(12) United States Patent
Cohen et al.

(10) Patent No.: US 6,884,600 B1
(45) Date of Patent: Apr. 26, 2005

(54) PROTEIN PHOSPHATASE-1 CATALYTIC SUBUNIT INTERACTIONS

(75) Inventors: Philip Cohen, Dundee (GB); Patricia Townsend Wade Cohen, Dundee (GB); David Barford, Oxford (GB)

(73) Assignee: Medical Research Council London (GB)

( * ) Notice: Subject to any disclaimer, the term of this patent is extended or adjusted under 35 U.S.C. 154(b) by 0 days.

(21) Appl. No.: 09/155,558

(22) PCT Filed: Apr. 1, 1997

(86) PCT No.: PCT/GB97/00898

§ 371 (c)(1),
(2), (4) Date: Mar. 17, 1999

(87) PCT Pub. No.: WO97/37224

PCT Pub. Date: Oct. 9, 1997

(30) Foreign Application Priority Data

Mar. 30, 1996 (GB) ............................................. 9606765
Dec. 19, 1996 (GB) ............................................. 9626362

(51) Int. Cl.[7] .......................... C12Q 1/44; C12N 15/09; C12N 9/12; A61K 38/00; C07K 1/00

(52) U.S. Cl. ........................ 435/21; 435/69.2; 435/194; 530/300; 530/350

(58) Field of Search ........................ 435/21, 194, 69.2, 435/195, 252.3, 320.1, 6, 325, 91.2; 530/300, 350; 536/23.1, 24.3

(56) References Cited

PUBLICATIONS

Gailly et al. European Journal of Biochemistry, (Jul. 15, 1996) 239 (2) : 326–32.*
Hubbard et al (1993) Trends Biochem Sci 18:172–177.
Egloff et al (1995) J Mol Biol 254:942–959.
Bollen et al (1992) Crit Rev Biochem Mol Biol 27(3):227–281.
Egloff et al (1997) EMBO J 16(8):1876–1887.
Chen et al (1994) FEBS Lett 356:51–56.
shimizu et al (1994) J Biol Chem 269:30407–30411.
Haystead et al (1995) FEBS Lett 377:123–127.
Moorhead et al (1994) FEBS Lett 356:46–50.
Doherty et al (1995) FEBS Lett 375:284–289.
Chen et al (1994) Diabetes 43:1234–1241.
Tang et al (1991) J Biol Chem 266:15782–15789.
Alessi et al (1992) Eur J Biochem 210:1023–1035.
Dent et al (1992) Eur J Biochem 210:1037–1044.
Cohen (1989) Ann Rev Biochem 58:453–508.
Alessi et al (1993) Eur J Biochem 213:1055–1066.
MacKintosh et al (1996) FEBS Lett 397:235–238.
Stark (1996) Yeast 12:1647–1675.
Johnson et al (1996) Eur J Biochem 239:317–325.
Cohen (1996) Adv Prot Phosphatases 8:371–376.
Barker et al (1993) Biochim Biophys Acta 1178:228–233.
Cohen et al (1988) Meth Enzymol 159:390–408.

(Continued)

Primary Examiner—Tekchand Saidha
(74) Attorney, Agent, or Firm—Rogalskyj & Weyand, LLP

(57) ABSTRACT

A method of identifying a compound which modulates the interaction between a PP1c and a regulatory subunit thereof, the method comprising determining whether a compound enhances or disrupts the interaction between (a) a PP1c or a fragment, variant, derivative or fusion thereof or a fusion of a fragment, variant or derivative and (b) a regulatory subunit which is able to bind to PP1c or a PP1c-binding fragment, variant, derivative or fusion of the subunit or a fusion of the fragment, variant or derivative. A method of affecting cellular metabolism or function, the method comprising administering to a cell (a) a compound which modulates the interaction between a PP1c and a regulatory subunit thereof or (b) a compound which mimics the effect of a regulatory subunit of PP1c or (c) a peptide capable of binding a PP1c and which affects the ability of PP1c to bind to a particular target and/or affects the regulation of PP1c activity, or a functional equivalent thereof.

19 Claims, 34 Drawing Sheets

OTHER PUBLICATIONS

Figure 1:
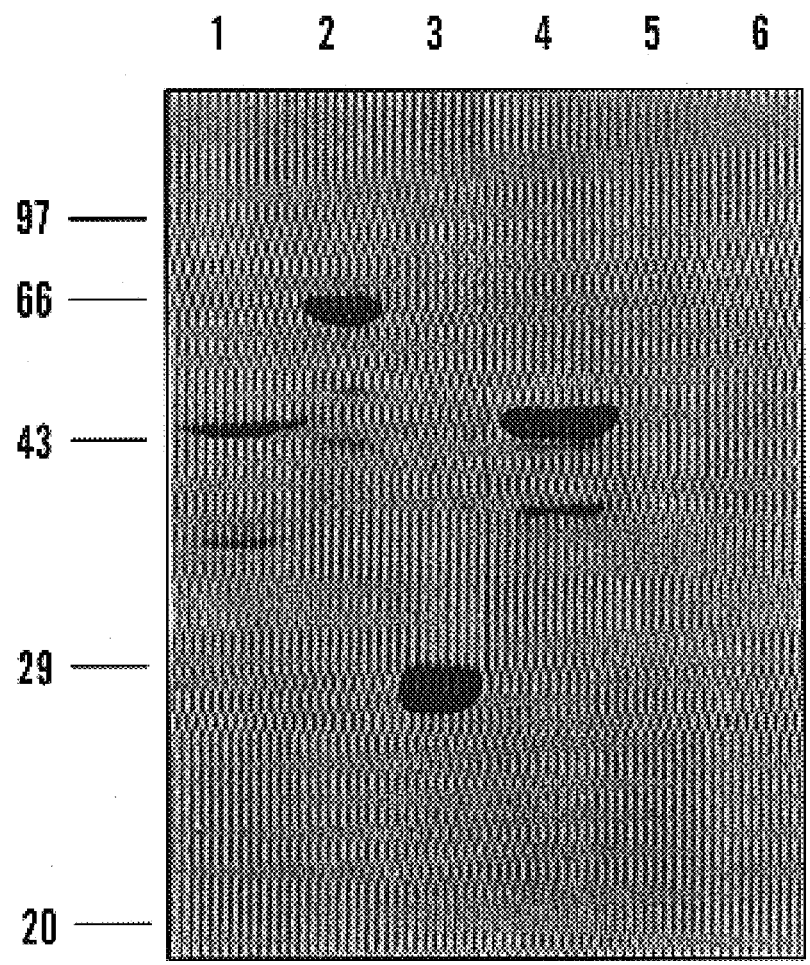

Mermoud et al (1992) Nucl Acids Res 20:5263–5269.
Moorhead et al (1995) FEBS Lett 362:101–105.
Shirazi et al (1994) J Biol Chem 269:31598–31606.
Helps et al (1995) FEBS Lett 377:295–300.
Okhura et al (1991) Cell 64:149–157.
Jagiello et al (1995) J Biol Chem 270:17257–17263.
Van Eynde et al (1995) J Biol Chem 270:28068–28074.
Durfee et al (1993) Genes & Dev 7:555–569.
Hirano et al (1995) J Biol Chem 270:19786–19790.
Cohen (1992) Trends Biochem Sci 17:408–413.
Stralfors et al (1986) Eur J Biochem 149:295–303.
Hirano et al (1996) FEBS Lett 389:191–194.
Beullens et al (1996) Eur J Biochem 239:183–189.
Hemmings et al (1990) J Biol Chem 265:20369–20376.
Desdouits et al (1995) Biochem Biophys Res Comm 206:653–658.
Aitken et al (1982) Eur J Biochem 126:235–246.
Williams et al (1986) J Biol Chem 261:1890–1903.
Alemany et al (1986) Eur J Biochem 156:101–110.
Barford et al (1994) J Mol Biol 235:763–766.
Barton et al (1994) Eur J Biochem 220:225–237.
Goldberg et al (1995) Nature 376:745–753.
Aitken et al (1982) FEBS Lett 147:54–58.
Endo et al (1996) Biochemistry 35:5220–5228.

* cited by examiner

| protein | putative PP1-binding motif | residues |
|---|---|---|
| GAC1 | S P E K N V R F A I E | 66-76 |
| PIG2 | S S G K S V R F A A H | 50-60 |
| GIP2 | I R S K S V H F D Q A | 217-227 |
| YIL045W | Q R S K S V H F D R V | 193-203 |
| YIL045W | V F V K N I Y F S N A | 412-422 |
| REG1 | T K N R H I H F N D R | 461-471 |
| REG2 | P R E R H I K F N D N | 164-174 |
| SCD5 | F K S K K V R F S E H | 270-280 |
| GIP1 | L S E K F I P F N N L | 180-190 |
| GIP1 | K K K R C V N F R N K | 441-451 |
| SHP1 | K V T R E I T F W K E | 232-242 |

*Fig. 12A*

| PROTEIN | PUTATIVE PP1-BINDING MOTIF | RESIDUES |
|---|---|---|
| GAC1 | S P E K N V R F A I E | 66-76 |
| PIG2 | S S G K S V R F A A H | 50-60 |
| GIP2 | I R S K S V H F D Q A | 217-227 |
| YIL045W | Q R S K S V H F D R V | 193-203 |
| YIL045W | V F V K N I Y F S N A | 412-422 |
| REG1 | T K N R H I H F N D R | 461-471 |
| REG2 | P R E R H I K F N D N | 164-174 |
| SCD5 | F K S K K V R F S E H | 270-280 |
| GIP1 | W N L K F I P F N N L | 180-190 |
| GIP1 | K K K R C V N F R N K | 441-451 |

*FIG. 12b*

```
Rat    MKMADAKQKRNEQLKRWIGSETDLEPPVVKRQ KTKVKFDDGAVFLAACSS    50
       |||||||||||||||||||||||||||||||  |||||||||||||||||||
Ch     MKMADAKQKRNEQLKRWIGSETDLEPPVVKRK KTKVKFDDGAVFLAACSS    50

Rat    GDTDEVLKLLHRGADINYANVDGLTALHQACI DDNVDMVKFLVENGANIN    100
       |||:|||:|| ||||||||||||||||||||| ||||||||||||||||||
Ch     GDTEEVLRLLERGADINYANVDGLTALHQACI DDNVDMVKFLVENGANIN    100

Rat    QPDNEGWIPLHAAASCGYLDIAEFLIGQGAHV GAVNSEGDTPLDIAEEEA    150
       |||||||||||||||||||||||||:|||||| ||||||||||||||||||
Ch     QPDNEGWIPLHAAASCGYLDIAEYLISQGAHV GAVNSEGDTPLDIAEEEA    150

Rat    MEELLQNEVNRQGVDIEAARKEEERIMLRDAR QWLNSGHISDVRHAKSGG    200
       ||||||||||||||||||||||||||||||| ||||||| |||||||||||
Ch     MEELLQNEVNRQGVDIEAARKEEERIMLRDAR QWLNSGHINDVRHAKSGG    200

Rat    TALHVAAAKGYTEVLKLLIQAGYDVNIKDYDG WTPLHAAAHWGKEEACRI    250
       |||||||||||||||||||||||||||||||| |||||||||||||||||||
Ch     TALHVAAAKGYTEVLKLLIQARYDVNIKDYDG WTPLHAAAHWGKEEACRI    250

Rat    LVDNLCDMETVNKVGQTAFDVADEDILGYLEE LQKKQNLLHSEKRDKKSP    300
       ||:|||||: |||||||||||||||||||||| |||||||||||||:||||
Ch     LVENLCDMEAVNKVGQTAFDVADEDILGYLEE LQKKQNLLHSEKREKKSP    300

Rat    LIESTANMENNQPQKTFKNKETLIIEPEKNAS RIESLEQEKADEEEEGKK    350
       ||||||::|||  |||||||||||:|||| |||| |||:|||||||||||||
Ch     LIESTANLDNNQTQKTFKNKETLIMEQEKNAS SIESLEHEKADEEEEGKK    350

Rat    DESSCSSEEDEEDDSESEAETDKTKPMASVTN AHTASTQAAPAAVTTPTL    400
       ||||||||:|:|||||||||| |:| |||||| |:| |::
Ch     DESSCSSEEEEDDDSESEAETDKAKTLA...NANTTSTQ..SASNTAPSV    395

Rat    SSNQGTPTSPVKKFPTSTTKISPKEEERKDES PASWRLGLRKTGSYGALA    450
       |||||||||||||:|||||||:|||||||||| |||||||||||||||||
Ch     AGGQGTPTSPLKKFPTSTTKVSPKEEERKDES PASWRLGLRKTGSYGALA    445

Rat    EITASKEAQKEKDTAGVIRSASSPRLSSSLDN KEKEKDNKGTRLAYVAPT    500
       |||||||||||||:||||||||||||||||||| |||||||:|||||||||
Ch     EITASKEAQKEKDSAGVIRSASSPRLSSSLDN KEKEKDGKGTRLAYVAPT    495

Rat    IPRRLGSTSDIEEKENRES..SNLRTSSSYTR RKWEDDLKKNSSIHEGST    548
       |||||:||||:||||| |:| ||| |||||:||| |:||| |
Ch     IPRRLASTSDIDEKENRDSSASSIRSGSSYAR RKWEEDVKKN.SLNEGPT    544

Rat    .....YHRSCSFGRRQDDLISCSVPSTTSTPT VTSAAGLQKSFLSSTSTT    552/593
            | || |||||||||:| |||| | |||||||:: ||
Ch     SLNTSYQRSGSFGRRQDDLVSSNVPSTAS..TVTSSAGLQKTLPASANTT    592

Rat    AKTPPGSSPAGTQSST SNRLWAEDSTEKEKDS APTAATILVAPTVVSAAA    587/643
       |: |: ||||||:||| |||||||||||||||| |:   |||:|| ||||
Ch     TKSTTGSTSAGVQSST SNRLWAEDSTEKEKDS VPTAVTVPVAPSVVNAAA    642

Rat    SSTTALTTTAGTLSS TSEVRERRRSYLTPVR DEESESQRKARSRQARQS    637/693
       :|||:|| :||||:|| ||||||||||||||||| |||||||||||||||||
Ch     .TTTAMTTATSGTVSS TSEVRERRRSYLTPVR DEESESQRKARSRQARQS    691

Rat    RRSTQGVTLTDLQEAEKTIGRSRSTRTREQEN EEKDKEEKEKQDKEKQEE    687/743
       |||||||||||||||||||||||||||||||| :||||||||||||||||
Ch     RRSTQGVTLTDLQEAEKTIGRSRSTRTREQEN EEKEKEEKEKQDKEKQEE    741

Rat    KKESEVSREDEYKQKYSRTYDETYARYRPVST SSSSTPSSSLSTLGSSL    737/793
       |||||   :::|:|:|:|||   :| | |||| || :|| |:|||| |||
Ch     KKESE.TKDDDYRQRYSRTVEEPYHRYRPTST .STSTSSTSSLSTSTSSL    789

Rat    YASSQLNRPNSLVGITSAYSRGLTKDNEREGE KKEEEKEGEDKSQPKSIR    787/843
       ||||||||||||:|||||||||:||| ||: |||| |||||||  |||||||
Ch     SSSSQLNRPNSLIGITSAYSRSGTKESEREGG KKEEEKE.EDKSQPKSIR    838

Rat    ERRRPREKRRSTGVSFWTQDSDENEQERQSDT EDGSSKRDTQTDSVSRYD    837/893
       |||||||||||||||||||||||||||:|:| |||:|:| |:|:||:|||
Ch     ERRRPREKRRSTGVSFWTQDSDENEQEHQSDS EEGTNKKETQSDSLSRYD    888

Rat    ..SSSTSSSDRYDSLLGRSASYSYLEERKPYG SRLEKDDSTDFKKLYEQI    885/941
         |||||||||:|| ||||:| |||||:|||| |||||||||||||||||
Ch     TGSLSVSSGDRYDSAQGRSGSQSYLEDRKPYC SRLEKEDSTDFKKLYEQI    938

Rat1/3                                                    ERRA    935/991
Rat2   LAENEKLKAQLHDTNMELTDLKLQLEKATQRQ ERFADRSLLEMEKRVTGK    935
       ||||||||||||||||||||||||||||||| |||| |||||||||||:||
Ch     LAENEKLKAQLHDTNMELTDLKLQLEKTTQRQ ERFADRSLLEMEKRVSGK    988

Rat1/3 LERRISEMEEELKMLPDLKADNQRLKDENGAL IRVISKLSK            976/1032
Rat2   SQYLLGGTKSSRKKNI                                     951
       |||||||| |||||:|
Ch     SQYLLGGKKSSRKKDI                                     1004
```

FIG. 17

Fig. 18B

PROTEIN PHOSPHATASE-1 CATALYTIC SUBUNIT INTERACTIONS

The present invention relates to peptides and protein-protein interactions and to the use of peptides, peptide analogues and compounds which modulate protein-protein interactions in the control of cellular metabolism and function.

Cellular metabolism or function is controlled by a number of regulatory agents, which are affected by extracellular factors, for example the physical condition of the cell or the binding of a messenger molecule to a receptor located on the cell surface. The extracellular factor may then initiate a cascade of secondary messenger reactions within the cell itself, leading ultimately to changes in some aspects(s) of metabolism or cell function.

It is well recognised by those skilled in the art that phosphorylation or dephosphorylation reactions often play a key role in regulating the activity of the proteins affected. Dephosphorylation reactions are catalysed by phosphatase enzymes, the activity of which may themselves be controlled by phosphorylation and/or dephosphorylation events. Whilst a substantial amount of knowledge has been accumulated regarding protein phosphatases as a group, the number and variety of these enzymes is such that detailed information concerning the mode of action of a specific phosphatase is not always available. There remains a need to further elucidate and characterise particular key enzymes.

The reversible phosphorylation of proteins regulates most aspects of cell life. About a third of all mammalian proteins are now thought to contain covalently bound phosphate and since protein kinases and phosphatases probably account for approximately 2–3% of all human gene products (Hunter, 1995), many of these enzymes must typically phosphorylate/dephosphorylate numerous proteins in vivo. However, it is becoming increasingly clear that some protein kinases and phosphatases do not find their physiological substrates by simple diffusion within cells and that they are frequently directed to particular loci in the vicinity of their substrates by interaction with targeting subunits. In this way, the actions of protein kinases and phosphatases with inherently broad specificities are restricted and their properties tailored to the needs of a particular subcellular location, organelle or process (reviewed in Hubbard and Cohen, 1993; Faux and Scott, 1996).

Protein phosphatase-1 (PP1), one of the major protein serine/threonine phosphatases of eukaryotic cells, participates in the control of a variety of cellular functions that include glycogen metabolism, muscle contraction, the exit from mitosis (reviewed in [1,2]) and the splicing of mRNA [3]. However, evidence has been accumulating that different processes are regulated by distinct forms of PP1 in which the phosphatase catalytic subunit (PP1c) is complexed to specific "targeting subunits". These proteins not only direct PP1c to particular subcellular locations, but modify its specificity in unique ways and confer regulation by extracellular agonists (reviewed in [2,3]).

Several targeting subunits have been isolated and characterised, including the $G_M$-subunit that targets PP1c to both the glycogen particles and sarcoplasmic reticulum of striated muscles [4,5], the $G_L$ subunit that targets PP1c to liver glycogen [6,7], the M-complexes responsible for the association of PP1c with the myofibrils of skeletal muscle [8,9] and smooth muscle [9-12], the p53 binding protein p53BP2 [13] and nuclear proteins such as sds22 [14] and NIPP1 [15,16]. PP1c is also reported to interact with other mammalian proteins such as the retinoblastoma gene product [17], ribosomal protein L5 [18], a 110 kDa nuclear protein that has yet to be identified [15] and two cytosolic proteins, termed inhibitor-1 and inhibitor-2. Inhibitor-1, and its homologue termed dopamine and cyclic AMP-regulated phosphoprotein (DARPP), become potent PP1 inhibitors after phosphorylation by cyclic AMP-dependent protein kinase (PKA). Inhibitor-1 is thought to inactivate PP1c released from glycogen particles when $G_M$ is phosphorylated by PKA [19]. Inhibitor-2 is present as a complex with PP1 in the cytosol, and there is evidence that one of its roles is to act like a molecular chaperone to ensure that the PP1 catalytic centre is folded correctly prior to its delivery to a specific targeting subunit [20]. It seems likely that many other PP1-targeting subunits will be identified over the next few years as a result of the introduction of powerful new techniques such as microcystin Sepharose affinity chromatography [8] and the yeast "two hybrid system" [13].

The forms of PP1c isolated so far each contain a single PP1c-binding subunit, implying that the interaction of different targeting subunits with PP1c may be mutually exclusive. This, in turn, suggests that the binding sites for targeting subunits may overlap, and that the proportion of PP1 directed to any particular location may be determined by the amounts of each targeting subunit synthesised and their relative affinities for PP1. However, the different targeting subunits show surprisingly little similarity to one another. $G_M$ and $G_L$ are structurally related, yet display only 23% amino acid sequence identity over the first 286 residues of $G_M$, while $G_L$ lacks the C-terminal 750 residues of $G_M$ [7]. p53BP2 [13] and the $M_{110}$ subunits from smooth muscle [10,11] and skeletal muscle [8] contain ankyrin repeats, but no other similarities have so far been detected between other PP1 targeting subunits.

The paradigm for the targeting subunit concept is protein phosphatase-1 (PP1), one of the major serine/threonine specific protein phosphatases of eukaryotic cells (Stralfors el al., 1985). This enzyme is involved in controlling diverse cellular functions including glycogen metabolism, muscle contraction, the exit from mitosis and the splicing of RNA (Cohen, 1989; Shenolikar, 1994; Wera and Hemmings, 1995). These different processes appear to be regulated by distinct PP1 holo-enzymes in which the same catalytic subunit (PP1c) is complexed to different targeting or regulatory subunits. The latter class of subunits act to confer in vivo substrate specificity not only by directing PP1c to the subcellular loci of its substrates, but also by enhancing or suppressing its activity towards different substrates. In addition, the regulatory subunits allow the activity of PP1 to be modulated by reversible protein phosphorylation and second messengers in response to extracellular stimuli.

Many regulatory subunits modulate the activity of PP1 towards its substrates. In the instance of the regulatory $M_{110}$ subunit that targets PP1c to myosin, the region on the $M_{110}$ subunit that enhances the dephosphorylation of myosin by PP1 has now been shown to be distinct from the region involved in targetting the PP1-M holoenzyme to myosin. These observations indicate that alterations in the substrate specificity of PP1c are likely to result from conformational changes induced by interactions with the targetting subunit and not simply as a direct result of targetting PP1c to its substrate. However, in the case of the glycogen binding subunit $G_M$, the dephosphorylation of glycogen phosphorylase and glycogen synthase was enhanced only under conditions when both the PP1-$G_M$ complex and its substrates were bound to glycogen (Hubbard and Cohen, 1989) suggesting that targetting alone may be sufficient to enhance specificity.

Whilst the identity of the PP1-binding site(s) on any targeting subunit is unknown, it has now been realised that the control of the substrate specificity and activity of this key regulatory enzyme and its interactions are of therapeutic importance. Disruption of PP1-targeting subunit interactions provide a way of altering selectively the state of phosphorylation, and hence the activities, of particular PP1 substrates. We have now identified relatively small peptides from the $G_M$ and $M_{110}$-subunits that interact with PP1, and which either disrupt or mimic the distinctive properties of myofibrillar and glycogen-associated forms of PP1. The binding of the G-subunit and the M-subunit of PP1 has also been found to be mutually exclusive.

A first aspect of the invention provides a method of identifying a compound which modulates the interaction between a PP1c and a regulatory subunit thereof, the method comprising determining whether a compound enhances or disrupts the interaction between (a) a PP1c or a fragment, variant, derivative or fusion thereof or a fusion of a fragment, variant or derivative and (b) a regulatory subunit which is able to bind to PP1c or a PP1c-binding fragment, variant, derivative or fusion of said subunit or a fusion of said fragment, variant or derivative.

Conveniently, the PP1c or a fragment, variant or derivative or fusion thereof or a fusion of a fragment, variant or derivative is one that is produced using recombinant DNA technology. By "fragment, variant, derivative or fusion of PP1c" we mean any such fragment, variant, derivative or fusion that retains the ability to interact with a regulatory subunit or a suitable PP1c-binding fragment, variant, derivative or fusion of said subunit or a fusion of said fragment, variant or derivative.

By "regulatory subunit" we mean any such regulatory subunit. Further subunits are being identified all the time. It is preferred if the regulatory subunit contains the consensus peptide sequence SEQ ID NO:35: Arg/Lys-Val/Ile-Xaa-Phe as described below.

By "PP1c-binding fragment, variant, derivative or fusion of said subunit or a fusion of said fragment, variant or derivative" we include any such fragments, variants, derivatives and fusions which are able to bind to PP1c. Conveniently, the fragments, variants, derivatives are made using recombinant DNA technology or, in the case of peptides and peptide derivatives and analogues they may be made using peptide synthetic methods.

The enhancement or disruption of the interaction between the said PP1c or a fragment, variant, derivative or fusion thereof or a fusion of a fragment, variant or derivative and the said regulatory subunit or a fragment, variant, derivative or fusion thereof or a fusion of a fragment, variant or derivative can be measured in vitro using methods well known in the art of biochemistry and including any methods which can be used to assess protein-protein, protein-peptide and protein-ligand interactions.

The said interaction can also be measured within a cell, for example using the yeast two-hybrid system as is well known in the art.

It should be appreciated that before the present invention the dissociation of a PP1c-regulatory subunit has not been achieved using a small molecule such as a peptide or a peptide analogue or derivative. Thus, it is preferred if the compounds screened in the method of the first aspect of the invention are small molecules and in particular that they are not intact regulatory subunits of PP1c.

By "small molecule" we include any compounds which have a molecular weight of less than 5000, preferably less than 2000 and more preferably less than 1000. Conveniently, the compounds screened are compounds which are able to enter a cell either passively via the cell membrane or via an active uptake system.

A second aspect of the invention provides a method of identifying a compound which mimics the effect of a regulatory subunit of PP1c, the method comprising contacting said compound with PP1c and determining whether, in the presence of the compound, PP1c adopts the function of properties of a PP1c in the presence of a given regulatory subunit.

By "mimics the effect of a regulatory subunit of PP1c" we include the meaning that the compound modifies a property of PP1c in such a way that PP1c acts, in at least one respect, like PP1c that is interacting with a regulatory subunit.

Examples of the properties of PP1c that may be modified, and examples of compounds which modify the properties of PP1c which are therefore identifiable in this method are given below.

Preferably, in the methods of the first and second aspects the said regulatory subunit of PP1c is any one of $M_{110}$, $G_L$, $G_M$, M-complexes, p53 BP2, sds22, NIPPI, L5, Inhibitor-1, Inhibitor-2, or DARPP.

More preferably, the regulatory subunit of PP1c is any one of $M_{110}$, $G_L$, $G_M$, M-complexes or p53BP2, and still more preferably the regulatory subunit of PP1c is $M_{110}$ or $G_M$.

In relation to the method of the first aspect of the invention the fragment of a regulatory subunit which is able to bind to PP1c is any of the peptides C63-T93 of SEQ ID NO:32, G63-N75 of SEQ ID NO:32, E2-R575 of SEQ ID NO:34, E2-P243 of SEQ ID NO:34, E2-D118 of SEQ ID NO:34, H10C-P350 of SEQ ID NO:34 and peptide 63–80 of SEQ ID NO:32 $G_M$ or functional equivalents thereof or peptides comprising said peptide sequences provided that they are not the complete $G_M$ regulatory subunit. Preferably the peptides are not E2-R575 of SEQ ID NO:34 or H100-P350 of SEQ ID NO:34.

As is described in more detail in the Examples, these peptides have been shown to bind to PP1c and it is convenient, in some circumstances, for the method to be carried out such that one of these peptide is displaced from, or the binding is enhanced to, PP1c. Suitably, the peptide may be labelled in a detectable manner to facilitate the detection of the interaction with PP1c. Conveniently, the peptide is labelled radioactively or fluorescently using methods well known in the art.

Also in relation to the method of the first aspect of the invention the fragment of a regulatory subunit which is able to bind to PP1c is any of the peptides M1-E309 of SEQ ID NO:33, M1-F38 of SEQ ID NO:33, M1-A150 of SEQ ID NO:33 or L24-Y496 of SEQ ID NO:33 of $M_{110}$ or functional equivalents thereof or peptides comprising said peptide sequences provided that they are not the complete $M_{110}$ regulatory subunit.

As is shown in more detail in the Examples these peptides have been shown to bind to PP1c.

Also in relation to the first aspect of the invention the PP1c-binding fragment, variant or derivative of said regulatory subunit or a fusion of said fragment, variant or derivative comprises the consensus peptide sequence SEQ ID NO:35: Arg/Lys-Val/Ile-Xaa-Phe wherein Xaa is any amino acid.

We have found that, surprisingly, many regulatory subunits that bind to PP1c contain the consensus peptide sequence Arg/Lys-Val/Ile-Xaa-Phe wherein Xaa is any amino acid, preferably a naturally occurring amino acid.

Typically, the PP1c-binding fragment, variant or derivative of said regulatory subunit or a fusion of said fragment, variant or derivative is a peptide (typically 8–400 amino acid residues, preferably 8–200, more preferably 8–10 and still more preferably 8–20 amino acid residues in length which comprises the given consensus peptide sequence).

It is preferred if the PP1c-binding fragment, variant or derivative comprises, in addition to the said consensus peptide sequence, at least one basic residue in the four residues N-terminal of the consensus peptide sequence. Preferably, there are at least two basic residues in this position, more preferably at least three such residues.

It is also preferred wherein in the consensus peptide sequence Xaa is not Asp or Glu because the negative charge is believed to interfere with binding to PP1c. Similarly, it is preferred if Xaa is not a large hydrophobic residue such as Phe, Tyr, Trp, Ile or Leu.

It is particularly preferred if the PP1c-binding fragment is a fragment of a regulatory subunit comprising the said consensus peptide sequence and therefore the peptide sequences which flank the consensus peptide sequence are the same as in the native regulatory subunit.

Preferably the PP1c-binding fragment is a fragment of any of the $M_{110}$, $G_L$, $G_M$, M-complexes, p53BP2, sds22, NIPPI, L5, Inhibitor-1, Inhibitor-2 or DARPP regulatory subunits comprising said consensus sequence.

Although the methods of the first and second aspects of the invention do not rely on any particular mechanism whereby the modulation or mimicking occurs, it is preferred if the compound binds to a PP1c. Alternatively, but still preferably, the compound binds to a regulatory subunit of PP1c.

A further aspect of the invention provides a compound identifiable by the method of the first or second aspects of the invention.

A further aspect of the invention provides a compound which modulates the interaction between a PP1c and a regulatory subunit thereof said compound comprising any of the peptides G63-T93 of SEQ ID NO:32, G63-N75 of SEQ ID NO:32, E2-R575 of SEQ ID NO:34, E2-P243 of SEQ ID NO:34, E2-D118 of SEQ ID NO:34, H100-P350 of SEQ Or NO:34 and peptide 63–80 of SEQ ID NO:32 $G_M$ or functional equivalents thereof or said compound comprising any of the peptides M1-E309 of SEQ ID NO:33, M1-F38 of SEQ ID NO:33, M1-A150 of SEQ ID NO:33 or L24-Y496 of SEQ ID NO:33 of $M_{110}$ or functional equivalents thereof or said compound comprising the consensus peptide sequence SEQ ID NO:35: Arg/Lys-Val/Ile-Xaa-Phe wherein Xaa is any naturally occurring amino acid or functional equivalents thereof, provided that the said compound is no a complete regulatory subunit of PP1c. Preferably the peptides are not E2-R575 of SEQ ID NO:34 or H100-P350 of SEQ ID NO:34.

By "functional equivalent" we include the meaning that the compound, although having a different structure to the said peptides, modulates the interaction between a PP1c and a regulatory subunit thereof in substantially the same way. For example, a functional equivalent may be a peptide in which conservative substitutions have been made. By "conservative substitution" is intended combinations such as Gly, Ala; Val, Ile, Leu; Asp, Glu; Asn, Gln; Ser, Thr; Lys, Arg; and Phe, Tyr. A functional equivalent may also be a peptide with the given sequence which has been adapted to be more likely to enter a cell. For example, fatty acids or other hydrophobic moieties may be attached to the peptide.

By the term "peptide" we mean derivatives of peptides which are resistant to proteolysis, for example those in which the N or C termini are blocked, or both are blocked, and it includes molecules in which one or more of the peptide linkages are modified so that the molecule retains substantially the same molecular configuration in the linkage but the linkage is more resistant to hydrolysis than a peptide linkage.

It is particularly preferred if the compound consists of the peptides G63-T93 of SEQ ID NO:32, G63-N75 of SEQ ID NO:32, E2-R575 of SEQ ID NO:34, E2-P243 of SEQ ID NO:34, E2-D118 of SEQ ID NO:34, H100-P350 of SEQ ID NO:34 or peptide 63 to 80 of SEQ ID NO:32 $G_M$ or functional equivalents thereof or if the compound consists of the peptides M1-E309 of SEQ ID NO:33, M1-F38 of SEQ ID NO:33, M1-A150 of SEQ ID NO:33 or L24-Y496 of SEQ ID NO:33 of $M_{110}$ or functional equivalents thereof. Preferably, the peptide is not E2-R575 of SEQ ID NO:34 or H100-P350 of SEQ ID NO:34.

A still further aspect of the invention provides a method of identifying a compound which modulates the interaction between a PP1c and a regulatory subunit thereof, or binds PP1c or mimics the effect of a regulatory subunit, the method comprising selecting a compound which is capable of adopting the same or substantially the same conformation as a peptide bound to the regulatory subunit-binding site of PP1c or the same or substantially the same conformation as the portion of PP1c which binds to said peptide. Suitably, the peptide comprises the consensus peptide sequence Arg/Lys-Val/Ile-Xaa-Phe wherein Xaa is any amino acid, preferably a naturally occurring amino acid. Conveniently, the said peptide consists of residues 63 to 75 of $G_M$.

It is particularly preferred if the conformation of the said peptide and the conformation of the said portion of PP1c is as defined by reference to the atomic coordinates given in Table A (see also Example 2). Example 2 provides further details of the peptide—PP1c interactions.

Table A provides the atomic coordinates for the given PP1c-peptide crystal structure.

A further aspect of the invention provides a compound identifiable by the aforementioned method of the invention.

It will be appreciated that the aforementioned compounds and peptides will be useful in medicine and, accordingly, the invention includes pharmaceutical compositions of the said compounds in combination with a pharmaceutically acceptable carrier.

The formulations may conveniently be presented in unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (eg povidone, gelatin, hydroxypropylmethyl cellulose), lubricant, inert diluent, preservative, disintegrant (eg sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

A further aspect of the invention provides a method of affecting cellular metabolism or function, the method comprising administering to a cell (a) a compound which modulates the interaction between a PP1c and a regulatory subunit thereof or (b) a compound which mimics the effect of a regulatory subunit of PP1c or (c) a peptide capable of binding a PP1c and which affects the ability of PP1c to bind to a particular target and/or affects the regulation of PP1c activity, or a functional equivalent thereof.

It will be appreciated that the said compounds are disclosed above with respect to specific compounds or with respect to methods of obtaining such compounds.

In particular, it is preferred if the compound administered to the cell is any one or more of the peptides G63-T93 of SEQ ID NO:32, G63-N75 of SEQ ID NO:32, E2-R575 of SEQ ID NO:34, E2-P243 of SEQ ID NO:34, E2-D118 of SEQ ID NO:34, H100-P350 of SEQ ID NO:34 and peptide 63–80 of SEQ ID NO:32 $G_M$ or functional equivalents thereof or peptides comprising said peptide sequences or any one or more of the peptides M1-E309 of SEQ ID NO:33, M1-F38 of SEQ ID NO:33, M1-A150 of SEQ ID NO:33 or L24-Y496 of SEQ ID NO:33 of $M_{110}$ or functional equivalents thereof or peptides comprising said peptide sequences. Preferably, the peptide is not E2-R575 of SEQ ID NO:34 or H100-P35C of SEQ ID NO:34.

In this embodiment it will be appreciated that functional equivalents include those compounds defined above as being functional equivalents, in particular, derivatives of peptides which are more readily able to enter a cell.

The compound may be administered to the cell in any suitable way, in particular in such a way that the compound will enter the cell in a suitable form to have its desired effect. Method of facilitating the entry of a compound into the cell are known in the art, for example, in relation to peptides the importins and penetrations may be used, or the peptides may be micro-injected or they may enter the cell in a suitable vehicle such as in a liposome.

Preferably, the cell is a cell in a mammalian body.

The aforementioned compounds of the invention or a formulation thereof may be administered by any conventional method including oral and parenteral (eg subcutaneous or intramuscular) injection. The treatment may consist of a single dose or a plurality of doses over a period of time.

Whilst it is possible for a compound of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof. Typically, the carriers will be water or saline which will be sterile and pyrogen free.

A further aspect of the invention provides a method of treating a patient in need of modulation of PP1c activity or function the method comprising administering to the patient an effective amount of a compound which modulates the interaction between a PP1c and a regulatory subunit thereof or (b) a compound which mimics the effect of a regulatory subunit of PP1c or (c) a peptide capable of binding a PP1c and which affects the ability of PP1c to bind to a particular target and/or affects the regulation of PP1c activity, or a functional equivalent thereof.

As will be apparent from what is described herein, protein phosphatase-1 (PP1) is one of the principal serine/threonine-specific protein phosphatases in human cells where it plays key roles in regulating a variety of physiological roles, including the metabolism of glycogen, the splicing of mRNA, the exit from mitosis and the contraction of smooth muscle. The different functions of PP1 are carried out by distinct species of this enzyme in which the same catalytic unit is complexed to different "targeting" subunits. The latter class of proteins direct PP1 to specific subcellular loci, tailor its properties to the needs of a particular locus and confer the ability to be regulated by extracellular signals (hormones, growth factors, neurotransmitters). Compounds as herein described that disrupt specific PP1-"targeting" subunits interactions or mimic the effect of a targeting subunit are likely to have a number of therapeutic uses as outlined below.

PP1 interacts with the M110-subunit which targets it to myosin in smooth muscle and enhances the rate at which PP1 dephosphorylates myosin. The dephosphorylation of myosin underlies the relaxation of smooth muscle. Thus compounds such as those disclosed herein which disrupt the interaction of PP1 with M110 in arterial muscle are expected to increase the phosphorylation of arterial myosin and elevate blood pressure.

The interaction of PP1 with M110 enhances the rate at which PP1 dephosphorylates myosin, but suppresses the rate at which it dephosphorylates glycogen phosphorylase. The disruption of the PP1-M110 interaction is therefore measured in a screen by looking for compounds which enhance the dephosphorylation of phosphorylase and/or suppress the dephosphorylation of the myosin P-light chain (see the Examples).

Compounds, such as those disclosed herein, that mimic the effect of the M110 subunit in stimulating myosin dephosphorylation are expected to be useful in lowering blood pressure. Such compounds are identified by their ability to stimulate the dephosphorylation of the myosin P-light chain by the catalytic subunit of PP1. An example of such an assay, which shows that the N-terminal 38 residues of the M110 subunit stimulate the dephosphorylation of the myosin P-light chain by PP1, is shown in the Examples.

The interaction of PP1 with $G_L$ targets the phosphatase to liver glycogen. This interaction enhances the dephosphorylation glycogen synthase which stimulates the conversion of glucose to glycogen. A compounds, such as those disclosed herein, disrupts the interaction between PP1 and $G_L$ is expected to be useful in treating hypoglycemia. The interaction of $G_L$ with PP1 strongly suppresses the rate at which PP1 dephosphorylates glycogen phosphorylase. A compound, such as those disclosed herein, which disrupts the interaction of PP1 with $G_L$ can be screened for very simply by its ability to increase the phosphorylase phosphatase activity of PP1 $G_L$. This can be carried out, for example, using rat liver glycogen pellet as described in the Examples. There is no need to use the purified enzyme.

PP1 interacts with p53 BP2 (Helps et al, 1995) a protein which is known to interact with the tumour suppressor p53. The phosphorylation of p53 is known to enhance its ability to bind to DNA and hence its ability to function as a tumour suppressor. p53BP2 may be a protein which targets PP1 to p53 stimulating the dephosphorylation and inactivation of p53. A compound, such as those disclosed herein, which disrupts the interaction of PP1 with p53BP2 may enhance the phosphorylation of p53 and its ability to function as a tumour suppressor. Since p53BP2 suppresses the dephosphorylation of glycogen phosphorylase (Helps et al, 1995), compounds that disrupt the p53BP2-PP1 complex can be screened by measuring the increase in rate of dephosphorylation of glycogen phosphorylase.

The present invention provides peptides able to bind to the catalytic sub-unit of protein phosphatase-1 (hereinafter referred to as PP1c). Generally the peptides affect the ability of PP1c to bind to particular target(s) and/or the regulation of PP1c activity.

Peptides can be designed based on the sequences of regulatory subunits, especially in relation to the peptide consensus sequence found therein and its flanking sequences. Peptides can be synthesised by methods well known in the art. For example, peptides may be synthesised by the Fmoc-polyamide mode of solid-phase peptide synthesis as disclosed by Lu et al (1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspanic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiocbem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

The peptides may be derived from the targeting subunit (s) of PP1c, in particular from the subunits $G_L$, $G_M$, $M_{110}$ and/or $M_{21}$. Additionally the peptides may be derived from other subunits such as different M-complexes, p53BP2, sds22, NIPP1, L5, Inhibitor-1, Inhibitor-2, DARPP or the like. Functional equivalents or portions of these peptides may also be used.

In a further aspect the present invention provides the use of peptides derived from targeting subunit(s) of PP1c, functional equivalents or portions thereof to affect cellular metabolism or function.

In a further aspect the present invention provides a method of treatment of the human or non-human (preferably mammalian) animal body, said method comprising altering the levels of peptides derived from targeting subunit(s) of PP1c, functional equivalents or portions thereof to an extent that cellular metabolism or function is affected.

Aspects of cellular metabolism that may be affected include (but are not limited to) glycogen metabolism, muscle metabolism, physiology and function.

Generally the levels of peptides or their activity will be enhanced in cells and this control may be achieved by causing higher levels of expression of nucleotides sequences encoding for such peptides (optionally linked to molecules which allow them to cross a cell membrane) or through the administration of such peptides or precursors thereof. Alternatively, in some circumstances, it may be more desirable to depress the levels of certain peptides or at least to depress the level of peptides in active form.

Preferred peptides according to the present invention are derivatives of $G_M$, especially G63-T93 of SEQ ID NO:32, G63-N75 of SEQ ID NO:32, E2-R575 of SEQ ID NO:34, E2-P243 of SEQ ID NO:34, E2-D118 of SEQ ID NO:34, H100-P350 of SEQ ID NO:34 and peptide 63 to 80 of SEQ ID NO:32, and derivatives of $M_{110}$, especially M1-E309 of SEQ ID NO:33, M1-F38 of SEQ ID NO:33, M1-A15C of SEQ ID NO:32, and L24-Y496 of SEQ ID NO:33. Preferably, the peptide is not E2-R575 of SEQ ID NO:34 or H100-P35C of SEQ ID NO:34.

Particularly preferred peptides are those derived from amino acid nos. 63 to 93 of SEQ ID NO:32, (including 63–80 and 63–75) of $G_M$; or from amino acids 1 to 309 of SEQ ID NO:33 (including from 1–150 and 1–38) of $M_{110}$.

The sequence of $G_M$ is given in Chen et al (1994) *Diabetes* 43, 1234–1241.

In yet further aspect the present invention provides chimeric proteins containing portions of other proteins or peptides or containing additional amino acids.

Additionally the present invention provides nucleotide sequences (optionally in the form of plasmids) encoding the peptides or chimeric proteins of interest. DNA which encodes the polypeptides or peptides of the invention or chimeric proteins can be made based on a knowledge of the peptide sequences disclosed herein. The DNA is then expressed in a suitable host to produce a polypeptide comprising the compound of the invention. Thus, the DNA encoding the polypeptide constituting the compound of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. No. 4,440,859 issued 3 Apr. 1984 to Rutter et at, U.S. Pat. No. 4,530,901 issued 23 Jul. 1985 to Weissman, U.S. Pat. No. 4,582,800 issued 15 Apr. 1986 to Crowl, U.S. Pat. No. 4,677,063 issued 30 Jun. 1987 to Mark et at, U.S. Pat. No. 4,678,751 issued 7 Jul. 1987 to Goeddel, U.S. Pat. No. 4,704,362 issued 3 Nov. 1987 to Itakura et at, U.S. Pat. No. 4,710,463 issued 1 Dec. 1987 to Murray, U.S. Pat. No. 4,757,006 issued 12 Jul. 1988 to Toole, Jr. et at, U.S. Pat. No. 4,766,075 issued 23 Aug. 1988 to Goeddel et at and U.S. Pat. No. 4,810,648 issued 7 Mar. 1989 to Stalker, all of which are incorporated herein by reference.

The DNA encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example Aspergillus), plant cells, animal cells and insect cells.

The vectors include a prokaryotic replicon, such as the ColE1 ori, for propagation in a prokaryote, even if the vector is to be used for expression in other, non-prokaryotic, cell types. The vectors can also include an appropriate promoter such as a prokaryolic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical manimalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403–406 and pRS413–416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413–416 are Yeast Centromere plasmids (YCps).

A variety of methods have been developed to operably link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences, at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) *Science* 239, 487–491.

In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art. In relation to the above section on DNA expression the term "polypeptide" includes peptides and chimeric proteins.

Further the present invention provides host cells transformed with suitable expression vectors and able to express the peptides. The host cells may be prokaryotic (e.g. *E. coli*) or eukaryotic (e.g. yeast, mammalian cell cultures).

Bacterial cells are preferred prokaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast and mammalian cells, preferably vertebrate cells such as those from a mouse, rat, monkey or human fibroblastic cell line. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, and monkey kidney-derived COS-1 cells available from the ATCC as CRL 1650.

Transformation of appropriate cell hosts with a DNA construct of the present invention is accomplished by well known methods that typically depend on the type of vector used. With regard to transformation of prokaryotic host cells, see, for example, Cohen et al (1972) *Proc. Natl. Acad. Sci. USA* 69, 2110 and Sambrook et al (1989) *Molecular Cloning, A Laboratory Manual*, Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104–109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming cells and is well known in the art for transforming yeast cell, bacterial cells and vertebrate cells.

For example, many bacterial species may be transformed by the methods described in Luchansky et al (1988) *Mol. Microbiol.* 2, 637–646 incorporated herein by reference. The greatest number of transformants is consistently recovered following electroporation of the DNA-cell mixture suspended in 2.5×PEB using 6250V per cm at 251 $\mu$FD.

Methods for transformation of yeast by electroporation are disclosed in Becker & Guarente (1990) *Methods Enzymol.* 194, 182.

Successfully transformed cells, ie cells that contain a DNA construct of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium.

In another aspect the present invention provides antibodies to PP1c which act in an analogous manner to the peptides of interest. Antibodies to the peptides themselves are also provided and these may themselves be used to affect cell metabolism or function.

Peptides in which one or more of the amino acid residues are chemically modified, before or after the peptide is synthesised, may be used providing that the function of the peptide, namely the production of specific antibodies in vivo, remains substantially unchanged. Such modifications include forming salts with acids or bases, especially physiologically acceptable organic or inorganic acids and bases, forming an ester or amide of a terminal carboxyl group, and attaching amino acid protecting groups such as N-t-butoxycarbonyl. Such modifications may protect the peptide from in vivo metabolism. The peptides may be present as single copies or as multiples, for example tandem repeats. Such tandem or multiple repeats may be sufficiently antigenic themselves to obviate the use of a carrier. It may be advantageous for the peptide to be formed as a loop, with the N-terminal and C-terminal ends joined together, or to add one or more Cys residues to an end to increase antigenicity and/or to allow disulphide bonds to be formed. If the peptide is covalently linked to a carrier, preferably a polypeptide, then the arrangement is preferably such that the peptide of the invention forms a loop.

According to current immunological theories, a carrier function should be present in any immunogenic formulation in order to stimulate, or enhance stimulation of, the immune system. It is thought that the best carriers embody (or, together with the antigen, create) a T-cell epitope. The peptides may be associated, for example by cross-linking, with a separate carrier, such as serum albumins, myoglobins, bacterial toxoids and keyhole limpet haemocyanin. More recently developed carriers which induce T-cell help in the immune response include the hepatitis-B core antigen (also called the nucleocapsid protein), presumed T-cell epitopes such as Thr-Ala-Ser-Gly-Val-Ala-Glu-Thr-Thr-Asn-Cys (SEQ ID No 1), beta-galactosidase and the 163–171 peptide of interleukin-1. The latter compound may variously be regarded as a carrier or as an adjuvant or as both. Alternatively, several copies of the same or different peptides of the invention may be cross-linked to one another; in this situation there is no separate carrier as such, but a carrier function may be provided by such cross-linking. Suitable cross-linking agents include those listed as such in the Sigma and Pierce catalogues, for example glutaraldehyde, carbodiimide and succinimidyl 4-(N-maleimidomethyl) cyclohexane-1-carboxylate, the latter agent exploiting the —SH group on the C-terminal cysteine residue (if present).

If the peptide is prepared by expression of a suitable nucleotide sequence in a suitable host, then it may be advantageous to express the peptide as a fusion product with a peptide sequence which acts as a carrier. Kabigen's "Ecosec" system is an example of such an arrangement.

The peptide of the invention may be linked to other antigens to provide a dual effect.

In a yet further aspect the present invention provides a method of diagnosis of abnormalities of cellular metabolism, said method comprising analysing the naturally occurring peptide(s) or the nucleotide sequences encoding therefore and comparing the results to the peptides described herein.

The peptides of the present invention may also be used in diagnosis and this aspect is also covered by the present invention.

The specificity of the catalytic subunit of protein phosphatase-1 (PP1c) is modified by regulatory subunits that target it to particular subcellular locations. For the first time we have identified PP1c-binding domains on $G_L$ and $G_M$, the subunits that target PP1c to hepatic and muscle glycogen, respectively, and on $M_{110}$, the subunit that targets PP1c to smooth muscle myosin. The peptide $G_M$-(G63-T93) interacted with PP1c and prevented $G_L$ from suppressing the dephosphorylation of glycogen phosphorylase, but it did not dissociate $G_L$ from PP1c or affect other characteristic properties of the $PP1_{GL}$ complex. These results indicate that $G_L$ contains two PP1c-binding sites, the region which suppresses the dephosphorylation of glycogen phosphorylase being distinct from that which enhances the dephosphorylation of glycogen synthase. At higher concentrations, $G_M$-(G63-N75) had the same effect as $G_M$-(G63-T93), but not if Ser67 was phosphorylated by cyclic AMP-dependent protein kinase. Thus phosphorylation of Ser67 dissociates $G_M$ from PP1c because phosphate is inserted into the PP1c-binding domain of $G_M$. The fragments $M_{110}$-(M1-E309) and $M_{110}$-(M1-F38), but not $M_{110}$-(D39-E309), mimicked the $M_{110}$ subunit in stimulating dephosphorylation of the smooth muscle myosin P-light chain and heavy meromyosin in vitro. However, in contrast to the $M_{110}$ subunit and $M_{110}$-(M1-E309), neither $M_{110}$-(M1-F38) nor $M_{110}$-(D39-E309) suppressed the PP1c-catalysed dephosphorylation of glycogen phosphorylase. These observations suggest that the region which stimulates the dephosphorylation of myosin is situated within the N-terminal 38 residues of the $M_{110}$ subunit, while the region which suppresses the dephosphorylation of glycogen phosphorylase requires the presence of at least part of the region 39–296 which contains seven ankyrin repeats. $M_{110}$-(M1-F38) displaced $G_L$ from PP1c, while $G_M$-(G63-T93) displaced $M_{110}$ from PP1c in vitro. These observations indicate that the region(s) of PP1c that interact with $G_M/G_L$ and $M_{110}$ overlap, explaining why different forms of PP1c contain just a single targeting subunit.

We also disclose the structure of PP1c in complex with a portion of a targeting subunit, and show that changing key amino acid residues in the subunit disrupts its interaction with PP1c. These studies identify a critical structural motif in targeting subunits involved in the interaction with PP1c as well as the recognition site on PP1c itself. These findings will facilitate the rational design of agents such as peptides or other forms of small cell-permeant molecules that act by disrupting PP1-targeting subunit interactions. Given the structural motif and the coordinates of the atoms in the crystal structure, it is within the scope of the abilities of a skilled molecular modeller to produce small cell-permeant molecules, which can enter cells naturally, and possess either the same motif, or an analogous structure to give the same functional properties to the molecule. Thus the small cell-permeant molecule can have a precise copy of the motif, or one which is functionally equivalent. The molecule can be a peptide, but other types of molecules, which are transferred across the plasma membrane of cells, may be preferred.

Several mammalian PP1c targeting subunits have been isolated and characterised, including the $G_M$ subunit that targets PP1c to both the glycogen particles and sarcoplasmic reticulum of striated muscles (Tang et al., 1991; Chen et al., 1994), the $G_L$ subunit that targets PP1c to liver glycogen (Moorhead et al., 1995; Doherty et al., 1995), the $M_{110}$ subunits responsible for the association of PP1c with the myofibrils of skeletal muscle (Moorhead et al., 1994; Alessi et al., 1992) and smooth muscle (Alessi et al., 1992; Chen et al., 1994), the p53 binding protein p53BP2 (Helps et al., 1995) and the nuclear protein NIPP-1 (Jagiello et al., 1995; Van Eynde et al., 1995). PP1c is also reported to interact with other mammalian proteins such as the retinoblastoma gene product (Durphee et al., 1993), an RNA splicing factor (Hirano et al., 1996), ribosomal proteins L5 (Hirano et al., 1995) and RIPP-1 (Beullens et al., 1996), a 110 kDa nuclear protein yet to be identified (Jagiello et al., 1995), kinesin-like proteins and small cytosolic proteins, inhibitor-1, DARPP-32 and inhibitor-2 (Cohen, 1989; Cohen, 1992, Hubbard and Cohen, 1993). Moreover, a number of distinct PP1-regulatory subunits have been identified in yeast (reviewed by Stark, 1996). We attempted to identify which regions of the $G_M$ and $M_{110}$ subunits were involved in binding to PP1c. These studies led to the identification of relatively small peptides from each targeting subunit that were capable of interacting with PP1c. Peptides comprising residues 63–93, 63–80 and 63–75 of $G_M$ bound to PP1c, dissociating it from $G_L$, while the N-terminal 38 residues of the $M_{110}$ subunit ($M_{110}$[1–38]) mimicked the intact $M_{110}$ subunit in enhancing the rate at which PP1c dephosphorylated the 20 kDa myosin light chain ($MLC_{20}$) subunit of smooth muscle myosin (Johnson et al., 1996).

The present invention thus provides peptides comprising the N-terminal 38 residues of the $M_{110}$ subunit, and those comprising residues 63–93, 63–80 and 63–75 of $G_M$.

Phosphorylation of Ser 67 of $G_M$ by protein kinase A (PKA) disrupts the interaction of $G_M$ with PP1c (Dent et al., 1990) and a similar disruption is also observed following the phosphorylation of Ser 67 of the $G_M$[63–75] peptide (Johnson et al., 1996). The finding that $G_M$[63–93] disrupted the interaction between PP1c and the $M_{110}$ subunit, and prevented $M_{110}$ from enhancing the $MLC_{20}$ phosphatase activity of PP1c implies that the binding of $M_{110}$ and $G_M$ to PP1c are mutually exclusive.

Thus the invention contemplates the substitution or modification of an amino acid in any such peptide.

To understand the basis for the recognition by PP1c of regulatory subunits, and peptides derived from these subunits, we co-crystallised a complex of PP1c with the $G_M$[63–75] peptide and determined the structure at 3.0 Å resolution. These experiments have demonstrated that residues 64 to 69 of the peptide are bound in an extended conformation to a hydrophobic channel within the C-terminal region of PP1c. The residues in $G_M$[63–75] that interact with PP1c lie in an Arg/Lys-Val/Ile-Xaa-Phe motif common to $M_{110}$[1–38] and almost all known mammalian PP1-binding proteins. Substituting Val or Phe by Ala in the $G_M$[163–75] peptide, and deleting the VxF motif from the $M_{110}$[1–38] peptide, abolished the ability of both peptides to interact with PP1c. These findings identify a recognition site on PP1c for a critical structural motif involved in the interaction of targeting subunits with PP1.

Particularly preferred peptides are derived from residues 63 to 69 of $G_M$ and comprise the motif Arg/Lys-Val/Ile-Xaa-Phe. Peptides derived from $M_{110}$ (or any other source) and also including the motif are also included in the scope of the invention.

Preferred peptides may also be substantially or wholly made up of hydrophobic residues.

The identification of this area of PP1c necessary for binding to the various subunits allows the design of agents to specifically disrupt the interaction at this area. Such disruption may, for example, increase the phosphorylation of the protein phospholamban in cardiac muscle and thus increase the force and rate of contraction of the muscle. This provides a possible treatment for congestive heart failure. Also, the specific disruption of the complex of PP1 and p53BP2 may prevent PP1 from dephosphorylating the tumour suppressor protein p53, thus enhancing phosphorylation of p53, its ability to bind to DNA, and thus its ability to act as a tumour suppressor.

The identification of the key motif in targetting subunits that bind to PP1 also provides the means to produce targetting subunits that can no longer interact with PP1. Overexpression of these mutant targetting subunits provides a powerful new way to determine the functions of different targetting subunits in vivo.

Abbreviations

PP1, protein phosphatase-1

PP1c, catalytic subunit of PP1

PP1, —isoform of PP1c $PP1_G$, glycogen-associated form of PP1

$PP1_M$, myosin-associated form of PP1

$G_M$, glycogen-binding subunit of PP1 from striated muscle $G_L$, glycogen-binding subunit of PP1 from liver NIPP1, nuclear inhibitor of PP1

DARPP, dopamine and cyclic AMP-regulated phosphoprotein $M_{21}$ and $M_{110}$, myofibrillar-binding subunits of PP1 with molecular masses of 21 kDa and 110 kDa respectively.

PKA, cyclic AMP-dependent protein kinase $PhMeSO_2F$, phenylmethylsuphonyl fluoride GST, glutathione-S-transferase $MLC_{20}$, myosin light chain of molecular mass 20 kDa.

The invention is now described in more detail by reference to the following Examples and Figures wherein:

FIG. 1 shows that the N-terminal 118 residues of human $G_M$ interact with PP1c.

GST-$G_M$ fusion proteins were electrophoresed on 10% SDS/polyacrylamide gels and stained with Coomassie blue (lanes 1–3) or, after transfer to nitrocellulose, probed with digoxygenin-labelled PP1γ (lanes 4–6) as in [9]. Lanes 1 and 4, GST-$G_M$-(E2-D118); Lanes 2 and 5, GST-$G_M$-(H100-P350); Lanes 3 and 6, GST. The positions of the marker proteins glycogen phosphorylase (97 kDa), bovine serum albumin (66 kDa), ovalbumin (43 kDa), carbonic anhydrase (29 kDa) and soybean trypsin inhibitor (20 kDa) are indicated.

Figure 2:
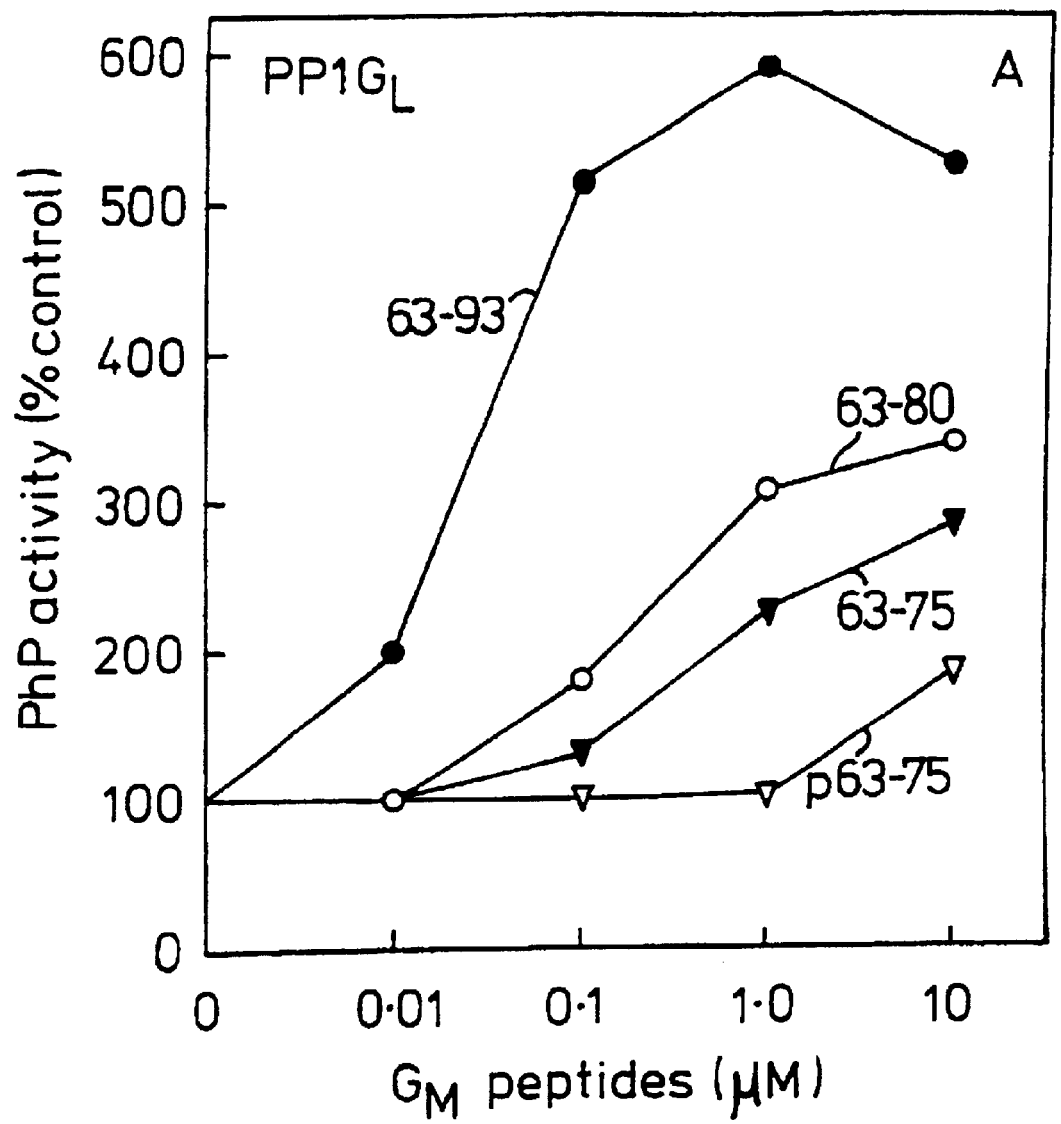

FIG. 2 shows that synthetic peptides between residues 63 and 93 of rabbit $G_M$ stimulate the phosphorylase phosphatase activity of $PP1_{GL}$.

Hepatic glycogen particles were diluted in assay buffer to 0.6 phosphorylase phosphatase (PhP) mU per ml, incubated for 15 minutes at 30° C. with $G_M$-(G63-T93) (closed circles), $G_M$-(G63-K80) (open circles) or $G_M$-(G63-N75) (closed triangles) and assayed as described in Example 1. The open triangles show the effect of $G_M$-(G63-N75) which had been phosphorylated at Ser67 by PKA (p$G_M$-(G63-N75)). Similar results were obtained in four experiments.

FIG. 3 shows that removal of the $M_{21}$ subunit from smooth muscle $PP1_M$ does not affect its MLC20 phosphatase:phosphorylase phosphatase activity ratio.

(A) Purified smooth muscle $PP1_M$ was electrophoresed on a 12% SDS/polyacrylamide gel, and either stained with Coomassie blue (lane 1) or immunoblotted [32] with antibodies specific for the $M_{21}$ subunit (lane 2) or the $M_{110}$ subunit (lane 3). The positions of the $M_{110}$ subunit, the $M_{21}$ subunit and PP1c are marked.

(B) Purified $PP1_M$ (lane 1) or $PP1_M$ lacking the $M_{21}$ subunit (lane 2) were electrophoresed on a 12% SDS polyacrylamide gel, transferred to nitrocellulose and immunoblotted with mixed, affinity-purified antibodies to the $M_{110}$ and $M_{21}$ subunits. The $M_{110}$ and $M_{21}$ subunits are marked. The activity ratio, $MLC_{20}$ phosphatase (MP):phosphorylase phosphatase (PhP) of the two preparations is also shown. Similar results were obtained in three different experiments. The activity ratio MP:PhP of PP1c is 0.07.

Figure 4:
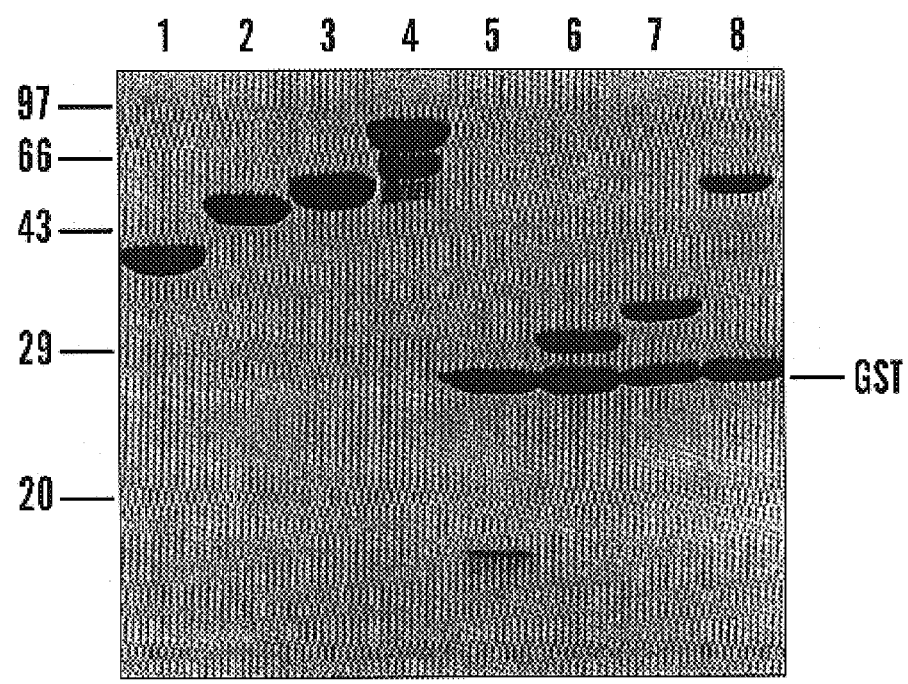

FIG. 4 shows expressed fragments of the $M_{110}$ subunit before and after cleavage of the GST-fusion proteins with thrombin.

Purified GST-fusion proteins were electrophoresed on a 15% SDS/polyacrylamide gel and stained with Coomassie blue. Lane 1, GST-$M_{110}$-(M1-A150); Lane 2, GST-$M_{110}$-(D39-E309); Lane 3, GST-$M_{110}$-(M1-E309); Lane 4, GST-$M_{110}$-(L24-Y496). Lanes 5–8 are the same as Lanes 1–4 except that the fusion proteins were cleaved with thrombin. The positions of the marker proteins glycogen phosphorylase (97 kDa), bovine serum albumin (66 kDa), ovalbumin (43 kDa), carbonic anhydrase (29 kDa), GST (26 kDa) and soybean trypsin inhibitor (20 kDa) are marked.

FIG. 5 shows the effect of $M_{110}$ subunit fragments on PP1c-catalysed dephosphorylation of $MLC_{20}$ and glycogen phosphorylase.

A,B; Effects of $M_{110}$-(M1-E309) (closed circles), $M_{110}$-(M1-F38) (open circles) and $M_{110}$-(D39-E309) (open triangles) on the $MLC_{20}$ phosphatase (B) and phosphorylase phosphatase (B) activities of PP1c were measured after incubating PP1c for 15 minutes at 30° C. with each fragment. The results are presented as a percentage of those obtained in experiments where the $M_{110}$ fragments were omitted.

C,D; The effect of $M_{110}$-(M1-A150) (open circles) and $M_{110}$-(L24-Y496) (closed circles) on the $MLC_{20}$ phosphatase (C) and phosphorylase phosphatase (D) activities of PP1c were measured as in A,B.

Figure 6:
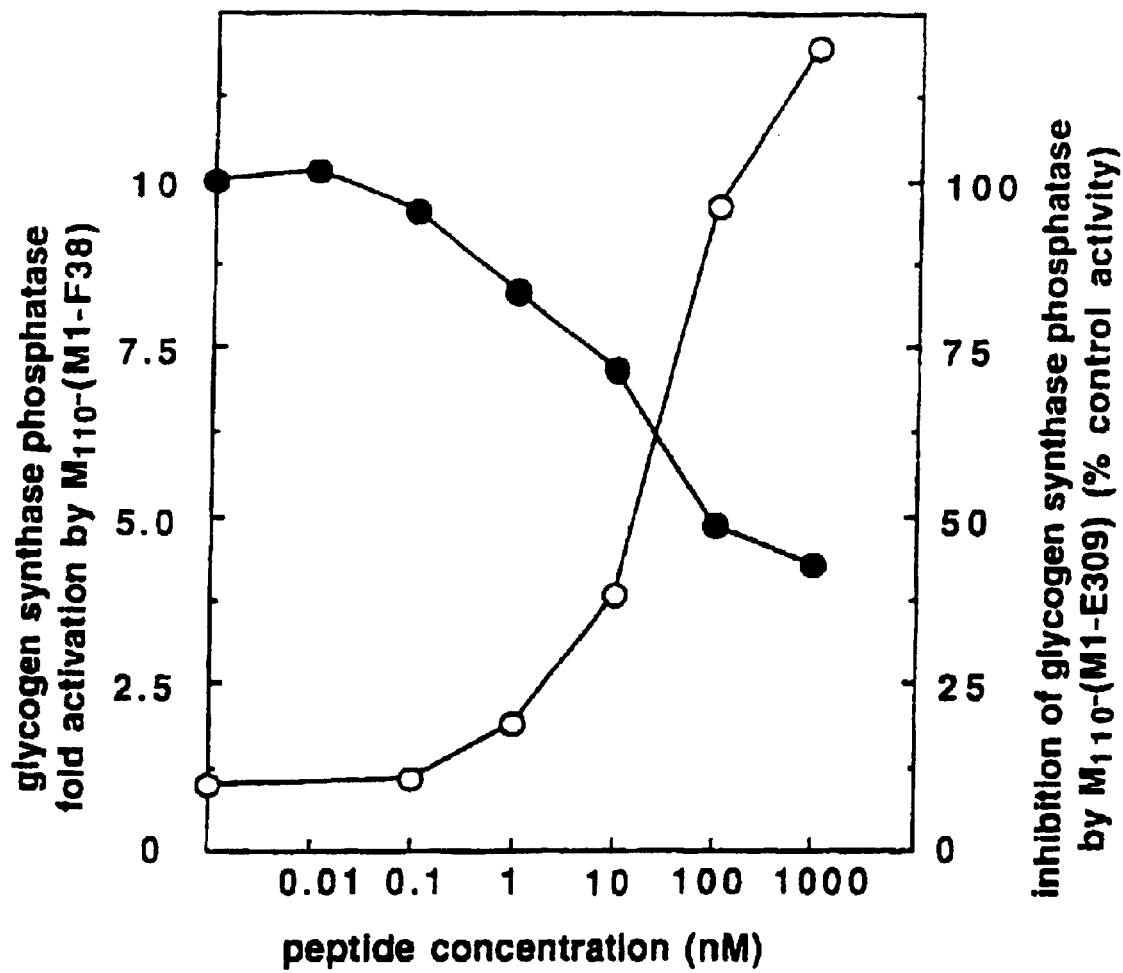

FIG. 6 shows the effect of $M_{110}$-(M1-F38) and $M_{110}$-(M1-E309) on the dephosphorylation of glycogen synthase by PP1c.

The glycogen synthase phosphatase activity of PP1c was measured after a 15 minute incubation at 30° C. with the indicated concentrations of $M_{110}$-(M1-F38) and $M_{110}$-(M1-E309). Similar results were obtained in three different experiments.

Figure 7A:
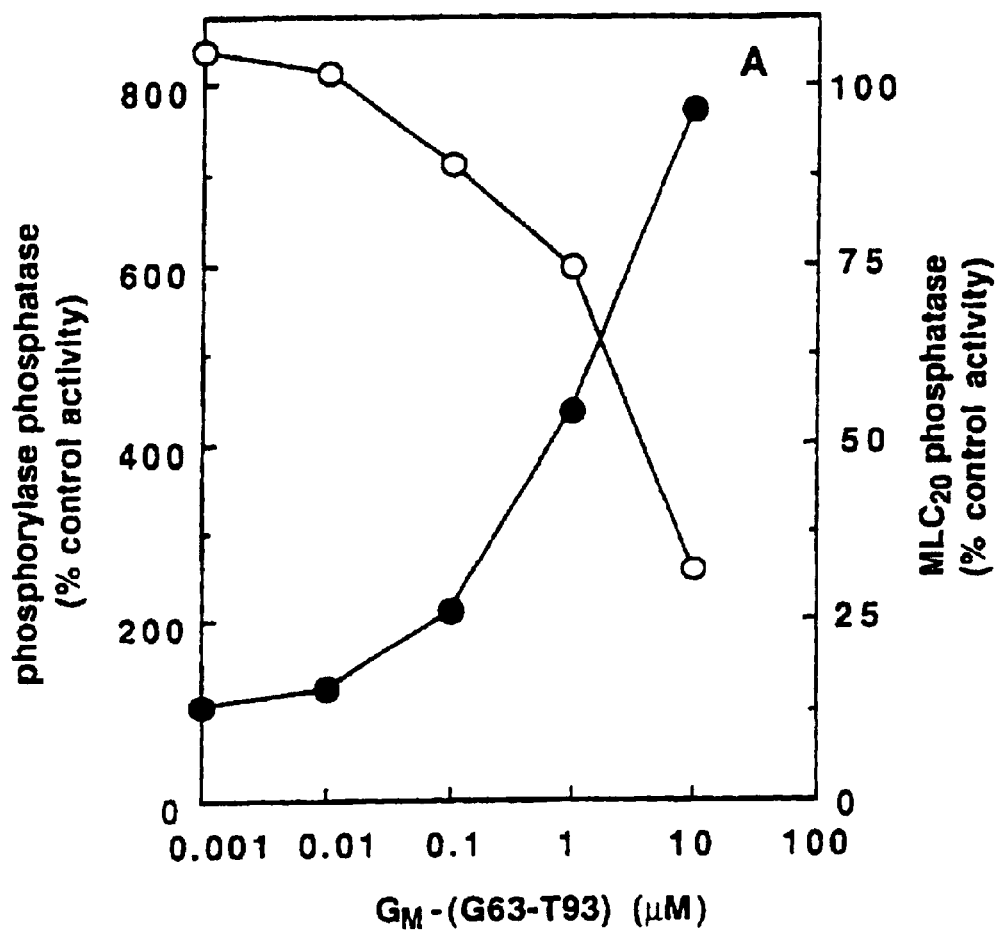

FIG. 7 shows that $G_M$-(G63-T93) dissociates $PP1_M$.

(A) The phosphorylase phosphatase (PhP) activity of $PP1_M$ (closed circles) and its $MLC_{20}$ phosphatase (MLCP) activity (open circles) were assayed after preincubation for 15 minutes at 30° C. with the indicated concentrations of $G_M$-(G63-T93). Activities are shown relative to control incubations in which $G_M$-(G63-T93) was omitted. Similar results were obtained in three experiments.

(B,C) PPIM was incubated for 15 minutes at 30° C. in the absence (B) and presence (C) of 10 M $G_M$-(G63-T93), then passed through a 30×1 cm column of Superose 12 equilibrated at ambient temperature in 50 mM Tris/HCl pH 7.5, 0.2M NaCl, 0.1 mM EGTA, 0.1% (by vol) 2-mercaptoethanol, 0.03% (by mass) Brij 35 in the absence (B) or presence (C) of 1 μM $G_M$-(G63-T93). Fractions (0.25 ml) were assayed for $MLC_{20}$ phosphatase (MLCP) in B and for phosphorylase phosphatase (PhP) activity in C. The arrows denote the position of ferritin (450 kDa) and ovalbumin (43 kDa).

Figure 8A:
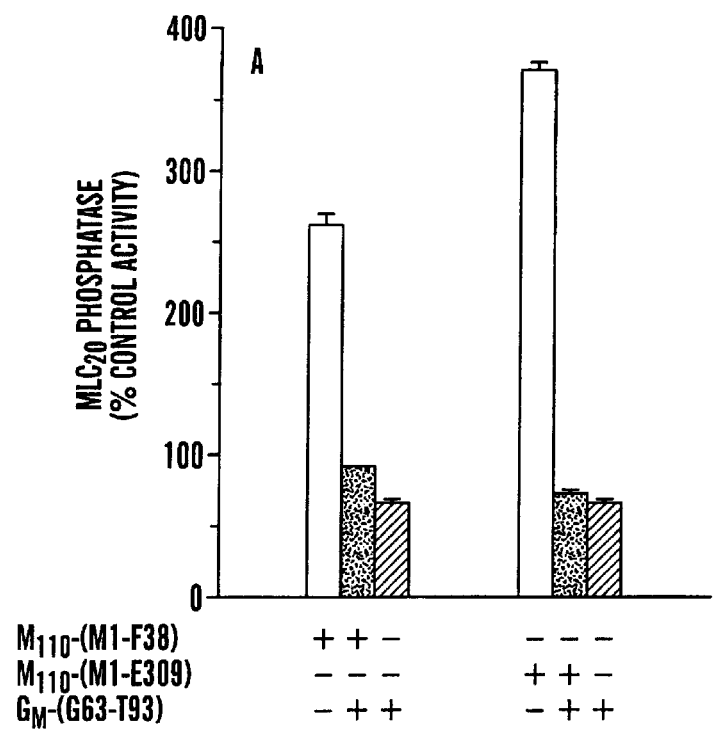

FIG. 8 shows that $G_M$-(G63-T93) prevents $M_{110}$-(M1-F38) or $M_{110}$-(M1-E309) from modulating the substrate specificity of PP1c.

(A) The $MLC_{20}$ phosphatase activity of PP1c was assayed after incubation for 15 minutes at 30° C. in the presence or absence of 1 μM $G_M$-(G63-T93) and either 0.1 μM $M_{110}$-(M1-F38) or 0.1 nM $M_{110}$-(M1-E309).

(B) The phosphorylase phosphatase activity of PP1c was assayed as in A in the presence or absence of 1 μM $G_M$-(G63-T93) and 1.0 nM $M_{110}$-(M1-E309). The results are presented (SEM for three experiments) as a percentage of the PP1c activity measured in the absence of $G_M$-(63-T93), $M_{110}$-(M1-F38) or $M_{110}$-(M1-E309).

Figure 9:
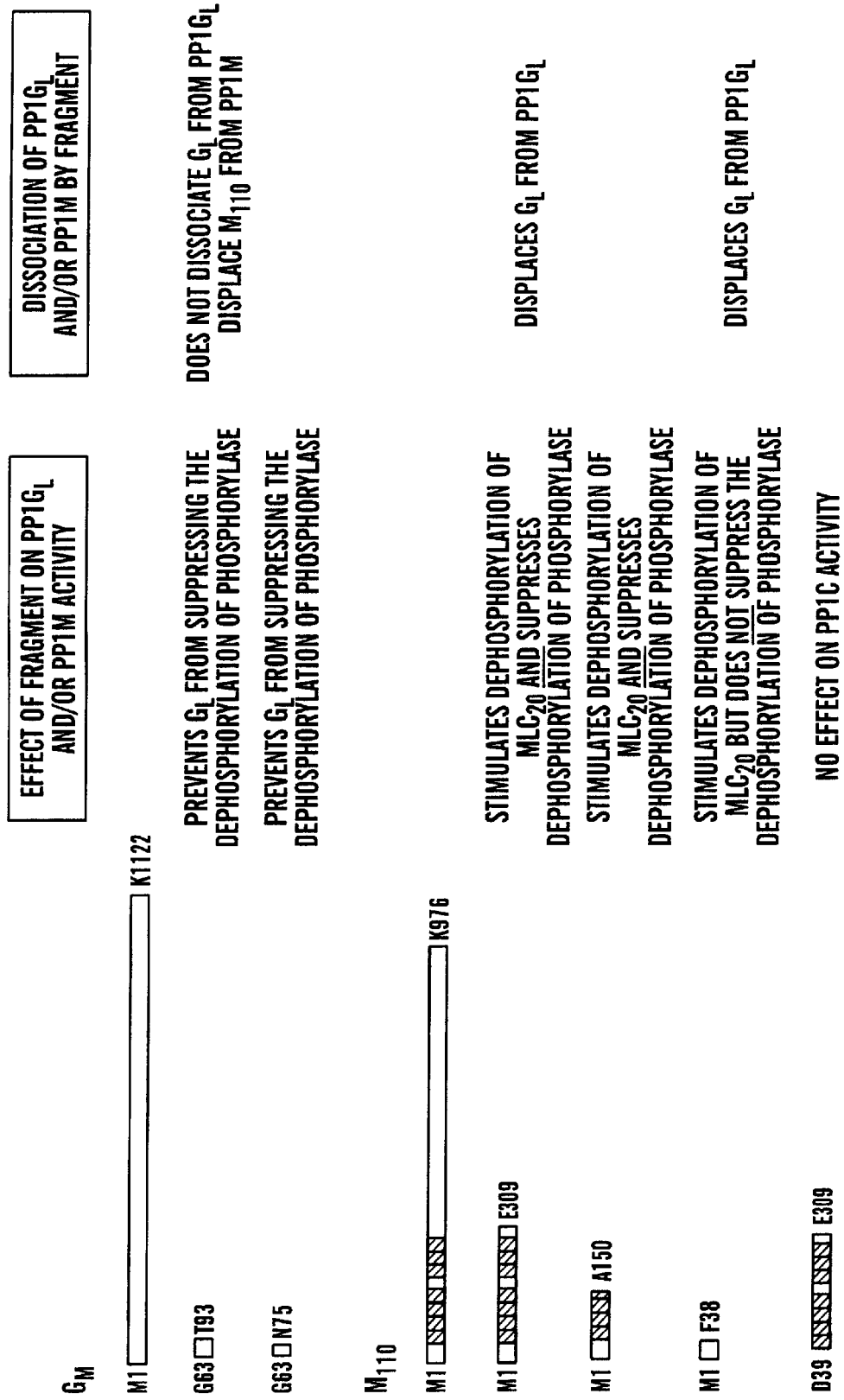

FIG. 9 shows the location of PP1c-binding domains on the $G_M$ and $M_{110}$ targeting subunits and their effects on PP1 activity.

The hatched boxes in the $M_{110}$ subunit denote the positions of the ankyrin repeats.

FIG. 10 shows a stereo view of the electron density corresponding to the peptide. A: Initial 2-fold averaged electron map. B: map calculated using 3Fo-2Fc coefficients and phases calculated from the final refined model. Displayed using TURBO-FRODO.

FIG. 11 shows the structure of PP1-$G_M$[63–75] peptide complex. A. Stereo view of a ribbons diagram of PP1c to indicate the position of the peptide binding channel at the interface of the two β-sheets of the β-sandwich. The peptide atoms are represented as ball-and-stick (MOLSCRIPT, Kraulis, 1991).

B. View of the surface of PP1c to show the hydrophobic peptide binding channel. Residues 63' to 69' (GRRVSFA) (SEQ ID No 2) of the $G_M$[63 75] peptide are shown as sticks. Drawn with TURBO-FRODO.

C. Stereo view of the $G_M$[63–75] peptide at the recognition site of PP1 to indicate polar interactions between peptide and protein and the formation of the β-sheet between Ser 67'—Ala 69' and 14 of PP1. Drawn with TURBO-FRODO.

E. Details of the structure of the peptide binding site to show hydrophobic interactions between PP1c and Val 66', Phe 68' and Ala 69' of the $G_M$[68–75] peptide (MOLSCRIPT, Kraulis, 1991).

FIG. 12 shows a sequence alignment of PP1-regulatory subunits in the vicinity of the (R/K)(V/I) x F motif. (A) mammalian PP1-binding subunits. $G_M$, Tang et al., 1991; G L, Docherty et al., 1995; $G_L$-related protein, Doherty et al., 1996; p53BP2, Helps et al., 1995; NIPP-1, Bollen et al., 1995; splicing factor PSF, Hirano et al., 1996; $M_{110}$ subunit, Chen et al., 1994; inhibitor-1, Aitken et al., 1982; DARPP-32, Williams et al., 1986. (B) PP1-binding proteins in *S. cerevisiae*. GAC1 (Francois et al., 1992); PIG2 GIP1, GIP2, YIL045W (Tu et al., 1996); REG1, REG2 (Tu and Carlson, 1995; Frederick and Tatchell, 1996); SCD5 (Nelson et al 1996; Tu et al 1996). The region homologous to the RRVSFA (SEQ ID No 3) motif in $G_M$ which intersects with PP1c is boxed.

FIG. 13 shows the disruption of the interactions between PP1c and the $G_L$ and $M_{110}$ subunits by a synthetic peptide from p53BP2. (A) PP1$_M$ from chicken gizzard smooth muscle (Alessi et al., 1992) was diluted and incubated for 15 min at 30° C. with the peptide GKRTNLRKTGSERIAHG-MRVKFNPLALLLDSC (SEQ ID No 4), corresponding to the sequence in p53BP2 that contains the RVXF motif. Reactions were started with either $^{32}$P-labelled $MLC_{20}$ or glycogen phosphorylase and the $MLC_{20}$ phosphatase (open circles) and phosphorylase phosphatase (PhP, closed circles) activities were determined. The results are expressed as a percentage of the activity determined in control incubations where the p53BP2 peptide was omitted (100%). Similar results were obtained in three separate experiments. (B) same as (A) except that the peptide was incubated with diluted hepatic glycogen particles containing PP1-$G_L$ before measuring the PhP activity. Similar results were obtained in three separate experiments.

Figure 14:
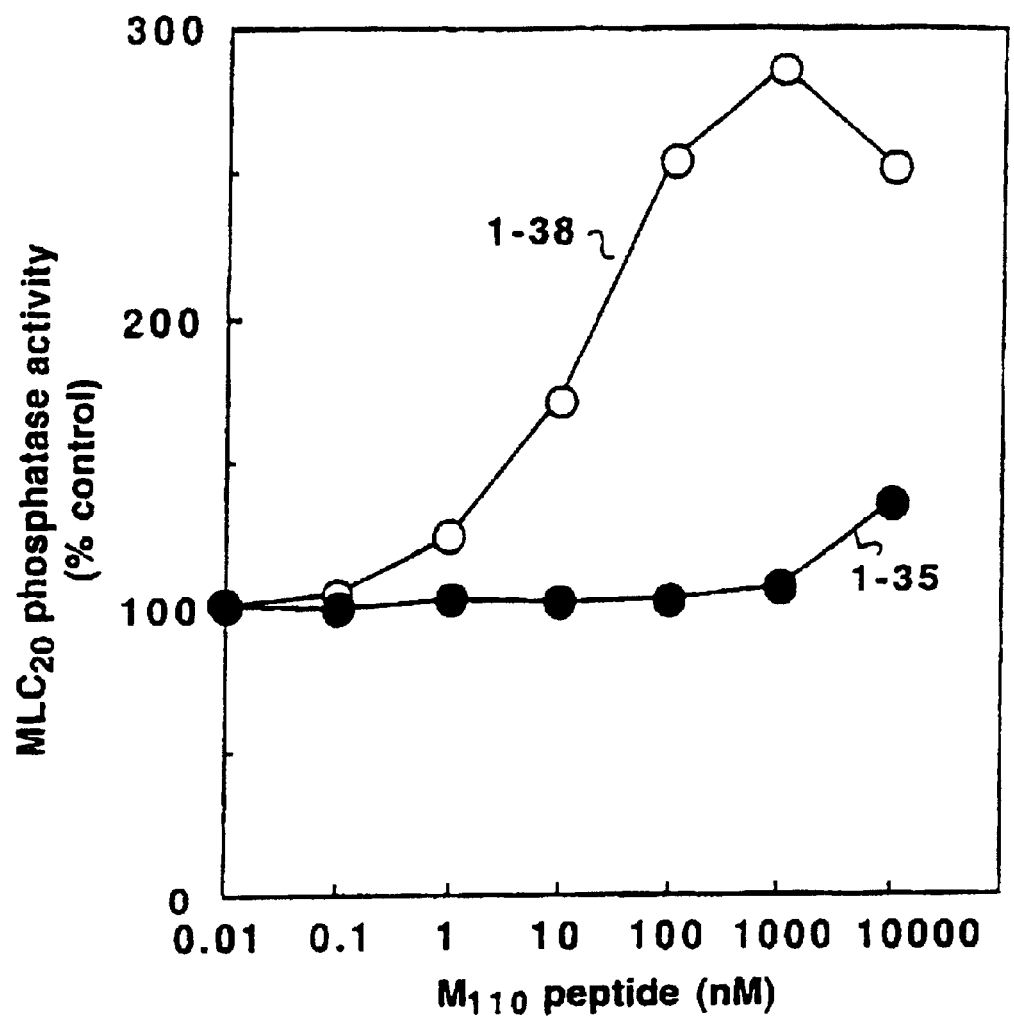

FIG. 14 shows the effect of $M_{110}$[M1-F38] and $M_{110}$[M1-K35] on the PP1c-catalysed dephosphorylation of $MLC_{20}$ $M_{110}$[M1-F38] (1–38, open circles) or $M_{110}$[M1-K35] (1–35, closed circles) were incubated with PP1c for 15 min at 30° C. and reactions started with the $^{32}$P-labelled $MLC_{20}$ substrate. The results are expressed as a % of the activity determined in control incubations where the $M_{110}$ peptides were omitted (100%). Similar results were obtained in three separate experiments.

Figure 15A:
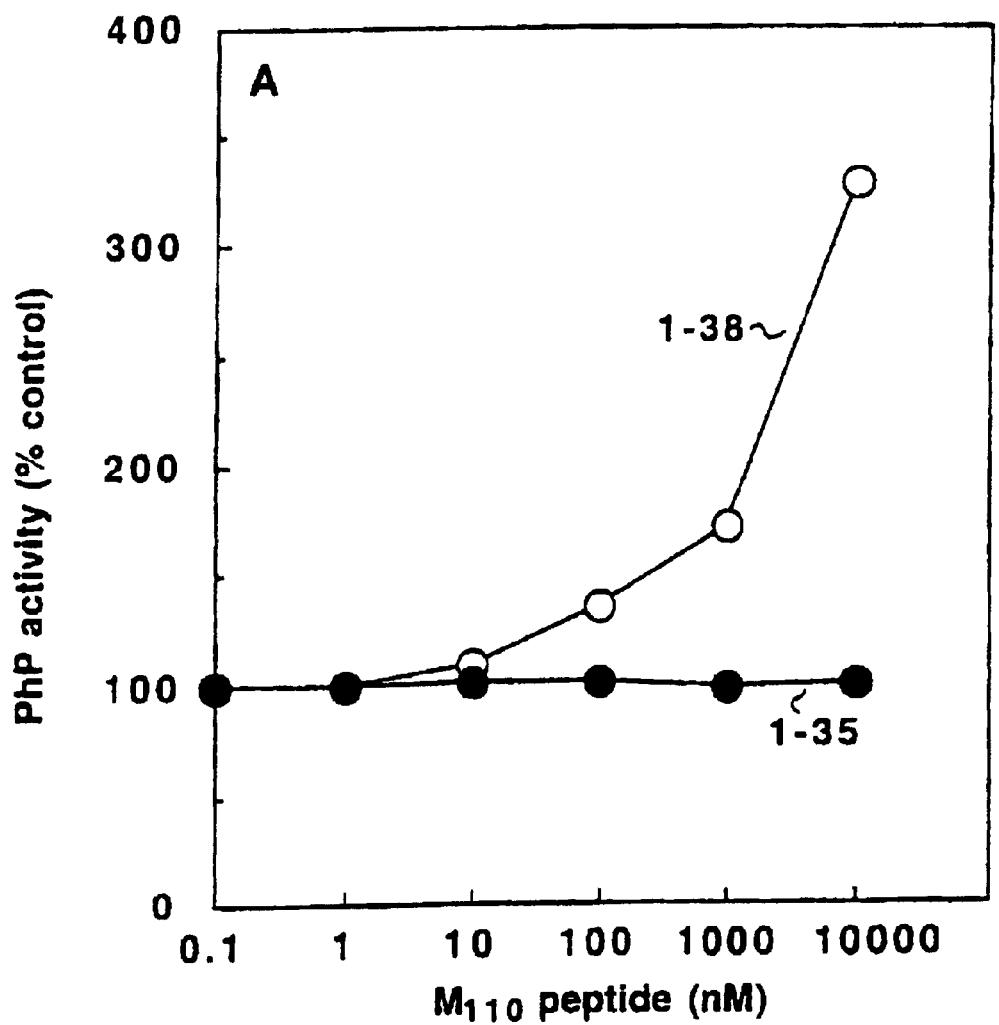
Figure 15B:
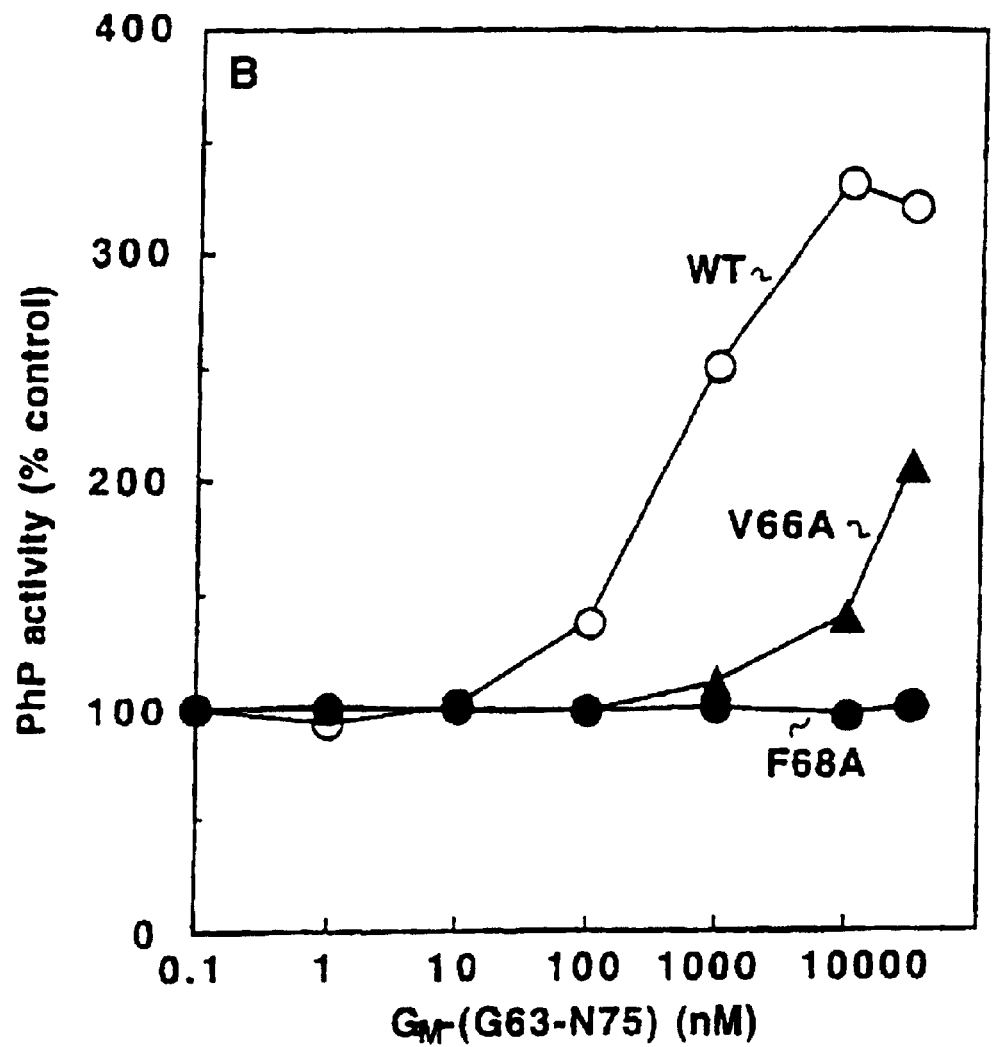

FIG. 15 shows the effect of synthetic peptides derived from the $M_{100}$ and $G_M$ subunits on the phosphorylase phosphatase activity of PP1-$G_L$. (A) Hepatic glycogen protein particles containing PP1-$G_L$ were diluted and incubated for 15 min at 30° C. with the indicated concentrations of either $M_{110}$[M1-F38] (open circles) or $M_{110}$[M1-K35] (closed circles) and the phosphatase reactions were initiated by addition of $^{32}$P-labelled glycogen phosphorylase. The results are expressed as a percentage of the activity determined in control incubations where the $M_{110}$ peptides were omitted. Similar results were obtained in three separate experiments. (B) The experiment was carried out as in (A), except that the peptide $G_M$[G63-N75] ("wild type", WT) and variants in which either Val 66 (V66A) (closed triangles) or Phe 68 (F68A) (closed circles) were changed to Ala, were used instead of the $M_{110}$ peptides. Similar results were obtained in three separate experiments.

Figure 16:

FIG. 16 shows a stereo view of a ribbons diagram of a model of PP1-phospho-inhibitor-1 complex. The side chains of Ile 10, Phe 12 and pThr 35 of phospho-inhibitor-1 are shown with the main-chain atoms of residues 8 to 36 of the inhibitor indicated as a shaded ribbon. Drawn with MOL-SCRIPT (Kraulis 1991).

FIG. 17 shows a comparison of rat and chicken gizzard $M_{110}$ and $M_{21}$ subunits (SEQ ID NOs:29 to 31).

Vertical lines indicate identical residues, colons denote similar residues in the rat and chicken $M_{110}$ sequences and deletions are shown by dots. (A) Comparison of $M_{110}$ subunits. Underlined residues in the rat $M_{110}$ subunit (Rat1) are deleted in some rat aorta forms and underlined residues in the chicken $M_{110}$ subunit (Ch1) are deleted in some chicken gizzard forms [5, 8]. Dashed lines above residues indicate amino acids deleted in the rat kidney $M_{110}$ subunit [9. The alternative C-terminal sequences of rat uterus $M_{110}$ subunit are shown as Rat1 and Rat2. Leucine residues in the C-terminal leucine zipper motif are double underlined. (B). The C-terminal sequence of the $M_{110}$ subunit is structurally related to the $M_{21}$ subunit. The sequence of the chicken $M_{21}$ subunit [5] is compared with the C-terminal sequences of Rat2 and Ch1 from A. Identities between Ch1 and Rat2 are shown in boldface type.

FIG. 18 shows immunoprecipitation and immunoblotting of $PP1_M$ in extracts from chicken gizzard myofibrils.

A. Antibodies specific for the $M_{110}$ and/or $M_{21}$ subunits immunoprecipitate most of the myosin P-light chain phosphatase activity in myofibrillar extracts. $PP1_M$ was immunoprecipitated with either control IgG, antibody raised against the $PP1_M$ holoenzyme, antibody specific for the $M_{110}$ subunit or antibody specific for the $M_{21}$ subunit, as described under Methods in Example 3. The figure shows activity present in the supernatant (S, open bars) or pellet (P, filled bars) as a percentage of that measured before centrifugation. The results shown are the average (±S.E.M.) for three separate experiments each assayed in duplicate. B, The $M_{110}$ and $M_{21}$ subunits are present in similar molar proportions in myofibrillar extracts and in purified $PP1_M$. 10 ng (track 1) or 3 ng (track 3) of purified $PP1_M$ or 12 μg (track 2) or 3.6 μg (track 4) of myofibrillar extract was electrophoresed on a 12% SDS/polyacrylamide gel, transferred to nitrocellulose and immunoblotted with mixed affinity-purified antibodies to the $M_{110}$ and $M_{21}$ subunits as in [22]. The positions of the two subunits are marked. The results indicate that $PP1_M$ comprises about 0.1% of the myofibrillar protein.

Figure 19A:
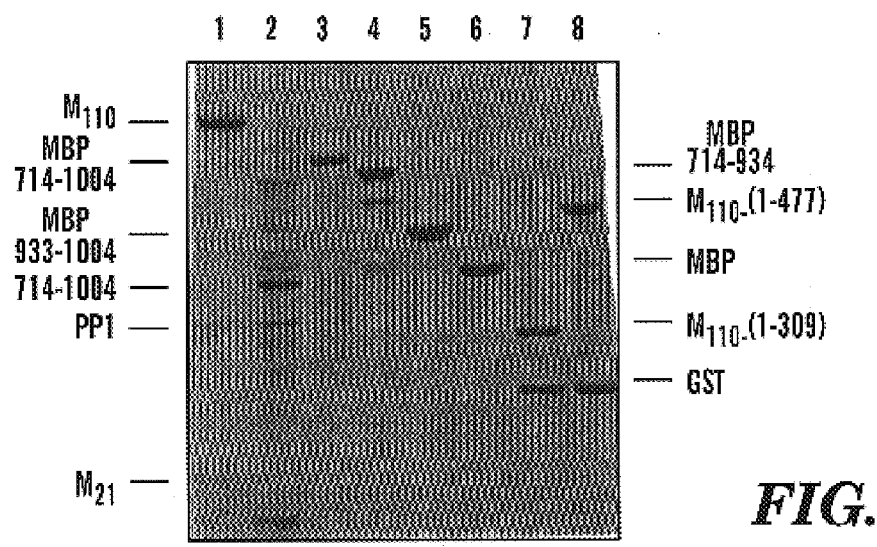

FIG. 19 shows the identification of the region on the $M_{110}$ subunit that interacts with the $M_{21}$ subunit.

A) $PP1_M$ 5 μg (track 1), 10 μg bacterial extract containing $M_{110}$-(R714-I1004) (track 2), MBP-$M_{110}$-(R714-I004) 1 μg (track 3), MBP-$M_{110}$-(R714-L934) 1 μg (track 4), MBP-$M_{110}$-(K933-I1004) 1 μg (track 5), MBP 1 μg (track 6), $M_{110}$-(M1-E309) 2 μg (lane 7) and $M_{110}$-(M1-S477) 2 μg (track 8) were run on a 12% SDS/polyacrylamide gel and stained with Coomassie Blue. B) same as A) except that 10-fold less protein was electrophoresed and after transfer to nitrocellulose the proteins were probed with digoxigenin-labelled $M_{21}$ subunit (0.2 μg/ml). C) same as B) except that, after electrophoresis, the proteins were transferred to nitrocellulose and probed with digoxigenin-labelled $M_{21}$-(M1-L146) (0.2 μg/ml).

Figure 20:
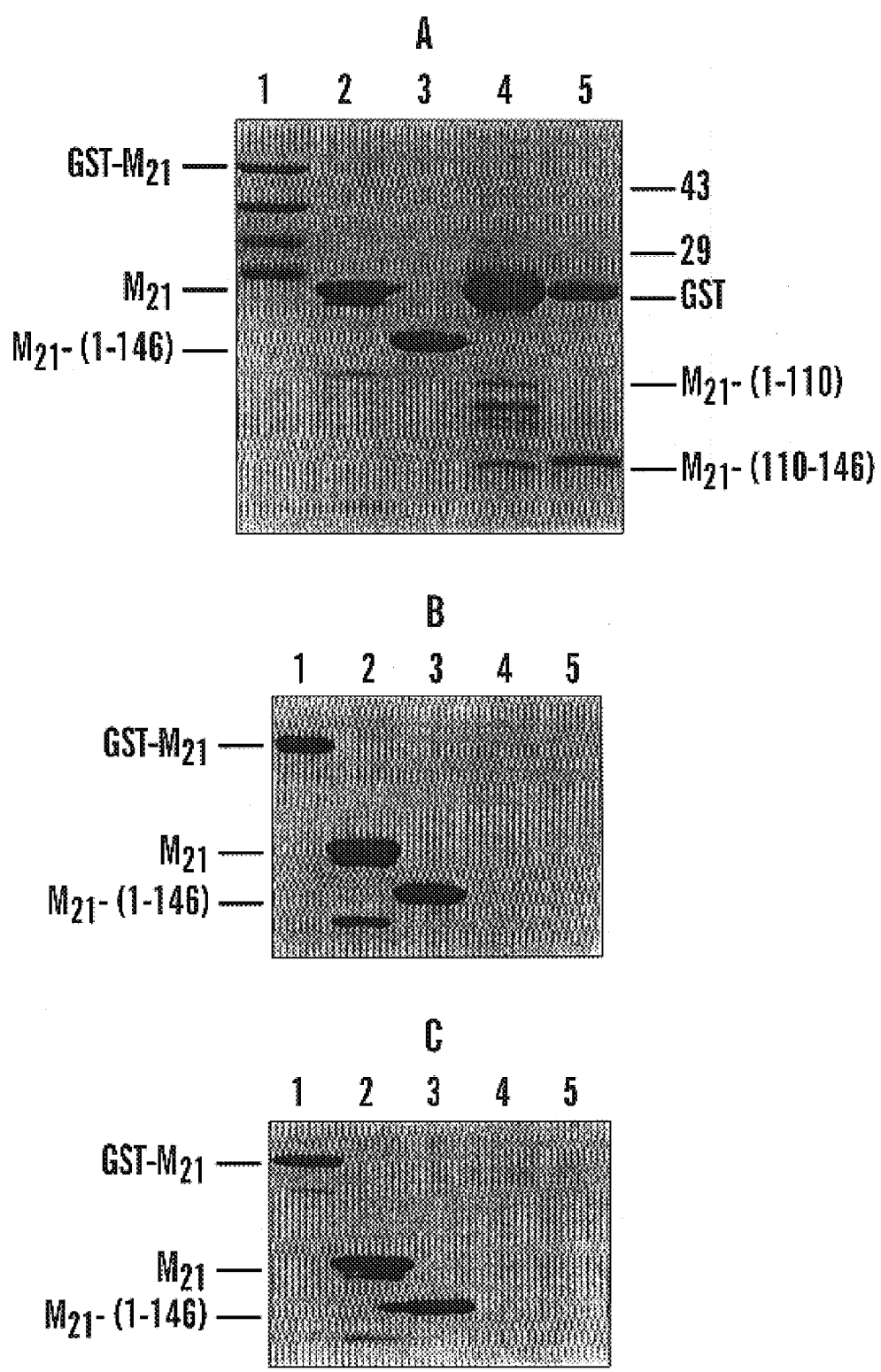

FIG. 20 shows the identification of the region of the $M_{21}$ subunit involved in interaction with the $M_{110}$ subunit and in dimerization.

A) GST-$M_{21}$ 5 μg (track 1), $M_{21}$ 5 μg (track 2), $M_{21}$-(M1-L146) 5 μg (track 3), $M_{21}$-(M1-E110) 20 μg (track 4) and $M_{21}$-(E110-K186) 5 μg (track 5) were run on 16.5% polyacrylamide gels and stained with Coomassie Blue. The marker proteins ovalbumin (43 kDa) and carbonic anhydrase (29 kDa) are indicated. B) GST-$M_{21}$ 0.5 μg (track 1), $M_{21}$ 0.5 μg (track 2), $M_{21}$-M1-L146) 0.5 μg (track 3), $M_{21}$-(M1-E110) 5 μg (track 4) and $M_{21}$-(E110-K186) 5 μg (track 5) were electrophoresed as in A) and after transfer to nitrocellulose the blots were probed with digoxigenin-labelled MBP-$M_{110}$-(K933-I1004) (0.2 μg/Ml). C) same as B) except that, after electrophoresis, the proteins were transferred to nitrocellulose and probed with digoxigenin-labelled $M_{21}$ subunit (0.2 μg/ml).

Figure 21:
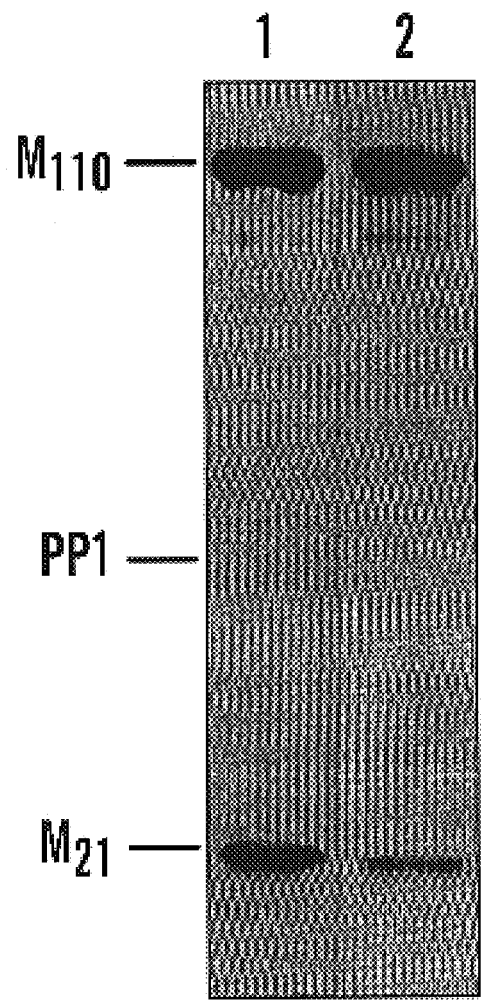

FIG. 21 shows that the $M_{21}$ subunit and $M_{21}$-(M1-L146) interact with the $M_{110}$ subunit and themselves, but not with PP1.

$PP1_M$ (0.5 μAg) was electrophoresed on a 12% SDS/polyacrylamide gel, transferred to nitrocellulose and probed with digoxigenin-labelled $M_{21}$ subunit (0.2 μg/ml) (track 1) or digoxigenin-labelled $M_{21}$-(M1-L146) (0.2 μg/ml) (track 2). The positions of the $M_{110}$ subunit, the $M_{21}$ subunit and PP1c are marked.

Figure 22:
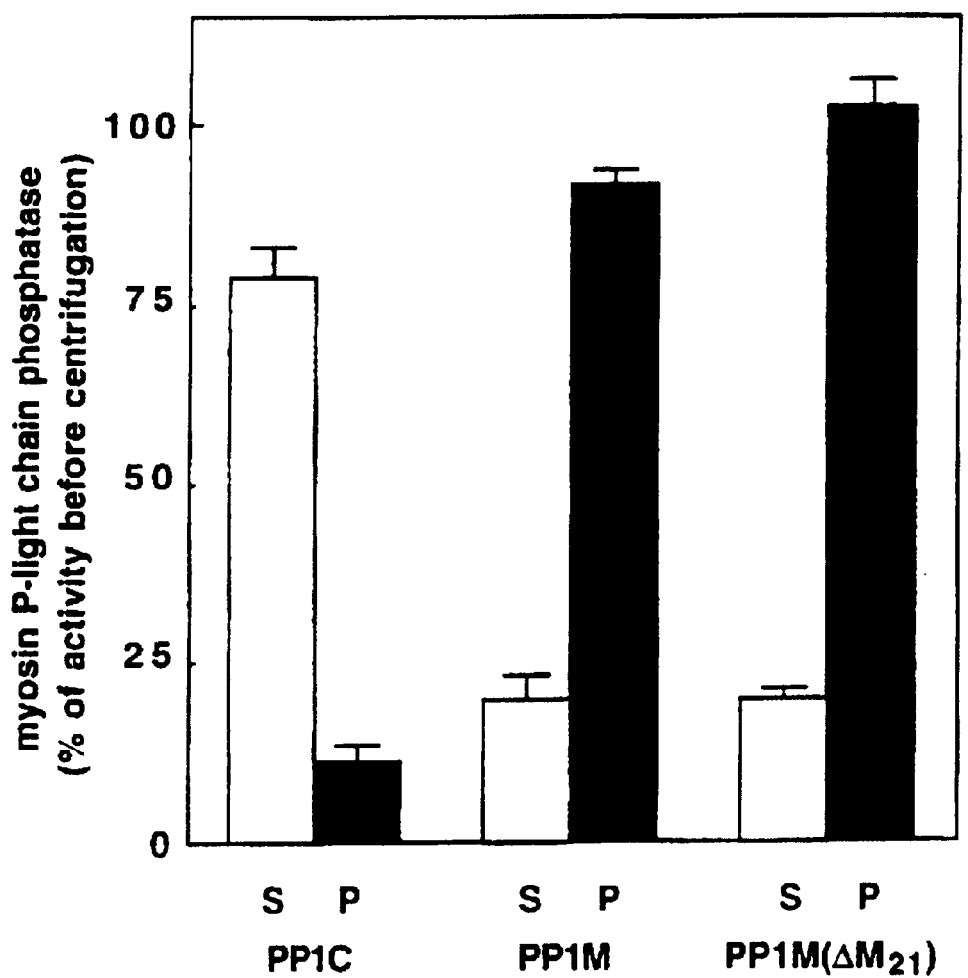

FIG. 22 shows that removal of the $M_{21}$ subunit from smooth muscle $PP1_M$ does not prevent it from being pelleted with myosin.

The PP1 catalytic subunit (PP1c), $PP1_M$, or $PP1_M$ lacking the $M_{21}$ subunit, $PP1_M(\Delta M_{21})$, each at 30 nM, were incubated for 15 min at 0° C. with 1 μM myosin and centrifuged (see Methods of Example 3). The figure shows the myosin P-light chain phosphatase activity present in the supernatant (S, open bars) or pellet (P, filled bars) as a percentage of that measured before centrifugation. The results shown are the average (±S.E.M.) for three separate experiments each assayed in duplicate.

Figure 23:
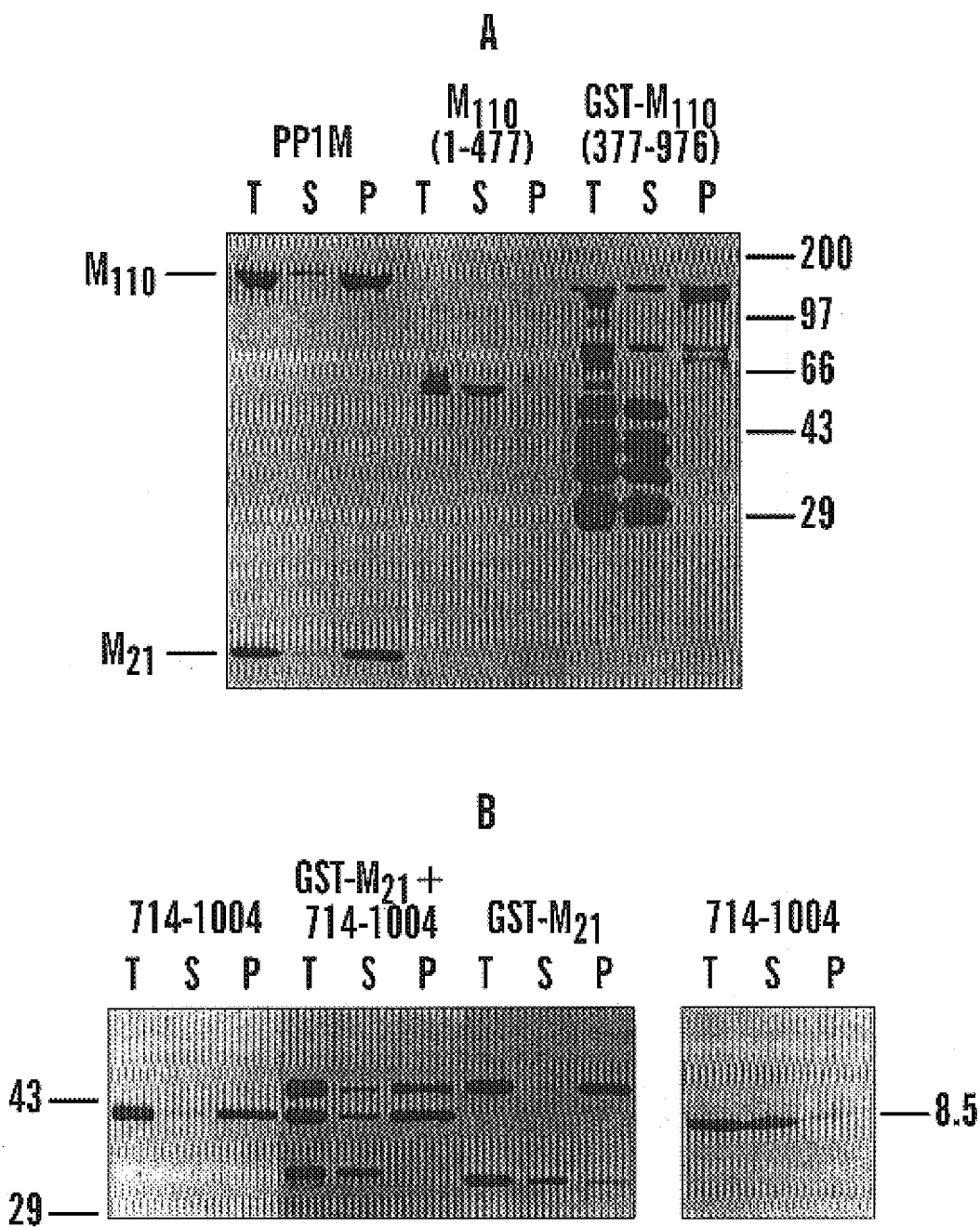

FIG. 23 shows the identification of a region of the $M_{110}$ subunit which binds to myosin.

(A); $PP1_M$, $M_{110}$-(M1-S477) and GST-$M_{110}$-(M377-K976), each at 30 nM were incubated for 15 min at 0° C. with 1 μM myosin and centrifuged. The supernatants (S), resuspended pellets (P) and the suspension before centrifugation (T, total) were electrophoresed on 12% SDS/polyacrylamide gels, transferred to nitrocellulose and immunoblotted with antibodies raised against the $PP1_M$ holoenzyme. No protein was pelleted in the absence of myosin (not shown). The positions of the marker proteins myosin heavy chain (200 kDa), glycogen phosphorylase (97 kDa), bovine serum albumin (66 kDa), ovalbumin (43 kDa), carbonic anhydrase (29 kDa) and soybean trypsin inhibitor (20 kDa) are indicated. (B) The experiments were carried out as in (A), except that the $M_{110}$ fragments and $M_{21}$ subunit were used at 100 nM, the 8.5 kDa $M_{110}$-(K933-I1004) fragment was electrophoresed on a 16.5% polyacrylamide gel and immunoblotting was carried out with affinity purified antibodies (see Methods). A small amount of $M_{110}$-(R714-I1004) pelleted in the absence of myosin. This was probably due to aggregation in the bacterial extract since this did not happen when it was complexed to the $M_{21}$ subunit (data not shown). No other protein was pelleted in the absence of myosin.

FIG. 24 shows that the isolated $M_{21}$ subunit binds to myosin.

(A); Myosin (1 μM) was mixed with 50 μM, 20 μM or 10 μM $M_{21}$ subunit to give the molar ratios $M_{21}$:myosin dimer indicated. After 15 min at 0° C., the solutions were centrifuged and the supernatants (S), resuspended pellets (P) and the suspension before centrifugation (T, total) were electrophoresed on 12% SDS/polyacrylamide gels and stained with Coomassie blue. The positions of the myosin heavy chain (MHC) and the $M_{21}$ subunit are indicated. The myosin light chains migrate faster than the $M_{21}$ subunit and are not visible at these loadings.

(B); Myosin (track A) was purified from chicken gizzard, and the myosin "rod" domain (track B) and light meromyosin (track C) produced by digestion of myosin with papain and chymotrypsin, respectively. These three proteins, all at 1 μM, were then mixed with $M_{21}$ subunit (track D) to give a molar ratio $M_{21}$:myosin dimer of 10:1 and, after 15 min at 0° C., the solutions were centrifuged and the supernatants (S), resuspended pellets (P) and the suspension before centrifugation (T, total) were electrophoresed on 12% SDS/polyacrylamide gels and stained with Coomassie blue. The slightly faster migrating band in the $M_{21}$ subunit preparation was shown by amino acid sequencing to be N-terminally truncated commencing at residue 16. (C); same as (B), except that $M_{21}$-(M1-L146) (track D) replaced the $M_{21}$ subunit.

Figure 25:
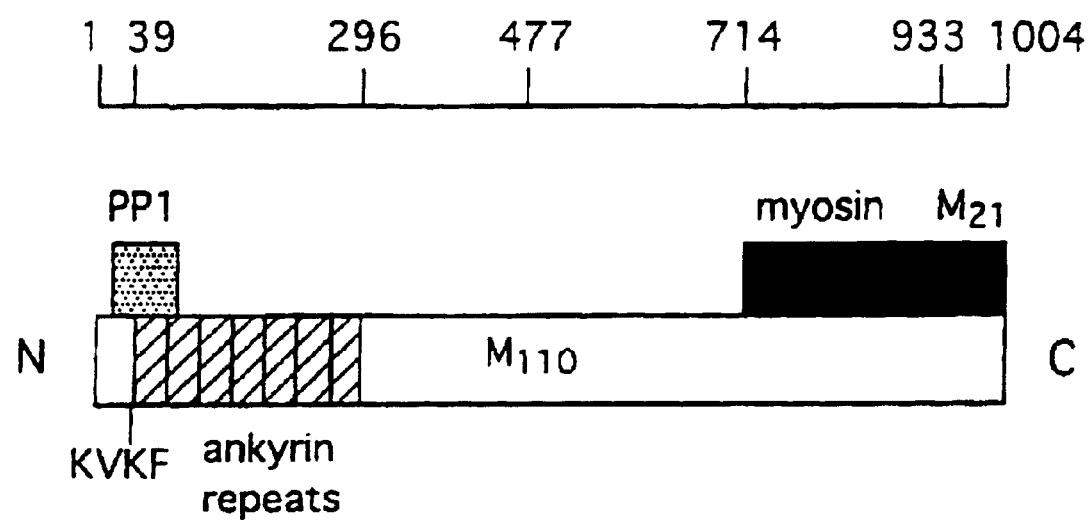

FIG. 25 gives a schematic representation of the regions on the $M_{110}$ subunit from chicken gizzard that interact with PP1c, myosin and the $M_{21}$ subunit.

PP1c binds to the KVKF (SEQ ID No 5) motif between residue 35 and 38, just N-terminal to the seven ankyrin repeats (hatched vertical lines) that suppress the dephosphorylation of substrates other than myosin. Residues 1–38 of the $M_{110}$ subunit enhance the dephosphorylation of myosin. The $M_{21}$ subunit binds to the C-terminal 72 residues of the $M_{110}$ subunit which are 43% identical in amino acid sequence to residues 87–161 of the $M_{21}$ subunit. The dephosphorylated form of myosin binds to $M_{110}$-(R714-I1004) but not to $M_{110}$-(K933-I1004), suggesting that myosin binds N-terminal to the $M_{21}$ subunit.

EXAMPLE 1

Identification of Protein Phosphatase 1-binding Domains on the Glycogen and Myofibrillar Targeting Subunits Materials and Methods Materials.

The myosin-associated form of PP1 ($PP1_M$) was from chicken gizzard [9] and the glycogen-associated form of PP1 ($PP1_G$) from rabbit skeletal muscle [2]. The β isoform of PP1c was released from $PP1_G$ by incubation for 2 hours in 2M LiBr, then purified by gel-filtration on a 30×1 cm column of Superose 12 (Pharmacia, Milton Keynes, U.K.) in the presence of 0.5M LiBr. Glycogen protein particles from rat liver [22] were used as the source of hepatic $PP1_G$. Digoxygenin-labelled PP1c ($γ_1$-isoform, hereafter termed PP1) was prepared as in [9]. $G_L$ was expressed in E. coli as a glutathione-S-transferase (GST) fusion protein [7], termed GST-$G_L$. The catalytic subunit of PP2A from bovine heart (PP2AC) was provided by Dr R. MacKintosh in this Unit. The phosphorylatable myosin light chain ($MLC_{20}$) and heavy meromyosin from chicken gizzard were a gift from Dr M. Ikebe (Case Western Reserve University, Cleveland, USA). Thrombin and benzamidine-Agarose were purchased from Sigma (Poole, UK).

Peptide Synthesis.

Peptides were synthesised on an Applied Biosystems 430A peptide synthesiser and their purity and concentration established by high performance liquid chromatography, mass spectrometry and amino acid analysis. The sequence of rabbit $G_M$-(G63-T93) is GRRVSFADNFGFNLVS-VKEFDTWELPSVSTT (SEQ ID No 6) and the sequence of $M_{110}$-(M1-F38) is MKMADAKQKRNEQLKRWIGSET-DLEPPVVKRQKTKVKF (SEQ ID No 7). The peptide $G_M$-(G63-T93) was cleaved with Lys-C endoproteinase (Boehringer) and the peptide $G_M$-(E81-T93) thus generated was purified on a $C_{18}$ column. The peptides $G_M$-(G63-K80) and $G_M$-(G63-N75), were synthesised, and the latter phosphorylated at Ser67 with the catalytic subunit of cyclic AMP-dependent protein kinase (PKA), then bound to a 1 ml $C_{18}$ column equilibrated in 0.1% (v/v) trifluoroacetic acid, washed with 0.1% trifluoroacetic acid to remove excess ATP, eluted with 0.1% trifluoroacetic acid containing 70% acetonitrile, dried and dissolved in water. The peptide $G_M$-(S40-Y55) was a gift from Dr Bruce Kemp (St Vincent's Institute, Australia).

Preparation of Phosphorylated Proteins and Phospharase Assays.

$^{32}$P-labelled rabbit skeletal muscle phosphorylase a (containing 1.0 mol phosphate per mol subunit) was prepared by phosphorylation with phosphorylase kinase [23], $^{32}$P-labelled rabbit skeletal muscle glycogen synthase (containing 1.5 mol/mol subunit in the sites 3 region) was prepared by phosphorylation with glycogen synthase kinase-3 [24]). $^{32}$P-labelled chicken gizzard $MLC_{20}$ and $^{32}$P-labelled chicken gizzard heavy meromyosin (containing 1.0 mol phosphate per mol subunit) were prepared by phosphorylation with smooth muscle myosin light chain kinase [9]. The dephosphorylation of phosphorylase a (10 μM), glycogen synthase (1 μM) and $MLC_{20}$ (1 μM) and heavy meromyosin (1 μM) was carried out as in [24]. One unit of activity (U) was that amount which released 1 mole of phosphate in one minute.

Construction of Vectors for the Expression of N-terminal Fragments of the $G_M$ Subunit as Glutathione-S-transferase (GSZ) Fusion Proteins in E. coli.

$G_M$-(E2-RS75) was produced by inserting a SmaI-SmaI restriction fragment, encoding amino acids 2–575 of human $G_M$, from clone H1G11 [5] into the SmaI site of pGEX-KG (Pharmacia, Milton Keynes, U.K.). This resulted in the addition after residues 2–575 of amino acids EFPVVVVEF (SEQ ID No 8) before the stop codon. $G_M$-(E2-P243) was made by deleting an NcoI-HindIII fragment of the $G_M$-(E2-R575) construct, resulting in termination after residue 243. $G_M$-(E2-D118), encoding amino acids 2–118, with a C-terminal addition of QLNSS was produced by deleting a BglII-HindIII fragment of the $G_M$-E2-R575) construct. $G_M$-H100-P350) encoding amino acids 100–350 was made by inserting an EcoRI-HindIII digested PCR fragment prepared using primers 5' GCCGAATTCACACAGAA-GAATATGTTTTAGCC 3' (SEQ ID No 9) and 5' GCCGAAGCTTATGGAAAATTGACTGGATCTGTTG 3' (SEQ ID No 10) into the same sites of pGEX-KG. Restriction sites in the primers are underlined.

Construction of Vectors for the Expression of Tile Chicken Gizzard $M_{21}$ Subunit in E. coli.

The entire coding region (M1-K186) of the $M_{21}$ subunit [10] was amplified by PCR using primers 5' CGCGCATAT-GTCGTCGCTGTTCACCAGG 3' (SEQ ID No 11) and 5' GGCGGATCCCTACTTGGAGAGTTTGC 3' (SEQ ID No 12), containing restriction sites NdeI and BamHI (underlined). After cleavage with the restriction enzymes, the PCR fragment was cloned into the same sites of the bacterial expression vector pT7-7.

Production of Fragments of the Chicken Gizzard and Rat Aorta $M_{110}$ subunits.

The C-terminal 291 residues $M_{110}$-(R714-I1004) of the chicken gizzard $M_{110}$ subunit were amplified by PCR using a primer 5' AGGAAGAATTCGTTCCACACGAAC 3' (SEQ ID No 13) containing an EcoRI restriction site (underlined) and a KS primer in the Bluescript vector of the cDNA clone [10]. The EcoRI digested PCR fragment was subcloned into the same site of pT7-7.

Rat aorta $M_{110}$ fragments were produced as GST-fusion proteins. $M_{110}$-(M1-A150) was amplified by PCR using primers A (5° CCTAGCCCGGGGATGAAGATGGCGGAC 3') (SEQ ID No 14) and B (5' GCGGAAGCTTATGCTTC-CTCCTCTGCAATATC 3') (SEQ ID No 15), containing SmaI and HindIII restriction sites (underlined) and the SmaI-HindIII digested PCR fragment subcloned into the same sites of pGEX-KG. $M_{110}$-(M1-E309) was produced by subcloning a SmaI-HindIII digested PCR fragment amplified using primers A and C (5' CTAGAAGCTTC-CATATTTGCTGTTGATTCAATC 3') (SEQ ID No 16) into the same sites of pGEX-KG. This resulted in one amino acid (A) being added after E309. $M_{110}$-(D39-E309) was produced by subcloning a SmaI-HindIII digested PCR fragment amplified using primers D (5'CCTAGCCCGGGGGACGATGGCGCCGTCTTCC 3') (SEQ ID No 17) and C into the same sites of pGEX-KG. An $M_{110}$-(L24-K976) was prepared by inserting a XhoI-XhoI restriction fragment of the entire $M_{110}$ cDNA in Bluescript into XhoI site of pGEX-KG, and $M_{110}$-(L24-Y496) expressed by deleting a NdeI-NdeI fragment of the L24-K976 construct and filling the overhanging ends before ligating them. This resulted in the addition after Y496 of amino acids MVAD (SEQ ID No 18) before the stop codon. The sequence of all subclones produced after PCR amplification were verified using an Applied Biosystems 373A automated DNA sequencer and Taq dye terminator cycle sequencing according to the manufacturer's instructions.

Expression of Proteins in E. coli.

All constructs were expressed in E. coli strain BL21(DE3) plysS. Cultures were grown at 37° C. in Luria-Bertani medium in the presence of 100 µg/ml ampicillin and 30 µg/ml chloramphenicol to an A600 of 0.4–0.6, and induced with 50 µg/ml isopropylthiogalactoside for 8 hours at 25° C. or overnight at ambient temperature. After centrifugation for 10 minutes at 7000×g (4° C.), cells from one liter of culture were resuspended in 20 ml of 50 mM Tris-HCl pH 8.0, 0.1 M NaCl, 1 mM EDTA, 0. 1% (by vol) 2-mercaptoethanol, 0.2 mM phenylmethylsulphonylfluoride ($PhMeSO_2F$), 1 mM benzamidine (buffer A) and frozen at −80° C. After thawing, sodium deoxycholate (1 mg/ml ), 8 mM $MgSO4$ and 10 g/ml DNAase I were added, the extract incubated until it was no longer viscous, then made 6 mM in EDTA, 1 mM in benzamidine and 0.2 mM in $PhMeSO_2F$ and centrifuged for 10 minutes at 10,000×g. The soluble GST-fusion proteins were then purified from the supernatant by affinity chromatography on glutathione-Sepharose (Pharmacia).

The $M_{21}$ subunit and $M_{110}$(R714-I1004) C-terminal fragment from chicken gizzard $M_{110}$ subunit, which were used for affinity purification of the anti-$M_{21}$ and anti-$M_{110}$ antibodies (see below) were obtained in inclusion bodies and therefore recovered in the pellets after centrifuging E. coli extracts at 10,000×g. $M_{110}$-(R714-I1004) was solubilised by resuspension in Buffer A containing 0.5% (by mass) Triton X-100 and was >95% pure. The $M_{21}$ subunit was not solubilised by this procedure but, after washing the pellets in 0.5% Triton X-100, was dissolved by sonication in 0.5% trifluoroacetic acid; its purity was about 20%.

$M_{110}$ GST-fusion proteins (1–9 mg/ml in 50 mM Tris/HCl, 2.5 mM $CaCl2$, 150 mM NaCl and 0. 1% (by vol) 2-mercaptoethanol) were cleaved by incubation for 20 minutes at 30° C. with 20 µg/ml thrombin. Benzamidine-Agarose (0.2 ml) was added and, after incubation (with rotation) for 30 minutes at ambient temperature, the benzamidine-Agarose containing the attached thrombin was removed, and the supernatant dialysed against 50 mM Tris-HCl pH 7.5, 0.1 mM EGTA, 0.1% (by vol) 2-mercaptoethanol, 10% glycerol and stored in aliquots at −80° C. After cleavage with thrombin, all fragments of the $M_{110}$ subunit, except $M_{110}$-(L24-Y496), commenced with the sequence GSPG (SEQ ID No 19) before the initiating residue of the GST-fusion proteins. The $M_{110}$-(24-Y496) was preceded by the sequence GSPGISGGGGGILDSMGR (SEQ ID No 20).

Production of Antibodies that Recognise the $M_{110}$ and $M_{21}$ Subunits of Chicken Gizzard $PP1_M$.

Polyclonal sheep antibodies to the $PP1_M$ holoenzyme were raised in the Scottish Antibody Production Unit (Carluke, Ayrshire, U.K.). Antibodies which recognise the $M_{110}$ subunit specifically were obtained by passing the antiserum down a 4 ml affinity column comprising 40 mg of $M_{110}$-(R714-I1004) coupled covalently to 1 g of dried CNBr-activated Sepharose 4B (Sigma). After washing with 10 column volumes of 50 mM Tris/HCl pH 7.5, 1% (by mass) Triton X-100, 0.1 mM EGTA, 0.1% (by vol) 2-mercaptoethanol (Buffer B) plus 0.5 M NaCl, followed by 10 volumes of Buffer B plus 1 M LiBr, the anti-$M_{110}$ antibody was eluted with 50 mM glycine pH 2.0, neutralised immediately with 1 M Tris/HCl pH 8.0 and stored in aliquots at −80° C. Antibodies which recognise the $M_{21}$ subunit specifically were obtained in an identical manner, except that the affinity column comprised about 40 mg of the expressed chicken gizzard $M_{21}$ subunit coupled to 6 g (dry weight) of CNBr-activated Sepharose.

Removal of the $M_{21}$ Subunit From $PP1_M$.

$PP1_M$ (0.01 ml, 0.4U/ml) was dissociated by incubation for 30 minutes with 500 µM arachidonic acid [25] and then for 30 minutes with 0.08 ml of packed Protein G-Sepharose coupled to 0.08 mg of affinity purified anti-$M_{21}$ antibody. The Protein G-Sepharose was pelleted, and the supernatant diluted at least 15-fold to allow the $M_{110}$ subunit and PP1c to recombine. The $M_{110}$-PP1c complex was further purified by gel filtration on Superose 12 (30×1 cm) to ensure complete removal of any free PP1c.

Results.

Identification of a PP1c-interaction Domain on the $G_M$-subunit of $PP1_{GM}$.

The amino acid sequence of rat hepatic $G_L$ is 23% identical (39% similar) to residues 1–286 of $G_M$ from human skeletal muscle [7]. There is no homology over the first 63 residues but identity is >40% over the regions 63–86, 144–166 and 186–227 of $G_M$ suggesting that one or more of these sequences comprise a PP1-binding domain. Fusion proteins in which GST was linked to fragments of $G_M$ were therefore tested for their ability to bind to PP1c. GST-$G_M$-(E2-D118) (FIG. 1) and GST-$G_M$-(E2-P243) (data not shown), but not GST-$G_M$-(H100-P350) or GST itself (FIG. 1) interacted with PP1 in Far Western experiments, indicating that the first 118 residues of $G_M$ contain a PP1c-binding domain. Moreover, a proteolytic fragment derived from GST-$G_M$-(E2-D118) whose molecular mass was 5 kDa less than GST-$G_M$-(E2-D118), but not a proteolytic fragment that was 6 kDa smaller, also interacted with PP1c (FIG. 1). Taken together, the observations suggested that the region comprising residues 63–86 was likely to bind to PP1c. We therefore synthesised $G_M$-(G63-T93) and examined its effect on the enzymatic properties of $PP1_{GL}$, the form of PP1 associated with rat hepatic protein-glycogen particles.

The interaction of PP1c with $G_L$ suppresses the dephosphorylation of muscle glycogen phosphorylase by 80% and enhances the dephosphorylation of muscle glycogen synthase by 2–3 fold [21, 26]. Disruption of the characteristic properties of hepatic $PP1_{GL}$ can therefore be monitored very simply by changes in its specificity. $G_M$-(G63-T93) induced a sixfold increase in the phosphorylase phosphatase activity of $PP1_{GL}$, the concentrations required for 50% activation being 30 nM (FIG. 2). $G_M$-(G63-T93) also prevented bacterially expressed GST-$G_L$ from suppressing the phosphorylase phosphatase activity of PP1c (data not shown). However, $G_M$-(G63-T93) had no effect on the glycogen synthase phosphatase activity of $PP1_{GL}$, nor was there any alteration of the other characteristic properties of $PP1_{GL}$, namely allosteric inhibition of the glycogen synthase phosphatase activity by phosphorylase a and binding to glycogen (data not shown). Thus the interaction of $G_M$-(G63-T93) with $PP1_{GL}$ does not displace $G_L$ from PP1c.

$G_M$-(G63-T93) also increased the phosphorylase phosphatase activity of PP1c, indicating that it binds to PP1c, rather than to $G_L$. However, the maximal stimulation was only 37+1.4% (SEM for three experiments), establishing that far greater activation of $PP1_{GL}$ is explained by the ability of $G_M$-(G63-T93) to overcome the suppressive effect of $G_L$ on the phosphorylase phosphatase activity of PP1c. Several other peptides, including a 32 residue peptide related to the C-terminus of ribosomal protein S6([G245, G246]S6[218–249]), $G_M$-(S40-Y55) and $G_M$-(E81-T93)

(data not shown), had no effect on the phosphorylase phosphatase activity of PP1$_{GL}$ or PP1c at concentrations up to 10 µM.

The peptides G$_M$-(G63-K80) and G$_M$-(G63-N75) also increased the phosphorylase phosphatase activity of PP1$_{GL}$, but were less effective than G$_M$-(G63-T93) and higher concentrations were needed (FIG. 2). G$_M$-(G63-K80) and G$_M$-(G63-N75) did not increase the phosphorylase phosphatase activity of PP1c significantly at concentrations up to 10 µM (data not shown). The phosphorylation of G$_M$ at Ser67 by cyclic AMP-dependent protein kinase (PKA) triggers the dissociation of PP1 from G$_M$ in vitro and in vivo [18] and phosphorylation of the peptide G$_M$-(G63-N75) at Ser67 prevented it from increasing the phosphorylase phosphatase activity of PP1$_{GL}$ (FIG. 2A). The increase in phosphorylase phosphatase activity observed at the highest phosphopeptide concentrations (10 µM) may be explained by trace contamination (<10%) with dephosphopeptide, resulting either from incomplete phosphorylation of Ser67 or slight dephosphorylation during the assay.

Identification of a PP1-interaction Domain on the M$_{110}$ Subunit.

Figure 3A:
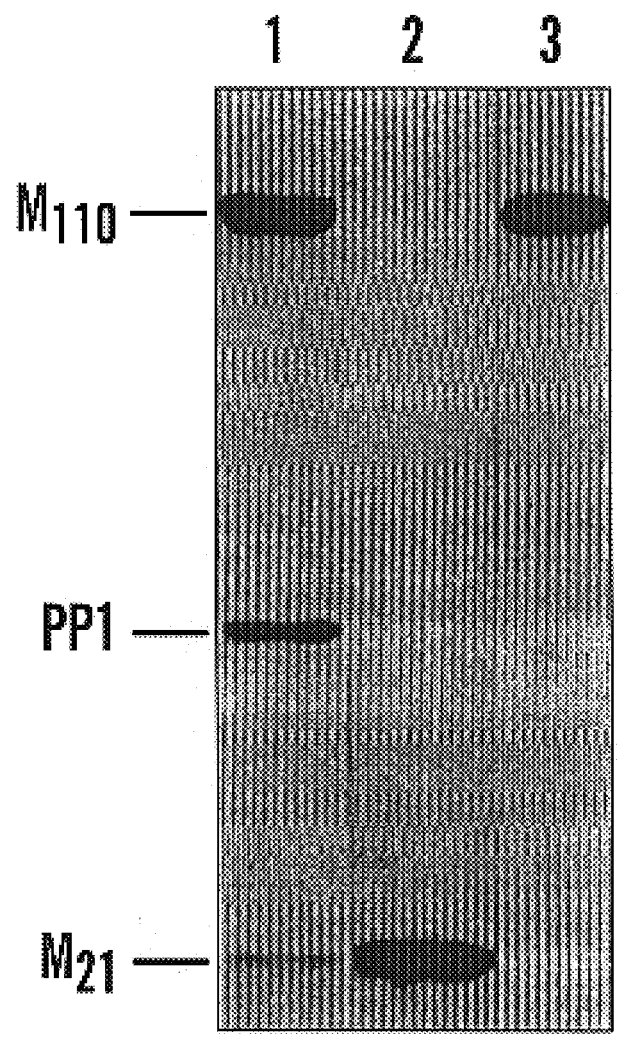
Figure 3B:
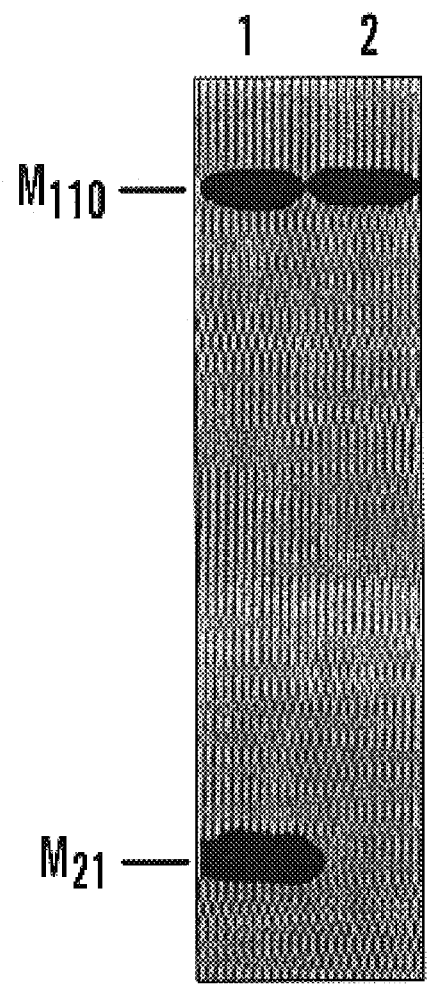

Antibodies were prepared that recognised either the M$_{110}$ or M$_{21}$ subunits of the myosin-associated form of PP1 (PP1$_M$) from chicken gizzard (FIG. 3A). Removal of the M$_{21}$ subunit using the M$_{21}$-specific antibody (FIG. 3B and see Methods) did not affect the activity of PP1$_M$ towards MLC$_{20}$ or phosphorylase, the MLC$_{20}$ phosphatase:phosphorylase phosphatase activity ratio (0.95±0.03) remaining 15-fold higher than PP1c (FIG. 3B). The M$_{21}$ subunit bound to M$_{110}$, but had no effect on the MLC$_{20}$ phosphatase or phosphorylase phosphatase activity of PP1c and did not bind to PP1c (D. Johnson unpublished). Thus M$_{110}$ is solely responsible for enhancing the dephosphorylation of MLC$_{20}$ and suppressing the dephosphorylation of glycogen phosphorylase by PP1c [9].

Figure 5A:
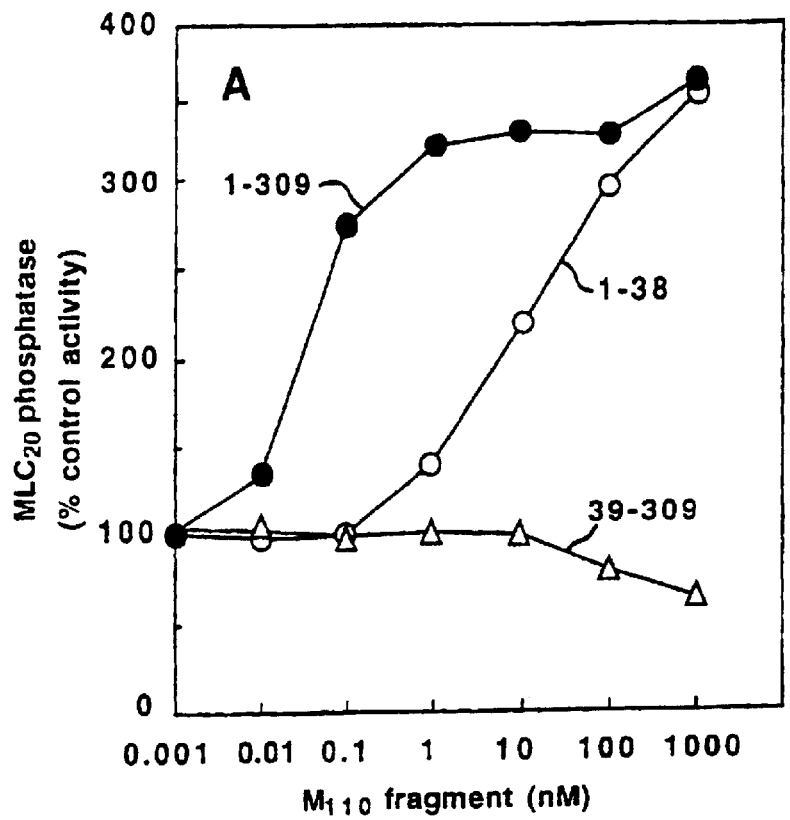
Figure 5B:
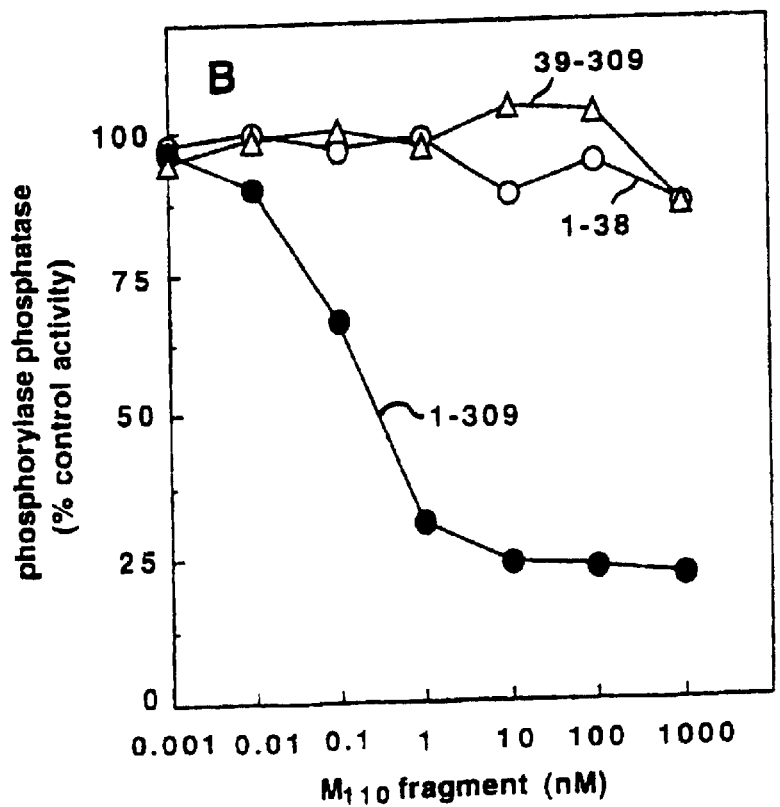
Figure 5C:
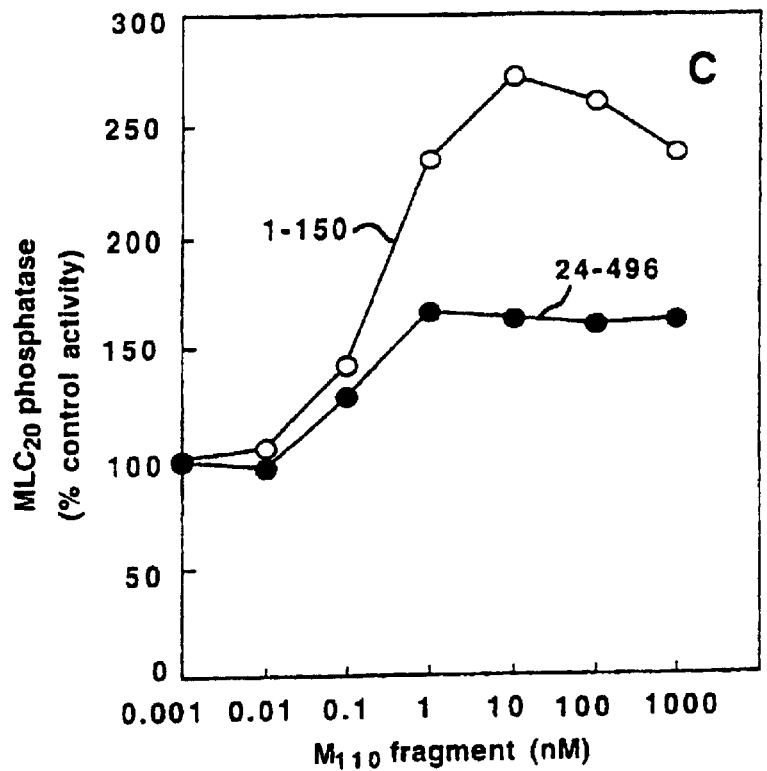
Figure 5D:
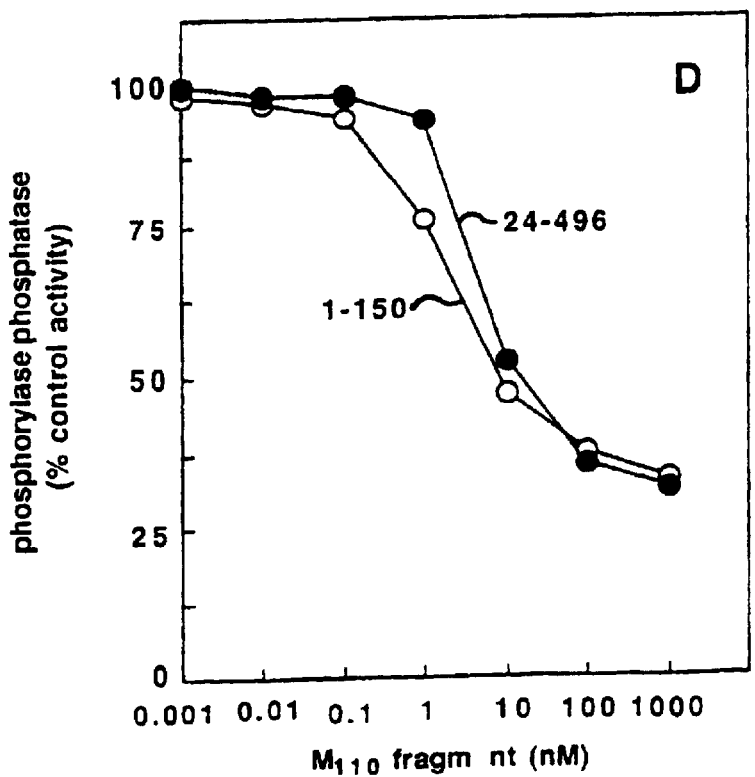

In order to identify which region(s) of M$_{110}$, modulates the specificity of PP1c, fusion proteins were constructed consisting of glutathione S-transferase (GST) followed by fragments of the M$_{110}$ subunit. After expression in *E. coli* and purification by affinity chromatography on glutathione-Sepharose, the fusion proteins were cleaved with thrombin to release GST from fragments of the M$_{110}$ subunit (FIG. 4 and see Methods). M$_{110}$-(M1-E309), which contains seven 33 residue ankyrin repeats located between residues 39–296, modified the specificity of PP1c in a similar manner to M$_{110}$ itself, increasing activity towards MLC$_{20}$ about 3-fold (FIG. 5A) and suppressing activity towards glycogen phosphorylase by about 80% (FIG. 5B). The concentration of M$_{110}$-(M1- E309) required to activate the MLC$_{20}$ phosphatase activity maximally (0.1 nM) was similar to the PP1c concentration in the assay, indicating an extremely high affinity for PP1c. M$_{110}$-(M1-A150) modified the specificity of PP1 similarly, but 10-fold higher concentrations were needed compared to M$_{110}$-(M1-E309) (FIGS. 5C and 5D).

If the GST tags were not cleaved with thrombin, a 10-fold higher concentration of M$_{110}$-(M1-E309) was needed to modulate the substrate specificity of PP1c, while M$_{110}$-(M1-A150) was unable to stimulate the MLC$_{20}$ phosphatase activity of PP1c at all (data not shown). GST itself did not interact with PP1c (FIG. 1), had no effect on either the MLC$_{20}$ phosphatase or phosphorylase phosphatase activity of PP1c (data not shown), and therefore was not removed from the solution after cleavage of the fusion proteins with thrombin.

In contrast to M$_{110}$-(M1-E309), M$_{110}$-(D39-E309) failed to stimulate the MLC$_{20}$ phosphatase activity of PP1c, or to inhibit its phosphorylase phosphatase activity (FIGS. 5A and 5B), suggesting that the extreme N-terminus of the M$_{110}$ subunit (i.e. before the start of the ankyrin repeats) might be important in modulating the specificity of PP1c. The peptide M$_{110}$-(M1-F38) was therefore synthesized and found to stimulate the MLC$_{20}$ phosphatase activity of PP1c to the same extent as M$_{110}$-(M1-E309), although the concentration required for half maximal activation (10 nM) was at least 100-fold higher (FIG. 5A). M$_{110}$-(M1-F38) stimulated the dephosphorylation of heavy meromyosin in a similar manner to the dephosphorylation of MLC$_{20}$ (data not shown). However, like M$_{110}$-(D39-E309), M$_{110}$-(M1-F38) did not inhibit the phosphorylase phosphatase activity of PP1c (FIG. 5B). These observations suggested that residues beyond 38 were needed to suppress phosphorylase phosphatase activity. Consistent with this, M$_{110}$-(L24-Y496) was less effective than M$_{110}$-(M1-A150) or M$_{110}$-(M1-E309) in stimulating the MLC$_{20}$ phosphatase activity of PP1c, but inhibited the phosphorylase phosphatase activity of PP1c in a similar manner to M$_{110}$-(M1-A150) (FIGS. 5C and 5D).

Although M$_{110}$-(D39-E309) and M$_{110}$-(M1-F38) had no effect on the phosphorylase phosphatase activity of PP1c when each peptide was included individually in the assays at concentrations up to 1 µM (FIG. 5), a 39±2% inhibition (SEM n=4) was observed when both peptides were both present at 1 µM. Surprisingly, M$_{110}$-(D39-E309) prevented (IC50=0.1 M) M$_{110}$-(M1-F38) from stimulating the MLC20 phosphatase activity of PP1c (data not shown). Thus M$_{110}$-(D39-E309) plus M$_{110}$-(M1-F38) do not faithfully mimic the effect of M$_{110}$-(M1-E309).

We have reported previously that the M$_{110}$/M$_{21}$ complex suppresses the dephosphorylation of glycogen synthase by PP1c [9] and, consistent with this finding, the dephosphorylation of glycogen synthase was also inhibited by M$_{110}$-(M1-E309) (FIG. 6B). However, the dephosphorylation of glycogen synthase was greatly enhanced by M$_{110}$-(M1-F38) (FIG. 6A).

The Binding of G$_M$ and the M$_{110}$ Subunit to PP1c is Mutually Exclusive.

Figure 7B:
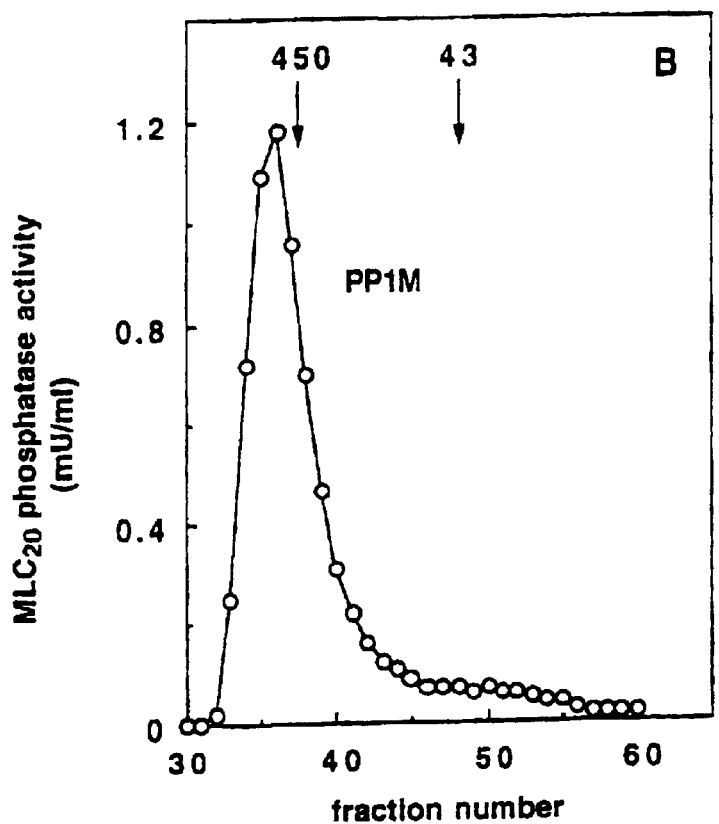
Figure 7C:
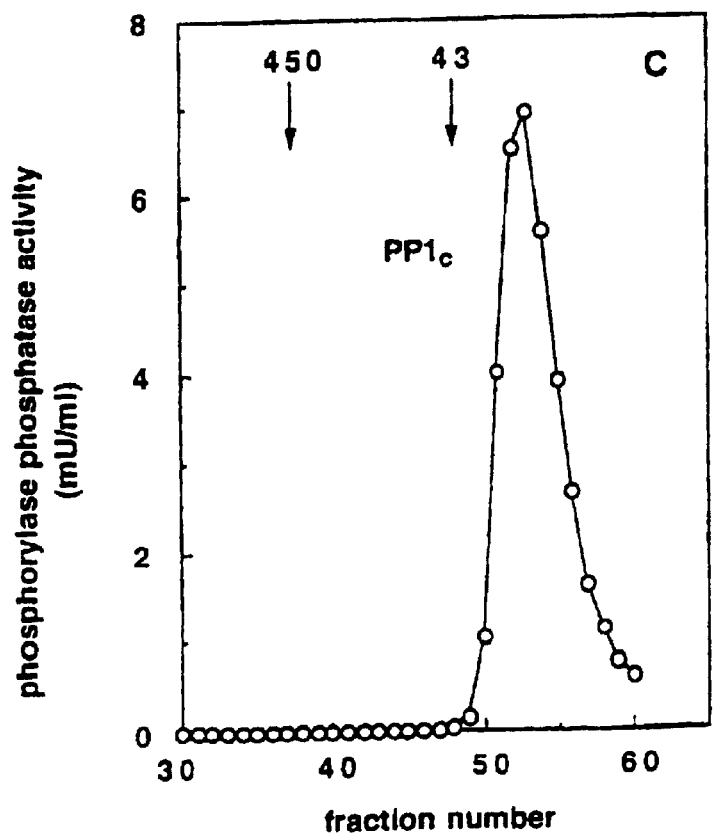
Figure 8B:
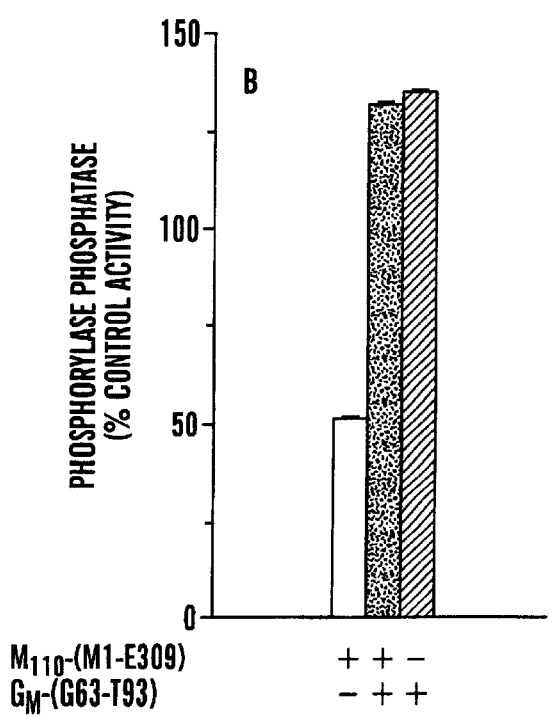

In order to investigate whether G$_M$ binds to the same region of PP1c as M$_{110}$, we next examined the effect of G$_M$-(G63-T93) on the properties of PP1$_M$. G$_M$-(G63-T93) at 10 µM increased the phosphorylase phosphatase activity of PP1$_M$ by about 7-fold and suppressed its MLC$_{20}$ phosphatase activity by 60–65% (FIG. 7A), indicating that the distinctive properties of PP1$_M$ had been disrupted. Gel-filtration experiments confirmed that G$^M$-(G63-T93) had displaced the M$_{110}$ subunit from PP1$_M$, dissociating it to PP1c (FIGS. 7B and 7C). G$_M$-(G63-T93) also prevented M$_{110}$-(M1-F38) or M$_{110}$-(M1-E309) from stimulating the MLC$_{20}$ phosphatase activity of PP1c (FIG. 8A), and prevented M$_{110}$-(M1-E309) from suppressing the phosphorylase phosphatase activity of PP1c (FIG. 8B).

Conversely, the presence of 10 µM M$_{110}$-(M1-F38) increased the phosphorylase phosphatase activity of PP1$_{GL}$ by 3.5-fold. This resulted from the partial dissociation to PP1c, because the enhanced phosphorylase phosphatase activity was not associated with glycogen, but recovered in the supernatant after centrifugation of the glycogen-protein particles (not shown).

Discussion.

We have identified a region on G$_M$ that binds to PP1c (FIG. 9). The peptides G$_M$-(G63-T93), G$_M$-(G63-K80) and G$_M$-(G63-N75) all prevented G$_L$ from suppressing the dephosphorylation of glycogen phosphorylase by PP1c and two lines of evidence indicate that these peptides interact with PP1c and not with G$_L$.

Firstly, the PP1c-catalysed dephosphorylation of glycogen phosphorylase is stimulated slightly by $G_M$-(G63-T93).

Secondly, PP1c crystallises in the presence of $G_M$-(G63-K80) or $G_M$-(G63-N75) in a different form than is observed in the absence of these peptides. PKA phosphorylates $G_M$ at Ser67 and the introduction of a negative charge directly into the PP1c-binding domain explains why phosphorylation of Ser67 triggers the dissociation of $G_M$ from PP1c [18]. Phosphorylation of $G_M$-(G63-N75) at Ser67 also prevented this peptide from interacting with PP1 in the $PP1_{GL}$ complex (FIG. 2).

Although $G_M$-($G^{63}$-$T^{93}$) prevented $G_L$ from suppressing the dephosphorylation of glycogen phosphorylase by PP1c, it did not dissociate $G_L$ from PP1c, nor did it affect the other characteristic properties of $PP1_{GL}$. Moreover, unlike $G_L$, $G_M$-(G63-T93) did not itself suppress the phosphorylase phosphatase activity of PP1c, but actually enhanced it slightly. These observations demonstrate that another region (s) on $G_L$ must interact with PP1c and that this other region(s) may play an important role in modulating the substrate specificity of PP1c. The presence of a second PP1c binding site in $G_M/G_L$ would be somewhat analogous to the situation found in inhibitor-1 and DARPP which also contain two PP1-binding sites, high (nM) affinity binding being generated by the conjugation of two low affinity binding sites that, individually, only interact with PP1 at tM concentrations [28]. The second PP1c-binding site on $G_M/G_L$ might correspond to one of the other regions where $G_M$ and $G_L$ show >40% identity (residues 144–166 and 186–227 of human $G_M$). Although $G_M$-(H100-P350) was not recognised by PP1c in Far Western experiments (FIG. 1) this result is not definitive because $G_M$-(H100-P350) may only interact with PP1c weakly. Alternatively, $G_M$-(H100-P350) might not fold correctly or fail to renature after SDS/polyacrylamide gel electrophoresis.

However, it is also possible that residues 144–166 and 186–227 of $G_M$ do not represent part of the second PP1c-binding domain, but part of the glycogen-binding domain. In this connection it should be recalled that residues 144–166 and 186–227 are the regions showing greatest similarity (25% identity) to GAC1, which appears to be a homologue of $G_M/G_L$ in budding yeast [7, 27, 28]. Curiously, GAC1 does not contain a region homologous to residues 63–93 of $G_M/G_L$. It would clearly be of interest to compare the effect of GAC1 on the enzymatic properties of PP1c with those of $G_M$ and $G_L$.

We have also identified a region on the $M_{110}$ subunit that binds to PP1c. An N-terminal fragment, M100-(M1-E309), enhanced the PP1c-catalysed dephosphorylation of $MLC_{20}$ and suppressed the dephosphorylation of glycogen phosphorylase in a similar manner to $M_{110}$ itself (FIG. 5). However, unlike $M_{110}$, this fragment does not bind to myosin. Thus the region which enhances the dephosphorylation of $MLC_{20}$ is distinct from the myosin-binding domain.

The fragment $M_{110}$-(M1-E309) contains seven ankyrin repeats lying between residues 39 and 296. However, $M_{110}$-(D39-E309) was ineffective as an activator of the $MLC_{20}$ phosphatase activity of PP1c or as an inhibitor of the phosphorylase phosphatase activity, and this led to the finding that a peptide comprising the N-terminal 38 residues of the $M_{110}$ subunit enhances the dephosphorylation of $MLC_{20}$ to the same extent as $M_{110}$-(M1-E309), although with lower potency. However, $M_{110}$-(M1-F38) did not inhibit the dephosphorylation of glycogen phosphorylase by PP1c suggesting that residues beyond 38 are required to suppress this activity. This view was reinforced by the finding that, although neither $M_{110}$-(M1-F38) nor $M_{110}$-(D39-E309) inhibited the phosphorylase phosphatase activity of PP1c when present individually, inhibition was observed in the presence of both peptides. Moreover $M_{110}$-(D39-E309) actually prevented $M_{110}$-(M1-F38) from stimulating the dephosphorylation of $MLC_{20}$.

These observations suggest that $M_{110}$-(D39-E309) can bind to $M_{110}$-(M1-F38) and/or PP1c. An interaction with PP1c seems likely because it has been found that $M_{110}$-(D39-E309) can enhance the phosphorylase activity of $PP1_{GL}$. The presence of a second PP1-binding site in the ankyrin-repeat domain of the $M_{110}$ subunit is also supported by the observation that higher concentrations of $M_{110}$-(M1-A150) and $M_{110}$-(M1-E309) are needed to inhibit the phosphorylase phosphatase activity of PP1c than are required to stimulate its $MLC_{20}$ phosphatase activity (see FIG. 5). The presence of at least two PP1-binding sites may explain why the $M_{110}$ subunit and PP1c interact at picomolar concentrations. The ankyrin repeat domain might suppress the dephosphorylation of some substrates (such as glycogen phosphorylase) by a steric mechanism, preventing them from gaining easy access to the catalytic centre. This scenario could explain why the dephosphorylation of glycogen synthase is greatly enhanced by $M_{110}$-(M1-F38) yet suppressed by $M_{110}$-(M1-E309) (FIG. 6).

$G_M$-(G63-T93) abolished the distinctive properties of $PP1_M$ (FIG. 7A), prevented $M_{110}$-(M1-F38) or $M_{110}$-(M1-E309) from modulating the substrate specificity of PP1c (FIG. 8) and displaced the $M_{110}$ subunit from $PP1_M$ (FIG. 7B). In addition, the peptide $M_{110}$-(M1-F38), was capable of displacing $G_L$ from $PP1_{GL}$. These findings indicate that the binding site(s) on PP1c for $G_M$ and the $M_{110}$ subunit are likely to overlap, explaining why different forms of PP1 contain a single PP1-targeting subunit. The three-dimensional structure of PP1c isoforms have recently been solved to high resolution [29,30], and PP1c crystallises in different forms in the presence of $G_M$-(G63-N75) or $G_M$-(G63-K80) or $M_{110}$-(M1-F38) than in the absence of these peptides.

Consistent with the results presented here, Gailly et al [31] have recently shown that $M_{110}$-(M1-F38) or $M_{110}$(M1-E309) enhance the ability of PP1c to stimulate the relaxation of microcystin-contracted permeabilised portal vein, while $G_M$-(G63-T93) inhibits the ability of $PP1_M$ to induce the relaxation of this smooth muscle. $G_M$-(G63-T93) also slowed the relaxation of permeabilised femoral artery, indicating that it competes with the endogenous $M_{110}$ subunit for PP1c [31]. Thus the PP1c-binding peptides described constitute useful pharmacological agents with which to explore the role and regulate the activity of PP1 in cell regulation.

EXAMPLE 2

Structural Basis for the Recognition of Regulatory Subunits by the Catalytic Subunit of Protein Phosphatase 1

Materials and Methods

Crystallisation and Data Collection

The catalytic subunit of PP1 1 was overproduced in *Escherischia coli* and purified as described previously (Alessi et al., 1993; Barford and Keller, 1994). The $G_M$[G63-N75] peptide, variants of this peptide in which Val 66' or Phe 68' were changed to Phe, and the peptides $M_{110}$[1–38] and $M_{110}$[1–35] were synthesised on an Applied Biosystems 430A peptide synthesiser and purified by chromatography on a C18 column (Johnson et al., 1996) by Mr F. B. Caudwell at Dundee. A three-fold molar excess of $G_M$[G63-N75] was added to the protein solution (8 mg/ml), which had been previously dialysed against 10 mM Tris-HCl (pH 7.8), 0.3 M NaCl, 0.4 mM MnCl$_2$ and 2 mM DTT. The complex was crystallised at 20° C. using the hanging drop vapour diffusion method, by mixing 2 ml of the protein-peptide solution and 2 ml of the precipitant solution containing 2.0 M ammonium sulphate, 2% (w/v) polyethylene glycol 400, 100 mM HEPES (pH 7.5) and 2 mM DTT. These conditions are very much in contrast to the relatively low ionic strength conditions from which the monoclinic PP1c crystals grew (Barford and Keller, 1994; Egloff et al., 1995). Crystals appeared after 3 months as a cluster. Individual crystals removed from the cluster had dimensions of ~25 μm×25 μm×5 μm. Crystals were frozen in a 100 K nitrogen gas stream and stored. Prior to freezing, crystals were incubated in a cryoprotectant solution consisting of an equilibration buffer; 2.0 M ammonium sulphate, 2% (w/v) PEG 400, 100 mM HEPES (pH 7.5) with increasing amounts of glycerol in steps of 7%, 15%, 22% and 30% (v/v).

A partial data set to 3.0 Å was collected on Beam Line PX 9.6, SRS, Daresbury, using a 30 cm diameter Mar Research image plate system. Data were processed and scaled using DENZO and SCALEPACK (Otwinowski, 1993). The crystal system is tetragonal with point group symmetry P422 and unit cell dimensions a=b=62.50 Å, c=361.30 Å. Systematic absences indicate a 21 screw axis along b. The Matthews coefficient was 2.38 Å$_3$ per Dalton, assuming 2 molecules per asymmetric unit. A second data-set was collected on BL4 at the ESRF, Grenoble. Substantial radiation damage was observed during data collection requiring that three crystals were used in total. Data collected from four crystal at Daresbury and the ESRF were merged together in SCALEPACK. Details of the data collection and processing statistics are given in Table 1.

Structure Determination

The structure of the PP1-G$_M$[63–75] complex was solved by molecular replacement using as a model the protein atoms coordinates of the 2.5 Å refined structure of the catalytic subunit of PP1γ1 determined by MAD methods (Egloff et al., 1995). Rotation and translation functions searches were performed with AMORE (Navaza, 1992). Using data between 8 and 3 Å resolution, the peak in the rotation search was 6.7 standard deviations (SD) above the mean. The translation search was best performed using data between 8 and 3.5 Å, giving a maximal peak at 13.8 SD above the mean for the space group P41212. After the first rigid body refinement performed in AMORE, the R-factor was 0.494 and the correlation factor 0.30.

Crystallographic Refinement

Figure 10A:
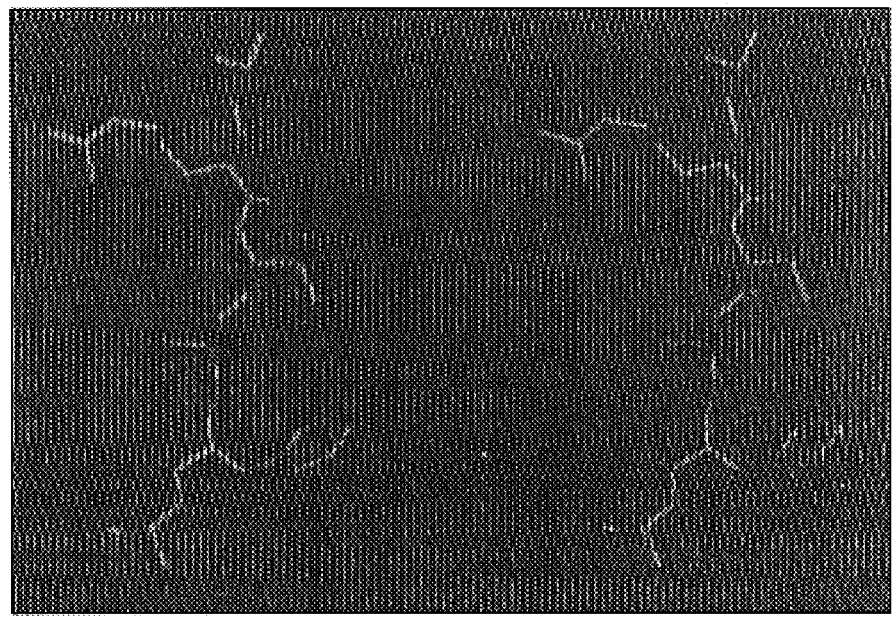
Figure 10B:
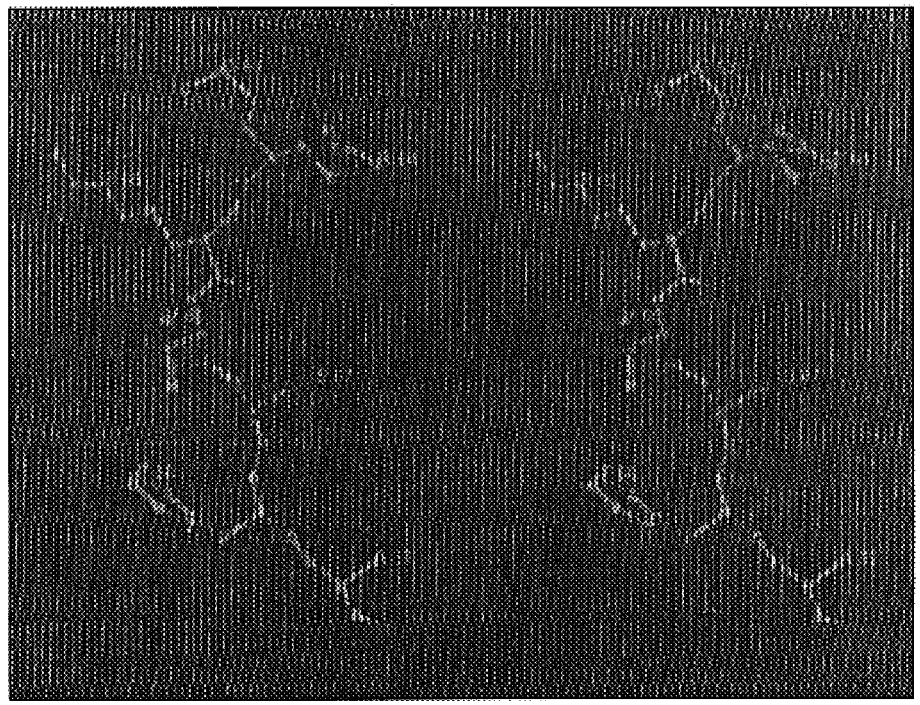

The solution from molecular replacement was optimized by 20 cycles of rigid body refinement performed with X-PLOR version 3.1 (Brunger, 1992), using data between 8.0 Å and 3.0 Å resolution. After a round of conjugate gradient positional refinement and simulated annealing molecular dynamics to 2000 K, followed by 25 cycles of grouped B-factor refinement (2 B-factor groups for each residue), the R factor (respectively free-R) was 0.295 (0.367). Fourier difference maps (Fo-Pc) and (3Fo-2Fc) revealed the presence of three strong peaks at (over three-times the sigma level of the map) at the catalytic site of PP1c. From the previously refined PP1c-structure, we identified two as manganese and iron ions. The third one, occupying the position of the tungstate ion in the PP1c-WO4 complex, was identified as sulphate. The initial difference Fourier maps also revealed strong electron density near the N-terminus of β14. The maps were improved by applying non-crystallographic symmetry 2-fold averaging using PHASES (Furey and Swaminathan, 1990). As shown in FIG. 1A, residues Val 66', Ser 67' and Phe 68' of the G$_M$[63–75] peptide were identified in the averaged map. These 3 residues, as well as the 2 metal and sulphate ions were built in each molecule, using the program TURBO-FRODO (Roussel and Cambillau, 1992). Refinement of this structure was performed by repeated rounds of manual rebuilding followed by conjugate gradient positional refinement and grouped B-factor refinement using X-PLOR. The final model contains protein residues Lys 6 to Ala 299 and peptide residues Arg 65' to Ala 69' in molecule 1, and protein residues Asn 8 to Lys 297 and peptide residues Gly 63' to Ala 69' in molecule 2. A few well defined water molecules were also observed in both initial (3Fo-2Fc) and (Fo-Fc) electron density maps. Eventually, 14 water molecules that were above 3 sigma in the (Fo-Fc) difference map, within hydrogen bond of the PP1-peptide complex or another solvent molecule and present in both molecules, were included in the model. The crystallographic and refinement data are summarized in Table 1. Representative electron density from the peptide before and after refinement is shown in FIGS. 10A and 10B, respectively. Solvent accessible surface areas were calculated using the method of Lee and Richards (1974).

Purification and Assay of PP1.

PP1c was isolated from the rabbit skeletal muscle PP1-G$_M$ complex as described previously (Johnson et al, 1996). Glycogen particles isolated from rat liver (Schelling el al, 1988) served as the source of PP1-G$_L$. The dephosphorylation of glycogen phosphorylase (10 μM) and the isolated MLC$_{20}$ of smooth muscle myosin (1 μM) by PP1c was carried out as described previously (Cohen et al., 1988; Alessi et al., 1992).

TABLE 1

Crystallographic data and refinement statistics

| Crystallographic data: | |
|---|---|
| Space group | P4$_1$2$_1$2 |
| Unit cell parameters (Å) | a = b = 62.50; c = 361.30 |
| Number of molecules per asymmetric unit | 2 |
| Temperature (K) | 100 |
| Total measured reflections | 290671 |
| Number of unique reflections | 15509 |
| Mean I/s(I) | 7.5 |
| Completeness (%) | 87 |
| Overall R-merge (%) | 14.7 |
| Refinement statistics: | |
| Number of reflections used for refinement | 13078 |
| Resolution range (Å) | 8.0–3.0 |
| R-work | 0.223 |
| R-free | 0.308 |
| Number of residues | protein    peptide |
| Molecule 1 | 294 (Lys 6 to 6 (ARVSFA) (SEQ ID No 21) Ala 299) 6 (RRVSFA) SEQ ID No 3) |
| Molecule 2 | 290 (Asn 8 to Lys 297) |
| R.m.s.d. from ideal bond lengths (Å) | 0.012 |
| R.m.s.d. from ideal angles (°) | 1.863 |
| Number of water molecules | |
| Molecule 1 | 7 |
| Molecule 2 | 7 |

TABLE 2

PP1-peptide polar interactions

| | Peptide atom | Protein atom | Water molecule | Distance (Å) |
|---|---|---|---|---|
| Molecule 1 | Arg 65' O | — | 7 W | 3.2 |
| | Val 66' N | Asp 242OD2 (**) | | 3.0 |
| | Ser 67' N | Leu 289 O | | 3.3 |
| | Ser 67' OG | | 7 W | 2.7 |
| | Ser 67' O | Cys 291 N (*) | | 3.2 |
| | Ala 69' N | Cys 291 O (*) | | 2.8 |
| Molecule 2 | Arg 64' NH1 | Glu 287 O (**) | | 2.6 |
| | Arg 65' O | | 7 W | 2.8 |
| | Val 66' N | Asp 242 OD2 (**) | | 3.2 |
| | Ser 67' N | Leu 289 O (*) | | 3.1 |
| | Ser 67' OG | | 7 W | 2.6 |
| | Ser 67' | Cys 291 N (*) | | 3.0 |
| | Ala 69' N | Cys 291 O (*) | | 3.3 |

PP1-peptide hydrophobic interactions

| Peptide residues | Protein residues |
|---|---|
| Val 66' | Ile 169 (*), Leu 243 (*), D242 (**), Leu 289 (*), Cys 291 (*) |
| Phe 68' | Phe 257 (*), Cys 291 (*), Phe 293 (*) |
| Ala 69' | Met290 (**) |

The star (*) indicates residues absolutely conserved in all protein phosphatase 1 sequences available so far, the double start (**) the residues mostly conserved (from sequence alignment from Barton et al, 1994).

Results and Discussion

Structure Determination.

Crystallographic data to 3.0 Å were measured at the ESRF beam-line BL4 at Grenoble and at PX9.6, Daresbury (Table 1). The relatively high merging R-factors and low I/(I values of the crystallographic data results from the weak diffraction observed from the PP1-$G_M$[63–73] crystals. This is attributable to both the small crystal size (~25 μm by 25 μm by 5 μm) and long c-axis of the unit cell. In addition, the high x-ray photon dose required to obtain usable diffraction images resulted in x-ray radiation damage to the crystals, despite being maintained at a temperature of 100 K during the course of the experiment. The structure was solve by the molecular replacement method using as a search model the 2.5 Å refined coordinates of PP1c (Egloff et al., 1995). Phases obtained from a single cycle of simulated annealing refinement of the protein coordinates alone using X-PLOR Brunger, 1992), and improved by 2-fold non-crystallographic symmetry averaging and solvent flattening, were used to calculate an electron density map. This map revealed clear density corresponding to residues Val 66', Ser 67' and Phe 68' (where ' denotes residues of the peptide) of the $G_M$ peptide and provided a starting point for further refinement of the PP1-$G_M$ peptide complex (FIG. 10A). The final model of the complex was refined at 3.0 Å resolution with a crystallographic R-factor of 0.22 and R-free of 0.31 (FIG. 10B). The two molecules of PP1c within the asymmetric unit are similar with a root mean square deviation between main chain atoms of 0.6 Å. Residues 6 to 299 and 8 to 297 from molecules 1 and 2 respectively, are visible in the electron density map. Similar to the structures of native $PP_{γ1}$ (Egloff et al., 1995) and PP1α in complex with microcystin LR (Goldberg et al., 1995), residues C-terminal to 299 are disordered.

Overall Structure of PP1

The conformation of PP1c in the PP1-$G_M$ complex is virtually identical to that of native PP1c in complex with tungstate (Egloff et al., 1995) with a root mean square deviation between equivalent main-chain atoms of 1.0 Å. PP1c is folded into a single elliptical domain consisting of a central β-sandwich of two mixed β-sheets surrounded on one side by 7α-helices and on the other by a sub-domain consisting of 3α-helices and a 3 stranded mixed α-sheet (FIG. 2A, B). The interface of the three β-sheets at the top of the β-sandwich creates a shallow catalytic site channel. Three loops connecting β-strands with α-helices within a β-α-β-α-β motif in sheet 1 (strand order β4-β3-β2-β13-β14) together with loops emanating from the opposite β-sheet (sheet 2; strand order, β1-β5-β6-β10-β12-β11) provide the catalytic site residues. The catalytic site of PP1 contains a binuclear metal site consisting of $Mn^{2+}$ and $Fe^{2+}$ (Egloff et al., 1995) and, in the PP1-$G_M$ complex, oxygen atoms of a sulphate ion of crystallisation coordinate both metal ions, similar to that seen in the PP1-tungstate (Egloff et al., 1995) and PP2B-phosphate complexes (Griffith et al, 1995).

PP1c-$G_M$[63–75] Peptide Interactions

Figure 11A:
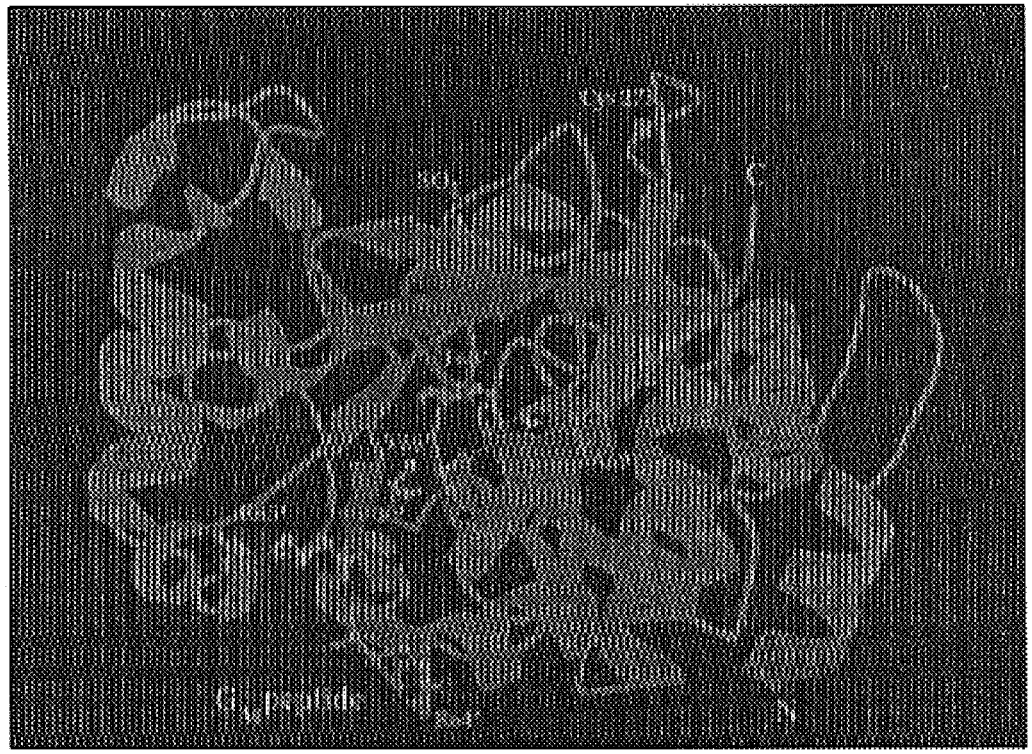
Figure 11B:
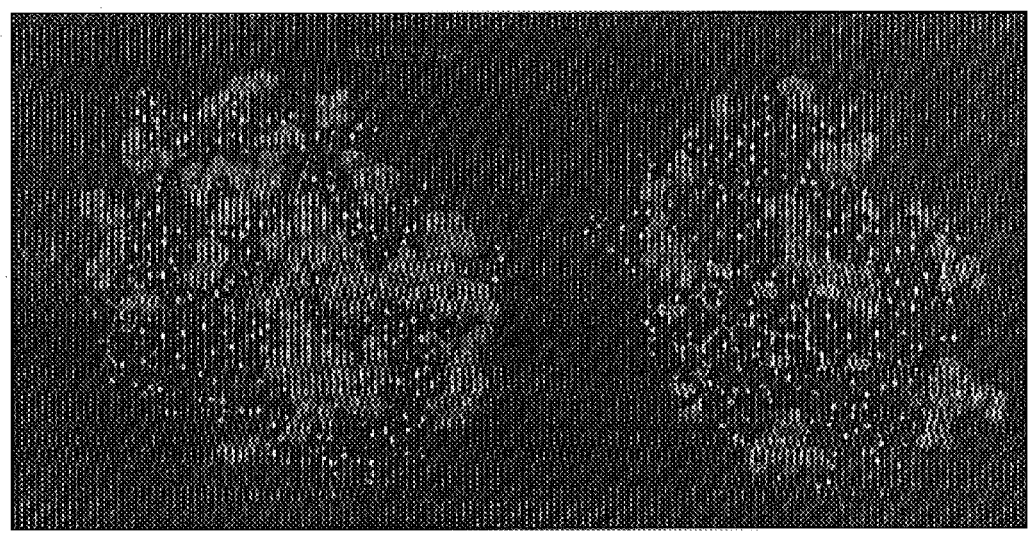
Figure 11C:
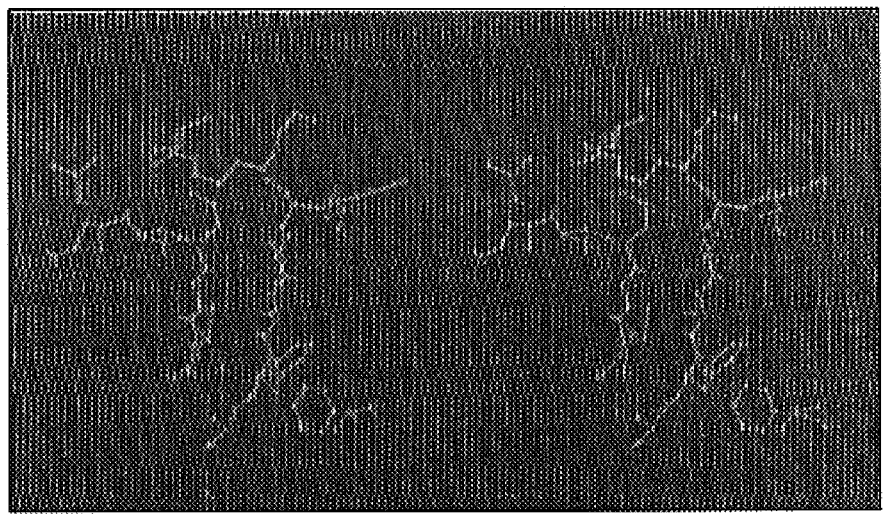
Figure 11E:
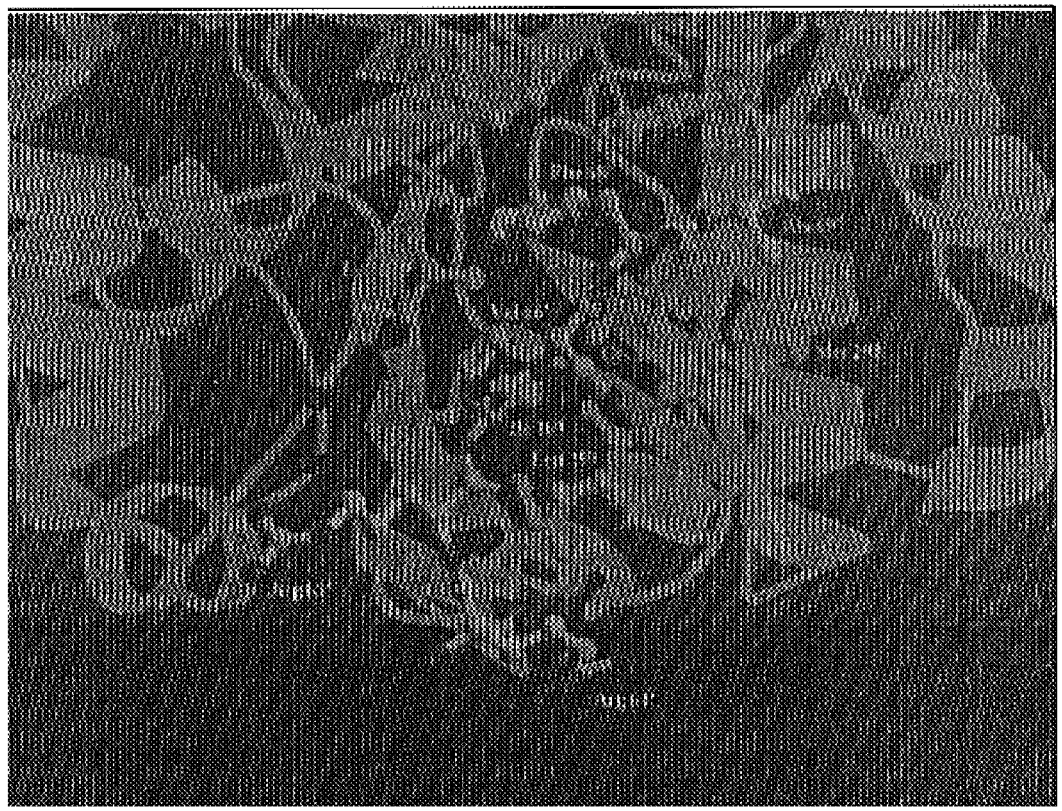

Six residues of the $G_M$[63–75] peptide (Arg 64' to Ala 69') are clearly visible in the electron density map of the complex of molecule 2, the remaining residues are not visible and assumed to be disordered (FIG. 10B). Density is not visible for Arg 64' of the peptide bound to molecule 1, otherwise equivalent residues of the peptide are similar within the two complexes. The six residues (RRVSFA) (SEQ ID No 3) of the $G_M$[63–75] peptide in complex 2 adopt an extended conformation and bind to a hydrophobic channel on the protein surface with dimensions 25 Å by 10 Å that is formed at the interface of the two β-sheets of the β-sandwich opposite to the catalytic site channel and therefore remote from the catalytic site (FIG. 11A). The residues that form this channel occur on three regions of PP1c, namely (i) the N-terminus of 5 and β5/β6 loop of sheet 2; (ii) the three edge β-strands of sheet 2: β10, β12, β11 and (iii) β13, the β13/β14 loop and β14 of the edge of sheet 1 (FIG. 11A). The total solvent accessible surface area buried on formation of the complex is 980 Å2. Three residues of the peptide (Ser 67' to Ala 69') form a β-strand which is incorporated into β-sheet 1 of PP1c as a sixth β-strand parallel to the N-terminus of the edge β-strand, β14 (residues Leu 289 to Leu 296) (FIG. 11C). Main-chain atoms of Ser 67' and Ala 69' form H-bonds to the main-chain atoms of residues of β14. In addition, the main-chain nitrogen of Val 66' forms a H-bond with the side-chain of Asp 242. Other polar interactions include the guanidinium group of Arg 64' with the mainchain carbonyl of Glu 287 and a salt bridge to Asp 166. Both Asp 166 and Asp 242 are invariant in mammalian PP1 genes. A water molecule bridges the main-chain carbonyl of Arg 65' and side-chain hydroxyl of Ser 67' with the main-chain carbonyl of Thr 288 of PP1c (FIG. 11C). A notable feature of the peptide binding site is the presence of a negatively charged region created by seven acidic residues (with one Lys residue) surrounding the hydrophobic channel at the N-terminus of the peptide in the vicinity of Arg 64' and Arg 65' that includes Asp 166 and Asp 242. This would suggest a favourable electrostatic environment for the side chains of Arg 64' and Arg 65'.

The predominant interactions between the peptide and PP1c involve hydrophobic contacts between the side chains of Val 66' and Phe 68' and solvent exposed, invariant, hydrophobic residues of PP1c that form the hydrophobic channel (FIG. 11C, E). In particular, the binding site for the side chain of Val 66' is formed from the side chains of Ile 169, Leu 243, Leu 289 and Cys 291, whereas that for the side chain of Phe 68' is formed from the side chains of Phe 257, Cys 291 and Phe 293. Details of peptide-PP1c contacts are given in Table 2. The structure of the $G_M$[63–75] peptide binding site is likely to be conserved in other forms of PP1 from diverse species. Each hydrophobic residue of PP1c that interacts with the Val 66' and Phe 68' residues of the $G_M$[63–75] peptide are invariant and the acidic residues that surround the N-terminus of the peptide binding site are highly conserved amongst all isoforms of PP1 from species as diverse as yeast, Drosophila, mammals and higher plants (Barton et al., 1994). However, since these residues are not conserved within the PP2A and PP2B sequences, these proteins will not recognise PP1-regulatory subunits.

Presence of an (R/K) (V/I)×F Motif in Other PP1c Regulatory Proteins

Figure 13A:
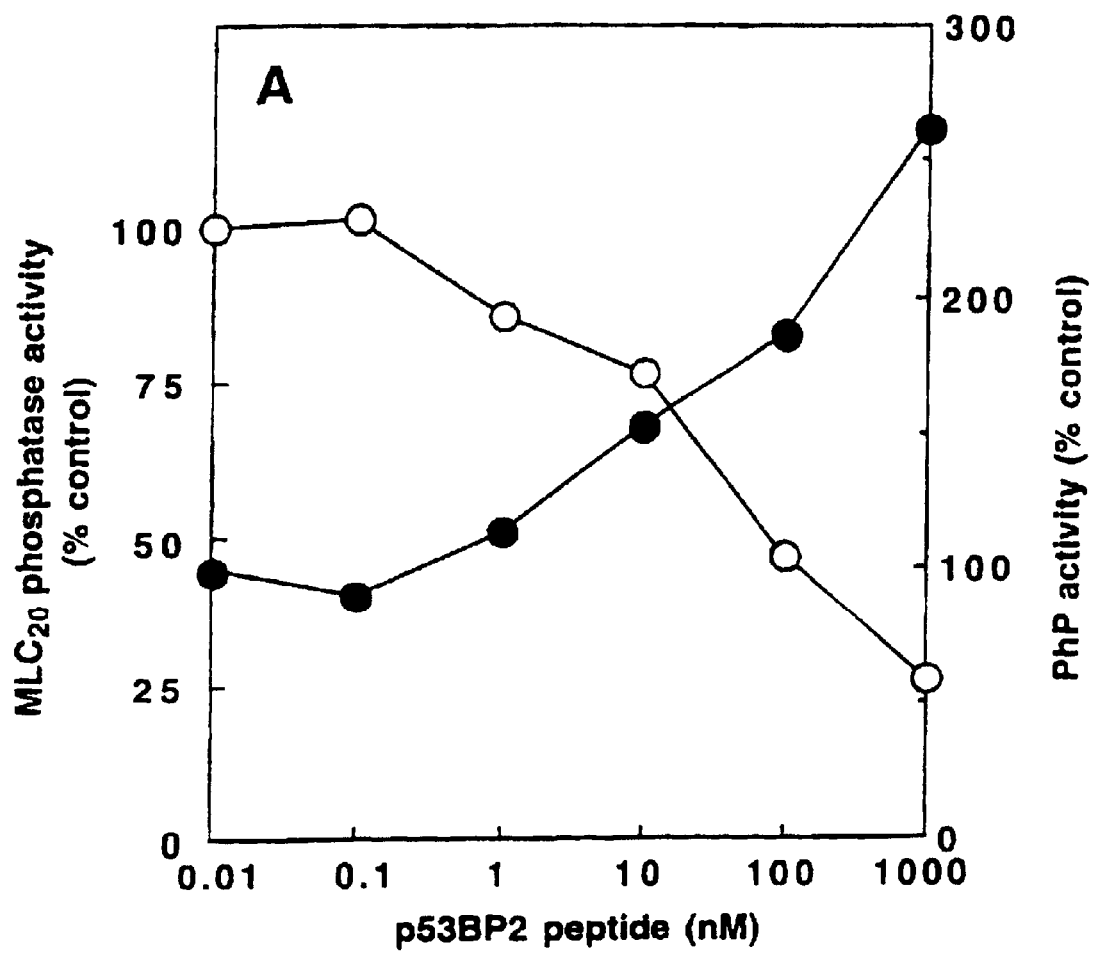
Figure 13B:
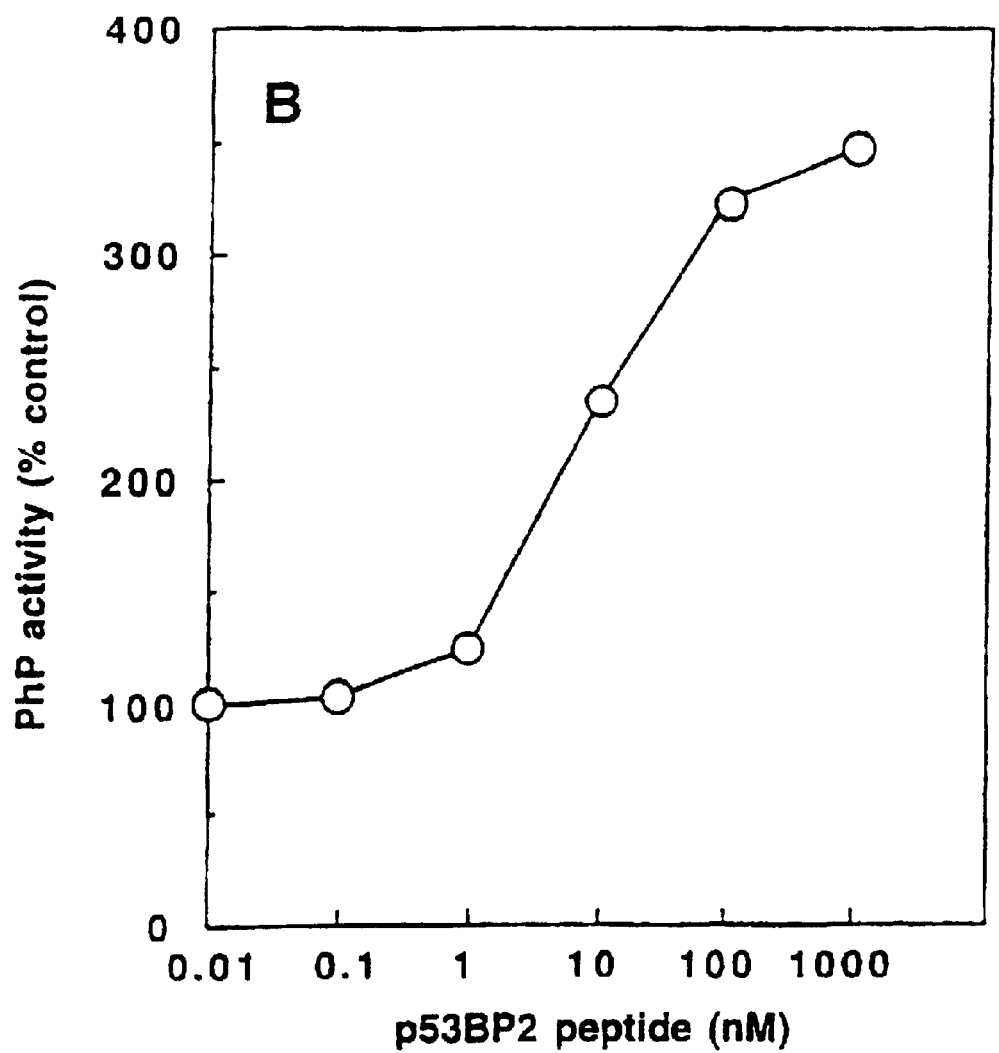

Over a dozen regulatory subunits of PP1c are now known which appear to bind to PP1c in a mutually exclusive manner that suggests either an overlapping binding site or sites. Sequence comparisons of these subunits reveals little similarity except for the motif (R/K) (V/I)×F, that is not only present in $G_M$[63×75] but also in $G_M$, $G_L$, $M_{110}$, NIPP-1, p53BP2, and an RNA splicing factor (FIG. 12A). Moreover, a 38 residue peptide from the 110kDa $M_{110}$ subunit that binds to PP1c contain this motif (Johnson et al, 1996), as do fragments of NIPP-1 (Beullens et al., 1992; Van Eynde et al, 1995), an RNA splicing factor (Hirano et al., 1996) and p53BP2 (Helps et al., 1995). A 32 residue peptide from p53BP2, which contains this motif, disrupted the interaction of the $M_{110}$ subunit with PP1c, as shown by a decrease in the rate of dephosphorylation of the $MLC_{20}$ subunit of smooth muscle myosin and by an increase in the rate of dephosphorylation of glycogen phosphorylase (FIG. 13A). This peptide also disrupted the interaction of the $G_L$ subunit with PP1c, as shown by an increase in the rate of dephosphorylation of glycogen phosphorylase (FIG. 13B). Peptides comprising the motif (R/K) (V/I)×F are thus encompassed within the scope of the invention.

In further support of the notion of a common PP1c recognition motif present within PP1-binding proteins, previous studies had revealed that the sequence KIQF (SEQ ID No 22) (similar to the R/KVxF motif) at the N-terminus of inhibitor 1 and its homologue DARPP-32 (FIG. 12A) is necessary for mediating the inhibitory effects of these proteins. Loss of Ile 10 of the KIQF (SEQ ID No 22) motif of inhibitor 1 disrupts the inhibitory effects on PP1c by phospho-inhibitor-1 (Aitken and Cohen, 1984; Endo et al., 1996) and the binding of either dephospho-inhibitor-1 or phospho-inhibitor-1 to PP1c (Endo et al., 1996). A similar result was found on disrupting the equivalent residue (Ile 9) of DARPP-32 (Hemmings et al., 1990; Desdouits et al., 1995). These results were interpreted to indicate that inhibitor-1 and DARPP-32 bind to PP1 through two low affinity binding sites, one that encompasses the sequence KIQF (SEQ ID No 22) and another which includes the phosphorylated Thr residue (35 in I-1, 34 in DARPP-32) and which presumably binds at the catalytic site. Analysis of the PP1-$G_M$[63–75] complex structure suggests that an isoleucine residue could be readily accommodated within the peptide binding site in place of Val 66' such that the additional methyl group on Ile compared to Val would contribute to favourable van der Waals interactions between the peptide and Leu 243 and Cys 291 of PP1. More bulky hydrophobic residues such as Leu, Met and Phe cannot be accommodated, however. It is interesting to note that as well as the (R/K) (V/I) x F motif shared by PP1-regulatory subunits, the four residues N-terminal to this motif contain an abundance of basic residues. These residues may provide further favourable interactions with the negative electrostatic surface potential at the N-terminus of the $G_M$(63–75) peptide binding site of PP1c.

Mutagenesis of the R/K) (V/I) x F motif

The structural studies presented here suggest a dominant role for Val 66' and Phe 68' in stabilising the interaction between $G_M$[63–75] and PP1c and this notion is further reinforced by the finding that other PP1-regulatory subunit sequences contain an (R/K)(V/I) x F motif yet share little overall sequence similarity. To test the hypothesis that Val 66' and Phe 68' are required for the interaction of $G_M$[63–75] with PP1c and also that the KVKF (SEQ ID No 5) sequence present within the $M_{110}$[M1-F38] peptide is important in mediating its interaction with PP1c, we synthesised variations of the $G_M$ and $M_{110}$ peptides where the R/KVxF motif was disrupted. The two variants of the $G_M$ peptide were Val 66' and Phe 68' to Ala substitutions. In order to disrupt the (R/K)(V/I) x F present within the $M_{110}$ peptide, a peptide corresponding to residues Met 1 to Lys 35 was synthesised which no longer contains the sequence VKF of the VxF motif, which is present at residues 36–38.

The results for the $M_{110}$[1–38] and $M_{110}$[1–35] peptides (FIGS. 14, 15) are unequivocal. Whereas $M_{110}$[1–38] stimulates the myosin light chain phosphatase activity of PP1c with a half-maximal effect at 10 nM reaching maximal (3-fold) activation at a peptide concentration of 1 μM as reported previously (Johnson et al, 1996), the $M_{110}$[1–35] peptide was at least 104-fold less effective at activating PP1c (FIG. 14). Unlike $M_{110}$[1–38], the $M_{110}$[1–35] peptide was also unable to activate the phosphorylase phosphatase activity of liver PP1-$G_L$. This latter result suggests two conclusions. Firstly, that although $M_{110}$[1–38] is able to bind to PP1c and disrupt the interactions between PP1c and the $G_L$-subunit, hence reversing the inhibitory effects of $G_L$ on the ability of PP1c to dephosphorylate phosphorylase, loss of the VKF sequence in the $M_{110}$[1–38] peptide abolishes the ability of the peptide to disrupt this interaction. Secondly, the recognition site on PP1c for the VKF sequence of the $M_{110}$[1–38] peptide must overlap with the binding site for the $G_L$ subunit, suggesting that the VKF sequence binds to the same site as the VSF sequence of $G_L$ that is identical with that present in the $G_M$[63–75] peptide. Similar conclusions may be reached from the results obtained from disrupting the VxF motif within the $G_M$[63–75] peptide (FIG. 16B). Substitution of Phe 68' for Ala abolishes completely the ability of $G_M$[63–75] to disrupt the PP1-$G_L$ complex, whereas replacement of Val 66' with Ala reduced the effectiveness of the disruption 100-fold.

Thus preferred peptides may comprise analogues of $G_M$ with substitutions at Val 66' and Phe 68' to some other amino acid such as Ala, so that binding of the PP1c to $G_M$ does not occur and the PP1c is not suitably directed or controlled. Alternatively, suitable peptides could comprise peptides suitable to compete for the binding site(s) of Val 66' and Phe 68' on PP1c. Such peptides can be added in sufficient quantities to compete for the Phe 68' and Val 66' binding site(s) on the PP1c, thereby disrupting the interaction of PP1c and natural $G_M$. Such peptides could comprise structural analogues of $G_M$ with Phe 68' and Val 66' in the same positions as $G_M$. Alternatively, other amino acids capable of mimicking the binding of Phe 68' and Val 66' could be used in these locations.

Regulation of the PP1-$G_M$ Complex by Phosphorylation of Ser 67'

Phosphorylation of Ser 67', corresponding to x of the VxF motif, by PKA promotes dissociiation of both $G_M$ and $G_M$[63–75] from PP1c. In vivo, this provides a mechanism of inhibiting PP1c during stimulation of skeletal muscle by adrenalin (Dent et al., 1990). The sequence of $G_M$ surrounding Ser 67' (RRVSFA) (SEQ ID No 3) conforms to a consensus PKA recognition sequence. Interestingly, the conformation of the peptide is similar to that of residues 18 to 23 corresponding to the pseudo-substrate sequence of PKI bound to the catalytic site of PKA (Knighton et al., 1990). Although the side chain of Ser 67' is exposed within the PP1c-peptide complex, overall the $G_M$ peptide is buried, and it is unlikely that Ser 67' would be a substrate for PKA when the peptide is bound to PP1c. This would suggest that PKA phosphorylates Ser 67' when $G_M$ is not associated with PP1c and that this phosphorylation prevents the re-association of PP1c with $G_M$. Since phosphorylation of Ser 67' promotes the dissociation of the PP1-$G_M$ complex both in vivo and in vitro, it is most likely that PKA phosphorylates Ser 67' of $G_M$ by competing with PP1c for the RRVSFA (SEQ ID No 3) sequence. This is consistent with a notion that the PP1-$G_M$ complex exists in dynamic equilibrium with free PP1c and $G_M$ subunits and that phosphorylation occurs on the regulatory subunit during transient dissociation from PP1c. In the PP1c-peptide complex, the side-chain of Ser 67' adopts the most favourable rotamer conformation. Analysis of the PP1c peptide complex structure suggests that incorporation of a phosphate group onto the side chain of Ser 67' with the same side-chain rotomer conformation would cause steric hindrance between the peptide and Met 290 of PP1 and also introduce a phosphate group into a region of negative charge at the PP1c surface (FIG. 11C). This may explain how phosphorylation of Set 67' prevents peptide association with PP1c, although it should be noted that rotation of the side-chain of Ser 67' would relieve this steric clash.

A similar mechanism of control may also operate for other PP1-regulatory subunits. For example, NIPP-1 a nuclear inhibitor of PP1, inhibits PP1 with an inhibitory constant of 1 pM (Beullens et al., 1992). Phosphorylation of NIPP-1 by PKA and/or casein kinase 2 in vitro abolishes this inhibition (Beullens et al., 1993; Van Eynde et al., 1994). Although the sites of phosphorylation on NIPP-1 that mediate these effects are not yet fully characterised it is known that these sites occur within the central ~120 residues of NIPP-1 that incorporates the (R/K)(V/I) x F motif (Van Eynde et al., 1995). Interestingly, a consensus phosphorylation site for PKA (RKNS) (SEQ ID No 23) occurs immediately N-terminal to this motif whereas one casein kinase 2 consensus phosphorylation site occurs between the Val and Phe of the motif and another occurs immediately C-terminal to the Phe residue (TFSEDDE) (SEQ ID No 24) (Van Eynde et al., 1995) (FIG. 12A). It is possible that PKA, casein kinase II or other kinases with similar specificity, release PP1c from inhibition by NIPP-1 by phosphorylating NIPP-1 at sites that block its interaction with the (R/K)(V/I) x F motif recognition site on PP1c.

Model of the PP1c-Phospho-Inhibitor 1 Complex

Our model for the interaction of a (R/K)(VII) x F motif with PP1c, together with previous kinetic data suggesting that the sequence KIQF (SEQ ID No 22) of inhibitor-1 (Aitken and Cohen, 1984; Endo et al., 1996) and DARPP-32 (Hemmings et al., 1990; Desdouits et al, 1995) interacts with PP1c, allowed us to construct a plausible model of a complex of PP1c with phospho-inhibitor 1. The major assumptions of this model were (1) the KIQF (SEQ ID No 22) sequence of inhibitor-1 binds to the same site as RVSF (SEQ ID No 25) of the $G_M$[63–75] sequence and (2) that the phosphothreonine residue 35 of phospho-inhibitor 1 binds at the phosphate binding site of the PP1c-catalytic site. Secondary structure predictions of inhibitor 1 (Rost and Sander, 1993; Rost, 1996) suggested that residues 9 to 14 and 23 to 31 adopt β-strand and α-helical conformations, respectively. The prediction of the sequence KIQF (SEQ ID No 22) as a β-strand is consistent with our assumption that this region of inhibitor-1 adopts the same conformation as RVSF (SEQ ID No 25) of the $G_M$ peptide when bound to the VxF recognition site of PP1c. We have positioned the residues RRPpTP (SEQ ID No 26) encompassing the pThr 35 site within the catalytic site channel in an extended conformation, with the phosphate group of the pThr 35 occupying the phosphate binding site of the catalytic site and the Oγ-atom of Thr 35 equivalent to the solvent exposed oxygen of a dianion that forms a H-bond to the side-chain of the putative general acid His 125 (Egloff et al., 1995; Griffith et al., 1995). The four consecutive Arg residues N-terminal to pThr 35 interact with Asp and Glu residues within an acidic groove of PP1c formed from the β7/β8 loop on one side and the β10/β11 loop and β11 strand on the other, similar to that proposed by Goldberg et al., (1995) for their model of DARPP-32 bound to PP1c. We propose that residues 20 to 30 of inhibitor-1 form an amphipathic helix which folds around the edge of the β-sandwich of PP1c. The N-terminus of this helix is disrupted by prolines at residues 19 and 23. Pro 19 and Pro 15 are probably responsible for introducing turns into the polypeptide chain that allows the β-strand encompassing the KIQF (SEQ ID No 22) sequence (residues 9 to 14) to connect with the α helix. The model of the phospho-inhibitor 1-PP1c complex is shown in FIG. 16.

Prediction of PP1 Recognition Motifs in Yeast PP1-Binding Proteins

The residues in mammalian PP1c that interact with the sequence RRVSFA (SEQ ID No 3) are conserved in S. cerevisiae PP1 suggesting that the proteins in S. cerevisiae known to interact with PP1 (reviewed by Stark, 1996) probably bind to a similar hydrophobic groove on the surface of the enzyme. Examination of their amino acid sequences revealed that a number of PP1-binding proteins in S. cerevisiae contained putative PP1-binding motifs that were similar to those present in mammalian PP1-binding proteins (FIG. 12A, B). The S. cerevisiae PP1-binding proteins not only contain a V/I x F motif, but also a basic residue equivalent to Arg 64' of $G_M$V the residue that contacts Asp 166, Leu 289 and the main-chain carbonyl of Glu 287 of PP1c. Several of the S. cerevisiae proteins also contain a further basic residue (His or Lys) at the position equivalent to Arg 65' of $G_M$. Another striking feature of the putative PP1-binding sequences in S. cerevisiae is the presence of a basic amino acid between the Val/Ile and Phe residues, as is also found in two mammalian PP1-regulatory subunits, the $M_{110}$ subunit and the p53BP2 (FIG. 12A).

The S. cerevisiae proteins GAC1 and PIG2 show some homology to residues 140–230 of mammalian $G_M$V and there is genetic and biochemical evidence that they may function to regulate glycogen metabolism in budding yeast (Francois et al., 1992). GIP2 also shares sequence similarity with residues 140–230 of mammalian $G_M$, while YIL045W is an open reading frame in the S. cerevisiae genome whose predicted amino acid sequence shows 41% sequence identity to GIP2. YIL045W contains two putative PP1-binding motifs and site directed mutagenesis will be needed to establish which (if either) of these sequences binds to PP1c. REG1 and REG2 are PP1-binding proteins that play a role in cell growth and, in the case of REG1, glucose repression (Tu and Carlson, 1995; Tu et al., 1996; Frederick and Tatchell, 1996). GIP1, which also contains two putative PP1-binding motifs, is expressed specifically during meiosis, affects the transcription of late meiotic genes and is essential for sporulation (Tu and Carlson, 1996). SCD5 is a PP1-interacting protein (Tu et al., 1996) that was first isolated as a multicopy suppressor of the inviability of clathrin heavy chain-deficient yeast (Nelson et al., 1996).

The findings herein demonstrate that the short peptide sequence, the (R/K)(V/I)XF motif, is critical for PP1c to interact with its regulatory subunits. PP1c (when complexed to its targeting subunits) plays key roles in the control of many cellular processed and it is reasonable to predict that over 100 pp1-binding proteins may exist in mammalian cells. Protein sequence data-base searching has revealed that the (R/K)(V/I)XF motifs are found in 10% of proteins. Thus if ~100 PP1-binding proteins occur in mammalian cells, only 1% of proteins with the (R/K)(V/I)XF motif will be PP1-binding proteins. The reasons why only a few proteins with the (R/K)(V/I)XF motif bind to PP1 are numerous. For example, not every residue may be tolerated at position X or immediately N-terminal or C-terminal to this motif. This study has shown that phosphoserine is not tolerated at position X and it is therefore likely that Asp or Glu will not be tolerated either. The structure of the PP1-$G_M$[63–75] complex suggests that large hydrophobic residues will also be excluded from position X. Moreover, the Val (or Ile) and Phe residues in many (R/K)(V/I)XF motifs will be buried in the hydrophobic core of the protein and hence be unable to interact with PP1, since this motif is predicted to form an amphipathic β-strand conformation. Thirdly, many of the (R/K)(V/I)XF motifs will be in extracellular proteins or extracelluar domains of transmembranc proteins and hence be unable to bind to PP1. Particular feature so the tertiary structure of PP1-binding proteins may allow exposure of this motif on the surface to allow interaction with PP1. Finally, there is evidence that a second PP1-binding site exists on the $G_M$ and $M_{110}$ subunits (Johnson et al., 1996) and the high affinity interaction of PP1c with protein inhibitor-1 is generated by the binding of PP1c to two low affinity sites (Desdouits et al., 1995), one of which is the KIQF sequence belonging to the (R/K)(V/I)XF motif.

The question of how regulatory subunits modulate the substrate specificity of PP1c requires the co-crystallisation of PP1c with a diverse array of regulatory subunits and substrates and is beyond the scope of this paper. However, two models to account for this property of regulatory subunits are that these subunits either alter the conformation of PP1c or simply target PP1 to its substrates. Both mechanisms may operate in vivo depending on the regulatory subunits and substrates. For example, evidence for the former model has recently been reported for the enhancement of myosin dephosphorylation by a complex of PP1c and the $M_{110}$ subunit (Johnson et al., 1996, 1997), whereas the enhancement of the dephosphorylation of glycogen phosphorylase and glycogen synthase by the PP1-$G_M$ complex is more consistent with the second model (Hubbard and Cohen, 1989).

The identification of the (R/K)(V/I)XF motif also suggests a new approach for determining the physiological roles of PP1-targeting subunits whose functions arc unknown. Thus mutation of the (R/K)(I/V)XF motif should disrupt the interaction of many targeting subunits with PP1c without affecting their binding to the target locus. Expression of these mutated proteins under an inducible promoter should lead to displacement of the normal targeting subunit (complexed to PP1c) from its target locus, without disrupting the functions of any other PP1c-targeting subunit complex. Finally, the structural information described here will also facilitate the rational design of drugs that act by disrupting PP1-targeting subunit interactions.

EXAMPLE 3

Identification of the Regions on the $M_{110}$ Subunit of Protein Phosphatase 1M that Interact with the $M_{110}$ Subunit and with Myosin Abbreviations—PP1$_M$, myofibril-associated form of protein phosphatase 1; PP1c, catalytic subunit of protein phosphatase-1; $M_{110}$ and $M_{21}$, 110 kDa and 21 kDa regulatory subunits of PP1$_M$; MBP, maltose-binding protein; GST, glutathione-S-transferase.

SUMMARY

We have previously isolated a form of protein phosphatase-1 (PP1$_M$) from avian smooth muscle myofibrils which is composed of the catalytic subunit of PP1 (PP1c) bound to an M-complex consisting of 110 kDa ($M_{110}$) and 21 kDa ($M_{21}$) subunits. The interaction of PP1c with an N-terminal region of the $M_{110}$ subunit enhances the dephosphorylation of myosin and suppresses the dephosphorylation of other substrates [Alessi, D. R., MacDougall, L. K., Sola, M. M., Ikebe, M. and Cohen, P. (1992) *Eur. J. Biochem* 210, 1023–1035; Chen, Y. H., Chen, M. X., Alessi, D. R., Campbell, D. G., Shanahan, C., Cohen, P. and Cohen, P. T. W. (1994) *FEBS Lett* 356, 51–56; Johnson, D. F., Moorhead, G., Caudwell, F. B., Cohen, P., Chen, Y. H., Chen, M. X. and Cohen, P. T. W. (1996) *Eur. J. Biochem.* 239, 317–325]. In this Example we establish that PP1$_M$ accounts for nearly all the myosin phosphatase activity in myofibrils, that the $M_{110}$ and $M_{21}$ subunits are present at similar concentrations in the myofibrillar fraction and that these subunits are entirely bound to PP1. We demonstrate that the $M_{21}$ subunit does not interact with PP1c, but with the C-terminal 72 residues of the $M_{110}$ subunit, a region which is 43% identical to residues 87–161 of the $M_{21}$ subunit. A fragment of the $M_{21}$ subunit, $M_{21}$-(M1-L146), lacking the C-terminal leucine zipper, also bound to the $M_{110}$ subunit, but two other fragments $M_{21}$-(M1-E110) and $M_{21}$-(E110-K186) did not. The $M_{110}$ and $M_{21}$ subunits were both found to be myosin-binding proteins. The C-terminal 291 residues of the $M_{110}$ subunit, but not the C-terminal 72 residues, bound to myosin, but the N-terminal fragments $M_{110}$-(M1-E309) and $M_{110}$-M1-S477) did not. Thus the region of the M,on subunit which stimulates the dephosphorylation of myosin by PP1c is distinct from the region which targets PP1$_M$ to myosin. Remarkably, each myosin dimer was capable of binding about 20 moles of $M_{21}$ subunit and many of the $M_{21}$-binding sites were located in the myosin "rod domain". The potential significance of this observation is discussed.

Introduction

Protein phosphatase-1 (PP1), one of the major serine/threonine-specific protein phosphatases in eukaryotic cells, is regulated by targetting subunits that direct it to particular subcellular loci, modify its substrate specificity and confer the ability to be regulated by extracellular signals (reviewed in [1, 2]). A significant proportion of the PP1 in vertebrate muscle extracts is associated with myofibrils and has enhanced activity towards the P-light chain of myosin and reduced activity towards other substrates, such as glycogen phosphorylase [3, 4]. When isolated from avian (chicken gizzard) [4, 5] or mammalian (pig bladder) [6] smooth muscle, this form of PP1 (PP1$_M$) was found to be composed of three subunits, namely the catalytic subunit of PP1 (PP1c) and two other proteins with molecular masses of 110 kDa and 21 kDa, termed the $M_{110}$ and $M_{21}$ subunits, respectively [4, 5]. The $M_{110}$ subunit is complexed to both PP1c and the $M_{21}$ subunit [4], and is the component which modulates the substrate specificity of PP1c because selective removal of the $M_{21}$ subunit from $PP1_M$ does not affect the rate at which either myosin or glycogen phosphorylase are dephosphorylated [7].

The $M_{110}$ subunit has been cloned from rat aorta [5], chicken gizzard [8] and rat kidney [9] cDNA libraries. The N-terminus of the $M_{110}$ subunit contains seven ankyrin repeats (residues 39–296 of the rat aorta protein), while alternative splicing in rat uterus [5] gives rise to two different C-termini (FIG. 17A), termed Rat1 and Rad2 (SEQ ID Nos 30 and 31). The C-terminus of Rat1 is virtually identical to the C-terminus of the $M_{110}$ subunit from chicken gizzard (SEQ ID No 29) (FIG. 17A). The sequence of the $M_{21}$ subunit from chicken gizzard is structurally related to the C-terminal region of the $M_{110}$ subunit, the most striking similarities occurring from residues 76–141 of the $M_{21}$ subunit and residues 921–984 of the chicken gizzard $M_{110}$ subunit (54% identity, FIG. 17B). However, the C-terminal 53 residues of the $M_{21}$ subunit from chicken gizzard are strikingly similar (83% identity) to the C-terminal 53 residues of the rat aorta sequence, both terminating in a leucine zipper (FIG. 17B, [5]).

Residues 1–309 of the $M_{110}$ subunit from rat aorta, $M_{110}$-(M1-E309), mimic the intact $M_{110}$ subunit in stimulating the dephosphorylation of myosin and in suppressing the dephosphorylation of glycogen phosphorylase by PP1c, but a slightly shorter construct $M_{110}$-(D39-E309) (which still contains the seven ankyrin repeats) is unable to modulate the specificity of PP1c [7]. This observation led to the finding that the N-terminal 38 residues, $M_{110}$-(M1-F38), bind to PP1c and enhance the dephosphorylation of myosin. However, $M_{110}$-(M1-F38) does not suppress the dephosphorylation of glycogen phosphorylase, suggesting that the ankyrin repeats either contain a second PP1c-binding site or prevent glycogen phosphorylase from binding to the active site of PP1c, perhaps by steric hindrance [7].

A 13 residue peptide $G_M$-(G63-N75) from the subunit ($G_M$) which targets PP1c to glycogen and the sarcoplasmic reticulum in striated muscle, has been co-crystallised with PP1c and the structure of the complex solved to 3 Å resolution [2]. These studies showed that a hexapeptide sequence in $G_M$-(G63-N75) (Arg-Arg-Val-Ser-Phe-Ala) (SEQ ID No 3) binds to a small hydrophobic groove on the surface of PP1c forming a β-sheet which runs parallel to another β-sheet in PP1c. Moreover, inspection of other mammalian PP1c-binding proteins reveals that almost all contain an Arg/Lys-Val/Ile-Xaa-Phe motif that is likely to be critical for interaction with PP1c [2]. For example, a Lys-Val-Lys-Phe (SEQ ID No 5) motif is present between residues 35 and 38 of the $M_{110}$ subunit and the deletion of residues 36–38 from $M_{110}$-(M1-F38) prevents this peptide from stimulating the dephosphorylation of myosin, and from disrupting the interaction of PP1c with other targetting subunits [2].

The finding that a region near the N-terminus of the $M_{110}$ subunit binds to PP1c and modulates its specificity raised the question of which region on the $M_{110}$ subunit interacted with the $M_{21}$ subunit, and how the $PP1_M$ complex is targeted to the myofibrils. In this Example we identify regions near the C-terminus of the $M_{110}$ subunit that interact with the $M_{21}$ subunit and with myosin, and demonstrate that the $M_{21}$ subunit is also a myosin-binding protein. These findings indicate that the domain of the $M_{110}$ subunit which enhances the dephosphorylation of the myosin P-light chain is distinct from the region which targets PP1c to the contractile apparatus.

Materials and Methods

Materials $PP1_M$ [4] and the dephosphorylated form of myosin [10] were isolated from chicken gizzard (SEQ ID No 29), and the rod-domain and light meromyosin were obtained by subdigestion of chicken gizzard myosin with papain and chymotrypsin, respectively [11]. $PP1_G$ was purified from rabbit skeletal muscle by Dr G. Moorhead in this laboratory [12] and PP1c dissociated from the glycogen-binding subunit by incubation for 2 h in 2 M LiBr and then purified by gel-filtration on a 30×1 cm column of Superose 12 (Pharmacia, Milton Keynes, UK) in the presence of LiBr (0.5 M). All other chemicals were from BDH Chemicals (Poole, UK) or Sigma (Poole, UK).

Construction of Vectors for the Expression of Fragments of the $M_{110}$ Subunit from Rat Aorta (Rat2 Sequence in FIG. 17A) as Glutathione-S-transferase (GST) Fusion Proteins in E. coli.

A construct pGEX-$M_{110}$-(M1-E309) for the expression of GST-$M_{110}$-(M1-E309) from rat aorta was produced as described previously [7]. A construct for the expression of GST-$M_{110}$-(M1-S477) was prepared by subcloning a XhoI-HindIII fragment (encoding L24-S477) of pKS-$M_{110}$-(M1-S477) described in [5] into the same sites of pGEX-$M_{110}$-(M1-E309). The resulting construct expressed a GST-$M_{110}$-(M1-S477) fusion protein with the additional amino acids SAANSISSLIHRD*(SEQ ID No 27) after S477. An expression construct for GST-$M_{110}$-(M377-K976) was produced by deleting a NcoI-NcoI fragment of the construct pGEX-$M_{110}$-(L24-K976) [7].

Construction of Vectors for the Expression of C-terminal Fragments of the $M_{110}$ Subunit from Chicken Gizzard (Ch1 Sequence in FIG. 17A, [5]) as Maltose Binding Protein (MBP) Fusion Proteins in E. coli.

A pT7.7 vector for the expression of the C-terminal 291 residues of the $M_{110}$ subunit from chicken gizzard, pT7-$M_{110}$-(R714-I1004) was described previously [7]. A construct for the expression of MBP-$M_{110}$-(R714-I1004) was produced by cloning an NdeI-BamHI fragment of pT7-$M_{110}$-l(R714-I1004) into the pMAL-HA vector (New England Biolabs). Removal of a HindIII-HindIII restriction fragment from pMBP-$M_{110}$-(R714-I1004) allowed expression of MBP-$M_{110}$-(R714-L934) with the sequence GTGR-RFTTS (SEQ ID No 28) added to its C-terminus. Removal of a NdeI-HindIII restriction fragment from pMBP-$M_{110}$-(R714-I1004), followed by filling in the overhanging ends and religating them, allowed expression of MBP-$M_{110}$-(K933-I1004).

Construction of Vectors for the Expression in E. coli. of the $M_{21}$ Subunit from Chicken Gizzard [5], with and Without the C-terminal Leucine Zipper Domain.

A pT7.7 vector for the expression of the entire coding region (M1-K186) of the $M_{21}$ subunit was described previously [7]. The leucine zipper motif of the $M_{21}$ subunit was deleted by removing a SacI-BamHI restriction fragment from pT7.7 $M_{21}$, filling in the overhanging ends and religating them. The construct expressed $M_{21}$-(M1-R144) with an extra I and L after residue 144. The $M_{21}$-(M1-R144) protein was insoluble when expressed and was purified as described for the expressed $M_{21}$ subunit [7].

Construction of Vectors for the Expression of the $M_{21}$ Subunit from Chicken Gizzard [5] and Fragments of the $M_{21}$ Subunit as Glutathione-S-transferase (GST) Fusion Proteins in E. coli.

A construct expressing GST-$M_{21}$ was produced by inserting a NdeI-HindIII fragment of pT7.7 $M_{21}$ encoding M1-K186 into the same sites of the pGEX vector modified to include an NdeI site. A construct expressing GST-M$_{21}$-(M1-E110) plus an additional Ala residue at the C-terminus was constructed by deleting a XhoI-HindIII fragment of pGEX-M$_{21}$, filling in the overhanging ends and religating them. In order to express GST-M$_{21}$-(E110-K186), a NdeI-XhoI restriction fragment of pGEX-M$_{21}$ was deleted and the overhanging ends filled in and religated.

Expression of Proteins in E. coli.

This was carried out essentially as described in [7], except that, after freezing the cells at −80° C. and thawing, the lysates were not treated with DNAase but sonicated for 4 min on ice (ensuring that the temperature remained below 4° C.) until the suspension was no longer viscous. The soluble GST-fusion proteins and MBP-fusion proteins were purified from the supernatant by affinity chromatography on glutathione-Sepharose (Sigma) and amylose resin (New England Biolabs), respectively, according to the instructions of the manufacturers. After expression in E. coli M$_{110}$-(R714-I1004) was the major soluble protein and all experiments with this fragment were performed using the bacterial extracts.

The chicken gizzard M$_{21}$ subunit was isolated from E. coli extracts as described [7]. M$_{21}$ subunit lacking the leucine zipper domain, M$_{21}$-(M1-L146), like the M$_{21}$ subunit itself, was obtained in inclusion bodies and therefore recovered in the pellet obtained after centrifugation of the bacterial lysates for 30 min at 28000×g. The inclusion bodies were washed three times in 50 mM Tris/HCl pH 7.5, 0.1M NaCl, 10 mM EDTA, 0.1% (by vol) 2-mercaptoethanol, 1 mM benzamidine, 0.2 mM phenylmethylsulphonyl fluoride and 0.5% (by mass) Triton X-100, then resuspended in 50 mM Tris/HCl pH 7.5, 1 mM EDTA, 1 mM EGTA, 0.03% (by mass) Brij-35, 0.1% (by vol) 2-mercaptoethanol. An aliquot (containing 3 mg protein) was made 0.5% (by vol) in trifluoroacetic acid, sonicated, centrifuged for 2 min at 13,000×g and the supernatant (containing the solubilised M$_{21}$ subunit) loaded on to a Vydac C18 column (Separations Group, Hesperia, Calif., USA) equilibrated in 0.1% (by vol) trifluoroacetic acid. The column was developed with a linear acetonitrile gradient at a flow rate of 1.0 ml/min with an increase in acetonitrile concentration of 1% per min. Homogeneous M$_{21}$ subunit, which eluted at 42% acetonitrile, and M$_{21}$-(M1-L146) which eluted at 40% acetonitrile were dried in a vacuum concentrator redissolved in water, redried and then dissolved in 50 mM Tris/HCl pH 7.5, 0.1 mM EGTA, 0.03% (by mass) Brij-35, 0.1% (by vol) 2-mercaptoethanol.

Removal of GST and MBP Tags from Fusion Proteins.

GST-M$_{110}$-(1–477) was cleaved with thrombin and the proteinase removed using benzamidine agarose [7]. GST-M$_{21}$-(E110-K186) (1 mg/ml) was cleaved by incubation for 1 h at 30° C. with 10 µg/ml thrombin, while GST-M$_{21}$-(M1-E110) (1 mg/ml) was cleaved by incubation for 3 h at 30° C. with 1 µg/ml thrombin, because it was more susceptible to degradation by thrombin. MBP-M$_{110}$(K933-I1004) (1 mg/ml) was cleaved by incubation for 8 h at 23° C. with Factor Xa (10 µg/ml). Other conditions and removal of Factor Xa were carried out as described for thrombin [7].

Preparation of Phosphorylated Myosin P-light Chain and Phosphatase Assays.

$^{32}$P-labelled myosin P-light chains containing 1.0 mol phosphate per mol subunit was prepared by phosphorylation with smooth muscle myosin light chain kinase [4]. The dephosphorylation of myosin P-light chain (1 µM) was carried out as in [4] and one unit of activity (U) was that amount which catalysed the release of 1 µmole of phosphate in one min. When assaying PP1$_M$ in immunoprecipitates from the myofibrillar extracts, the tubes were shaken continuously and 3 nM okadaic acid was included to inhibit any PP2A present.

Immunoprecipitation of PP1$_M$ from Myofibrillar Extracts.

Antibodies raised against the PP1$_M$ holoenzyme (1 µg), which recognise both the M$_{110}$ and M$_{21}$ subunits, but not PP1c, affinity purified antibodies specific for either the M$_{110}$ subunit or M$_{21}$ subunit (5 µg) [7], and control IgG (5 µg) were conjugated separately to 10 µl of pelleted protein G-Sepharose. After incubation for 30 min at 4° C., the Protein G-Sepharose-antibody conjugate was washed three times with 50 mM Tris/HCl pH 7.5, 0.1 mM EGTA, 0.03% (by mass) Brij-35, 0.3M NaCl, 0.1% (by vol) 2-mercaptoethanol before addition of a 100 µl of myofibrillar extract (prepared as in [4]) which had been diluted 10-fold in 50 mM Tris/HCl pH 7.5, 0.1 mM EGTA, 0.1% (by vol) 2-mercaptoethanol, 0.2 mM phenylmethylsulphonyl fluoride, 1 mM benzamidine, 10 µg/ml leupeptin containing 1 mg/ml bovine serum albumin. After incubation for 1 h at 4° C., with shaking, a 10 µl aliquot of the suspension was removed to measure the total activity. The remaining 90 µl was centrifuged for 1 min at 13,000×g, the supernatant was removed, and the pellet washed twice in dilution buffer containing 0.2 M NaCl and 0.03% (by mass) Brij-35 (but no bovine serum albumin), once in dilution buffer and then resuspended in 90 µl of dilution buffer. Myosin P-light chain phosphatase activity was then measured in the supernatant and the resuspended pellet at a further 30-fold final dilution.

Myosin binding assays. Myosin (0.5 mg/ml, 1 µM in terms of myosin heavy chains) in 10 mM Hepes pH 7.5, 50 mM KCl, 5 mM MgCl2, 0.1% (by vol) 2-mercaptoethanol, was mixed with PP1$_M$, M$_{21}$ subunit, or fragments of the M$_{110}$ and M$_{21}$ subunits, at the concentrations indicated in figure legends. After incubation for 15 min at 0° C., the solutions were centrifuged for 2 min at 13,000×g, the supernatants removed, and the pellets washed twice in 10 mM Hepes pH 7.5, 50 mM KCl, 5 mM MgCl2, 0.1% (by vol) 2-mercaptoethanol before resuspension in 50 mM Tris-HCl pH 7.5, 0.1 mM EGTA, 0.03% (by mass) Brij 35, 0.6 M NaCl, 0.1% (by vol) 2-mercaptoethanol. Aliquots of the supernatant, the resuspended pellet and the suspension before centrifugation were either assayed for myosin P-light chain phosphatase activity or denatured in SDS and analysed by SDS/polyacrylamide gel electrophoresis.

Preparation of a Complex Between GST-M$_{21}$ and M$_{110}$-(R714-I1004).

GST-M$_{21}$ (10 µg) was mixed with 80 µl of bacterial extract expressing M$_{110}$-(R714-I1004). After incubation for 15 min at ambient temperature the solution was added to 20 µl (packed volume) of glutathione-Sepharose equilibrated in 50 mM Tris HCl pH 7.5, 0.1 mM EGTA, 0.03% (by mass) Brij 35, 0.1% (by vol) 2-mercaptoethanol, 0.2 mM phenylmethylsulphonyl fluoride, 1 mM benzamidine and 0.15 M NaCl. After incubation for 30 min at 4° C. with shaking, the Sepharose was washed three times in the same buffer before eluting the complex with buffer containing 20 mM glutathione pH 8.0.

Other Procedures.

Proteins were labelled with digoxigenin and Far Western analyses carried out as described [4], except that the digoxigenin-labelled probe was used at a concentration of 0.2 µg/ml instead of 2 µg/ml. SDS/polyacrylamide gel electrophoresis was carried out on 7.5–15% gels according to Laemmli [13] and on 16.5% gels according to Schagger and von Jagow [14]. Protein was estimated according to Bradford [15].

Results

PP1$_M$ Accounts for Nearly all the Myosin Phosphatase Activity in Extracts Prepared from Chicken Gizzard Moyfibrils.

Figure 18A:
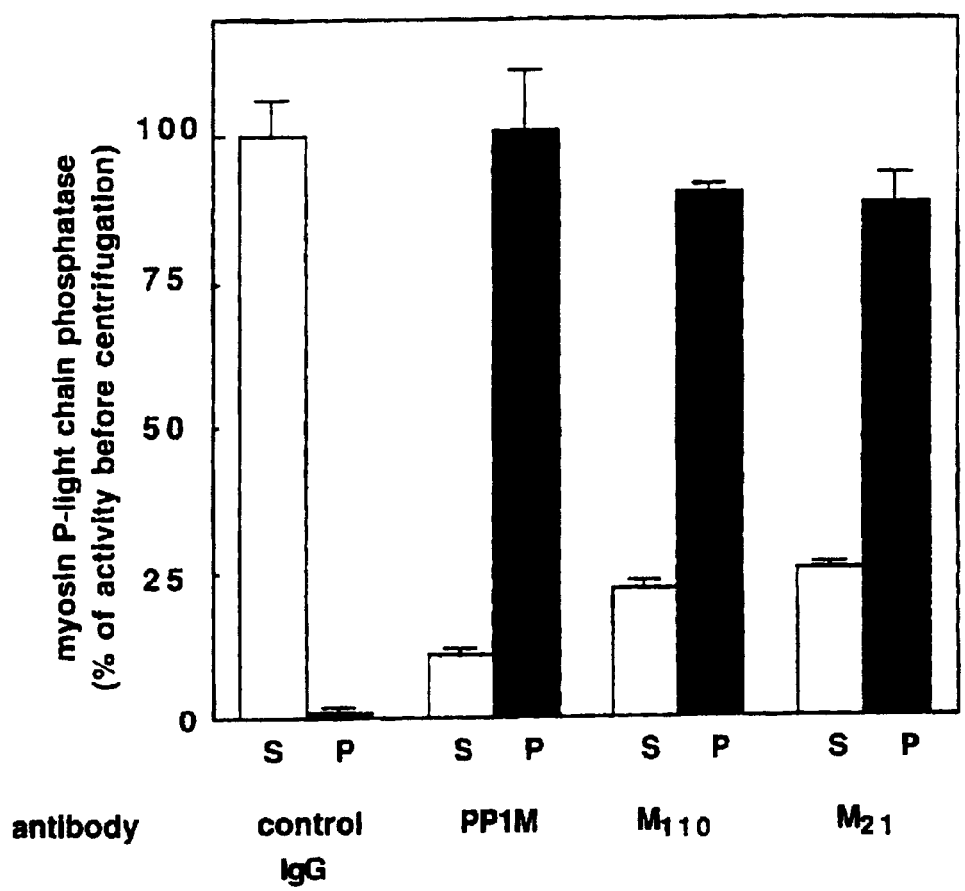

80–90% of the myosin phosphatase activity present in chicken gizzard homogenates is recovered in the myofibrils [4]. In the present study, we used antibodies that recognise the $M_{110}$ and/or the $M_{21}$ subunits of chicken gizzard $PP1_M$ [7] to immunoprecipitate the myosin P-light chain phosphatase activity from the myofibrillar extracts. About 90% of the activity was immunoprecipitated by antibodies raised against the $PP1_M$ holoenzyme (FIG. 18A) which recognise both the $M_{110}$ and $M_{21}$ subunits in immunoblotting experiments, but not PP1c. Similarly, about 80% of the myosin P-light chain phosphatase activity in the myofibrillar extracts was immunoprecipitated by either the anti-$M_{110}$ antibody or by the anti-$M_{21}$ antibody (FIG. 18A). Thus, most of the myosin P-light chain phosphatase activity in myofibrillar extracts is catalysed by PP1c present as a complex containing both the $M_{110}$ and the $M_{21}$ subunits.

Immunoblotting experiments demonstrated that the ratio $M_{110}:M_{21}$ in myofibrillar extracts was identical to the ratio of these subunits in purified $PP1_M$ (FIG. 18B), which is 1:1 [4]. These immunoblotting experiments also demonstrated that $PP1_M$ comprises 0.1% of the protein in the myofibrillar extract (see legend to FIG. 18B), identical to the proportion estimated from the fold-purification needed to obtain pure $PP1_M$ from this fraction (see Table 1 in Ref 4). These experiments imply that $PP1_M$ accounts for virtually all the myosin phosphatase activity associated with myofibrils, and that neither the $M_{110}$ nor the $M_{21}$ subunit is present in a significant molar excess over PP1c in the myofibrils.

Identification of a Region on the $M_{110}$ Subunit that Binds to the $M_{21}$ Subunit.

Figure 19B:
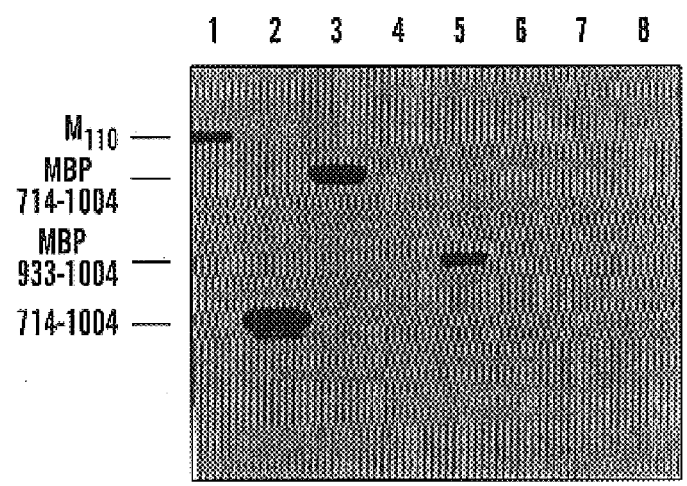
Figure 19C:
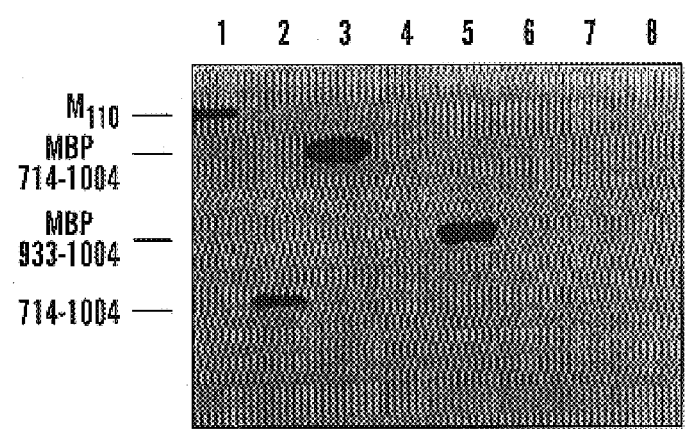

$PP1_M$ and several fragments of the $M_{110}$ subunit, were subjected to SDS/polyacrylamide gel electrophoresis (FIG. 19A) and, after transfer to nitrocellulose, the blots were probed with digoxigenin-labelled $M_{21}$ subunit (FIG. 19B). These experiments showed that the $M_{21}$ subunit recognised the full length $M_{110}$ subunit (FIG. 19B, track 1), $M_{110}$-(R714-I1004) (FIG. 19B, tracks 2 and 3) and $M_{110}$-(K933-I1004) (FIG. 19B, track 5), but not $M_{110}$-(R714-L934) (FIG. 19B, track 4), $M_{110}$-(M1-E309) (FIG. 19B, track 7) or $M_{110}$-(M1-S477) (FIG. 19B, track 8). Thus, the $M_{21}$ subunit binds to the C-terminal 72 residues of the $M_{110}$ subunit. The specificity of this interaction was indicated by the observation that digoxigenin-labelled $M_{21}$ subunit recognised only $M_{110}$-(R714-I1004) and no other protein in the E. coli extract (track 2 in FIGS. 19A and 19B), nor did it recognise the MBP or GST tags, PP1c (FIGS. 19A and 19B) or any of the molecular mass markers (data not shown).

Consistent with the results in FIG. 19, digoxigenin-labelled MBP-$M_{110}$-(R714-I1004) (data not shown) and MBP-$M_{110}$-(K933-I1004) (FIG. 20B), but not digoxigenin-labelled MBP-$M_{110}$-(R714-L934) (data not shown), recognised the full length $M_{21}$ subunit and $M_{21}$(M1-L146) in Far Western blotting experiments.

The Region of the $M_{21}$ Subunit that Interacts with the $M_{110}$ Subunit.

Digoxigenin-labelled $M_{21}$-(M1-L146) recognised the same fragments of the $M_{110}$ subunit as the full length $M_{21}$ protein (FIG. 19C), demonstrating that the C-terminal leucine zipper of the $M_{21}$ subunit is not required for interaction with the $M_{1110}$ subunit. However, neither digoxigenin-labelled GST-$M_{21}$-(M1-E110) nor digoxigenin-labelled GST-$M_{21}$-(E110-K186) recognised $M_{110}$-(K933-I1004) in Far Western blotting experiments (data not shown). Consistent with these findings, digoxigenin-labelled $M_{110}$-(K933-I1004) recognised the full length $M_{21}$ protein and $M_{21}$-(M1-L146), but not $M_{21}$-(M1-E110) or $M_{21}$-(E110-K186) in Far Western blotting experiments (FIGS. 20A and B). However, digoxigenin-labelled $M_{110}$-(K933-I1004) did recognise a proteolytic fragment of the $M_{21}$ subunit with an apparent molecular mass only slightly larger than $M_{21}$-(M1-E110) (FIG. 20B, track 2 and compare tracks 2 and 4 in FIG. 20A). These results are considered further under Discussion.

The Isolated $M_{21}$ Subunit Dimerizes and the Region Involved in Dimerization is Identical to that which Interacts with the $M_{110}$ Subunit.

Although the $M_{110}$ subunit binds to both PP1c and the $M_{21}$ subunit [4], and removal of the $M_{21}$ subunit does not alter the specificity of the $PP1_M$ complex [7], an interaction between the $M_{21}$ subunit and PP1c had not been excluded. In order to examine this point, PP1c and the $M_{21}$ subunit were mixed together and subjected to gel filtration on Superose 12. The $M_{21}$ subunit eluted just before the 37 kDa PP1c protein, demonstrating that they do not form a high affinity complex and suggesting that the isolated $M_{21}$ subunit dimerizes (data not shown). These results were supported by the finding that digoxigenin-labelled full length $M_{21}$ subunit recognised the $M_{21}$ subunit as well as the $M_{110}$ subunit, but not PP1c, in Far Western blotting experiments (FIG. 21, track 1). Similar results were obtained with $M_{21}$-(M1-L146) (FIG. 21, track 2). Digoxigenin-labelled $M_{21}$ subunit, like digoxigenin-labelled $M_{110}$-(K933-I1004), recognised a fragment of the $M_{21}$ subunit that migrated slightly more slowly than $M_{21}$-(M1-E110), but did not recognise $M_{21}$-(M1-E110) or $M_{21}$-(E110-K186) (Tracks 2, 4 and 5 in FIGS. 20B and 20C).

Identification of a Region on the $M_{110}$ Subunit that Binds to Myosin.

When $PP1_M$ (30 nM) was mixed with chicken gizzard myosin (1 μM) and centrifuged to pellet the myosin, 85% of the myosin P-light chain phosphatase was recovered in the pellet (FIGS. 22 and 23A). In contrast, neither PP1c (FIG. 22) nor bovine serum albumin (data not shown) bound to myosin under these conditions. After removal of the $M_{21}$ subunit from $PP1_M$ [7], the $M_{110}$-PP1c complex ($PP1_M$ ($\Delta M_{21}$) still pelleted with myosin in a similar manner to $PP1_M$ itself (FIG. 22), indicating that the $M_{110}$ subunit is a myosin-binding protein.

In order to identify the myosin-binding domain(s), several fragments of the $M_{110}$ subunit were expressed and purified from E. coli extracts and their binding to myosin was studied. GST-$M_{110}$-(M1-S477), like GST-$M_{110}$-(M1-E309) [7], stimulated the PP1c-catalysed dephosphorylation of the myosin P-light chain and inhibited the dephosphorylation of glycogen phosphorylase in a similar manner to the full length $M_{110}$ subunit (data not shown). However, neither GST-$M_{110}$-(M1-S477) nor GST-$M_{110}$-(M1-E309) bound to myosin (data not shown), even after removal of the GST-tag from GST-$M_{110}$-(M1-S477) (FIG. 23A).

A fragment comprising GST-$M_{110}$-(M377-K976) from rat aorta migrated as multiple bands on SDS/polyacrylamide gels after purification on glutathione-Sepharose (FIG. 23A), indicating cleavage at multiple sites within the $M_{110}$ subunit. Only the largest fragment, with an apparent molecular mass corresponding to undegraded GST-$M_{110}$-(M377-K976) bound to myosin (FIG. 23A), suggesting that the myosin binding site(s) was located towards the C-terminus of the $M_{110}$ subunit. Consistent with this finding, $M_{110}$-(R714-I1004) from chicken gizzard also bound to myosin (FIG. 23B). However, $M_{110}$-(K933-I1004), which bound to the $M_{21}$ subunit (FIG. 20B), did not bind to myosin in these experiments (FIG. 23B).

The $M_{21}$ Subunit, and a Complex Between $M_{21}$ and $M_{110}$-(R714-I1004) Bind to Myosin.

After purification on glutathione-Sepharose, GST-$M_{21}$ migrated as four protein staining bands (track 1 in FIG.

20A), the two species of highest apparent molecular mass being recognised by the anti-$M_{21}$ antibody (FIG. 23B). The apparent molecular mass of the slowest migrating band (47 kDa) corresponds to undegraded GST-$M_{21}$ and this species bound to myosin (FIG. 23B). The next most slowly migrating band had an apparent molecular mass of 38 kDa, slightly less than that of GST-$M_{21}$-(M1-E110) (data not shown) indicating that it corresponds to GST fused to about the first 100 residues of the $M_{21}$ subunit; this fragment hardly bound to myosin (FIG. 23B).

Bacterial extracts expressing $M_{110}$-(R714-I1004) were mixed with GST-$M_{21}$ and the resulting complex was purified on glutathione-Sepharose. This complex bound quantitatively to myosin (FIG. 23B). In contrast, the GST-$M_{21}$ fragment of apparent molecular mass 38 kDa was not complexed to $M_{110}$-(R714-I1004) and did not bind to myosin (FIG. 23B). The C-terminal fragment of the $M_{21}$ subunit, $M_{21}$-(E110-K186) also did not bind to myosin under these conditions (data not shown).

Multiple Binding Sites for the $M_{21}$ Subunit on the Myosin Molecule.

Figure 24A:
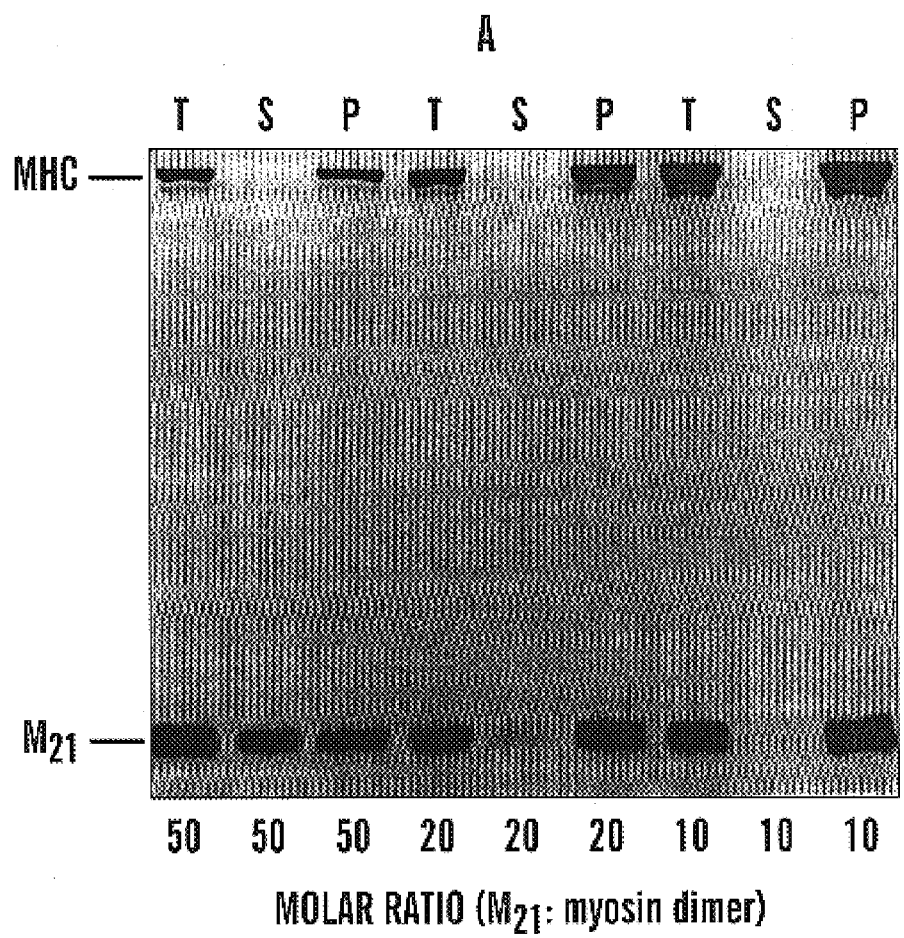
Figure 24B:
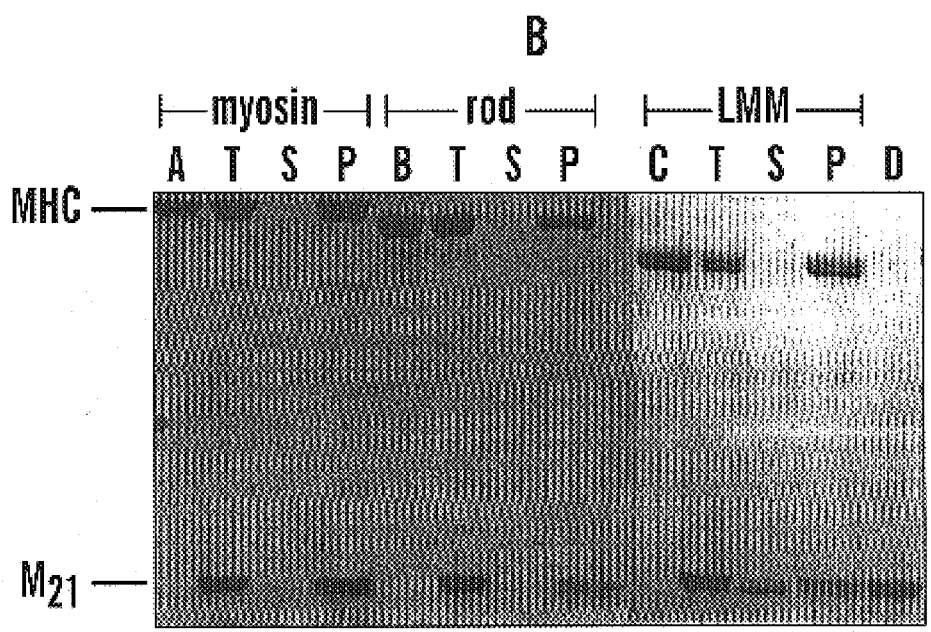
Figure 24C:
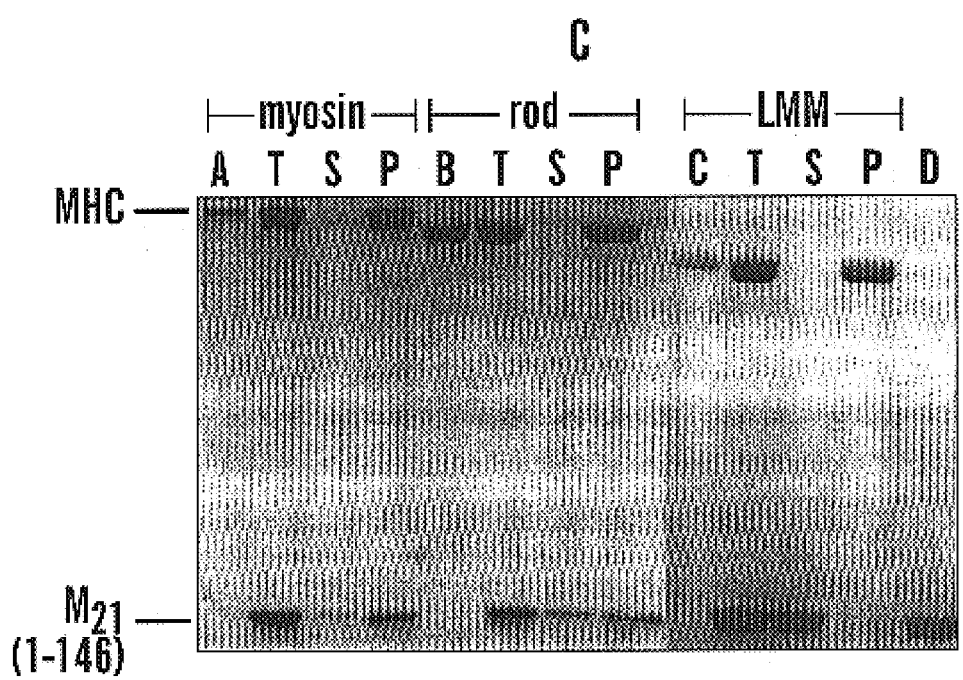

The molar ratio myosin:$PP1_M$ in chicken gizzard is about 80:1 in vivo [4] and the myosin binding experiments described above were therefore carried out using a large (ten fold) molar excess of myosin over either the $M_{21}$ or the $M_{110}$ subunit. However, further experiments carried out with the $M_{21}$ subunit in excess revealed that, remarkably, 20 or more moles of $M_{21}$ subunit could be bound to each myosin dimer (FIG. 24A). Many of the binding sites were located in the region of myosin involved in filament formation, because the $M_{21}$ subunit was pelleted with the myosin "rod" domain even when the molar ratio $M_{21}$:myosin dimer was 10:1 (FIG. 24B). A shorter portion of the rod, termed light meromyosin, also bound the $M_{21}$ subunit avidly. However, a fragment of the $M_{21}$ subunit lacking the first 15 residues from the N-terminus, which was a contaminant in this preparation, did not bind to light meromyosin (FIG. 24B), although it bound to the longer myosin rod (FIG. 24B). The $M_{21}$ subunit lacking the C-terminal leucine zipper, $M_{21}$-(M1-L146), bound to both myosin and the rod domain, but fewer moles of $M_{21}$-(M1-L146) could be bound and this C-terminally truncated species did not bind to light meromyosin under the conditions studied (FIG. 24C).

Multiple Forms of the $M_{110}$ Subunit

Comparison of two different clones encoding the $M_{110}$ subunit from chicken gizzard revealed a 123 bp (41 amino acid) deletion/insertion after Asn-511 (FIG. 17, [8]). Since the rat aorta sequence [5] showed considerable variation from the chicken sequences in this region, compared to the high degree of sequence similarity throughout most of the rest of the molecule (FIG. 17), it seemed probable that forms of the rat $M_{110}$ subunit also existed that varied in this middle section of the protein. PCR of the "variable region" of several rat aorta clones gave fragments of either 608 bp or 776 bp. Direct sequencing of these fragments showed an in frame insertion of 168bp (56 amino acids) after Ser-552 (FIG. 1); i.e. a slightly different position from the deletion reported for the chicken gizzard $M_{110}$ subunit (FIG. 17). Furthermore, a different 62 amino acid deletion/insertion in this section is apparent by comparison of the rat aorta sequences with that of the $M_{110}$ protein from rat kidney (FIG. 1) [9]. While it is likely that most of these variations arise by alternative splicing of the mNRNA, Southern blotting of rat genomic DNA revealed the presence of two closely related genes (data not shown).

Discussion

The contraction of smooth muscle is triggered by phosphorylation of the P-light chain of myosin catalysed by myosin light chain kinase. However, the identity of the myosin P-light chain phosphatase remained unclear for many years. In 1992 we reported that 80–90% of the myosin phosphatase activity in chicken gizzard homogenates was associated with myofibrils and purified a myosin phosphatase to homogeneity from this fraction [4]. This enzyme, termed $PP1_M$, was found to be composed of the β-isoform of PP1c (termed the δ-isoform in [16]) and an "M-complex" consisting of two other subunits [4] whose molecular masses were 21 kDa ($M_{21}$) [5] and 110 kDa ($M_{110}$) [5, 8], respectively. Further evidence that a form of PP1 was the major myosin phosphatase in smooth muscle was indicated by the finding that tautomycin (a much more potent inhibitor of PP1 than PP2A [17]) stimulated the contraction of permeabilised mammalian smooth muscle fibres at much lower concentrations than okadaic acid [18] (a much more potent inhibitor of PP2A than PP1 [19]).

Two further pieces of evidence presented in this Example establish that $PP1_M$ accounts for most, if not all, of the myosin phosphatase activity associated with chicken gizzard myofibrils, reinforcing the view that it is likely to be the major myosin P-light chain phosphatase in vivo. Firstly, nearly all the myosin P-light chain phosphatase activity was immunoprecipitated by antibodies that recognise either the $M_{110}$ or the $M_{21}$ subunit specifically (FIG. 18A). Secondly, $PP1_M$ was found to represent 0.1% of the protein in the myofibrillar extracts whether its concentration was calculated from the increase in specific activity needed for purification to homogeneity [4] or from immunoblotting experiments with the anti-$M_{110}$ and anti-$M_{21}$ antibodies (FIG. 18B). Had another enzyme been the major myosin phosphatase in the myofibrillar extracts the enrichment estimated by immunoblotting with anti-$M_{110}$ and anti-$M_{21}$ antibodies would have been much higher.

The experiments presented in FIG. 18 also demonstrate that the $M_{110}$ and $M_{21}$ subunits are not present in myofibrillar extracts in a significant molar excess over PP1c and that all the $M_{110}$ subunits are complexed to $M_{21}$ subunit and vice versa. The $M_{21}$ subunit was found to bind to the C-terminal 72 residues of the chicken gizzard $M_{110}$ subunit (FIGS. 19 and 25), a region whose amino acid sequence is 43% identical to residues 87–161 of the $M_{21}$ subunit (FIG. 17B). The C-terminal leucine zipper of the $M_{21}$ subunit (residues 145–186) is not required for interaction with the $M_{110}$ subunit, and the site on the $M_{21}$ subunit which interacts with the $M_{110}$ subunit lies within about the N-terminal 120 residues (FIG. 20B). Interestingly, the same region is essential for the dimerisation of the $M_{21}$ subunit (compare FIGS. 20B and 20C), suggesting that the region(s) involved in interaction is probably located between residues 60 and 120 of the $M_{21}$ subunit and 906–965 of the $M_{110}$ subunit from chicken gizzard; i.e. the regions with greatest amino acid identity between these two proteins (FIG. 17). More digoxigenin-labelled $M_{21}$ subunit bound to the $M_{110}$ subunit than to the $M_{21}$ subunit in Far Western blotting experiments (FIG. 21), consistent with the observation that $M_{110}/M_{21}$ heterodimers form in vivo, but not $M_{21}/M_{21}$ homodimers. The finding that the C-terminus of the $M_{110}$ subunit interacts with the $M_{21}$ subunit explains why preparations of $PP1_M$ comprising PP1c complexed to N-terminal fragments of the $M_{110}$ subunit do not contain the $M_{21}$ subunit [8, 20].

$PP1_M$ binds to the dephosphorylated form of myosin and our data demonstrate that the $M_{110}$ subunit (FIG. 22) and the $M_{21}$ subunit (FIG. 23B and FIG. 24) are both myosin-binding proteins. The C-terminal 600 residues of the $M_{110}$ subunit from rat aorta, $M_{110}$-(M377-K976) (FIG. 23A) and the C-terminal 291 residues of the $M_{110}$ subunit from chicken gizzard, $M_{110}$-(R714-I1004), bound to myosin, but the C-terminal 72 residues of the $M_{110}$ subunit, $M_{110}$-(K933-I1004), did not (FIG. 23B), indicating that a myosin-binding domain is likely to be situated in the $M_{110}$ subunit just N-terminal to the $M_{21}$-binding domain (FIG. 25). In contrast, two N-terminal fragments of the $M_{110}$ subunit $M_{110}$-(M1-S477) (FIG. 23A) and $M_{110}$-(M1-E309) (data not shown) did not bind to myosin under the conditions studied. Since $M_{110}$-(M1-E309) [7] and $M_{110}$-(M1-S477) (data not shown) stimulate the dephosphorylation of myosin and inhibit the dephosphorylation of glycogen phosphorylase by PP1c, and in a similar manner to full length $M_{110}$ subunit, these results show that the region of the $M_{110}$ subunit which stimulates the dephosphorylation of the myosin P-light chain is distinct from that which binds the dephosphorylated form of myosin and thereby targets $PP1_M$ to the contractile apparatus.

Digestion of chicken gizzard $PP1_M$ with chymotrypsin cleaves the $M_{110}$ subunit to a fragment with an apparent molecular mass of 58 kDa and a form of PP1, termed here $PP1_M*$, can then be isolated by gel-filtration which appears to comprise just the 58 kDa fragment and PP1c in a 1:1 molar ratio [8]. The 58 kDa fragment, like the $M_{110}$ subunit, has a blocked N-terminus and seven tryptic peptides isolated were located between residues 286 and 467, suggesting that the 58 kDa fragment corresponds to the N-terminal portion of the $M_{110}$ subunit [8]. $PP1_M*$ was reported to bind to myosin, albeit less effectively than PPIM [8], suggesting the presence of a myosin-binding domain within the 58 kDa fragment. This result is in apparent conflict with the present study, because the fragment $M_{110}$-(M1-S477), which also migrates on SDS/polyacrylamide gels with an apparent molecular mass of 58 kDa, did not bind to dephosphorylated myosin under conditions where 80–90% of the $PP1_M$ and $M_{110}$-(R714-I1004) was pelleted with myosin (FIG. 23A). One possible explanation for this discrepancy is that $PP1_M*$ also contains small myosin-binding fragments from the C-terminus of the $M_{110}$ subunit which still interact with the N-terminal 58 kDa fragment, but are too small to be detected by SDS/polyacrylamide gel electrophoresis. In a separate study heavy meromyosin (50 $\mu$g) was found to bind partially to 2 mg of $M_{110}$-(1–633) coupled to Affigel 15, at very low ionic strength but not at 150–200 mM NaCl [21]. The significance of this observation is unclear because of the extremely high concentration of the $M_{110}$-(1–633) used in these experiments. The average intracellular concentration of $PP1_M$ in chicken gizzard is about 1 $\mu$M, 100-fold lower than the concentration of myosin. In the present study, we analysed the binding of the $M_{110}$ subunit and its subfragments (30–100 nM) to myosin (1 $\mu$M) using low concentrations of these proteins to try and ensure that only high affinity binding sites were identified.

The isolated $M_{21}$ subunit also bound to myosin and up to 20 moles of $M_{21}$ subunit could be bound to each myosin dimer (FIG. 24). These observations indicate that each myosin molecule contains multiple binding sites for the $M_{21}$ subunit, many of which are located within the "rod domain" (FIGS. 24B and 24C). In vivo, the molar ratio $PP1_M$:myosin is about 1:80 and yet, during muscle relaxation, all the myosin P-light chains can be dephosphorylated by $PP1_M$ within seconds. This implies that $PP1_M$ must be highly mobile within the myofibrils and move extremely rapidly from one myosin molecule to another. The "off rates" for binding of $PP1_M$ to myosin must therefore be very fast as well as the "on rates". It is tempting to speculate that the presence of multiple binding sites on myosin for the $M_{21}$ subunit (and perhaps for the $M_{110}$ subunit as well) allows $PP1_M$ to "slide" rapidly from one myosin molecule to another.

EXAMPLE 4

Design of Small Molecules to Modulate the Properties of PP1

Table A is a print-out of the atomic coordinates of the protein phosphatase-1 peptide coordinates as deduced in Example 2. The format is Protein Data Bank. The structure of the protein phosphatase-1 catalytic subunit (PP1c) in complex with a 13-residue peptide ($G_M$ peptide) corresponding to a site of interaction between PP1c and the glycogen targeting subunit provides a frame-work for the rational design of small molecules to modulate the functions and properties of PP1 in vivo. Knowledge of the structural nature of the interactions between the $G_M$ peptide and PP1c allows the design of inhibitors that mimic these interactions. These inhibitors may be designed for increased potency, cell permeability and with improved pharmokinetic properties.

Computer graphics systems may be used to design such inhibitors in conjunction with computer graphics modelling software such as SYBIL available from: Tripos Inc, 16995 S Hanley Road, St Louis, Miss. 63144-2913, USA and LUDI available from: Molecular Simulations Inc, 9685 Scranton Road, San Diego, Calif. 92121-3752, USA, and in conjunction with the atomic coordinates shown in Table A.

EXAMPLE 5

Effect of Peptide Derived from p53BP2 Binding Site to PP1 in Vivo

The function of p53BP2 is ascertained by examining the in vivo effect of peptides based on the sequence of the p53BP2 binding site to PP1. This may be done by reference to the consensus peptide sequence described in the previous Examples and by reference to the crystal structure in Example 2. The peptide is introduced into cultured cells using penetratin available from Appligene. Other importins may also be used. Alternatively cDNA specifying p53BP2 proteins mutant in the p53BP2 binding site to PP1 are transfected in cultured cells. The effect of these agents on the cell cycle and apoptosis are assessed by a number of methods, for example WAF1 ELISA and Nuclear Matrix Protein ELISA assays (Amersham).

The effect of the p53BP2 peptide is to modulate the interaction between PP1 and p53BP2 in vivo and affect cell regulation and apoptosis. The p53BP2 peptide may also be micro-injected into the cell.

TABLE A

| ATOM | 1 | N | LYS | 6 | −10.263 | 46.372 | 91.126 | 1.00 | 53.07 | 0 |
|---|---|---|---|---|---|---|---|---|---|---|
| ATOM | 3 | CA | LYS | 6 | −9.182 | 46.177 | 90.159 | 1.00 | 53.07 | 0 |
| ATOM | 4 | CB | LYS | 6 | −9.220 | 47.277 | 89.092 | 1.00 | 45.20 | 0 |
| ATOM | 5 | CG | LYS | 6 | −10.284 | 47.095 | 88.015 | 1.00 | 45.20 | 0 |
| ATOM | 6 | CD | LYS | 6 | −9.809 | 46.200 | 86.868 | 1.00 | 45.20 | 0 |
| ATOM | 7 | CE | LYS | 6 | −8.832 | 46.919 | 85.927 | 1.00 | 45.20 | 0 |
| ATOM | 8 | NZ | LYS | 6 | −7.498 | 47.216 | 86.540 | 1.00 | 45.20 | 0 |
| ATOM | 12 | C | LYS | 6 | −7.814 | 46.179 | 90.835 | 1.00 | 53.07 | 0 |
| ATOM | 13 | O | LYS | 6 | −6.854 | 45.624 | 90.303 | 1.00 | 45.20 | 0 |
| ATOM | 14 | N | LEU | 7 | −7.746 | 46.816 | 92.005 | 1.00 | 42.33 | 0 |
| ATOM | 16 | CA | LEU | 7 | −6.527 | 46.941 | 92.800 | 1.00 | 43.14 | 0 |
| ATOM | 17 | CB | LEU | 7 | −6.840 | 47.599 | 94.141 | 1.00 | 24.45 | 0 |
| ATOM | 18 | CG | LEU | 7 | −5.670 | 47.782 | 95.106 | 1.00 | 18.34 | 0 |
| ATOM | 19 | CD1 | LEU | 7 | −4.775 | 48.881 | 94.589 | 1.00 | 25.09 | 0 |
| ATOM | 20 | CD2 | LEU | 7 | −6.186 | 48.121 | 96.496 | 1.00 | 22.21 | 0 |
| ATOM | 21 | C | LEU | 7 | −5.892 | 45.594 | 93.063 | 1.00 | 42.81 | 0 |
| ATOM | 22 | O | LEU | 7 | −6.497 | 44.723 | 93.675 | 1.00 | 23.55 | 0 |
| ATOM | 23 | N | ASN | 8 | −4.656 | 45.424 | 92.627 | 1.00 | 17.03 | 0 |
| ATOM | 25 | CA | ASN | 8 | −4.000 | 44.156 | 92.846 | 1.00 | 11.65 | 0 |
| ATOM | 26 | CB | ASN | 8 | −3.204 | 43.744 | 91.610 | 1.00 | 18.54 | 0 |
| ATOM | 27 | CG | ASN | 8 | −3.486 | 42.312 | 91.193 | 1.00 | 15.30 | 0 |
| ATOM | 28 | OD1 | ASN | 8 | −4.643 | 41.903 | 91.068 | 1.00 | 14.53 | 0 |
| ATOM | 29 | ND2 | ASN | 8 | −2.429 | 41.538 | 90.993 | 1.00 | 7.61 | 0 |
| ATOM | 32 | C | ASN | 8 | −3.110 | 44.207 | 94.079 | 1.00 | 11.35 | 0 |
| ATOM | 33 | O | ASN | 8 | −1.906 | 44.515 | 93.985 | 1.00 | 12.23 | 0 |
| ATOM | 34 | N | ILE | 9 | −3.716 | 43.900 | 95.232 | 1.00 | 12.56 | 0 |
| ATOM | 36 | CA | ILE | 9 | −3.018 | 43.894 | 96.523 | 1.00 | 14.41 | 0 |
| ATOM | 37 | CB | ILE | 9 | −3.955 | 43.439 | 97.690 | 1.00 | 2.00 | 0 |
| ATOM | 38 | CG2 | ILE | 9 | −3.155 | 42.828 | 98.812 | 1.00 | 2.00 | 0 |
| ATOM | 39 | CG1 | ILE | 9 | −4.742 | 44.634 | 98.244 | 1.00 | 2.00 | 0 |
| ATOM | 40 | CD1 | ILE | 9 | −3.865 | 45.837 | 98.581 | 1.00 | 2.00 | 0 |
| ATOM | 41 | C | ILE | 9 | −1.796 | 42.996 | 96.501 | 1.00 | 10.07 | 0 |
| ATOM | 42 | O | ILE | 9 | −0.759 | 43.351 | 97.045 | 1.00 | 2.00 | 0 |
| ATOM | 43 | N | ASP | 10 | −1.916 | 41.845 | 95.849 | 1.00 | 2.00 | 0 |
| ATOM | 45 | CA | ASP | 10 | −0.822 | 40.887 | 95.782 | 1.00 | 2.00 | 0 |
| ATOM | 46 | CB | ASP | 10 | −1.336 | 39.562 | 95.208 | 1.00 | 45.77 | 0 |
| ATOM | 47 | CG | ASP | 10 | −2.234 | 38.801 | 96.191 | 1.00 | 46.34 | 0 |
| ATOM | 48 | OD1 | ASP | 10 | −3.054 | 39.444 | 96.879 | 1.00 | 50.94 | 0 |
| ATOM | 49 | OD2 | ASP | 10 | −2.123 | 37.558 | 96.281 | 1.00 | 55.84 | 0 |
| ATOM | 50 | C | ASP | 10 | 0.426 | 41.369 | 95.036 | 1.00 | 2.00 | 0 |
| ATOM | 51 | O | ASP | 10 | 1.540 | 41.181 | 95.516 | 1.00 | 43.44 | 0 |
| ATOM | 52 | N | SER | 11 | 0.245 | 41.993 | 93.874 | 1.00 | 2.00 | 0 |
| ATOM | 54 | CA | SER | 11 | 1.387 | 42.494 | 93.112 | 1.00 | 2.00 | 0 |
| ATOM | 55 | CB | SER | 11 | 0.987 | 42.834 | 91.678 | 1.00 | 24.54 | 0 |
| ATOM | 56 | OG | SER | 11 | −0.025 | 43.819 | 91.653 | 1.00 | 26.40 | 0 |
| ATOM | 58 | C | SER | 11 | 1.964 | 43.727 | 93.804 | 1.00 | 2.00 | 0 |
| ATOM | 59 | O | SER | 11 | 3.168 | 44.010 | 93.702 | 1.00 | 23.86 | 0 |
| ATOM | 60 | N | ILE | 12 | 1.099 | 44.467 | 94.493 | 1.00 | 19.26 | 0 |
| ATOM | 62 | CA | ILE | 12 | 1.536 | 45.641 | 95.226 | 1.00 | 19.26 | 0 |
| ATOM | 63 | CB | ILE | 12 | 0.345 | 46.351 | 95.878 | 1.00 | 2.00 | 0 |
| ATOM | 64 | CG2 | ILE | 12 | 0.831 | 47.364 | 96.909 | 1.00 | 2.00 | 0 |
| ATOM | 65 | CG1 | ILE | 12 | −0.499 | 46.986 | 94.775 | 1.00 | 2.00 | 0 |
| ATOM | 66 | CD1 | ILE | 12 | −1.722 | 47.687 | 95.245 | 1.00 | 2.00 | 0 |
| ATOM | 67 | C | ILE | 12 | 2.501 | 45.112 | 96.275 | 1.00 | 19.26 | 0 |
| ATOM | 68 | O | ILE | 12 | 3.684 | 45.445 | 96.264 | 1.00 | 2.00 | 0 |
| ATOM | 69 | N | ILE | 13 | 1.987 | 44.246 | 97.141 | 1.00 | 2.00 | 0 |
| ATOM | 71 | CA | ILE | 13 | 2.764 | 43.605 | 98.199 | 1.00 | 2.00 | 0 |
| ATOM | 72 | CB | ILE | 13 | 1.899 | 42.504 | 98.897 | 1.00 | 2.00 | 0 |
| ATOM | 73 | CG2 | ILE | 13 | 2.747 | 41.645 | 99.810 | 1.00 | 2.00 | 0 |
| ATOM | 74 | CG1 | ILE | 13 | 0.764 | 43.154 | 99.691 | 1.00 | 2.00 | 0 |
| ATOM | 75 | CD1 | ILE | 13 | −0.213 | 42.167 | 100.331 | 1.00 | 2.00 | 0 |
| ATOM | 76 | C | ILE | 13 | 4.039 | 42.960 | 97.602 | 1.00 | 2.00 | 0 |
| ATOM | 77 | O | ILE | 13 | 5.142 | 43.099 | 98.158 | 1.00 | 2.00 | 0 |
| ATOM | 78 | N | GLN | 14 | 3.864 | 42.278 | 96.462 | 1.00 | 2.00 | 0 |
| ATOM | 80 | CA | GLN | 14 | 4.937 | 41.582 | 95.740 | 1.00 | 2.00 | 0 |
| ATOM | 81 | CB | GLN | 14 | 4.415 | 41.065 | 94.391 | 1.00 | 21.13 | 0 |
| ATOM | 82 | CG | GLN | 14 | 5.467 | 40.470 | 93.454 | 1.00 | 32.43 | 0 |
| ATOM | 83 | CD | GLN | 14 | 5.655 | 41.284 | 92.171 | 1.00 | 28.89 | 0 |
| ATOM | 84 | OE1 | GLN | 14 | 4.726 | 41.428 | 91.363 | 1.00 | 30.84 | 0 |
| ATOM | 85 | NE2 | GLN | 14 | 6.861 | 41.818 | 91.977 | 1.00 | 29.15 | 0 |
| ATOM | 88 | C | GLN | 14 | 6.088 | 42.519 | 95.515 | 1.00 | 2.00 | 0 |
| ATOM | 89 | O | GLN | 14 | 7.206 | 42.249 | 95.934 | 1.00 | 24.80 | 0 |
| ATOM | 90 | N | ARG | 15 | 5.789 | 43.625 | 94.848 | 1.00 | 15.16 | 0 |
| ATOM | 92 | CA | ARG | 15 | 6.776 | 44.638 | 94.552 | 1.00 | 15.16 | 0 |
| ATOM | 93 | CB | ARG | 15 | 6.122 | 45.812 | 93.846 | 1.00 | 8.83 | 0 |
| ATOM | 94 | CG | ARG | 15 | 6.530 | 45.981 | 92.388 | 1.00 | 8.83 | 0 |
| ATOM | 95 | CD | ARG | 15 | 5.543 | 46.882 | 91.684 | 1.00 | 8.83 | 0 |
| ATOM | 96 | NE | ARG | 15 | 4.195 | 46.322 | 91.761 | 1.00 | 8.83 | 0 |
| ATOM | 98 | CZ | ARG | 15 | 3.094 | 46.998 | 91.465 | 1.00 | 8.83 | 0 |

TABLE A-continued

| | | | | | | | | | | |
|---|---|---|---|---|---|---|---|---|---|---|
| ATOM | 99 | NH1 | ARG | 15 | 3.178 | 48.261 | 91.073 | 1.00 | 9.33 | 0 |
| ATOM | 102 | NH2 | ARG | 15 | 1.907 | 46.413 | 91.567 | 1.00 | 8.83 | 0 |
| ATOM | 105 | C | ARG | 15 | 7.405 | 45.106 | 95.841 | 1.00 | 15.16 | 0 |
| ATOM | 106 | O | ARG | 15 | 8.622 | 45.124 | 95.952 | 1.00 | 13.09 | 0 |
| ATOM | 107 | N | LEU | 16 | 6.575 | 45.462 | 96.820 | 1.00 | 2.00 | 0 |
| ATOM | 109 | CA | LEU | 16 | 7.049 | 45.924 | 98.124 | 1.00 | 2.00 | 0 |
| ATOM | 110 | CB | LEU | 16 | 5.853 | 46.215 | 99.033 | 1.00 | 2.00 | 0 |
| ATOM | 111 | CG | LEU | 16 | 4.982 | 47.420 | 98.662 | 1.00 | 2.00 | 0 |
| ATOM | 112 | CD1 | LEU | 16 | 3.630 | 47.302 | 99.324 | 1.00 | 2.00 | 0 |
| ATOM | 113 | CD2 | LEU | 16 | 5.664 | 48.707 | 99.056 | 1.00 | 2.00 | 0 |
| ATOM | 114 | C | LEU | 16 | 8.014 | 44.942 | 98.809 | 1.00 | 2.00 | 0 |
| ATOM | 115 | O | LEU | 16 | 9.031 | 45.354 | 99.361 | 1.00 | 2.00 | 0 |
| ATOM | 116 | N | LEU | 17 | 7.712 | 43.650 | 98.770 | 1.00 | 12.70 | 0 |
| ATOM | 118 | CA | LEU | 17 | 8.590 | 42.652 | 99.395 | 1.00 | 4.33 | 0 |
| ATOM | 119 | CB | LEU | 17 | 7.812 | 41.387 | 99.780 | 1.00 | 4.50 | 0 |
| ATOM | 120 | CG | LEU | 17 | 6.740 | 41.515 | 100.838 | 1.00 | 4.52 | 0 |
| ATOM | 121 | CD1 | LEU | 17 | 6.338 | 40.159 | 101.302 | 1.00 | 11.14 | 0 |
| ATOM | 122 | CD2 | LEU | 17 | 7.285 | 42.318 | 101.997 | 1.00 | 6.93 | 0 |
| ATOM | 123 | C | LEU | 17 | 9.796 | 42.225 | 98.548 | 1.00 | 7.39 | 0 |
| ATVH | 124 | O | LEU | 17 | 10.751 | 41.652 | 99.086 | 1.00 | 15.30 | 0 |
| ATOM | 125 | N | GLU | 18 | 9.758 | 42.492 | 97.238 | 1.00 | 65.13 | 0 |
| ATOM | 127 | CA | GLU | 18 | 10.847 | 42.104 | 96.329 | 1.00 | 70.48 | 0 |
| ATOM | 128 | CD | GLU | 18 | 10.505 | 42.471 | 94.883 | 1.00 | 89.02 | 0 |
| ATOM | 129 | CG | GLU | 18 | 10.769 | 43.929 | 94.547 | 1.00 | 97.06 | 0 |
| ATOM | 130 | CD | GLU | 18 | 10.677 | 44.239 | 93.069 | 1.00 | 39.46 | 0 |
| ATOM | 131 | OE1 | GLU | 18 | 11.030 | 43.351 | 92.256 | 1.00 | 39.46 | 0 |
| ATOM | 132 | OE2 | GLU | 18 | 10.265 | 45.375 | 92.727 | 1.00 | 39.46 | 0 |
| ATOM | 133 | C | GLU | 18 | 12.199 | 42.724 | 96.687 | 1.00 | 70.82 | 0 |
| ATOM | 134 | O | GLU | 18 | 13.244 | 42.249 | 96.240 | 1.00 | 88.34 | 0 |
| ATOM | 135 | N | VAL | 19 | 12.172 | 43.793 | 97.480 | 1.00 | 28.97 | 0 |
| ATOM | 137 | CA | VAL | 19 | 13.394 | 44.470 | 97.891 | 1.00 | 28.97 | 0 |
| ATOM | 138 | CB | VAL | 19 | 13.139 | 45.968 | 96.207 | 1.00 | 6.66 | 0 |
| ATOM | 139 | CG1 | VAL | 19 | 12.746 | 46.702 | 96.942 | 1.00 | 6.86 | 0 |
| ATOM | 140 | CG2 | VAL | 19 | 12.044 | 46.117 | 99.231 | 1.00 | 4.03 | 0 |
| ATOM | 141 | C | VAL | 19 | 14.079 | 43.805 | 99.081 | 1.00 | 28.97 | 0 |
| ATOM | 142 | O | VAL | 19 | 15.134 | 44.258 | 99.514 | 1.00 | 13.23 | 0 |
| ATOM | 143 | N | ARG | 20 | 13.490 | 42.736 | 99.615 | 1.00 | 2.00 | 0 |
| ATOM | 145 | CA | ARG | 20 | 14.093 | 42.016 | 100.748 | 1.00 | 2.00 | 0 |
| ATOM | 146 | CB | ARG | 20 | 13.242 | 40.812 | 101.142 | 1.00 | 17.66 | 0 |
| ATOM | 147 | CG | ARG | 20 | 12.043 | 41.138 | 101.990 | 1.00 | 16.46 | 0 |
| ATOM | 148 | CD | ARG | 20 | 11.192 | 39.899 | 102.195 | 1.00 | 21.30 | 0 |
| ATOM | 149 | NE | ARG | 20 | 12.006 | 38.733 | 102.532 | 1.00 | 18.45 | 0 |
| ATOM | 151 | CZ | ARG | 20 | 11.559 | 37.481 | 102.546 | 1.00 | 23.19 | 0 |
| ATOM | 152 | NH1 | ARG | 20 | 10.288 | 37.232 | 102.249 | 1.00 | 28.11 | 0 |
| ATOM | 155 | NH2 | ARG | 20 | 12.383 | 36.477 | 102.836 | 1.00 | 21.96 | 0 |
| ATOM | 158 | C | ARG | 20 | 15.480 | 41.521 | 100.333 | 1.00 | 2.00 | 0 |
| ATOM | 159 | O | ARG | 20 | 15.609 | 40.778 | 99.353 | 1.00 | 20.52 | 0 |
| ATOM | 160 | N | GLY | 21 | 16.514 | 41.956 | 101.047 | 1.00 | 61.97 | 0 |
| ATOM | 162 | CA | GLY | 21 | 17.863 | 41.527 | 100.718 | 1.00 | 65.49 | 0 |
| ATOM | 163 | C | GLY | 21 | 18.702 | 42.522 | 99.930 | 1.00 | 66.05 | 0 |
| ATOM | 164 | O | GLY | 21 | 19.933 | 42.409 | 99.889 | 1.00 | 13.74 | 0 |
| ATOM | 165 | N | SER | 22 | 18.055 | 43.490 | 99.290 | 1.00 | 19.66 | 0 |
| ATOM | 167 | CA | SER | 22 | 18.790 | 44.491 | 98.523 | 1.00 | 17.08 | 0 |
| ATOM | 168 | CB | SER | 22 | 17.874 | 45.159 | 97.481 | 1.00 | 26.61 | 0 |
| ATOM | 169 | OG | SER | 22 | 16.821 | 45.908 | 98.074 | 1.00 | 32.17 | 0 |
| ATOM | 171 | C | SER | 22 | 19.371 | 45.538 | 99.466 | 1.00 | 17.54 | 0 |
| ATOM | 172 | O | SER | 22 | 19.047 | 45.558 | 100.657 | 1.00 | 21.05 | 0 |
| ATOM | 173 | N | LYS | 23 | 20.222 | 46.409 | 98.935 | 1.00 | 53.24 | 0 |
| ATOM | 175 | CA | LYS | 23 | 20.828 | 47.458 | 99.740 | 1.00 | 49.50 | 0 |
| ATOM | 176 | CB | LYS | 23 | 21.565 | 48.471 | 98.852 | 1.00 | 94.25 | 0 |
| ATOM | 177 | CG | LYS | 23 | 20.639 | 49.422 | 98.085 | 1.00 | 59.71 | 0 |
| ATOM | 178 | CD | LYS | 23 | 21.341 | 50.716 | 97.688 | 1.00 | 94.25 | 0 |
| ATOM | 179 | CE | LYS | 23 | 20.346 | 51.775 | 97.214 | 1.00 | 59.77 | 0 |
| ATOM | 180 | NZ | LYS | 23 | 19.448 | 52.240 | 98.306 | 1.00 | 59.94 | 0 |
| ATOM | 184 | C | LYS | 23 | 19.739 | 48.190 | 100.528 | 1.00 | 49.47 | 0 |
| ATOM | 185 | O | LYS | 23 | 18.659 | 48.488 | 99.998 | 1.00 | 59.94 | 0 |
| ATOM | 186 | N | PRO | 24 | 19.990 | 48.458 | 101.813 | 1.00 | 37.72 | 0 |
| ATOM | 187 | CD | PRO | 24 | 21.185 | 48.148 | 102.614 | 1.00 | 2.00 | 0 |
| ATOM | 188 | CA | PRO | 24 | 18.987 | 49.165 | 102.613 | 1.00 | 36.73 | 0 |
| ATOM | 189 | CB | PRO | 24 | 19.618 | 49.217 | 104.004 | 1.00 | 2.00 | 0 |
| ATOM | 190 | CG | PRO | 24 | 21.109 | 49.208 | 103.704 | 1.00 | 2.00 | 0 |
| ATOM | 191 | C | PRO | 24 | 18.798 | 50.551 | 102.019 | 1.00 | 33.26 | 0 |
| ATOM | 192 | O | PRO | 24 | 19.752 | 51.325 | 101.938 | 1.00 | 2.00 | 0 |
| ATOM | 193 | N | GLY | 25 | 17.579 | 50.835 | 101.575 | 1.00 | 22.79 | 0 |
| ATOM | 195 | CA | GLY | 25 | 17.275 | 52.119 | 100.981 | 1.00 | 22.84 | 0 |
| ATOM | 196 | C | GLY | 25 | 16.653 | 51.904 | 99.624 | 1.00 | 18.00 | 0 |
| ATOM | 197 | O | GLY | 25 | 16.098 | 52.827 | 99.037 | 1.00 | 28.24 | 0 |
| ATOM | 198 | N | LYS | 26 | 16.750 | 50.679 | 99.116 | 1.00 | 2.00 | 0 |
| ATOM | 200 | CA | LYS | 26 | 16.174 | 50.351 | 97.817 | 1.00 | 2.00 | 0 |

TABLE A-continued

| ATOM | 201 | CB | LYS | 26 | 16.469 | 48.892 | 97.458 | 1.00 | 45.45 | 0 |
|---|---|---|---|---|---|---|---|---|---|---|
| ATOM | 202 | CG | LYS | 26 | 15.931 | 48.437 | 96.110 | 1.00 | 55.13 | 0 |
| ATOM | 203 | CD | LYS | 26 | 16.209 | 49.435 | 94.979 | 1.00 | 59.31 | 0 |
| ATOM | 204 | CE | LYS | 26 | 17.694 | 49.644 | 94.691 | 1.00 | 60.93 | 0 |
| ATOM | 205 | NZ | LYS | 26 | 17.883 | 50.619 | 93.569 | 1.00 | 68.30 | 0 |
| ATOM | 209 | C | LYS | 26 | 14.674 | 50.624 | 97.856 | 1.00 | 2.00 | 0 |
| ATOM | 210 | O | LYS | 26 | 13.916 | 49.964 | 98.566 | 1.00 | 42.74 | 0 |
| ATOM | 211 | N | ASN | 27 | 14.278 | 51.648 | 97.111 | 1.00 | 2.00 | 0 |
| ATOM | 213 | CA | ASN | 27 | 12.894 | 52.086 | 97.027 | 1.00 | 2.00 | 0 |
| ATOM | 214 | CB | ASN | 27 | 12.836 | 53.526 | 96.517 | 1.00 | 50.37 | 0 |
| ATOM | 215 | CG | ASN | 27 | 13.257 | 54.525 | 97.563 | 1.00 | 56.29 | 0 |
| ATOM | 216 | OD1 | ASN | 27 | 12.929 | 54.381 | 98.740 | 1.00 | 61.45 | 0 |
| ATOM | 217 | ND2 | ASN | 27 | 13.982 | 55.551 | 97.142 | 1.00 | 59.50 | 0 |
| ATOM | 220 | C | ASN | 27 | 11.964 | 51.219 | 96.183 | 1.00 | 2.00 | 0 |
| ATOM | 221 | O | ASN | 27 | 12.384 | 50.256 | 95.540 | 1.00 | 54.11 | 0 |
| ATOM | 222 | N | VAL | 28 | 10.689 | 51.590 | 96.209 | 1.00 | 12.34 | 0 |
| ATOM | 224 | CA | VAL | 28 | 9.646 | 50.910 | 95.473 | 1.00 | 12.71 | 0 |
| ATOM | 225 | CB1 | VAL | 28 | 9.126 | 49.693 | 96.283 | 1.00 | 2.00 | 0 |
| ATOM | 226 | CG1 | VAL | 28 | 8.777 | 50.111 | 97.684 | 1.00 | 2.00 | 0 |
| ATOM | 227 | CG2 | VAL | 28 | 7.932 | 49.053 | 95.599 | 1.00 | 2.00 | 0 |
| ATOM | 228 | C | VAL | 28 | 8.549 | 51.935 | 95.145 | 1.00 | 19.22 | 0 |
| ATOM | 229 | O | VAL | 28 | 7.757 | 52.363 | 96.000 | 1.00 | 2.00 | 0 |
| ATOM | 230 | N | GLN | 29 | 8.548 | 52.372 | 93.892 | 1.00 | 26.36 | 0 |
| ATOM | 232 | CA | GLN | 29 | 7.586 | 53.365 | 93.424 | 1.00 | 27.97 | 0 |
| ATOM | 233 | CB | GLN | 29 | 8.203 | 54.239 | 92.325 | 1.00 | 11.00 | 0 |
| ATOM | 234 | CG | GLN | 29 | 7.479 | 55.543 | 92.080 | 1.00 | 8.47 | 0 |
| ATOM | 235 | CD | GLN | 29 | 7.684 | 56.541 | 93.201 | 1.00 | 11.72 | 0 |
| ATOM | 236 | OE1 | GLN | 29 | 7.097 | 57.619 | 93.198 | 1.00 | 13.39 | 0 |
| ATOM | 237 | NE2 | GLN | 29 | 8.525 | 56.195 | 94.159 | 1.00 | 12.03 | 0 |
| ATOM | 240 | C | GLN | 29 | 6.347 | 52.688 | 92.887 | 1.00 | 27.73 | 0 |
| ATOM | 241 | O | GLN | 29 | 6.401 | 51.934 | 91.926 | 1.00 | 8.22 | 0 |
| ATOM | 242 | N | LEU | 30 | 5.229 | 52.941 | 93.531 | 1.00 | 2.00 | 0 |
| ATOM | 244 | CA | LEU | 30 | 3.978 | 52.359 | 93.087 | 1.00 | 2.00 | 0 |
| ATOM | 245 | CB | LEU | 30 | 3.157 | 51.859 | 94.279 | 1.00 | 18.06 | 0 |
| ATOM | 246 | CG | LEU | 30 | 3.381 | 50.416 | 94.729 | 1.00 | 18.06 | 0 |
| ATOM | 247 | CD1 | LEU | 30 | 4.857 | 50.152 | 94.928 | 1.00 | 18.06 | 0 |
| ATOM | 248 | CD2 | LEU | 30 | 2.603 | 50.171 | 96.009 | 1.00 | 18.06 | 0 |
| ATOM | 249 | C | LEU | 30 | 3.223 | 53.441 | 92.348 | 1.00 | 2.00 | 0 |
| ATOM | 250 | O | LEU | 30 | 3.363 | 54.621 | 92.664 | 1.00 | 18.06 | 0 |
| ATOM | 251 | N | GLN | 31 | 2.441 | 53.050 | 91.355 | 1.00 | 75.78 | 0 |
| ATOM | 253 | CA | GLN | 31 | 1.679 | 54.026 | 90.599 | 1.00 | 80.15 | 0 |
| ATOM | 254 | CB | GLN | 31 | 0.782 | 53.336 | 89.593 | 1.00 | 2.00 | 0 |
| ATOM | 255 | CG | GLN | 31 | 1.448 | 52.204 | 68.883 | 1.00 | 2.00 | 0 |
| ATOM | 256 | CD | GLN | 31 | 0.498 | 51.469 | 87.976 | 1.00 | 2.00 | 0 |
| ATOM | 257 | OE1 | GLN | 31 | 0.933 | 50.694 | 87.122 | 1.00 | 2.00 | 0 |
| ATOM | 258 | NE2 | GLN | 31 | −0.809 | 51.698 | 88.150 | 1.00 | 2.00 | 0 |
| ATOM | 261 | C | GLN | 31 | 0.819 | 54.783 | 91.585 | 1.00 | 79.69 | 0 |
| ATOM | 262 | O | GLN | 31 | 0.276 | 54.187 | 92.512 | 1.00 | 2.00 | 0 |
| ATOM | 263 | N | GLU | 32 | 0.716 | 56.091 | 91.380 | 1.00 | 2.00 | 0 |
| ATOM | 265 | CA | GLU | 32 | −0.074 | 56.979 | 92.228 | 1.00 | 2.00 | 0 |
| ATOM | 266 | CB | GLU | 32 | −0.236 | 58.333 | 91.523 | 1.00 | 57.69 | 0 |
| ATOM | 267 | CG | GLU | 32 | −1.206 | 59.320 | 92.181 | 1.00 | 62.36 | 0 |
| ATOM | 268 | CD | GLU | 32 | −1.652 | 60.426 | 91.226 | 1.00 | 60.46 | 0 |
| ATOM | 269 | OE1 | GLU | 32 | −2.596 | 61.176 | 91.570 | 1.00 | 59.61 | 0 |
| ATOM | 270 | OE2 | GLU | 32 | −1.059 | 60.543 | 90.128 | 1.00 | 62.85 | 0 |
| ATOM | 271 | C | GLU | 32 | −1.449 | 56.370 | 92.539 | 1.00 | 2.00 | 0 |
| ATOM | 272 | O | GLU | 32 | −1.875 | 56.341 | 93.695 | 1.00 | 53.86 | 0 |
| ATOM | 273 | N | ASN | 33 | −2.127 | 55.865 | 91.517 | 1.00 | 6.25 | 0 |
| ATOM | 275 | CA | ASN | 33 | −3.445 | 55.278 | 91.714 | 1.00 | 7.45 | 0 |
| ATOM | 276 | CB | ASN | 33 | −4.134 | 55.026 | 90.364 | 1.00 | 30.19 | 0 |
| ATOM | 277 | CG | ASN | 33 | −3.291 | 54.199 | 89.412 | 1.00 | 30.49 | 0 |
| ATOM | 278 | OD1 | ASN | 33 | −2.592 | 53.261 | 89.810 | 1.00 | 32.73 | 0 |
| ATOM | 279 | ND2 | ASN | 33 | −3.349 | 54.551 | 88.141 | 1.00 | 33.00 | 0 |
| ATOM | 282 | C | ASN | 33 | −3.448 | 54.002 | 92.565 | 1.00 | 10.76 | 0 |
| ATOM | 283 | O | ASN | 33 | −4.466 | 53.670 | 93.182 | 1.00 | 23.15 | 0 |
| ATOM | 284 | N | GLU | 34 | −2.322 | 53.292 | 92.598 | 1.00 | 27.56 | 0 |
| ATOM | 286 | CA | GLU | 34 | −2.217 | 52.081 | 93.402 | 1.00 | 24.54 | 0 |
| ATOM | 287 | CB | GLU | 34 | −1.005 | 51.251 | 92.985 | 1.00 | 23.44 | 0 |
| ATOM | 288 | CG | GLU | 34 | −1.203 | 50.479 | 91.698 | 1.00 | 22.75 | 0 |
| ATOM | 289 | CD | GLU | 34 | −0.120 | 49.438 | 91.479 | 1.00 | 28.72 | 0 |
| ATOM | 290 | OE1 | GLU | 34 | −0.443 | 48.226 | 91.460 | 1.00 | 34.33 | 0 |
| ATOM | 291 | OE2 | GLU | 34 | 1.055 | 49.834 | 91.330 | 1.00 | 31.11 | 0 |
| ATOM | 292 | C | GLU | 34 | −2.106 | 52.470 | 94.871 | 1.00 | 25.10 | 0 |
| ATOM | 293 | O | GLU | 34 | −2.797 | 51.923 | 95.716 | 1.00 | 19.23 | 0 |
| ATOM | 294 | N | ILE | 35 | −1.244 | 53.430 | 95.172 | 1.00 | 14.94 | 0 |
| ATOM | 296 | CA | ILE | 35 | −1.083 | 53.889 | 96.541 | 1.00 | 28.22 | 0 |
| ATOM | 297 | CB | ILE | 35 | 0.045 | 54.888 | 96.632 | 1.00 | 2.00 | 0 |
| ATOM | 298 | CG2 | ILE | 35 | 0.013 | 55.607 | 97.961 | 1.00 | 2.00 | 0 |
| ATOM | 299 | CG1 | ILE | 35 | 1.354 | 54.154 | 96.395 | 1.00 | 2.00 | 0 |

TABLE A-continued

| | | | | | | | | | |
|---|---|---|---|---|---|---|---|---|---|
| ATOM | 300 | CD1 | ILE | 35 | 2.554 | 55.045 | 96.414 | 1.00 | 2.00 | 0 |
| ATOM | 301 | C | ILE | 35 | −2.368 | 54.536 | 97.034 | 1.00 | 13.21 | 0 |
| ATOM | 302 | O | ILE | 35 | −2.794 | 54.302 | 98.172 | 1.00 | 2.00 | 0 |
| ATOM | 303 | N | ARG | 36 | −2.985 | 55.340 | 96.171 | 1.00 | 2.00 | 0 |
| ATOM | 305 | CA | ARG | 36 | −4.237 | 56.015 | 96.506 | 1.00 | 2.00 | 0 |
| ATOM | 306 | CB | ARG | 36 | −4.578 | 57.082 | 95.446 | 1.00 | 8.06 | 0 |
| ATOM | 307 | CG | ARG | 36 | −5.725 | 56.703 | 94.502 | 1.00 | 14.08 | 0 |
| ATOM | 308 | CD | ARG | 36 | −6.059 | 57.824 | 93.555 | 1.00 | 20.55 | 0 |
| ATOM | 309 | NE | ARG | 36 | −6.465 | 59.029 | 94.267 | 1.00 | 14.43 | 0 |
| ATOM | 311 | CZ | ARG | 36 | −7.726 | 59.383 | 94.491 | 1.00 | 22.93 | 0 |
| ATOM | 312 | NH1 | ARG | 36 | −8.729 | 58.618 | 94.064 | 1.00 | 22.80 | 0 |
| ATOM | 315 | NH2 | ARG | 36 | −7.987 | 60.518 | 95.134 | 1.00 | 19.87 | 0 |
| ATOM | 318 | C | ARG | 36 | −5.394 | 55.005 | 96.657 | 1.00 | 2.00 | 0 |
| ATOM | 319 | O | ARG | 36 | −6.415 | 55.305 | 97.279 | 1.00 | 2.00 | 0 |
| ATOM | 320 | N | GLY | 37 | −5.240 | 53.828 | 96.059 | 1.00 | 2.00 | 0 |
| ATOM | 322 | CA | GLY | 37 | −6.264 | 52.814 | 96.177 | 1.00 | 2.00 | 0 |
| ATOM | 323 | C | GLY | 37 | −6.118 | 52.251 | 97.575 | 1.00 | 2.00 | 0 |
| ATOM | 324 | O | GLY | 37 | −7.106 | 52.030 | 98.289 | 1.00 | 2.00 | 0 |
| ATOM | 325 | N | LEU | 38 | −4.864 | 52.039 | 97.975 | 1.00 | 8.88 | 0 |
| ATOM | 327 | CA | LEU | 38 | −4.558 | 51.515 | 99.288 | 1.00 | 8.88 | 0 |
| ATOM | 328 | CB | LEU | 38 | −3.061 | 51.550 | 99.559 | 1.00 | 2.00 | 0 |
| ATOM | 329 | CG | LEU | 38 | −2.202 | 50.559 | 98.784 | 1.00 | 2.00 | 0 |
| ATOM | 330 | CD1 | LEU | 38 | −0.765 | 50.804 | 99.171 | 1.00 | 2.00 | 0 |
| ATOM | 331 | CD2 | LEU | 38 | −2.614 | 49.106 | 99.063 | 1.00 | 2.00 | 0 |
| ATOM | 332 | C | LEU | 38 | −5.278 | 52.406 | 100.258 | 1.00 | 8.88 | 0 |
| ATOM | 333 | O | LEU | 38 | −6.130 | 51.928 | 101.002 | 1.00 | 2.00 | 0 |
| ATOM | 334 | N | CYS | 39 | −4.976 | 53.705 | 100.216 | 1.00 | 2.00 | 0 |
| ATOM | 336 | CA | CYS | 39 | −5.613 | 54.690 | 101.099 | 1.00 | 2.00 | 0 |
| ATOM | 337 | CB | CYS | 39 | −5.339 | 56.096 | 100.607 | 1.00 | 2.00 | 0 |
| ATOM | 338 | SG | CYS | 39 | −3.719 | 56.686 | 100.830 | 1.00 | 2.00 | 0 |
| ATOM | 339 | C | CYS | 39 | −7.140 | 54.555 | 101.201 | 1.00 | 2.00 | 0 |
| ATOM | 340 | O | CYS | 39 | −7.708 | 54.580 | 102.296 | 1.00 | 2.00 | 0 |
| ATOM | 341 | N | LEU | 40 | −7.793 | 54.412 | 100.053 | 1.00 | 2.00 | 0 |
| ATOM | 343 | CA | LEU | 40 | −9.233 | 54.330 | 99.999 | 1.00 | 2.00 | 0 |
| ATOM | 344 | CB | LEU | 40 | −9.735 | 54.704 | 98.599 | 1.00 | 2.00 | 0 |
| ATOM | 345 | CG | LEU | 40 | −10.127 | 56.184 | 98.419 | 1.00 | 2.00 | 0 |
| ATOM | 346 | CD1 | LEU | 40 | −9.020 | 57.095 | 98.939 | 1.00 | 2.00 | 0 |
| ATOM | 347 | CD2 | LEU | 40 | −10.401 | 56.484 | 96.960 | 1.00 | 2.00 | 0 |
| ATOM | 348 | C | LEU | 40 | −9.817 | 53.014 | 100.426 | 1.00 | 2.00 | 0 |
| ATOM | 349 | O | LEU | 40 | −10.853 | 52.987 | 101.071 | 1.00 | 2.00 | 0 |
| ATOM | 350 | N | LYS | 41 | −9.174 | 51.916 | 100.081 | 1.00 | 7.31 | 0 |
| ATOM | 352 | CA | LYS | 41 | −9.721 | 50.630 | 100.468 | 1.00 | 7.31 | 0 |
| ATOM | 353 | CB | LYS | 41 | −9.123 | 49.517 | 99.598 | 1.00 | 2.00 | 0 |
| ATOM | 354 | CG | LYS | 41 | −9.685 | 48.157 | 99.884 | 1.00 | 2.00 | 0 |
| ATOM | 355 | CD | LYS | 41 | −11.188 | 48.216 | 99.923 | 1.00 | 2.00 | 0 |
| ATOM | 356 | CE | LYS | 41 | −11.746 | 46.968 | 100.560 | 1.00 | 2.00 | 0 |
| ATOM | 357 | NZ | LYS | 41 | −11.188 | 45.721 | 99.910 | 1.00 | 2.00 | 0 |
| ATOM | 361 | C | LYS | 41 | 9.475 | 50.376 | 101.963 | 1.00 | 7.31 | 0 |
| ATOM | 362 | O | LYS | 41 | −10.375 | 49.934 | 102.674 | 1.00 | 2.00 | 0 |
| ATOM | 363 | N | SER | 42 | −8.266 | 50.666 | 102.440 | 1.00 | 3.34 | 0 |
| ATOM | 365 | CA | SER | 42 | −7.935 | 50.477 | 103.844 | 1.00 | 3.34 | 0 |
| ATOM | 366 | CB | SER | 42 | −6.496 | 50.854 | 104.094 | 1.00 | 2.00 | 0 |
| ATOM | 367 | OG | SER | 42 | −6.315 | 52.215 | 103.766 | 1.00 | 2.00 | 0 |
| ATOM | 369 | C | SER | 42 | −8.844 | 51.398 | 104.650 | 1.00 | 7.34 | 0 |
| ATOM | 370 | O | SER | 42 | −9.504 | 50.955 | 105.600 | 1.00 | 2.00 | 0 |
| ATOM | 371 | N | ARG | 43 | −8.906 | 52.671 | 104.247 | 1.00 | 2.00 | 0 |
| ATOM | 373 | CA | ARG | 43 | −9.746 | 53.650 | 104.928 | 1.00 | 2.00 | 0 |
| ATOM | 374 | CB | ARG | 43 | −9.856 | 54.946 | 104.135 | 1.00 | 2.00 | 0 |
| ATOM | 375 | CG | ARG | 43 | −10.530 | 56.063 | 104.917 | 1.00 | 2.00 | 0 |
| ATOM | 376 | CD | ARG | 43 | −11.541 | 56.826 | 104.097 | 1.00 | 2.00 | 0 |
| ATOM | 377 | NE | ARG | 43 | −11.803 | 58.137 | 104.679 | 1.00 | 2.00 | 0 |
| ATOM | 379 | CZ | ARG | 43 | −13.010 | 58.603 | 105.005 | 1.00 | 2.00 | 0 |
| ATOM | 380 | NH1 | ARG | 43 | −14.112 | 57.877 | 104.826 | 1.00 | 2.00 | 0 |
| ATOM | 383 | NH2 | ARG | 43 | −13.120 | 59.827 | 105.502 | 1.00 | 2.00 | 0 |
| ATOM | 386 | C | ARG | 43 | −11.136 | 53.103 | 105.104 | 1.00 | 2.00 | 0 |
| ATOM | 387 | O | ARG | 43 | −11.800 | 53.385 | 106.083 | 1.00 | 2.00 | 0 |
| ATOM | 388 | N | GLU | 44 | −11.574 | 52.321 | 104.130 | 1.00 | 19.11 | 0 |
| ATOM | 390 | CA | GLU | 44 | −12.901 | 51.727 | 104.146 | 1.00 | 19.41 | 0 |
| ATOM | 391 | CB | GLU | 44 | −13.179 | 51.107 | 102.776 | 1.00 | 23.41 | 0 |
| ATOM | 392 | CG | GLU | 44 | −14.599 | 50.695 | 102.542 | 1.00 | 34.12 | 0 |
| ATOM | 393 | CD | GLU | 44 | −14.711 | 49.574 | 101.532 | 1.00 | 38.72 | 0 |
| ATOM | 394 | OE1 | GLU | 44 | −15.634 | 49.626 | 100.699 | 1.00 | 43.51 | 0 |
| ATOM | 395 | OE2 | GLU | 44 | −13.886 | 48.639 | 101.576 | 1.00 | 35.90 | 0 |
| ATOM | 396 | C | GLU | 44 | −12.987 | 50.674 | 105.260 | 1.00 | 20.56 | 0 |
| ATOM | 397 | O | GLU | 44 | −13.967 | 50.622 | 106.007 | 1.00 | 24.61 | 0 |
| ATOM | 398 | N | ILE | 45 | −11.945 | 49.857 | 105.379 | 1.00 | 8.30 | 0 |
| ATOM | 400 | CA | ILE | 45 | −11.896 | 48.811 | 106.384 | 1.00 | 8.30 | 0 |
| ATOM | 401 | CB | ILE | 45 | −10.720 | 47.876 | 106.133 | 1.00 | 2.00 | 0 |
| ATOM | 402 | CG2 | ILE | 45 | −10.795 | 46.678 | 107.049 | 1.00 | 2.00 | 0 |

TABLE A-continued

| ATOM | 403 | CG1 | ILE | 45 | −10.774 | 47.382 | 104.698 | 1.00 | 2.00 | 0 |
|------|-----|-----|-----|----|---------|--------|---------|------|------|---|
| ATOM | 404 | CD1 | ILE | 45 | −9.559 | 46.593 | 104.285 | 1.00 | 2.00 | 0 |
| ATOM | 405 | C | ILE | 45 | −11.775 | 49.401 | 107.784 | 1.00 | 8.30 | 0 |
| ATOM | 406 | O | ILE | 45 | −12.249 | 48.819 | 108.756 | 1.00 | 2.00 | 0 |
| ATOM | 407 | N | PHE | 46 | −11.134 | 50.550 | 107.905 | 1.00 | 2.00 | 0 |
| ATOM | 409 | CA | PHE | 46 | −11.013 | 51.154 | 109.214 | 1.00 | 2.00 | 0 |
| ATOM | 410 | CB | PHE | 46 | −10.076 | 52.352 | 109.176 | 1.00 | 2.00 | 0 |
| ATOM | 411 | CG | PHE | 46 | −8.665 | 51.992 | 108.843 | 1.00 | 2.00 | 0 |
| ATOM | 412 | CD1 | PHE | 46 | −7.829 | 52.906 | 108.223 | 1.00 | 2.00 | 0 |
| ATOM | 413 | CD2 | PHE | 46 | −8.168 | 50.726 | 109.151 | 1.00 | 2.00 | 0 |
| ATOM | 414 | CE1 | PHE | 46 | −6.516 | 52.558 | 107.915 | 1.00 | 2.00 | 0 |
| ATOM | 415 | CE2 | PHE | 46 | −6.859 | 50.375 | 108.845 | 1.00 | 2.00 | 0 |
| ATOM | 416 | CZ | PHE | 46 | −6.027 | 51.289 | 108.227 | 1.00 | 2.00 | 0 |
| ATOM | 417 | C | PHE | 46 | −12.396 | 51.561 | 109.686 | 1.00 | 2.00 | 0 |
| ATOM | 418 | O | PHE | 46 | −12.840 | 51.109 | 110.731 | 1.00 | 2.00 | 0 |
| ATOM | 419 | N | LEU | 47 | −13.106 | 52.358 | 108.896 | 1.00 | 2.00 | 0 |
| ATOM | 421 | CA | LEU | 47 | −14.441 | 52.807 | 109.277 | 1.00 | 2.00 | 0 |
| ATOM | 422 | CB | LEU | 47 | −15.043 | 53.705 | 108.190 | 1.00 | 2.00 | 0 |
| ATOM | 423 | CG | LEU | 47 | −14.641 | 55.181 | 108.110 | 1.00 | 2.00 | 0 |
| ATOM | 424 | CD1 | LEU | 47 | −14.094 | 55.641 | 109.462 | 1.00 | 2.00 | 0 |
| ATOM | 425 | CD2 | LEU | 47 | −13.619 | 55.397 | 107.030 | 1.00 | 2.00 | 0 |
| ATOM | 426 | C | LEU | 47 | −15.424 | 51.677 | 109.578 | 1.00 | 2.00 | 0 |
| ATOM | 427 | O | LEU | 47 | −16.432 | 51.905 | 110.243 | 1.00 | 2.00 | 0 |
| ATOM | 428 | N | SER | 48 | −15.145 | 50.469 | 109.091 | 1.00 | 2.00 | 0 |
| ATOM | 430 | CA | SER | 48 | −16.037 | 49.339 | 109.305 | 1.00 | 2.00 | 0 |
| ATOM | 431 | CB | SER | 48 | −16.121 | 48.483 | 108.039 | 1.00 | 23.35 | 0 |
| ATOM | 432 | OG | SER | 48 | −14.844 | 48.045 | 107.622 | 1.00 | 30.63 | 0 |
| ATOM | 434 | C | SER | 48 | −15.624 | 48.473 | 110.482 | 1.00 | 2.00 | 0 |
| ATOM | 435 | O | SER | 48 | −16.184 | 47.390 | 110.700 | 1.00 | 28.70 | 0 |
| ATOM | 436 | N | GLN | 49 | −14.627 | 48.922 | 111.225 | 1.00 | 61.72 | 0 |
| ATOM | 438 | CA | GLN | 49 | −14.175 | 48.193 | 112.394 | 1.00 | 63.25 | 0 |
| ATOM | 439 | CB | GLN | 49 | −12.763 | 47.645 | 112.173 | 1.00 | 13.32 | 0 |
| ATOM | 440 | CG | GLN | 49 | −12.668 | 46.511 | 111.146 | 1.00 | 7.00 | 0 |
| ATOM | 441 | CD | GLN | 49 | −11.246 | 45.952 | 110.995 | 1.00 | 8.88 | 0 |
| ATOM | 442 | OE1 | GLN | 49 | −10.251 | 46.640 | 111.258 | 1.00 | 9.23 | 0 |
| ATOM | 443 | NE2 | GLN | 49 | −11.151 | 44.700 | 110.573 | 1.00 | 7.45 | 0 |
| ATOM | 446 | C | GLN | 49 | −14.210 | 49.205 | 113.540 | 1.00 | 63.04 | 0 |
| ATOM | 447 | O | GLN | 49 | −13.864 | 50.373 | 113.357 | 1.00 | 14.61 | 0 |
| ATOM | 448 | N | PRO | 50 | −14.645 | 48.778 | 114.734 | 1.00 | 34.58 | 0 |
| ATOM | 449 | CD | PRO | 50 | −14.967 | 47.399 | 115.118 | 1.00 | 4.65 | 0 |
| ATOM | 450 | CA | PRO | 50 | −14.728 | 49.657 | 115.901 | 1.00 | 34.58 | 0 |
| ATOM | 451 | CB | PRO | 50 | −15.037 | 48.678 | 117.032 | 1.00 | 2.00 | 0 |
| ATOM | 452 | CG | PRO | 50 | −14.496 | 47.365 | 116.531 | 1.00 | 2.00 | 0 |
| ATOM | 453 | C | PRO | 50 | −13.459 | 50.468 | 116.164 | 1.00 | 34.58 | 0 |
| ATOM | 454 | O | PRO | 50 | −12.356 | 50.002 | 115.884 | 1.00 | 2.95 | 0 |
| ATOM | 455 | N | ILE | 51 | −13.626 | 51.673 | 116.708 | 1.00 | 2.00 | 0 |
| ATOM | 457 | CA | ILE | 51 | −12.499 | 52.550 | 117.015 | 1.00 | 2.00 | 0 |
| ATOM | 458 | CB | ILE | 51 | −13.001 | 53.975 | 117.318 | 1.00 | 2.00 | 0 |
| ATOM | 459 | CG2 | ILE | 51 | −13.642 | 54.035 | 118.673 | 1.00 | 2.00 | 0 |
| ATOM | 460 | CG1 | ILE | 51 | −11.850 | 54.958 | 117.295 | 1.00 | 2.00 | 0 |
| ATOM | 461 | CD1 | ILE | 51 | −12.328 | 56.370 | 117.351 | 1.00 | 2.00 | 0 |
| ATOM | 462 | C | ILE | 51 | −11.650 | 51.996 | 118.172 | 1.00 | 2.00 | 0 |
| ATOM | 463 | O | ILE | 51 | −10.456 | 52.303 | 118.283 | 1.00 | 2.00 | 0 |
| ATOM | 464 | N | LEU | 52 | −12.284 | 51.187 | 119.028 | 1.00 | 2.00 | 0 |
| ATOM | 466 | CA | LEU | 52 | −11.622 | 50.522 | 120.159 | 1.00 | 2.00 | 0 |
| ATOM | 467 | CB | LEU | 52 | −12.391 | 50.746 | 121.473 | 1.00 | 2.00 | 0 |
| ATOM | 468 | CG | LEU | 52 | −11.655 | 50.518 | 122.808 | 1.00 | 2.00 | 0 |
| ATOM | 469 | CD1 | LEU | 52 | −12.559 | 50.899 | 123.944 | 1.00 | 2.00 | 0 |
| ATOM | 470 | CD2 | LEU | 52 | −11.233 | 49.085 | 122.973 | 1.00 | 2.00 | 0 |
| ATOM | 471 | C | LEU | 52 | −11.660 | 49.033 | 119.770 | 1.00 | 2.00 | 0 |
| ATOM | 472 | O | LEU | 52 | −12.652 | 48.331 | 120.006 | 1.00 | 2.00 | 0 |
| ATOM | 473 | N | LEU | 53 | −10.584 | 48.576 | 119.136 | 1.00 | 2.00 | 0 |
| ATOM | 475 | CA | LEU | 53 | −10.464 | 47.204 | 118.667 | 1.00 | 2.00 | 0 |
| ATOM | 476 | CB | LEU | 53 | −9.066 | 46.982 | 118.069 | 1.00 | 2.00 | 0 |
| ATOM | 477 | CG | LEU | 53 | −8.802 | 47.038 | 116.555 | 1.00 | 2.00 | 0 |
| ATOM | 478 | CD1 | LEU | 53 | −9.835 | 47.889 | 115.810 | 1.00 | 2.00 | 0 |
| ATOM | 479 | CD2 | LEU | 53 | −7.401 | 47.550 | 116.353 | 1.00 | 2.00 | 0 |
| ATOM | 480 | C | LEU | 53 | −10.686 | 46.230 | 119.792 | 1.00 | 2.00 | 0 |
| ATOM | 481 | O | LEU | 53 | −10.365 | 46.522 | 120.937 | 1.00 | 2.00 | 0 |
| ATOM | 482 | N | GLU | 54 | −11.251 | 45.076 | 119.472 | 1.00 | 19.77 | 0 |
| ATOM | 484 | CA | GLU | 54 | −11.465 | 44.049 | 120.474 | 1.00 | 20.13 | 0 |
| ATOM | 485 | CB | GLU | 54 | −12.955 | 43.809 | 120.714 | 1.00 | 56.32 | 0 |
| ATOM | 486 | CG | GLU | 54 | −13.244 | 43.362 | 122.135 | 1.00 | 66.19 | 0 |
| ATOM | 487 | CD | GLU | 54 | −14.668 | 42.873 | 122.346 | 1.00 | 69.64 | 0 |
| ATOM | 488 | OE1 | GLU | 54 | −15.613 | 43.627 | 122.024 | 1.00 | 78.06 | 0 |
| ATOM | 489 | OE2 | GLU | 54 | −14.839 | 41.734 | 122.848 | 1.00 | 73.27 | 0 |
| ATOM | 490 | C | GLU | 54 | −10.798 | 42.820 | 119.882 | 1.00 | 19.77 | 0 |
| ATOM | 491 | O | GLU | 54 | −11.451 | 41.949 | 119.313 | 1.00 | 48.57 | 0 |
| ATOM | 492 | N | LEU | 55 | −9.473 | 42.800 | 119.974 | 1.00 | 2.00 | 0 |

TABLE A-continued

| | | | | | | | | | |
|---|---|---|---|---|---|---|---|---|---|
| ATOM | 494 | CA | LEU | 55 | −8.666 | 41.712 | 119.452 | 1.00 | 2.00 | 0 |
| ATOM | 495 | CB | LEU | 55 | −7.245 | 42.188 | 119.176 | 1.00 | 2.00 | 0 |
| ATOM | 496 | CG | LEU | 55 | −7.148 | 43.458 | 118.336 | 1.00 | 2.00 | 0 |
| ATOM | 497 | CD1 | LEU | 55 | −5.695 | 43.728 | 117.961 | 1.00 | 2.00 | 0 |
| ATOM | 498 | CD2 | LEU | 55 | −8.024 | 43.298 | 117.108 | 1.00 | 2.00 | 0 |
| ATOM | 499 | C | LEU | 55 | −8.624 | 40.586 | 120.456 | 1.00 | 2.00 | 0 |
| ATOM | 500 | O | LEU | 55 | −8.724 | 40.807 | 121.664 | 1.00 | 10.45 | 0 |
| ATOM | 501 | N | GLU | 56 | −8.448 | 39.374 | 119.961 | 1.00 | 2.00 | 0 |
| ATOM | 503 | CA | GLU | 56 | −8.407 | 38.224 | 120.826 | 1.00 | 2.00 | 0 |
| ATOM | 504 | CB | GLU | 56 | −9.741 | 37.467 | 120.729 | 1.00 | 18.79 | 0 |
| ATOM | 505 | CG | GLU | 56 | −10.989 | 38.283 | 121.171 | 1.00 | 30.34 | 0 |
| ATOM | 506 | CD | GLU | 56 | −11.012 | 38.677 | 122.658 | 1.00 | 42.94 | 0 |
| ATOM | 507 | OE1 | GLU | 56 | −11.188 | 37.789 | 123.526 | 1.00 | 44.70 | 0 |
| ATOM | 508 | OE2 | GLU | 56 | −10.872 | 39.882 | 122.955 | 1.00 | 47.48 | 0 |
| ATOM | 509 | C | GLU | 56 | −7.244 | 37.343 | 120.393 | 1.00 | 2.00 | 0 |
| ATOM | 510 | O | GLU | 56 | −6.292 | 37.839 | 119.800 | 1.00 | 3.40 | 0 |
| ATOM | 511 | N | ALA | 57 | −7.312 | 36.062 | 120.765 | 1.00 | 65.90 | 0 |
| ATOM | 513 | CA | ALA | 57 | −6.336 | 35.026 | 120.405 | 1.00 | 62.88 | 0 |
| ATOM | 514 | CB | ALA | 57 | −6.750 | 34.434 | 119.039 | 1.00 | 26.61 | 0 |
| ATOM | 515 | C | ALA | 57 | −4.867 | 35.474 | 120.387 | 1.00 | 68.03 | 0 |
| ATOM | 516 | O | ALA | 57 | −4.543 | 36.519 | 120.932 | 1.00 | 14.05 | 0 |
| ATOM | 517 | N | PRO | 58 | −3.951 | 34.632 | 119.857 | 1.00 | 2.00 | 0 |
| ATOM | 518 | CD | PRO | 58 | −4.109 | 33.203 | 119.533 | 1.00 | 9.23 | 0 |
| ATOM | 519 | CA | PRO | 58 | −2.526 | 34.988 | 119.782 | 1.00 | 2.00 | 0 |
| ATOM | 520 | CB | PRO | 58 | −1.852 | 33.645 | 119.501 | 1.00 | 9.23 | 0 |
| ATOM | 521 | CG | PRO | 58 | −2.881 | 32.926 | 118.711 | 1.00 | 9.49 | 0 |
| ATOM | 522 | C | PRO | 58 | −2.176 | 36.002 | 118.672 | 1.00 | 2.00 | 0 |
| ATOM | 523 | O | PRO | 58 | −2.688 | 35.901 | 117.540 | 1.00 | 12.29 | 0 |
| ATOM | 524 | N | LEU | 59 | −1.284 | 36.947 | 118.975 | 1.00 | 17.05 | 0 |
| ATOM | 526 | CA | LEU | 59 | −0.856 | 37.944 | 117.989 | 1.00 | 17.05 | 0 |
| ATOM | 527 | CB | LEU | 59 | −1.862 | 39.100 | 117.895 | 1.00 | 2.00 | 0 |
| ATOM | 528 | CG | LEU | 59 | −1.842 | 40.166 | 118.993 | 1.00 | 2.00 | 0 |
| ATOM | 529 | CD1 | LEU | 59 | −2.880 | 41.252 | 118.706 | 1.00 | 2.00 | 0 |
| ATOM | 530 | CD2 | LEU | 59 | −2.117 | 39.498 | 120.339 | 1.00 | 2.00 | 0 |
| ATOM | 531 | C | LEU | 59 | 0.510 | 38.501 | 118.351 | 1.00 | 17.05 | 0 |
| ATOM | 532 | O | LEU | 59 | 1.030 | 38.229 | 119.429 | 1.00 | 2.00 | 0 |
| ATOM | 533 | N | LYS | 60 | 1.103 | 39.259 | 117.438 | 1.00 | 21.64 | 0 |
| ATOM | 535 | CA | LYS | 60 | 2.399 | 39.872 | 117.688 | 1.00 | 21.64 | 0 |
| ATOM | 536 | CB | LYS | 60 | 3.358 | 39.655 | 116.513 | 1.00 | 10.44 | 0 |
| ATOM | 537 | CG | LYS | 60 | 3.185 | 38.327 | 115.768 | 1.00 | 11.70 | 0 |
| ATOM | 538 | CD | LYS | 60 | 3.556 | 37.101 | 116.608 | 1.00 | 12.19 | 0 |
| ATOM | 539 | CE | LYS | 60 | 5.034 | 36.783 | 116.544 | 1.00 | 8.37 | 0 |
| ATOM | 540 | NZ | LYS | 60 | 5.824 | 37.927 | 117.066 | 1.00 | 8.37 | 0 |
| ATOM | 544 | C | LYS | 60 | 2.063 | 41.353 | 117.804 | 1.00 | 21.64 | 0 |
| ATOM | 545 | O | LYS | 60 | 1.142 | 41.832 | 117.128 | 1.00 | 13.47 | 0 |
| ATOM | 546 | N | ILE | 61 | 2.757 | 42.072 | 118.680 | 1.00 | 20.60 | 0 |
| ATOM | 548 | CA | ILE | 61 | 2.499 | 43.496 | 118.822 | 1.00 | 22.32 | 0 |
| ATOM | 549 | CB | ILE | 61 | 2.032 | 43.859 | 120.240 | 1.00 | 2.00 | 0 |
| ATOM | 550 | CG2 | ILE | 61 | 1.485 | 45.288 | 120.239 | 1.00 | 2.00 | 0 |
| ATOM | 551 | CG1 | ILE | 61 | 0.940 | 42.881 | 120.702 | 1.00 | 2.00 | 0 |
| ATOM | 552 | CD1 | ILE | 61 | 0.019 | 43.422 | 121.783 | 1.00 | 2.00 | 0 |
| ATOM | 553 | C | ILE | 61 | 3.791 | 44.220 | 118.494 | 1.00 | 23.52 | 0 |
| ATOM | 554 | O | ILE | 61 | 4.862 | 43.752 | 118.868 | 1.00 | 2.00 | 0 |
| ATOM | 555 | N | CYS | 62 | 3.698 | 45.341 | 117.787 | 1.00 | 2.00 | 0 |
| ATOM | 557 | CA | CYS | 62 | 4.874 | 46.095 | 117.393 | 1.00 | 2.00 | 0 |
| ATOM | 558 | CB | CYS | 62 | 5.147 | 45.925 | 115.895 | 1.00 | 11.47 | 0 |
| ATOM | 559 | SG | CYS | 62 | 5.439 | 44.252 | 115.266 | 1.00 | 11.47 | 0 |
| ATOM | 560 | C | CYS | 62 | 4.607 | 47.560 | 117.658 | 1.00 | 2.00 | 0 |
| ATOM | 561 | O | CYS | 62 | 3.451 | 47.957 | 117.751 | 1.00 | 11.47 | 0 |
| ATOM | 562 | N | GLY | 63 | 5.662 | 48.367 | 117.739 | 1.00 | 2.00 | 0 |
| ATOM | 564 | CA | GLY | 63 | 5.507 | 49.789 | 117.971 | 1.00 | 2.00 | 0 |
| ATOM | 565 | C | GLY | 63 | 6.548 | 50.610 | 117.222 | 1.00 | 2.00 | 0 |
| ATOM | 566 | O | GLY | 63 | 7.624 | 50.109 | 116.897 | 1.00 | 11.39 | 0 |
| ATOM | 567 | N | ASP | 64 | 6.216 | 51.870 | 116.959 | 1.00 | 2.00 | 0 |
| ATOM | 569 | CA | ASP | 64 | 7.068 | 52.834 | 116.255 | 1.00 | 3.88 | 0 |
| ATOM | 570 | CB | ASP | 64 | 7.805 | 53.721 | 117.245 | 1.00 | 6.62 | 0 |
| ATOM | 571 | CG | ASP | 64 | 6.873 | 54.589 | 118.025 | 1.00 | 6.62 | 0 |
| ATOM | 572 | OD1 | ASP | 64 | 5.996 | 54.019 | 118.708 | 1.00 | 12.70 | 0 |
| ATOM | 573 | OD2 | ASP | 64 | 7.003 | 55.829 | 117.946 | 1.00 | 12.70 | 0 |
| ATOM | 574 | C | ASP | 64 | 8.064 | 52.362 | 115.221 | 1.00 | 14.37 | 0 |
| ATOM | 575 | O | ASP | 64 | 9.221 | 52.080 | 115.557 | 1.00 | 8.57 | 0 |
| ATOM | 576 | N | ILE | 65 | 7.619 | 52.326 | 113.963 | 1.00 | 5.19 | 0 |
| ATOM | 578 | CA | ILE | 65 | 8.471 | 51.924 | 112.849 | 1.00 | 3.07 | 0 |
| ATOM | 579 | CB | ILE | 65 | 7.663 | 51.310 | 111.672 | 1.00 | 2.00 | 0 |
| ATOM | 580 | CG2 | ILE | 65 | 8.609 | 50.903 | 110.535 | 1.00 | 2.00 | 0 |
| ATOM | 581 | CG1 | ILE | 65 | 6.871 | 50.095 | 112.151 | 1.00 | 2.00 | 0 |
| ATOM | 582 | CD1 | ILE | 65 | 7.723 | 49.023 | 112.763 | 1.00 | 2.00 | 0 |
| ATOM | 583 | C | ILE | 65 | 9.185 | 53.177 | 112.357 | 1.00 | 2.24 | 0 |
| ATOM | 584 | O | ILE | 65 | 10.379 | 53.148 | 112.101 | 1.00 | 2.00 | 0 |

TABLE A-continued

| | | | | | | | | | |
|---|---|---|---|---|---|---|---|---|---|
| ATOM | 585 | N | HIS | 66 | 8.451 | 54.276 | 112.235 | 1.00 | 2.00 | 0 |
| ATOM | 587 | CA | HIS | 66 | 9.022 | 55.536 | 111.776 | 1.00 | 2.00 | 0 |
| ATOM | 588 | C | HIS | 66 | 9.847 | 55.525 | 110.502 | 1.00 | 2.00 | 0 |
| ATOM | 589 | O | HIS | 66 | 11.042 | 55.818 | 110.539 | 1.00 | 12.38 | 0 |
| ATOM | 590 | CB | HIS | 66 | 9.846 | 56.182 | 112.88 | 1.00 | 8.25 | 0 |
| ATOM | 591 | CG | HIS | 66 | 9.040 | 57.046 | 113.782 | 1.00 | 8.25 | 0 |
| ATOM | 592 | ND1 | HIS | 66 | 8.104 | 57.949 | 113.337 | 1.00 | 8.25 | 0 |
| ATOM | 594 | CD2 | HIS | 66 | 9.001 | 57.109 | 115.133 | 1.00 | 8.25 | 0 |
| ATOM | 595 | NE2 | HIS | 66 | 8.042 | 58.043 | 115.526 | 1.00 | 6.25 | 0 |
| ATOM | 596 | CE1 | HIS | 66 | 7.536 | 58.516 | 114.399 | 1.00 | 8.25 | 0 |
| ATOM | 597 | N | GLY | 67 | 9.197 | 55.195 | 109.385 | 1.00 | 11.52 | 0 |
| ATOM | 599 | CA | GLY | 67 | 9.835 | 55.174 | 108.078 | 1.00 | 11.52 | 0 |
| ATOM | 600 | C | GLY | 67 | 11.029 | 54.266 | 107.868 | 1.00 | 11.52 | 0 |
| ATOM | 601 | O | GLY | 67 | 11.782 | 54.462 | 106.915 | 1.00 | 81.94 | 0 |
| ATOM | 602 | N | GLN | 68 | 11.214 | 53.272 | 108.730 | 1.00 | 18.96 | 0 |
| ATOM | 604 | CA | GLN | 68 | 12.353 | 52.364 | 108.602 | 1.00 | 20.32 | 0 |
| ATOM | 605 | CB | GLN | 68 | 13.007 | 52.139 | 109.957 | 1.00 | 6.39 | 0 |
| ATOM | 606 | CG | GLN | 68 | 13.261 | 53.407 | 110.711 | 1.00 | 4.06 | 0 |
| ATOM | 607 | CD | GLN | 68 | 14.315 | 53.239 | 111.757 | 1.00 | 7.01 | 0 |
| ATOM | 608 | OE1 | GLN | 68 | 15.013 | 54.197 | 112.111 | 1.00 | 8.21 | 0 |
| ATOM | 609 | NE2 | GLN | 68 | 14.453 | 52.020 | 112.270 | 1.00 | 5.84 | 0 |
| ATOM | 612 | C | GLN | 68 | 11.916 | 51.039 | 108.010 | 1.00 | 18.72 | 0 |
| ATOM | 613 | O | GLN | 68 | 12.018 | 49.975 | 108.634 | 1.00 | 10.73 | 0 |
| ATOM | 614 | N | TYR | 69 | 11.450 | 51.119 | 106.777 | 1.00 | 5.70 | 0 |
| ATOM | 616 | CA | TYR | 69 | 10.959 | 49.970 | 106.054 | 1.00 | 5.52 | 0 |
| ATOM | 617 | CB | TYR | 69 | 10.807 | 50.313 | 104.587 | 1.00 | 2.00 | 0 |
| ATOM | 618 | CG | TYR | 69 | 9.988 | 49.322 | 103.841 | 1.00 | 2.00 | 0 |
| ATOM | 619 | CD1 | TYR | 69 | 8.658 | 49.099 | 104.187 | 1.00 | 2.00 | 0 |
| ATOM | 620 | CE1 | TYR | 69 | 7.873 | 48.194 | 103.477 | 1.00 | 2.00 | 0 |
| ATOM | 621 | CD2 | TYR | 69 | 10.526 | 48.611 | 102.762 | 1.00 | 2.00 | 0 |
| ATOM | 622 | CE2 | TYR | 69 | 9.751 | 47.701 | 102.038 | 1.00 | 2.00 | 0 |
| ATOM | 623 | CZ | TYR | 69 | 8.431 | 47.506 | 102.408 | 1.00 | 2.00 | 0 |
| ATOM | 624 | OH | TYR | 69 | 7.656 | 46.632 | 101.715 | 1.00 | 2.00 | 0 |
| ATOM | 626 | C | TYR | 69 | 11.815 | 48.730 | 106.188 | 1.00 | 8.52 | 0 |
| ATOM | 627 | O | TYR | 69 | 11.284 | 47.641 | 106.393 | 1.00 | 2.00 | 0 |
| ATOM | 628 | N | TYR | 70 | 13.132 | 48.877 | 106.093 | 1.00 | 2.00 | 0 |
| ATOM | 630 | CA | TYR | 70 | 13.992 | 47.703 | 106.186 | 1.00 | 2.00 | 0 |
| ATOM | 631 | CB | TYR | 70 | 15.420 | 48.031 | 105.741 | 1.00 | 64.80 | 0 |
| ATOM | 632 | CG | TYR | 70 | 15.533 | 47.964 | 104.231 | 1.00 | 70.91 | 0 |
| ATOM | 633 | CD1 | TYR | 70 | 15.026 | 48.993 | 103.431 | 1.00 | 73.06 | 0 |
| ATOM | 634 | CE1 | TYR | 70 | 15.082 | 48.924 | 102.041 | 1.00 | 68.38 | 0 |
| ATOM | 635 | CD2 | TYR | 70 | 16.107 | 46.857 | 103.597 | 1.00 | 73.86 | 0 |
| ATOM | 636 | CE2 | TYR | 70 | 16.171 | 46.780 | 102.200 | 1.00 | 70.94 | 0 |
| ATOM | 637 | CZ | TYR | 70 | 15.654 | 47.820 | 101.433 | 1.00 | 72.52 | 0 |
| ATOM | 638 | OH | TYR | 70 | 15.712 | 47.779 | 100.062 | 1.00 | 70.35 | 0 |
| ATOM | 640 | C | TYR | 70 | 13.943 | 47.007 | 107.538 | 1.00 | 2.00 | 0 |
| ATOM | 641 | O | TYR | 70 | 13.967 | 45.771 | 107.610 | 1.00 | 64.08 | 0 |
| ATOM | 642 | N | ASP | 71 | 13.821 | 47.789 | 108.608 | 1.00 | 7.87 | 0 |
| ATOM | 644 | CA | ASP | 71 | 13.728 | 47.203 | 109.927 | 1.00 | 6.73 | 0 |
| ATOM | 645 | CB | ASP | 71 | 14.030 | 48.242 | 110.998 | 1.00 | 14.88 | 0 |
| ATOM | 646 | CG | ASP | 71 | 15.514 | 48.600 | 111.054 | 1.00 | 25.87 | 0 |
| ATOM | 647 | OD1 | ASP | 71 | 15.826 | 49.778 | 111.293 | 1.00 | 24.58 | 0 |
| ATOM | 648 | OD2 | ASP | 71 | 16.375 | 47.714 | 110.861 | 1.00 | 21.52 | 0 |
| ATOM | 649 | C | ASP | 71 | 12.331 | 46.622 | 110.051 | 1.00 | 6.73 | 0 |
| ATOM | 650 | O | ASP | 71 | 12.116 | 45.697 | 110.826 | 1.00 | 14.14 | 0 |
| ATOM | 651 | N | LEU | 72 | 11.399 | 47.148 | 109.250 | 1.00 | 2.00 | 0 |
| ATOM | 653 | CA | LEU | 72 | 10.015 | 46.654 | 109.208 | 1.00 | 2.00 | 0 |
| ATOM | 654 | CB | LEU | 72 | 9.094 | 47.613 | 108.456 | 1.00 | 2.00 | 0 |
| ATOM | 655 | CG | LEU | 72 | 7.771 | 46.946 | 108.067 | 1.00 | 2.00 | 0 |
| ATOM | 656 | CD1 | LEU | 72 | 7.025 | 46.562 | 109.342 | 1.00 | 2.00 | 0 |
| ATOM | 657 | CD2 | LEU | 72 | 6.935 | 47.867 | 107.208 | 1.00 | 2.00 | 0 |
| ATOM | 658 | C | LEU | 72 | 10.014 | 45.320 | 108.476 | 1.00 | 2.00 | 0 |
| ATOM | 659 | O | LEU | 72 | 9.259 | 44.401 | 108.814 | 1.00 | 2.00 | 0 |
| ATOM | 660 | N | LEU | 73 | 10.848 | 45.231 | 107.449 | 1.00 | 44.35 | 0 |
| ATOM | 662 | CA | LEU | 73 | 10.968 | 44.005 | 106.693 | 1.00 | 42.59 | 0 |
| ATOM | 663 | CB | LEU | 73 | 11.846 | 44.218 | 105.460 | 1.00 | 2.00 | 0 |
| ATOM | 664 | CG | LEU | 73 | 11.248 | 44.759 | 104.160 | 1.00 | 2.00 | 0 |
| ATOM | 665 | CD1 | LEU | 73 | 12.324 | 44.728 | 103.101 | 1.00 | 2.00 | 0 |
| ATOM | 666 | CD2 | LEU | 73 | 10.052 | 43.920 | 103.725 | 1.00 | 2.00 | 0 |
| ATOM | 667 | C | LEU | 73 | 11.603 | 42.978 | 107.629 | 1.00 | 42.42 | 0 |
| ATOM | 668 | O | LEU | 73 | 11.059 | 41.890 | 107.817 | 1.00 | 2.00 | 0 |
| ATOM | 669 | N | ARG | 74 | 12.729 | 43.354 | 108.241 | 1.00 | 2.00 | 0 |
| ATOM | 671 | CA | ARG | 74 | 13.462 | 42.494 | 109.179 | 1.00 | 2.00 | 0 |
| ATOM | 672 | CB | ARG | 74 | 14.591 | 43.285 | 109.840 | 1.00 | 31.22 | 0 |
| ATOM | 673 | CG | ARG | 74 | 15.909 | 43.478 | 108.958 | 1.00 | 31.18 | 0 |
| ATOM | 674 | CD | ARG | 74 | 16.944 | 44.146 | 109.710 | 1.00 | 37.63 | 0 |
| ATOM | 675 | NE | ARG | 74 | 17.250 | 43.459 | 110.960 | 1.00 | 37.44 | 0 |
| ATOM | 677 | CZ | ARG | 74 | 17.210 | 44.041 | 112.157 | 1.00 | 41.10 | 0 |
| ATOM | 678 | NH1 | ARG | 74 | 16.888 | 45.327 | 112.265 | 1.00 | 39.99 | 0 |

TABLE A-continued

| | | | | | | | | | |
|---|---|---|---|---|---|---|---|---|---|
| ATOM | 681 | NH2 | ARG | 74 | 17.476 | 43.339 | 113.254 | 1.00 | 39.22 | 0 |
| ATOM | 684 | C | ARG | 74 | 12.569 | 41.896 | 110.259 | 1.00 | 2.00 | 0 |
| ATOM | 685 | O | ARG | 74 | 12.621 | 40.703 | 110.544 | 1.00 | 29.18 | 0 |
| ATOM | 686 | N | LEU | 75 | 11.747 | 42.742 | 110.853 | 1.00 | 2.00 | 0 |
| ATOM | 688 | CA | LEU | 75 | 10.818 | 42.331 | 111.901 | 1.00 | 2.00 | 0 |
| ATOM | 689 | CB | LEU | 75 | 10.069 | 43.580 | 112.407 | 1.00 | 3.53 | 0 |
| ATOM | 690 | CG | LEU | 75 | 8.704 | 43.654 | 113.091 | 1.00 | 3.53 | 0 |
| ATOM | 691 | CD1 | LEU | 75 | 8.554 | 45.074 | 113.606 | 1.00 | 3.53 | 0 |
| ATOM | 692 | CD2 | LEU | 75 | 7.561 | 43.337 | 112.138 | 1.00 | 3.53 | 0 |
| ATOM | 693 | C | LEU | 75 | 9.850 | 41.279 | 111.384 | 1.00 | 2.00 | 0 |
| ATOM | 694 | O | LEU | 75 | 9.594 | 40.284 | 112.043 | 1.00 | 3.53 | 0 |
| ATOM | 695 | N | PHE | 76 | 9.325 | 41.514 | 110.190 | 1.00 | 2.00 | 0 |
| ATOM | 697 | CA | PHE | 76 | 8.382 | 40.604 | 109.573 | 1.00 | 2.00 | 0 |
| ATOM | 698 | CB | PHE | 76 | 7.883 | 41.173 | 108.255 | 1.00 | 2.00 | 0 |
| ATOM | 699 | CG | PHE | 76 | 6.626 | 41.966 | 108.382 | 1.00 | 2.00 | 0 |
| ATOM | 700 | CD1 | PHE | 76 | 6.447 | 43.124 | 107.642 | 1.00 | 2.00 | 0 |
| ATOM | 701 | CD2 | PHE | 76 | 5.616 | 41.550 | 109.240 | 1.00 | 2.00 | 0 |
| ATOM | 702 | CE1 | PHE | 76 | 5.277 | 43.852 | 107.753 | 1.00 | 2.00 | 0 |
| ATOM | 703 | CE2 | PHE | 76 | 4.447 | 42.270 | 109.358 | 1.00 | 2.00 | 0 |
| ATOM | 704 | CZ | PHE | 76 | 4.272 | 43.423 | 108.615 | 1.00 | 2.00 | 0 |
| ATOM | 705 | C | PHE | 76 | 9.016 | 39.271 | 109.322 | 1.00 | 2.00 | 0 |
| ATOM | 706 | O | PHE | 76 | 8.339 | 38.260 | 109.363 | 1.00 | 2.00 | 0 |
| ATOM | 707 | N | GLU | 77 | 10.316 | 39.283 | 109.043 | 1.00 | 2.00 | 0 |
| ATOM | 709 | CA | GLU | 77 | 11.080 | 38.065 | 108.789 | 1.00 | 2.00 | 0 |
| ATOM | 710 | CB | GLU | 77 | 12.436 | 38.409 | 108.191 | 1.00 | 84.85 | 0 |
| ATOM | 711 | CG | GLU | 77 | 12.331 | 39.117 | 106.861 | 1.00 | 89.26 | 0 |
| ATOM | 712 | CD | GLU | 77 | 13.651 | 39.690 | 106.391 | 1.00 | 98.60 | 0 |
| ATOM | 713 | OE1 | GLU | 77 | 13.627 | 40.493 | 105.434 | 1.00 | 98.04 | 0 |
| ATOM | 714 | OE2 | GLU | 77 | 14.709 | 39.345 | 106.973 | 1.00 | 0.97 | 0 |
| ATOM | 715 | C | GLU | 77 | 11.262 | 37.316 | 110.100 | 1.00 | 2.00 | 0 |
| ATOM | 716 | O | GLU | 77 | 11.469 | 36.103 | 110.099 | 1.00 | 80.75 | 0 |
| ATOM | 717 | N | TYR | 78 | 11.182 | 38.045 | 111.216 | 1.00 | 15.29 | 0 |
| ATOM | 719 | CA | TYR | 78 | 11.325 | 37.449 | 112.538 | 1.00 | 15.29 | 0 |
| ATOM | 720 | CB | TYR | 78 | 11.945 | 38.455 | 113.514 | 1.00 | 67.13 | 0 |
| ATOM | 721 | CG | TYR | 78 | 12.459 | 37.828 | 114.796 | 1.00 | 69.14 | 0 |
| ATOM | 722 | CD1 | TYR | 78 | 11.822 | 36.717 | 115.368 | 1.00 | 76.95 | 0 |
| ATOM | 723 | CE1 | TYR | 78 | 12.278 | 36.142 | 116.548 | 1.00 | 77.96 | 0 |
| ATOM | 724 | CD2 | TYR | 78 | 13.577 | 38.346 | 115.446 | 1.00 | 75.81 | 0 |
| ATOM | 725 | CE2 | TYR | 78 | 14.044 | 37.775 | 116.638 | 1.00 | 77.77 | 0 |
| ATOM | 726 | CZ | TYR | 78 | 13.387 | 36.673 | 117.181 | 1.00 | 77.18 | 0 |
| ATOM | 727 | OH | TYR | 78 | 13.826 | 36.115 | 118.365 | 1.00 | 87.14 | 0 |
| ATOM | 729 | C | TYR | 78 | 9.967 | 36.964 | 113.053 | 1.00 | 15.29 | 0 |
| ATOM | 730 | O | TYR | 78 | 9.811 | 35.796 | 113.403 | 1.00 | 62.78 | 0 |
| ATOM | 731 | N | GLY | 79 | 8.992 | 37.863 | 113.117 | 1.00 | 2.00 | 0 |
| ATOM | 733 | CA | GLY | 79 | 7.675 | 37.485 | 113.582 | 1.00 | 2.00 | 0 |
| ATOM | 734 | C | GLY | 79 | 6.977 | 36.532 | 112.629 | 1.00 | 2.00 | 0 |
| ATOM | 735 | O | GLY | 79 | 6.226 | 35.649 | 113.052 | 1.00 | 34.11 | 0 |
| ATOM | 736 | N | GLY | 80 | 7.237 | 36.699 | 111.338 | 1.00 | 49.23 | 0 |
| ATOM | 738 | CA | GLY | 80 | 6.601 | 35.870 | 110.330 | 1.00 | 48.34 | 0 |
| ATOM | 739 | C | GLY | 80 | 5.699 | 36.782 | 109.520 | 1.00 | 47.91 | 0 |
| ATOM | 740 | O | GLY | 80 | 4.955 | 37.572 | 110.097 | 1.00 | 15.83 | 0 |
| ATOM | 741 | N | PHE | 81 | 5.759 | 36.692 | 108.193 | 1.00 | 2.00 | 0 |
| ATOM | 743 | CA | PHE | 81 | 4.948 | 37.558 | 107.343 | 1.00 | 2.00 | 0 |
| ATOM | 744 | CB | PHE | 81 | 5.386 | 37.403 | 105.880 | 1.00 | 2.00 | 0 |
| ATOM | 745 | CG | PHE | 81 | 6.673 | 38.134 | 105.556 | 1.00 | 2.00 | 0 |
| ATOM | 746 | CD1 | PHE | 81 | 7.899 | 37.506 | 105.685 | 1.00 | 2.00 | 0 |
| ATOM | 747 | CD2 | PHE | 81 | 6.652 | 39.467 | 105.139 | 1.00 | 2.00 | 0 |
| ATOM | 748 | CE1 | PHE | 81 | 9.082 | 38.193 | 105.405 | 1.00 | 2.00 | 0 |
| ATOM | 749 | CE2 | PHE | 81 | 7.829 | 40.154 | 104.859 | 1.00 | 2.00 | 0 |
| ATOM | 750 | CZ | PHE | 81 | 9.044 | 39.517 | 104.992 | 1.00 | 2.00 | 0 |
| ATOM | 751 | C | PHE | 81 | 3.428 | 37.380 | 107.548 | 1.00 | 2.00 | 0 |
| ATOM | 752 | O | PHE | 81 | 2.918 | 36.257 | 107.636 | 1.00 | 2.00 | 0 |
| ATOM | 753 | N | PRO | 82 | 2.694 | 38.505 | 107.618 | 1.00 | 2.00 | 0 |
| ATOM | 754 | CD | PRO | 82 | 3.317 | 39.807 | 107.337 | 1.00 | 21.23 | 0 |
| ATOM | 755 | CA | PRO | 82 | 1.261 | 38.702 | 107.820 | 1.00 | 2.00 | 0 |
| ATOM | 756 | CB | PRO | 82 | 0.996 | 39.979 | 107.079 | 1.00 | 20.78 | 0 |
| ATOM | 757 | CG | PRO | 82 | 2.144 | 40.765 | 107.502 | 1.00 | 22.98 | 0 |
| ATOM | 758 | C | PRO | 82 | 0.273 | 37.623 | 107.490 | 1.00 | 2.00 | 0 |
| ATOM | 759 | O | PRO | 82 | −0.761 | 37.529 | 108.161 | 1.00 | 36.87 | 0 |
| ATOM | 760 | N | PRO | 83 | 0.501 | 36.841 | 106.423 | 1.00 | 27.66 | 0 |
| ATOM | 761 | CD | PRO | 83 | 1.439 | 36.880 | 105.290 | 1.00 | 2.85 | 0 |
| ATOM | 762 | CA | PRO | 83 | −0.514 | 35.812 | 106.201 | 1.00 | 30.55 | 0 |
| ATOM | 763 | CB | PRO | 83 | 0.089 | 34.958 | 105.083 | 1.00 | 5.44 | 0 |
| ATOM | 764 | CG | PRO | 83 | 1.550 | 35.427 | 104.971 | 1.00 | 10.08 | 0 |
| ATOM | 765 | C | PRO | 83 | −0.791 | 34.990 | 107.460 | 1.00 | 24.53 | 0 |
| ATOM | 766 | O | PRO | 83 | −1.947 | 34.863 | 107.882 | 1.00 | 5.06 | 0 |
| ATOM | 767 | N | GLU | 84 | 0.284 | 34.504 | 108.080 | 1.00 | 63.06 | 0 |
| ATOM | 769 | CA | GLU | 84 | 0.190 | 33.665 | 109.268 | 1.00 | 65.66 | 0 |
| ATOM | 770 | CB | GLU | 84 | 1.448 | 32.797 | 109.382 | 1.00 | 61.87 | 0 |

TABLE A-continued

| | | | | | | | | | |
|---|---|---|---|---|---|---|---|---|---|
| ATOM | 771 | CG | GLU | 84 | 1.194 | 31.402 | 109.979 | 1.00 | 75.07 | 0 |
| ATOM | 772 | CD | GLU | 84 | 0.401 | 30.452 | 109.056 | 1.00 | 79.88 | 0 |
| ATOM | 773 | OE1 | GLU | 84 | 1.015 | 29.508 | 108.504 | 1.00 | 76.25 | 0 |
| ATOM | 774 | OE2 | GLU | 84 | −0.832 | 30.635 | 108.891 | 1.00 | 74.31 | 0 |
| ATOM | 775 | C | GLU | 84 | −0.066 | 34.394 | 110.588 | 1.00 | 66.47 | 0 |
| ATOM | 776 | O | GLU | 84 | −1.194 | 34.406 | 111.085 | 1.00 | 61.22 | 0 |
| ATOM | 777 | N | SER | 85 | 0.984 | 34.978 | 111.161 | 1.00 | 66.52 | 0 |
| ATOM | 779 | CA | SER | 85 | 0.882 | 35.691 | 112.431 | 1.00 | 64.76 | 0 |
| ATOM | 780 | CB | SER | 85 | 2.266 | 36.145 | 112.900 | 1.00 | 2.00 | 0 |
| ATOM | 781 | OG | SER | 85 | 3.198 | 35.078 | 112.871 | 1.00 | 2.00 | 0 |
| ATOM | 783 | C | SER | 85 | −0.013 | 36.917 | 112.349 | 1.00 | 62.83 | 0 |
| ATOM | 784 | O | SER | 85 | −0.005 | 37.633 | 111.341 | 1.00 | 2.00 | 0 |
| ATOM | 785 | N | ASN | 86 | −0.785 | 37.146 | 113.412 | 1.00 | 2.00 | 0 |
| ATOM | 787 | CA | ASN | 86 | −1.647 | 38.321 | 113.490 | 1.00 | 2.00 | 0 |
| ATOM | 788 | CB | ASN | 86 | −2.747 | 38.123 | 114.520 | 1.00 | 2.00 | 0 |
| ATOM | 789 | CG | ASN | 86 | −3.887 | 37.283 | 113.994 | 1.00 | 10.84 | 0 |
| ATOM | 790 | OD1 | ASN | 86 | −3.763 | 36.629 | 112.957 | 1.00 | 12.15 | 0 |
| ATOM | 791 | ND2 | ASN | 86 | −5.017 | 37.300 | 114.705 | 1.00 | 6.45 | 0 |
| ATOM | 794 | C | ASN | 86 | −0.742 | 39.467 | 113.912 | 1.00 | 2.00 | 0 |
| ATOM | 795 | O | ASN | 86 | 0.363 | 39.229 | 114.423 | 1.00 | 2.00 | 0 |
| ATOM | 796 | N | TYR | 87 | −1.183 | 40.703 | 113.723 | 1.00 | 2.00 | 0 |
| ATOM | 798 | CA | TYR | 87 | −0.337 | 41.830 | 114.081 | 1.00 | 2.00 | 0 |
| ATOM | 799 | CB | TYR | 87 | 0.529 | 42.253 | 112.870 | 1.00 | 2.00 | 0 |
| ATOM | 800 | CG | TYR | 87 | 1.802 | 41.448 | 112.684 | 1.00 | 2.00 | 0 |
| ATOM | 801 | CD1 | TYR | 87 | 1.879 | 40.421 | 111.749 | 1.00 | 2.00 | 0 |
| ATOM | 802 | CE1 | TYR | 87 | 3.039 | 39.689 | 111.598 | 1.00 | 2.00 | 0 |
| ATOM | 803 | CD2 | TYR | 87 | 2.930 | 41.714 | 113.458 | 1.00 | 2.00 | 0 |
| ATOM | 804 | CE2 | TYR | 87 | 4.080 | 40.991 | 113.313 | 1.00 | 2.00 | 0 |
| ATOM | 805 | CZ | TYR | 87 | 4.127 | 39.986 | 112.384 | 1.00 | 2.00 | 0 |
| ATOM | 806 | OH | TYR | 87 | 5.280 | 39.281 | 112.259 | 1.00 | 2.00 | 0 |
| ATOM | 808 | C | TYR | 87 | −1.104 | 43.029 | 114.588 | 1.00 | 2.00 | 0 |
| ATOM | 809 | O | TYR | 87 | −2.264 | 43.238 | 114.216 | 1.00 | 2.00 | 0 |
| ATOM | 810 | N | LEU | 88 | −0.440 | 43.810 | 115.435 | 1.00 | 2.00 | 0 |
| ATOM | 812 | CA | LEU | 88 | −1.015 | 45.026 | 115.987 | 1.00 | 2.00 | 0 |
| ATOM | 813 | CB | LEU | 88 | −1.615 | 44.766 | 117.375 | 1.00 | 2.00 | 0 |
| ATOM | 814 | CG | LEU | 88 | −2.364 | 45.917 | 118.062 | 1.00 | 2.00 | 0 |
| ATOM | 815 | CD1 | LEU | 88 | −3.657 | 46.225 | 117.348 | 1.00 | 2.00 | 0 |
| ATOM | 816 | CD2 | LEU | 88 | −2.675 | 45.551 | 119.493 | 1.00 | 2.00 | 0 |
| ATOM | 817 | C | LEU | 88 | 0.119 | 46.034 | 116.084 | 1.00 | 2.00 | 0 |
| ATOM | 818 | O | LEU | 88 | 1.082 | 45.814 | 116.814 | 1.00 | 2.00 | 0 |
| ATDM | 819 | N | PHE | 89 | 0.061 | 47.108 | 115.309 | 1.00 | 2.00 | 0 |
| ATOM | 821 | CA | PHE | 89 | 1.114 | 48.117 | 115.393 | 1.00 | 2.00 | 0 |
| ATOM | 822 | CB | PHE | 89 | 1.567 | 48.599 | 114.004 | 1.00 | 2.00 | 0 |
| ATOM | 823 | CG | PHE | 89 | 2.305 | 47.563 | 113.221 | 1.00 | 2.00 | 0 |
| ATOM | 824 | CD1 | PHE | 89 | 1.617 | 46.543 | 112.578 | 1.00 | 2.00 | 0 |
| ATOM | 825 | CD2 | PHE | 89 | 3.683 | 47.581 | 113.159 | 1.00 | 2.00 | 0 |
| ATOM | 826 | CE1 | PHE | 89 | 2.284 | 45.547 | 111.885 | 1.00 | 2.00 | 0 |
| ATOM | 827 | CE2 | PHE | 89 | 4.379 | 46.586 | 112.464 | 1.00 | 2.00 | 0 |
| ATOM | 828 | CZ | PHE | 89 | 3.673 | 45.565 | 111.826 | 1.00 | 2.00 | 0 |
| ATOM | 829 | C | PHE | 89 | 0.495 | 49.250 | 116.197 | 1.00 | 2.00 | 0 |
| ATOM | 830 | O | PHE | 89 | −0.664 | 49.615 | 115.985 | 1.00 | 2.00 | 0 |
| ATOM | 831 | N | LEU | 90 | 1.271 | 49.797 | 117.124 | 1.00 | 4.99 | 0 |
| ATOM | 833 | CA | LEU | 90 | 0.810 | 50.856 | 118.014 | 1.00 | 4.99 | 0 |
| ATOM | 834 | CB | LEU | 90 | 1.519 | 50.702 | 119.370 | 1.00 | 2.00 | 0 |
| ATOM | 835 | CG | LEU | 90 | 1.516 | 49.291 | 119.991 | 1.00 | 2.00 | 0 |
| ATOM | 836 | CD1 | LEU | 90 | 2.488 | 49.246 | 121.147 | 1.00 | 2.00 | 0 |
| ATOM | 837 | CD2 | LEU | 90 | 0.111 | 48.870 | 120.402 | 1.00 | 2.00 | 0 |
| ATOM | 838 | C | LEU | 90 | 1.000 | 52.275 | 117.463 | 1.00 | 4.99 | 0 |
| ATOM | 839 | O | LEU | 90 | 1.382 | 53.196 | 118.200 | 1.00 | 2.00 | 0 |
| ATOM | 840 | N | GLY | 91 | 0.734 | 52.459 | 116.175 | 1.00 | 14.03 | 0 |
| ATOM | 842 | CA | GLY | 91 | 0.884 | 53.774 | 115.588 | 1.00 | 14.03 | 0 |
| ATOM | 843 | C | GLY | 91 | 2.307 | 54.139 | 115.209 | 1.00 | 14.03 | 0 |
| ATOM | 844 | O | GLY | 91 | 3.220 | 53.312 | 115.267 | 1.00 | 32.27 | 0 |
| ATOM | 845 | N | ASP | 92 | 2.471 | 55.400 | 114.820 | 1.00 | 2.00 | 0 |
| ATOM | 847 | CA | ASP | 92 | 3.736 | 55.978 | 114.382 | 1.00 | 2.00 | 0 |
| ATOM | 848 | CB | ASP | 92 | 4.670 | 56.170 | 115.576 | 1.00 | 2.00 | 0 |
| ATOM | 849 | CG | ASP | 92 | 4.185 | 57.239 | 116.525 | 1.00 | 2.00 | 0 |
| ATOM | 850 | OD1 | ASP | 92 | 3.449 | 56.145 | 116.063 | 1.00 | 2.00 | 0 |
| ATOM | 851 | OD2 | ASP | 92 | 4.541 | 57.177 | 117.725 | 1.00 | 2.00 | 0 |
| ATOM | 852 | C | ASP | 92 | 4.427 | 55.205 | 113.259 | 1.00 | 2.00 | 0 |
| ATOM | 853 | O | ASP | 92 | 5.515 | 54.631 | 113.422 | 1.00 | 2.00 | 0 |
| ATOM | 854 | N | TYR | 93 | 3.792 | 55.234 | 112.096 | 1.00 | 2.00 | 0 |
| ATOM | 856 | CA | TYR | 93 | 4.301 | 54.523 | 110.938 | 1.00 | 2.00 | 0 |
| ATOM | 857 | CB | TYR | 93 | 3.149 | 53.907 | 110.171 | 1.00 | 2.00 | 0 |
| ATOM | 858 | CG | TYR | 93 | 2.122 | 53.226 | 111.029 | 1.00 | 2.00 | 0 |
| ATOM | 859 | CD1 | TYR | 93 | 0.875 | 53.801 | 111.227 | 1.00 | 2.00 | 0 |
| ATOM | 860 | CE1 | TYR | 93 | −0.086 | 53.176 | 112.004 | 1.00 | 2.00 | 0 |
| ATOM | 861 | CD2 | TYR | 93 | 2.390 | 52.002 | 111.628 | 1.00 | 2.00 | 0 |
| ATOM | 862 | CE2 | TYR | 93 | 1.445 | 51.362 | 112.405 | 1.00 | 2.00 | 0 |

TABLE A-continued

| | | | | | | | | | | |
|---|---|---|---|---|---|---|---|---|---|---|
| ATOM | 863 | CZ | TYR | 93 | 0.204 | 51.951 | 112.593 | 1.00 | 2.00 | 0 |
| ATOM | 864 | OH | TYR | 93 | −0.736 | 51.315 | 113.379 | 1.00 | 2.00 | 0 |
| ATOM | 866 | C | TYR | 93 | 5.088 | 55.399 | 109.992 | 1.00 | 2.00 | 0 |
| ATOM | 867 | O | TYR | 93 | 5.998 | 54.922 | 109.335 | 1.00 | 2.00 | 0 |
| ATOM | 868 | N | VAL | 94 | 4.718 | 56.667 | 109.904 | 1.00 | 2.00 | 0 |
| ATOM | 870 | CA | VAL | 94 | 5.380 | 57.607 | 109.004 | 1.00 | 2.00 | 0 |
| ATOM | 871 | CB | VAL | 94 | 4.322 | 58.340 | 108.112 | 1.00 | 2.00 | 0 |
| ATOM | 872 | CG1 | VAL | 94 | 3.365 | 57.315 | 107.523 | 1.00 | 2.00 | 0 |
| ATOM | 873 | CG2 | VAL | 94 | 3.551 | 59.356 | 108.903 | 1.00 | 2.00 | 0 |
| ATOM | 874 | C | VAL | 94 | 6.253 | 58.614 | 109.780 | 1.00 | 2.00 | 0 |
| ATOM | 875 | O | VAL | 94 | 6.447 | 58.457 | 110.985 | 1.00 | 2.00 | 0 |
| ATOM | 876 | N | ASP | 95 | 6.774 | 59.629 | 109.094 | 1.00 | 8.40 | 0 |
| ATOM | 878 | CA | ASP | 95 | 7.641 | 60.648 | 109.689 | 1.00 | 2.00 | 0 |
| ATOM | 879 | CB | ASP | 95 | 6.967 | 61.356 | 110.868 | 1.00 | 39.32 | 0 |
| ATOM | 880 | CG | ASP | 95 | 5.975 | 62.433 | 110.449 | 1.00 | 45.35 | 0 |
| ATOM | 881 | OD1 | ASP | 95 | 6.227 | 63.167 | 109.471 | 1.00 | 44.75 | 0 |
| ATOM | 882 | OD2 | ASP | 95 | 4.937 | 62.561 | 111.127 | 1.00 | 53.79 | 0 |
| ATOM | 883 | C | ASP | 95 | 8.975 | 60.074 | 110.155 | 1.00 | 2.71 | 0 |
| ATOM | 884 | O | ASP | 95 | 9.092 | 58.877 | 110.421 | 1.00 | 37.69 | 0 |
| ATOM | 885 | N | ARG | 96 | 9.972 | 60.949 | 110.252 | 1.00 | 21.97 | 0 |
| ATOM | 887 | CA | ARG | 96 | 11.322 | 60.589 | 110.685 | 1.00 | 27.39 | 0 |
| ATOM | 888 | CB | ARG | 96 | 11.285 | 59.989 | 112.099 | 1.00 | 18.63 | 0 |
| ATOM | 889 | CG | ARG | 96 | 12.037 | 60.816 | 113.128 | 1.00 | 24.81 | 0 |
| ATOM | 890 | CD | ARG | 96 | 11.255 | 62.052 | 113.581 | 1.00 | 32.64 | 0 |
| ATOM | 891 | NE | ARG | 96 | 10.551 | 61.833 | 114.850 | 1.00 | 39.46 | 0 |
| ATOM | 893 | CZ | ARG | 96 | 9.890 | 62.774 | 115.525 | 1.00 | 39.86 | 0 |
| ATOM | 894 | NH1 | ARG | 96 | 9.824 | 64.018 | 115.066 | 1.00 | 40.95 | 0 |
| ATOM | 897 | NH2 | ARG | 96 | 9.290 | 62.471 | 116.670 | 1.00 | 44.56 | 0 |
| ATOM | 900 | C | ARG | 96 | 12.109 | 59.659 | 109.732 | 1.00 | 24.24 | 0 |
| ATOM | 901 | C | ARG | 96 | 13.114 | 60.072 | 109.135 | 1.00 | 13.09 | 0 |
| ATOM | 902 | N | GLY | 97 | 11.668 | 58.411 | 109.592 | 1.00 | 19.94 | 0 |
| ATOM | 904 | CA | GLY | 97 | 12.359 | 57.480 | 108.716 | 1.00 | 20.45 | 0 |
| ATOM | 905 | C | GLY | 97 | 12.412 | 57.920 | 107.269 | 1.00 | 23.76 | 0 |
| ATOM | 906 | O | GLY | 97 | 11.516 | 58.617 | 106.773 | 1.00 | 84.64 | 0 |
| ATOM | 907 | N | LYS | 98 | 13.460 | 57.469 | 106.584 | 1.00 | 47.57 | 0 |
| ATOM | 909 | CA | LYS | 98 | 13.698 | 57.806 | 105.182 | 1.00 | 46.79 | 0 |
| ATOM | 910 | CB | LYS | 98 | 15.147 | 57.462 | 104.832 | 1.00 | 31.45 | 0 |
| ATOM | 911 | CG | LYS | 98 | 16.169 | 58.397 | 105.487 | 1.00 | 30.73 | 0 |
| ATOM | 912 | CD | LYS | 98 | 17.606 | 59.061 | 105.087 | 1.00 | 32.79 | 0 |
| ATOM | 913 | CE | LYS | 98 | 18.605 | 59.089 | 105.627 | 1.00 | 30.08 | 0 |
| ATOM | 914 | NZ | LYS | 98 | 20.036 | 58.743 | 105.315 | 1.00 | 31.54 | 0 |
| ATOM | 918 | C | LYS | 98 | 12.741 | 57.196 | 104.146 | 1.00 | 44.78 | 0 |
| ATOM | 919 | O | LYS | 98 | 12.613 | 57.707 | 103.040 | 1.00 | 31.43 | 0 |
| ATOM | 920 | N | GLN | 99 | 12.059 | 56.120 | 104.517 | 1.00 | 2.00 | 0 |
| ATOM | 922 | CA | GLN | 99 | 11.132 | 55.430 | 103.639 | 1.00 | 2.00 | 0 |
| ATOM | 923 | CB | GLN | 99 | 11.654 | 54.023 | 103.337 | 1.00 | 11.21 | 0 |
| ATOM | 924 | CG | GLN | 99 | 12.945 | 53.993 | 102.552 | 1.00 | 6.66 | 0 |
| ATOM | 925 | CD | GLN | 99 | 13.361 | 52.586 | 102.177 | 1.00 | 11.01 | 0 |
| ATOM | 926 | OE1 | GLN | 99 | 13.802 | 51.805 | 103.031 | 1.00 | 10.44 | 0 |
| ATOM | 927 | NE2 | GLN | 99 | 13.229 | 52.247 | 100.895 | 1.00 | 8.18 | 0 |
| ATOM | 930 | C | GLN | 99 | 9.741 | 55.328 | 104.245 | 1.00 | 2.00 | 0 |
| ATOM | 931 | O | GLN | 99 | 9.177 | 54.238 | 104.317 | 1.00 | 6.66 | 0 |
| ATOM | 932 | N | SER | 100 | 9.178 | 56.460 | 104.657 | 1.00 | 24.01 | 0 |
| ATOM | 934 | CA | SER | 100 | 7.839 | 56.475 | 105.257 | 1.00 | 24.01 | 0 |
| ATOM | 935 | CB | SER | 100 | 7.481 | 57.897 | 105.739 | 1.00 | 2.00 | 0 |
| ATOM | 936 | OG | SER | 100 | 8.479 | 58.490 | 106.556 | 1.00 | 2.00 | 0 |
| ATOM | 938 | C | SBR | 100 | 6.749 | 55.987 | 104.272 | 1.00 | 24.01 | 0 |
| ATOM | 939 | O | SER | 100 | 5.703 | 55.463 | 104.680 | 1.00 | 2.00 | 0 |
| ATOM | 940 | N | LEU | 101 | 7.015 | 56.153 | 102.977 | 1.00 | 27.83 | 0 |
| ATOM | 942 | CA | LEU | 101 | 6.064 | 55.786 | 101.913 | 1.00 | 27.83 | 0 |
| ATOM | 943 | CB | LEU | 101 | 6.551 | 56.416 | 100.599 | 1.00 | 3.66 | 0 |
| ATOM | 944 | CG | LEU | 101 | 5.593 | 57.224 | 99.721 | 1.00 | 3.66 | 0 |
| ATOM | 945 | CD1 | LEU | 101 | 4.209 | 56.591 | 99.749 | 1.00 | 3.66 | 0 |
| ATOM | 946 | CD2 | LEU | 101 | 5.532 | 58.653 | 100.208 | 1.00 | 3.66 | 0 |
| ATOM | 947 | C | LEU | 101 | 5.852 | 54.284 | 101.689 | 1.00 | 27.83 | 0 |
| ATOM | 948 | O | LEU | 101 | 4.731 | 53.851 | 101.467 | 1.00 | 3.66 | 0 |
| ATOM | 949 | N | GLU | 102 | 6.901 | 53.480 | 101.725 | 1.00 | 2.00 | 0 |
| ATOM | 951 | CA | GLU | 102 | 6.713 | 52.055 | 101.490 | 1.00 | 2.00 | 0 |
| ATOM | 952 | CB | GLU | 102 | 7.976 | 51.470 | 100.870 | 1.00 | 13.98 | 0 |
| ATOM | 953 | CG | GLU | 102 | 9.211 | 52.208 | 101.294 | 1.00 | 13.98 | 0 |
| ATOM | 954 | CD | GLU | 102 | 10.116 | 52.539 | 100.136 | 1.00 | 13.98 | 0 |
| ATOM | 955 | OE1 | GLU | 102 | 10.151 | 53.727 | 99.737 | 1.00 | 13.98 | 0 |
| ATOM | 956 | OE2 | GLU | 102 | 10.772 | 51.599 | 99.643 | 1.00 | 13.98 | 0 |
| ATOM | 957 | C | GLU | 102 | 6.307 | 51.324 | 102.763 | 1.00 | 2.00 | 0 |
| ATOM | 958 | O | GLU | 102 | 5.686 | 50.263 | 102.729 | 1.00 | 13.98 | 0 |
| ATOM | 959 | N | THR | 103 | 6.664 | 51.901 | 103.897 | 1.00 | 2.00 | 0 |
| ATOM | 961 | CA | THR | 103 | 6.293 | 51.330 | 105.173 | 1.00 | 2.00 | 0 |
| ATOM | 962 | CB | THR | 103 | 6.923 | 52.098 | 106.309 | 1.00 | 2.00 | 0 |
| ATOM | 963 | OG1 | THR | 103 | 8.313 | 52.297 | 106.028 | 1.00 | 2.00 | 0 |

TABLE A-continued

| | | | | | | | | | |
|---|---|---|---|---|---|---|---|---|---|
| ATOM | 965 | CG2 | THR | 103 | 6.758 | 51.329 | 107.599 | 1.00 | 2.00 | 0 |
| ATOM | 966 | C | THR | 103 | 4.775 | 51.440 | 105.296 | 1.00 | 2.00 | 0 |
| ATOM | 967 | O | THR | 103 | 4.081 | 50.428 | 105.394 | 1.00 | 2.00 | 0 |
| ATOM | 968 | N | ILE | 104 | 4.256 | 52.667 | 105.257 | 1.00 | 2.00 | 0 |
| ATOM | 970 | CA | ILE | 104 | 2.824 | 52.873 | 105.363 | 1.00 | 2.00 | 0 |
| ATOM | 971 | CB | ILE | 104 | 2.486 | 54.389 | 105.300 | 1.00 | 12.72 | 0 |
| ATOM | 972 | CG2 | ILE | 104 | 2.856 | 54.965 | 103.956 | 1.00 | 12.35 | 0 |
| ATOM | 973 | CG1 | ILE | 104 | 0.996 | 54.615 | 105.548 | 1.00 | 13.84 | 0 |
| ATOM | 974 | CD1 | ILE | 104 | 0.459 | 53.940 | 106.787 | 1.00 | 12.35 | 0 |
| ATOM | 975 | C | ILE | 104 | 2.074 | 52.062 | 104.294 | 1.00 | 2.00 | 0 |
| ATOM | 976 | O | ILE | 104 | 0.975 | 51.581 | 104.544 | 1.00 | 18.28 | 0 |
| ATOM | 977 | N | CYS | 105 | 2.690 | 51.868 | 103.127 | 1.00 | 23.45 | 0 |
| ATOM | 979 | CA | CYS | 105 | 2.080 | 51.092 | 102.042 | 1.00 | 21.74 | 0 |
| ATOM | 980 | CB | CYS | 105 | 2.722 | 51.458 | 100.708 | 1.00 | 20.76 | 0 |
| ATOM | 981 | SG | CYS | 105 | 2.010 | 52.958 | 99.957 | 1.00 | 18.03 | 0 |
| ATOM | 982 | C | CYS | 105 | 2.061 | 49.563 | 102.214 | 1.00 | 17.08 | 0 |
| ATOM | 983 | O | CYS | 105 | 1.114 | 48.915 | 101.781 | 1.00 | 20.76 | 0 |
| ATOM | 984 | N | LEU | 106 | 3.089 | 48.952 | 102.833 | 1.00 | 2.00 | 0 |
| ATOM | 986 | CA | LEU | 106 | 3.124 | 47.526 | 103.073 | 1.00 | 2.00 | 0 |
| ATOM | 987 | CB | LEU | 106 | 4.519 | 47.042 | 103.495 | 1.00 | 2.00 | 0 |
| ATOM | 988 | CG | LEU | 106 | 4.680 | 45.544 | 103.802 | 1.00 | 2.00 | 0 |
| ATOM | 989 | CD1 | LEU | 106 | 4.200 | 44.694 | 102.639 | 1.00 | 2.00 | 0 |
| ATOM | 990 | CD2 | LEU | 106 | 6.133 | 45.247 | 104.053 | 1.00 | 2.00 | 0 |
| ATOM | 991 | C | LEU | 106 | 2.154 | 47.179 | 104.178 | 1.00 | 2.00 | 0 |
| ATOM | 992 | O | LEU | 106 | 1.589 | 46.088 | 104.192 | 1.00 | 2.00 | 0 |
| ATOM | 993 | N | LEU | 107 | 1.992 | 48.107 | 105.116 | 1.00 | 2.00 | 0 |
| ATOM | 995 | CA | LEU | 107 | 1.078 | 47.922 | 106.226 | 1.00 | 2.00 | 0 |
| ATOM | 996 | CB | LEU | 107 | 1.347 | 48.967 | 107.319 | 1.00 | 2.00 | 0 |
| ATOM | 997 | CG | LEU | 107 | 2.761 | 48.857 | 107.911 | 1.00 | 2.00 | 0 |
| ATOM | 998 | CD1 | LEU | 107 | 3.106 | 50.016 | 108.815 | 1.00 | 2.00 | 0 |
| ATOM | 999 | CD2 | LEU | 107 | 2.868 | 47.535 | 108.638 | 1.00 | 2.00 | 0 |
| ATOM | 1000 | C | LEU | 107 | −0.339 | 48.035 | 105.683 | 1.00 | 2.00 | 0 |
| ATOM | 1001 | O | LEU | 107 | −1.153 | 47.125 | 105.873 | 1.00 | 2.00 | 0 |
| ATOM | 1002 | N | LEU | 108 | −0.623 | 49.126 | 104.971 | 1.00 | 2.00 | 0 |
| ATOM | 1004 | CA | LEU | 108 | −1.953 | 49.340 | 104.394 | 1.00 | 2.00 | 0 |
| ATOM | 1005 | CB | LEU | 108 | −2.020 | 50.666 | 103.637 | 1.00 | 2.00 | 0 |
| ATOM | 1006 | CG | LEU | 108 | −2.103 | 51.925 | 104.499 | 1.00 | 2.00 | 0 |
| ATOM | 1007 | CD1 | LEU | 108 | −2.244 | 53.164 | 103.618 | 1.00 | 2.00 | 0 |
| ATOM | 1008 | CD2 | LEU | 108 | −3.281 | 51.792 | 105.433 | 1.00 | 2.00 | 0 |
| ATOM | 1009 | C | LEU | 108 | −2.352 | 48.206 | 103.455 | 1.00 | 2.00 | 0 |
| ATOM | 1010 | O | LEU | 108 | −3.533 | 47.846 | 103.369 | 1.00 | 2.00 | 0 |
| ATOM | 1011 | N | ALA | 109 | −1.366 | 47.643 | 102.762 | 1.00 | 2.00 | 0 |
| ATOM | 1013 | CA | ALA | 109 | −1.608 | 46.539 | 101.839 | 1.00 | 2.00 | 0 |
| ATOM | 1014 | CB | ALA | 109 | −0.336 | 46.209 | 101.087 | 1.00 | 33.06 | 0 |
| ATOM | 1015 | C | ALA | 109 | −2.091 | 45.316 | 102.605 | 1.00 | 2.00 | 0 |
| ATOM | 1016 | O | ALA | 109 | −3.146 | 44.746 | 102.305 | 1.00 | 24.92 | 0 |
| ATOM | 1017 | N | TYR | 110 | −1.311 | 44.929 | 103.609 | 1.00 | 5.11 | 0 |
| ATOM | 1019 | CA | TYR | 110 | −1.625 | 43.781 | 104.452 | 1.00 | 2.00 | 0 |
| ATOM | 1020 | CB | TYR | 110 | −0.495 | 43.564 | 105.438 | 1.00 | 2.00 | 0 |
| ATOM | 1021 | CG | TYR | 110 | 0.674 | 42.771 | 104.922 | 1.00 | 2.00 | 0 |
| ATOM | 1022 | CD1 | TYR | 110 | 1.966 | 43.235 | 105.092 | 1.00 | 2.00 | 0 |
| ATOM | 1023 | CE1 | TYR | 110 | 3.053 | 42.474 | 104.706 | 1.00 | 2.00 | 0 |
| ATOM | 1024 | CD2 | TYR | 110 | 0.494 | 41.517 | 104.340 | 1.00 | 2.00 | 0 |
| ATOM | 1025 | CE2 | TYR | 110 | 1.578 | 40.743 | 103.950 | 1.00 | 2.00 | 0 |
| ATOM | 1026 | CZ | TYR | 110 | 2.859 | 41.230 | 104.139 | 1.00 | 2.00 | 0 |
| ATOM | 1027 | OH | TYR | 110 | 3.963 | 40.483 | 103.779 | 1.00 | 2.00 | 0 |
| ATOM | 1029 | C | TYR | 110 | −2.948 | 43.940 | 105.215 | 1.00 | 2.00 | 0 |
| ATOM | 1030 | O | TYR | 110 | −3.663 | 42.961 | 105.441 | 1.00 | 2.00 | 0 |
| ATOM | 1031 | N | LYS | 111 | −3.265 | 45.168 | 105.618 | 1.00 | 2.00 | 0 |
| AYOM | 1033 | CA | LYS | 111 | −4.508 | 45.430 | 106.333 | 1.00 | 2.00 | 0 |
| ATOM | 1034 | CB | LYS | 111 | −4.619 | 46.904 | 106.708 | 1.00 | 2.00 | 0 |
| ATOM | 1035 | CG | LYS | 111 | −5.942 | 47.262 | 107.393 | 1.00 | 2.00 | 0 |
| ATOM | 1036 | CD | LYS | 111 | −6.065 | 46.501 | 108.685 | 1.00 | 2.00 | 0 |
| ATOM | 1037 | CE | LYS | 111 | −7.410 | 46.743 | 109.354 | 1.00 | 2.00 | 0 |
| ATOM | 1038 | NZ | LYS | 111 | −7.643 | 45.735 | 110.428 | 1.00 | 2.00 | 0 |
| ATOM | 1042 | C | LYS | 111 | −5.698 | 45.051 | 105.465 | 1.00 | 2.00 | 0 |
| ATOM | 1043 | O | LYS | 111 | −6.655 | 44.431 | 105.951 | 1.00 | 2.00 | 0 |
| ATOM | 1044 | N | ILE | 112 | −5.624 | 45.455 | 104.192 | 1.00 | 2.00 | 0 |
| ATOM | 1046 | CA | ILE | 112 | −6.651 | 45.192 | 103.177 | 1.00 | 2.00 | 0 |
| ATOM | 1047 | CB | ILE | 112 | −6.361 | 45.978 | 101.875 | 1.00 | 25.04 | 0 |
| ATOM | 1048 | CG2 | ILE | 112 | −7.414 | 45.656 | 100.814 | 1.00 | 25.04 | 0 |
| ATOM | 1049 | CG1 | ILE | 112 | −6.339 | 47.482 | 102.166 | 1.00 | 25.04 | 0 |
| ATOM | 1050 | CD1 | ILE | 112 | −5.857 | 48.336 | 101.012 | 1.00 | 25.04 | 0 |
| ATOM | 1051 | C | ILE | 112 | −6.706 | 43.706 | 102.829 | 1.00 | 2.00 | 0 |
| ATOM | 1052 | O | ILE | 112 | −7.793 | 43.156 | 102.568 | 1.00 | 25.04 | 0 |
| ATOM | 1053 | N | LYS | 113 | −5.537 | 43.067 | 102.816 | 1.00 | 2.00 | 0 |
| ATOM | 1055 | CA | LYS | 113 | 5.447 | 41.649 | 102.513 | 1.00 | 2.00 | 0 |
| ATOM | 1056 | CB | LYS | 113 | −4.001 | 41.285 | 102.181 | 1.00 | 8.72 | 0 |
| ATOM | 1057 | CG | LYS | 113 | −3.852 | 39.909 | 101.596 | 1.00 | 8.72 | 0 |

TABLE A-continued

| | | | | | | | | | |
|---|---|---|---|---|---|---|---|---|---|
| ATOM | 1058 | CD | LYS | 113 | −2.780 | 39.871 | 100.521 | 1.00 | 8.72 | 0 |
| ATOM | 1059 | CE | LYS | 113 | −2.618 | 38.467 | 99.975 | 1.00 | 8.72 | 0 |
| ATOM | 1060 | NZ | LYS | 113 | −3.952 | 37.873 | 99.637 | 1.00 | 8.72 | 0 |
| ATOM | 1064 | C | LYS | 113 | −5.987 | 40.780 | 103.667 | 1.00 | 2.00 | 0 |
| ATOM | 1065 | O | LYS | 113 | −6.620 | 39.742 | 103.435 | 1.00 | 8.72 | 0 |
| ATOM | 1066 | N | TYR | 114 | −5.744 | 41.200 | 104.906 | 1.00 | 9.02 | 0 |
| ATOM | 1068 | CA | TYR | 114 | −6.226 | 40.455 | 106.068 | 1.00 | 8.11 | 0 |
| ATOM | 1069 | CB | TYR | 114 | −5.122 | 39.580 | 106.666 | 1.00 | 12.47 | 0 |
| ATOM | 1070 | CC | TYR | 114 | −4.138 | 38.988 | 105.689 | 1.00 | 12.47 | 0 |
| ATOM | 1071 | CD1 | TYR | 114 | −3.027 | 39.715 | 105.278 | 1.00 | 12.47 | 0 |
| ATOM | 1072 | CE1 | TYR | 114 | −2.111 | 39.191 | 104.397 | 1.00 | 12.47 | 0 |
| ATOM | 1073 | CD2 | TYR | 114 | −4.307 | 37.709 | 105.188 | 1.00 | 12.47 | 0 |
| ATOM | 1074 | CE2 | TYR | 114 | −3.395 | 37.168 | 104.302 | 1.00 | 12.47 | 0 |
| ATOM | 1075 | CZ | TYR | 114 | −2.296 | 37.917 | 103.908 | 1.00 | 12.47 | 0 |
| ATOM | 1076 | OH | TYR | 114 | −1.378 | 37.404 | 103.013 | 1.00 | 12.47 | 0 |
| ATOM | 1078 | C | TYR | 114 | −6.729 | 41.417 | 107.155 | 1.00 | 9.76 | 0 |
| ATOM | 1079 | O | TYR | 114 | −6.058 | 41.636 | 108.169 | 1.00 | 12.47 | 0 |
| ATOM | 1080 | N | PRO | 115 | −7.928 | 41.985 | 106.968 | 1.00 | 34.30 | 0 |
| ATOM | 1081 | CD | PRO | 115 | −8.843 | 41.845 | 105.826 | 1.00 | 24.86 | 0 |
| ATOM | 1082 | CA | PRO | 115 | −8.488 | 42.912 | 107.944 | 1.00 | 34.30 | 0 |
| ATOM | 1083 | CB | PRO | 115 | −9.862 | 43.227 | 107.365 | 1.00 | 24.86 | 0 |
| ATOM | 1084 | CG | PRO | 115 | −9.640 | 43.117 | 105.921 | 1.00 | 24.86 | 0 |
| ATOM | 1085 | C | PRO | 115 | −8.586 | 42.310 | 109.335 | 1.00 | 34.30 | 0 |
| ATOM | 1086 | O | PRO | 115 | −8.017 | 42.937 | 110.285 | 1.00 | 24.86 | 0 |
| ATOM | 1087 | N | GLU | 116 | −9.275 | 41.181 | 109.445 | 1.00 | 2.00 | 0 |
| ATOM | 1089 | CA | GLU | 116 | −9.477 | 40.538 | 110.742 | 1.00 | 2.00 | 0 |
| ATOM | 1090 | CB | GLU | 116 | −10.577 | 39.469 | 110.637 | 1.00 | 35.30 | 0 |
| ATOM | 1091 | CG | GLU | 116 | −11.673 | 39.726 | 109.593 | 1.00 | 37.08 | 0 |
| ATOM | 1092 | CD | GLU | 116 | −12.739 | 40.728 | 110.027 | 1.00 | 43.38 | 0 |
| ATOM | 1093 | OE1 | GLU | 116 | −13.060 | 41.641 | 109.235 | 1.00 | 47.93 | 0 |
| ATOM | 1094 | OE2 | GLU | 116 | −13.274 | 40.599 | 111.147 | 1.00 | 48.80 | 0 |
| ATOM | 1095 | C | GLU | 116 | −8.213 | 39.902 | 111.358 | 1.00 | 2.00 | 0 |
| ATOM | 1096 | O | GLU | 116 | −8.296 | 39.287 | 112.424 | 1.00 | 32.95 | 0 |
| ATOM | 1097 | N | ASN | 117 | −7.054 | 40.067 | 110.712 | 1.00 | 2.00 | 0 |
| ATOM | 1099 | CA | ASN | 117 | −5.820 | 39.455 | 111.211 | 1.00 | 2.00 | 0 |
| ATOM | 1100 | CB | ASN | 117 | −5.457 | 38.220 | 110.375 | 1.00 | 6.12 | 0 |
| ATOM | 1101 | CG | ASN | 117 | −6.552 | 37.174 | 110.353 | 1.00 | 8.10 | 0 |
| ATOM | 1102 | OD1 | ASN | 117 | −7.584 | 37.351 | 109.700 | 1.00 | 17.57 | 0 |
| ATOM | 1103 | ND2 | ASN | 117 | −6.328 | 36.071 | 111.048 | 1.00 | 14.33 | 0 |
| ATOM | 1106 | C | ASN | 117 | −4.613 | 40.372 | 111.211 | 1.00 | 2.00 | 0 |
| ATOM | 1107 | O | ASN | 117 | −3.496 | 39.952 | 111.506 | 1.00 | 8.94 | 0 |
| ATOM | 1108 | N | PHE | 118 | −4.821 | 41.620 | 110.862 | 1.00 | 2.00 | 0 |
| ATOM | 1110 | CA | PHE | 118 | −3.715 | 42.559 | 110.815 | 1.00 | 2.00 | 0 |
| ATOM | 1111 | CB | PHE | 118 | −3.135 | 42.617 | 109.395 | 1.00 | 2.00 | 0 |
| ATOM | 1112 | CG | PHE | 118 | −1.902 | 43.471 | 109.256 | 1.00 | 2.00 | 0 |
| ATOM | 1113 | CD1 | PHE | 118 | −0.647 | 42.886 | 109.155 | 1.00 | 2.00 | 0 |
| ATOM | 1114 | CD2 | PHE | 118 | −1.995 | 44.857 | 109.177 | 1.00 | 2.00 | 0 |
| ATOM | 1115 | CE1 | PHE | 118 | 0.503 | 43.680 | 108.972 | 1.00 | 2.00 | 0 |
| ATOM | 1116 | CE2 | PHE | 118 | −0.657 | 45.647 | 108.997 | 1.00 | 2.00 | 0 |
| ATOM | 1117 | CZ | PHE | 118 | 0.393 | 45.060 | 108.894 | 1.00 | 2.00 | 0 |
| ATOM | 1118 | C | PHE | 118 | −4.392 | 43.854 | 111.194 | 1.00 | 2.00 | 0 |
| ATOM | 1119 | O | PHE | 118 | −5.384 | 44.259 | 110.576 | 1.00 | 2.00 | 0 |
| ATOM | 1120 | N | PHE | 119 | −3.874 | 44.483 | 112.240 | 1.00 | 12.11 | 0 |
| ATOM | 1122 | CA | PHE | 119 | −4.467 | 45.700 | 112.721 | 1.00 | 12.11 | 0 |
| ATOM | 1123 | CB | PHE | 119 | −5.174 | 45.400 | 114.022 | 1.00 | 2.00 | 0 |
| ATOM | 1124 | CG | PHE | 119 | −6.229 | 44.355 | 113.889 | 1.00 | 2.00 | 0 |
| ATOM | 1125 | CD1 | PHE | 119 | −5.903 | 43.008 | 113.975 | 1.00 | 2.00 | 0 |
| ATOM | 1126 | CD2 | PHE | 119 | −7.556 | 44.716 | 113.655 | 1.00 | 2.00 | 0 |
| ATOM | 1127 | CE1 | PHE | 119 | −6.881 | 42.035 | 113.829 | 1.00 | 2.00 | 0 |
| ATOM | 1128 | CE2 | PHE | 119 | −8.546 | 43.753 | 113.506 | 1.00 | 2.00 | 0 |
| ATOM | 1129 | CZ | PHE | 119 | −8.209 | 42.410 | 113.592 | 1.00 | 2.00 | 0 |
| ATOM | 1130 | C | PHE | 119 | −3.472 | 46.806 | 112.905 | 1.00 | 12.11 | 0 |
| ATOM | 1131 | O | PHE | 119 | −2.342 | 46.577 | 113.346 | 1.00 | 2.00 | 0 |
| ATOM | 1132 | N | LEU | 120 | −3.893 | 48.008 | 112.537 | 1.00 | 2.00 | 0 |
| ATOM | 1134 | CA | LEU | 120 | −3.043 | 49.179 | 112.672 | 1.00 | 2.00 | 0 |
| ATOM | 1135 | CB | LEU | 120 | −2.770 | 49.809 | 111.303 | 1.00 | 2.00 | 0 |
| ATOM | 1136 | CG | LEU | 120 | −2.127 | 48.910 | 110.259 | 1.00 | 2.00 | 0 |
| ATOM | 1137 | CD1 | LEU | 120 | −2.147 | 49.623 | 108.924 | 1.00 | 2.00 | 0 |
| ATOM | 1138 | CD2 | LEU | 120 | −0.731 | 46.539 | 110.685 | 1.00 | 2.00 | 0 |
| ATOM | 1139 | C | LEU | 120 | −3.766 | 50.176 | 113.559 | 1.00 | 2.00 | 0 |
| ATOM | 1140 | O | LEU | 120 | −4.963 | 50.401 | 113.375 | 1.00 | 2.00 | 0 |
| ATOM | 1141 | N | LEU | 121 | −3.069 | 50.730 | 114.542 | 1.00 | 2.00 | 0 |
| ATOM | 1143 | CA | LEU | 121 | −3.670 | 51.714 | 115.415 | 1.00 | 2.00 | 0 |
| ATOM | 1144 | CB | LEU | 121 | −3.351 | 51.428 | 116.890 | 1.00 | 2.00 | 0 |
| ATOM | 1145 | CG | LEU | 121 | −4.142 | 50.320 | 117.598 | 1.00 | 2.00 | 0 |
| ATOM | 1146 | CD1 | LEU | 121 | −3.648 | 50.150 | 119.012 | 1.00 | 2.00 | 0 |
| ATOM | 1147 | CD2 | LEU | 121 | −5.609 | 50.657 | 117.581 | 1.00 | 2.00 | 0 |
| ATOM | 1148 | C | LEU | 121 | −3.100 | 53.060 | 115.004 | 1.00 | 2.00 | 0 |
| ATOM | 1149 | O | LEU | 121 | −2.213 | 53.148 | 114.166 | 1.00 | 2.00 | 0 |

TABLE A-continued

| ATOM | 1150 | N | ARG | 122 | −3.631 | 54.118 | 115.592 | 1.00 | 2.00 | 0 |
|---|---|---|---|---|---|---|---|---|---|---|
| ATOM | 1152 | CA | ARG | 122 | −3.162 | 55.434 | 115.251 | 1.00 | 2.00 | 0 |
| ATOM | 1153 | CB | ARG | 122 | −4.336 | 56.404 | 115.224 | 1.00 | 2.00 | 0 |
| ATOM | 1154 | CG | ARG | 122 | −4.047 | 57.765 | 114.619 | 1.00 | 2.00 | 0 |
| ATOM | 1155 | CD | ARG | 122 | −5.298 | 58.565 | 114.683 | 1.00 | 2.00 | 0 |
| ATOM | 1156 | NE | ARG | 122 | −5.207 | 59.851 | 114.014 | 1.00 | 2.00 | 0 |
| ATOM | 1158 | CZ | ARG | 122 | −6.274 | 60.578 | 113.685 | 1.00 | 2.00 | 0 |
| ATOM | 1159 | NH1 | ARG | 122 | −7.512 | 60.131 | 113.956 | 1.00 | 2.00 | 0 |
| ATOM | 1162 | NH2 | ARG | 122 | −6.104 | 61.762 | 113.102 | 1.00 | 2.00 | 0 |
| ATOM | 1165 | C | ARG | 122 | −2.104 | 55.942 | 116.208 | 1.00 | 2.00 | 0 |
| ATOM | 1166 | O | ARG | 122 | −2.163 | 55.716 | 117.423 | 1.00 | 2.00 | 0 |
| ATOM | 1167 | N | GLY | 123 | −1.135 | 56.635 | 115.631 | 1.00 | 2.00 | 0 |
| ATOM | 1169 | CA | GLY | 123 | −0.073 | 57.235 | 116.399 | 1.00 | 2.00 | 0 |
| ATOM | 1170 | C | GLY | 123 | −0.205 | 58.730 | 116.198 | 1.00 | 2.00 | 0 |
| ATOM | 1171 | O | GLY | 123 | −0.865 | 59.177 | 115.262 | 1.00 | 86.19 | 0 |
| ATOM | 1172 | N | ASN | 124 | 0.437 | 59.508 | 117.058 | 1.00 | 2.00 | 0 |
| ATOM | 1174 | CA | ASN | 124 | 0.390 | 60.956 | 116.958 | 1.00 | 2.00 | 0 |
| ATOM | 1175 | CB | ASN | 124 | 1.003 | 61.584 | 118.199 | 1.00 | 4.11 | 0 |
| ATOM | 1176 | CG | ASN | 124 | 2.477 | 61.333 | 118.313 | 1.00 | 8.88 | 0 |
| ATOM | 1177 | OD1 | ASN | 124 | 2.940 | 60.187 | 118.486 | 1.00 | 8.54 | 0 |
| ATOM | 1178 | ND2 | ASN | 124 | 3.240 | 62.400 | 118.236 | 1.00 | 6.38 | 0 |
| ATOM | 1181 | C | ASN | 124 | 1.103 | 61.455 | 115.708 | 1.00 | 2.00 | 0 |
| ATOM | 1182 | O | ASN | 124 | 1.143 | 62.664 | 115.430 | 1.00 | 5.53 | 0 |
| ATOM | 1183 | N | HIS | 125 | 1.678 | 60.515 | 114.963 | 1.00 | 18.81 | 0 |
| ATOM | 1185 | CA | HIS | 125 | 2.372 | 60.815 | 113.723 | 1.00 | 19.06 | 0 |
| ATOM | 1186 | CB | HIS | 125 | 3.759 | 60.186 | 113.744 | 1.00 | 13.41 | 0 |
| ATOM | 1187 | CG | HIS | 125 | 4.790 | 61.072 | 114.362 | 1.00 | 13.65 | 0 |
| ATOM | 1188 | CD2 | HIS | 125 | 4.765 | 61.811 | 115.493 | 1.00 | 8.85 | 0 |
| ATOM | 1189 | ND1 | HIS | 125 | 6.006 | 61.322 | 113.772 | 1.00 | 14.49 | 0 |
| ATOM | 1191 | CE1 | HIS | 125 | 6.686 | 62.182 | 114.503 | 1.00 | 13.93 | 0 |
| ATOM | 1192 | NE2 | HIS | 125 | 5.954 | 62.496 | 115.554 | 1.00 | 12.46 | 0 |
| ATOM | 1194 | C | HIS | 125 | 1.555 | 60.338 | 112.523 | 1.00 | 16.39 | 0 |
| ATOM | 1195 | O | HIS | 125 | 2.090 | 59.905 | 111.513 | 1.00 | 13.34 | 0 |
| ATOM | 1196 | N | GLU | 126 | 0.241 | 60.382 | 112.686 | 1.00 | 2.00 | 0 |
| ATOM | 1198 | CA | GLU | 126 | −0.731 | 60.018 | 111.664 | 1.00 | 2.00 | 0 |
| ATOM | 1199 | CB | GLU | 126 | −1.462 | 58.725 | 112.050 | 1.00 | 2.00 | 0 |
| ATOM | 1200 | CG | GLU | 126 | −0.783 | 57.443 | 111.570 | 1.00 | 2.00 | 0 |
| ATOM | 1201 | CD | GLU | 126 | 0.578 | 57.217 | 112.190 | 1.00 | 2.00 | 0 |
| ATOM | 1202 | OE1 | GLU | 126 | 1.615 | 57.346 | 111.504 | 1.00 | 2.00 | 0 |
| ATOM | 1203 | OE2 | GLU | 126 | 0.610 | 56.898 | 113.385 | 1.00 | 2.00 | 0 |
| ATOM | 1204 | C | GLU | 126 | −1.683 | 61.211 | 111.705 | 1.00 | 2.00 | 0 |
| ATOM | 1205 | O | GLU | 126 | −2.903 | 61.073 | 111.837 | 1.00 | 2.00 | 0 |
| ATOM | 1206 | N | CYS | 127 | −1.097 | 62.392 | 111.578 | 1.00 | 2.00 | 0 |
| ATOM | 1208 | CA | CYS | 127 | −1.860 | 63.608 | 111.681 | 1.00 | 2.00 | 0 |
| ATOM | 1209 | CB | CYS | 127 | −2.037 | 63.960 | 113.167 | 1.00 | 26.08 | 0 |
| ATOM | 1210 | SG | CYS | 127 | −3.052 | 65.420 | 113.546 | 1.00 | 39.49 | 0 |
| ATOM | 1211 | C | CYS | 127 | −1.142 | 64.731 | 110.976 | 1.00 | 2.00 | 0 |
| ATOM | 1212 | O | CYS | 127 | 0.048 | 64.974 | 111.204 | 1.00 | 23.46 | 0 |
| ATOM | 1213 | N | ALA | 128 | −1.912 | 65.421 | 110.142 | 1.00 | 2.00 | 0 |
| ATOM | 1215 | CA | ALA | 128 | −1.489 | 66.551 | 109.335 | 1.00 | 2.00 | 0 |
| ATOM | 1216 | CB | ALA | 128 | −2.686 | 67.412 | 109.031 | 1.00 | 2.00 | 0 |
| ATOM | 1217 | C | ALA | 128 | −0.385 | 67.413 | 109.910 | 1.00 | 2.00 | 0 |
| ATOM | 1218 | O | ALA | 128 | 0.690 | 67.456 | 109.346 | 1.00 | 2.00 | 0 |
| ATOM | 1219 | N | SER | 129 | −0.649 | 68.097 | 111.021 | 1.00 | 2.00 | 0 |
| ATOM | 1221 | CA | SER | 129 | 0.331 | 68.981 | 111.675 | 1.00 | 2.00 | 0 |
| ATOM | 1222 | CB | SER | 129 | −0.288 | 69.580 | 112.937 | 1.00 | 28.29 | 0 |
| ATOM | 1223 | OG | SER | 129 | −0.836 | 68.562 | 113.760 | 1.00 | 32.64 | 0 |
| ATOM | 1225 | C | SER | 129 | 1.671 | 68.344 | 112.042 | 1.00 | 2.00 | 0 |
| ATOM | 1226 | O | SER | 129 | 2.669 | 69.048 | 112.186 | 1.00 | 24.43 | 0 |
| ATOM | 1227 | N | ILE | 130 | 1.687 | 67.027 | 112.226 | 1.00 | 2.00 | 0 |
| ATOM | 1229 | CA | ILE | 130 | 2.920 | 66.343 | 112.572 | 1.00 | 2.00 | 0 |
| ATOM | 1230 | CB | ILE | 130 | 2.671 | 65.177 | 113.588 | 1.00 | 2.00 | 0 |
| ATOM | 1231 | CG2 | ILE | 130 | 3.999 | 64.584 | 114.058 | 1.00 | 2.00 | 0 |
| ATOM | 1232 | CG1 | ILE | 130 | 2.012 | 65.717 | 114.854 | 1.00 | 2.00 | 0 |
| ATOM | 1233 | CD1 | ILE | 130 | 2.828 | 66.820 | 115.554 | 1.00 | 2.00 | 0 |
| ATOM | 1234 | C | ILE | 130 | 3.563 | 65.829 | 111.289 | 1.00 | 2.00 | 0 |
| ATOM | 1235 | O | ILE | 130 | 4.776 | 65.962 | 111.113 | 1.00 | 2.00 | 0 |
| ATOM | 1236 | N | ASN | 131 | 2.751 | 65.253 | 110.397 | 1.00 | 15.50 | 0 |
| ATOM | 1238 | CA | ASN | 131 | 3.209 | 64.747 | 109.091 | 1.00 | 12.35 | 0 |
| ATOM | 1239 | CB | ASN | 131 | 2.027 | 64.290 | 108.231 | 1.00 | 2.00 | 0 |
| ATOM | 1240 | CG | ASN | 131 | 1.487 | 62.929 | 108.632 | 1.00 | 2.00 | 0 |
| ATOM | 1241 | OD1 | ASN | 131 | 1.712 | 62.438 | 109.750 | 1.00 | 2.00 | 0 |
| ATOM | 1242 | ND2 | ASN | 131 | 0.745 | 62.313 | 107.718 | 1.00 | 2.00 | 0 |
| ATOM | 1245 | C | ASN | 131 | 3.849 | 65.914 | 106.374 | 1.00 | 28.24 | 0 |
| ATOM | 1246 | O | ASN | 131 | 5.001 | 65.854 | 107.951 | 1.00 | 2.00 | 0 |
| ATOM | 1247 | N | ARG | 132 | 3.051 | 66.971 | 108.255 | 1.00 | 2.00 | 0 |
| ATOM | 1249 | CA | ARG | 132 | 3.386 | 66.234 | 107.627 | 1.00 | 2.00 | 0 |
| ATOM | 1250 | CB | ARG | 132 | 2.327 | 69.269 | 108.006 | 1.00 | 22.25 | 0 |
| ATOM | 1251 | CG | ARG | 132 | 2.505 | 70.673 | 107.477 | 1.00 | 26.48 | 0 |

TABLE A-continued

| | | | | | | | | | |
|---|---|---|---|---|---|---|---|---|---|
| ATOM | 1252 | CD | ARG | 132 | 2.505 | 70.734 | 105.962 | 1.00 | 27.28 | 0 |
| ATOM | 1253 | NE | ARG | 132 | 3.849 | 70.533 | 105.434 | 1.00 | 36.02 | 0 |
| ATOM | 1255 | CZ | ARG | 132 | 4.577 | 71.479 | 104.852 | 1.00 | 34.03 | 0 |
| ATOM | 1256 | NH1 | ARG | 132 | 4.080 | 72.697 | 104.711 | 1.00 | 30.29 | 0 |
| ATOM | 1259 | NH2 | ARG | 132 | 5.808 | 71.211 | 104.424 | 1.00 | 37.77 | 0 |
| ATOM | 1262 | C | ARG | 132 | 4.768 | 68.731 | 107.990 | 1.00 | 2.00 | 0 |
| ATOM | 1263 | O | ARG | 132 | 5.359 | 69.477 | 107.225 | 1.00 | 27.60 | 0 |
| ATOM | 1264 | N | ILE | 133 | 5.314 | 68.324 | 109.127 | 1.00 | 2.00 | 0 |
| ATOM | 1266 | CA | ILE | 133 | 6.652 | 68.601 | 109.457 | 1.00 | 2.00 | 0 |
| ATOM | 1267 | CB | ILE | 133 | 6.652 | 69.644 | 110.746 | 1.00 | 20.12 | 0 |
| ATOM | 1268 | CG2 | ILE | 133 | 6.215 | 71.055 | 110.441 | 1.00 | 19.34 | 0 |
| ATOM | 1269 | CG1 | ILE | 133 | 5.761 | 68.999 | 111.800 | 1.00 | 21.76 | 0 |
| ATOM | 1270 | CD1 | ILE | 133 | 5.687 | 69.792 | 113.065 | 1.00 | 22.74 | 0 |
| ATOM | 1271 | C | ILE | 133 | 7.794 | 67.779 | 109.553 | 1.00 | 2.00 | 0 |
| ATOM | 1272 | O | ILE | 133 | 8.915 | 68.073 | 109.127 | 1.00 | 21.74 | 0 |
| ATOM | 1273 | N | TYR | 134 | 7.521 | 66.583 | 110.080 | 1.00 | 2.00 | 0 |
| ATOM | 1275 | CA | TYR | 134 | 8.571 | 65.567 | 110.270 | 1.00 | 2.00 | 0 |
| ATOM | 1276 | CB | TYR | 134 | 8.330 | 64.766 | 111.561 | 1.00 | 27.01 | 0 |
| ATOM | 1277 | CG | TYR | 134 | 8.270 | 65.648 | 112.767 | 1.00 | 19.94 | 0 |
| ATOM | 1278 | CD1 | TYR | 134 | 7.092 | 65.789 | 113.486 | 1.00 | 23.86 | 0 |
| ATOM | 1279 | CE1 | TYR | 134 | 7.016 | 66.651 | 114.557 | 1.00 | 24.86 | 0 |
| ATOM | 1280 | CD2 | TYR | 134 | 9.380 | 66.392 | 113.160 | 1.00 | 24.55 | 0 |
| ATOM | 1281 | CE2 | TYR | 134 | 9.312 | 67.254 | 114.228 | 1.00 | 23.33 | 0 |
| ATOM | 1282 | CZ | TYR | 134 | 8.128 | 67.384 | 114.925 | 1.00 | 28.93 | 0 |
| ATOM | 1283 | OH | TYR | 134 | 8.043 | 68.259 | 115.984 | 1.00 | 27.73 | 0 |
| ATOM | 1285 | C | TYR | 134 | 8.823 | 64.606 | 109.139 | 1.00 | 2.00 | 0 |
| ATOM | 1286 | O | TYR | 134 | 8.996 | 63.404 | 109.368 | 1.00 | 24.62 | 0 |
| ATOM | 1287 | N | GLY | 135 | 8.847 | 65.127 | 107.922 | 1.00 | 11.68 | 0 |
| ATOM | 1289 | CA | GLY | 135 | 9.134 | 64.275 | 106.787 | 1.00 | 10.40 | 0 |
| ATOM | 1290 | C | GLY | 135 | 8.028 | 63.772 | 105.882 | 1.00 | 9.03 | 0 |
| ATOM | 1291 | O | GLY | 135 | 8.010 | 64.127 | 104.713 | 1.00 | 20.70 | 0 |
| ATOM | 1292 | N | PHE | 136 | 7.110 | 62.963 | 106.393 | 1.00 | 2.00 | 0 |
| ATOM | 1294 | CA | PHE | 136 | 6.062 | 62.412 | 105.549 | 1.00 | 2.00 | 0 |
| ATOM | 1295 | CB | PHE | 136 | 4.951 | 61.757 | 106.347 | 1.00 | 2.00 | 0 |
| ATOM | 1296 | CG | PHE | 136 | 4.091 | 60.831 | 105.524 | 1.00 | 2.00 | 0 |
| ATOM | 1297 | CD1 | PHE | 136 | 4.664 | 59.734 | 104.870 | 1.00 | 2.00 | 0 |
| ATOM | 1298 | CD2 | PHE | 136 | 2.713 | 61.036 | 105.424 | 1.00 | 2.00 | 0 |
| ATOM | 1299 | CE1 | PHE | 136 | 3.882 | 58.846 | 104.131 | 1.00 | 2.00 | 0 |
| ATOM | 1300 | CE2 | PHE | 136 | 1.915 | 60.155 | 104.688 | 1.00 | 2.00 | 0 |
| ATOM | 1301 | CZ | PHE | 136 | 2.507 | 59.050 | 104.037 | 1.00 | 2.00 | 0 |
| ATOM | 1302 | C | PHE | 136 | 5.421 | 63.358 | 104.563 | 1.00 | 2.00 | 0 |
| ATOM | 1303 | O | PHE | 136 | 5.121 | 62.926 | 103.445 | 1.00 | 2.00 | 0 |
| ATOM | 1304 | N | TYR | 137 | 5.199 | 64.616 | 104.940 | 1.00 | 2.00 | 0 |
| ATOM | 1306 | CA | TYR | 137 | 4.606 | 65.530 | 103.977 | 1.00 | 2.00 | 0 |
| ATOM | 1307 | CB | TYR | 137 | 4.243 | 66.859 | 104.598 | 1.00 | 2.00 | 0 |
| ATOM | 1308 | CG | TYR | 137 | 3.886 | 67.921 | 103.564 | 1.00 | 2.00 | 0 |
| ATOM | 1309 | CD1 | TYR | 137 | 2.550 | 68.203 | 103.257 | 1.00 | 2.00 | 0 |
| ATOM | 1310 | CE1 | TYR | 137 | 2.228 | 69.196 | 102.327 | 1.00 | 2.00 | 0 |
| ATOM | 1311 | CD2 | TYR | 137 | 4.893 | 68.666 | 102.901 | 1.00 | 2.00 | 0 |
| ATOM | 1312 | CE2 | TYR | 137 | 4.576 | 69.644 | 101.985 | 1.00 | 2.00 | 0 |
| ATOM | 1313 | CZ | TYR | 137 | 3.247 | 69.903 | 101.707 | 1.00 | 2.00 | 0 |
| ATOM | 1314 | OH | TYR | 137 | 2.920 | 70.893 | 100.823 | 1.00 | 2.00 | 0 |
| ATOM | 1316 | C | TYR | 137 | 5.566 | 65.785 | 102.822 | 1.00 | 2.00 | 0 |
| ATOM | 1317 | O | TYR | 137 | 5.187 | 65.669 | 101.646 | 1.00 | 2.00 | 0 |
| ATOM | 1318 | N | ASP | 138 | 6.802 | 66.153 | 103.155 | 1.00 | 2.00 | 0 |
| ATOM | 1320 | CA | ASP | 138 | 7.822 | 66.439 | 102.147 | 1.00 | 2.00 | 0 |
| ATOM | 1321 | CB | ASP | 138 | 9.102 | 66.971 | 102.810 | 1.00 | 28.59 | 0 |
| ATOM | 1322 | CG | ASP | 138 | 8.832 | 68.173 | 103.705 | 1.00 | 31.85 | 0 |
| ATOM | 1323 | OD1 | ASP | 138 | 8.999 | 69.327 | 103.255 | 1.00 | 34.04 | 0 |
| ATOM | 1324 | OD2 | ASP | 138 | 8.432 | 67.963 | 104.867 | 1.00 | 31.26 | 0 |
| ATOM | 1325 | C | ASP | 138 | 8.118 | 65.203 | 101.308 | 1.00 | 2.00 | 0 |
| ATOM | 1326 | O | ASP | 138 | 8.322 | 65.309 | 100.102 | 1.00 | 27.39 | 0 |
| ATOM | 1327 | N | GLU | 139 | 8.097 | 64.030 | 101.926 | 1.00 | 31.40 | 0 |
| ATOM | 1329 | CA | GLU | 139 | 8.366 | 62.797 | 101.200 | 1.00 | 28.32 | 0 |
| ATOM | 1330 | C | GLU | 139 | 8.380 | 61.608 | 102.149 | 1.00 | 2.00 | 0 |
| ATOM | 1331 | CG | GLU | 139 | 8.965 | 60.361 | 101.526 | 1.00 | 4.78 | 0 |
| ATOM | 1332 | CD | GLU | 139 | 9.167 | 59.231 | 102.525 | 1.00 | 3.01 | 0 |
| ATOM | 1333 | OE1 | GLU | 139 | 9.135 | 58.050 | 102.087 | 1.00 | 2.00 | 0 |
| ATOM | 1334 | OE2 | GLU | 139 | 9.372 | 59.518 | 103.738 | 1.00 | 4.61 | 0 |
| ATOM | 1335 | C | GLU | 139 | 7.323 | 62.572 | 100.117 | 1.00 | 30.47 | 0 |
| ATOM | 1336 | O | GLU | 139 | 7.660 | 62.419 | 98.941 | 1.00 | 2.00 | 0 |
| ATOM | 1337 | N | CYS | 140 | 6.055 | 62.553 | 100.511 | 1.00 | 12.32 | 0 |
| ATOM | 1339 | CA | CYS | 140 | 4.981 | 62.355 | 99.553 | 1.00 | 3.99 | 0 |
| ATOM | 1340 | CB | CYS | 140 | 3.625 | 62.543 | 100.221 | 1.00 | 18.56 | 0 |
| ATOM | 1341 | SG | CYS | 140 | 3.313 | 61.308 | 101.477 | 1.00 | 23.54 | 0 |
| ATOM | 1342 | C | CYS | 140 | 5.128 | 63.346 | 98.416 | 1.00 | 12.32 | 0 |
| ATOM | 1343 | O | CYS | 140 | 5.117 | 62.961 | 97.257 | 1.00 | 21.26 | 0 |
| ATOM | 1344 | N | LYS | 141 | 5.305 | 64.616 | 98.763 | 1.00 | 41.55 | 0 |
| ATOM | 1346 | CA | LYS | 141 | 5.446 | 65.696 | 97.786 | 1.00 | 40.86 | 0 |

TABLE A-continued

| ATOM | 1347 | CB | LYS | 141 | 5.655 | 67.023 | 98.531 | 1.00 | 38.66 | 0 |
|---|---|---|---|---|---|---|---|---|---|---|
| ATOM | 1348 | CG | LYS | 141 | 5.853 | 68.246 | 97.646 | 1.00 | 32.19 | 0 |
| ATOM | 1349 | CD | LYS | 141 | 5.886 | 69.522 | 98.468 | 1.00 | 35.28 | 0 |
| ATOM | 1350 | CE | LYS | 141 | 5.895 | 70.750 | 97.584 | 1.00 | 36.09 | 0 |
| ATOM | 1351 | NZ | LYS | 141 | 5.552 | 71.948 | 98.380 | 1.00 | 40.44 | 0 |
| ATOM | 1355 | C | LYS | 141 | 6.586 | 65.467 | 96.791 | 1.00 | 40.27 | 0 |
| ATOM | 1356 | O | LYS | 141 | 6.431 | 65.642 | 95.582 | 1.00 | 28.60 | 0 |
| ATOM | 1357 | N | ARG | 142 | 7.731 | 65.073 | 97.319 | 1.00 | 23.84 | 0 |
| ATOM | 1359 | CA | ARG | 142 | 8.912 | 64.834 | 96.512 | 1.00 | 23.84 | 0 |
| ATOM | 1360 | CB | ARG | 142 | 10.097 | 64.566 | 97.444 | 1.00 | 22.75 | 0 |
| ATOM | 1361 | CG | ARG | 142 | 11.368 | 64.101 | 96.778 | 1.00 | 24.10 | 0 |
| ATOM | 1362 | CD | ARG | 142 | 12.474 | 64.073 | 97.799 | 1.00 | 33.58 | 0 |
| ATOM | 1363 | NE | ARG | 142 | 12.099 | 63.283 | 98.963 | 1.00 | 37.62 | 0 |
| ATOM | 1365 | CZ | ARG | 142 | 12.464 | 62.018 | 99.150 | 1.00 | 46.30 | 0 |
| ATOM | 1366 | NH1 | ARG | 142 | 13.224 | 61.404 | 98.249 | 1.00 | 44.23 | 0 |
| ATOM | 1369 | NH2 | ARG | 142 | 12.060 | 61.363 | 100.234 | 1.00 | 42.22 | 0 |
| ATOM | 1372 | C | ARG | 142 | 8.732 | 63.689 | 95.519 | 1.00 | 23.84 | 0 |
| ATOM | 1373 | O | ARG | 142 | 8.995 | 63.838 | 94.330 | 1.00 | 24.93 | 0 |
| ATOM | 1374 | N | ARG | 143 | 8.268 | 62.550 | 95.999 | 1.00 | 2.00 | 0 |
| ATOM | 1376 | CA | ARG | 143 | 8.104 | 61.413 | 95.125 | 1.00 | 2.00 | 0 |
| ATOM | 1377 | CB | ARG | 143 | 8.267 | 60.134 | 95.941 | 1.00 | 2.86 | 0 |
| ATOM | 1378 | CG | ARG | 143 | 9.686 | 59.941 | 96.455 | 1.00 | 2.86 | 0 |
| ATOM | 1379 | CD | ARG | 143 | 9.792 | 58.874 | 97.530 | 1.00 | 8.64 | 0 |
| ATOM | 1380 | NE | ARG | 143 | 9.490 | 57.527 | 97.049 | 1.00 | 4.03 | 0 |
| ATOM | 1382 | CZ | ARG | 143 | 9.492 | 56.439 | 97.816 | 1.00 | 6.91 | 0 |
| ATOM | 1383 | NH1 | ARG | 143 | 9.782 | 56.527 | 99.115 | 1.00 | 7.13 | 0 |
| ATOM | 1386 | NH2 | ARG | 143 | 9.203 | 55.257 | 97.287 | 1.00 | 12.97 | 0 |
| ATOM | 1389 | C | ARG | 143 | 6.796 | 61.411 | 94.367 | 1.00 | 2.00 | 0 |
| ATOM | 1390 | O | ARG | 143 | 6.707 | 60.818 | 93.295 | 1.00 | 12.04 | 0 |
| ATOM | 1391 | N | TYR | 144 | 5.791 | 62.097 | 94.897 | 1.00 | 2.00 | 0 |
| ATOM | 1393 | CA | TYR | 144 | 4.459 | 62.120 | 94.274 | 1.00 | 2.00 | 0 |
| ATOM | 1394 | CB | TYR | 144 | 3.509 | 61.150 | 95.021 | 1.00 | 2.00 | 0 |
| ATOM | 1395 | CG | TYR | 144 | 3.902 | 59.689 | 94.953 | 1.00 | 2.00 | 0 |
| ATOM | 1396 | CD1 | TYR | 144 | 4.946 | 59.203 | 95.716 | 1.00 | 2.00 | 0 |
| ATOM | 1397 | CE1 | TYR | 144 | 5.336 | 57.885 | 95.635 | 1.00 | 2.00 | 0 |
| ATOM | 1398 | CD2 | TYR | 144 | 3.248 | 58.804 | 94.102 | 1.00 | 2.00 | 0 |
| ATOM | 1399 | CE2 | TYR | 144 | 3.633 | 57.483 | 94.017 | 1.00 | 2.00 | 0 |
| ATOM | 1400 | CZ | TYR | 144 | 4.683 | 57.034 | 94.786 | 1.00 | 2.00 | 0 |
| ATOM | 1401 | OH | TYR | 144 | 5.113 | 55.738 | 94.703 | 1.00 | 2.00 | 0 |
| ATOM | 1403 | C | TYR | 144 | 3.789 | 63.502 | 94.169 | 1.00 | 2.00 | 0 |
| ATOM | 1404 | O | TYR | 144 | 4.129 | 64.316 | 93.297 | 1.00 | 2.00 | 0 |
| ATOM | 1405 | N | ASN | 145 | 2.827 | 63.750 | 95.058 | 1.00 | 2.00 | 0 |
| ATOM | 1407 | CA | ASN | 145 | 2.081 | 65.000 | 95.083 | 1.00 | 2.00 | 0 |
| ATOM | 1408 | CB | ASN | 145 | 1.159 | 65.078 | 93.867 | 1.00 | 7.57 | 0 |
| ATOM | 1409 | CG | ASN | 145 | 0.255 | 63.861 | 93.748 | 1.00 | 5.76 | 0 |
| ATOM | 1410 | OD1 | ASN | 145 | −0.823 | 63.826 | 94.329 | 1.00 | 9.42 | 0 |
| ATOM | 1411 | ND2 | ASN | 145 | 0.702 | 62.851 | 93.007 | 1.00 | 5.88 | 0 |
| ATOM | 1414 | C | ASN | 145 | 1.229 | 65.137 | 96.354 | 1.00 | 2.00 | 0 |
| ATOM | 1415 | O | ASN | 145 | 0.760 | 64.143 | 96.938 | 1.00 | 11.61 | 0 |
| ATOM | 1416 | N | ILE | 146 | 1.001 | 66.391 | 96.737 | 1.00 | 2.00 | 0 |
| ATOM | 1418 | CA | ILE | 146 | 0.217 | 66.745 | 97.901 | 1.00 | 2.00 | 0 |
| ATOM | 1419 | CB | ILE | 146 | 0.168 | 68.278 | 98.048 | 1.00 | 2.00 | 0 |
| ATOM | 1420 | CG2 | ILE | 146 | −0.607 | 68.690 | 99.278 | 1.00 | 2.00 | 0 |
| ATOM | 1421 | CG1 | ILE | 146 | 1.591 | 69.798 | 98.201 | 1.00 | 2.00 | 0 |
| ATOM | 1422 | CD1 | ILE | 146 | 1.679 | 70.270 | 99.360 | 1.00 | 2.00 | 0 |
| ATOM | 1423 | C | ILE | 146 | −1.181 | 66.143 | 97.851 | 1.00 | 2.00 | 0 |
| ATOM | 1424 | O | ILE | 146 | −1.805 | 65.927 | 98.881 | 1.00 | 2.00 | 0 |
| ATOM | 1425 | N | LYS | 147 | −1.680 | 65.839 | 96.668 | 1.00 | 2.00 | 0 |
| ATOM | 1427 | CA | LYS | 147 | −3.000 | 65.241 | 96.594 | 1.00 | 2.00 | 0 |
| ATOM | 1428 | CB | LYS | 147 | −3.412 | 65.007 | 95.131 | 1.00 | 15.32 | 0 |
| ATOM | 1429 | CG | LYS | 147 | −4.880 | 64.643 | 94.902 | 1.00 | 21.64 | 0 |
| ATOM | 1430 | CD | LYS | 147 | −5.024 | 63.248 | 94.280 | 1.00 | 29.48 | 0 |
| ATOM | 1431 | CE | LYS | 147 | −4.704 | 62.128 | 95.300 | 1.00 | 25.79 | 0 |
| ATOM | 1432 | NZ | LYS | 147 | −4.388 | 60.777 | 94.716 | 1.00 | 22.31 | 0 |
| ATOM | 1436 | C | LYS | 147 | −2.864 | 63.928 | 97.345 | 1.00 | 2.00 | 0 |
| ATOM | 1437 | O | LYS | 147 | −3.652 | 63.630 | 96.233 | 1.00 | 8.30 | 0 |
| ATOM | 1438 | N | LEU | 148 | −1.815 | 63.180 | 97.023 | 1.00 | 9.36 | 0 |
| ATOM | 1440 | CA | LEU | 148 | −1.582 | 61.892 | 97.651 | 1.00 | 9.36 | 0 |
| ATOM | 1441 | CB | LEU | 148 | −0.360 | 61.202 | 97.037 | 1.00 | 2.00 | 0 |
| ATOM | 1442 | CG | LEU | 148 | −0.207 | 59.721 | 97.415 | 1.00 | 2.00 | 0 |
| ATOM | 1443 | CD1 | LEU | 148 | −1.398 | 58.910 | 96.924 | 1.00 | 2.00 | 0 |
| ATOM | 1444 | CD2 | LEU | 148 | 1.078 | 59.168 | 96.835 | 1.00 | 2.00 | 0 |
| ATOM | 1445 | C | LEU | 148 | −1.423 | 62.040 | 99.157 | 1.00 | 9.36 | 0 |
| ATOM | 1446 | O | LEU | 148 | −2.097 | 61.351 | 99.899 | 1.00 | 2.00 | 0 |
| ATOM | 1447 | N | TRP | 149 | −0.555 | 62.943 | 99.611 | 1.00 | 2.00 | 0 |
| ATOM | 1449 | CA | TRP | 149 | −0.360 | 63.166 | 101.042 | 1.00 | 2.00 | 0 |
| ATOM | 1450 | CB | TRP | 149 | 0.559 | 64.359 | 101.276 | 1.00 | 9.48 | 0 |
| ATOM | 1451 | CG | TRP | 149 | 0.690 | 64.767 | 102.748 | 1.00 | 13.35 | 0 |
| ATOM | 1452 | CD2 | TRP | 149 | 0.095 | 65.915 | 103.387 | 1.00 | 9.36 | 0 |

TABLE A-continued

| | | | | | | | | |
|---|---|---|---|---|---|---|---|---|
| ATOM | 1453 | CE2 | TRP | 149 | 0.512 | 65.907 | 104.725 | 1.00 | 12.67 | 0 |
| ATOM | 1454 | CE3 | TRP | 149 | −0.751 | 66.946 | 102.951 | 1.00 | 9.36 | 0 |
| ATOM | 1455 | CD1 | TRP | 149 | 1.415 | 64.135 | 103.713 | 1.00 | 12.84 | 0 |
| ATOM | 1456 | NE1 | TRP | 149 | 1.315 | 64.811 | 104.895 | 1.00 | 14.40 | 0 |
| ATOM | 1458 | CZ2 | TRP | 149 | 0.119 | 66.880 | 105.632 | 1.00 | 10.82 | 0 |
| ATOM | 1459 | CZ3 | TRP | 149 | −1.138 | 67.912 | 103.858 | 1.00 | 10.25 | 0 |
| ATOM | 1460 | CH2 | TRP | 149 | −0.702 | 67.870 | 105.182 | 1.00 | 21.34 | 0 |
| ATOM | 1461 | C | TRP | 149 | −1.712 | 63.427 | 101.707 | 1.00 | 2.00 | 0 |
| ATOM | 1462 | O | TRP | 149 | −2.095 | 62.726 | 102.647 | 1.00 | 9.36 | 0 |
| ATOM | 1463 | N | LYS | 150 | −2.429 | 64.434 | 101.216 | 1.00 | 2.00 | 0 |
| ATOM | 1465 | CA | LYS | 150 | −3.756 | 64.777 | 101.725 | 1.00 | 2.00 | 0 |
| ATOM | 1466 | CB | LYS | 150 | −4.392 | 65.810 | 100.819 | 1.00 | 25.82 | 0 |
| ATOM | 1467 | CG | LYS | 150 | −3.695 | 67.135 | 100.844 | 1.00 | 27.78 | 0 |
| ATOM | 1468 | CD | LYS | 150 | −4.145 | 67.981 | 99.676 | 1.00 | 24.78 | 0 |
| ATOM | 1469 | CE | LYS | 150 | −4.236 | 69.442 | 100.053 | 1.00 | 28.33 | 0 |
| ATOM | 1470 | NZ | LYS | 150 | −5.243 | 69.673 | 101.132 | 1.00 | 35.49 | 0 |
| ATOM | 1474 | C | LYS | 150 | −4.661 | 63.536 | 101.786 | 1.00 | 2.00 | 0 |
| ATOM | 1475 | O | LYS | 150 | −5.468 | 63.397 | 102.701 | 1.00 | 28.71 | 0 |
| ATOM | 1476 | N | THR | 151 | −4.525 | 62.638 | 100.809 | 1.00 | 2.00 | 0 |
| ATOM | 1478 | CA | THR | 151 | −5.315 | 61.403 | 100.758 | 1.00 | 2.00 | 0 |
| ATOM | 1479 | CB | THR | 151 | −5.111 | 60.670 | 99.408 | 1.00 | 18.71 | 0 |
| ATOM | 1480 | OG1 | THR | 151 | −5.491 | 61.532 | 98.332 | 1.00 | 21.97 | 0 |
| ATOM | 1482 | CG2 | THR | 151 | −5.964 | 59.434 | 99.332 | 1.00 | 19.85 | 0 |
| ATOM | 1483 | C | THR | 151 | −4.920 | 60.487 | 101.925 | 1.00 | 2.00 | 0 |
| ATOM | 1484 | O | THR | 151 | −5.760 | 59.773 | 102.489 | 1.00 | 14.71 | 0 |
| ATOM | 1485 | N | PHE | 152 | −3.645 | 60.529 | 102.297 | 1.00 | 2.00 | 0 |
| ATOM | 1487 | CA | PHE | 152 | −3.161 | 59.729 | 103.398 | 1.00 | 2.00 | 0 |
| ATOM | 1488 | CB | PHE | 152 | −1.638 | 59.759 | 103.502 | 1.00 | 13.78 | 0 |
| ATOM | 1489 | CG | PHE | 152 | −0.956 | 58.5B6 | 102.830 | 1.00 | 13.78 | 0 |
| ATOM | 1490 | CD1 | PHE | 152 | 0.034 | 58.792 | 101.864 | 1.00 | 13.78 | 0 |
| ATOM | 1491 | CD2 | PHE | 152 | −1.289 | 57.277 | 103.178 | 1.00 | 13.78 | 0 |
| ATOM | 1492 | CE1 | PHE | 152 | 0.679 | 57.717 | 101.260 | 1.00 | 13.78 | 0 |
| ATOM | 1493 | CE2 | PHE | 152 | −0.648 | 56.194 | 102.578 | 1.00 | 13.78 | 0 |
| ATOM | 1494 | CZ | PHE | 152 | 0.340 | 56.417 | 101.617 | 1.00 | 13.78 | 0 |
| ATOM | 1495 | C | PHE | 152 | −3.767 | 60.246 | 104.673 | 1.00 | 2.00 | 0 |
| ATOM | 1496 | O | PHE | 152 | −4.380 | 59.470 | 105.397 | 1.00 | 13.78 | 0 |
| ATOM | 1497 | N | THR | 153 | −3.657 | 61.547 | 104.944 | 1.00 | 2.00 | 0 |
| ATOM | 1499 | CA | THR | 153 | −4.217 | 62.064 | 106.192 | 1.00 | 2.00 | 0 |
| ATOM | 1500 | CB | THR | 153 | −4.166 | 63.604 | 106.318 | 1.00 | 19.49 | 0 |
| ATOM | 1501 | OG1 | THR | 153 | −4.912 | 64.207 | 105.265 | 1.00 | 24.34 | 0 |
| ATOM | 1503 | CG2 | THR | 153 | −2.739 | 64.095 | 106.293 | 1.00 | 23.93 | 0 |
| ATOM | 1504 | C | THR | 153 | −5.653 | 61.007 | 106.348 | 1.00 | 2.00 | 0 |
| ATOM | 1505 | O | THR | 153 | −6.054 | 61.158 | 107.414 | 1.00 | 29.22 | 0 |
| ATOM | 1506 | N | ASP | 154 | −6.415 | 61.667 | 105.276 | 1.00 | 2.00 | 0 |
| ATOM | 1508 | CA | ASP | 154 | −7.801 | 61.250 | 105.332 | 1.00 | 2.00 | 0 |
| ATOM | 1509 | CB | ASP | 154 | −8.442 | 61.393 | 103.945 | 1.00 | 21.48 | 0 |
| ATOM | 1510 | CG | ASP | 154 | −9.965 | 61.345 | 103.987 | 1.00 | 21.21 | 0 |
| ATOM | 1511 | OD1 | ASP | 154 | −10.576 | 61.750 | 102.971 | 1.00 | 27.37 | 0 |
| ATOM | 1512 | OD2 | ASP | 154 | −10.548 | 60.912 | 105.018 | 1.00 | 20.95 | 0 |
| ATOM | 1513 | C | ASP | 154 | −7.889 | 59.806 | 105.801 | 1.00 | 2.00 | 0 |
| ATOM | 1514 | O | ASP | 154 | −8.783 | 59.444 | 106.569 | 1.00 | 11.19 | 0 |
| ATOM | 1515 | N | CYS | 155 | −6.968 | 58.981 | 105.319 | 1.00 | 2.00 | 0 |
| ATOM | 1517 | CA | CYS | 155 | −6.951 | 57.571 | 105.691 | 1.00 | 2.00 | 0 |
| ATOM | 1518 | CB | CYS | 155 | −5.904 | 56.822 | 104.865 | 1.00 | 2.00 | 0 |
| ATOM | 1519 | SG | CYS | 155 | −5.770 | 55.072 | 105.254 | 1.00 | 2.00 | 0 |
| ATOM | 1520 | C | CYS | 155 | −6.627 | 57.479 | 107.178 | 1.00 | 2.00 | 0 |
| ATOM | 1521 | O | CYS | 155 | −7.267 | 56.741 | 107.931 | 1.00 | 2.00 | 0 |
| ATOM | 1522 | N | PHE | 156 | −5.641 | 58.273 | 107.593 | 1.00 | 8.58 | 0 |
| ATOM | 1524 | CA | PHE | 156 | −5.172 | 58.366 | 108.954 | 1.00 | 8.58 | 0 |
| ATOM | 1525 | CB | PHE | 156 | −4.056 | 59.409 | 109.018 | 1.00 | 2.00 | 0 |
| ATOM | 1526 | CG | PHE | 156 | −2.766 | 58.945 | 108.437 | 1.00 | 2.00 | 0 |
| ATOM | 1527 | CD1 | PHE | 156 | −2.537 | 57.585 | 108.206 | 1.00 | 2.00 | 0 |
| ATOM | 1528 | CD2 | PHE | 156 | −1.756 | 59.847 | 108.160 | 1.00 | 2.00 | 0 |
| ATOM | 1529 | CE1 | PHE | 156 | −1.309 | 57.130 | 107.710 | 1.00 | 2.00 | 0 |
| ATOM | 1530 | CE2 | PHE | 156 | −0.518 | 59.400 | 107.662 | 1.00 | 2.00 | 0 |
| ATOM | 1531 | CZ | PHE | 156 | −0.295 | 58.039 | 107.439 | 1.00 | 2.00 | 0 |
| ATOM | 1532 | C | PHE | 156 | −6.287 | 58.743 | 109.931 | 1.00 | 8.58 | 0 |
| ATOM | 1533 | O | PHE | 156 | −6.463 | 58.119 | 110.974 | 1.00 | 2.00 | 0 |
| ATOM | 1534 | N | ASN | 157 | −7.055 | 59.758 | 109.572 | 1.00 | 2.00 | 0 |
| ATOM | 1536 | CA | ASN | 157 | −8.144 | 60.233 | 110.405 | 1.00 | 2.00 | 0 |
| ATOM | 1537 | CB | ASN | 157 | −8.811 | 61.475 | 109.779 | 1.00 | 2.00 | 0 |
| ATOM | 1538 | CG | ASN | 157 | −7.861 | 62.661 | 109.577 | 1.00 | 2.00 | 0 |
| ATOM | 1539 | OD1 | ASN | 157 | −8.226 | 63.629 | 108.922 | 1.00 | 2.00 | 0 |
| ATOM | 1540 | ND2 | ASN | 157 | −6.669 | 62.601 | 110.143 | 1.00 | 2.00 | 0 |
| ATOM | 1543 | C | ASN | 157 | −9.230 | 59.179 | 110.631 | 1.00 | 2.00 | 0 |
| ATOM | 1544 | O | ASN | 157 | −10.242 | 59.489 | 111.240 | 1.00 | 2.00 | 0 |
| ATOM | 1545 | N | CYS | 158 | −9.064 | 57.962 | 110.120 | 1.00 | 2.00 | 0 |
| ATOM | 1547 | CA | CYS | 158 | −10.074 | 56.914 | 110.304 | 1.00 | 2.00 | 0 |
| ATOM | 1548 | CB | CYS | 158 | −10.751 | 56.567 | 108.970 | 1.00 | 2.00 | 0 |

TABLE A-continued

| ATOM | 1549 | SG | CYS | 158 | −11.898 | 57.864 | 108.331 | 1.00 | 2.00 | 0 |
| --- | --- | --- | --- | --- | --- | --- | --- | --- | --- | --- |
| ATOM | 1550 | C | CYS | 158 | −9.482 | 55.665 | 110.924 | 1.00 | 2.00 | 0 |
| ATOM | 1551 | O | CYS | 158 | −10.148 | 54.648 | 111.049 | 1.00 | 2.00 | 0 |
| ATOM | 1552 | N | LEU | 159 | −8.216 | 55.772 | 111.304 | 1.00 | 2.00 | 0 |
| ATOM | 1554 | CA | LEU | 159 | −7.433 | 54.714 | 111.945 | 1.00 | 2.00 | 0 |
| ATOM | 1555 | CB | LEU | 159 | −5.985 | 55.219 | 112.037 | 1.00 | 2.00 | 0 |
| ATOM | 1556 | CG | LEU | 159 | −4.747 | 54.363 | 111.781 | 1.00 | 2.00 | 0 |
| ATOM | 1557 | CD1 | LEU | 159 | −4.993 | 53.449 | 110.617 | 1.00 | 2.00 | 0 |
| ATOM | 1558 | CD2 | LEU | 159 | −3.536 | 55.269 | 111.503 | 1.00 | 2.00 | 0 |
| ATOM | 1559 | C | LEU | 159 | −8.010 | 54.454 | 113.361 | 1.00 | 2.00 | 0 |
| ATOM | 1560 | O | LEU | 159 | −8.548 | 55.367 | 113.980 | 1.00 | 2.00 | 0 |
| ATOM | 1561 | N | PRO | 160 | −7.951 | 53.209 | 113.871 | 1.00 | 2.00 | 0 |
| ATOM | 1562 | CD | PRO | 160 | −7.504 | 51.978 | 113.208 | 1.00 | 2.00 | 0 |
| ATOM | 1563 | CA | PRO | 160 | −8.473 | 52.896 | 115.209 | 1.00 | 2.00 | 0 |
| ATOM | 1564 | CB | PRO | 160 | −8.398 | 51.375 | 115.269 | 1.00 | 2.00 | 0 |
| ATOM | 1565 | CG | PRO | 160 | −8.416 | 50.956 | 113.838 | 1.00 | 2.00 | 0 |
| ATOM | 1566 | C | PRO | 160 | −7.535 | 53.516 | 116.228 | 1.00 | 2.00 | 0 |
| ATOM | 1567 | O | PRO | 160 | −6.329 | 53.463 | 116.031 | 1.00 | 2.00 | 0 |
| ATOM | 1568 | N | ILE | 161 | −8.062 | 54.073 | 117.315 | 1.00 | 10.42 | 0 |
| ATOM | 1570 | CA | ILE | 161 | −7.206 | 54.717 | 118.312 | 1.00 | 10.42 | 0 |
| ATOM | 1571 | CB | ILE | 161 | −7.862 | 55.995 | 118.918 | 1.00 | 2.00 | 0 |
| ATOM | 1572 | CG2 | ILE | 161 | −8.493 | 56.837 | 117.823 | 1.00 | 2.00 | 0 |
| ATOM | 1573 | CG1 | ILE | 161 | −8.899 | 55.612 | 119.987 | 1.00 | 2.00 | 0 |
| ATOM | 1574 | CD1 | ILE | 161 | −9.428 | 56.766 | 120.775 | 1.00 | 2.00 | 0 |
| ATOM | 1575 | C | ILE | 161 | −6.741 | 53.859 | 119.492 | 1.00 | 10.42 | 0 |
| ATOM | 1576 | O | ILE | 161 | −5.808 | 54.254 | 120.193 | 1.00 | 2.00 | 0 |
| ATOM | 1577 | N | ALA | 162 | −7.387 | 52.712 | 119.720 | 1.00 | 16.67 | 0 |
| ATOM | 1579 | CA | ALA | 162 | −7.036 | 51.832 | 120.837 | 1.00 | 16.67 | 0 |
| ATOM | 1580 | CB | ALA | 162 | −7.580 | 52.409 | 122.120 | 1.00 | 2.00 | 0 |
| ATOM | 1581 | C | ALA | 162 | −7.567 | 50.414 | 120.637 | 1.00 | 16.67 | 0 |
| ATOM | 1582 | O | ALA | 162 | −8.494 | 50.203 | 119.861 | 1.00 | 2.00 | 0 |
| ATOM | 1583 | N | ALA | 163 | −6.984 | 49.455 | 121.356 | 1.00 | 2.00 | 0 |
| ATOM | 1585 | CA | ALA | 163 | −7.379 | 48.052 | 121.267 | 1.00 | 2.00 | 0 |
| ATOM | 1586 | CB | ALA | 163 | −6.559 | 47.374 | 120.197 | 1.00 | 14.80 | 0 |
| ATOM | 1587 | C | ALA | 163 | −7.232 | 47.283 | 122.604 | 1.00 | 2.00 | 0 |
| ATOM | 1588 | O | ALA | 163 | −6.373 | 47.620 | 123.425 | 1.00 | 8.24 | 0 |
| ATOM | 1589 | N | ILE | 164 | −8.069 | 46.263 | 122.813 | 1.00 | 8.09 | 0 |
| ATOM | 1591 | CA | ILE | 164 | −8.036 | 45.424 | 124.018 | 1.00 | 8.09 | 0 |
| ATOM | 1592 | CB | ILE | 164 | −9.323 | 45.590 | 124.860 | 1.00 | 10.56 | 0 |
| ATOM | 1593 | CG2 | ILE | 164 | −9.200 | 44.830 | 126.150 | 1.00 | 10.56 | 0 |
| ATOM | 1594 | CG1 | ILE | 164 | −9.566 | 47.055 | 125.187 | 1.00 | 10.56 | 0 |
| ATOM | 1595 | CD1 | ILE | 164 | −10.886 | 47.285 | 125.837 | 1.00 | 10.56 | 0 |
| ATOM | 1596 | C | ILE | 164 | −7.910 | 43.938 | 123.623 | 1.00 | 8.09 | 0 |
| ATOM | 1597 | O | ILE | 164 | −8.866 | 43.328 | 123.127 | 1.00 | 10.56 | 0 |
| ATOM | 1598 | N | VAL | 165 | −6.739 | 43.353 | 123.856 | 1.00 | 20.53 | 0 |
| ATOM | 1600 | CA | VAL | 165 | −6.510 | 41.958 | 123.503 | 1.00 | 21.83 | 0 |
| ATOM | 1601 | CB | VAL | 165 | −5.041 | 41.664 | 123.243 | 1.00 | 2.00 | 0 |
| ATOM | 1602 | CG1 | VAL | 165 | −4.905 | 40.241 | 122.717 | 1.00 | 2.00 | 0 |
| ATOM | 1603 | CG2 | VAL | 165 | −4.460 | 42.686 | 122.273 | 1.00 | 2.00 | 0 |
| ATOM | 1604 | C | VAL | 165 | −6.973 | 40.987 | 124.570 | 1.00 | 22.04 | 0 |
| ATOM | 1605 | O | VAL | 165 | −6.546 | 41.064 | 125.728 | 1.00 | 2.00 | 0 |
| ATOM | 1606 | N | ASP | 166 | −7.841 | 40.066 | 124.163 | 1.00 | 10.50 | 0 |
| ATOM | 1608 | CA | ASP | 166 | −8.401 | 39.057 | 125.046 | 1.00 | 16.73 | 0 |
| ATOM | 1609 | CB | ASP | 166 | −7.348 | 37.980 | 125.337 | 1.00 | 24.26 | 0 |
| ATOM | 1610 | CG | ASP | 166 | −7.245 | 36.914 | 124.212 | 1.00 | 24.02 | 0 |
| ATOM | 1611 | OD1 | ASP | 166 | −8.258 | 36.207 | 123.944 | 1.00 | 22.39 | 0 |
| ATOM | 1612 | OD2 | ASP | 166 | −6.145 | 36.776 | 123.611 | 1.00 | 26.91 | 0 |
| ATOM | 1613 | C | ASP | 166 | −8.963 | 39.674 | 126.326 | 1.00 | 15.15 | 0 |
| ATOM | 1614 | O | ASP | 166 | −9.139 | 39.006 | 127.336 | 1.00 | 12.89 | 0 |
| ATOM | 1615 | N | GLU | 167 | −9.262 | 40.967 | 126.231 | 1.00 | 2.00 | 0 |
| ATOM | 1617 | CA | GLU | 167 | −9.833 | 41.811 | 127.289 | 1.00 | 2.00 | 0 |
| ATOM | 1618 | CB | GLU | 167 | −11.280 | 41.394 | 127.555 | 1.00 | 83.32 | 0 |
| ATOM | 1619 | CG | GLU | 167 | −12.129 | 41.397 | 126.273 | 1.00 | 2.00. | 0 |
| ATOM | 1620 | CD | GLU | 167 | −11.819 | 42.603 | 125.305 | 1.00 | 2.00 | 0 |
| ATOM | 1621 | OE1 | GLU | 167 | −11.133 | 42.398 | 124.242 | 1.00 | 2.00 | 0 |
| ATOM | 1622 | OE2 | GLU | 167 | −12.268 | 43.750 | 125.622 | 1.00 | 2.00 | 0 |
| ATOM | 1623 | C | GLU | 167 | −9.056 | 41.981 | 128.585 | 1.00 | 2.00 | 0 |
| ATOM | 1624 | O | GLU | 167 | −9.634 | 42.138 | 129.657 | 1.00 | 74.79 | 0 |
| ATOM | 1625 | N | LYS | 168 | −7.733 | 41.984 | 128.460 | 1.00 | 22.77 | 0 |
| ATOM | 1627 | CA | LYS | 168 | −6.829 | 42.154 | 129.589 | 1.00 | 14.49 | 0 |
| ATOM | 1628 | CB | LYS | 168 | −6.098 | 40.844 | 129.910 | 1.00 | 21.81 | 0 |
| ATOM | 1629 | CG | LYS | 168 | −6.956 | 39.798 | 130.600 | 1.00 | 17.49 | 0 |
| ATOM | 1630 | CD | LYS | 168 | −7.677 | 40.404 | 131.802 | 1.00 | 18.27 | 0 |
| ATOM | 1631 | CE | LYS | 168 | −8.654 | 39.411 | 132.466 | 1.00 | 26.28 | 0 |
| ATOM | 1632 | NZ | LYS | 168 | −9.658 | 40.080 | 133.373 | 1.00 | 29.04 | 0 |
| ATOM | 1636 | C | LYS | 166 | −5.811 | 43.225 | 129.237 | 1.00 | 11.04 | 0 |
| ATOM | 1637 | O | LYS | 168 | −5.665 | 44.214 | 129.947 | 1.00 | 17.06 | 0 |
| ATOM | 1638 | N | ILE | 169 | −5.109 | 43.015 | 128.131 | 1.00 | 2.00 | 0 |
| ATOM | 1640 | CA | ILE | 169 | −4.093 | 43.950 | 127.663 | 1.00 | 2.00 | 0 |

TABLE A-continued

| | | | | | | | | | |
|---|---|---|---|---|---|---|---|---|---|
| ATOM | 1641 | CB | ILE | 169 | −3.151 | 43.267 | 126.648 | 1.00 | 2.00 | 0 |
| ATOM | 1642 | CG2 | ILE | 169 | −1.989 | 44.184 | 126.302 | 1.00 | 2.00 | 0 |
| ATOM | 1643 | CG1 | ILE | 169 | −2.632 | 41.952 | 127.215 | 1.00 | 2.00 | 0 |
| ATOM | 1644 | CD1 | ILE | 169 | −1.691 | 41.218 | 126.297 | 1.00 | 2.00 | 0 |
| ATOM | 1645 | C | ILE | 169 | −4.731 | 45.144 | 126.964 | 1.00 | 2.00 | 0 |
| ATOM | 1646 | O | ILE | 169 | −5.393 | 44.973 | 125.938 | 1.00 | 2.00 | 0 |
| ATOM | 1647 | N | PHE | 170 | −4.572 | 46.337 | 127.524 | 1.00 | 17.81 | 0 |
| ATOM | 1649 | CA | PHE | 170 | −5.110 | 47.525 | 126.877 | 1.00 | 19.78 | 0 |
| ATOM | 1650 | CB | PHE | 170 | −5.486 | 48.610 | 127.885 | 1.00 | 2.00 | 0 |
| ATOM | 1651 | CG | PHE | 170 | −5.895 | 49.920 | 127.252 | 1.00 | 2.00 | 0 |
| ATOM | 1652 | CD1 | PHE | 170 | −7.095 | 50.028 | 126.538 | 1.00 | 2.00 | 0 |
| ATOM | 1653 | CD2 | PHE | 170 | −5.092 | 51.056 | 127.390 | 1.00 | 2.00 | 0 |
| ATOM | 1654 | CE1 | PHE | 170 | −7.493 | 51.248 | 125.976 | 1.00 | 2.00 | 0 |
| ATOM | 1655 | CE2 | PHE | 170 | −5.473 | 52.282 | 126.836 | 1.00 | 2.00 | 0 |
| ATOM | 1656 | CZ | PHE | 170 | −6.680 | 52.377 | 126.127 | 1.00 | 2.00 | 0 |
| ATOM | 1657 | C | PHE | 170 | −3.943 | 47.992 | 126.038 | 1.00 | 23.45 | 0 |
| ATOM | 1658 | O | PHE | 170 | −2.809 | 47.983 | 126.518 | 1.00 | 2.00 | 0 |
| ATOM | 1659 | N | CYS | 171 | −4.208 | 48.375 | 124.790 | 1.00 | 2.00 | 0 |
| ATOM | 1661 | CA | CYS | 171 | −3.158 | 48.836 | 123.868 | 1.00 | 2.00 | 0 |
| ATOM | 1662 | CB | CYS | 171 | −2.952 | 47.643 | 122.766 | 1.00 | 26.14 | 0 |
| ATOM | 1663 | SG | CYS | 171 | −2.524 | 46.203 | 123.305 | 1.00 | 16.13 | 0 |
| ATOM | 1664 | C | CYS | 171 | −3.499 | 50.189 | 123.310 | 1.00 | 2.00 | 0 |
| ATOM | 1665 | O | CYS | 171 | −4.652 | 50.453 | 122.943 | 1.00 | 26.14 | 0 |
| ATOM | 1666 | N | CYS | 172 | −2.495 | 51.058 | 123.265 | 1.00 | 2.00 | 0 |
| ATOM | 1668 | CA | CYS | 172 | −2.635 | 52.378 | 122.668 | 1.00 | 2.00 | 0 |
| ATOM | 1669 | CB | CYS | 172 | −3.403 | 53.356 | 123.597 | 1.00 | 14.54 | 0 |
| ATOM | 1670 | SG | CYS | 172 | −2.593 | 53.995 | 125.094 | 1.00 | 15.67 | 0 |
| ATOM | 1671 | C | CYS | 172 | −1.231 | 52.890 | 122.287 | 1.00 | 2.00 | 0 |
| ATOM | 1672 | O | CYS | 172 | −0.227 | 52.277 | 122.657 | 1.00 | 7.48 | 0 |
| ATOM | 1673 | N | HIS | 173 | −1.154 | 53.951 | 121.488 | 1.00 | 2.00 | 0 |
| ATOM | 1675 | CA | HIS | 173 | 0.146 | 54.461 | 121.112 | 1.00 | 2.00 | 0 |
| ATOM | 1676 | C | HIS | 173 | 0.815 | 55.130 | 122.297 | 1.00 | 2.00 | 0 |
| ATOM | 1677 | O | HIS | 173 | 1.893 | 54.707 | 122.722 | 1.00 | 2.00 | 0 |
| ATOM | 1678 | CB | HIS | 173 | 0.056 | 55.457 | 119.944 | 1.00 | 2.00 | 0 |
| ATOM | 1679 | CG | HIS | 173 | 1.377 | 56.074 | 119.588 | 1.00 | 2.00 | 0 |
| ATOM | 1680 | ND1 | HIS | 173 | 2.487 | 55.347 | 119.234 | 1.00 | 2.00 | 0 |
| ATOM | 1682 | CD2 | HIS | 173 | 1.774 | 57.372 | 119.565 | 1.00 | 2.00 | 0 |
| ATOM | 1683 | NE2 | HIS | 173 | 3.123 | 57.441 | 119.241 | 1.00 | 2.00 | 0 |
| ATOM | 1684 | CE1 | HIS | 173 | 3.492 | 56.189 | 119.045 | 1.00 | 2.00 | 0 |
| ATOM | 1685 | N | GLY | 174 | 0.168 | 56.172 | 122.817 | 1.00 | 2.00 | 0 |
| ATOM | 1697 | CA | GLY | 174 | 0.711 | 56.933 | 123.935 | 1.00 | 2.00 | 0 |
| ATOM | 1688 | C | GLY | 174 | 0.568 | 56.450 | 125.386 | 1.00 | 2.00 | 0 |
| ATOM | 1689 | O | GLY | 174 | 1.556 | 56.111 | 126.041 | 1.00 | 2.00 | 0 |
| ATOM | 1690 | N | GLY | 175 | −0.648 | 56.453 | 125.913 | 1.00 | 16.98 | 0 |
| ATOM | 1692 | CA | GLY | 175 | −0.830 | 56.028 | 127.283 | 1.00 | 16.98 | 0 |
| ATOM | 1693 | C | GLY | 175 | −2.227 | 56.343 | 127.763 | 1.00 | 16.98 | 0 |
| ATOM | 1694 | O | GLY | 175 | −3.190 | 56.231 | 126.999 | 1.00 | 66.77 | 0 |
| ATOM | 1695 | N | LEU | 176 | −2.341 | 56.764 | 129.021 | 1.00 | 11.28 | 0 |
| ATOM | 1697 | CA | LEU | 176 | −3.637 | 57.063 | 129.604 | 1.00 | 11.28 | 0 |
| ATOM | 1698 | CB | LEU | 176 | −3.740 | 56.427 | 130.976 | 1.00 | 2.00 | 0 |
| ATOM | 1699 | CG | LEU | 176 | −3.443 | 54.934 | 130.966 | 1.00 | 2.00 | 0 |
| ATOM | 1700 | CD1 | LEU | 176 | −3.469 | 54.407 | 132.374 | 1.00 | 2.00 | 0 |
| ATOM | 1701 | CD2 | LEU | 176 | −4.463 | 54.218 | 130.121 | 1.00 | 2.00 | 0 |
| ATOM | 1702 | C | LEU | 176 | −3.876 | 58.545 | 129.692 | 1.00 | 11.28 | 0 |
| ATOM | 1703 | O | LEU | 176 | −2.943 | 59.329 | 129.645 | 1.00 | 2.00 | 0 |
| ATOM | 1704 | N | SER | 177 | −5.138 | 58.913 | 129.850 | 1.00 | 6.18 | 0 |
| ATOM | 1706 | CA | SER | 177 | −5.567 | 60.304 | 129.918 | 1.00 | 6.86 | 0 |
| ATOM | 1707 | CB | SER | 177 | −6.476 | 60.587 | 128.718 | 1.00 | 12.19 | 0 |
| ATOM | 1708 | OG | SER | 177 | −7.189 | 61.804 | 128.835 | 1.00 | 12.19 | 0 |
| ATOM | 1710 | C | SER | 177 | −6.356 | 60.573 | 131.193 | 1.00 | 7.79 | 0 |
| ATOM | 1711 | O | SER | 177 | −7.170 | 59.749 | 131.606 | 1.00 | 12.19 | 0 |
| ATOM | 1712 | N | PRO | 178 | −6.150 | 61.736 | 131.824 | 1.00 | 2.00 | 0 |
| ATOM | 1713 | CD | PRO | 178 | −5.223 | 62.827 | 131.505 | 1.00 | 29.89 | 0 |
| ATOM | 1714 | CA | PRO | 178 | −6.895 | 62.054 | 133.041 | 1.00 | 2.00 | 0 |
| ATOM | 1715 | CB | PRO | 178 | −6.231 | 63.337 | 133.518 | 1.00 | 25.57 | 0 |
| ATOM | 1716 | CG | PRO | 178 | −5.842 | 63.973 | 132.274 | 1.00 | 21.36 | 0 |
| ATOM | 1717 | C | PRO | 178 | −8.394 | 62.266 | 132.757 | 1.00 | 2.00 | 0 |
| ATOM | 1718 | O | PRO | 178 | −9.140 | 62.740 | 133.617 | 1.00 | 24.04 | 0 |
| ATOM | 1719 | N | ASP | 179 | −8.821 | 61.933 | 131.543 | 1.00 | 38.94 | 0 |
| ATOM | 1721 | CA | ASP | 179 | −10.206 | 62.078 | 131.129 | 1.00 | 37.05 | 0 |
| ATOM | 1722 | CB | ASP | 179 | −10.264 | 62.870 | 129.837 | 1.00 | 33.34 | 0 |
| ATOM | 1723 | CG | ASP | 179 | −9.964 | 64.320 | 130.048 | 1.00 | 30.55 | 0 |
| ATOM | 1724 | OD1 | ASP | 179 | −10.923 | 65.045 | 130.386 | 1.00 | 31.71 | 0 |
| ATOM | 1725 | OD2 | ASP | 179 | −8.796 | 64.728 | 129.889 | 1.00 | 32.17 | 0 |
| ATOM | 1726 | C | ASP | 179 | −10.871 | 60.735 | 130.923 | 1.00 | 40.05 | 0 |
| ATOM | 1727 | O | ASP | 179 | −12.096 | 60.638 | 130.873 | 1.00 | 34.46 | 0 |
| ATOM | 1728 | N | LEU | 180 | −10.057 | 59.699 | 130.791 | 1.00 | 15.43 | 0 |
| ATOM | 1730 | CA | LEU | 180 | −10.570 | 58.362 | 130.590 | 1.00 | 12.98 | 0 |
| ATOM | 1731 | CB | LEU | 180 | −9.446 | 57.467 | 130.058 | 1.00 | 2.00 | 0 |

TABLE A-continued

| | | | | | | | | | |
|---|---|---|---|---|---|---|---|---|---|
| ATOM | 1732 | CG | LEU | 180 | −9.867 | 56.186 | 129.336 | 1.00 | 2.00 | 0 |
| ATOM | 1733 | CD1 | LEU | 180 | −10.706 | 56.511 | 128.110 | 1.00 | 2.00 | 0 |
| ATOM | 1734 | CD2 | LEU | 180 | −8.633 | 55.413 | 128.953 | 1.00 | 2.00 | 0 |
| ATOM | 1735 | C | LEU | 180 | −11.157 | 57.806 | 131.902 | 1.00 | 14.43 | 0 |
| ATOM | 1736 | O | LEU | 180 | −10.470 | 57.709 | 132.931 | 1.00 | 2.00 | 0 |
| ATOM | 1737 | N | GLN | 181 | −12.448 | 57.492 | 131.862 | 1.00 | 5.88 | 0 |
| ATOM | 1739 | CA | GLN | 181 | −13.184 | 56.917 | 132.992 | 1.00 | 5.88 | 0 |
| ATOM | 1740 | CB | GLN | 181 | −14.379 | 57.787 | 133.375 | 1.00 | 32.99 | 0 |
| ATOM | 1741 | CG | GLN | 181 | −14.002 | 59.152 | 133.900 | 1.00 | 36.07 | 0 |
| ATOM | 1742 | CD | GLN | 181 | −15.101 | 60.172 | 133.676 | 1.00 | 38.35 | 0 |
| ATOM | 1743 | OE1 | GLN | 181 | −16.285 | 59.886 | 133.877 | 1.00 | 41.53 | 0 |
| ATOM | 1744 | NE2 | GLN | 181 | −14.717 | 61.366 | 133.242 | 1.00 | 38.39 | 0 |
| ATOM | 1747 | C | GLN | 181 | −13.672 | 55.563 | 132.500 | 1.00 | 5.88 | 0 |
| ATOM | 1748 | O | GLN | 181 | −13.572 | 54.554 | 133.205 | 1.00 | 24.31 | 0 |
| ATOM | 1749 | N | SER | 182 | −14.188 | 55.544 | 131.274 | 1.00 | 2.20 | 0 |
| ATOM | 1751 | CA | SER | 182 | −14.651 | 54.310 | 130.664 | 1.00 | 9.71 | 0 |
| ATOM | 1752 | CB | SER | 182 | −16.174 | 54.255 | 130.614 | 1.00 | 15.80 | 0 |
| ATOM | 1753 | OG | SER | 182 | −16.668 | 54.856 | 129.433 | 1.00 | 17.25 | 0 |
| ATOM | 1755 | C | SER | 182 | −14.112 | 54.177 | 129.248 | 1.00 | 3.77 | 0 |
| ATOM | 1756 | O | SER | 182 | −13.359 | 55.019 | 126.751 | 1.00 | 15.80 | 0 |
| ATOM | 1757 | N | MET | 183 | −14.526 | 53.091 | 126.615 | 1.00 | 2.00 | 0 |
| ATOM | 1759 | CA | MET | 163 | −14.156 | 52.780 | 127.251 | 1.00 | 2.00 | 0 |
| ATOM | 1760 | CB | MET | 183 | −14.100 | 51.272 | 127.064 | 1.00 | 2.00 | 0 |
| ATOM | 1761 | CG | MET | 183 | −13.171 | 50.616 | 128.048 | 1.00 | 2.00 | 0 |
| ATOM | 1762 | SD | MET | 183 | −11.620 | 51.473 | 128.022 | 1.00 | 2.00 | 0 |
| ATOM | 1763 | CE | MET | 183 | −10.520 | 50.135 | 127.900 | 1.00 | 2.00 | 0 |
| ATOM | 1764 | C | MET | 183 | −15.204 | 53.373 | 126.326 | 1.00 | 2.00 | 0 |
| ATOM | 1765 | O | MET | 183 | −14.959 | 53.550 | 125.129 | 1.00 | 2.00 | 0 |
| ATOM | 1766 | N | GLU | 184 | −16.370 | 53.700 | 126.882 | 1.00 | 2.00 | 0 |
| ATOM | 1768 | CA | GLU | 184 | −17.432 | 54.280 | 126.082 | 1.00 | 2.00 | 0 |
| ATOM | 1769 | CB | GLU | 184 | −18.668 | 54.531 | 126.910 | 1.00 | 6.25 | 0 |
| ATOM | 1770 | CG | GLU | 184 | −19.830 | 54.977 | 126.073 | 1.00 | 8.82 | 0 |
| ATOM | 1771 | CD | GLU | 184 | −20.273 | 53.927 | 125.068 | 1.00 | 13.01 | 0 |
| ATOM | 1772 | OE1 | GLU | 184 | −19.846 | 52.744 | 125.181 | 1.00 | 14.09 | 0 |
| ATOM | 1773 | OE2 | GLU | 184 | −21.064 | 54.293 | 124.164 | 1.00 | 20.29 | 0 |
| ATOM | 1774 | C | GLU | 184 | −16.978 | 55.586 | 125.481 | 1.00 | 2.00 | 0 |
| ATOM | 1775 | O | GLU | 184 | −17.399 | 55.946 | 124.392 | 1.00 | 23.33 | 0 |
| ATOM | 1776 | N | GLN | 185 | −16.117 | 56.295 | 126.198 | 1.00 | 12.32 | 0 |
| ATOM | 1778 | CA | GLN | 185 | −15.599 | 57.561 | 125.714 | 1.00 | 14.30 | 0 |
| ATOM | 1779 | CB | GLN | 185 | −14.697 | 58.190 | 126.758 | 1.00 | 43.49 | 0 |
| ATOM | 1780 | CG | GLN | 185 | −15.454 | 58.629 | 127.990 | 1.00 | 47.40 | 0 |
| ATOM | 1781 | CD | GLN | 185 | −14.537 | 58.929 | 129.139 | 1.00 | 49.32 | 0 |
| ATOM | 1782 | OE1 | GLN | 185 | −13.994 | 58.016 | 129.753 | 1.00 | 56.49 | 0 |
| ATOM | 1783 | NE2 | GLN | 185 | −14.350 | 60.208 | 129.437 | 1.00 | 49.76 | 0 |
| ATOM | 1786 | C | GLN | 185 | −14.834 | 57.307 | 124.432 | 1.00 | 16.93 | 0 |
| ATOM | 1787 | O | GLN | 185 | −14.973 | 58.053 | 123.461 | 1.00 | 43.79 | 0 |
| ATOM | 1788 | N | ILE | 186 | −14.044 | 56.238 | 124.420 | 1.00 | 5.67 | 0 |
| ATOM | 1790 | CA | ILE | 186 | −13.280 | 55.880 | 123.235 | 1.00 | 5.67 | 0 |
| ATOM | 1791 | CB | ILE | 186 | −12.436 | 54.613 | 123.470 | 1.00 | 16.18 | 0 |
| ATOM | 1792 | CG2 | ILE | 186 | −11.675 | 54.243 | 122.208 | 1.00 | 11.85 | 0 |
| ATOM | 1793 | CG1 | ILE | 186 | −11.489 | 54.825 | 124.642 | 1.00 | 13.18 | 0 |
| ATOM | 1794 | CD1 | ILE | 186 | −10.545 | 55.954 | 124.459 | 1.00 | 17.92 | 0 |
| ATOM | 1795 | C | ILE | 186 | −14.294 | 55.566 | 122.143 | 1.00 | 5.67 | 0 |
| ATOM | 1796 | O | ILE | 186 | −14.260 | 56.145 | 121.060 | 1.00 | 19.35 | 0 |
| ATOM | 1797 | N | ARG | 187 | −15.207 | 54.655 | 122.471 | 1.00 | 17.59 | 0 |
| ATOM | 1799 | CA | ARG | 187 | −16.243 | 54.205 | 121.561 | 1.00 | 16.33 | 0 |
| ATOM | 1800 | CB | ARG | 187 | −17.141 | 53.165 | 122.237 | 1.00 | 20.41 | 0 |
| ATOM | 1801 | CG | ARG | 187 | −16.468 | 51.900 | 122.723 | 1.00 | 29.32 | 0 |
| ATOM | 1802 | CD | ARG | 187 | −17.497 | 51.006 | 123.447 | 1.00 | 31.43 | 0 |
| ATOM | 1803 | NE | ARG | 187 | −16.888 | 49.888 | 124.165 | 1.00 | 38.34 | 0 |
| ATOM | 1805 | CZ | ARG | 187 | −16.311 | 48.838 | 123.580 | 1.00 | 34.30 | 0 |
| ATOM | 1806 | NH1 | ARG | 187 | −16.256 | 48.747 | 122.252 | 1.00 | 41.37 | 0 |
| ATOM | 1809 | NH2 | ARG | 187 | −15.783 | 47.873 | 124.322 | 1.00 | 34.50 | 0 |
| ATOM | 1812 | C | ARG | 187 | −17.148 | 55.302 | 121.011 | 1.00 | 15.89 | 0 |
| ATOM | 1813 | O | ARG | 187 | −17.937 | 55.032 | 120.108 | 1.00 | 20.82 | 0 |
| ATOM | 1814 | N | ARG | 188 | −17.071 | 56.524 | 121.529 | 1.00 | 2.00 | 0 |
| ATOM | 1816 | CA | ARG | 188 | −17.964 | 57.557 | 121.012 | 1.00 | 2.00 | 0 |
| ATOM | 1817 | CE | ARG | 188 | −18.878 | 58.105 | 122.106 | 1.00 | 31.38 | 0 |
| ATOM | 1818 | CG | ARG | 188 | −18.184 | 56.827 | 123.228 | 1.00 | 29.44 | 0 |
| ATOM | 1819 | CD | ARG | 188 | −19.202 | 59.586 | 124.034 | 1.00 | 31.32 | 0 |
| ATOM | 1820 | NE | ARG | 188 | −20.410 | 58.802 | 124.237 | 1.00 | 33.18 | 0 |
| ATOM | 1822 | CZ | ARG | 188 | −21.637 | 59.285 | 124.112 | 1.00 | 29.63 | 0 |
| ATOM | 1823 | NH1 | ARG | 188 | −21.827 | 60.561 | 123.777 | 1.00 | 36.26 | 0 |
| ATOM | 1826 | NH2 | ARG | 188 | −23.671 | 58.484 | 124.332 | 1.00 | 32.06 | 0 |
| ATOM | 1829 | C | ARG | 188 | −17.255 | 58.692 | 120.332 | 1.00 | 2.00 | 0 |
| ATOM | 1830 | O | ARG | 188 | −17.758 | 59.904 | 120.250 | 1.00 | 31.89 | 0 |
| ATOM | 1831 | N | ILE | 189 | −16.070 | 58.369 | 119.846 | 1.00 | 17.06 | 0 |
| ATOM | 1833 | CA | ILE | 189 | −15.263 | 59.333 | 119.136 | 1.00 | 16.98 | 0 |
| ATOM | 1834 | CB | ILE | 189 | −13.759 | 59.043 | 119.345 | 1.00 | 16.67 | 0 |

TABLE A-continued

| ATOM | 1835 | CG2 | ILE | 189 | −12.924 | 59.973 | 118.493 | 1.00 | 17.43 | 0 |
| ATOM | 1836 | CG1 | ILE | 189 | −13.411 | 59.205 | 120.826 | 1.00 | 17.65 | 0 |
| ATOM | 1837 | CD1 | ILE | 189 | −11.970 | 58.946 | 121.173 | 1.00 | 16.74 | 0 |
| ATOM | 1838 | C | ILE | 189 | −15.620 | 59.244 | 117.656 | 1.00 | 19.51 | 0 |
| ATOM | 1839 | O | ILE | 189 | −15.448 | 58.184 | 117.044 | 1.00 | 25.93 | 0 |
| ATOM | 1840 | N | MET | 190 | −16.158 | 60.342 | 117.108 | 1.00 | 22.12 | 0 |
| ATOM | 1842 | CA | MET | 190 | −16.514 | 60.420 | 115.685 | 1.00 | 24.92 | 0 |
| ATOM | 1843 | CB | MET | 190 | −17.051 | 61.812 | 115.320 | 1.00 | 46.39 | 0 |
| ATOM | 1844 | CG | MET | 190 | −17.366 | 61.977 | 113.826 | 1.00 | 46.97 | 0 |
| ATOM | 1845 | SD | MET | 190 | −17.820 | 63.658 | 113.312 | 1.00 | 58.03 | 0 |
| ATOM | 1846 | CE | MET | 190 | −16.271 | 64.266 | 112.598 | 1.00 | 52.38 | 0 |
| ATOM | 1847 | C | MET | 190 | −15.173 | 60.194 | 115.015 | 1.00 | 25.36 | 0 |
| ATOM | 1848 | O | MET | 190 | −14.287 | 61.041 | 115.106 | 1.00 | 32.57 | 0 |
| ATOM | 1849 | N | ARG | 191 | −15.023 | 59.057 | 114.346 | 1.00 | 2.00 | 0 |
| ATOM | 1851 | CA | ARG | 191 | −13.732 | 58.738 | 113.772 | 1.00 | 2.00 | 0 |
| ATOM | 1852 | CB | ARG | 191 | −13.731 | 57.394 | 113.089 | 1.00 | 2.00 | 0 |
| ATOM | 1853 | CG | ARG | 191 | −12.300 | 56.900 | 112.821 | 1.00 | 11.31 | 0 |
| ATOM | 1854 | CD | ARG | 191 | −11.978 | 55.799 | 113.752 | 1.00 | 11.31 | 0 |
| ATOM | 1855 | NE | ARG | 191 | −13.139 | 54.935 | 113.762 | 1.00 | 2.00 | 0 |
| ATOM | 1857 | CZ | ARG | 191 | −13.124 | 53.663 | 113.416 | 1.00 | 2.00 | 0 |
| ATOM | 1858 | NH1 | ARG | 191 | −11.985 | 53.085 | 113.047 | 1.00 | 2.00 | 0 |
| ATOM | 1861 | NH2 | ARG | 191 | −14.263 | 52.984 | 113.430 | 1.00 | 2.00 | 0 |
| ATOM | 1864 | C | ARG | 191 | −13.084 | 59.769 | 112.857 | 1.00 | 2.00 | 0 |
| ATOM | 1865 | O | ARG | 191 | −11.995 | 60.267 | 113.202 | 1.00 | 6.10 | 0 |
| ATOM | 1866 | N | PRO | 192 | −13.685 | 60.065 | 111.670 | 1.00 | 37.06 | 0 |
| ATOM | 1867 | CD | PRO | 192 | −14.912 | 59.530 | 111.045 | 1.00 | 2.00 | 0 |
| ATOM | 1868 | CA | PRO | 192 | −13.048 | 61.068 | 110.799 | 1.00 | 36.28 | 0 |
| ATOM | 1869 | CB | PRO | 192 | −14.114 | 61.335 | 109.749 | 1.00 | 2.00 | 0 |
| ATOM | 1870 | CG | PRO | 192 | −14.743 | 59.973 | 109.602 | 1.00 | 2.00 | 0 |
| ATOM | 1871 | C | PRO | 192 | −12.787 | 62.261 | 111.693 | 1.00 | 37.24 | 0 |
| ATOM | 1872 | O | PRO | 192 | −13.697 | 63.033 | 112.004 | 1.00 | 2.00 | 0 |
| ATOM | 1873 | N | THR | 193 | −11.552 | 62.348 | 112.168 | 1.00 | 2.00 | 0 |
| ATOM | 1875 | CA | THR | 193 | −11.182 | 63.396 | 113.089 | 1.00 | 2.00 | 0 |
| ATOM | 1876 | CB | THR | 193 | −11.627 | 63.063 | 114.540 | 1.00 | 22.05 | 0 |
| ATOM | 1877 | OG1 | THR | 193 | −11.349 | 64.183 | 115.392 | 1.00 | 31.69 | 0 |
| ATOM | 1879 | CG2 | THR | 193 | −10.862 | 61.859 | 115.089 | 1.00 | 21.46 | 0 |
| ATOM | 1880 | C | THR | 193 | −9.700 | 63.661 | 113.152 | 1.00 | 2.00 | 0 |
| ATOM | 1881 | O | THR | 193 | −8.865 | 62.795 | 112.860 | 1.00 | 17.62 | 0 |
| ATOM | 1882 | N | ASP | 194 | −9.394 | 64.879 | 113.572 | 1.00 | 2.00 | 0 |
| ATOM | 1884 | CA | ASP | 194 | −8.031 | 65.311 | 113.744 | 1.00 | 2.00 | 0 |
| ATOM | 1885 | CB | ASP | 194 | −7.927 | 66.805 | 113.431 | 1.00 | 49.25 | 0 |
| ATOM | 1886 | CG | ASP | 194 | −6.561 | 67.197 | 112.912 | 1.00 | 49.25 | 0 |
| ATOM | 1887 | OD1 | ASP | 194 | −6.132 | 68.334 | 113.194 | 1.00 | 49.25 | 0 |
| ATOM | 1888 | OD2 | ASP | 194 | −5.920 | 66.371 | 112.217 | 1.00 | 49.25 | 0 |
| ATOM | 1889 | C | ASP | 194 | −7.686 | 65.041 | 115.216 | 1.00 | 2.00 | 0 |
| ATOM | 1890 | O | ASP | 194 | −8.571 | 64.978 | 116.077 | 1.00 | 54.62 | 0 |
| ATOM | 1891 | N | VAL | 195 | −6.408 | 64.836 | 115.488 | 1.00 | 17.01 | 0 |
| ATOM | 1893 | CA | VAL | 195 | −5.948 | 64.611 | 116.839 | 1.00 | 12.88 | 0 |
| ATOM | 1894 | CB | VAL | 195 | −4.509 | 64.017 | 116.818 | 1.00 | 9.98 | 0 |
| ATOM | 1895 | CG1 | VAL | 195 | −3.934 | 63.875 | 118.239 | 1.00 | 9.98 | 0 |
| ATOM | 1896 | CG2 | VAL | 195 | −4.532 | 62.675 | 116.124 | 1.00 | 9.98 | 0 |
| ATOM | 1897 | C | VAL | 195 | −5.971 | 65.994 | 117.511 | 1.00 | 12.88 | 0 |
| ATOM | 1898 | O | VAL | 195 | −5.343 | 66.934 | 117.038 | 1.00 | 9.98 | 0 |
| ATOM | 1899 | N | PRO | 196 | −6.771 | 66.152 | 118.567 | 1.00 | 16.08 | 0 |
| ATOM | 1900 | CD | PRO | 196 | −7.805 | 65.214 | 119.033 | 1.00 | 26.02 | 0 |
| ATOM | 1901 | CA | PRO | 196 | −6.862 | 67.429 | 119.284 | 1.00 | 21.91 | 0 |
| ATOM | 1902 | CB | PRO | 196 | −8.026 | 67.195 | 120.240 | 1.00 | 25.86 | 0 |
| ATOM | 1903 | CG | PRO | 196 | −8.874 | 66.153 | 119.496 | 1.00 | 25.31 | 0 |
| ATOM | 1904 | C | PRO | 196 | −5.560 | 67.735 | 120.027 | 1.00 | 24.64 | 0 |
| ATOM | 1905 | O | PRO | 196 | −4.809 | 66.818 | 120.349 | 1.00 | 23.54 | 0 |
| ATOM | 1906 | N | ASP | 197 | −5.291 | 69.010 | 120.302 | 1.00 | 39.93 | 0 |
| ATOM | 1908 | CA | ASP | 197 | −4.058 | 69.377 | 121.005 | 1.00 | 38.76 | 0 |
| ATOM | 1909 | CB | ASP | 197 | −3.605 | 70.789 | 120.612 | 1.00 | 78.93 | 0 |
| ATOM | 1910 | CG | ASP | 197 | −4.726 | 71.800 | 120.658 | 1.00 | 84.50 | 0 |
| ATOM | 1911 | OD1 | ASP | 197 | −5.071 | 72.263 | 121.768 | 1.00 | 83.41 | 0 |
| ATOM | 1912 | OD2 | ASP | 197 | −5.258 | 72.134 | 119.578 | 1.00 | 90.03 | 0 |
| ATOM | 1913 | C | ASP | 197 | −4.162 | 69.256 | 122.520 | 1.00 | 41.64 | 0 |
| ATOM | 1914 | O | ASP | 197 | −3.227 | 69.577 | 123.255 | 1.00 | 85.35 | 0 |
| ATOM | 1915 | N | GLN | 198 | −5.316 | 68.789 | 122.973 | 1.00 | 2.00 | 0 |
| ATOM | 1917 | CA | GLN | 198 | −5.581 | 66.588 | 124.385 | 1.00 | 2.00 | 0 |
| ATOM | 1918 | CB | GLN | 198 | −5.686 | 69.937 | 125.120 | 1.00 | 27.32 | 0 |
| ATOM | 1919 | CG | GLN | 198 | −6.621 | 70.967 | 124.503 | 1.00 | 32.39 | 0 |
| ATOM | 1920 | CD | GLN | 198 | −7.981 | 71.041 | 125.192 | 1.00 | 29.94 | 0 |
| ATOM | 1921 | OE1 | GLN | 198 | −8.108 | 70.793 | 126.397 | 1.00 | 32.81 | 0 |
| ATOM | 1922 | NE2 | GLN | 198 | −9.007 | 71.391 | 124.424 | 1.00 | 29.42 | 0 |
| ATOM | 1925 | C | GLN | 198 | −6.863 | 67.793 | 124.492 | 1.00 | 2.00 | 0 |
| ATOM | 1926 | O | GLN | 198 | −7.748 | 67.909 | 123.640 | 1.00 | 26.90 | 0 |
| ATOM | 1927 | N | GLY | 199 | −6.943 | 66.949 | 125.509 | 1.00 | 15.20 | 0 |
| ATOM | 1929 | CA | GLY | 199 | −8.137 | 66.148 | 125.692 | 1.00 | 15.56 | 0 |

TABLE A-continued

| ATOM | 1930 | C | GLY | 199 | −7.820 | 64.670 | 125.631 | 1.00 | 13.32 | 0 |
|---|---|---|---|---|---|---|---|---|---|---|
| ATOM | 1931 | O | GLY | 199 | −6.655 | 64.283 | 125.502 | 1.00 | 2.00 | 0 |
| ATOM | 1932 | N | LEU | 200 | −8.857 | 63.842 | 125.684 | 1.00 | 2.00 | 0 |
| ATOM | 1934 | CA | LEU | 200 | −8.690 | 62.402 | 125.666 | 1.00 | 2.00 | 0 |
| ATOM | 1935 | CB | LEU | 200 | −10.049 | 61.701 | 125.667 | 1.00 | 2.00 | 0 |
| ATOM | 1936 | CG | LEU | 200 | −9.945 | 60.224 | 126.081 | 1.00 | 2.00 | 0 |
| ATOM | 1937 | CD1 | LEU | 200 | −11.126 | 59.800 | 126.947 | 1.00 | 2.00 | 0 |
| ATOM | 1938 | CD2 | LEU | 200 | −9.842 | 59.380 | 124.847 | 1.00 | 2.00 | 0 |
| ATOM | 1939 | C | LEU | 200 | −7.850 | 61.875 | 124.521 | 1.00 | 2.00 | 0 |
| ATOM | 1940 | O | LEU | 200 | −6.764 | 61.323 | 124.764 | 1.00 | 2.00 | 0 |
| ATOM | 1941 | N | LEU | 201 | −8.344 | 62.045 | 123.283 | 1.00 | 2.00 | 0 |
| ATOM | 1943 | CA | LEU | 201 | −7.663 | 61.566 | 122.070 | 1.00 | 2.00 | 0 |
| ATOM | 1944 | CB | LEU | 201 | −8.378 | 62.041 | 120.811 | 1.00 | 2.00 | 0 |
| ATOM | 1945 | CG | LEU | 201 | −8.369 | 61.100 | 119.589 | 1.00 | 2.00 | 0 |
| ATOM | 1946 | CD1 | LEU | 201 | −8.895 | 61.855 | 118.375 | 1.00 | 2.00 | 0 |
| ATOM | 1947 | CD2 | LEU | 201 | −6.981 | 60.569 | 119.277 | 1.00 | 2.00 | 0 |
| ATOM | 1948 | C | LEU | 201 | −6.246 | 62.078 | 122.059 | 1.00 | 2.00 | 0 |
| ATOM | 1949 | O | LEU | 201 | −5.319 | 61.347 | 121.715 | 1.00 | 2.00 | 0 |
| ATOM | 1950 | N | CYS | 202 | −6.071 | 63.333 | 122.446 | 1.00 | 2.00 | 0 |
| ATOM | 1952 | CA | CYS | 202 | −4.733 | 63.891 | 122.484 | 1.00 | 2.00 | 0 |
| ATOM | 1953 | CB | CYS | 202 | −4.722 | 65.306 | 123.024 | 1.00 | 2.00 | 0 |
| ATOM | 1954 | SG | CYS | 202 | −3.012 | 65.850 | 123.209 | 1.00 | 2.00 | 0 |
| ATOM | 1955 | C | CYS | 202 | −3.850 | 63.076 | 123.394 | 1.00 | 2.00 | 0 |
| ATOM | 1956 | O | CYS | 202 | −2.719 | 62.715 | 123.036 | 1.00 | 2.00 | 0 |
| ATOM | 1957 | N | ASP | 203 | −4.385 | 62.798 | 124.584 | 1.00 | 15.07 | 0 |
| ATOM | 1959 | CA | ASP | 203 | −3.673 | 62.057 | 125.611 | 1.00 | 11.86 | 0 |
| ATOM | 1960 | CB | ASP | 203 | −4.429 | 62.142 | 126.931 | 1.00 | 13.71 | 0 |
| ATOM | 1961 | CG | ASP | 203 | −4.449 | 63.538 | 127.497 | 1.00 | 15.77 | 0 |
| ATOM | 1962 | OD1 | ASP | 203 | −3.529 | 64.315 | 127.162 | 1.00 | 11.73 | 0 |
| ATOM | 1963 | OD2 | ASP | 203 | −5.380 | 63.861 | 128.271 | 1.00 | 16.16 | 0 |
| ATOM | 1964 | C | ASP | 203 | −3.369 | 60.615 | 125.262 | 1.00 | 13.81 | 0 |
| ATOM | 1965 | O | ASP | 203 | −2.254 | 60.155 | 125.492 | 1.00 | 23.94 | 0 |
| ATOM | 1966 | N | LEU | 204 | −4.330 | 59.902 | 124.695 | 1.00 | 10.49 | 0 |
| ATOM | 1968 | CA | LEU | 204 | −4.097 | 58.509 | 124.332 | 1.00 | 10.49 | 0 |
| ATOM | 1969 | CB | LEU | 204 | −5.351 | 57.912 | 123.717 | 1.00 | 10.22 | 0 |
| ATOM | 1970 | CG | LEU | 204 | −6.478 | 57.606 | 124.696 | 1.00 | 10.22 | 0 |
| ATOM | 1971 | CD1 | LEU | 204 | −7.667 | 57.281 | 123.866 | 1.00 | 10.22 | 0 |
| ATOM | 1972 | CD2 | LEU | 204 | −6.143 | 56.441 | 125.620 | 1.00 | 10.22 | 0 |
| ATOM | 1973 | C | LEU | 204 | −2.930 | 58.347 | 123.361 | 1.00 | 10.49 | 0 |
| ATOM | 1974 | O | LEU | 204 | −2.204 | 57.352 | 123.392 | 1.00 | 10.22 | 0 |
| ATOM | 1975 | N | LEU | 205 | −2.748 | 59.336 | 122.501 | 1.00 | 2.00 | 0 |
| ATOM | 1977 | CA | LEU | 205 | −1.679 | 59.301 | 121.525 | 1.00 | 2.00 | 0 |
| ATOM | 1978 | CB | LEU | 205 | −2.161 | 59.933 | 120.219 | 1.00 | 2.00 | 0 |
| ATOM | 1979 | CG | LEU | 205 | −3.459 | 59.463 | 119.551 | 1.00 | 2.00 | 0 |
| ATOM | 1980 | CD1 | LEU | 205 | −3.595 | 60.238 | 118.259 | 1.00 | 2.00 | 0 |
| ATOM | 1981 | CD2 | LEU | 205 | −3.459 | 57.954 | 119.269 | 1.00 | 2.00 | 0 |
| ATOM | 1982 | C | LEU | 205 | −0.409 | 60.018 | 121.967 | 1.00 | 2.00 | 0 |
| ATOM | 1983 | O | LEU | 205 | 0.620 | 59.890 | 121.314 | 1.00 | 2.00 | 0 |
| ATOM | 1984 | N | TRP | 206 | −0.472 | 60.756 | 123.072 | 1.00 | 10.02 | 0 |
| ATOM | 1986 | CA | TRP | 206 | 0.678 | 61.526 | 123.545 | 1.00 | 10.02 | 0 |
| ATOM | 1987 | CB | TRP | 206 | 0.362 | 62.994 | 123.408 | 1.00 | 2.00 | 0 |
| ATOM | 1988 | CG | TRP | 206 | 0.413 | 63.485 | 122.052 | 1.00 | 2.00 | 0 |
| ATOM | 1989 | CD2 | TRP | 206 | 1.532 | 64.103 | 121.420 | 1.00 | 2.00 | 0 |
| ATOM | 1990 | CE2 | TRP | 206 | 1.105 | 64.535 | 120.148 | 1.00 | 2.00 | 0 |
| ATOM | 1991 | CE3 | TRP | 206 | 2.854 | 64.355 | 121.813 | 1.00 | 2.00 | 0 |
| ATOM | 1992 | CD1 | TRP | 206 | −0.616 | 63.541 | 121.162 | 1.00 | 2.00 | 0 |
| ATOM | 1993 | NE1 | TRP | 206 | −0.212 | 64.178 | 120.017 | 1.00 | 2.00 | 0 |
| ATOM | 1995 | CZ2 | TRP | 206 | 1.950 | 65.207 | 119.263 | 1.00 | 2.00 | 0 |
| ATOM | 1996 | CZ3 | TRP | 206 | 3.697 | 65.024 | 120.932 | 1.00 | 2.00 | 0 |
| ATOM | 1997 | CH2 | TRP | 206 | 3.238 | 65.443 | 119.669 | 1.00 | 2.00 | 0 |
| ATOM | 1998 | C | TRP | 206 | 1.246 | 61.330 | 124.955 | 1.00 | 10.02 | 0 |
| ATOM | 1999 | 0 | TRP | 206 | 2.419 | 61.639 | 125.194 | 1.00 | 2.00 | 0 |
| ATOM | 2000 | N | SER | 207 | 0.418 | 60.967 | 125.886 | 1.00 | 2.00 | 0 |
| ATOM | 2002 | CA | SER | 207 | 0.830 | 60.690 | 127.267 | 1.00 | 2.00 | 0 |
| ATOM | 2003 | CB | SER | 207 | −0.363 | 60.273 | 128.121 | 1.00 | 29.76 | 0 |
| ATOM | 2004 | OG | SER | 207 | −0.482 | 61.120 | 129.256 | 1.00 | 35.73 | 0 |
| ATOM | 2006 | C | SER | 207 | 1.951 | 59.699 | 127.446 | 1.00 | 2.00 | 0 |
| ATOM | 2007 | O | SER | 207 | 2.075 | 58.743 | 126.681 | 1.00 | 31.05 | 0 |
| ATOM | 2008 | N | ASP | 208 | 2.777 | 59.943 | 128.462 | 1.00 | 2.00 | 0 |
| ATOM | 2010 | CA | ASP | 208 | 3.899 | 59.056 | 128.764 | 1.00 | 2.00 | 0 |
| ATOM | 2011 | CB | ASP | 208 | 5.257 | 59.714 | 128.505 | 1.00 | 42.39 | 0 |
| ATOM | 2012 | CG | ASP | 208 | 5.296 | 60.532 | 127.256 | 1.00 | 46.59 | 0 |
| ATOM | 2013 | OD1 | ASP | 208 | 5.695 | 61.706 | 127.362 | 1.00 | 48.93 | 0 |
| ATOM | 2014 | OD2 | ASP | 208 | 4.959 | 60.008 | 126.180 | 1.00 | 44.70 | 0 |
| ATOM | 2015 | C | ASP | 208 | 3.903 | 58.705 | 130.231 | 1.00 | 2.00 | 0 |
| ATOM | 2016 | O | ASP | 208 | 3.580 | 59.537 | 131.072 | 1.00 | 45.54 | 0 |
| ATOM | 2017 | N | PRO | 209 | 4.244 | 57.457 | 130.559 | 1.00 | 10.98 | 0 |
| ATOM | 2018 | CD | PRO | 209 | 4.509 | 56.316 | 129.673 | 1.00 | 2.00 | 0 |
| ATOM | 2019 | CA | PRO | 209 | 4.299 | 57.040 | 131.957 | 1.00 | 10.98 | 0 |

TABLE A-continued

| | | | | | | | | | |
|---|---|---|---|---|---|---|---|---|---|
| ATOM | 2020 | CB | PRO | 209 | 4.407 | 55.522 | 131.845 | 1.00 | 2.00 | 0 |
| ATOM | 2021 | CG | PRO | 209 | 5.197 | 55.356 | 130.604 | 1.00 | 2.00 | 0 |
| ATOM | 2022 | C | PRO | 209 | 5.584 | 57.675 | 132.507 | 1.00 | 10.98 | 0 |
| ATOM | 2023 | O | PRO | 209 | 6.448 | 58.078 | 131.712 | 1.00 | 2.00 | 0 |
| ATOM | 2024 | N | ASP | 210 | 5.724 | 57.774 | 133.833 | 1.00 | 2.00 | 0 |
| ATOM | 2026 | CA | ASP | 210 | 6.931 | 58.360 | 134.413 | 1.00 | 2.00 | 0 |
| ATOM | 2027 | CB | ASP | 210 | 6.755 | 59.863 | 134.614 | 1.00 | 31.00 | 0 |
| ATOM | 2028 | CG | ASP | 210 | 8.050 | 60.570 | 134.990 | 1.00 | 36.69 | 0 |
| ATOM | 2029 | OD1 | ASP | 210 | 9.132 | 59.956 | 134.874 | 1.00 | 33.32 | 0 |
| ATOM | 2030 | OD2 | ASP | 210 | 7.989 | 61.756 | 135.396 | 1.00 | 38.93 | 0 |
| ATOM | 2031 | C | ASP | 210 | 7.304 | 57.734 | 135.729 | 1.00 | 2.00 | 0 |
| ATOM | 2032 | O | ASP | 210 | 6.448 | 57.320 | 136.496 | 1.00 | 28.60 | 0 |
| ATOM | 2033 | N | LYS | 211 | 8.608 | 57.666 | 135.966 | 1.00 | 4.23 | 0 |
| ATOM | 2035 | CA | LYS | 211 | 9.170 | 57.136 | 137.211 | 1.00 | 9.37 | 0 |
| ATOM | 2036 | CB | LYS | 211 | 10.647 | 56.760 | 137.024 | 1.00 | 17.66 | 0 |
| ATOM | 2037 | CG | LYS | 211 | 10.941 | 55.441 | 136.345 | 1.00 | 29.60 | 0 |
| ATOM | 2038 | CD | LYS | 211 | 12.451 | 55.184 | 136.403 | 1.00 | 32.82 | 0 |
| ATOM | 2039 | CE | LYS | 211 | 12.852 | 53.831 | 135.809 | 1.00 | 42.70 | 0 |
| ATOM | 2040 | NZ | LYS | 211 | 14.336 | 53.616 | 135.852 | 1.00 | 41.45 | 0 |
| ATOM | 2044 | C | LYS | 211 | 9.100 | 58.157 | 138.367 | 1.00 | 7.69 | 0 |
| ATOM | 2045 | O | LYS | 211 | 8.746 | 57.803 | 139.481 | 1.00 | 18.85 | 0 |
| ATOM | 2046 | N | ASP | 212 | 9.456 | 59.414 | 138.093 | 1.00 | 2.00 | 0 |
| ATOM | 2048 | CA | ASP | 212 | 9.468 | 60.483 | 139.101 | 1.00 | 2.00 | 0 |
| ATOM | 2049 | CB | ASP | 212 | 10.322 | 61.669 | 138.624 | 1.00 | 39.78 | 0 |
| ATOM | 2050 | CG | ASP | 212 | 11.483 | 61.254 | 137.754 | 1.00 | 46.31 | 0 |
| ATOM | 2051 | OD1 | ASP | 212 | 11.823 | 62.030 | 136.834 | 1.00 | 41.85 | 0 |
| ATOM | 2052 | OD2 | ASP | 212 | 12.051 | 60.166 | 137.987 | 1.00 | 46.28 | 0 |
| ATOM | 2053 | C | ASP | 212 | 8.074 | 61.033 | 139.412 | 1.00 | 2.00 | 0 |
| ATOM | 2054 | O | ASP | 212 | 7.943 | 62.164 | 139.903 | 1.00 | 41.82 | 0 |
| ATOM | 2055 | N | VAL | 213 | 7.040 | 60.250 | 139.124 | 1.00 | 2.00 | 0 |
| ATOM | 2057 | CA | VAL | 213 | 5.669 | 60.690 | 139.340 | 1.00 | 2.00 | 0 |
| ATOM | 2058 | CB | VAL | 213 | 5.137 | 61.376 | 138.050 | 1.00 | 2.00 | 0 |
| ATOM | 2059 | CG1 | VAL | 213 | 3.652 | 61.247 | 137.922 | 1.00 | 2.00 | 0 |
| ATOM | 2060 | CG2 | VAL | 213 | 5.505 | 62.826 | 138.076 | 1.00 | 2.00 | 0 |
| ATOM | 2061 | C | VAL | 213 | 4.767 | 59.526 | 139.763 | 1.00 | 2.00 | 0 |
| ATOM | 2062 | O | VAL | 213 | 5.007 | 58.356 | 139.390 | 1.00 | 2.00 | 0 |
| ATOM | 2063 | N | LEU | 214 | 3.748 | 59.844 | 140.564 | 1.00 | 21.53 | 0 |
| ATOM | 2065 | CA | LEU | 214 | 2.815 | 58.830 | 141.022 | 1.00 | 19.34 | 0 |
| ATOM | 2066 | CB | LEU | 214 | 2.742 | 58.809 | 142.543 | 1.00 | 14.66 | 0 |
| ATOM | 2067 | CG | LEU | 214 | 2.371 | 57.438 | 143.097 | 1.00 | 15.86 | 0 |
| ATOM | 2068 | CD1 | LEU | 214 | 3.507 | 56.477 | 142.816 | 1.00 | 9.71 | 0 |
| ATOM | 2069 | CD2 | LEU | 214 | 2.109 | 57.530 | 144.588 | 1.00 | 17.44 | 0 |
| ATOM | 2070 | C | LEU | 214 | 1.433 | 59.068 | 140.439 | 1.00 | 19.87 | 0 |
| ATOM | 2071 | O | LEU | 214 | 0.757 | 58.124 | 140.033 | 1.00 | 9.54 | 0 |
| ATOM | 2072 | N | GLY | 215 | 1.003 | 60.322 | 140.411 | 1.00 | 16.98 | 0 |
| ATOM | 2074 | CA | GLY | 215 | −0.299 | 60.640 | 139.852 | 1.00 | 11.19 | 0 |
| ATOM | 2075 | C | GLY | 215 | −0.081 | 61.255 | 138.487 | 1.00 | 12.07 | 0 |
| ATOM | 2076 | O | GLY | 215 | 0.772 | 60.796 | 137.739 | 1.00 | 10.02 | 0 |
| ATOM | 2077 | N | TRP | 216 | −0.824 | 62.303 | 138.167 | 1.00 | 2.00 | 0 |
| ATOM | 2079 | CA | TRP | 216 | −0.684 | 62.979 | 136.890 | 1.00 | 2.00 | 0 |
| ATOM | 2080 | CB | TRP | 216 | −2.030 | 63.535 | 136.458 | 1.00 | 2.00 | 0 |
| ATOM | 2081 | CG | TRP | 216 | −2.903 | 62.452 | 136.050 | 1.00 | 2.00 | 0 |
| ATOM | 2082 | CD2 | TRP | 216 | −2.840 | 61.741 | 134.804 | 1.00 | 2.00 | 0 |
| ATOM | 2083 | CE2 | TRP | 216 | −3.806 | 60.713 | 134.865 | 1.00 | 2.00 | 0 |
| ATOM | 2084 | CE3 | TRP | 216 | −2.050 | 61.865 | 133.648 | 1.00 | 2.00 | 0 |
| ATOM | 2085 | CD1 | TRP | 216 | −3.879 | 61.860 | 136.789 | 1.00 | 2.00 | 0 |
| ATOM | 2086 | NE1 | TRP | 216 | −4.425 | 60.811 | 136.087 | 1.00 | 2.00 | 0 |
| ATOM | 2088 | CZ2 | TRP | 216 | −4.005 | 59.812 | 133.809 | 1.00 | 2.00 | 0 |
| ATOM | 2089 | CZ3 | TRP | 216 | −2.251 | 60.970 | 132.605 | 1.00 | 2.00 | 0 |
| ATOM | 2090 | CH2 | TRP | 216 | −3.217 | 59.961 | 132.695 | 1.00 | 2.00 | 0 |
| ATOM | 2091 | C | TRP | 216 | 0.310 | 64.101 | 136.985 | 1.00 | 2.00 | 0 |
| ATOM | 2092 | O | TRP | 216 | 0.261 | 64.883 | 137.926 | 1.00 | 2.00 | 0 |
| ATOM | 2093 | N | GLY | 217 | 1.213 | 64.182 | 136.021 | 1.00 | 12.63 | 0 |
| ATOM | 2095 | CA | GLY | 217 | 2.199 | 65.245 | 136.028 | 1.00 | 15.52 | 0 |
| ATOM | 2096 | C | GLY | 217 | 2.312 | 65.928 | 134.675 | 1.00 | 10.15 | 0 |
| ATOM | 2097 | O | GLY | 217 | 1.627 | 65.559 | 133.720 | 1.00 | 26.84 | 0 |
| ATOM | 2098 | N | GLU | 218 | 3.189 | 66.923 | 134.594 | 1.00 | 23.86 | 0 |
| ATOM | 2100 | CA | GLU | 218 | 3.434 | 67.686 | 133.364 | 1.00 | 22.47 | 0 |
| ATOM | 2101 | CB | GLU | 218 | 4.198 | 68.978 | 133.729 | 1.00 | 65.82 | 0 |
| ATOM | 2102 | CG | GLU | 218 | 5.082 | 69.595 | 132.641 | 1.00 | 67.96 | 0 |
| ATOM | 2103 | CD | GLU | 218 | 6.577 | 69.562 | 132.987 | 1.00 | 67.00 | 0 |
| ATOM | 2104 | OE1 | GLU | 218 | 7.056 | 70.519 | 133.631 | 1.00 | 68.41 | 0 |
| ATOM | 2105 | OE2 | GLU | 218 | 7.276 | 68.589 | 132.616 | 1.00 | 63.29 | 0 |
| ATOM | 2106 | C | GLU | 218 | 4.232 | 66.841 | 132.371 | 1.00 | 25.48 | 0 |
| ATOM | 2107 | O | GLU | 218 | 4.808 | 65.820 | 132.750 | 1.00 | 67.07 | 0 |
| ATOM | 2108 | N | ASN | 219 | 4.253 | 67.245 | 131.103 | 1.00 | 21.19 | 0 |
| ATOM | 2110 | CA | ASN | 219 | 5.039 | 66.510 | 130.108 | 1.00 | 21.18 | 0 |
| ATOM | 2111 | CB | ASN | 219 | 4.140 | 65.888 | 129.048 | 1.00 | 10.60 | 0 |
| ATOM | 2112 | CG | ASN | 219 | 4.832 | 64.791 | 128.282 | 1.00 | 14.78 | 0 |

TABLE A-continued

| | | | | | | | | | |
|---|---|---|---|---|---|---|---|---|---|
| ATOM | 2113 | OD1 | ASN | 219 | 6.052 | 64.646 | 128.341 | 1.00 | 9.20 | 0 |
| ATOM | 2114 | ND2 | ASN | 219 | 4.057 | 64.003 | 127.560 | 1.00 | 8.28 | 0 |
| ATOM | 2117 | C | ASN | 219 | 6.058 | 67.411 | 129.425 | 1.00 | 21.70 | 0 |
| ATOM | 2118 | O | ASN | 219 | 5.776 | 68.576 | 129.151 | 1.00 | 9.52 | 0 |
| ATOM | 2119 | N | ASP | 220 | 7.246 | 66.886 | 129.151 | 1.00 | 35.32 | 0 |
| ATOM | 2121 | CA | ASP | 220 | 8.266 | 67.690 | 128.485 | 1.00 | 34.19 | 0 |
| ATOM | 2122 | CB | ASP | 220 | 9.585 | 66.900 | 128.358 | 1.00 | 48.55 | 0 |
| ATOM | 2123 | CG | ASP | 220 | 9.469 | 65.673 | 127.447 | 1.00 | 92.38 | 0 |
| ATOM | 2124 | OD1 | ASP | 220 | 9.083 | 64.584 | 127.938 | 1.00 | 48.43 | 0 |
| ATOM | 2125 | OD2 | ASP | 220 | 9.778 | 65.797 | 126.237 | 1.00 | 92.09 | 0 |
| ATOM | 2126 | O | ASP | 220 | 7.763 | 68.148 | 127.100 | 1.00 | 33.44 | 0 |
| ATOM | 2127 | O | ASP | 220 | 8.045 | 69.262 | 126.661 | 1.00 | 47.84 | 0 |
| ATOM | 2128 | N | ARG | 221 | 6.986 | 67.287 | 126.444 | 1.00 | 22.98 | 0 |
| ATOM | 2130 | CA | ARG | 221 | 6.427 | 67.552 | 125.127 | 1.00 | 22.11 | 0 |
| ATOM | 2131 | CB | ARG | 221 | 5.578 | 66.382 | 124.672 | 1.00 | 2.00 | 0 |
| ATOM | 2132 | CG | ARG | 221 | 6.251 | 65.056 | 124.739 | 1.00 | 2.00 | 0 |
| ATOM | 2133 | CD | ARG | 221 | 5.241 | 63.981 | 124.421 | 1.00 | 2.00 | 0 |
| ATOM | 2134 | NE | ARG | 221 | 5.828 | 62.658 | 124.590 | 1.00 | 2.00 | 0 |
| ATOM | 2136 | CZ | ARG | 221 | 6.785 | 62.154 | 123.811 | 1.00 | 2.00 | 0 |
| ATOM | 2137 | NH1 | ARG | 221 | 7.255 | 62.866 | 122.790 | 1.00 | 2.00 | 0 |
| ATOM | 2140 | NH2 | ARG | 221 | 7.285 | 60.947 | 124.064 | 1.00 | 2.00 | 0 |
| ATOM | 2143 | C | ARG | 221 | 5.546 | 68.776 | 125.109 | 1.00 | 18.96 | 0 |
| ATOM | 2144 | O | ARG | 221 | 5.164 | 69.239 | 124.052 | 1.00 | 2.00 | 0 |
| ATOM | 2145 | N | GLY | 222 | 5.188 | 69.280 | 126.280 | 1.00 | 2.00 | 0 |
| ATOM | 2147 | CA | GLY | 222 | 4.328 | 70.447 | 126.343 | 1.00 | 2.00 | 0 |
| ATOM | 2148 | C | GLY | 222 | 2.939 | 70.103 | 125.844 | 1.00 | 2.00 | 0 |
| ATOM | 2149 | O | GLY | 222 | 2.142 | 70.988 | 125.509 | 1.00 | 29.15 | 0 |
| ATOM | 2150 | N | VAL | 223 | 2.658 | 68.804 | 125.776 | 1.00 | 2.00 | 0 |
| ATOM | 2152 | CA | VAL | 223 | 1.356 | 66.313 | 125.342 | 1.00 | 2.00 | 0 |
| ATOM | 2153 | CB | VAL | 223 | 1.364 | 67.860 | 123.839 | 1.00 | 2.00 | 0 |
| ATOM | 2154 | CG1 | VAL | 223 | −0.063 | 67.688 | 123.280 | 1.00 | 2.00 | 0 |
| ATOM | 2155 | CG2 | VAL | 223 | 2.258 | 68.762 | 123.004 | 1.00 | 2.00 | 0 |
| ATOM | 2156 | C | VAL | 223 | 1.071 | 67.125 | 126.250 | 1.00 | 2.00 | 0 |
| ATOM | 2157 | O | VAL | 223 | 2.004 | 66.431 | 126.656 | 1.00 | 2.00 | 0 |
| ATOM | 2158 | N | SER | 224 | −0.205 | 66.897 | 126.550 | 1.00 | 12.21 | 0 |
| ATOM | 2160 | CA | SER | 224 | −0.661 | 65.825 | 127.440 | 1.00 | 15.55 | 0 |
| ATOM | 2161 | CB | SER | 224 | −0.609 | 64.453 | 126.759 | 1.00 | 6.64 | 0 |
| ATOM | 2162 | OG | SER | 224 | 0.713 | 64.003 | 126.546 | 1.00 | 10.80 | 0 |
| ATOM | 2164 | C | SER | 224 | 0.077 | 65.779 | 128.787 | 1.00 | 20.53 | 0 |
| ATOM | 2165 | O | SER | 224 | 0.814 | 66.706 | 129.153 | 1.00 | 8.42 | 0 |
| ATOM | 2166 | N | PHE | 225 | −0.124 | 64.700 | 129.533 | 1.00 | 6.68 | 0 |
| ATOM | 2168 | CA | PHE | 225 | 0.484 | 64.586 | 130.839 | 1.00 | 6.68 | 0 |
| ATOM | 2169 | CB | PHE | 225 | −0.625 | 64.489 | 131.890 | 1.00 | 14.03 | 0 |
| ATOM | 2170 | CG | PHE | 225 | −1.670 | 65.552 | 131.758 | 1.00 | 11.21 | 0 |
| ATOM | 2171 | CD1 | PHE | 225 | −2.925 | 65.248 | 131.239 | 1.00 | 11.66 | 0 |
| ATOM | 2172 | CD2 | PHE | 225 | −1.396 | 66.869 | 132.131 | 1.00 | 11.41 | 0 |
| ATOM | 2173 | CE1 | PHE | 225 | −3.899 | 66.241 | 131.086 | 1.00 | 11.76 | 0 |
| ATOM | 2174 | CE2 | PHE | 225 | −2.363 | 67.869 | 131.983 | 1.00 | 14.72 | 0 |
| ATOM | 2175 | CZ | PHE | 225 | −3.618 | 67.553 | 131.458 | 1.00 | 16.73 | 0 |
| ATOM | 2176 | C | PHE | 225 | 1.405 | 63.392 | 130.957 | 1.00 | 6.68 | 0 |
| ATOM | 2177 | O | PHE | 225 | 1.902 | 62.850 | 129.966 | 1.00 | 15.31 | 0 |
| ATOM | 2178 | N | THR | 226 | 1.663 | 63.022 | 132.203 | 1.00 | 2.00 | 0 |
| ATOM | 2180 | CA | THR | 226 | 2.473 | 61.872 | 132.509 | 1.00 | 2.00 | 0 |
| ATOM | 2181 | CB | THR | 226 | 3.898 | 62.226 | 132.853 | 1.00 | 13.51 | 0 |
| ATOM | 2182 | OG1 | THR | 226 | 4.607 | 61.012 | 133.094 | 1.00 | 13.51 | 0 |
| ATOM | 2184 | CG2 | THR | 226 | 3.961 | 63.081 | 134.086 | 1.00 | 13.51 | 0 |
| ATOM | 2185 | C | THR | 226 | 1.809 | 61.217 | 133.686 | 1.00 | 2.00 | 0 |
| ATOM | 2186 | O | THR | 226 | 1.039 | 61.861 | 134.394 | 1.00 | 13.51 | 0 |
| ATOM | 2187 | N | PHE | 227 | 2.086 | 59.938 | 133.883 | 1.00 | 2.00 | 0 |
| ATOM | 2189 | CA | PHE | 227 | 1.466 | 59.191 | 134.957 | 1.00 | 2.00 | 0 |
| ATOM | 2190 | CB | PHE | 227 | 0.206 | 58.448 | 134.472 | 1.00 | 18.74 | 0 |
| ATOM | 2191 | CG | PHE | 227 | 0.362 | 57.793 | 133.131 | 1.00 | 21.51 | 0 |
| ATOM | 2192 | CD1 | PHE | 227 | 0.717 | 56.453 | 133.034 | 1.00 | 18.55 | 0 |
| ATOM | 2193 | CD2 | PHE | 227 | 0.188 | 58.532 | 133.954 | 1.00 | 20.45 | 0 |
| ATOM | 2194 | CE1 | PHE | 227 | 0.902 | 55.857 | 131.787 | 1.00 | 19.97 | 0 |
| ATOM | 2195 | CE2 | PHE | 227 | 0.371 | 57.948 | 130.698 | 1.00 | 14.44 | 0 |
| ATOM | 2196 | CZ | PHE | 227 | 0.729 | 56.612 | 130.612 | 1.00 | 17.09 | 0 |
| ATOM | 2197 | C | PHE | 227 | 2.427 | 58.224 | 135.562 | 1.00 | 2.00 | 0 |
| ATOM | 2198 | O | PHE | 227 | 3.282 | 57.668 | 134.888 | 1.00 | 20.11 | 0 |
| ATOM | 2199 | N | GLY | 228 | 2.294 | 58.066 | 136.867 | 1.00 | 21.90 | 0 |
| ATOM | 2201 | CA | GLY | 228 | 3.143 | 57.165 | 137.607 | 1.00 | 20.86 | 0 |
| ATOM | 2202 | C | GLY | 228 | 2.424 | 55.859 | 137.815 | 1.00 | 24.57 | 0 |
| ATOM | 2203 | O | GLY | 228 | 1.365 | 55.615 | 137.223 | 1.00 | 2.00 | 0 |
| ATOM | 2204 | N | ALA | 229 | 2.974 | 55.041 | 138.704 | 1.00 | 2.00 | 0 |
| ATOM | 2206 | CA | ALA | 229 | 2.422 | 53.722 | 138.971 | 1.00 | 2.00 | 0 |
| ATOM | 2207 | CB | ALA | 229 | 3.372 | 52.924 | 139.835 | 1.00 | 2.00 | 0 |
| ATOM | 2208 | C | ALA | 229 | 1.055 | 53.706 | 139.576 | 1.00 | 2.00 | 0 |
| ATOM | 2209 | O | ALA | 229 | 0.359 | 52.705 | 139.460 | 1.00 | 2.00 | 0 |
| ATOM | 2210 | N | GLU | 230 | 0.666 | 54.802 | 140.220 | 1.00 | 2.00 | 0 |

TABLE A-continued

| | | | | | | | | | |
|---|---|---|---|---|---|---|---|---|---|
| ATOM | 2212 | CA | GLU | 230 | −0.648 | 54.881 | 140.875 | 1.00 | 2.00 | 0 |
| ATOM | 2213 | CB | GLU | 230 | −0.787 | 56.193 | 141.647 | 1.00 | 66.07 | 0 |
| ATOM | 2214 | CG | GLU | 230 | −1.123 | 56.014 | 143.111 | 1.00 | 71.18 | 0 |
| ATOM | 2215 | CD | GLU | 230 | −2.376 | 55.175 | 143.337 | 1.00 | 2.00 | 0 |
| ATOM | 2216 | OE1 | GLU | 230 | −2.275 | 53.918 | 143.199 | 1.00 | 2.00 | 0 |
| ATOM | 2217 | OE2 | GLU | 230 | −3.448 | 55.773 | 143.663 | 1.00 | 2.00 | 0 |
| ATOM | 2218 | C | GLU | 230 | −1.769 | 54.777 | 139.862 | 1.00 | 2.00 | 0 |
| ATOM | 2219 | O | GLU | 230 | −2.649 | 53.922 | 139.966 | 1.00 | 60.28 | 0 |
| ATOM | 2220 | N | VAL | 231 | −1.684 | 55.652 | 138.861 | 1.00 | 12.41 | 0 |
| ATOM | 2222 | CA | VAL | 231 | −2.649 | 55.749 | 137.772 | 1.00 | 9.72 | 0 |
| ATOM | 2223 | CB | VAL | 231 | −2.186 | 56.789 | 136.717 | 1.00 | 2.00 | 0 |
| ATOM | 2224 | CG1 | VAL | 231 | −3.304 | 57.063 | 135.718 | 1.00 | 2.00 | 0 |
| ATOM | 2225 | CG2 | VAL | 231 | −1.728 | 58.077 | 137.396 | 1.00 | 2.00 | 0 |
| ATOM | 2226 | C | VAL | 231 | −2.816 | 54.393 | 137.102 | 1.00 | 11.88 | 0 |
| ATOM | 2227 | O | VAL | 231 | −3.937 | 53.966 | 136.849 | 1.00 | 2.00 | 0 |
| ATOM | 2228 | N | VAL | 232 | −1.695 | 53.723 | 136.832 | 1.00 | 2.00 | 0 |
| ATOM | 2230 | CA | VAL | 232 | −1.678 | 52.397 | 136.203 | 1.00 | 2.00 | 0 |
| ATOM | 2231 | CB | VAL | 232 | −0.245 | 51.817 | 136.151 | 1.00 | 2.00 | 0 |
| ATOM | 2232 | CG1 | VAL | 232 | −0.264 | 50.442 | 135.548 | 1.00 | 2.00 | 0 |
| ATOM | 2233 | CG2 | VAL | 232 | 0.664 | 52.724 | 135.376 | 1.00 | 2.00 | 0 |
| ATOM | 2234 | C | VAL | 232 | −2.533 | 51.413 | 136.992 | 1.00 | 2.00 | 0 |
| ATOM | 2235 | O | VAL | 232 | −3.449 | 50.787 | 136.454 | 1.00 | 2.00 | 0 |
| ATOM | 2236 | N | ALA | 233 | −2.217 | 51.292 | 138.275 | 1.00 | 38.57 | 0 |
| ATOM | 2238 | CA | ALA | 233 | −2.920 | 50.395 | 139.173 | 1.00 | 38.57 | 0 |
| ATOM | 2239 | CB | ALA | 233 | −2.297 | 50.487 | 140.542 | 1.00 | 13.20 | 0 |
| ATOM | 2240 | C | ALA | 233 | −4.426 | 50.681 | 139.245 | 1.00 | 38.57 | 0 |
| ATOM | 2241 | O | ALA | 233 | −5.255 | 49.763 | 139.166 | 1.00 | 9.05 | 0 |
| ATOM | 2242 | N | LYS | 234 | −4.780 | 51.954 | 139.397 | 1.00 | 2.00 | 0 |
| ATOM | 2244 | CA | LYS | 234 | −6.177 | 52.355 | 139.477 | 1.00 | 2.00 | 0 |
| ATOM | 2245 | CB | LYS | 234 | −6.270 | 53.843 | 139.803 | 1.00 | 22.96 | 0 |
| ATOM | 2246 | CG | LYS | 234 | −5.776 | 54.160 | 141.205 | 1.00 | 31.42 | 0 |
| ATOM | 2247 | CD | LYS | 234 | −6.667 | 53.499 | 142.257 | 1.00 | 42.09 | 0 |
| ATOM | 2248 | CE | LYS | 234 | −5.916 | 53.151 | 143.543 | 1.00 | 40.07 | 0 |
| ATOM | 2249 | NZ | LYS | 234 | −5.104 | 51.892 | 143.444 | 1.00 | 41.59 | 0 |
| ATOM | 2253 | C | LYS | 234 | −6.920 | 52.036 | 138.183 | 1.00 | 2.00 | 0 |
| ATOM | 2254 | O | LYS | 234 | −7.936 | 51.319 | 138.206 | 1.00 | 20.45 | 0 |
| ATOM | 2255 | N | PHE | 235 | −6.389 | 52.532 | 137.061 | 1.00 | 14.37 | 0 |
| ATOM | 2257 | CA | PHE | 235 | −6.973 | 52.319 | 135.733 | 1.00 | 14.37 | 0 |
| ATOM | 2258 | CB | PHE | 235 | −6.055 | 52.880 | 134.640 | 1.00 | 2.00 | 0 |
| ATOM | 2259 | CG | PHE | 235 | −6.438 | 52.452 | 133.249 | 1.00 | 2.00 | 0 |
| ATOM | 2260 | CD1 | PHE | 235 | −7.352 | 53.199 | 132.502 | 1.00 | 2.00 | 0 |
| ATOM | 2261 | CD2 | PHE | 235 | −5.924 | 51.270 | 132.706 | 1.00 | 2.00 | 0 |
| ATOM | 2262 | CE1 | PHE | 235 | −7.760 | 52.777 | 131.236 | 1.00 | 2.00 | 0 |
| ATOM | 2263 | CE2 | PHE | 235 | −6.316 | 50.834 | 131.452 | 1.00 | 2.00 | 0 |
| ATOM | 2264 | CZ | PHE | 235 | −7.242 | 51.588 | 130.710 | 1.00 | 2.00 | 0 |
| ATOM | 2265 | C | PHE | 235 | −7.229 | 50.849 | 135.444 | 1.00 | 14.37 | 0 |
| ATOM | 2266 | O | PHE | 235 | −8.312 | 50.471 | 134.977 | 1.00 | 2.00 | 0 |
| ATOM | 2267 | N | LEU | 236 | −6.217 | 50.029 | 135.690 | 1.00 | 3.08 | 0 |
| ATOM | 2269 | CA | LEU | 236 | −6.339 | 48.606 | 135.447 | 1.00 | 5.72 | 0 |
| ATOM | 2270 | CB | LEU | 236 | −5.018 | 47.900 | 135.731 | 1.00 | 2.00 | 0 |
| ATOM | 2271 | CG | LEU | 236 | −3.915 | 48.136 | 134.710 | 1.00 | 2.00 | 0 |
| ATOM | 2272 | CD1 | LEU | 236 | −2.699 | 47.332 | 135.096 | 1.00 | 2.00 | 0 |
| ATOM | 2273 | CD2 | LEU | 236 | −4.405 | 47.737 | 133.321 | 1.00 | 2.00 | 0 |
| ATOM | 2274 | C | LEU | 236 | −7.452 | 47.978 | 136.278 | 1.00 | 10.30 | 0 |
| ATOM | 2275 | O | LEU | 236 | −8.389 | 47.398 | 135.712 | 1.00 | 2.00 | 0 |
| ATOM | 2276 | N | HIS | 237 | −7.368 | 48.118 | 137.606 | 1.00 | 8.44 | 0 |
| ATOM | 2278 | CA | HIS | 237 | −8.368 | 47.540 | 138.504 | 1.00 | 8.44 | 0 |
| ATOM | 2279 | CB | HIS | 237 | −8.088 | 47.885 | 139.980 | 1.00 | 38.56 | 0 |
| ATOM | 2280 | CG | HIS | 237 | −9.141 | 47.360 | 140.935 | 1.00 | 46.82 | 0 |
| ATOM | 2281 | CD2 | HIS | 237 | −10.323 | 47.916 | 141.329 | 1.00 | 46.01 | 0 |
| ATOM | 2282 | ND1 | HIS | 237 | −9.035 | 46.173 | 141.599 | 1.00 | 46.3B | 0 |
| ATOM | 2284 | CE1 | HIS | 237 | −10.103 | 45.989 | 142.355 | 1.00 | 50.85 | 0 |
| ATOM | 2285 | NE2 | HIS | 237 | −10.900 | 47.031 | 142.210 | 1.00 | 49.26 | 0 |
| ATOM | 2287 | C | HIS | 237 | −9.747 | 48.033 | 138.138 | 1.00 | 8.44 | 0 |
| ATOM | 2288 | O | HIS | 237 | −10.672 | 47.232 | 138.027 | 1.00 | 35.43 | 0 |
| ATOM | 2289 | N | LYS | 238 | −9.882 | 49.346 | 137.947 | 1.00 | 2.00 | 0 |
| ATOM | 2291 | CA | LYS | 238 | −11.183 | 49.923 | 137.607 | 1.00 | 2.00 | 0 |
| ATOM | 2292 | CB | LYS | 238 | −11.071 | 51.424 | 137.327 | 1.00 | 28.00 | 0 |
| ATOM | 2293 | CG | LYS | 238 | −12.427 | 52.103 | 137.104 | 1.00 | 29.80 | 0 |
| ATOM | 2294 | CD | LYS | 238 | −12.322 | 53.628 | 136.829 | 1.00 | 36.02 | 0 |
| ATOM | 2295 | CE | LYS | 238 | −11.917 | 54.444 | 136.083 | 1.00 | 32.99 | 0 |
| ATOM | 2296 | NZ | LYS | 238 | −11.833 | 55.925 | 137.845 | 1.00 | 30.09 | 0 |
| ATOM | 2300 | C | LYS | 238 | −11.776 | 49.215 | 136.403 | 1.00 | 2.00 | 0 |
| ATOM | 2301 | O | LYS | 238 | −12.991 | 49.205 | 136.234 | 1.00 | 29.21 | 0 |
| ATOM | 2302 | N | HIS | 239 | −10.913 | 46.607 | 135.584 | 1.00 | 2.00 | 0 |
| ATOM | 2304 | CA | HIS | 239 | −11.340 | 47.897 | 134.384 | 1.00 | 2.00 | 0 |
| ATOM | 2305 | CB | HIS | 239 | −10.784 | 48.603 | 133.148 | 1.00 | 2.00 | 0 |
| ATOM | 2306 | CG | HIS | 239 | −11.125 | 50.056 | 133.091 | 1.00 | 2.00 | 0 |
| ATOM | 2307 | CD2 | HIS | 239 | −12.282 | 50.689 | 132.785 | 1.00 | 2.00 | 0 |

TABLE A-continued

| | | | | | | | | | |
|---|---|---|---|---|---|---|---|---|---|
| ATOM | 2308 | ND1 | HIS | 239 | −10.217 | 51.046 | 133.397 | 1.00 | 2.00 | 0 |
| ATOM | 2310 | CE1 | HIS | 239 | −10.797 | 52.225 | 133.284 | 1.00 | 2.00 | 0 |
| ATOM | 2311 | NE2 | HIS | 239 | −12.052 | 52.036 | 132.914 | 1.00 | 2.00 | 0 |
| ATOM | 2313 | C | HIS | 239 | −10.946 | 46.417 | 134.352 | 1.00 | 2.00 | 0 |
| ATOM | 2314 | O | HIS | 239 | −10.938 | 45.798 | 133.295 | 1.00 | 2.00 | 0 |
| ATOM | 2315 | N | ASP | 240 | −10.642 | 45.838 | 135.503 | 1.00 | 37.96 | 0 |
| ATOM | 2317 | CA | ASP | 240 | −10.251 | 44.433 | 135.564 | 1.00 | 37.83 | 0 |
| ATOM | 2318 | CB | ASP | 240 | −11.482 | 43.512 | 135.737 | 1.00 | 39.81 | 0 |
| ATOM | 2319 | CG | ASP | 240 | −12.676 | 43.919 | 134.870 | 1.00 | 47.06 | 0 |
| ATOM | 2320 | OD1 | ASP | 240 | −12.687 | 43.571 | 133.666 | 1.00 | 50.73 | 0 |
| ATOM | 2321 | OD2 | ASP | 240 | −13.610 | 44.578 | 135.396 | 1.00 | 47.58 | 0 |
| ATOM | 2322 | C | ASP | 240 | −9.393 | 43.985 | 134.385 | 1.00 | 37.76 | 0 |
| ATOM | 2323 | O | ASP | 240 | −9.626 | 42.933 | 133.797 | 1.00 | 40.81 | 0 |
| ATOM | 2324 | N | LEU | 241 | −8.417 | 44.823 | 134.040 | 1.00 | 2.00 | 0 |
| ATOM | 2326 | CA | LEU | 241 | −7.462 | 44.551 | 132.955 | 1.00 | 2.00 | 0 |
| ATOM | 2327 | CB | LEU | 241 | −7.066 | 45.858 | 132.229 | 1.00 | 2.00 | 0 |
| ATOM | 2328 | CG | LEU | 241 | −8.185 | 46.590 | 131.429 | 1.00 | 2.00 | 0 |
| ATOM | 2329 | CD1 | LEU | 241 | −7.795 | 48.047 | 131.224 | 1.00 | 2.00 | 0 |
| ATOM | 2330 | CD2 | LEU | 241 | −8.435 | 45.899 | 130.087 | 1.00 | 2.00 | 0 |
| ATOM | 2331 | C | LEU | 241 | −6.225 | 43.925 | 133.601 | 1.00 | 2.00 | 0 |
| ATOM | 2332 | O | LEU | 241 | −6.157 | 43.832 | 134.818 | 1.00 | 2.00 | 0 |
| ATOM | 2333 | N | ASP | 242 | −5.235 | 43.534 | 132.817 | 1.00 | 2.00 | 0 |
| ATOM | 2335 | CA | ASP | 242 | −4.046 | 42.895 | 133.380 | 1.00 | 2.00 | 0 |
| ATOM | 2336 | CB | ASP | 242 | −3.974 | 41.455 | 132.915 | 1.00 | 25.69 | 0 |
| ATOM | 2337 | CG | ASP | 242 | −4.683 | 40.511 | 133.822 | 1.00 | 12.63 | 0 |
| ATOM | 2338 | CD1 | ASP | 242 | −5.751 | 40.853 | 134.365 | 1.00 | 16.91 | 0 |
| ATOM | 2339 | OD2 | ASP | 242 | −4.149 | 39.404 | 133.976 | 1.00 | 15.37 | 0 |
| ATOM | 2340 | C | AEP | 242 | −2.711 | 43.506 | 133.033 | 1.00 | 2.00 | 0 |
| ATOM | 2341 | O | ASP | 242 | −1.702 | 43.214 | 133.671 | 1.00 | 25.69 | 0 |
| ATOM | 2342 | N | LEU | 243 | −2.689 | 44.317 | 131.994 | 1.00 | 23.97 | 0 |
| ATOM | 2344 | CA | LEU | 243 | −1.440 | 44.899 | 131.539 | 1.00 | 18.84 | 0 |
| ATOM | 2345 | CB | LEU | 243 | −0.644 | 43.799 | 130.822 | 1.00 | 2.00 | 0 |
| ATOM | 2346 | CG | LEU | 243 | 0.698 | 43.831 | 130.097 | 1.00 | 2.00 | 0 |
| ATOM | 2347 | CD1 | LEU | 243 | 0.410 | 43.690 | 128.660 | 1.00 | 2.00 | 0 |
| ATOM | 2348 | CD2 | LEU | 243 | 1.526 | 45.058 | 130.397 | 1.00 | 2.00 | 0 |
| ATOM | 2349 | C | LEU | 243 | −1.804 | 46.013 | 130.590 | 1.00 | 19.91 | 0 |
| ATOM | 2350 | O | LEU | 243 | −2.960 | 46.149 | 130.183 | 1.00 | 2.00 | 0 |
| ATOM | 2351 | N | ILE | 244 | −0.834 | 46.849 | 130.283 | 1.00 | 24.04 | 0 |
| ATOM | 2353 | CA | ILE | 244 | −1.070 | 47.919 | 129.354 | 1.00 | 22.40 | 0 |
| ATOM | 2354 | CG2 | ILE | 244 | −1.164 | 49.269 | 130.067 | 1.00 | 2.00 | 0 |
| ATOM | 2355 | CG2 | ILE | 244 | −1.235 | 50.405 | 129.026 | 1.00 | 2.00 | 0 |
| ATOM | 2356 | CG1 | ILE | 244 | −2.395 | 49.255 | 130.994 | 1.00 | 2.00 | 0 |
| ATOM | 2357 | CD1 | ILE | 244 | −2.607 | 50.530 | 131.803 | 1.00 | 2.00 | 0 |
| ATOM | 2358 | C | ILE | 244 | 0.069 | 47.902 | 128.369 | 1.00 | 25.54 | 0 |
| ATOM | 2359 | O | ILE | 244 | 1.234 | 47.715 | 128.755 | 1.00 | 2.00 | 0 |
| ATOM | 2360 | N | CYS | 245 | −0.286 | 48.063 | 127.096 | 1.00 | 2.00 | 0 |
| ATOM | 2362 | CA | CYS | 245 | 0.675 | 48.074 | 126.019 | 1.00 | 2.00 | 0 |
| ATOM | 2363 | CB | CYS | 245 | 0.403 | 46.930 | 125.077 | 1.00 | 7.03 | 0 |
| ATOM | 2364 | SG | CYS | 245 | 1.849 | 45.913 | 124.986 | 1.00 | 12.49 | 0 |
| ATOM | 2365 | C | CYS | 245 | 0.668 | 49.389 | 125.275 | 1.00 | 2.00 | 0 |
| ATOM | 2366 | O | CYS | 245 | −0.362 | 49.842 | 124.792 | 1.00 | 8.03 | 0 |
| ATOM | 2367 | N | ARG | 246 | 1.829 | 50.014 | 125.235 | 1.00 | 2.00 | 0 |
| ATOM | 2369 | CA | ARG | 246 | 1.987 | 51.277 | 124.562 | 1.00 | 2.00 | 0 |
| ATOM | 2370 | CB | ARG | 246 | 1.763 | 52.438 | 125.541 | 1.00 | 2.00 | 0 |
| ATOM | 2371 | CG | ARG | 246 | 2.658 | 52.453 | 126.783 | 1.00 | 2.00 | 0 |
| ATOM | 2372 | CD | ARG | 246 | 3.969 | 53.245 | 126.623 | 1.00 | 2.00 | 0 |
| ATOM | 2373 | NE | ARG | 246 | 3.714 | 54.656 | 126.323 | 1.00 | 2.00 | 0 |
| ATOM | 2375 | CZ | ARG | 246 | 4.610 | 55.622 | 126.519 | 1.00 | 2.00 | 0 |
| ATOM | 2376 | NH1 | ARG | 246 | 5.842 | 55.334 | 126.895 | 1.00 | 2.00 | 0 |
| ATOM | 2379 | NH2 | ARG | 246 | 4.263 | 56.881 | 126.289 | 1.00 | 2.00 | 0 |
| ATOM | 2382 | C | ARG | 246 | 3.374 | 51.342 | 123.938 | 1.00 | 2.00 | 0 |
| ATOM | 2383 | O | ARG | 246 | 4.216 | 50.471 | 124.168 | 1.00 | 2.00 | 0 |
| ATOM | 2384 | N | ALA | 247 | 3.605 | 52.345 | 123.108 | 1.00 | 2.00 | 0 |
| ATOM | 2386 | CA | ALA | 247 | 4.906 | 52.489 | 122.484 | 1.00 | 2.00 | 0 |
| ATOM | 2387 | CB | ALA | 247 | 4.791 | 52.272 | 120.975 | 1.00 | 61.76 | 0 |
| ATOM | 2388 | C | ALA | 247 | 5.351 | 53.902 | 122.819 | 1.00 | 2.00 | 0 |
| ATOM | 2389 | O | ALA | 247 | 5.806 | 54.172 | 123.922 | 1.00 | 61.76 | 0 |
| ATOM | 2390 | N | HIS | 248 | 5.187 | 54.801 | 121.870 | 1.00 | 2.00 | 0 |
| ATOM | 2392 | CA | HIS | 248 | 5.512 | 56.193 | 122.042 | 1.00 | 2.00 | 0 |
| ATOM | 2393 | C | HIS | 248 | 6.959 | 56.579 | 122.361 | 1.00 | 2.00 | 0 |
| ATOM | 2394 | O | HIS | 248 | 7.507 | 57.453 | 121.672 | 1.00 | 2.00 | 0 |
| ATOM | 2395 | CB | HIS | 248 | 4.539 | 56.793 | 123.054 | 1.00 | 2.00 | 0 |
| ATOM | 2396 | CG | HIS | 248 | 4.255 | 58.246 | 122.837 | 1.00 | 2.00 | 0 |
| ATOM | 2397 | ND | HIS | 248 | 5.262 | 59.147 | 122.594 | 1.00 | 2.00 | 0 |
| ATOM | 2398 | CE1 | HIS | 248 | 4.677 | 60.327 | 122.535 | 1.00 | 2.00 | 0 |
| ATOM | 2399 | CD2 | HIS | 248 | 3.074 | 58.906 | 122.913 | 1.00 | 2.00 | 0 |
| ATOM | 2400 | NE2 | HIS | 248 | 3.359 | 60.234 | 122.721 | 1.00 | 2.00 | 0 |
| ATOM | 2402 | N | GLN | 249 | 7.588 | 55.942 | 123.348 | 1.00 | 7.57 | 0 |
| ATOM | 2404 | CA | GLN | 249 | 8.967 | 56.283 | 123.731 | 1.00 | 7.57 | 0 |

TABLE A-continued

| | | | | | | | | | |
|---|---|---|---|---|---|---|---|---|---|
| ATOM | 2405 | CB | GLN | 249 | 9.010 | 56.722 | 125.192 | 1.00 | 30.82 | 0 |
| ATOM | 2406 | CG | GLN | 249 | 7.987 | 57.759 | 125.566 | 1.00 | 32.63 | 0 |
| ATOM | 2407 | CD | GLN | 249 | 8.159 | 58.253 | 126.983 | 1.00 | 33.33 | 0 |
| ATOM | 2408 | OE1 | GLN | 249 | 7.871 | 59.406 | 127.274 | 1.00 | 39.63 | 0 |
| ATOM | 2409 | NE2 | GLN | 249 | 8.640 | 57.389 | 127.874 | 1.00 | 32.74 | 0 |
| ATOM | 2412 | C | GLN | 249 | 10.052 | 55.222 | 123.529 | 1.00 | 7.57 | 0 |
| ATOM | 2413 | O | GLN | 249 | 9.884 | 54.057 | 123.888 | 1.00 | 28.32 | 0 |
| ATOM | 2414 | N | VAL | 250 | 11.185 | 55.664 | 122.988 | 1.00 | 20.32 | 0 |
| ATOM | 2416 | CA | VAL | 250 | 12.339 | 54.805 | 122.735 | 1.00 | 20.32 | 0 |
| ATOM | 2417 | CB | VAL | 250 | 13.571 | 55.628 | 122.300 | 1.00 | 6.81 | 0 |
| ATOM | 2418 | CG1 | VAL | 250 | 14.641 | 54.714 | 121.706 | 1.00 | 6.81 | 0 |
| ATOM | 2419 | CG2 | VAL | 250 | 13.161 | 56.708 | 121.311 | 1.00 | 6.81 | 0 |
| ATOM | 2420 | C | VAL | 250 | 12.733 | 54.034 | 123.998 | 1.00 | 20.32 | 0 |
| ATOM | 2421 | O | VAL | 250 | 12.471 | 54.474 | 125.120 | 1.00 | 6.81 | 0 |
| ATOM | 2422 | N | VAL | 251 | 13.372 | 52.887 | 123.797 | 1.00 | 2.00 | 0 |
| ATOM | 2424 | CA | VAL | 251 | 13.820 | 52.023 | 124.871 | 1.00 | 2.00 | 0 |
| ATOM | 2425 | CB | VAL | 251 | 12.655 | 51.150 | 125.391 | 1.00 | 9.99 | 0 |
| ATOM | 2426 | CG1 | VAL | 251 | 11.778 | 51.967 | 126.311 | 1.00 | 9.99 | 0 |
| ATOM | 2427 | CG2 | VAL | 251 | 11.803 | 50.661 | 124.247 | 1.00 | 9.99 | 0 |
| ATOM | 2428 | C | VAL | 251 | 14.960 | 51.167 | 124.316 | 1.00 | 2.00 | 0 |
| ATOM | 2429 | O | VAL | 251 | 14.792 | 50.470 | 123.319 | 1.00 | 9.99 | 0 |
| ATOM | 2430 | N | GLU | 252 | 16.118 | 51.224 | 124.972 | 1.00 | 21.55 | 0 |
| ATOM | 2432 | CA | GLU | 252 | 17.312 | 50.509 | 124.519 | 1.00 | 19.34 | 0 |
| ATOM | 2433 | CB | GLU | 252 | 18.152 | 50.605 | 125.542 | 1.00 | 11.04 | 0 |
| ATOM | 2434 | CG | GLU | 252 | 19.819 | 50.220 | 124.933 | 1.00 | 18.95 | 0 |
| ATOM | 2435 | CD | GLU | 252 | 20.926 | 49.966 | 125.962 | 1.00 | 20.92 | 0 |
| ATOM | 2436 | OE1 | GLU | 252 | 21.938 | 49.303 | 125.597 | 1.00 | 17.37 | 0 |
| ATOM | 2437 | OE2 | GLU | 252 | 20.782 | 50.422 | 127.126 | 1.00 | 29.06 | 0 |
| ATOM | 2438 | C | GLU | 252 | 17.144 | 49.055 | 124.145 | 1.00 | 19.22 | 0 |
| ATOM | 2439 | O | GLU | 252 | 17.838 | 48.571 | 123.261 | 1.00 | 8.64 | 0 |
| ATOM | 2440 | N | ASP | 253 | 16.240 | 48.356 | 124.815 | 1.00 | 2.00 | 0 |
| ATOM | 2442 | CA | ASP | 253 | 16.025 | 46.936 | 124.544 | 1.00 | 2.00 | 0 |
| ATOM | 2443 | CB | ASP | 253 | 16.125 | 46.144 | 125.850 | 1.00 | 78.16 | 0 |
| ATOM | 2444 | CG | ASP | 253 | 17.543 | 46.106 | 126.401 | 1.00 | 84.05 | 0 |
| ATOM | 2445 | OD1 | ASP | 253 | 18.060 | 44.995 | 126.635 | 1.00 | 89.15 | 0 |
| ATOM | 2446 | OD2 | ASP | 253 | 18.148 | 47.181 | 126.598 | 1.00 | 87.62 | 0 |
| ATOM | 2447 | C | ASP | 253 | 14.710 | 46.645 | 123.836 | 1.00 | 2.00 | 0 |
| ATOM | 2448 | O | ASP | 253 | 14.201 | 45.528 | 123.881 | 1.00 | 63.68 | 0 |
| ATOM | 2449 | N | GLY | 254 | 14.161 | 47.660 | 123.181 | 1.00 | 2.00 | 0 |
| ATOM | 2451 | CA | GLY | 254 | 12.919 | 47.483 | 122.457 | 1.00 | 2.00 | 0 |
| ATOM | 2452 | C | GLY | 254 | 11.715 | 47.547 | 123.354 | 1.00 | 2.00 | 0 |
| ATOM | 2453 | O | GLY | 254 | 10.694 | 48.124 | 122.993 | 1.00 | 43.70 | 0 |
| ATOM | 2454 | N | TYR | 255 | 11.823 | 46.922 | 124.516 | 1.00 | 2.00 | 0 |
| ATOM | 2456 | CA | TYR | 255 | 10.749 | 46.956 | 125.484 | 1.00 | 2.00 | 0 |
| ATOM | 2457 | CB | TYR | 255 | 10.047 | 45.614 | 125.571 | 1.00 | 2.00 | 0 |
| ATOM | 2458 | CG | TYR | 255 | 10.853 | 44.510 | 126.185 | 1.00 | 2.00 | 0 |
| ATOM | 2459 | CD1 | TYR | 255 | 12.103 | 44.175 | 125.696 | 1.00 | 2.00 | 0 |
| ATOM | 2460 | CE1 | TYR | 255 | 12.824 | 43.121 | 126.248 | 1.00 | 2.00 | 0 |
| ATOM | 2461 | CD2 | TYR | 255 | 10.337 | 43.770 | 127.246 | 1.00 | 2.00 | 0 |
| ATOM | 2462 | CE2 | TYR | 255 | 11.041 | 42.721 | 127.802 | 1.00 | 2.00 | 0 |
| ATOM | 2463 | CZ | TYR | 255 | 12.279 | 42.397 | 127.301 | 1.00 | 2.00 | 0 |
| ATOM | 2464 | OH | TYR | 255 | 12.946 | 41.328 | 127.839 | 1.00 | 2.00 | 0 |
| ATOM | 2466 | C | TYR | 255 | 11.262 | 47.375 | 126.847 | 1.00 | 2.00 | 0 |
| ATOM | 2467 | O | TYR | 255 | 12.453 | 47.283 | 127.150 | 1.00 | 2.00 | 0 |
| ATOM | 2468 | N | GLU | 256 | 10.336 | 47.853 | 127.656 | 1.00 | 2.00 | 0 |
| ATOM | 2470 | CA | GLU | 256 | 10.632 | 48.341 | 128.979 | 1.00 | 2.00 | 0 |
| ATOM | 2471 | CB | GLU | 256 | 11.092 | 49.798 | 128.910 | 1.00 | 20.70 | 0 |
| ATOM | 2472 | CG | GLU | 256 | 11.264 | 50.457 | 130.269 | 1.00 | 27.98 | 0 |
| ATOM | 2473 | CD | GLU | 256 | 11.485 | 51.961 | 130.179 | 1.00 | 31.28 | 0 |
| ATOM | 2474 | OE1 | GLU | 256 | 10.726 | 52.725 | 130.834 | 1.00 | 33.21 | 0 |
| ATOM | 2475 | OE2 | GLU | 256 | 12.418 | 52.378 | 129.453 | 1.00 | 39.87 | 0 |
| ATOM | 2476 | C | GLU | 256 | 9.362 | 48.238 | 129.800 | 1.00 | 2.00 | 0 |
| ATOM | 2477 | O | GLU | 256 | 8.299 | 48.743 | 129.420 | 1.00 | 18.74 | 0 |
| ATOM | 2478 | N | PHE | 257 | 9.474 | 47.540 | 130.919 | 1.00 | 2.00 | 0 |
| ATOM | 2480 | CA | PHE | 257 | 8.357 | 47.364 | 131.806 | 1.00 | 2.00 | 0 |
| ATOM | 2481 | CB | PHE | 257 | 8.578 | 46.139 | 132.661 | 1.00 | 2.00 | 0 |
| ATOM | 2482 | CG | PHE | 257 | 8.222 | 44.865 | 131.978 | 1.00 | 2.00 | 0 |
| ATOM | 2483 | CD1 | PHE | 257 | 9.187 | 43.926 | 131.694 | 1.00 | 2.00 | 0 |
| ATOM | 2484 | CD2 | PHE | 257 | 6.906 | 44.594 | 131.649 | 1.00 | 2.00 | 0 |
| ATOM | 2485 | CE1 | PHE | 257 | 8.849 | 42.740 | 131.101 | 1.00 | 2.00 | 0 |
| ATOM | 2486 | CE2 | PHE | 257 | 6.560 | 43.417 | 131.058 | 1.00 | 2.00 | 0 |
| ATOM | 2487 | CZ | PHE | 257 | 7.533 | 42.461 | 130.781 | 1.00 | 2.00 | 0 |
| ATOM | 2488 | C | PHE | 257 | 8.257 | 48.593 | 132.671 | 1.00 | 2.00 | 0 |
| ATOM | 2489 | O | PHE | 257 | 9.215 | 49.360 | 132.782 | 1.00 | 2.00 | 0 |
| ATOM | 2490 | N | PHE | 258 | 7.104 | 48.777 | 133.286 | 1.00 | 25.02 | 0 |
| ATOM | 2492 | CA | PHE | 258 | 6.884 | 49.916 | 134.147 | 1.00 | 25.02 | 0 |
| ATOM | 2493 | CB | PHE | 258 | 6.417 | 51.086 | 133.299 | 1.00 | 2.00 | 0 |
| ATOM | 2494 | CG | PHE | 258 | 5.831 | 52.237 | 134.072 | 1.00 | 2.00 | 0 |
| ATOM | 2495 | CD1 | PHE | 258 | 6.625 | 53.325 | 134.431 | 1.00 | 2.00 | 0 |

TABLE A-continued

| ATOM | 2496 | CD2 | PHE | 258 | 4.468 | 52.271 | 134.369 | 1.00 | 2.00 | 0 |
|---|---|---|---|---|---|---|---|---|---|---|
| ATOM | 2497 | CE1 | PHE | 258 | 6.070 | 54.439 | 135.070 | 1.00 | 2.00 | 0 |
| ATOM | 2498 | CE2 | PHE | 258 | 3.900 | 53.369 | 135.003 | 1.00 | 2.00 | 0 |
| ATOM | 2499 | CZ | PHE | 258 | 4.698 | 54.461 | 135.356 | 1.00 | 2.00 | 0 |
| ATOM | 2500 | C | PHE | 258 | 5.837 | 49.508 | 135.160 | 1.00 | 25.02 | 0 |
| ATOM | 2501 | O | PHE | 258 | 4.965 | 48.675 | 134.859 | 1.00 | 2.00 | 0 |
| ATOM | 2502 | N | ALA | 259 | 5.953 | 50.063 | 136.368 | 1.00 | 13.61 | 0 |
| ATOM | 2504 | CA | ALA | 259 | 5.027 | 49.775 | 137.457 | 1.00 | 11.22 | 0 |
| ATOM | 2505 | CB | ALA | 259 | 3.626 | 50.318 | 137.122 | 1.00 | 2.00 | 0 |
| ATOM | 2506 | C | ALA | 259 | 4.951 | 48.286 | 137.729 | 1.00 | 12.73 | 0 |
| ATOM | 2507 | O | ALA | 259 | 3.876 | 47.718 | 137.660 | 1.00 | 2.00 | 0 |
| ATOM | 2508 | N | LYS | 260 | 6.091 | 47.657 | 138.016 | 1.00 | 2.00 | 0 |
| ATOM | 2510 | CA | LYS | 260 | 6.140 | 46.214 | 138.304 | 1.00 | 9.39 | 0 |
| ATOM | 2511 | CB | LYS | 260 | 5.594 | 45.925 | 139.704 | 1.00 | 20.75 | 0 |
| ATOM | 2512 | CG | LYS | 260 | 6.589 | 46.151 | 140.844 | 1.00 | 28.17 | 0 |
| ATOM | 2513 | CD | LYS | 260 | 6.797 | 47.622 | 141.177 | 1.00 | 36.91 | 0 |
| ATOM | 2514 | CE | LYS | 260 | 7.615 | 47.765 | 142.449 | 1.00 | 36.02 | 0 |
| ATOM | 2515 | NZ | LYS | 260 | 6.919 | 47.158 | 143.633 | 1.00 | 29.33 | 0 |
| ATOM | 2519 | C | LYS | 260 | 5.370 | 45.375 | 137.279 | 1.00 | 2.00 | 0 |
| ATOM | 2520 | O | LYS | 260 | 4.443 | 44.633 | 137.641 | 1.00 | 15.95 | 0 |
| ATOM | 2521 | N | ARG | 261 | 5.764 | 45.531 | 136.004 | 1.00 | 2.00 | 0 |
| ATOM | 2523 | CA | ARG | 261 | 5.173 | 44.843 | 134.851 | 1.00 | 2.00 | 0 |
| ATOM | 2524 | CB | ARG | 261 | 5.410 | 43.335 | 134.964 | 1.00 | 21.35 | 0 |
| ATOM | 2525 | CG | ARG | 261 | 6.881 | 42.969 | 134.928 | 1.00 | 21.35 | 0 |
| ATOM | 2526 | CD | ARG | 261 | 7.088 | 41.473 | 134.970 | 1.00 | 9.03 | 0 |
| ATOM | 2527 | NE | ARG | 261 | 8.408 | 41.097 | 134.460 | 1.00 | 14.18 | 0 |
| ATOM | 2529 | CZ | ARG | 261 | 8.801 | 39.842 | 134.222 | 1.00 | 14.38 | 0 |
| ATOM | 2530 | NH1 | ARG | 261 | 7.976 | 38.820 | 134.462 | 1.00 | 16.12 | 0 |
| ATOM | 2533 | NH2 | ARG | 261 | 10.018 | 39.603 | 133.729 | 1.00 | 18.11 | 0 |
| ATOM | 2536 | C | ARG | 261 | 3.692 | 45.136 | 134.592 | 1.00 | 2.00 | 0 |
| ATOM | 2537 | O | ARG | 261 | 3.009 | 44.343 | 133.933 | 1.00 | 21.35 | 0 |
| ATOM | 2538 | N | GLN | 262 | 3.215 | 46.283 | 135.092 | 1.00 | 7.73 | 0 |
| ATOM | 2540 | CA | GLN | 262 | 1.821 | 46.727 | 134.927 | 1.00 | 7.73 | 0 |
| ATOM | 2541 | CB | GLN | 262 | 1.379 | 47.620 | 136.100 | 1.00 | 2.00 | 0 |
| ATOM | 2542 | CG | GLN | 262 | 1.106 | 46.888 | 137.434 | 1.00 | 2.00 | 0 |
| ATOM | 2543 | CD | GLN | 262 | 0.859 | 47.840 | 138.601 | 1.00 | 2.00 | 0 |
| ATOM | 2544 | OE1 | GLN | 262 | −0.277 | 48.137 | 138.930 | 1.00 | 2.00 | 0 |
| ATOM | 2545 | NE | GLN | 262 | 1.922 | 48.304 | 139.237 | 1.00 | 2.00 | 0 |
| ATOM | 2548 | C | GLN | 262 | 1.635 | 47.495 | 133.628 | 1.00 | 7.73 | 0 |
| ATOM | 2549 | O | GLN | 262 | 0.526 | 47.650 | 133.154 | 1.00 | 2.00 | 0 |
| ATOM | 2550 | N | LEU | 263 | 2.730 | 47.996 | 133.078 | 1.00 | 2.00 | 0 |
| ATOM | 2552 | CA | LEU | 263 | 2.723 | 48.726 | 131.819 | 1.00 | 2.00 | 0 |
| ATOM | 2553 | CB | LEU | 263 | 2.754 | 50.244 | 132.069 | 1.00 | 2.00 | 0 |
| ATOM | 2554 | CG | LEU | 263 | 3.070 | 51.201 | 130.890 | 1.00 | 2.00 | 0 |
| ATOM | 2555 | CD1 | LEU | 263 | 2.404 | 52.532 | 131.133 | 1.00 | 2.00 | 0 |
| ATOM | 2556 | CD2 | LEU | 263 | 4.575 | 51.408 | 130.679 | 1.00 | 2.00 | 0 |
| ATOM | 2557 | C | LEU | 263 | 3.991 | 48.305 | 131.089 | 1.00 | 2.00 | 0 |
| ATOM | 2558 | O | LEU | 263 | 5.018 | 48.082 | 131.736 | 1.00 | 2.00 | 0 |
| ATOM | 2559 | N | VAL | 264 | 3.932 | 48.207 | 129.759 | 1.00 | 42.92 | 0 |
| ATOM | 2561 | CA | VAL | 264 | 5.105 | 47.858 | 128.949 | 1.00 | 41.59 | 0 |
| ATOM | 2562 | CB | VAL | 264 | 5.014 | 46.373 | 128.433 | 1.00 | 2.00 | 0 |
| ATOM | 2563 | CG1 | VAL | 264 | 3.952 | 46.242 | 127.372 | 1.00 | 2.00 | 0 |
| ATOM | 2564 | CG2 | VAL | 264 | 6.349 | 45.908 | 127.929 | 1.00 | 2.00 | 0 |
| ATOM | 2565 | C | VAL | 264 | 5.193 | 48.840 | 127.772 | 1.00 | 42.79 | 0 |
| ATOM | 2566 | O | VAL | 264 | 4.164 | 49.261 | 127.242 | 1.00 | 2.00 | 0 |
| ATOM | 2567 | N | THR | 265 | 6.409 | 49.237 | 127.400 | 1.00 | 2.00 | 0 |
| ATOM | 2569 | CA | THR | 265 | 6.639 | 50.177 | 126.292 | 1.00 | 2.00 | 0 |
| ATOM | 2570 | CB | THR | 265 | 7.420 | 51.412 | 126.789 | 1.00 | 2.00 | 0 |
| ATOM | 2571 | OG1 | THR | 265 | 6.534 | 52.253 | 127.531 | 1.00 | 2.00 | 0 |
| ATOM | 2573 | CG2 | THR | 265 | 8.021 | 52.191 | 125.648 | 1.00 | 2.00 | 0 |
| ATOM | 2574 | C | THR | 265 | 7.405 | 49.523 | 125.132 | 1.00 | 2.00 | 0 |
| ATOM | 2575 | O | THR | 265 | 8.612 | 49.245 | 125.246 | 1.00 | 2.00 | 0 |
| ATOM | 2576 | N | LEU | 266 | 6.712 | 49.280 | 124.019 | 1.00 | 7.19 | 0 |
| ATOM | 2578 | CA | LEU | 266 | 7.330 | 48.653 | 122.857 | 1.00 | 7.19 | 0 |
| ATOM | 2579 | CB | LEU | 266 | 6.338 | 47.721 | 122.176 | 1.00 | 2.00 | 0 |
| ATOM | 2580 | CG | LEU | 266 | 5.815 | 46.505 | 122.948 | 1.00 | 2.00 | 0 |
| ATOM | 2581 | CD1 | LEU | 266 | 4.859 | 45.733 | 122.057 | 1.00 | 2.00 | 0 |
| ATOM | 2582 | CD2 | LEU | 266 | 6.955 | 45.599 | 123.368 | 1.00 | 2.00 | 0 |
| ATOM | 2583 | C | LEU | 266 | 7.898 | 49.618 | 121.819 | 1.00 | 7.19 | 0 |
| ATOM | 2584 | O | LEU | 266 | 7.329 | 50.675 | 121.537 | 1.00 | 2.00 | 0 |
| ATOM | 2585 | N | PHE | 267 | 9.033 | 49.249 | 121.247 | 1.00 | 2.00 | 0 |
| ATOM | 2587 | CA | PHE | 267 | 9.665 | 50.068 | 120.222 | 1.00 | 2.00 | 0 |
| ATOM | 2588 | CB | PHE | 267 | 10.763 | 50.960 | 120.821 | 1.00 | 2.00 | 0 |
| ATOM | 2589 | CG | PHE | 267 | 10.937 | 52.260 | 120.091 | 1.00 | 2.00 | 0 |
| ATOM | 2590 | CD1 | PHE | 267 | 9.985 | 53.261 | 120.206 | 1.00 | 2.00 | 0 |
| ATOM | 2591 | CD2 | PHE | 267 | 12.021 | 52.468 | 119.255 | 1.00 | 2.00 | 0 |
| ATOM | 2592 | CE1 | PHE | 267 | 10.108 | 54.445 | 119.493 | 1.00 | 2.00 | 0 |
| ATOM | 2593 | CE2 | PHE | 267 | 12.146 | 53.652 | 118.540 | 1.00 | 2.00 | 0 |
| ATOM | 2594 | CZ | PHE | 267 | 11.187 | 54.636 | 118.661 | 1.00 | 2.00 | 0 |

TABLE A-continued

| | | | | | | | | | |
|---|---|---|---|---|---|---|---|---|---|
| ATOM | 2595 | C | PHE | 267 | 10.246 | 49.076 | 119.227 | 1.00 | 2.00 | 0 |
| ATOM | 2596 | O | PHE | 267 | 11.418 | 48.693 | 119.321 | 1.00 | 2.00 | 0 |
| ATOM | 2597 | N | SER | 268 | 9.387 | 48.638 | 118.302 | 1.00 | 12.94 | 0 |
| ATOM | 2599 | CA | SER | 268 | 9.707 | 47.648 | 117.267 | 1.00 | 12.94 | 0 |
| ATOM | 2600 | CB | SER | 268 | 8.420 | 47.043 | 116.723 | 1.00 | 11.11 | 0 |
| ATOM | 2601 | OG | SER | 268 | 7.593 | 46.579 | 117.771 | 1.00 | 11.11 | 0 |
| ATOM | 2603 | C | SER | 268 | 10.450 | 48.231 | 116.103 | 1.00 | 12.94 | 0 |
| ATOM | 2604 | O | SER | 268 | 10.150 | 49.344 | 115.711 | 1.00 | 11.11 | 0 |
| ATOM | 2605 | N | ALA | 269 | 11.391 | 47.454 | 115.556 | 1.00 | 71.01 | 0 |
| ATOM | 2607 | CA | ALA | 269 | 12.222 | 47.779 | 114.378 | 1.00 | 71.72 | 0 |
| ATOM | 2608 | CB | ALA | 269 | 11.383 | 48.513 | 113.295 | 1.00 | 82.00 | 0 |
| ATOM | 2609 | C | ALA | 269 | 13.585 | 48.469 | 114.543 | 1.00 | 74.82 | 0 |
| ATOM | 2610 | O | ALA | 269 | 14.609 | 47.889 | 114.186 | 1.00 | 91.21 | 0 |
| ATOM | 2611 | N | PRO | 270 | 13.619 | 49.704 | 115.076 | 1.00 | 28.82 | 0 |
| ATOM | 2612 | CD | PRO | 270 | 12.436 | 50.466 | 115.513 | 1.00 | 2.00 | 0 |
| ATOM | 2613 | CA | PRO | 270 | 14.788 | 50.542 | 115.316 | 1.00 | 31.86 | 0 |
| ATOM | 2614 | CB | PRO | 270 | 14.340 | 51.374 | 116.502 | 1.00 | 2.00 | 0 |
| ATOM | 2615 | CG | PRO | 270 | 13.034 | 51.783 | 116.023 | 1.00 | 2.00 | 0 |
| ATOM | 2616 | C | PRO | 270 | 16.254 | 50.192 | 115.428 | 1.00 | 29.52 | 0 |
| ATOM | 2617 | O | PRO | 270 | 16.716 | 49.072 | 115.272 | 1.00 | 2.00 | 0 |
| ATOM | 2618 | N | ASN | 271 | 16.928 | 51.318 | 115.593 | 1.00 | 2.00 | 0 |
| ATOM | 2620 | CA | ASN | 271 | 18.346 | 51.621 | 115.754 | 1.00 | 2.00 | 0 |
| ATOM | 2621 | CB | ASN | 271 | 19.168 | 50.935 | 114.663 | 1.00 | 35.96 | 0 |
| ATOM | 2622 | CG | ASN | 271 | 18.483 | 50.953 | 113.300 | 1.00 | 61.96 | 0 |
| ATOM | 2623 | OD1 | ASN | 271 | 17.605 | 51.787 | 113.034 | 1.00 | 36.11 | 0 |
| ATOM | 2624 | ND2 | ASN | 271 | 18.872 | 50.015 | 112.432 | 1.00 | 36.31 | 0 |
| ATOM | 2627 | C | ASN | 271 | 18.199 | 53.143 | 115.475 | 1.00 | 2.00 | 0 |
| ATOM | 2628 | O | ASN | 271 | 19.072 | 53.807 | 114.915 | 1.00 | 61.69 | 0 |
| ATOM | 2629 | N | TYR | 272 | 17.039 | 53.638 | 115.930 | 1.00 | 2.00 | 0 |
| ATOM | 2631 | CA | TYR | 272 | 16.489 | 54.978 | 115.793 | 1.00 | 2.00 | 0 |
| ATOM | 2632 | CB | TYR | 272 | 15.772 | 55.358 | 117.090 | 1.00 | 17.33 | 0 |
| ATOM | 2633 | CG | TYR | 272 | 14.528 | 56.208 | 116.897 | 1.00 | 10.41 | 0 |
| ATOM | 2634 | CD1 | TYR | 272 | 13.458 | 55.769 | 116.105 | 1.00 | 11.86 | 0 |
| ATOM | 2635 | CE1 | TYR | 272 | 12.313 | 56.571 | 115.917 | 1.00 | 14.32 | 0 |
| ATOM | 2636 | CD2 | TYR | 272 | 14.421 | 57.454 | 117.492 | 1.00 | 10.66 | 0 |
| ATOM | 2637 | CE2 | TYR | 272 | 13.287 | 58.256 | 117.312 | 1.00 | 15.43 | 0 |
| ATOM | 2638 | CZ | TYR | 272 | 12.243 | 57.813 | 116.529 | 1.00 | 9.40 | 0 |
| ATOM | 2639 | OH | TYR | 272 | 11.143 | 58.636 | 116.375 | 1.00 | 17.38 | 0 |
| ATOM | 2641 | C | TYR | 272 | 17.332 | 56.132 | 115.299 | 1.00 | 2.03 | 0 |
| ATOM | 2642 | O | TYR | 272 | 18.356 | 56.471 | 115.888 | 1.00 | 29.84 | 0 |
| ATOM | 2643 | N | CYS | 273 | 16.860 | 56.731 | 114.201 | 1.00 | 7.24 | 0 |
| ATOM | 2645 | CA | CYS | 273 | 17.490 | 57.875 | 113.553 | 1.00 | 6.82 | 0 |
| ATOM | 2646 | CB | CYS | 273 | 17.201 | 59.167 | 114.331 | 1.00 | 11.61 | 0 |
| ATOM | 2647 | SG | CYS | 273 | 15.496 | 59.459 | 114.843 | 1.00 | 10.42 | 0 |
| ATOM | 2648 | C | CYS | 273 | 19.010 | 57.724 | 113.411 | 1.00 | 6.43 | 0 |
| ATOM | 2649 | O | CYS | 273 | 19.738 | 58.717 | 113.512 | 1.00 | 9.04 | 0 |
| ATOM | 2650 | N | GLY | 274 | 19.498 | 56.502 | 113.185 | 1.00 | 13.82 | 0 |
| ATOM | 2652 | CA | GLY | 274 | 20.934 | 56.303 | 113.044 | 1.00 | 13.82 | 0 |
| ATOM | 2653 | C | GLY | 274 | 21.710 | 57.029 | 114.134 | 1.00 | 13.82 | 0 |
| ATOM | 2654 | O | GLY | 274 | 22.817 | 57.515 | 113.906 | 1.00 | 39.65 | 0 |
| ATOM | 2655 | N | GLU | 275 | 21.120 | 57.085 | 115.326 | 1.00 | 92.80 | 0 |
| ATOM | 2657 | CA | GLU | 275 | 21.719 | 57.764 | 116.467 | 1.00 | 91.32 | 0 |
| ATOM | 2658 | CB | GLU | 275 | 21.479 | 59.276 | 116.340 | 1.00 | 25.01 | 0 |
| ATOM | 2659 | CG | GLU | 275 | 19.994 | 59.656 | 116.224 | 1.00 | 31.82 | 0 |
| ATOM | 2660 | CD | GLU | 275 | 19.730 | 61.158 | 116.060 | 1.00 | 30.92 | 0 |
| ATOM | 2661 | OE1 | GLU | 275 | 18.951 | 61.713 | 116.868 | 1.00 | 38.31 | 0 |
| ATOM | 2662 | OE2 | GLU | 275 | 20.276 | 61.787 | 115.125 | 1.00 | 34.18 | 0 |
| ATOM | 2663 | C | GLU | 275 | 21.137 | 57.260 | 117.794 | 1.00 | 90.32 | 0 |
| ATOM | 2664 | O | GLU | 275 | 20.941 | 58.047 | 118.716 | 1.00 | 23.69 | 0 |
| ATOM | 2665 | N | PHE | 276 | 20.868 | 55.958 | 117.901 | 1.00 | 16.78 | 0 |
| ATOM | 2667 | CA | PHE | 276 | 20.303 | 55.412 | 119.134 | 1.00 | 17.07 | 0 |
| ATOM | 2668 | CB | PHE | 276 | 18.774 | 55.551 | 119.125 | 1.00 | 37.20 | 0 |
| ATOM | 2669 | CG | PHE | 276 | 18.280 | 56.876 | 119.652 | 1.00 | 35.89 | 0 |
| ATOM | 2670 | CD1 | PHE | 276 | 17.522 | 57.726 | 118.849 | 1.00 | 35.53 | 0 |
| ATOM | 2671 | CD2 | PHE | 276 | 18.572 | 57.273 | 120.949 | 1.00 | 39.17 | 0 |
| ATOM | 2672 | CE1 | PHE | 276 | 17.067 | 58.945 | 119.329 | 1.00 | 31.45 | 0 |
| ATOM | 2673 | CE2 | PHE | 276 | 18.123 | 58.485 | 121.434 | 1.00 | 36.03 | 0 |
| ATOM | 2674 | CZ | PHE | 276 | 17.367 | 59.324 | 120.621 | 1.00 | 39.75 | 0 |
| ATOM | 2675 | C | PHE | 276 | 20.681 | 53.992 | 119.597 | 1.00 | 17.79 | 0 |
| ATOM | 2676 | O | PHE | 276 | 20.463 | 53.669 | 120.772 | 1.00 | 36.38 | 0 |
| ATOM | 2677 | N | ASP | 277 | 21.213 | 53.140 | 118.712 | 1.00 | 27.69 | 0 |
| ATOM | 2679 | CA | ASP | 277 | 21.638 | 51.772 | 119.093 | 1.00 | 27.89 | 0 |
| ATOM | 2680 | CB | ASP | 277 | 22.884 | 51.848 | 120.016 | 1.00 | 0.27 | 0 |
| ATOM | 2681 | CG | ASP | 277 | 23.231 | 50.508 | 120.716 | 1.00 | 39.20 | 0 |
| ATOM | 2682 | OD1 | ASP | 277 | 23.163 | 50.470 | 121.964 | 1.00 | 39.20 | 0 |
| ATOM | 2683 | OD2 | ASP | 277 | 23.576 | 49.508 | 120.036 | 1.00 | 39.20 | 0 |
| ATOM | 2684 | C | ASP | 277 | 20.560 | 50.892 | 119.742 | 1.00 | 26.41 | 0 |
| ATOM | 2685 | O | ASP | 277 | 20.761 | 49.675 | 119.918 | 1.00 | 0.76 | 0 |
| ATOM | 2686 | N | ASN | 278 | 19.428 | 51.491 | 120.101 | 1.00 | 2.00 | 0 |

TABLE A-continued

| | | | | | | | | | |
|---|---|---|---|---|---|---|---|---|---|
| ATOM | 2688 | CA | ASN | 278 | 18.344 | 50.758 | 120.722 | 1.00 | 2.00 | 0 |
| ATOM | 2689 | CB | ASN | 278 | 17.142 | 51.676 | 120.920 | 1.00 | 2.00 | 0 |
| ATOM | 2690 | CG | ASN | 278 | 16.394 | 51.930 | 119.639 | 1.00 | 2.00 | 0 |
| ATOM | 2691 | OD1 | ASN | 278 | 16.867 | 52.643 | 118.765 | 1.00 | 2.00 | 0 |
| ATOM | 2692 | ND2 | ASN | 278 | 15.225 | 51.324 | 119.510 | 1.00 | 2.00 | 0 |
| ATOM | 2695 | C | ASN | 278 | 17.938 | 49.602 | 119.829 | 1.00 | 2.00 | 0 |
| ATOM | 2696 | O | ASN | 278 | 17.970 | 49.710 | 118.600 | 1.00 | 2.00 | 0 |
| ATOM | 2697 | N | ALA | 279 | 17.603 | 48.487 | 120.454 | 1.00 | 14.31 | 0 |
| ATOM | 2699 | CA | ALA | 279 | 17.133 | 47.320 | 119.734 | 1.00 | 14.31 | 0 |
| ATOM | 2700 | CB | ALA | 279 | 17.281 | 46.081 | 120.594 | 1.00 | 2.00 | 0 |
| ATOM | 2701 | C | ALA | 279 | 15.655 | 47.631 | 119.498 | 1.00 | 14.31 | 0 |
| ATOM | 2702 | O | ALA | 279 | 15.155 | 48.645 | 119.996 | 1.00 | 2.00 | 0 |
| ATOM | 2703 | N | GLY | 280 | 14.959 | 46.786 | 118.743 | 1.00 | 2.00 | 0 |
| ATOM | 2705 | CA | GLY | 280 | 13.549 | 47.014 | 118.484 | 1.00 | 2.00 | 0 |
| ATOM | 2706 | C | GLY | 280 | 12.864 | 45.783 | 118.992 | 1.00 | 2.00 | 0 |
| ATOM | 2707 | O | GLY | 280 | 13.381 | 44.698 | 118.799 | 1.00 | 9.35 | 0 |
| ATOM | 2708 | N | ALA | 281 | 11.725 | 45.906 | 119.643 | 1.00 | 2.00 | 0 |
| ATOM | 2710 | CA | ALA | 281 | 11.082 | 44.702 | 120.167 | 1.00 | 2.00 | 0 |
| ATOM | 2711 | CB | ALA | 281 | 10.799 | 44.850 | 121.658 | 1.00 | 2.00 | 0 |
| ATOM | 2712 | C | ALA | 281 | 9.815 | 44.345 | 119.437 | 1.00 | 2.00 | 0 |
| ATOM | 2713 | O | ALA | 281 | 9.451 | 44.992 | 118.473 | 1.00 | 2.00 | 0 |
| ATOM | 2714 | N | MET | 282 | 9.140 | 43.312 | 119.918 | 1.00 | 14.19 | 0 |
| ATOM | 2716 | CA | MET | 282 | 7.907 | 42.833 | 119.315 | 1.00 | 14.19 | 0 |
| ATOM | 2717 | CB | MET | 282 | 8.232 | 42.115 | 117.995 | 1.00 | 25.98 | 0 |
| ATOM | 2718 | CG | MET | 282 | 7.056 | 41.885 | 117.060 | 1.00 | 24.91 | 0 |
| ATOM | 2719 | SD | MET | 282 | 7.304 | 40.449 | 115.980 | 1.00 | 25.45 | 0 |
| ATOM | 2720 | CE | MET | 282 | 9.044 | 40.644 | 115.525 | 1.00 | 21.20 | 0 |
| ATOM | 2721 | C | MET | 282 | 7.397 | 41.851 | 120.363 | 1.00 | 14.19 | 0 |
| ATOM | 2722 | O | MET | 282 | 8.142 | 40.972 | 120.790 | 1.00 | 24.98 | 0 |
| ATOM | 2723 | N | MET | 283 | 6.148 | 42.004 | 120.788 | 1.00 | 2.00 | 0 |
| ATOM | 2725 | CA | MET | 283 | 5.592 | 41.143 | 121.825 | 1.00 | 2.00 | 0 |
| ATOM | 2726 | CB | MET | 283 | 4.940 | 41.991 | 122.929 | 1.00 | 19.29 | 0 |
| ATOM | 2727 | CG | MET | 283 | 4.481 | 41.205 | 124.142 | 1.00 | 19.76 | 0 |
| ATOM | 2728 | SD | MET | 283 | 3.228 | 42.077 | 125.116 | 1.00 | 20.92 | 0 |
| ATOM | 2729 | CE | MET | 283 | 4.204 | 43.235 | 125.966 | 1.00 | 17.38 | 0 |
| ATOM | 2730 | C | MET | 283 | 4.592 | 40.125 | 121.339 | 1.00 | 2.00 | 0 |
| ATOM | 2731 | O | MET | 283 | 3.456 | 40.470 | 121.036 | 1.00 | 16.17 | 0 |
| ATOM | 2732 | N | SER | 284 | 5.012 | 35.571 | 121.291 | 1.00 | 2.00 | 0 |
| ATOM | 2734 | CA | SER | 284 | 4.148 | 37.777 | 120.869 | 1.00 | 2.00 | 0 |
| ATOM | 2735 | CB | SER | 284 | 4.991 | 36.664 | 120.220 | 1.00 | 20.90 | 0 |
| ATOM | 2736 | OG | SER | 284 | 6.376 | 36.771 | 120.528 | 1.00 | 23.67 | 0 |
| ATOM | 2738 | C | SBR | 284 | 3.275 | 37.202 | 122.018 | 1.00 | 2.00 | 0 |
| ATOM | 2739 | O | SER | 284 | 3.777 | 36.595 | 122.978 | 1.00 | 26.24 | 0 |
| ATOM | 2740 | N | VAL | 285 | 1.967 | 37.402 | 121.894 | 1.00 | 2.00 | 0 |
| ATOM | 2742 | CA | VAL | 285 | 0.979 | 36.940 | 122.859 | 1.00 | 2.00 | 0 |
| ATOM | 2743 | CB | VAL | 285 | −0.091 | 38.026 | 123.056 | 1.00 | 2.00 | 0 |
| ATOM | 2744 | CG1 | VAL | 285 | −0.952 | 37.714 | 124.262 | 1.00 | 2.00 | 0 |
| ATOM | 2745 | CG2 | VAL | 285 | 0.572 | 39.381 | 123.171 | 1.00 | 2.00 | 0 |
| ATOM | 2746 | C | VAL | 285 | 0.274 | 35.644 | 122.417 | 1.00 | 2.00 | 0 |
| ATGK | 2747 | O | VAL | 285 | −0.572 | 35.672 | 121.532 | 1.00 | 2.00 | 0 |
| ATOM | 2748 | N | ASP | 286 | 0.609 | 34.512 | 123.026 | 1.00 | 2.00 | 0 |
| ATOM | 2750 | CA | ASP | 286 | −0.056 | 33.258 | 122.663 | 1.00 | 2.00 | 0 |
| ATOM | 2751 | CB | ASP | 286 | 0.771 | 32.019 | 123.071 | 1.00 | 22.05 | 0 |
| ATOM | 2752 | CG | ASP | 286 | 1.192 | 32.020 | 124.531 | 1.00 | 24.93 | 0 |
| ATOM | 2753 | OD1 | ASP | 286 | 0.578 | 32.742 | 125.344 | 1.00 | 32.49 | 0 |
| ATOM | 2754 | OD2 | ASP | 286 | 2.152 | 31.285 | 124.866 | 1.00 | 28.80 | 0 |
| ATOM | 2755 | C | ASP | 286 | −1.494 | 33.141 | 123.181 | 1.00 | 2.00 | 0 |
| ATOM | 2756 | O | ASP | 286 | −1.993 | 34.023 | 123.881 | 1.00 | 12.72 | 0 |
| ATOM | 2757 | N | GLU | 287 | −2.144 | 32.036 | 122.817 | 1.00 | 28.94 | 0 |
| ATOM | 2759 | CA | GLU | 287 | −3.543 | 31.744 | 123.153 | 1.00 | 28.07 | 0 |
| ATOM | 2760 | CB | GLU | 287 | −3.912 | 30.340 | 122.657 | 1.00 | 59.96 | 0 |
| ATOM | 2761 | CG | GLU | 287 | −3.610 | 30.049 | 121.177 | 1.00 | 66.13 | 0 |
| ATOM | 2762 | CD | GLU | 287 | −2.139 | 29.730 | 120.890 | 1.00 | 70.85 | 0 |
| ATOM | 2763 | OE1 | GLU | 287 | −1.712 | 29.890 | 119.723 | 1.00 | 75.38 | 0 |
| ATOM | 2764 | OE2 | GLU | 287 | −1.412 | 29.315 | 121.822 | 1.00 | 73.00 | 0 |
| ATOM | 2765 | C | GLU | 287 | −3.876 | 31.836 | 124.638 | 1.00 | 30.16 | 0 |
| ATOM | 2766 | O | GLU | 287 | −5.017 | 32.074 | 125.029 | 1.00 | 62.37 | 0 |
| ATOM | 2767 | N | THR | 288 | −2.852 | 31.654 | 125.455 | 1.00 | 41.83 | 0 |
| ATOM | 2769 | CA | THR | 288 | −2.995 | 31.665 | 126.894 | 1.00 | 36.69 | 0 |
| ATOM | 2770 | CB | THR | 288 | −2.269 | 30.449 | 127.457 | 1.00 | 11.26 | 0 |
| ATOM | 2771 | OG1 | THR | 288 | −0.865 | 30.552 | 127.171 | 1.00 | 11.65 | 0 |
| ATOM | 2773 | CG2 | THR | 288 | −2.827 | 29.171 | 126.800 | 1.00 | 11.00 | 0 |
| ATOM | 2774 | C | THR | 288 | −2.461 | 32.947 | 127.533 | 1.00 | 36.73 | 0 |
| ATOM | 2775 | O | THR | 288 | −2.015 | 32.948 | 128.675 | 1.00 | 18.83 | 0 |
| ATOM | 2776 | N | LEU | 289 | −2.492 | 34.034 | 126.776 | 1.00 | 6.34 | 0 |
| ATOM | 2778 | CA | LEU | 289 | −2.027 | 35.334 | 127.232 | 1.00 | 2.00 | 0 |
| ATOM | 2779 | CB | LEU | 289 | −3.081 | 35.946 | 125.155 | 1.00 | 2.00 | 0 |
| ATOM | 2780 | CG | LEU | 289 | −4.282 | 36.465 | 127.346 | 1.00 | 2.00 | 0 |
| ATOM | 2751 | CD1 | LEU | 289 | −5.390 | 36.973 | 128.263 | 1.00 | 2.00 | 0 |

TABLE A-continued

| | | | | | | | | | |
|---|---|---|---|---|---|---|---|---|---|
| ATOM | 2782 | CD2 | LEU | 289 | −3.817 | 37.593 | 126.412 | 1.00 | 2.00 | 0 |
| ATOM | 2783 | C | LEU | 289 | −0.615 | 35.454 | 127.826 | 1.00 | 2.00 | 0 |
| ATOM | 2784 | O | LEU | 289 | −0.299 | 36.445 | 128.493 | 1.00 | 2.00 | 0 |
| ATOM | 2785 | N | MET | 290 | 0.244 | 34.475 | 127.566 | 1.00 | 20.85 | 0 |
| ATOM | 2787 | CA | MET | 290 | 1.619 | 34.548 | 128.046 | 1.00 | 23.75 | 0 |
| ATOM | 2788 | CB | MET | 290 | 2.238 | 33.156 | 128.212 | 1.00 | 24.81 | 0 |
| ATOM | 2789 | CG | NET | 290 | 3.717 | 33.200 | 128.623 | 1.00 | 23.46 | 0 |
| ATOM | 2790 | SD | MET | 290 | 4.726 | 31.867 | 127.935 | 1.00 | 26.75 | 0 |
| ATOM | 2791 | CE | MET | 290 | 5.196 | 32.555 | 126.310 | 1.00 | 29.16 | 0 |
| ATOM | 2792 | C | MET | 290 | 2.430 | 35.332 | 127.015 | 1.00 | 19.20 | 0 |
| ATOM | 2793 | O | MET | 290 | 2.545 | 34.910 | 125.858 | 1.00 | 29.26 | 0 |
| ATOM | 2794 | N | CYS | 291 | 3.003 | 36.454 | 127.449 | 1.00 | 2.00 | 0 |
| ATOM | 2796 | CA | CYS | 291 | 3.797 | 37.336 | 126.590 | 1.00 | 2.00 | 0 |
| ATOM | 2797 | CB | CYS | 291 | 1.624 | 38.773 | 127.062 | 1.00 | 17.87 | 0 |
| ATOM | 2798 | SG | CYS | 291 | 1.913 | 39.123 | 127.404 | 1.00 | 13.14 | 0 |
| ATOM | 2799 | C | CYS | 291 | 5.293 | 37.034 | 126.465 | 1.00 | 2.00 | 0 |
| ATOM | 2800 | O | CYS | 291 | 5.958 | 36.694 | 127.448 | 1.00 | 23.09 | 0 |
| ATOM | 2801 | N | SER | 292 | 5.808 | 37.187 | 125.244 | 1.00 | 5.71 | 0 |
| ATOM | 2803 | CA | SER | 292 | 7.223 | 36.977 | 124.928 | 1.00 | 9.30 | 0 |
| ATOM | 2804 | CB | SER | 292 | 7.385 | 35.709 | 124.098 | 1.00 | 12.57 | 0 |
| ATOM | 2805 | OG | SER | 292 | 6.548 | 34.675 | 124.593 | 1.00 | 20.05 | 0 |
| ATOM | 2807 | C | SER | 292 | 7.691 | 38.195 | 124.113 | 1.00 | 4.04 | 0 |
| ATOM | 2808 | O | SER | 292 | 6.867 | 38.867 | 123.485 | 1.00 | 14.24 | 0 |
| ATOM | 2809 | N | PHE | 293 | 8.993 | 38.487 | 124.128 | 1.00 | 2.00 | 0 |
| ATOM | 2811 | CA | PHE | 293 | 9.526 | 39.623 | 123.385 | 1.00 | 2.00 | 0 |
| ATOM | 2812 | CB | PHE | 293 | 10.077 | 40.676 | 124.337 | 1.00 | 17.01 | 0 |
| ATOM | 2813 | CG | PHE | 293 | 9.063 | 41.244 | 125.270 | 1.00 | 19.48 | 0 |
| ATOM | 2814 | CD1 | PHE | 293 | 8.772 | 40.611 | 126.466 | 1.00 | 23.05 | 0 |
| ATOM | 2815 | CD2 | PHE | 293 | 8.414 | 42.426 | 124.967 | 1.00 | 21.44 | 0 |
| ATOM | 2816 | CE1 | PHE | 293 | 7.852 | 41.146 | 127.352 | 1.00 | 24.82 | 0 |
| ATOM | 2817 | CE2 | PHE | 293 | 7.494 | 42.968 | 125.845 | 1.00 | 20.24 | 0 |
| ATOM | 2818 | CZ | PHE | 293 | 7.213 | 42.325 | 127.044 | 1.00 | 22.28 | 0 |
| ATOM | 2819 | C | PHE | 293 | 10.641 | 39.259 | 122.412 | 1.00 | 2.00 | 0 |
| ATOM | 2820 | O | PHE | 293 | 11.715 | 38.839 | 122.853 | 1.00 | 17.14 | 0 |
| ATOM | 2821 | N | GLN | 294 | 10.390 | 39.418 | 121.104 | 1.00 | 2.00 | 0 |
| ATOM | 2823 | CA | GLN | 294 | 11.404 | 39.162 | 120.060 | 1.00 | 2.00 | 0 |
| ATOM | 2824 | CB | GLN | 294 | 10.748 | 38.742 | 118.743 | 1.00 | 14.58 | 0 |
| ATOM | 2825 | CG | GLN | 294 | 10.074 | 37.383 | 116.798 | 1.00 | 22.67 | 0 |
| ATOM | 2826 | CD | GLN | 294 | 8.684 | 37.387 | 116.179 | 1.00 | 24.62 | 0 |
| ATOM | 2827 | OE1 | GLN | 294 | 7.835 | 38.206 | 116.535 | 1.00 | 27.17 | 0 |
| ATOM | 2828 | NE2 | GLN | 294 | 8.441 | 36.456 | 117.258 | 1.00 | 25.84 | 0 |
| ATOM | 2831 | C | GLN | 294 | 12.182 | 40.464 | 119.855 | 1.00 | 2.00 | 0 |
| ATOM | 2832 | O | GLN | 294 | 11.587 | 41.528 | 119.660 | 1.00 | 20.63 | 0 |
| ATOM | 2833 | N | ILE | 295 | 13.507 | 40.379 | 119.893 | 1.00 | 11.23 | 0 |
| ATOM | 2835 | CA | ILE | 295 | 14.356 | 41.569 | 119.772 | 1.00 | 12.32 | 0 |
| ATOM | 2836 | CB | ILE | 295 | 15.400 | 41.624 | 120.968 | 1.00 | 10.45 | 0 |
| ATOM | 2837 | CG2 | ILE | 295 | 16.277 | 42.875 | 120.886 | 1.00 | 10.45 | 0 |
| ATOM | 2838 | CG1 | ILE | 295 | 14.674 | 41.607 | 122.324 | 1.00 | 10.45 | 0 |
| ATOM | 2839 | CD1 | ILE | 295 | 13.756 | 42.807 | 122.580 | 1.00 | 10.45 | 0 |
| ATOM | 2840 | C | ILE | 295 | 15.126 | 41.703 | 118.453 | 1.00 | 7.79 | 0 |
| ATOM | 2841 | O | ILE | 295 | 15.723 | 40.741 | 117.974 | 1.00 | 10.45 | 0 |
| ATOM | 2842 | N | LEU | 296 | 15.087 | 42.900 | 117.873 | 1.00 | 11.71 | 0 |
| ATOM | 2844 | CA | LEU | 296 | 15.824 | 43.235 | 116.658 | 1.00 | 13.33 | 0 |
| ATOM | 2845 | CB | LEU | 296 | 14.987 | 44.102 | 115.717 | 1.00 | 24.46 | 0 |
| ATOM | 2846 | CG | LEU | 296 | 13.835 | 43.467 | 114.946 | 1.00 | 22.89 | 0 |
| ATOM | 2847 | CD1 | LEU | 296 | 12.626 | 43.340 | 115.862 | 1.00 | 22.12 | 0 |
| ATOM | 2848 | CD2 | LEU | 296 | 13.499 | 44.331 | 113.732 | 1.00 | 19.71 | 0 |
| ATOM | 2849 | C | LEU | 296 | 16.965 | 44.070 | 117.224 | 1.00 | 13.82 | 0 |
| ATOM | 2850 | O | LEU | 296 | 16.785 | 45.260 | 117.485 | 1.00 | 13.73 | 0 |
| ATOM | 2851 | N | LYS | 297 | 18.135 | 43.454 | 117.381 | 1.00 | 2.00 | 0 |
| ATOM | 2853 | CA | LYS | 297 | 19.319 | 44.087 | 117.997 | 1.00 | 2.00 | 0 |
| ATOM | 2854 | CB | LYS | 297 | 20.224 | 42.971 | 118.527 | 1.00 | 79.20 | 0 |
| ATOM | 2855 | CG | LYS | 297 | 20.792 | 42.094 | 117.419 | 1.00 | 79.65 | 0 |
| ATOM | 2856 | CD | LYS | 297 | 21.898 | 41.187 | 117.915 | 1.00 | 76.76 | 0 |
| ATOM | 2857 | CE | LYS | 297 | 22.543 | 40.430 | 116.762 | 1.00 | 71.01 | 0 |
| ATOM | 2858 | NZ | LYS | 297 | 23.644 | 39.543 | 117.232 | 1.00 | 66.76 | 0 |
| ATOM | 2862 | C | LYS | 297 | 20.259 | 45.149 | 117.376 | 1.00 | 2.00 | 0 |
| ATOM | 2863 | O | LYS | 297 | 21.255 | 45.501 | 118.013 | 1.00 | 94.11 | 0 |
| ATOM | 2864 | N | PRO | 298 | 19.995 | 45.656 | 116.152 | 1.00 | 40.11 | 0 |
| ATOM | 2865 | CD | PRO | 298 | 18.942 | 45.297 | 115.188 | 1.00 | 2.00 | 0 |
| ATOM | 2866 | CA | PRO | 298 | 20.900 | 46.658 | 115.553 | 1.00 | 40.11 | 0 |
| ATOM | 2667 | CB | PRO | 298 | 20.220 | 46.981 | 114.227 | 1.00 | 2.00 | 0 |
| ATOM | 2868 | CG | PRO | 298 | 19.570 | 45.700 | 113.886 | 1.00 | 2.00 | 0 |
| ATOM | 2869 | C | PRO | 298 | 21.264 | 47.935 | 116.312 | 1.00 | 40.11 | 0 |
| ATOM | 2870 | O | PRO | 298 | 21.041 | 48.056 | 117.514 | 1.00 | 2.00 | 0 |
| ATOM | 2871 | N | ALA | 299 | 21.854 | 48.878 | 115.574 | 1.00 | 61.74 | 0 |
| ATOM | 2873 | CA | ALA | 299 | 22.276 | 50.176 | 116.101 | 1.00 | 61.74 | 0 |
| ATOM | 2874 | CB | ALA | 299 | 23.627 | 50.063 | 116.799 | 1.00 | 2.00 | 0 |
| ATOM | 2875 | C | ALA | 299 | 22.373 | 51.193 | 114.973 | 1.00 | 61.74 | 0 |

TABLE A-continued

| | | | | | | | | | |
|---|---|---|---|---|---|---|---|---|---|
| ATOM | 2876 | O | ALA | 299 | 21.893 | 52.319 | 115.105 | 1.00 | 2.00 | 0 |
| ATOM | 2677 | N | ASN | 508 | 41.191 | 29.848 | 91.500 | 1.00 | 48.97 | 0 |
| ATOM | 2879 | CA | ASN | 508 | 39.902 | 30.150 | 90.896 | 1.00 | 48.97 | 0 |
| ATOM | 2880 | CB | ASN | 508 | 38.951 | 30.831 | 91.887 | 1.00 | 0.74 | 0 |
| ATOM | 2881 | CG | ASN | 508 | 37.666 | 31.359 | 91.203 | 1.00 | 0.74 | 0 |
| ATOM | 2882 | OD1 | ASN | 508 | 36.879 | 30.587 | 90.592 | 1.00 | 0.74 | 0 |
| ATOM | 2883 | ND2 | ASN | 508 | 37.453 | 32.682 | 91.290 | 1.00 | 0.74 | 0 |
| ATOM | 2886 | C | ASN | 508 | 40.096 | 31.041 | 89.687 | 1.00 | 48.97 | 0 |
| ATOM | 2887 | O | ASN | 508 | 40.274 | 32.266 | 89.798 | 1.00 | 0.74 | 0 |
| ATOM | 2888 | N | ILE | 509 | 40.006 | 30.387 | 88.533 | 1.00 | 17.27 | 0 |
| ATOM | 2890 | CA | ILE | 509 | 40.188 | 30.983 | 87.224 | 1.00 | 18.75 | 0 |
| ATOM | 2891 | CB | ILE | 509 | 40.088 | 29.889 | 86.127 | 1.00 | 44.37 | 0 |
| ATOM | 2892 | CG2 | ILE | 509 | 38.650 | 29.700 | 85.673 | 1.00 | 52.59 | 0 |
| ATOM | 2893 | CG1 | ILE | 509 | 41.013 | 30.238 | 84.966 | 1.00 | 44.31 | 0 |
| ATOM | 2894 | CD1 | ILE | 509 | 42.489 | 30.093 | 85.305 | 1.00 | 44.07 | 0 |
| ATOM | 2895 | C | ILE | 509 | 39.196 | 32.089 | 86.957 | 1.00 | 18.83 | 0 |
| ATOM | 2896 | O | ILE | 509 | 39.463 | 32.956 | 86.131 | 1.00 | 44.94 | 0 |
| ATOM | 2897 | N | ASP | 510 | 38.070 | 32.071 | 87.670 | 1.00 | 2.00 | 0 |
| ATOM | 2899 | CA | ASP | 510 | 37.048 | 33.088 | 87.485 | 1.00 | 2.00 | 0 |
| ATOM | 2900 | CB | ASP | 510 | 35.711 | 32.605 | 88.031 | 1.00 | 52.76 | 0 |
| ATOM | 2901 | CG | ASP | 510 | 35.029 | 31.634 | 87.089 | 1.00 | 54.58 | 0 |
| ATOM | 2902 | OD1 | ASP | 510 | 34.008 | 32.015 | 86.483 | 1.00 | 54.54 | 0 |
| ATOM | 2903 | OD2 | ASP | 510 | 35.521 | 30.497 | 86.944 | 1.00 | 58.16 | 0 |
| ATOM | 2904 | C | ASP | 510 | 37.403 | 34.442 | 88.056 | 1.00 | 2.00 | 0 |
| ATOM | 2905 | O | ASP | 510 | 37.016 | 35.464 | 87.490 | 1.00 | 52.34 | 0 |
| ATOM | 2906 | N | SER | 511 | 38.143 | 34.471 | 89.160 | 1.00 | 2.00 | 0 |
| ATOM | 2908 | CA | SER | 511 | 38.548 | 35.763 | 89.739 | 1.00 | 2.00 | 0 |
| ATOM | 2909 | CB | SER | 511 | 39.372 | 35.570 | 91.015 | 1.00 | 53.95 | 0 |
| ATOM | 2910 | OG | SER | 511 | 38.631 | 34.907 | 92.020 | 1.00 | 50.17 | 0 |
| ATOM | 2912 | C | SER | 511 | 39.447 | 36.379 | 88.690 | 1.00 | 2.00 | 0 |
| ATOM | 2913 | O | SER | 511 | 39.228 | 37.488 | 88.203 | 1.00 | 59.62 | 0 |
| ATOM | 2914 | N | ILE | 512 | 40.453 | 35.584 | 88.349 | 1.00 | 45.56 | 0 |
| ATOM | 2916 | CA | ILE | 512 | 41.462 | 35.892 | 87.361 | 1.00 | 40.32 | 0 |
| ATOM | 2917 | CB | ILE | 512 | 42.224 | 34.598 | 87.035 | 1.00 | 2.00 | 0 |
| ATOM | 2918 | CG2 | ILE | 512 | 43.250 | 34.842 | 85.943 | 1.00 | 2.00 | 0 |
| ATOM | 2919 | CG1 | ILE | 512 | 42.897 | 34.092 | 88.316 | 1.00 | 2.00 | 0 |
| ATOM | 2920 | CD1 | ILE | 512 | 43.635 | 32.772 | 88.174 | 1.00 | 2.00 | 0 |
| ATOM | 2921 | C | ILE | 512 | 40.843 | 36.514 | 86.105 | 1.00 | 41.22 | 0 |
| ATOM | 2922 | O | ILE | 512 | 41.051 | 37.700 | 85.848 | 1.00 | 2.00 | 0 |
| ATOM | 2923 | N | ILE | 513 | 40.061 | 35.728 | 85.358 | 1.00 | 2.00 | 0 |
| ATOM | 2925 | CA | ILE | 513 | 39.408 | 36.195 | 84.136 | 1.00 | 2.00 | 0 |
| ATOM | 2926 | CB | ILE | 513 | 38.435 | 35.123 | 83.529 | 1.00 | 2.00 | 0 |
| ATOM | 2927 | CG2 | ILE | 513 | 37.560 | 35.757 | 82.455 | 1.00 | 2.00 | 0 |
| ATOM | 2928 | CG1 | ILE | 513 | 39.227 | 33.963 | 82.890 | 1.00 | 2.00 | 0 |
| ATOM | 2929 | CD1 | ILE | 513 | 38.365 | 32.796 | 82.367 | 1.00 | 2.00 | 0 |
| ATOM | 2930 | C | ILE | 513 | 38.640 | 37.493 | 84.335 | 1.00 | 2.00 | 0 |
| ATOM | 2931 | O | ILE | 513 | 38.764 | 38.403 | 83.519 | 1.00 | 2.00 | 0 |
| ATOM | 2932 | N | GLN | 514 | 37.858 | 37.611 | 85.402 | 1.00 | 12.46 | 0 |
| ATOM | 2934 | CA | GLN | 514 | 37.117 | 38.853 | 85.581 | 1.00 | 12.46 | 0 |
| ATOM | 2935 | CB | GLN | 514 | 35.985 | 38.678 | 86.591 | 1.00 | 26.62 | 0 |
| ATOM | 2936 | CG | GLN | 514 | 36.384 | 38.251 | 87.972 | 1.00 | 26.62 | 0 |
| ATOM | 2937 | CD | GLN | 514 | 35.195 | 38.279 | 88.929 | 1.00 | 26.62 | 0 |
| ATOM | 2938 | OE1 | GLN | 514 | 34.582 | 39.337 | 89.140 | 1.00 | 26.62 | 0 |
| ATOM | 2939 | NE2 | GLN | 514 | 34.851 | 37.116 | 89.502 | 1.00 | 26.62 | 0 |
| ATOM | 2942 | C | GLN | 514 | 38.009 | 40.055 | 85.936 | 1.00 | 12.46 | 0 |
| ATOM | 2943 | O | GLN | 514 | 37.686 | 41.205 | 85.613 | 1.00 | 26.62 | 0 |
| ATOM | 2944 | N | ARG | 515 | 39.147 | 39.773 | 86.564 | 1.00 | 6.50 | 0 |
| ATOM | 2946 | CA | ARG | 515 | 40.090 | 40.810 | 86.937 | 1.00 | 7.53 | 0 |
| ATOM | 2947 | CB | ARG | 515 | 41.125 | 40.251 | 87.917 | 1.00 | 8.04 | 0 |
| ATOM | 2948 | CG | ARG | 515 | 40.626 | 40.257 | 89.362 | 1.00 | 8.04 | 0 |
| ATOM | 2949 | CD | ARG | 515 | 41.182 | 39.117 | 90.212 | 1.00 | 8.04 | 0 |
| ATOM | 2950 | NE | ARG | 515 | 42.609 | 39.250 | 90.490 | 1.00 | 8.04 | 0 |
| ATOM | 2952 | CZ | ARG | 515 | 43.355 | 38.276 | 90.998 | 1.00 | 8.04 | 0 |
| ATOM | 2953 | NH1 | ARG | 515 | 42.505 | 37.103 | 91.275 | 1.00 | 8.04 | 0 |
| ATOM | 2956 | NH2 | ARG | 515 | 44.646 | 38.478 | 91.228 | 1.00 | 8.04 | 0 |
| ATOM | 2959 | C | ARG | 515 | 40.745 | 41.325 | 85.669 | 1.00 | 12.92 | 0 |
| ATOM | 2960 | O | ARG | 515 | 40.840 | 42.537 | 85.464 | 1.00 | 8.04 | 0 |
| ATOM | 2961 | N | LEU | 516 | 41.167 | 40.398 | 84.810 | 1.00 | 8.93 | 0 |
| ATOM | 2963 | CA | LEU | 516 | 41.788 | 40.727 | 83.525 | 1.00 | 6.71 | 0 |
| ATOM | 2964 | CB | LEU | 516 | 42.172 | 39.431 | 82.786 | 1.00 | 2.00 | 0 |
| ATOM | 2965 | CG | LEU | 516 | 43.298 | 38.561 | 83.385 | 1.00 | 2.00 | 0 |
| ATOM | 2966 | CD1 | LEU | 516 | 43.057 | 37.096 | 83.082 | 1.00 | 2.00 | 0 |
| ATOM | 2967 | CD2 | LEU | 516 | 44.650 | 38.986 | 82.843 | 1.00 | 2.00 | 0 |
| ATOM | 2968 | C | LEU | 516 | 40.809 | 41.562 | 82.675 | 1.00 | 5.82 | 0 |
| ATOM | 2969 | O | LEU | 516 | 41.187 | 42.516 | 82.002 | 1.00 | 2.00 | 0 |
| ATOM | 2970 | N | LEU | 517 | 39.534 | 41.228 | 82.755 | 1.00 | 2.00 | 0 |
| ATOM | 2972 | CA | LEU | 517 | 38.519 | 41.928 | 81.993 | 1.00 | 2.73 | 0 |
| ATOM | 2973 | CB | LEU | 517 | 37.336 | 40.993 | 81.752 | 1.00 | 7.08 | 0 |
| ATOM | 2974 | CG | LEU | 517 | 37.203 | 40.297 | 80.398 | 1.00 | 3.18 | 0 |

TABLE A-continued

| | | | | | | | | | |
|---|---|---|---|---|---|---|---|---|---|
| ATOM | 2975 | CD1 | LEU | 517 | 38.524 | 39.694 | 79.950 | 1.00 | 12.86 | 0 |
| ATOM | 2976 | CD2 | LEU | 517 | 36.133 | 39.227 | 80.518 | 1.00 | 9.89 | 0 |
| ATOM | 2977 | C | LEU | 517 | 37.989 | 43.262 | 82.536 | 1.00 | 9.79 | 0 |
| ATOM | 2978 | O | LEU | 517 | 37.169 | 43.908 | 81.858 | 1.00 | 16.46 | 0 |
| ATOM | 2979 | N | GLU | 518 | 38.409 | 43.708 | 83.722 | 1.00 | 2.00 | 0 |
| ATOM | 2981 | CA | GLU | 518 | 37.845 | 44.981 | 84.178 | 1.00 | 2.00 | 0 |
| ATOM | 2982 | CB | GLU | 518 | 37.621 | 45.015 | 85.699 | 1.00 | 2.00 | 0 |
| ATOM | 2983 | CG | GLU | 518 | 36.908 | 46.315 | 86.231 | 1.00 | 2.00 | 0 |
| ATOM | 2964 | CD | GLU | 518 | 35.550 | 46.705 | 85.526 | 1.00 | 2.00 | 0 |
| ATOM | 2985 | OE1 | GLU | 518 | 34.554 | 47.001 | 86.262 | 1.00 | 2.00 | 0 |
| ATOM | 2986 | OE2 | GLU | 518 | 35.481 | 46.748 | 84.252 | 1.00 | 2.00 | 0 |
| ATOM | 2987 | C | GLU | 518 | 38.618 | 46.200 | 83.677 | 1.00 | 2.00 | 0 |
| ATOM | 2988 | O | GLU | 518 | 38.121 | 47.335 | 83.729 | 1.00 | 2.00 | 0 |
| ATOM | 2989 | N | VAL | 519 | 39.828 | 45.978 | 83.166 | 1.00 | 21.94 | 0 |
| ATOM | 2991 | CA | VAL | 519 | 40.582 | 47.094 | 82.589 | 1.00 | 19.66 | 0 |
| ATOM | 2992 | CB | VAL | 519 | 42.078 | 46.804 | 82.428 | 1.00 | 40.73 | 0 |
| ATOM | 2993 | CG1 | VAL | 519 | 42.759 | 46.806 | 83.771 | 1.00 | 42.53 | 0 |
| ATOM | 2994 | CG2 | VAL | 519 | 42.272 | 45.488 | 81.684 | 1.00 | 37.62 | 0 |
| ATOM | 2995 | C | VAL | 519 | 40.007 | 47.307 | 81.196 | 1.00 | 22.58 | 0 |
| ATOM | 2996 | O | VAL | 519 | 40.402 | 48.229 | 80.493 | 1.00 | 48.07 | 0 |
| ATOM | 2997 | N | ARG | 520 | 39.066 | 46.442 | 80.815 | 1.00 | 26.87 | 0 |
| ATOM | 2999 | CA | ARG | 520 | 38.410 | 46.495 | 79.515 | 1.00 | 28.58 | 0 |
| ATOM | 3000 | CB | ARG | 520 | 37.216 | 45.534 | 79.480 | 1.00 | 40.18 | 0 |
| ATOM | 3001 | CG | ARG | 520 | 36.878 | 45.043 | 78.086 | 1.00 | 44.14 | 0 |
| ATOM | 3002 | CD | ARG | 520 | 35.994 | 43.814 | 78.116 | 1.00 | 47.95 | 0 |
| ATOM | 3003 | NE | ARG | 520 | 34.592 | 44.131 | 77.872 | 1.00 | 44.40 | 0 |
| ATOM | 3005 | CZ | ARG | 520 | 33.565 | 43.402 | 78.308 | 1.00 | 51.11 | 0 |
| ATOM | 3006 | NH1 | ARG | 520 | 33.767 | 42.298 | 79.022 | 1.00 | 48.24 | 0 |
| ATOM | 3009 | NH2 | ARG | 520 | 32.325 | 43.778 | 78.026 | 1.00 | 49.03 | 0 |
| ATOM | 3012 | C | ARG | 520 | 37.946 | 47.899 | 79.147 | 1.00 | 28.36 | 0 |
| ATOM | 3013 | O | ARG | 520 | 37.881 | 48.247 | 77.964 | 1.00 | 46.63 | 0 |
| ATOM | 3014 | N | GLY | 521 | 37.639 | 48.703 | 80.158 | 1.00 | 27.79 | 0 |
| ATOM | 3016 | CA | GLY | 521 | 37.186 | 50.056 | 79.905 | 1.00 | 30.97 | 0 |
| ATOM | 3017 | C | GLY | 521 | 38.158 | 51.099 | 80.400 | 1.00 | 32.39 | 0 |
| ATOM | 3018 | O | GLY | 521 | 37.739 | 52.124 | 80.940 | 1.00 | 54.55 | 0 |
| ATOM | 3019 | N | SER | 522 | 39.451 | 50.840 | 80.225 | 1.00 | 46.95 | 0 |
| ATOM | 3021 | CA | SER | 522 | 40.495 | 51.761 | 80.663 | 1.00 | 47.91 | 0 |
| ATOM | 3022 | CB | SER | 522 | 41.300 | 51.146 | 81.801 | 1.00 | 33.41 | 0 |
| ATOM | 3023 | OG | SER | 522 | 40.459 | 50.694 | 82.844 | 1.00 | 32.38 | 0 |
| ATOM | 3025 | C | SER | 522 | 41.436 | 52.094 | 79.517 | 1.00 | 49.38 | 0 |
| ATOM | 3026 | O | SER | 522 | 41.495 | 51.378 | 78.513 | 1.00 | 34.02 | 0 |
| ATOM | 3027 | N | LYS | 523 | 42.174 | 53.184 | 79.679 | 1.00 | 84.47 | 0 |
| ATOM | 3029 | CA | LYS | 523 | 43.127 | 53.640 | 78.674 | 1.00 | 81.24 | 0 |
| ATOM | 3030 | CB | LYS | 523 | 44.035 | 54.715 | 79.274 | 1.00 | 43.78 | 0 |
| ATOM | 3031 | CG | LYS | 523 | 43.307 | 55.987 | 79.619 | 1.00 | 44.40 | 0 |
| ATOM | 3032 | CD | LYS | 523 | 44.206 | 56.990 | 80.322 | 1.00 | 68.84 | 0 |
| ATOM | 3033 | CE | LYS | 523 | 43.493 | 58.336 | 80.458 | 1.00 | 44.38 | 0 |
| ATOM | 3034 | NZ | LYS | 523 | 42.092 | 58.186 | 80.983 | 1.00 | 44.06 | 0 |
| ATOM | 3038 | C | LYS | 523 | 44.000 | 52.501 | 78.173 | 1.00 | 80.03 | 0 |
| ATOM | 3039 | O | LYS | 523 | 44.314 | 51.584 | 78.937 | 1.00 | 43.77 | 0 |
| ATOM | 3040 | N | PRO | 524 | 44.360 | 52.514 | 76.873 | 1.00 | 2.00 | 0 |
| ATOM | 3041 | CD | PRO | 524 | 43.901 | 53.427 | 75.811 | 1.00 | 84.06 | 0 |
| ATOM | 3042 | CA | PRO | 524 | 45.218 | 51.459 | 76.316 | 1.00 | 2.00 | 0 |
| ATOM | 3043 | CB | PRO | 524 | 45.357 | 51.871 | 74.850 | 1.00 | 62.26 | 0 |
| ATOM | 3044 | CG | PRO | 524 | 44.057 | 52.574 | 74.576 | 1.00 | 78.74 | 0 |
| ATOM | 3045 | C | PRO | 524 | 46.576 | 51.489 | 77.063 | 1.00 | 2.00 | 0 |
| ATOM | 3046 | O | PRO | 524 | 47.510 | 52.190 | 76.653 | 1.00 | 76.15 | 0 |
| ATOM | 3047 | N | GLY | 525 | 46.647 | 50.742 | 78.166 | 1.00 | 33.80 | 0 |
| ATOM | 3049 | CA | GLY | 525 | 47.846 | 50.682 | 78.984 | 1.00 | 98.68 | 0 |
| ATOM | 3050 | C | GLY | 525 | 47.575 | 50.197 | 80.403 | 1.00 | 99.00 | 0 |
| ATOM | 3051 | O | GLY | 525 | 48.427 | 49.555 | 81.013 | 1.00 | 2.00 | 0 |
| ATOM | 3052 | N | LYS | 526 | 46.397 | 50.496 | 80.942 | 1.00 | 49.37 | 0 |
| ATOM | 3054 | CA | LYS | 526 | 46.047 | 50.070 | 82.297 | 1.00 | 44.35 | 0 |
| ATOM | 3055 | CB | LYS | 526 | 44.537 | 50.226 | 82.505 | 1.00 | 0.79 | 0 |
| ATOM | 3056 | CG | LYS | 526 | 44.013 | 49.851 | 83.911 | 1.00 | 0.82 | 0 |
| ATOM | 3057 | CD | LYS | 526 | 44.370 | 50.915 | 84.950 | 1.00 | 0.29 | 0 |
| ATOM | 3058 | CE | LYS | 526 | 44.413 | 50.312 | 86.354 | 1.00 | 28.48 | 0 |
| ATOM | 3059 | NZ | LYS | 526 | 45.166 | 51.143 | 87.348 | 1.00 | 28.16 | 0 |
| ATOM | 3063 | C | LYS | 526 | 46.461 | 48.602 | 82.479 | 1.00 | 41.81 | 0 |
| ATOM | 3064 | O | LYS | 526 | 45.984 | 47.727 | 81.760 | 1.00 | 0.75 | 0 |
| ATOM | 3065 | N | ASN | 527 | 47.372 | 46.337 | 83.412 | 1.00 | 6.60 | 0 |
| ATOM | 3067 | CA | ASN | 527 | 47.861 | 46.972 | 83.639 | 1.00 | 6.60 | 0 |
| ATOM | 3068 | CB | ASN | 527 | 49.208 | 46.977 | 84.361 | 1.00 | 20.38 | 0 |
| ATOM | 3069 | CG | ASN | 527 | 50.300 | 47.733 | 83.645 | 1.00 | 30.42 | 0 |
| ATOM | 3070 | OD1 | ASN | 527 | 50.695 | 48.820 | 84.068 | 1.00 | 29.99 | 0 |
| ATOM | 3071 | ND2 | ASN | 527 | 50.818 | 47.148 | 82.561 | 1.00 | 30.17 | 0 |
| ATOM | 3074 | C | ASN | 527 | 46.895 | 46.135 | 84.463 | 1.00 | 6.60 | 0 |
| ATOM | 3075 | O | ASN | 527 | 45.866 | 46.628 | 84.924 | 1.00 | 23.47 | 0 |
| ATOM | 3076 | N | VAL | S28 | 47.271 | 44.866 | 84.647 | 1.00 | 26.67 | 0 |

TABLE A-continued

| | | | | | | | | | |
|---|---|---|---|---|---|---|---|---|---|
| ATOM | 3078 | CA | VAL | 528 | 46.541 | 43.874 | 85.443 | 1.00 | 26.67 | 0 |
| ATOM | 3079 | CB | VAL | 528 | 45.575 | 43.004 | 84.603 | 1.00 | 33.44 | 0 |
| ATOM | 3080 | CG1 | VAL | 528 | 44.909 | 41.956 | 85.488 | 1.00 | 33.01 | 0 |
| ATOM | 3081 | CG2 | VAL | 528 | 44.524 | 43.858 | 83.956 | 1.00 | 35.61 | 0 |
| ATOM | 3082 | C | VAL | 528 | 47.607 | 42.940 | 86.018 | 1.00 | 26.67 | 0 |
| ATOM | 3083 | O | VAL | 528 | 48.054 | 42.003 | 85.348 | 1.00 | 36.85 | 0 |
| ATOM | 3084 | N | GLN | 529 | 48.048 | 43.231 | 87.239 | 1.00 | 2.00 | 0 |
| ATOM | 3086 | CA | GLN | 529 | 49.061 | 42.407 | 87.920 | 1.00 | 2.00 | 0 |
| ATOM | 3087 | CB | GLN | 529 | 49.968 | 43.297 | 88.787 | 1.00 | 30.41 | 0 |
| ATOM | 3088 | CG | GLN | 529 | 51.142 | 42.569 | 89.428 | 1.00 | 32.34 | 0 |
| ATOM | 3089 | CD | GLN | 529 | 52.380 | 42.558 | 86.558 | 1.00 | 31.37 | 0 |
| ATOM | 3090 | OE1 | GLN | 529 | 53.436 | 43.035 | 88.962 | 1.00 | 35.47 | 0 |
| ATOM | 3091 | NE2 | GLN | 529 | 52.259 | 42.014 | 87.361 | 1.00 | 30.69 | 0 |
| ATOM | 3094 | C | GLN | 529 | 48.350 | 41.347 | 88.792 | 1.00 | 2.00 | 0 |
| ATOM | 3095 | O | GLN | 529 | 47.545 | 41.689 | 89.663 | 1.00 | 32.29 | 0 |
| ATOM | 3096 | N | LEU | 530 | 48.624 | 40.072 | 88.536 | 1.00 | 2.00 | 0 |
| ATOM | 3098 | CA | LEU | 530 | 47.994 | 39.002 | 89.303 | 1.00 | 2.00 | 0 |
| ATOM | 3099 | CB | LEU | 530 | 47.462 | 37.911 | 88.381 | 1.00 | 12.99 | 0 |
| ATOM | 3100 | CG | LEU | 530 | 46.535 | 38.302 | 87.248 | 1.00 | 12.99 | 0 |
| ATOM | 3101 | CD1 | LEU | 530 | 47.297 | 38.159 | 85.956 | 1.00 | 12.99 | 0 |
| ATOM | 3102 | CD2 | LEU | 530 | 45.313 | 37.403 | 87.243 | 1.00 | 12.99 | 0 |
| ATOM | 3103 | C | LEU | 530 | 49.002 | 38.365 | 90.236 | 1.00 | 2.00 | 0 |
| ATOM | 3104 | O | LEU | 530 | 50.207 | 38.543 | 90.067 | 1.00 | 12.99 | 0 |
| ATOM | 3105 | N | GLN | 531 | 48.516 | 37.622 | 91.221 | 1.00 | 2.00 | 0 |
| ATOM | 3107 | CA | GLN | 531 | 49.418 | 36.932 | 92.117 | 1.00 | 2.00 | 0 |
| ATOM | 3108 | CB | GLN | 531 | 46.634 | 36.051 | 93.090 | 1.00 | 61.54 | 0 |
| ATOM | 3109 | CG | GLN | 531 | 48.376 | 36.639 | 94.465 | 1.00 | 62.91 | 0 |
| ATOM | 3110 | CD | GLN | 531 | 47.221 | 37.603 | 94.487 | 1.00 | 63.71 | 0 |
| ATOM | 3111 | OE1 | GLN | 531 | 47.322 | 36.684 | 95.053 | 1.00 | 59.60 | 0 |
| ATOM | 3112 | NE2 | GLN | 531 | 46.111 | 37.219 | 93.876 | 1.00 | 61.96 | 0 |
| ATOM | 3115 | C | GLN | 531 | 50.337 | 36.040 | 91.266 | 1.00 | 2.00 | 0 |
| ATOM | 3116 | O | GLN | 531 | 49.859 | 35.276 | 90.422 | 1.00 | 67.15 | 0 |
| ATOM | 3117 | N | GLU | 532 | 51.647 | 36.153 | 91.480 | 1.00 | 2.00 | 0 |
| ATOM | 3119 | CA | GLU | 532 | 52.655 | 35.349 | 90.766 | 1.00 | 2.00 | 0 |
| ATOM | 3120 | CB | GLU | 532 | 54.056 | 35.623 | 91.336 | 1.00 | 19.01 | 0 |
| ATOM | 3121 | CG | GLU | 532 | 55.176 | 34.623 | 90.966 | 1.00 | 22.74 | 0 |
| ATOM | 3122 | CD | GLU | 532 | 56.496 | 34.871 | 91.746 | 1.00 | 25.50 | 0 |
| ATOM | 3123 | OE1 | GLU | 532 | 56.845 | 36.042 | 92.058 | 1.00 | 20.16 | 0 |
| ATOM | 3124 | OE2 | GLU | 532 | 57.195 | 33.879 | 92.051 | 1.00 | 20.82 | 0 |
| ATOM | 3125 | C | GLU | 532 | 52.345 | 33.866 | 90.900 | 1.00 | 2.00 | 0 |
| ATOM | 3126 | O | GLU | 532 | 52.833 | 33.059 | 90.116 | 1.00 | 17.28 | 0 |
| ATOM | 3127 | N | ASN | 533 | 51.568 | 33.509 | 91.918 | 1.00 | 26.78 | 0 |
| ATOM | 3129 | CA | ASN | 533 | 51.181 | 32.120 | 92.127 | 1.00 | 27.69 | 0 |
| ATOM | 3130 | CB | ASN | 533 | 50.751 | 31.857 | 93.587 | 1.00 | 42.65 | 0 |
| ATOM | 3131 | CG | ASN | 533 | 49.834 | 32.944 | 94.154 | 1.00 | 49.17 | 0 |
| ATOM | 3132 | OD1 | ASN | 533 | 50.274 | 34.070 | 94.392 | 1.00 | 50.06 | 0 |
| ATOM | 3133 | ND2 | ASN | 533 | 48.568 | 32.605 | 94.387 | 1.00 | 50.92 | 0 |
| ATOM | 3136 | C | ASN | 533 | 50.053 | 31.770 | 91.165 | 1.00 | 26.24 | 0 |
| ATOM | 3137 | O | ASN | 533 | 49.918 | 30.615 | 90.747 | 1.00 | 41.80 | 0 |
| ATOM | 3138 | N | GLU | 534 | 49.253 | 32.777 | 90.815 | 1.00 | 24.76 | 0 |
| ATOM | 3140 | CA | GLU | 534 | 48.146 | 32.592 | 89.893 | 1.00 | 19.83 | 0 |
| ATOM | 3141 | CB | GLU | 534 | 47.228 | 33.801 | 89.916 | 1.00 | 17.15 | 0 |
| ATOM | 3142 | CG | GLU | 534 | 46.509 | 33.924 | 91.239 | 1.00 | 23.75 | 0 |
| ATOM | 3143 | CD | GLU | 534 | 45.598 | 35.132 | 91.321 | 1.00 | 25.22 | 0 |
| ATOM | 3144 | OE1 | GLU | 534 | 44.490 | 34.997 | 91.890 | 1.00 | 24.06 | 0 |
| ATOM | 3145 | OE2 | GLU | 534 | 45.991 | 36.215 | 90.822 | 1.00 | 29.17 | 0 |
| ATOM | 3146 | C | GLU | 534 | 48.712 | 32.365 | 88.510 | 1.00 | 21.16 | 0 |
| ATOM | 3147 | O | GLU | 534 | 48.235 | 31.500 | 87.779 | 1.00 | 14.12 | 0 |
| ATOM | 3148 | N | ILE | 535 | 49.747 | 33.122 | 88.156 | 1.00 | 2.00 | 0 |
| ATOM | 3150 | CA | ILE | 535 | 50.389 | 32.942 | 86.859 | 1.00 | 2.00 | 0 |
| ATOM | 3151 | CB | ILE | 535 | 51.442 | 34.023 | 86.570 | 1.00 | 2.00 | 0 |
| ATOM | 3152 | CG2 | ILE | 535 | 52.050 | 33.784 | 85.190 | 1.00 | 2.00 | 0 |
| ATOM | 3153 | CG1 | ILE | 535 | 50.793 | 35.411 | 86.641 | 1.00 | 2.00 | 0 |
| ATOM | 3154 | CD1 | ILE | 535 | 51.537 | 36.488 | 85.849 | 1.00 | 2.00 | 0 |
| ATOM | 3155 | C | ILE | 535 | 51.060 | 31.565 | 86.797 | 1.00 | 2.00 | 0 |
| ATOM | 3156 | O | ILE | 535 | 50.788 | 30.780 | 85.876 | 1.00 | 2.00 | 0 |
| ATOM | 3157 | N | ARG | 536 | 51.914 | 31.256 | 87.778 | 1.00 | 2.00 | 0 |
| ATOM | 3159 | CA | ARG | 536 | 52.583 | 29.951 | 87.793 | 1.00 | 2.00 | 0 |
| ATOM | 3160 | CB | ARG | 536 | 53.495 | 29.818 | 89.011 | 1.00 | 39.13 | 0 |
| ATOM | 3161 | CG | ARG | 536 | 52.808 | 29.604 | 90.341 | 1.00 | 45.43 | 0 |
| ATOM | 3162 | CD | ARG | 536 | 53.839 | 29.648 | 91.474 | 1.00 | 49.26 | 0 |
| ATOM | 3163 | NE | ARG | 536 | 55.059 | 28.910 | 91.132 | 1.00 | 56.04 | 0 |
| ATOM | 3165 | CZ | ARG | 536 | 55.110 | 27.603 | 90.876 | 1.00 | 55.24 | 0 |
| ATOM | 3166 | NH1 | ARG | 536 | 54.011 | 26.860 | 90.920 | 1.00 | 53.92 | 0 |
| ATOM | 3169 | NH2 | ARG | 536 | 56.267 | 27.032 | 90.576 | 1.00 | 44.45 | 0 |
| ATOM | 3172 | C | ARG | 536 | 51.562 | 28.811 | 87.742 | 1.00 | 2.00 | 0 |
| ATOM | 3173 | O | ARG | 536 | 51.806 | 27.778 | 87.126 | 1.00 | 37.01 | 0 |
| ATOM | 3174 | N | GLY | 537 | 50.406 | 29.033 | 88.363 | 1.00 | 2.00 | 0 |
| ATOM | 3176 | CA | GLY | 537 | 49.345 | 28.046 | 88.340 | 1.00 | 2.00 | 0 |

TABLE A-continued

| ATOM | 3177 | C | GLY | 537 | 48.690 | 28.000 | 86.970 | 1.00 | 2.00 | 0 |
|---|---|---|---|---|---|---|---|---|---|---|
| ATOM | 3178 | O | GLY | 537 | 48.292 | 26.924 | 86.512 | 1.00 | 2.00 | 0 |
| ATOM | 3179 | N | LEU | 538 | 48.574 | 29.164 | 86.319 | 1.00 | 9.51 | 0 |
| ATOM | 3181 | CA | LEU | 538 | 47.979 | 29.276 | 84.977 | 1.00 | 7.63 | 0 |
| ATOM | 3182 | CB | LEU | 538 | 47.930 | 30.736 | 84.513 | 1.00 | 2.00 | 0 |
| ATOM | 3183 | CG | LEU | 538 | 46.654 | 31.524 | 84.772 | 1.00 | 2.00 | 0 |
| ATOM | 3184 | CD1 | LEU | 538 | 46.865 | 32.966 | 84.408 | 1.00 | 2.00 | 0 |
| ATOM | 3185 | CD2 | LEU | 538 | 45.531 | 30.940 | 83.972 | 1.00 | 2.00 | 0 |
| ATOM | 3186 | C | LEU | 538 | 48.816 | 28.472 | 84.000 | 1.00 | 12.73 | 0 |
| ATOM | 3187 | O | LEU | 538 | 48.295 | 27.635 | 83.271 | 1.00 | 2.00 | 0 |
| ATOM | 3188 | N | CYS | 539 | 50.120 | 28.724 | 84.000 | 1.00 | 2.00 | 0 |
| ATOM | 3190 | CA | CYS | 539 | 51.036 | 28.001 | 83.132 | 1.00 | 2.00 | 0 |
| ATOM | 3191 | CB | CYS | 539 | 52.473 | 28.494 | 83.337 | 1.00 | 20.52 | 0 |
| ATOM | 3192 | SC | CYS | 539 | 52.713 | 30.280 | 83.567 | 1.00 | 19.48 | 0 |
| ATOM | 3193 | C | CYS | 539 | 50.957 | 26.501 | 83.474 | 1.00 | 2.00 | 0 |
| ATOM | 3194 | O | CYS | 539 | 50.854 | 25.658 | 82.588 | 1.00 | 29.69 | 0 |
| ATOM | 3195 | N | LEU | 540 | 50.984 | 26.191 | 84.769 | 1.00 | 26.60 | 0 |
| ATOM | 3197 | CA | LEU | 540 | 50.919 | 24.819 | 85.265 | 1.00 | 26.60 | 0 |
| ATOM | 3198 | CB | LEU | 540 | 51.106 | 24.818 | 86.786 | 1.00 | 2.00 | 0 |
| ATOM | 3199 | CG | LEU | 540 | 52.539 | 24.770 | 87.339 | 1.00 | 2.00 | 0 |
| ATOM | 3200 | CD1 | LEU | 540 | 53.001 | 23.360 | 87.385 | 1.00 | 2.00 | 0 |
| ATOM | 3201 | CD2 | LEU | 540 | 53.492 | 25.577 | 86.497 | 1.00 | 2.00 | 0 |
| ATOM | 3202 | C | LEU | 540 | 49.635 | 24.061 | 84.899 | 1.00 | 26.60 | 0 |
| ATOM | 3203 | O | LEU | 540 | 49.677 | 22.856 | 84.619 | 1.00 | 2.00 | 0 |
| ATOM | 3204 | N | LYS | 541 | 48.500 | 24.756 | 84.901 | 1.00 | 13.81 | 0 |
| ATOM | 3206 | CA | LYS | 541 | 47.219 | 24.126 | 84.561 | 1.00 | 17.46 | 0 |
| ATOM | 3207 | CB | LYS | 541 | 46.046 | 24.964 | 65.108 | 1.00 | 14.61 | 0 |
| ATOM | 3208 | CG | LYS | 541 | 45.844 | 24.880 | 86.624 | 1.00 | 22.53 | 0 |
| ATOM | 3209 | CD | LYS | 541 | 44.709 | 25.777 | 87.150 | 1.00 | 31.64 | 0 |
| ATOM | 3210 | CE | LYS | 541 | 45.175 | 27.201 | 87.517 | 1.00 | 37.15 | 0 |
| ATOM | 3211 | NZ | LYS | 541 | 44.147 | 28.010 | 88.284 | 1.00 | 27.95 | 0 |
| ATOM | 3215 | C | LYS | 541 | 47.047 | 23.891 | 83.046 | 1.00 | 16.97 | 0 |
| ATOM | 3216 | O | LYS | 541 | 46.862 | 22.745 | 82.608 | 1.00 | 8.92 | 0 |
| ATOM | 3217 | N | SER | 542 | 47.131 | 24.963 | 82.253 | 1.00 | 2.00 | 0 |
| ATOM | 3219 | CA | SER | 542 | 46.975 | 24.877 | 80.791 | 1.00 | 2.00 | 0 |
| ATOM | 3220 | CB | SER | 542 | 47.165 | 26.256 | 80.150 | 1.00 | 2.00 | 0 |
| ATOM | 3221 | OG | SER | 542 | 48.499 | 26.703 | 80.298 | 1.00 | 2.00 | 0 |
| ATOM | 3223 | C | SER | 542 | 47.915 | 23.870 | 80.107 | 1.00 | 2.00 | 0 |
| ATOM | 3224 | O | SER | 542 | 47.450 | 22.991 | 79.377 | 1.00 | 2.00 | 0 |
| ATOM | 3225 | N | ARG | 543 | 49.223 | 24.016 | 80.338 | 1.00 | 8.64 | 0 |
| ATOM | 3227 | CA | ARG | 543 | 50.244 | 23.128 | 79.772 | 1.00 | 8.64 | 0 |
| ATOM | 3228 | CB | ARG | 543 | 51.607 | 23.381 | 80.434 | 1.00 | 2.00 | 0 |
| ATOM | 3229 | CG | ARG | 543 | 52.676 | 22.339 | 80.116 | 1.00 | 4.46 | 0 |
| ATOM | 3230 | CD | ARG | 543 | 53.757 | 22.313 | 81.173 | 1.00 | 2.00 | 0 |
| ATOM | 3231 | NE | ARG | 543 | 54.989 | 21.663 | 80.708 | 1.00 | 2.00 | 0 |
| ATOM | 3233 | CZ | ARG | 543 | 55.326 | 20.395 | 80.952 | 1.00 | 2.00 | 0 |
| ATOM | 3234 | NH1 | ARG | 543 | 54.523 | 19.606 | 81.656 | 1.00 | 3.99 | 0 |
| ATOM | 3237 | NH2 | ARG | 543 | 56.483 | 19.915 | 80.508 | 1.00 | 2.00 | 0 |
| ATOM | 3240 | C | ARG | 543 | 49.873 | 21.660 | 79.981 | 1.00 | 8.64 | 0 |
| ATOM | 3241 | O | ARG | 543 | 50.187 | 20.806 | 79.146 | 1.00 | 5.52 | 0 |
| ATOM | 3242 | N | GLU | 544 | 49.227 | 21.352 | 81.098 | 1.00 | 42.94 | 0 |
| ATOM | 3244 | CA | GLU | 544 | 48.834 | 19.978 | 81.355 | 1.00 | 44.22 | 0 |
| ATOM | 3245 | CB | GLU | 544 | 48.308 | 19.841 | 82.778 | 1.00 | 37.01 | 0 |
| ATOM | 3246 | CG | GLU | 544 | 48.175 | 18.415 | 83.249 | 1.00 | 41.48 | 0 |
| ATOM | 3247 | CD | GLU | 544 | 47.561 | 18.341 | 84.626 | 1.00 | 46.37 | 0 |
| ATOM | 3248 | OE1 | GLU | 544 | 46.433 | 18.858 | 84.791 | 1.00 | 53.09 | 0 |
| ATOM | 3249 | OE2 | GLU | 544 | 48.202 | 17.777 | 85.543 | 1.00 | 47.19 | 0 |
| ATOM | 3250 | C | GLU | 544 | 47.763 | 19.584 | 80.339 | 1.00 | 40.49 | 0 |
| ATOM | 3251 | O | GLU | 544 | 47.742 | 18.450 | 79.867 | 1.00 | 34.80 | 0 |
| ATOM | 3252 | N | ILE | 545 | 46.898 | 20.538 | 79.994 | 1.00 | 2.00 | 0 |
| ATOM | 3254 | CA | ILE | 545 | 45.823 | 20.315 | 79.017 | 1.00 | 2.00 | 0 |
| ATOM | 3255 | CB | ILE | 545 | 44.805 | 21.487 | 78.959 | 1.00 | 11.87 | 0 |
| ATOM | 3256 | CG2 | ILE | 545 | 43.645 | 21.102 | 78.064 | 1.00 | 6.53 | 0 |
| ATOM | 3257 | CG1 | ILE | 545 | 44.288 | 21.836 | 80.353 | 1.00 | 16.65 | 0 |
| ATOM | 3258 | CD1 | ILE | 545 | 43.267 | 22.955 | 80.361 | 1.00 | 13.01 | 0 |
| ATOM | 3259 | C | ILE | 545 | 46.377 | 20.149 | 77.605 | 1.00 | 2.00 | 0 |
| ATOM | 3260 | O | ILE | 545 | 45.960 | 19.267 | 76.868 | 1.00 | 9.05 | 0 |
| ATOM | 3261 | N | PHE | 546 | 47.302 | 21.018 | 77.227 | 1.00 | 2.00 | 0 |
| ATOM | 3263 | CA | PHE | 546 | 47.895 | 20.945 | 75.918 | 1.00 | 2.00 | 0 |
| ATOM | 3264 | CB | PHE | 546 | 49.058 | 21.906 | 75.816 | 1.00 | 2.00 | 0 |
| ATOM | 3265 | CG | PHE | 546 | 48.653 | 23.335 | 75.875 | 1.00 | 2.00 | 0 |
| ATOM | 3266 | CD1 | PHE | 546 | 49.512 | 24.293 | 76.399 | 1.00 | 2.00 | 0 |
| ATOM | 3267 | CD2 | PHE | 546 | 47.411 | 23.730 | 75.426 | 1.00 | 2.00 | 0 |
| ATOM | 3268 | CE1 | PHE | 546 | 49.127 | 25.630 | 76.473 | 1.00 | 2.00 | 0 |
| ATOM | 3269 | CE2 | PHE | 546 | 47.023 | 25.050 | 75.496 | 1.00 | 2.00 | 0 |
| ATOM | 3270 | CZ | PHE | 546 | 47.881 | 26.006 | 76.020 | 1.00 | 2.00 | 0 |
| ATOM | 3271 | C | PHE | 546 | 48.374 | 19.538 | 75.658 | 1.00 | 2.00 | 0 |
| ATOM | 3272 | O | PHE | 546 | 48.141 | 18.990 | 74.596 | 1.00 | 2.00 | 0 |
| ATOM | 3273 | N | LEU | 547 | 49.012 | 18.935 | 76.647 | 1.00 | 2.00 | 0 |

TABLE A-continued

| ATOM | 3275 | CA | LEU | 547 | 49.527 | 17.582 | 76.506 | 1.00 | 2.00 | 0 |
| --- | --- | --- | --- | --- | --- | --- | --- | --- | --- | --- |
| ATOM | 3276 | CB | LEU | 547 | 50.499 | 17.289 | 77.654 | 1.00 | 6.91 | 0 |
| ATOM | 3277 | CG | LEU | 547 | 51.754 | 18.159 | 77.582 | 1.00 | 8.40 | 0 |
| ATOM | 3278 | CD1 | LEU | 547 | 52.096 | 18.701 | 78.934 | 1.00 | 16.17 | 0 |
| ATOM | 3279 | CD2 | LEU | 547 | 52.905 | 17.363 | 77.029 | 1.00 | 11.72 | 0 |
| ATOM | 3280 | C | LEU | 547 | 48.422 | 16.526 | 76.434 | 1.00 | 2.00 | 0 |
| ATOM | 3281 | O | LEU | 547 | 48.642 | 15.414 | 75.946 | 1.00 | 6.91 | 0 |
| ATOM | 3282 | N | SER | 548 | 47.230 | 16.881 | 76.903 | 1.00 | 5.34 | 0 |
| ATOM | 3284 | CA | SER | 548 | 46.091 | 15.964 | 76.898 | 1.00 | 5.34 | 0 |
| ATOM | 3285 | CB | SER | 548 | 45.099 | 16.356 | 77.993 | 1.00 | 36.19 | 0 |
| ATOM | 3286 | OG | SER | 548 | 45.611 | 17.389 | 78.821 | 1.00 | 39.64 | 0 |
| ATOM | 3288 | C | SER | 548 | 45.374 | 15.975 | 75.552 | 1.00 | 5.34 | 0 |
| ATOM | 3289 | O | SER | 548 | 44.299 | 15.381 | 75.406 | 1.00 | 36.66 | 0 |
| ATOM | 3290 | N | GLN | 549 | 45.968 | 16.649 | 74.569 | 1.00 | 23.79 | 0 |
| ATOM | 3292 | CA | GLN | 549 | 45.384 | 16.754 | 73.242 | 1.00 | 23.94 | 0 |
| ATOM | 3293 | CB | GLN | 549 | 44.751 | 18.128 | 73.084 | 1.00 | 46.80 | 0 |
| ATOM | 3294 | CG | GLN | 549 | 43.567 | 18.354 | 73.990 | 1.00 | 38.43 | 0 |
| ATOM | 3295 | CD | GLN | 549 | 43.180 | 19.800 | 74.054 | 1.00 | 38.53 | 0 |
| ATOM | 3296 | OE1 | GLN | 549 | 43.934 | 20.672 | 73.624 | 1.00 | 46.42 | 0 |
| ATOM | 3297 | NE2 | GLN | 549 | 42.002 | 20.074 | 74.595 | 1.00 | 39.54 | 0 |
| ATOM | 3300 | C | GLN | 549 | 46.456 | 16.547 | 72.182 | 1.00 | 25.87 | 0 |
| ATOM | 3301 | O | GLN | 549 | 47.634 | 16.766 | 72.451 | 1.00 | 42.01 | 0 |
| ATOM | 3302 | N | PRO | 550 | 46.068 | 16.105 | 70.963 | 1.00 | 2.00 | 0 |
| ATOM | 3303 | CD | PRO | 550 | 44.729 | 15.738 | 70.469 | 1.00 | 36.68 | 0 |
| ATOM | 3304 | CA | PRO | 550 | 47.075 | 15.894 | 69.921 | 1.00 | 2.00 | 0 |
| ATOM | 3305 | CB | PRO | 550 | 46.253 | 15.350 | 68.750 | 1.00 | 36.68 | 0 |
| ATOM | 3306 | CG | PRO | 550 | 44.886 | 15.915 | 68.988 | 1.00 | 36.68 | 0 |
| ATOM | 3307 | C | PRO | 550 | 47.816 | 17.184 | 69.580 | 1.00 | 2.00 | 0 |
| ATOM | 3308 | O | PRO | 550 | 47.318 | 18.280 | 69.840 | 1.00 | 36.68 | 0 |
| ATOM | 3309 | N | ILE | 551 | 49.013 | 17.046 | 69.015 | 1.00 | 2.00 | 0 |
| ATOM | 3311 | CA | ILE | 551 | 49.824 | 18.198 | 68.626 | 1.00 | 2.00 | 0 |
| ATOM | 3312 | CB | ILE | 551 | 51.293 | 17.788 | 68.510 | 1.00 | 2.00 | 0 |
| ATOM | 3313 | CG2 | ILE | 551 | 51.490 | 16.914 | 67.292 | 1.00 | 2.00 | 0 |
| ATOM | 3314 | CG1 | ILE | 551 | 52.182 | 19.021 | 68.475 | 1.00 | 2.00 | 0 |
| ATOM | 3315 | CD1 | ILE | 551 | 53.648 | 18.701 | 68.468 | 1.00 | 2.00 | 0 |
| ATOM | 3316 | C | ILE | 551 | 49.295 | 18.705 | 67.281 | 1.00 | 2.00 | 0 |
| ATOM | 3317 | O | ILE | 551 | 49.596 | 19.807 | 66.840 | 1.00 | 2.00 | 0 |
| ATOM | 3318 | N | LEU | 552 | 48.514 | 17.863 | 66.627 | 1.00 | 2.00 | 0 |
| ATOM | 3320 | CA | LEU | 552 | 47.896 | 18.202 | 65.369 | 1.00 | 2.00 | 0 |
| ATOM | 3321 | CB | LEU | 552 | 48.287 | 17.148 | 64.320 | 1.00 | 2.00 | 0 |
| ATOM | 3322 | CG | LEU | 552 | 47.809 | 17.215 | 62.867 | 1.00 | 2.00 | 0 |
| ATOM | 3323 | CD1 | LEU | 552 | 48.082 | 15.532 | 62.209 | 1.00 | 2.00 | 0 |
| ATOM | 3324 | CD2 | LEU | 552 | 48.544 | 16.174 | 62.131 | 1.00 | 2.00 | 0 |
| ATOM | 3325 | C | LEU | 552 | 46.397 | 18.180 | 65.728 | 1.00 | 2.00 | 0 |
| ATOM | 3326 | O | LEU | 552 | 45.753 | 17.124 | 65.734 | 1.00 | 2.00 | 0 |
| ATOM | 3327 | N | LEU | 553 | 45.881 | 19.352 | 66.100 | 1.00 | 20.15 | 0 |
| ATOM | 3329 | CA | LEU | 553 | 44.485 | 19.512 | 66.517 | 1.00 | 20.15 | 0 |
| ATOM | 3330 | CB | LEU | 553 | 44.240 | 20.926 | 67.055 | 1.00 | 2.00 | 0 |
| ATOM | 3331 | CG | LEU | 553 | 44.374 | 21.262 | 68.543 | 1.00 | 2.00 | 0 |
| ATOM | 3332 | CD1 | LEU | 553 | 45.224 | 20.282 | 69.290 | 1.00 | 2.00 | 0 |
| ATOM | 3333 | CD2 | LEU | 553 | 44.942 | 22.639 | 68.638 | 1.00 | 2.00 | 0 |
| ATOM | 3334 | C | LEU | 553 | 43.495 | 19.229 | 65.410 | 1.00 | 20.15 | 0 |
| ATOM | 3335 | O | LEU | 553 | 43.604 | 19.780 | 64.309 | 1.00 | 2.00 | 0 |
| ATOM | 3336 | N | GLU | 554 | 42.524 | 18.375 | 65.724 | 1.00 | 14.62 | 0 |
| ATOM | 3338 | CA | GLU | 554 | 41.476 | 17.983 | 64.786 | 1.00 | 13.80 | 0 |
| ATOM | 3339 | CB | GLU | 554 | 41.135 | 16.492 | 64.956 | 1.00 | 57.31 | 0 |
| ATOM | 3340 | CG | GLU | 554 | 42.326 | 15.550 | 65.177 | 1.00 | 69.83 | 0 |
| ATOM | 3341 | CD | GLU | 554 | 43.168 | 15.310 | 63.927 | 1.00 | 73.58 | 0 |
| ATOM | 3342 | OE1 | GLU | 554 | 42.918 | 15.957 | 62.887 | 1.00 | 82.45 | 0 |
| ATOM | 3343 | OE2 | GLU | 554 | 44.090 | 14.465 | 63.988 | 1.00 | 79.54 | 0 |
| ATOM | 3344 | C | GLU | 554 | 40.241 | 18.823 | 65.105 | 1.00 | 12.33 | 0 |
| ATOM | 3345 | O | GLU | 554 | 39.253 | 18.311 | 65.638 | 1.00 | 51.99 | 0 |
| ATOM | 3346 | N | LEU | 555 | 40.296 | 20.112 | 64.792 | 1.00 | 2.00 | 0 |
| ATOM | 3348 | CA | LEU | 555 | 39.176 | 21.007 | 65.077 | 1.00 | 2.00 | 0 |
| ATOM | 3349 | CB | LEU | 555 | 39.628 | 22.456 | 64.911 | 1.00 | 2.00 | 0 |
| ATOM | 3350 | CG | LEU | 555 | 40.660 | 22.840 | 65.972 | 1.00 | 2.00 | 0 |
| ATOM | 3351 | CD1 | LEU | 555 | 41.274 | 24.194 | 65.697 | 1.00 | 2.00 | 0 |
| ATOM | 3352 | CD2 | LEU | 555 | 39.959 | 22.839 | 67.294 | 1.00 | 2.00 | 0 |
| ATOM | 3353 | C | LEU | 555 | 37.932 | 20.734 | 64.237 | 1.00 | 2.00 | 0 |
| ATOM | 3354 | O | LEU | 555 | 37.862 | 19.731 | 63.537 | 1.00 | 2.00 | 0 |
| ATOM | 3355 | N | GLU | 556 | 36.933 | 21.603 | 64.345 | 1.00 | 2.00 | 0 |
| ATOM | 3357 | CA | GLU | 556 | 35.716 | 21.460 | 63.569 | 1.00 | 2.00 | 0 |
| ATOM | 3358 | CB | GLU | 556 | 35.028 | 20.115 | 63.846 | 1.00 | 32.90 | 0 |
| ATOM | 3359 | CG | GLU | 556 | 34.175 | 20.063 | 65.100 | 1.00 | 48.42 | 0 |
| ATOM | 3360 | CD | GLU | 556 | 32.935 | 19.176 | 64.941 | 1.00 | 58.49 | 0 |
| ATOM | 3361 | OE1 | GLU | 556 | 32.792 | 18.188 | 65.711 | 1.00 | 60.59 | 0 |
| ATOM | 3362 | OE2 | GLU | 556 | 32.101 | 19.477 | 64.047 | 1.00 | 59.64 | 0 |
| ATOM | 3363 | C | GLU | 556 | 34.736 | 22.583 | 63.826 | 1.00 | 2.00 | 0 |
| ATOM | 3364 | O | GLU | 556 | 35.067 | 23.580 | 64.446 | 1.00 | 16.83 | 0 |

TABLE A-continued

| | | | | | | | | | | |
|---|---|---|---|---|---|---|---|---|---|---|
| ATOM | 3365 | N | ALA | 557 | 33.544 | 22.423 | 63.257 | 1.00 | 2.00 | 0 |
| ATOM | 3367 | CA | ALA | 557 | 32.398 | 23.330 | 63.427 | 1.00 | 2.00 | 0 |
| ATOM | 3368 | CB | ALA | 557 | 31.747 | 23.013 | 64.788 | 1.00 | 47.62 | 0 |
| ATOM | 3369 | C | ALA | 557 | 32.701 | 24.826 | 63.286 | 1.00 | 2.00 | 0 |
| ATOM | 3370 | O | ALA | 557 | 33.711 | 25.191 | 62.671 | 1.00 | 40.85 | 0 |
| ATOM | 3371 | N | PRO | 558 | 31.811 | 25.711 | 63.802 | 1.00 | 2.00 | 0 |
| ATOM | 3372 | CD | PRO | 558 | 30.459 | 25.558 | 64.353 | 1.00 | 2.44 | 0 |
| ATOM | 3373 | CA | PRO | 558 | 32.123 | 27.139 | 63.658 | 1.00 | 2.00 | 0 |
| ATOM | 3374 | CB | PRO | 558 | 30.786 | 27.826 | 63.951 | 1.00 | 2.53 | 0 |
| ATOM | 3375 | CG | PRO | 558 | 29.798 | 26.759 | 63.843 | 1.00 | 2.44 | 0 |
| ATOM | 3376 | C | PRO | 558 | 33.190 | 27.648 | 64.627 | 1.00 | 2.00 | 0 |
| ATOM | 3377 | O | PRO | 558 | 32.975 | 27.616 | 65.844 | 1.00 | 7.53 | 0 |
| ATOM | 3378 | N | LEU | 559 | 34.325 | 28.119 | 64.112 | 1.00 | 2.00 | 0 |
| ATOM | 3380 | CA | LEU | 559 | 35.349 | 28.689 | 64.982 | 1.00 | 2.00 | 0 |
| ATOM | 3381 | CB | LEU | 559 | 36.568 | 27.769 | 65.148 | 1.00 | 2.00 | 0 |
| ATOM | 3382 | CG | LEU | 559 | 37.592 | 27.571 | 64.050 | 1.00 | 2.00 | 0 |
| ATOM | 3383 | CD1 | LEU | 559 | 38.620 | 26.563 | 64.476 | 1.00 | 2.00 | 0 |
| ATOM | 3384 | CD2 | LEU | 559 | 36.885 | 27.083 | 62.830 | 1.00 | 2.00 | 0 |
| ATOM | 3385 | C | LEU | 559 | 35.769 | 30.038 | 64.435 | 1.00 | 2.00 | 0 |
| ATOM | 3386 | O | LEU | 559 | 35.444 | 30.389 | 63.311 | 1.00 | 2.00 | 0 |
| ATOM | 3387 | N | LYS | 560 | 36.461 | 30.804 | 65.260 | 1.00 | 2.00 | 0 |
| ATOM | 3389 | CA | LYS | 560 | 36.932 | 32.115 | 64.889 | 1.00 | 2.00 | 0 |
| ATOM | 3390 | CB | LYS | 560 | 36.359 | 33.143 | 65.843 | 1.00 | 20.44 | 0 |
| ATOM | 3391 | CG | LYS | 560 | 36.612 | 34.562 | 65.427 | 1.00 | 20.44 | 0 |
| ATOM | 3392 | CD | LYS | 560 | 35.574 | 35.512 | 66.018 | 1.00 | 20.44 | 0 |
| ATOM | 3393 | CE | LYS | 560 | 34.253 | 35.452 | 65.275 | 1.00 | 20.44 | 0 |
| ATOM | 3394 | NZ | LYS | 560 | 33.706 | 34.083 | 65.225 | 1.00 | 20.44 | 0 |
| ATOM | 3398 | C | LYS | 560 | 38.426 | 31.990 | 65.052 | 1.00 | 2.00 | 0 |
| ATOM | 3399 | O | LYS | 560 | 38.908 | 31.624 | 66.117 | 1.00 | 20.44 | 0 |
| ATOM | 3400 | N | ILE | 561 | 39.164 | 32.244 | 63.986 | 1.00 | 2.00 | 0 |
| ATOM | 3402 | CA | ILE | 561 | 40.606 | 32.106 | 64.017 | 1.00 | 2.00 | 0 |
| ATOM | 3403 | CB | ILE | 561 | 41.095 | 31.318 | 62.750 | 1.00 | 2.00 | 0 |
| ATOM | 3404 | CG2 | ILE | 561 | 42.566 | 30.913 | 62.891 | 1.00 | 2.00 | 0 |
| ATOM | 3405 | CG1 | ILE | 561 | 40.204 | 30.076 | 62.558 | 1.00 | 2.00 | 0 |
| ATOM | 3406 | CD1 | ILE | 561 | 40.806 | 28.940 | 61.761 | 1.00 | 2.00 | 0 |
| ATOM | 3407 | C | ILE | 561 | 41.247 | 33.488 | 64.102 | 1.00 | 2.00 | 0 |
| ATOM | 3408 | O | ILE | 561 | 40.703 | 34.450 | 63.543 | 1.00 | 2.00 | 0 |
| ATOM | 3409 | N | CYS | 562 | 42.365 | 33.586 | 64.833 | 1.00 | 2.00 | 0 |
| ATOM | 3411 | CA | CYS | 562 | 43.124 | 34.829 | 65.001 | 1.00 | 2.00 | 0 |
| ATOM | 3412 | CB | CYS | 562 | 42.793 | 35.464 | 66.339 | 1.00 | 13.31 | 0 |
| ATOM | 3413 | SG | CYS | 562 | 41.073 | 35.733 | 66.574 | 1.00 | 13.31 | 0 |
| ATOM | 3414 | C | CYS | 562 | 44.642 | 34.599 | 64.928 | 1.00 | 2.00 | 0 |
| ATOM | 3415 | O | CYS | 562 | 45.151 | 33.551 | 65.373 | 1.00 | 13.31 | 0 |
| ATOM | 3416 | N | GLY | 563 | 45.362 | 35.540 | 64.348 | 1.00 | 2.00 | 0 |
| ATOM | 3418 | CA | GLY | 563 | 46.805 | 35.424 | 64.252 | 1.00 | 2.00 | 0 |
| ATOM | 3419 | C | GLY | 563 | 47.546 | 36.260 | 65.291 | 1.00 | 2.00 | 0 |
| ATOM | 3420 | O | GLY | 563 | 46.997 | 36.556 | 66.351 | 1.00 | 5.66 | 0 |
| ATOM | 3421 | N | ASP | 564 | 48.780 | 36.649 | 64.958 | 1.00 | 2.00 | 0 |
| ATOM | 3423 | CA | ASP | 564 | 49.657 | 37.452 | 65.811 | 1.00 | 2.00 | 0 |
| ATOM | 3424 | CB | ASP | 564 | 50.705 | 38.191 | 64.964 | 1.00 | 2.00 | 0 |
| ATOM | 3425 | CG | ASP | 564 | 51.724 | 37.270 | 64.321 | 1.00 | 2.00 | 0 |
| ATOM | 3426 | OD1 | ASP | 564 | 51.390 | 36.565 | 63.334 | 1.00 | 2.00 | 0 |
| ATOM | 3427 | OD2 | ASP | 564 | 52.876 | 37.249 | 64.786 | 1.00 | 2.00 | 0 |
| ATOM | 3428 | C | ASP | 564 | 48.981 | 38.497 | 66.693 | 1.00 | 2.00 | 0 |
| ATOM | 3429 | O | ASP | 564 | 48.395 | 39.442 | 66.189 | 1.00 | 2.00 | 0 |
| ATOM | 3430 | N | ILE | 565 | 49.094 | 38.327 | 68.009 | 1.00 | 31.53 | 0 |
| ATOM | 3432 | CA | ILE | 565 | 48.537 | 39.294 | 68.953 | 1.00 | 35.54 | 0 |
| ATOM | 3433 | CB | ILE | 565 | 47.810 | 38.612 | 70.135 | 1.00 | 9.39 | 0 |
| ATOM | 3434 | CG2 | ILE | 565 | 47.139 | 39.664 | 70.996 | 1.00 | 9.39 | 0 |
| ATOM | 3435 | CG1 | ILE | 565 | 46.710 | 37.685 | 69.622 | 1.00 | 9.39 | 0 |
| ATOM | 3436 | CD1 | ILE | 565 | 45.611 | 38.424 | 68.906 | 1.00 | 9.39 | 0 |
| ATOM | 3437 | C | ILE | 565 | 49.681 | 40.168 | 69.489 | 1.00 | 32.16 | 0 |
| ATOM | 3438 | O | ILE | 565 | 49.491 | 41.356 | 69.756 | 1.00 | 9.39 | 0 |
| ATOM | 3439 | N | HIS | 566 | 50.659 | 39.560 | 69.637 | 1.00 | 14.33 | 0 |
| ATOM | 3441 | CA | HIS | 566 | 52.082 | 40.219 | 70.111 | 1.00 | 15.67 | 0 |
| ATOM | 3442 | C | HIS | 566 | 51.958 | 41.227 | 71.245 | 1.00 | 16.54 | 0 |
| ATOM | 3443 | O | HIS | 566 | 52.427 | 42.359 | 71.127 | 1.00 | 15.89 | 0 |
| ATOM | 3444 | CB | HIS | 566 | 52.811 | 40.882 | 68.943 | 1.00 | 9.53 | 0 |
| ATOM | 3445 | CG | HIS | 566 | 53.652 | 39.936 | 68.153 | 1.00 | 9.53 | 0 |
| ATOM | 3446 | ND1 | HIS | 566 | 54.829 | 39.391 | 68.605 | 1.00 | 9.53 | 0 |
| ATOM | 3448 | CD2 | HIS | 566 | 53.470 | 39.432 | 66.910 | 1.00 | 9.53 | 0 |
| ATOM | 3449 | NE2 | HIS | 566 | 54.525 | 38.582 | 66.589 | 1.00 | 9.53 | 0 |
| ATOM | 3450 | CE1 | HIS | 566 | 55.312 | 38.600 | 67.652 | 1.00 | 9.53 | 0 |
| ATOM | 3451 | N | GLY | 567 | 51.337 | 40.808 | 72.345 | 1.00 | 2.00 | 0 |
| ATOM | 3453 | CA | GLY | 567 | 51.170 | 41.686 | 73.490 | 1.00 | 2.00 | 0 |
| ATOM | 3454 | C | GLY | 567 | 50.249 | 42.894 | 73.375 | 1.00 | 2.00 | 0 |
| ATOM | 3455 | O | GLY | 567 | 50.269 | 43.764 | 74.254 | 1.00 | 3.59 | 0 |
| ATOM | 3456 | N | GLN | 568 | 49.455 | 42.973 | 72.314 | 1.00 | 36.66 | 0 |
| ATOM | 3458 | CA | GLN | 568 | 48.527 | 44.086 | 72.141 | 1.00 | 34.60 | 0 |

TABLE A-continued

| ATOM | 3459 | CB | GLN | 568 | 48.164 | 44.236 | 70.667 | 1.00 | 2.50 | 0 |
|---|---|---|---|---|---|---|---|---|---|---|
| ATOM | 3460 | CG | GLN | 568 | 49.345 | 44.164 | 69.715 | 1.00 | 3.37 | 0 |
| ATOM | 3461 | CD | GLN | 568 | 49.768 | 45.507 | 69.144 | 1.00 | 3.10 | 0 |
| ATOM | 3462 | OE1 | GLN | 568 | 50.958 | 45.769 | 68.974 | 1.00 | 4.87 | 0 |
| ATOM | 3463 | NE2 | GLN | 568 | 48.800 | 46.349 | 68.833 | 1.00 | 18.91 | 0 |
| ATOM | 3466 | C | GLN | 568 | 47.280 | 43.730 | 72.950 | 1.00 | 34.26 | 0 |
| ATOM | 3467 | O | GLN | 568 | 46.253 | 43.365 | 72.380 | 1.00 | 7.33 | 0 |
| ATOM | 3468 | N | TYR | 569 | 47.363 | 43.864 | 74.272 | 1.00 | 2.00 | 0 |
| ATOM | 3470 | CA | TYR | 569 | 46.263 | 43.485 | 75.161 | 1.00 | 2.00 | 0 |
| ATOM | 3471 | CB | TYR | 569 | 46.664 | 43.687 | 76.620 | 1.00 | 26.93 | 0 |
| ATOM | 3472 | CG | TYR | 569 | 45.692 | 43.048 | 77.600 | 1.00 | 27.02 | 0 |
| ATOM | 3473 | CD1 | TYR | 569 | 45.401 | 41.684 | 77.520 | 1.00 | 22.43 | 0 |
| ATOM | 3474 | CE1 | TYR | 569 | 44.496 | 41.097 | 78.393 | 1.00 | 24.12 | 0 |
| ATOM | 3475 | CD2 | TYR | 569 | 45.049 | 43.807 | 78.575 | 1.00 | 24.68 | 0 |
| ATOM | 3476 | CE2 | TYR | 569 | 44.139 | 43.223 | 79.449 | 1.00 | 24.01 | 0 |
| ATOM | 3477 | CZ | TYR | 569 | 43.866 | 41.869 | 79.352 | 1.00 | 28.35 | 0 |
| ATOM | 3478 | OH | TYR | 569 | 42.950 | 41.282 | 80.197 | 1.00 | 35.43 | 0 |
| ATOM | 3480 | C | TYR | 569 | 44.888 | 44.085 | 74.946 | 1.00 | 2.00 | 0 |
| ATOM | 3481 | O | TYR | 569 | 43.885 | 43.374 | 75.015 | 1.00 | 29.07 | 0 |
| ATOM | 3482 | N | TYR | 570 | 44.817 | 45.384 | 74.710 | 1.00 | 11.04 | 0 |
| ATOM | 3484 | CA | TYR | 570 | 43.515 | 45.999 | 74.510 | 1.00 | 14.25 | 0 |
| ATOM | 3485 | CB | TYR | 570 | 43.599 | 47.505 | 74.766 | 1.00 | 46.12 | 0 |
| ATOM | 3486 | CG | TYR | 570 | 43.577 | 47.792 | 76.261 | 1.00 | 51.43 | 0 |
| ATOM | 3487 | CD1 | TYR | 570 | 44.749 | 47.743 | 77.025 | 1.00 | 48.11 | 0 |
| ATOM | 3488 | CE1 | TYR | 570 | 44.715 | 47.952 | 78.398 | 1.00 | 52.04 | 0 |
| ATOM | 3489 | CD2 | TYR | 570 | 42.375 | 48.063 | 76.917 | 1.00 | 49.50 | 0 |
| ATOM | 3490 | CE2 | TYR | 570 | 42.340 | 48.272 | 78.277 | 1.00 | 51.48 | 0 |
| ATOM | 3491 | CZ | TYR | 570 | 43.507 | 48.215 | 79.010 | 1.00 | 53.24 | 0 |
| ATOM | 3492 | OH | TYR | 570 | 43.452 | 48.426 | 80.359 | 1.00 | 54.97 | 0 |
| ATOM | 3494 | C | TYR | 570 | 42.929 | 45.6S3 | 73.152 | 1.00 | 13.58 | 0 |
| ATOM | 3495 | O | TYR | 570 | 41.708 | 45.654 | 72.967 | 1.00 | 43.14 | 0 |
| ATOM | 3496 | N | ASP | 571 | 43.813 | 45.311 | 72.217 | 1.00 | 12.28 | 0 |
| ATOM | 3498 | CA | ASP | 571 | 43.402 | 44.903 | 70.891 | 1.00 | 11.58 | 0 |
| ATOM | 3499 | CB | ASP | 571 | 44.590 | 44.870 | 69.975 | 1.00 | 6.85 | 0 |
| ATOM | 3500 | CG | ASP | 571 | 45.128 | 46.237 | 69.733 | 1.00 | 12.88 | 0 |
| ATOM | 3501 | OD1 | ASP | 571 | 46.254 | 46.522 | 70.185 | 1.00 | 19.21 | 0 |
| ATOM | 3502 | OD2 | ASP | 571 | 44.402 | 47.044 | 69.110 | 1.00 | 16.01 | 0 |
| ATOM | 3503 | C | ASP | 571 | 42.818 | 43.539 | 71.062 | 1.00 | 14.93 | 0 |
| ATOM | 3504 | O | ASP | 571 | 41.775 | 43.247 | 70.507 | 1.00 | 19.59 | 0 |
| ATOM | 3505 | N | LEU | 572 | 43.487 | 42.707 | 71.853 | 1.00 | 2.00 | 0 |
| ATOM | 3507 | CA | LEU | 572 | 42.977 | 41.378 | 72.147 | 1.00 | 2.00 | 0 |
| ATOM | 3508 | CB | LEU | 572 | 43.909 | 40.641 | 73.110 | 1.00 | 2.00 | 0 |
| ATOM | 3509 | CG | LEU | 572 | 43.302 | 39.416 | 73.820 | 1.00 | 2.00 | 0 |
| ATOM | 3510 | CD1 | LEU | 572 | 43.061 | 38.267 | 72.832 | 1.00 | 2.00 | 0 |
| ATOM | 3511 | CD2 | LEU | 572 | 44.227 | 38.982 | 74.955 | 1.00 | 2.00 | 0 |
| ATOM | 3512 | C | LEU | 572 | 41.579 | 41.554 | 72.771 | 1.00 | 2.00 | 0 |
| ATOM | 3513 | O | LEU | 572 | 40.678 | 40.758 | 72.512 | 1.00 | 2.00 | 0 |
| ATOM | 3514 | N | LEU | 573 | 41.395 | 42.604 | 73.572 | 1.00 | 9.95 | 0 |
| ATOM | 3516 | CA | LEU | 573 | 40.092 | 42.874 | 74.195 | 1.00 | 6.25 | 0 |
| ATOM | 3517 | CB | LEU | 573 | 40.224 | 43.910 | 75.317 | 1.00 | 2.00 | 0 |
| ATOM | 3518 | CG | LEU | 573 | 40.807 | 43.360 | 76.625 | 1.00 | 2.00 | 0 |
| ATOM | 3519 | CD1 | LEU | 573 | 40.667 | 44.416 | 77.717 | 1.00 | 2.00 | 0 |
| ATOM | 3520 | CD2 | LEU | 573 | 40.079 | 42.053 | 77.033 | 1.00 | 2.00 | 0 |
| ATOM | 3521 | C | LEU | 573 | 39.055 | 43.344 | 73.170 | 1.00 | 4.08 | 0 |
| ATOM | 3522 | O | LEU | 573 | 37.865 | 42.974 | 73.260 | 1.00 | 2.00 | 0 |
| ATOM | 3523 | N | ARG | 574 | 39.518 | 44.153 | 72.203 | 1.00 | 13.12 | 0 |
| ATOM | 3525 | CA | ARG | 574 | 38.682 | 44.665 | 71.115 | 1.00 | 12.30 | 0 |
| ATOM | 3526 | CB | ARG | 574 | 39.491 | 45.598 | 70.212 | 1.00 | 30.04 | 0 |
| ATOM | 3527 | CG | ARG | 574 | 39.704 | 46.994 | 70.757 | 1.00 | 31.00 | 0 |
| ATOM | 3528 | CD | ARG | 574 | 40.697 | 47.811 | 69.915 | 1.00 | 35.07 | 0 |
| ATOM | 3529 | NE | ARG | 574 | 40.294 | 47.989 | 68.514 | 1.00 | 36.10 | 0 |
| ATOM | 3531 | CZ | ARG | 574 | 41.018 | 48.625 | 67.587 | 1.00 | 36.14 | 0 |
| ATOM | 3532 | NH1 | ARG | 574 | 42.198 | 49.162 | 67.890 | 1.00 | 35.84 | 0 |
| ATOM | 3535 | NH2 | ARG | 574 | 40.565 | 48.713 | 66.341 | 1.00 | 40.46 | 0 |
| ATOM | 3538 | C | ARG | 574 | 38.265 | 43.440 | 70.324 | 1.00 | 10.99 | 0 |
| ATOM | 3539 | O | ARG | 574 | 37.092 | 43.253 | 70.004 | 1.00 | 30.16 | 0 |
| ATOM | 3540 | N | LEU | 575 | 39.260 | 42.591 | 70.066 | 1.00 | 2.00 | 0 |
| ATOM | 3542 | CA | LEU | 575 | 39.156 | 41.339 | 69.323 | 1.00 | 2.00 | 0 |
| ATOM | 3543 | CB | LEU | 575 | 40.471 | 40.576 | 69.502 | 1.00 | 18.14 | 0 |
| ATOM | 3544 | CG | LEU | 575 | 41.058 | 39.569 | 68.514 | 1.00 | 18.14 | 0 |
| ATOM | 3545 | CD1 | LEU | 575 | 40.112 | 38.378 | 68.370 | 1.00 | 18.14 | 0 |
| ATOM | 3546 | CD2 | LEU | 575 | 41.355 | 40.249 | 67.176 | 1.00 | 18.14 | 0 |
| ATOM | 3547 | C | LEU | 575 | 37.970 | 40.494 | 69.801 | 1.00 | 2.00 | 0 |
| ATOM | 3548 | O | LEU | 575 | 37.121 | 40.081 | 69.001 | 1.00 | 18.14 | 0 |
| ATOM | 3549 | N | PHE | 576 | 37.908 | 40.247 | 71.103 | 1.00 | 29.25 | 0 |
| ATOM | 3551 | CA | PHE | 576 | 36.823 | 39.459 | 71.664 | 1.00 | 32.60 | 0 |
| ATOM | 3552 | CB | PHE | 576 | 37.115 | 39.098 | 73.119 | 1.00 | 2.00 | 0 |
| ATOM | 3553 | CG | PHE | 576 | 38.116 | 38.001 | 73.270 | 1.00 | 2.00 | 0 |
| ATOM | 3554 | CD1 | PHE | 576 | 39.158 | 36.111 | 74.184 | 1.00 | 2.00 | 0 |

TABLE A-continued

| ATOM | 3555 | CD2 | PHE | 576 | 38.022 | 36.855 | 72.491 | 1.00 | 2.00 | 0 |
| --- | --- | --- | --- | --- | --- | --- | --- | --- | --- | --- |
| ATOM | 3556 | CE1 | PHE | 576 | 40.097 | 37.098 | 74.324 | 1.00 | 2.00 | 0 |
| ATOM | 3557 | CE2 | PHE | 576 | 38.960 | 35.828 | 72.621 | 1.00 | 2.00 | 0 |
| ATOM | 3558 | CZ | PHE | 576 | 40.000 | 35.953 | 73.540 | 1.00 | 2.00 | 0 |
| ATOM | 3559 | C | PHE | 576 | 35.479 | 40.164 | 71.573 | 1.00 | 29.95 | 0 |
| ATOM | 3560 | O | PHE | 576 | 34.433 | 39.517 | 71.648 | 1.00 | 2.00 | 0 |
| ATOM | 3561 | N | GLU | 577 | 35.504 | 41.484 | 71.421 | 1.00 | 21.04 | 0 |
| ATOM | 3563 | CA | GLU | 577 | 34.273 | 42.259 | 71.307 | 1.00 | 23.59 | 0 |
| ATOM | 3564 | CB | GLU | 577 | 34.561 | 43.731 | 71.566 | 1.00 | 40.21 | 0 |
| ATOM | 3565 | CG | GLU | 577 | 35.032 | 44.001 | 72.971 | 1.00 | 50.88 | 0 |
| ATOM | 3566 | CD | GLU | 577 | 35.688 | 45.347 | 73.113 | 1.00 | 55.67 | 0 |
| ATOM | 3567 | OE1 | GLU | 577 | 36.439 | 45.522 | 74.099 | 1.00 | 60.01 | 0 |
| ATOM | 3568 | OE2 | GLU | 577 | 35.461 | 46.224 | 72.245 | 1.00 | 63.14 | 0 |
| ATOM | 3569 | C | GLU | 577 | 33.654 | 42.091 | 69.928 | 1.00 | 25.67 | 0 |
| ATOM | 3570 | O | GLU | 577 | 32.435 | 42.156 | 69.772 | 1.00 | 44.83 | 0 |
| ATOM | 3571 | N | TYR | 578 | 34.509 | 41.901 | 68.928 | 1.00 | 51.92 | 0 |
| ATOM | 3573 | CA | TYR | 578 | 34.052 | 41.700 | 67.561 | 1.00 | 48.79 | 0 |
| ATOM | 3574 | CB | TYR | 578 | 35.208 | 41.834 | 66.564 | 1.00 | 35.56 | 0 |
| ATOM | 3575 | CG | TYR | 578 | 35.703 | 43.245 | 66.356 | 1.00 | 40.25 | 0 |
| ATOM | 3576 | CD1 | TYR | 578 | 35.598 | 43.865 | 65.111 | 1.00 | 40.27 | 0 |
| ATOM | 3577 | CE1 | TYR | 578 | 36.062 | 45.168 | 64.917 | 1.00 | 44.74 | 0 |
| ATOM | 3578 | CD2 | TYR | 578 | 36.281 | 43.960 | 67.399 | 1.00 | 45.71 | 0 |
| ATOM | 3579 | CE2 | TYR | 578 | 36.747 | 45.258 | 67.217 | 1.00 | 42.53 | 0 |
| ATOM | 3580 | CZ | TYR | 578 | 36.636 | 45.853 | 65.979 | 1.00 | 49.98 | 0 |
| ATOM | 3581 | OH | TYR | 578 | 37.106 | 47.131 | 65.812 | 1.00 | 54.82 | 0 |
| ATOM | 3583 | C | TYR | 578 | 33.467 | 40.303 | 67.458 | 1.00 | 49.18 | 0 |
| ATOM | 3584 | O | TYR | 578 | 32.316 | 40.124 | 67.081 | 1.00 | 35.27 | 0 |
| ATOM | 3585 | N | GLY | 579 | 34.271 | 39.307 | 67.797 | 1.00 | 2.60 | 0 |
| ATOM | 3587 | CA | GLY | 579 | 33.787 | 37.949 | 67.713 | 1.00 | 6.22 | 0 |
| ATOM | 3588 | C | GLY | 579 | 32.737 | 37.628 | 68.755 | 1.00 | 8.52 | 0 |
| ATOM | 3589 | O | GLY | 579 | 31.555 | 37.446 | 68.437 | 1.00 | 39.88 | 0 |
| ATOM | 3590 | N | GLY | 580 | 33.194 | 37.557 | 70.006 | 1.00 | 2.00 | 0 |
| ATOM | 3592 | CA | GLY | 580 | 32.342 | 37.236 | 71.140 | 1.00 | 2.00 | 0 |
| ATOM | 3593 | C | GLY | 580 | 33.191 | 36.491 | 72.151 | 1.00 | 2.00 | 0 |
| ATOM | 3594 | O | GLY | 580 | 33.725 | 35.415 | 71.853 | 1.00 | 44.94 | 0 |
| ATOM | 3595 | N | PHE | 581 | 33.307 | 37.067 | 73.348 | 1.00 | 15.06 | 0 |
| ATOM | 3597 | CA | PHE | 581 | 34.116 | 36.500 | 74.432 | 1.00 | 12.63 | 0 |
| ATOM | 3598 | CB | PHE | 581 | 33.857 | 37.263 | 75.744 | 1.00 | 2.00 | 0 |
| ATOM | 3599 | CG | PHE | 581 | 34.679 | 38.542 | 75.885 | 1.00 | 2.00 | 0 |
| ATOM | 3600 | CD1 | PHE | 581 | 34.136 | 39.783 | 75.557 | 1.00 | 2.00 | 0 |
| ATOM | 3601 | CD2 | PHE | 581 | 35.999 | 38.495 | 76.346 | 1.00 | 2.00 | 0 |
| ATOM | 3602 | CE1 | PHE | 581 | 34.894 | 40.941 | 75.687 | 1.00 | 2.00 | 0 |
| ATOM | 3603 | CE2 | PHE | 581 | 36.757 | 39.659 | 76.475 | 1.00 | 2.00 | 0 |
| ATOM | 3604 | CZ | PHE | 581 | 36.204 | 40.875 | 76.146 | 1.00 | 2.00 | 0 |
| ATOM | 3605 | C | PHE | 581 | 33.913 | 34.999 | 74.611 | 1.00 | 12.63 | 0 |
| ATOM | 3606 | O | PHE | 581 | 32.782 | 34.521 | 74.647 | 1.00 | 2.00 | 0 |
| ATOM | 3607 | N | PRO | 582 | 35.021 | 34.243 | 74.737 | 1.00 | 21.81 | 0 |
| ATOM | 3608 | CD | PRO | 582 | 36.360 | 34.852 | 74.820 | 1.00 | 85.20 | 0 |
| ATOM | 3609 | CA | PRO | 582 | 35.141 | 32.795 | 74.910 | 1.00 | 24.62 | 0 |
| ATOM | 3610 | CP | PRO | 582 | 36.398 | 32.675 | 75.737 | 1.00 | 86.40 | 0 |
| ATOM | 3611 | CG | PRO | 582 | 37.266 | 33.636 | 75.008 | 1.00 | 87.84 | 0 |
| ATOM | 3612 | C | PRO | 582 | 33.966 | 31.958 | 75.425 | 1.00 | 28.53 | 0 |
| ATOM | 3613 | O | PRO | 582 | 33.816 | 30.796 | 75.012 | 1.00 | 0.58 | 0 |
| ATOM | 3614 | N | PRO | 583 | 33.160 | 32.466 | 76.374 | 1.00 | 13.00 | 0 |
| ATOM | 3615 | CD | PRO | 583 | 33.090 | 33.632 | 77.269 | 1.00 | 51.24 | 0 |
| ATOM | 3616 | CA | PRO | 583 | 32.099 | 31.500 | 76.681 | 1.00 | 13.55 | 0 |
| ATOM | 3617 | CB | PRO | 583 | 31.281 | 32.215 | 77.759 | 1.00 | 53.59 | 0 |
| ATOM | 3618 | CG | PRO | 583 | 31.616 | 33.699 | 77.550 | 1.00 | 50.46 | 0 |
| ATOM | 3619 | C | PRO | 583 | 31.296 | 31.283 | 75.389 | 1.00 | 14.03 | 0 |
| ATOM | 3620 | O | PRO | 583 | 30.950 | 30.152 | 75.043 | 1.00 | 48.29 | 0 |
| ATOM | 3621 | N | GLU | 584 | 31.089 | 32.383 | 74.663 | 1.00 | 35.81 | 0 |
| ATOM | 3623 | CA | GLU | 584 | 30.333 | 32.439 | 73.412 | 1.00 | 39.44 | 0 |
| ATOM | 3624 | CB | GLU | 584 | 30.122 | 33.913 | 73.043 | 1.00 | 78.69 | 0 |
| ATOM | 3625 | CG | GLU | 584 | 28.955 | 34.213 | 72.117 | 1.00 | 90.10 | 0 |
| ATOM | 3626 | CD | GLU | 584 | 28.662 | 35.712 | 72.022 | 1.00 | 95.41 | 0 |
| ATOM | 3627 | OE1 | GLU | 584 | 28.313 | 36.190 | 70.918 | 1.00 | 90.41 | 0 |
| ATOM | 3628 | OE2 | GLU | 584 | 28.782 | 36.418 | 73.053 | 1.00 | 95.61 | 0 |
| ATOM | 3629 | C | GLU | 584 | 30.975 | 31.676 | 72.244 | 1.00 | 36.17 | 0 |
| ATOM | 3630 | O | GLU | 584 | 30.780 | 30.466 | 72.106 | 1.00 | 78.39 | 0 |
| ATOM | 3631 | N | SER | 585 | 31.737 | 32.381 | 71.406 | 1.00 | 12.28 | 0 |
| ATOM | 3633 | CA | SER | 585 | 32.394 | 31.779 | 70.245 | 1.00 | 6.77 | 0 |
| ATOM | 3634 | CD | SER | 585 | 32.720 | 32.857 | 69.209 | 1.00 | 31.98 | 0 |
| ATOM | 3635 | OG | SER | 585 | 31.558 | 33.556 | 68.809 | 1.00 | 27.38 | 0 |
| ATOM | 3637 | C | SER | 585 | 33.669 | 30.995 | 70.539 | 1.00 | 9.84 | 0 |
| ATOM | 3638 | O | SER | 585 | 34.382 | 31.258 | 71.502 | 1.00 | 35.35 | 0 |
| ATOM | 3639 | N | ASN | 586 | 33.947 | 30.037 | 69.664 | 1.00 | 2.00 | 0 |
| ATOM | 3641 | CA | ASN | 586 | 35.136 | 29.197 | 69.749 | 1.00 | 2.00 | 0 |
| ATOM | 3642 | CB | ASN | 586 | 34.909 | 27.854 | 69.066 | 1.00 | 2.87 | 0 |
| ATOM | 3643 | CG | ASN | 586 | 33.728 | 27.107 | 69.625 | 1.00 | 10.37 | 0 |

TABLE A-continued

| | | | | | | | | | |
|---|---|---|---|---|---|---|---|---|---|
| ATOM | 3644 | OD1 | ASN | 586 | 33.497 | 25.960 | 69.265 | 1.00 | 11.13 | 0 |
| ATOM | 3645 | ND2 | ASN | 586 | 32.967 | 27.745 | 70.506 | 1.00 | 4.44 | 0 |
| ATOM | 3648 | C | ASN | 586 | 36.251 | 29.937 | 69.029 | 1.00 | 2.00 | 0 |
| ATOM | 3649 | O | ASN | 586 | 36.017 | 30.574 | 68.007 | 1.00 | 2.87 | 0 |
| ATOM | 3650 | N | TYR | 587 | 37.458 | 29.858 | 69.564 | 1.00 | 13.99 | 0 |
| ATOM | 3652 | CA | TYR | 587 | 38.571 | 30.554 | 68.966 | 1.00 | 13.99 | 0 |
| ATOM | 3653 | CB | TYR | 587 | 39.049 | 31.706 | 69.876 | 1.00 | 2.00 | 0 |
| ATOM | 3654 | CG | TYR | 587 | 38.177 | 32.946 | 69.873 | 1.00 | 2.00 | 0 |
| ATOM | 3655 | CD1 | TYR | 587 | 36.998 | 33.004 | 70.638 | 1.00 | 2.00 | 0 |
| ATOM | 3656 | CE1 | TYR | 587 | 36.177 | 34.138 | 70.624 | 1.00 | 2.00 | 0 |
| ATOM | 3657 | CD2 | TYR | 587 | 38.519 | 34.061 | 69.088 | 1.00 | 2.00 | 0 |
| ATOM | 3658 | CE2 | TYR | 587 | 37.701 | 35.205 | 69.065 | 1.00 | 2.00 | 0 |
| ATOM | 3659 | CZ | TYR | 587 | 36.532 | 35.231 | 69.840 | 1.00 | 2.00 | 0 |
| ATOM | 3660 | OH | TYR | 587 | 35.743 | 36.352 | 69.838 | 1.00 | 2.00 | 0 |
| ATOM | 3662 | C | TYR | 587 | 39.721 | 29.608 | 68.745 | 1.00 | 13.99 | 0 |
| ATOM | 3663 | O | TYR | 587 | 39.812 | 28.562 | 69.392 | 1.00 | 2.00 | 0 |
| ATOM | 3664 | N | LEU | 586 | 40.584 | 29.987 | 67.809 | 1.00 | 2.00 | 0 |
| ATOM | 3666 | CA | LEU | 588 | 41.803 | 29.261 | 67.493 | 1.00 | 2.00 | 0 |
| ATOM | 3667 | CB | LEU | 588 | 41.681 | 29.482 | 66.195 | 1.00 | 10.69 | 0 |
| ATOM | 3668 | CG | LEU | 588 | 43.032 | 27.907 | 65.781 | 1.00 | 10.69 | 0 |
| ATOM | 3669 | CD1 | LEU | 588 | 43.568 | 27.073 | 66.912 | 1.00 | 10.69 | 0 |
| ATOM | 3670 | CD2 | LEU | 588 | 42.912 | 27.079 | 64.533 | 1.00 | 10.69 | 0 |
| ATOM | 3671 | C | LEU | 588 | 42.809 | 30.375 | 67.301 | 1.00 | 2.00 | 0 |
| ATOM | 3672 | O | LEU | 588 | 42.547 | 31.301 | 66.532 | 1.00 | 10.69 | 0 |
| ATOM | 3673 | N | PHE | 589 | 43.924 | 30.333 | 66.026 | 1.00 | 2.00 | 0 |
| ATOM | 3675 | CA | PHE | 589 | 44.938 | 31.363 | 67.865 | 1.00 | 2.00 | 0 |
| ATOM | 3676 | CB | PHE | 589 | 45.289 | 32.013 | 69.200 | 1.00 | 2.00 | 0 |
| ATOM | 3677 | CG | PHE | 589 | 44.279 | 33.026 | 69.652 | 1.00 | 2.00 | 0 |
| ATOM | 3678 | CD1 | PHE | 589 | 43.136 | 32.633 | 70.326 | 1.00 | 2.00 | 0 |
| ATOM | 3679 | CD2 | PHE | 589 | 44.471 | 34.376 | 69.391 | 1.00 | 2.00 | 0 |
| ATOM | 3680 | CE1 | PHE | 589 | 42.203 | 33.567 | 70.732 | 1.00 | 2.00 | 0 |
| ATOM | 3681 | CE2 | PHE | 589 | 43.542 | 35.321 | 69.793 | 1.00 | 2.00 | 0 |
| ATOM | 3682 | CZ | PHE | 589 | 42.408 | 34.918 | 70.463 | 1.00 | 2.00 | 0 |
| ATOM | 3683 | C | PHE | 589 | 46.140 | 30.717 | 67.219 | 1.00 | 2.00 | 0 |
| ATOM | 3684 | O | PHE | 589 | 46.532 | 29.610 | 67.602 | 1.00 | 2.00 | 0 |
| ATOM | 3685 | N | LEU | 590 | 46.715 | 31.411 | 66.235 | 1.00 | 2.00 | 0 |
| ATOM | 3687 | CA | LEU | 590 | 47.845 | 30.892 | 65.459 | 1.00 | 2.00 | 0 |
| ATOM | 3688 | CB | LEU | 590 | 47.650 | 31.303 | 63.988 | 1.00 | 9.73 | 0 |
| ATOM | 3689 | CG | LEU | 590 | 46.273 | 31.022 | 63.356 | 1.00 | 9.73 | 0 |
| ATOM | 3690 | CD1 | LEU | 590 | 46.162 | 31.702 | 62.014 | 1.00 | 9.73 | 0 |
| ATOM | 3691 | CD2 | LEU | 590 | 46.056 | 29.529 | 63.211 | 1.00 | 9.73 | 0 |
| ATOM | 3692 | C | LEU | 590 | 49.277 | 31.221 | 65.947 | 1.00 | 2.00 | 0 |
| ATOM | 3693 | O | LEU | 590 | 50.263 | 30.856 | 65.296 | 1.00 | 9.73 | 0 |
| ATOM | 3694 | N | GLY | 591 | 49.389 | 31.929 | 67.071 | 1.00 | 2.00 | 0 |
| ATOM | 3696 | CA | GLY | 591 | 50.703 | 32.223 | 67.626 | 1.00 | 2.00 | 0 |
| ATOM | 3697 | C | GLY | S91 | 51.132 | 33.648 | 67.923 | 1.00 | 2.00 | 0 |
| ATOM | 3698 | O | GLY | 591 | 50.369 | 34.620 | 67.769 | 1.00 | 2.00 | 0 |
| ATOM | 3699 | N | ASP | 592 | 52.387 | 33.741 | 68.358 | 1.00 | 2.00 | 0 |
| ATOM | 3701 | CA | ASP | 592 | 53.033 | 35.000 | 68.707 | 1.00 | 2.00 | 0 |
| ATOM | 3702 | CB | ASP | 592 | 53.424 | 35.746 | 67.448 | 1.00 | 6.15 | a |
| ATOM | 3703 | CG | ASP | 592 | 54.521 | 35.051 | 66.686 | 1.00 | 16.84 | 0 |
| ATOM | 3704 | OD1 | ASP | 592 | 54.955 | 35.606 | 65.657 | 1.00 | 11.71 | 0 |
| ATOM | 3705 | OD2 | ASP | S92 | 54.943 | 33.949 | 67.114 | 1.00 | 18.80 | 0 |
| ATOM | 3706 | C | ASP | 592 | 52.194 | 35.887 | 69.598 | 1.00 | 2.00 | 0 |
| ATOM | 3707 | O | ASP | 592 | 51.813 | 36.995 | 69.211 | 1.00 | 6.68 | 0 |
| ATOM | 3708 | N | TYR | 593 | 51.927 | 35.370 | 70.800 | 1.00 | 12.61 | 0 |
| ATOM | 3710 | CA | TYR | 593 | 51.127 | 36.036 | 71.822 | 1.00 | 12.61 | 0 |
| ATOM | 3711 | CB | TYR | 593 | 50.602 | 35.017 | 72.827 | 1.00 | 2.00 | 0 |
| ATOM | 3712 | CG | TYR | 593 | 49.994 | 33.790 | 72.200 | 1.00 | 2.00 | 0 |
| ATOM | 3713 | CD1 | TYR | 593 | 50.558 | 32.532 | 72.382 | 1.00 | 2.00 | 0 |
| ATOM | 3714 | CE1 | TYR | 593 | 49.995 | 31.401 | 71.793 | 1.00 | 2.00 | 0 |
| ATOM | 3715 | CD2 | TYR | 593 | 48.852 | 33.886 | 71.413 | 1.00 | 2.00 | 0 |
| ATOM | 3716 | CE2 | TYR | 593 | 48.284 | 32.772 | 70.822 | 1.00 | 2.00 | 0 |
| ATOM | 3717 | CZ | TYR | 593 | 48.856 | 31.540 | 71.013 | 1.00 | 2.00 | 0 |
| ATOM | 3718 | OH | TYR | 593 | 48.267 | 30.459 | 70.412 | 1.00 | 2.00 | 0 |
| ATOM | 3720 | C | TYR | 593 | 51.995 | 37.019 | 72.560 | 1.00 | 12.61 | 0 |
| ATOM | 3721 | O | TYR | 593 | 51.526 | 38.079 | 72.981 | 1.00 | 2.00 | 0 |
| ATOM | 3722 | N | VAL | 594 | 53.270 | 36.660 | 72.692 | 1.00 | 2.00 | 0 |
| ATOM | 3724 | CA | VAL | 594 | 54.238 | 37.463 | 73.420 | 1.00 | 2.00 | 0 |
| ATOM | 3725 | CB | VAL | 594 | 54.913 | 36.599 | 74.501 | 1.00 | 30.06 | 0 |
| ATOM | 3726 | CG1 | VAL | 594 | 53.855 | 35.785 | 75.241 | 1.00 | 30.06 | 0 |
| ATOM | 3727 | CG2 | VAL | 594 | 55.950 | 35.684 | 73.875 | 1.00 | 30.06 | 0 |
| ATOM | 3728 | C | VAL | 594 | 55.309 | 38.154 | 72.563 | 1.00 | 2.00 | 0 |
| ATOM | 3729 | O | VAL | 594 | 55.408 | 37.919 | 71.356 | 1.00 | 30.06 | 0 |
| ATOM | 3730 | N | ASP | 595 | 56.112 | 38.991 | 73.218 | 1.00 | 2.00 | 0 |
| ATOM | 3732 | CA | ASP | 595 | 57.184 | 39.776 | 72.601 | 1.00 | 2.00 | 0 |
| ATOM | 3733 | CB | ASP | 595 | 58.073 | 38.903 | 71.705 | 1.00 | 33.25 | 0 |
| ATOM | 3734 | CG | ASP | 595 | 58.911 | 37.890 | 72.502 | 1.00 | 42.03 | 0 |
| ATOM | 3735 | OD1 | ASP | 595 | 59.240 | 38.147 | 73.679 | 1.00 | 40.72 | 0 |

TABLE A-continued

| ATOM | 3736 | OD2 | ASP | 595 | 59.256 | 36.831 | 71.941 | 1.00 | 46.45 | 0 |
|---|---|---|---|---|---|---|---|---|---|---|
| ATOM | 3737 | C | ASP | 595 | 56.547 | 40.920 | 71.818 | 1.00 | 2.00 | 0 |
| ATOM | 3738 | O | ASP | 595 | 55.335 | 40.901 | 71.575 | 1.00 | 29.29 | 0 |
| ATOM | 3739 | N | ARG | 596 | 57.342 | 41.927 | 71.460 | 1.00 | 2.00 | 0 |
| ATOM | 3741 | CA | ARG | 596 | 56.843 | 43.096 | 70.716 | 1.00 | 2.00 | 0 |
| ATOM | 3742 | CB | ARG | 596 | 56.146 | 42.658 | 69.416 | 1.00 | 7.10 | 0 |
| ATOM | 3743 | CG | ARG | 596 | 57.043 | 41.863 | 68.457 | 1.00 | 13.06 | 0 |
| ATOM | 3744 | CD | ARG | 596 | 58.035 | 42.755 | 67.729 | 1.00 | 17.94 | 0 |
| ATOM | 3745 | NE | ARG | 596 | 59.293 | 42.081 | 67.407 | 1.00 | 25.56 | 0 |
| ATOM | 3747 | CZ | ARG | 596 | 59.402 | 40.954 | 66.709 | 1.00 | 35.06 | 0 |
| ATOM | 3748 | NH1 | ARG | 596 | 58.325 | 40.338 | 66.236 | 1.00 | 31.67 | 0 |
| ATOM | 3751 | NH2 | ARG | 596 | 60.604 | 40.438 | 66.486 | 1.00 | 31.81 | 0 |
| ATOM | 3754 | C | ARG | 596 | 55.898 | 43.996 | 71.547 | 1.00 | 2.00 | 0 |
| ATOM | 3755 | O | ARG | 596 | 56.269 | 45.112 | 71.922 | 1.00 | 7.10 | 0 |
| ATOM | 3756 | N | GLY | 597 | 54.692 | 43.521 | 71.847 | 1.00 | 32.20 | 0 |
| ATOM | 3758 | CA | GLY | 597 | 53.763 | 44.323 | 72.632 | 1.00 | 30.86 | 0 |
| ATOM | 3759 | C | GLY | 597 | 54.199 | 44.603 | 74.062 | 1.00 | 35.68 | 0 |
| ATOM | 3760 | O | GLY | 597 | 55.120 | 43.976 | 74.570 | 1.00 | 2.00 | 0 |
| ATOM | 3761 | N | LYS | 598 | 53.520 | 45.539 | 74.720 | 1.00 | 20.71 | 0 |
| ATOM | 3763 | CA | LYS | 598 | 53.845 | 45.911 | 76.097 | 1.00 | 17.90 | 0 |
| ATOM | 3764 | CB | LYS | 598 | 53.686 | 47.427 | 76.271 | 1.00 | 54.79 | 0 |
| ATOM | 3765 | CG | LYS | 598 | 54.813 | 48.259 | 75.655 | 1.00 | 53.06 | 0 |
| ATOM | 3766 | CD | LYS | 598 | 56.159 | 48.031 | 76.359 | 1.00 | 56.27 | 0 |
| ATOM | 3767 | CE | LYS | 598 | 56.120 | 48.441 | 77.838 | 1.00 | 53.59 | 0 |
| ATOM | 3768 | NZ | LYS | 598 | 57.407 | 48.186 | 78.548 | 1.00 | 56.50 | 0 |
| ATOM | 3772 | C | LYS | 598 | 53.064 | 45.179 | 77.210 | 1.00 | 18.19 | 0 |
| ATOM | 3773 | O | LYS | 598 | 53.384 | 45.314 | 78.395 | 1.00 | 55.50 | 0 |
| ATOM | 3774 | N | GLN | 599 | 52.053 | 44.400 | 76.832 | 1.00 | 2.00 | 0 |
| ATOM | 3776 | CA | GLN | 599 | 51.244 | 43.666 | 77.795 | 1.00 | 2.00 | 0 |
| ATOM | 3777 | CB | GLN | 599 | 49.820 | 44.244 | 77.839 | 1.00 | 24.44 | 0 |
| ATOM | 3778 | CG | GLN | 599 | 49.780 | 45.701 | 78.304 | 1.00 | 31.08 | 0 |
| ATOM | 3779 | CD | GLN | 599 | 48.398 | 46.169 | 78.728 | 1.00 | 27.33 | 0 |
| ATOM | 3780 | OE1 | GLN | 599 | 47.537 | 46.449 | 77.895 | 1.00 | 26.31 | 0 |
| ATOM | 3781 | NE2 | GLN | 599 | 48.188 | 46.277 | 80.029 | 1.00 | 27.77 | 0 |
| ATOM | 3784 | C | GLN | 599 | 51.215 | 42.163 | 77.514 | 1.00 | 2.00 | 0 |
| ATOM | 3785 | O | GLN | 599 | 50.183 | 41.515 | 77.626 | 1.00 | 24.92 | 0 |
| ATOM | 3786 | N | SER | 600 | 52.371 | 41.602 | 77.198 | 1.00 | 2.00 | 0 |
| ATOM | 3788 | CA | SER | 600 | 52.445 | 40.180 | 76.921 | 1.00 | 2.00 | 0 |
| ATOM | 3789 | CD | SER | 600 | 53.975 | 39.781 | 76.547 | 1.00 | 2.00 | 0 |
| ATOM | 3790 | OG | SER | 600 | 54.381 | 40.577 | 75.480 | 1.00 | 2.00 | 0 |
| ATOM | 3792 | C | SER | 600 | 51.968 | 39.304 | 78.078 | 1.00 | 2.00 | 0 |
| ATOM | 3793 | O | SER | 600 | 51.589 | 38.153 | 77.856 | 1.00 | 2.00 | 0 |
| ATOM | 3794 | N | LEU | 601 | 51.990 | 39.830 | 79.306 | 1.00 | 2.00 | 0 |
| ATOM | 3796 | CA | LEU | 601 | 51.566 | 39.055 | 80.486 | 1.00 | 2.00 | 0 |
| ATOM | 3797 | CB | LEU | 601 | 52.120 | 39.628 | 81.801 | 1.00 | 2.00 | 0 |
| ATOM | 3798 | CG | LEU | 601 | 53.573 | 39.753 | 62.260 | 1.00 | 2.00 | 0 |
| ATOM | 3791 | CD1 | LEU | 601 | 54.290 | 38.405 | 82.228 | 1.00 | 2.00 | 0 |
| ATOM | 3800 | CD2 | LEU | 601 | 54.244 | 40.799 | 81.399 | 1.00 | 2.00 | 0 |
| ATOM | 3801 | C | LEU | 601 | 50.058 | 39.002 | 80.635 | 1.00 | 2.00 | 0 |
| ATOM | 3802 | O | LEU | 601 | 49.498 | 37.949 | 80.921 | 1.00 | 4.13 | 0 |
| ATOM | 3803 | N | GLU | 602 | 49.412 | 40.154 | 80.490 | 1.00 | 2.00 | 0 |
| ATOM | 3805 | CA | GLU | 602 | 47.969 | 40.227 | 80.608 | 1.00 | 2.00 | 0 |
| ATOM | 3806 | CB | GLU | 602 | 47.486 | 41.676 | 80.495 | 1.00 | 5.18 | 0 |
| ATOM | 3807 | CG | GLU | 602 | 47.752 | 42.552 | 81.739 | 1.00 | 5.18 | 0 |
| ATOM | 3808 | CD | GLU | 602 | 49.152 | 43.180 | 81.773 | 1.00 | 5.18 | 0 |
| ATOM | 3809 | OE1 | GLU | 602 | 50.146 | 42.439 | 81.854 | 1.00 | 5.18 | 0 |
| ATOM | 3810 | OE2 | GLU | 602 | 49.266 | 44.424 | 81.732 | 1.00 | 5.18 | 0 |
| ATOM | 3811 | C | GLU | 602 | 47.413 | 39.391 | 79.479 | 1.00 | 2.00 | 0 |
| ATOM | 3812 | O | GLU | 602 | 46.452 | 38.661 | 79.661 | 1.00 | 5.18 | 0 |
| ATOM | 3813 | N | THR | 603 | 48.072 | 39.477 | 78.323 | 1.00 | 56.10 | 0 |
| ATOM | 3815 | CA | THR | 603 | 47.705 | 38.748 | 77.110 | 1.00 | 56.10 | 0 |
| ATOM | 3816 | CB | THR | 603 | 48.585 | 39.206 | 75.941 | 1.00 | 8.67 | 0 |
| ATOM | 3817 | OG1 | THR | 603 | 48.197 | 40.527 | 75.557 | 1.00 | 8.67 | 0 |
| ATOM | 3819 | CG2 | THR | 603 | 48.437 | 38.272 | 74.748 | 1.00 | 8.67 | 0 |
| ATOM | 3820 | C | THR | 603 | 47.794 | 37.228 | 77.228 | 1.00 | 56.10 | 0 |
| ATOM | 3821 | O | THR | 603 | 46.804 | 36.522 | 77.060 | 1.00 | 8.67 | 0 |
| ATOM | 3822 | N | ILE | 604 | 48.980 | 36.713 | 77.505 | 1.00 | 2.00 | 0 |
| ATOM | 3824 | CA | ILE | 604 | 49.137 | 35.273 | 77.630 | 1.00 | 2.00 | 0 |
| ATOM | 3825 | CB | ILE | 604 | 50.643 | 34.900 | 77.738 | 1.00 | 2.00 | 0 |
| ATOM | 3826 | CG2 | ILE | 604 | 51.244 | 35.475 | 79.009 | 1.00 | 2.00 | 0 |
| ATOM | 3827 | CG1 | ILE | 604 | 50.812 | 33.382 | 77.627 | 1.00 | 2.00 | 0 |
| ATOM | 3828 | CD1 | ILE | 604 | 50.177 | 32.766 | 76.369 | 1.00 | 2.00 | 0 |
| ATOM | 3829 | C | ILE | 604 | 48.314 | 34.710 | 78.808 | 1.00 | 2.00 | 0 |
| ATOM | 3830 | O | ILE | 604 | 47.886 | 33.565 | 78.779 | 1.00 | 2.00 | 0 |
| ATOM | 3831 | N | CYS | 605 | 48.057 | 35.526 | 79.821 | 1.00 | 17.68 | 0 |
| ATOM | 3833 | CA | CYS | 605 | 47.283 | 35.072 | 80.962 | 1.00 | 16.48 | 0 |
| ATOM | 3834 | CB | CYS | 605 | 47.434 | 36.026 | 82.138 | 1.00 | 12.63 | 0 |
| ATOM | 3835 | SG | CYS | 605 | 48.994 | 35.843 | 82.980 | 1.00 | 18.12 | 0 |
| ATOM | 3836 | C | CYS | 605 | 45.824 | 34.923 | 80.630 | 1.00 | 10.22 | 0 |

TABLE A-continued

| | | | | | | | | | |
|---|---|---|---|---|---|---|---|---|---|
| ATOM | 3837 | O | CYS | 605 | 45.185 | 33.963 | 81.068 | 1.00 | 8.59 | 0 |
| ATOM | 3838 | N | LEU | 606 | 45.280 | 35.856 | 79.861 | 1.00 | 2.00 | 0 |
| ATOM | 3840 | CA | LEU | 606 | 43.874 | 35.771 | 79.504 | 1.00 | 2.00 | 0 |
| ATOM | 3841 | CB | LEU | 606 | 43.396 | 37.087 | 78.881 | 1.00 | 2.00 | 0 |
| ATOM | 3842 | CG | LEU | 606 | 41.886 | 37.223 | 78.636 | 1.00 | 2.00 | 0 |
| ATOM | 3843 | CD1 | LEU | 606 | 41.081 | 36.716 | 79.867 | 1.00 | 2.00 | 0 |
| ATOM | 3844 | CD2 | LEU | 606 | 41.551 | 38.688 | 78.326 | 1.00 | 2.00 | 0 |
| ATOM | 3845 | C | LEU | 606 | 43.589 | 34.599 | 78.559 | 1.00 | 2.00 | 0 |
| ATOM | 3846 | O | LEU | 606 | 42.503 | 34.012 | 78.612 | 1.00 | 2.00 | 0 |
| ATOM | 3847 | N | LEU | 607 | 44.562 | 34.246 | 77.713 | 1.00 | 9.59 | 0 |
| ATOM | 3849 | CA | LEU | 607 | 44.392 | 33.137 | 76.772 | 1.00 | 9.59 | 0 |
| ATOM | 3850 | CB | LEU | 607 | 45.394 | 33.246 | 75.604 | 1.00 | 9.66 | 0 |
| ATOM | 3851 | CG | LEU | 607 | 45.302 | 34.531 | 74.755 | 1.00 | 9.66 | 0 |
| ATOM | 3852 | CD1 | LEU | 607 | 46.376 | 34.564 | 73.709 | 1.00 | 9.66 | 0 |
| ATOM | 3853 | CD2 | LEU | 607 | 43.951 | 34.634 | 74.114 | 1.00 | 9.66 | 0 |
| ATOM | 3854 | C | LEU | 607 | 44.509 | 31.781 | 77.476 | 1.00 | 9.59 | 0 |
| ATOM | 3855 | O | LEU | 607 | 43.772 | 30.841 | 77.148 | 1.00 | 9.66 | 0 |
| ATOM | 3856 | N | LEU | 608 | 45.412 | 31.688 | 78.452 | 1.00 | 67.56 | 0 |
| ATOM | 3858 | CA | LEU | 608 | 45.599 | 30.460 | 79.230 | 1.00 | 67.56 | 0 |
| ATOM | 3859 | CB | LEU | 608 | 46.872 | 30.529 | 80.054 | 1.00 | 2.00 | 0 |
| ATOM | 3860 | CG | LEU | 608 | 48.168 | 30.385 | 79.273 | 1.00 | 2.00 | 0 |
| ATOM | 3861 | CD1 | LEU | 608 | 49.357 | 30.366 | 80.234 | 1.00 | 2.00 | 0 |
| ATOM | 3862 | CD2 | LEU | 608 | 48.109 | 29.107 | 78.462 | 1.00 | 2.00 | 0 |
| ATOM | 3863 | C | LEU | 608 | 44.427 | 30.217 | 80.170 | 1.00 | 67.56 | 0 |
| ATOM | 3864 | O | LEU | 608 | 44.097 | 29.059 | 50.477 | 1.00 | 2.00 | 0 |
| ATOM | 3865 | N | ALA | 609 | 43.833 | 31.313 | 60.653 | 1.00 | 2.00 | 0 |
| ATOM | 3867 | CA | ALA | 609 | 42.667 | 31.250 | 81.531 | 1.00 | 2.00 | 0 |
| ATOM | 3868 | CB | ALA | 609 | 42.322 | 32.637 | 82.044 | 1.00 | 2.00 | 0 |
| ATOM | 3869 | C | ALA | 609 | 41.496 | 30.677 | 80.734 | 1.00 | 2.00 | 0 |
| ATOM | 3870 | O | ALA | 609 | 40.833 | 29.747 | 81.162 | 1.00 | 2.00 | 0 |
| ATOM | 3871 | N | TYR | 610 | 41.263 | 31.231 | 79.552 | 1.00 | 2.00 | 0 |
| ATOM | 3873 | CA | TYR | 610 | 40.186 | 30.771 | 78.686 | 1.00 | 2.00 | 0 |
| ATOM | 3874 | CB | TYR | 610 | 40.046 | 31.717 | 77.504 | 1.00 | 2.00 | 0 |
| ATOM | 3875 | CG | TYR | 610 | 39.274 | 32.974 | 77.820 | 1.00 | 2.00 | 0 |
| ATOM | 3876 | CD1 | TYR | 610 | 39.685 | 34.202 | 77.315 | 1.00 | 2.00 | 0 |
| ATOM | 3877 | CE1 | TYR | 610 | 38.952 | 35.359 | 77.558 | 1.00 | 2.00 | 0 |
| ATOM | 3878 | CD2 | TYR | 610 | 38.108 | 32.933 | 78.589 | 1.00 | 2.00 | 0 |
| ATOM | 3879 | CE2 | TYR | 610 | 37.367 | 34.091 | 78.841 | 1.00 | 2.00 | 0 |
| ATOM | 3880 | CZ | TYR | 610 | 37.797 | 35.298 | 78.319 | 1.00 | 2.00 | 0 |
| ATOM | 3881 | OH | TYR | 610 | 37.086 | 36.452 | 78.533 | 1.00 | 2.00 | 0 |
| ATOM | 3883 | C | TYR | 610 | 40.431 | 29.342 | 78.205 | 1.00 | 2.00 | 0 |
| ATOM | 3884 | O | TYR | 610 | 39.481 | 28.575 | 78.006 | 1.00 | 2.00 | 0 |
| ATOM | 3885 | N | LYS | 611 | 41.703 | 26.991 | 78.017 | 1.00 | 2.00 | 0 |
| ATOM | 3887 | CA | LYS | 611 | 42.063 | 27.648 | 77.600 | 1.00 | 2.00 | 0 |
| ATOM | 3888 | CB | LYS | 611 | 43.551 | 27.532 | 77.308 | 1.00 | 3.53 | 0 |
| ATOM | 3889 | CG | LYS | 611 | 43.926 | 26.136 | 76.803 | 1.00 | 3.53 | 0 |
| ATOM | 3890 | CD | LYS | 611 | 43.240 | 25.837 | 75.467 | 1.00 | 3.53 | 0 |
| ATOM | 3891 | CE | LYS | 611 | 43.476 | 24.412 | 74.980 | 1.00 | 3.53 | 0 |
| ATOM | 3892 | NZ | LYS | 611 | 42.391 | 23.502 | 75.421 | 1.00 | 3.53 | 0 |
| ATOM | 3896 | C | LYS | 611 | 41.717 | 26.666 | 76.700 | 1.00 | 2.00 | 0 |
| ATOM | 3897 | O | LYS | 611 | 41.142 | 25.616 | 78.431 | 1.00 | 3.53 | 0 |
| ATOM | 3898 | N | ILE | 612 | 42.084 | 26.990 | 79.938 | 1.00 | 26.02 | 0 |
| ATOM | 3900 | CA | ILE | 612 | 41.780 | 26.115 | 81.069 | 1.00 | 26.02 | 0 |
| ATOM | 3901 | CB | ILE | 612 | 42.543 | 26.535 | 82.336 | 1.00 | 2.00 | 0 |
| ATOM | 3902 | CG2 | ILE | 612 | 42.232 | 25.576 | 83.475 | 1.00 | 2.00 | 0 |
| ATOM | 3903 | CG1 | ILE | 612 | 44.041 | 26.511 | 82.063 | 1.00 | 2.00 | 0 |
| ATOM | 3904 | CD1 | ILE | 612 | 44.860 | 27.144 | 83.135 | 1.00 | 2.00 | 0 |
| ATOM | 3905 | C | ILE | 612 | 40.284 | 26.149 | 81.365 | 1.00 | 26.02 | 0 |
| ATOM | 3906 | O | ILE | 612 | 39.698 | 25.131 | 81.739 | 1.00 | 2.00 | 0 |
| ATOM | 3907 | N | LYS | 613 | 39.683 | 27.326 | 81.181 | 1.00 | 2.00 | 0 |
| ATOM | 3909 | CA | LYS | 613 | 38.257 | 27.556 | 81.414 | 1.00 | 2.00 | 0 |
| ATOM | 3910 | CD | LYS | 613 | 37.966 | 29.056 | 81.402 | 1.00 | 10.53 | 0 |
| ATOM | 3911 | CG | LYS | 613 | 36.528 | 29.437 | 81.650 | 1.00 | 10.53 | 0 |
| ATOM | 3912 | CD | LYS | 613 | 36.070 | 29.072 | 83.035 | 1.00 | 10.53 | 0 |
| ATOM | 3913 | CE | LYS | 613 | 34.717 | 29.693 | 83.364 | 1.00 | 10.53 | 0 |
| ATOM | 3914 | NZ | LYS | 613 | 33.611 | 29.182 | 82.523 | 1.00 | 10.53 | 0 |
| ATOM | 3918 | C | LYS | 613 | 37.379 | 26.847 | 80.384 | 1.00 | 2.00 | 0 |
| ATOM | 3919 | O | LYS | 613 | 36.335 | 26.293 | 80.739 | 1.00 | 10.53 | 0 |
| ATOM | 3920 | N | TYR | 614 | 37.819 | 26.842 | 79.121 | 1.00 | 24.09 | 0 |
| ATOM | 3922 | CA | TYR | 614 | 37.079 | 26.214 | 78.016 | 1.00 | 27.84 | 0 |
| ATOM | 3923 | CB | TYR | 614 | 36.473 | 27.301 | 77.125 | 1.00 | 2.00 | 0 |
| ATOM | 3924 | CG | TYR | 614 | 35.679 | 26.363 | 77.855 | 1.00 | 2.00 | 0 |
| ATOM | 3925 | CD1 | TYR | 614 | 36.123 | 29.689 | 77.892 | 1.00 | 2.00 | 0 |
| ATOM | 3926 | CE1 | TYR | 614 | 35.409 | 30.671 | 78.567 | 1.00 | 2.00 | 0 |
| ATOM | 3927 | CD2 | TYR | 614 | 34.490 | 28.048 | 78.516 | 1.00 | 2.00 | 0 |
| ATOM | 3928 | CE2 | TYR | 614 | 33.766 | 29.020 | 79.199 | 1.00 | 2.00 | 0 |
| ATOM | 3929 | CZ | TYR | 614 | 34.232 | 30.330 | 79.227 | 1.00 | 2.00 | 0 |
| ATOM | 3930 | OH | TYR | 614 | 33.560 | 31.293 | 79.960 | 1.00 | 2.00 | 0 |
| ATOM | 3932 | C | TYR | 614 | 37.976 | 25.317 | 77.146 | 1.00 | 25.93 | 0 |

TABLE A-continued

| | | | | | | | | | | |
|---|---|---|---|---|---|---|---|---|---|---|
| ATOM | 3933 | O | TYR | 614 | 38.012 | 25.474 | 75.935 | 1.00 | 2.00 | 0 |
| ATOM | 3934 | N | PRO | 615 | 38.641 | 24.310 | 77.733 | 1.00 | 21.49 | 0 |
| ATOM | 3935 | CD | PRO | 615 | 38.494 | 23.854 | 79.123 | 1.00 | 11.83 | 0 |
| ATOM | 3936 | CA | PRO | 615 | 39.541 | 23.406 | 76.995 | 1.00 | 22.47 | 0 |
| ATOM | 3937 | CB | PRO | 615 | 39.950 | 22.384 | 78.055 | 1.00 | 11.83 | 0 |
| ATOM | 3938 | CG | PRO | 615 | 38.773 | 22.382 | 78.995 | 1.00 | 11.83 | 0 |
| ATOM | 3939 | C | PRO | 615 | 39.078 | 22.714 | 75.720 | 1.00 | 20.23 | 0 |
| ATOM | 3940 | O | PRO | 615 | 39.873 | 22.026 | 75.074 | 1.00 | 11.83 | 0 |
| ATOM | 3941 | N | GLU | 616 | 37.813 | 22.879 | 75.350 | 1.00 | 15.62 | 0 |
| ATOM | 3943 | CA | GLU | 616 | 37.296 | 22.213 | 74.159 | 1.00 | 16.61 | 0 |
| ATOM | 3944 | CB | GLU | 616 | 36.240 | 21.179 | 74.566 | 1.00 | 26.75 | 0 |
| ATOM | 3945 | CG | GLU | 616 | 36.644 | 20.253 | 75.695 | 1.00 | 30.68 | 0 |
| ATOM | 3946 | CD | GLU | 616 | 37.872 | 19.416 | 75.382 | 1.00 | 40.71 | 0 |
| ATOM | 3947 | OE1 | GLU | 616 | 38.747 | 19.294 | 76.273 | 1.00 | 39.65 | 0 |
| ATOM | 3948 | OE2 | GLU | 616 | 37.960 | 18.874 | 74.256 | 1.00 | 39.29 | 0 |
| ATOM | 3949 | C | GLU | 616 | 36.681 | 23.175 | 73.140 | 1.00 | 13.01 | 0 |
| ATOM | 3950 | O | GLU | 616 | 36.276 | 22.765 | 72.046 | 1.00 | 20.06 | 0 |
| ATOM | 3951 | N | ASN | 617 | 36.620 | 24.453 | 73.499 | 1.00 | 2.00 | 0 |
| ATOM | 3953 | CA | ASN | 617 | 36.027 | 25.467 | 72.636 | 1.00 | 2.00 | 0 |
| ATOM | 3954 | CB | ASN | 617 | 34.678 | 25.896 | 73.218 | 1.00 | 42.63 | 0 |
| ATOM | 3955 | CG | ASN | 617 | 33.743 | 24.720 | 73.456 | 1.00 | 47.29 | 0 |
| ATOM | 3956 | OD1 | ASN | 617 | 33.800 | 24.064 | 74.500 | 1.00 | 50.83 | 0 |
| ATOM | 3957 | ND2 | ASN | 617 | 32.883 | 24.443 | 72.485 | 1.00 | 53.65 | 0 |
| ATOM | 3960 | C | ASN | 617 | 36.941 | 26.686 | 72.476 | 1.00 | 2.00 | 0 |
| ATOM | 3961 | O | ASN | 617 | 36.500 | 27.747 | 72.032 | 1.00 | 45.01 | 0 |
| ATOM | 3962 | N | PHE | 618 | 38.215 | 26.517 | 72.812 | 1.00 | 14.67 | 0 |
| ATOM | 3964 | CA | PHE | 618 | 39.192 | 27.596 | 72.736 | 1.00 | 14.67 | 0 |
| ATOM | 3965 | CB | PHE | 618 | 39.146 | 28.387 | 74.044 | 1.00 | 2.00 | 0 |
| ATOM | 3966 | CG | PHE | 618 | 40.042 | 29.585 | 74.073 | 1.00 | 2.00 | 0 |
| ATOM | 3967 | CD1 | PHE | 618 | 39.501 | 30.871 | 74.058 | 1.00 | 2.00 | 0 |
| ATOM | 3968 | CD2 | PHE | 618 | 41.422 | 29.441 | 74.147 | 1.00 | 2.00 | 0 |
| ATOM | 3969 | CE1 | PHE | 618 | 40.322 | 32.007 | 74.119 | 1.00 | 2.00 | 0 |
| ATOM | 3970 | CE2 | PHE | 618 | 42.254 | 30.562 | 74.209 | 1.00 | 2.00 | 0 |
| ATOM | 3971 | CZ | PHE | 618 | 41.696 | 31.854 | 74.195 | 1.00 | 2.00 | 0 |
| ATOM | 3972 | C | PHE | 618 | 40.540 | 26.907 | 72.570 | 1.00 | 14.67 | 0 |
| ATOM | 3973 | O | PHE | 618 | 40.893 | 26.066 | 73.394 | 1.00 | 2.00 | 0 |
| ATOM | 3974 | N | PHE | 619 | 41.285 | 27.239 | 71.514 | 1.00 | 2.00 | 0 |
| ATOM | 3976 | CA | PHE | 619 | 42.583 | 26.599 | 71.271 | 1.00 | 2.00 | 0 |
| ATOM | 3977 | CB | PHE | 619 | 42.468 | 25.622 | 70.111 | 1.00 | 2.00 | 0 |
| ATOM | 3978 | CG | PHE | 619 | 41.404 | 24.595 | 70.311 | 1.00 | 2.00 | 0 |
| ATOM | 3979 | CD1 | PHE | 619 | 40.063 | 24.936 | 70.159 | 1.00 | 2.00 | 0 |
| ATOM | 3980 | CD2 | PHE | 619 | 41.738 | 23.291 | 70.678 | 1.00 | 2.00 | 0 |
| ATOM | 3981 | CE1 | PHE | 619 | 39.068 | 23.997 | 70.370 | 1.00 | 2.00 | 0 |
| ATOM | 3982 | CE2 | PHE | 619 | 40.750 | 22.337 | 70.892 | 1.00 | 2.00 | 0 |
| ATOM | 3983 | CZ | PHE | 619 | 39.408 | 22.689 | 70.738 | 1.00 | 2.00 | 0 |
| ATOM | 3984 | C | PHE | 619 | 43.719 | 27.566 | 71.005 | 1.00 | 2.00 | 0 |
| ATOM | 3985 | O | PHE | 619 | 43.501 | 26.698 | 70.564 | 1.00 | 2.00 | 0 |
| ATOM | 3986 | N | LEU | 620 | 44.936 | 27.115 | 71.282 | 1.00 | 2.00 | 0 |
| ATOM | 3988 | CA | LEU | 620 | 46.118 | 27.933 | 71.073 | 1.00 | 2.00 | 0 |
| ATOM | 3989 | CB | LEU | 620 | 46.647 | 28.507 | 72.393 | 1.00 | 2.00 | 0 |
| ATOM | 3990 | CG | LEU | 620 | 45.826 | 29.389 | 73.321 | 1.00 | 2.00 | 0 |
| ATOM | 3991 | CD1 | LEU | 620 | 46.741 | 29.868 | 74.437 | 1.00 | 2.00 | 0 |
| ATOM | 3992 | CD2 | LEU | 620 | 45.247 | 30.563 | 72.565 | 1.00 | 2.00 | 0 |
| ATOM | 3993 | C | LEU | 620 | 47.225 | 27.093 | 70.438 | 1.00 | 2.00 | 0 |
| ATOM | 3994 | O | LEU | 620 | 47.548 | 25.987 | 70.910 | 1.00 | 2.00 | 0 |
| ATOM | 3995 | N | LEU | 621 | 47.805 | 27.634 | 69.376 | 1.00 | 2.00 | 0 |
| ATOM | 3997 | CA | LEU | 621 | 48.880 | 26.971 | 68.669 | 1.00 | 2.00 | 0 |
| ATOM | 3998 | CB | LEU | 621 | 48.577 | 26.929 | 67.162 | 1.00 | 2.00 | 0 |
| ATOM | 3999 | CG | LEU | 621 | 47.256 | 26.280 | 66.739 | 1.00 | 2.00 | 0 |
| ATOM | 4000 | CD1 | LEU | 621 | 47.021 | 26.511 | 65.253 | 1.00 | 2.00 | 0 |
| ATOM | 4001 | CD2 | LEU | 621 | 47.281 | 24.813 | 67.062 | 1.00 | 2.00 | 0 |
| ATOM | 4002 | C | LEU | 621 | 50.162 | 27.756 | 68.943 | 1.00 | 2.00 | 0 |
| ATOM | 4003 | O | LEU | 621 | 50.121 | 28.937 | 69.285 | 1.00 | 2.00 | 0 |
| ATOM | 4004 | N | ARG | 622 | 51.296 | 27.092 | 68.774 | 1.00 | 2.00 | 0 |
| ATOM | 4006 | CA | ARG | 622 | 52.593 | 27.690 | 69.013 | 1.00 | 2.00 | 0 |
| ATOM | 4007 | CB | ARG | 622 | 53.620 | 26.578 | 69.231 | 1.00 | 5.18 | 0 |
| ATOM | 4008 | CG | ARG | 622 | 54.967 | 27.052 | 69.716 | 1.00 | 5.18 | 0 |
| ATOM | 4009 | CD | ARG | 622 | 55.802 | 25.891 | 70.196 | 1.00 | 5.18 | 0 |
| ATOM | 4010 | NE | ARG | 622 | 56.969 | 26.357 | 70.941 | 1.00 | 5.18 | 0 |
| ATOM | 4012 | CZ | ARG | 622 | 57.830 | 25.553 | 71.557 | 1.00 | 5.18 | 0 |
| ATOM | 4013 | NH1 | ARG | 622 | 57.659 | 24.240 | 71.525 | 1.00 | 6.18 | 0 |
| ATOM | 4016 | NH2 | ARG | 622 | 58.870 | 26.056 | 72.199 | 1.00 | 5.18 | 0 |
| ATOM | 4019 | C | ARG | 622 | 53.070 | 28.615 | 67.894 | 1.00 | 2.00 | 0 |
| ATOM | 4020 | O | ARG | 622 | 53.032 | 28.270 | 66.702 | 1.00 | 16.40 | 0 |
| ATOM | 4021 | N | GLY | 623 | 53.508 | 29.805 | 68.286 | 1.00 | 19.04 | 0 |
| ATOM | 4023 | CA | GLY | 623 | 54.043 | 30.749 | 67.328 | 1.00 | 20.78 | 0 |
| ATOM | 4024 | C | GLY | 623 | 55.551 | 30.573 | 67.390 | 1.00 | 18.09 | 0 |
| ATOM | 4025 | O | GLY | 623 | 56.069 | 29.805 | 68.212 | 1.00 | 2.00 | 0 |
| ATOM | 4026 | N | ASN | 624 | 56.281 | 31.266 | 66.530 | 1.00 | 32.06 | 0 |

TABLE A-continued

| | | | | | | | | | |
|---|---|---|---|---|---|---|---|---|---|
| ATOM | 4028 | CA | ASN | 624 | 57.728 | 31.144 | 66.566 | 1.00 | 32.95 | 0 |
| ATOM | 4029 | CB | ASN | 624 | 58.345 | 31.543 | 65.220 | 1.00 | 12.63 | 0 |
| ATOM | 4030 | CG | ASN | 624 | 58.120 | 33.002 | 64.857 | 1.00 | 8.84 | 0 |
| ATOM | 4031 | OD1 | ASN | 624 | 57.381 | 33.754 | 65.538 | 1.00 | 9.47 | 0 |
| ATOM | 4032 | ND2 | ASN | 624 | 58.721 | 33.413 | 63.757 | 1.00 | 8.50 | 0 |
| ATOM | 4035 | C | ASN | 624 | 58.260 | 31.988 | 67.721 | 1.00 | 32.42 | 0 |
| ATOM | 4036 | O | ASN | 624 | 59.442 | 31.926 | 68.066 | 1.00 | 7.81 | 0 |
| ATOM | 4037 | N | HIS | 625 | 57.359 | 32.757 | 68.335 | 1.00 | 7.71 | 0 |
| ATOM | 4039 | CA | HIS | 625 | 57.687 | 33.614 | 69.477 | 1.00 | 8.83 | 0 |
| ATOM | 4040 | CB | HIS | 625 | 57.030 | 34.987 | 69.320 | 1.00 | 2.00 | 0 |
| ATOM | 4041 | CG | HIS | 625 | 57.909 | 35.998 | 68.656 | 1.00 | 2.00 | 0 |
| ATOM | 4042 | CD2 | HIS | 625 | 59.042 | 35.854 | 67.933 | 1.00 | 2.00 | 0 |
| ATOM | 4043 | ND1 | HIS | 625 | 57.668 | 37.351 | 68.721 | 1.00 | 2.00 | 0 |
| ATOM | 4045 | CE1 | HIS | 625 | 58.618 | 37.999 | 68.069 | 1.00 | 2.00 | 0 |
| ATOM | 4046 | NE2 | HIS | 625 | 59.464 | 37.113 | 67.582 | 1.00 | 2.00 | 0 |
| ATOM | 4048 | C | HIS | 625 | 57.278 | 32.960 | 70.807 | 1.00 | 8.94 | 0 |
| ATOM | 4049 | O | HIS | 625 | 57.188 | 33.644 | 71.825 | 1.00 | 2.00 | 0 |
| ATOM | 4050 | N | GLU | 626 | 56.984 | 31.691 | 70.767 | 1.00 | 2.00 | 0 |
| ATOM | 4052 | CA | GLU | 626 | 56.629 | 30.914 | 71.945 | 1.00 | 2.00 | 0 |
| ATOM | 4053 | CB | GLU | 626 | 55.404 | 30.026 | 71.666 | 1.00 | 23.06 | 0 |
| ATOM | 4054 | CG | GLU | 626 | 54.051 | 30.627 | 72.039 | 1.00 | 18.70 | 0 |
| ATOM | 4055 | CD | GLU | 626 | 53.812 | 31.997 | 71.445 | 1.00 | 17.00 | 0 |
| ATOM | 4056 | OE1 | GLU | 626 | 53.516 | 32.922 | 72.217 | 1.00 | 20.31 | 0 |
| ATOM | 4057 | OE2 | GLU | 626 | 53.911 | 32.165 | 70.214 | 1.00 | 23.26 | 0 |
| ATOM | 4058 | C | GLU | 626 | 57.888 | 30.068 | 72.029 | 1.00 | 2.00 | 0 |
| ATOM | 4059 | O | GLU | 626 | 57.851 | 28.841 | 71.921 | 1.00 | 23.50 | 0 |
| ATOM | 4060 | N | CYS | 627 | 59.015 | 30.748 | 72.184 | 1.00 | 2.00 | 0 |
| ATOM | 4062 | CA | CYS | 627 | 60.290 | 30.067 | 72.218 | 1.00 | 2.00 | 0 |
| ATOM | 4063 | CB | CYS | 627 | 60.832 | 29.957 | 70.789 | 1.00 | 7.85 | 0 |
| ATOM | 4064 | SG | CYS | 627 | 62.235 | 29.843 | 70.575 | 1.00 | 19.90 | 0 |
| ATOM | 4065 | C | CYS | 627 | 61.260 | 30.842 | 73.105 | 1.00 | 2.00 | 0 |
| ATOM | 4066 | O | CYS | 627 | 61.355 | 32.066 | 73.008 | 1.00 | 8.12 | 0 |
| ATOM | 4067 | N | ALA | 628 | 61.971 | 30.116 | 73.970 | 1.00 | 19.49 | 0 |
| ATOM | 4069 | CA | ALA | 628 | 62.934 | 30.702 | 74.900 | 1.00 | 19.49 | 0 |
| ATOM | 4070 | CB | ALA | 628 | 63.704 | 29.601 | 75.567 | 1.00 | 2.00 | 0 |
| ATOM | 4071 | C | ALA | 628 | 63.890 | 31.662 | 74.206 | 1.00 | 19.49 | 0 |
| ATOM | 4072 | O | ALA | 628 | 63.921 | 32.859 | 74.484 | 1.00 | 2.00 | 0 |
| ATOM | 4073 | N | SER | 629 | 64.660 | 31.101 | 73.291 | 1.00 | 10.83 | 0 |
| ATOM | 4075 | CA | SER | 629 | 65.637 | 31.813 | 72.478 | 1.00 | 14.60 | 0 |
| ATOM | 4076 | CB | SER | 629 | 66.057 | 30.877 | 71.355 | 1.00 | 15.99 | 0 |
| ATOM | 4077 | OG | SER | 629 | 65.846 | 29.522 | 71.762 | 1.00 | 20.43 | 0 |
| ATOM | 4079 | C | SER | 629 | 65.119 | 33.131 | 71.899 | 1.00 | 19.16 | 0 |
| ATOM | 4080 | O | SER | 629 | 65.869 | 34.085 | 71.759 | 1.00 | 13.43 | 0 |
| ATOM | 4081 | N | ILE | 630 | 63.834 | 33.167 | 71.566 | 1.00 | 2.00 | 0 |
| ATOM | 4083 | CA | ILE | 630 | 63.198 | 34.354 | 71.022 | 1.00 | 2.00 | 0 |
| ATOM | 4084 | CB | ILE | 630 | 62.076 | 33.973 | 70.017 | 1.00 | 2.00 | 0 |
| ATOM | 4085 | CG2 | ILE | 630 | 61.675 | 35.174 | 69.202 | 1.00 | 2.00 | 0 |
| ATOM | 4086 | CG1 | ILE | 630 | 62.604 | 32.998 | 68.980 | 1.00 | 2.00 | 0 |
| ATOM | 4087 | CD1 | ILE | 630 | 63.664 | 33.598 | 68.080 | 1.00 | 2.00 | 0 |
| ATOM | 4088 | C | ILE | 630 | 62.636 | 35.281 | 72.131 | 1.00 | 2.00 | 0 |
| ATOM | 4089 | O | ILE | 630 | 62.866 | 36.492 | 72.068 | 1.00 | 2.00 | 0 |
| ATOM | 4090 | N | ASN | 631 | 61.932 | 34.729 | 73.137 | 1.00 | 10.29 | 0 |
| ATOM | 4092 | CA | ASN | 631 | 61.350 | 35.504 | 74.272 | 1.00 | 9.61 | 0 |
| ATOM | 4093 | CB | ASN | 631 | 60.759 | 34.597 | 75.349 | 1.00 | 8.67 | 0 |
| ATOM | 4094 | CG | ASN | 631 | 59.555 | 33.848 | 74.891 | 1.00 | 17.37 | 0 |
| ATOM | 4095 | OD1 | ASN | 631 | 59.189 | 33.896 | 73.722 | 1.00 | 21.10 | 0 |
| ATOM | 4096 | ND2 | ASN | 631 | 58.926 | 33.124 | 75.815 | 1.00 | 15.25 | 0 |
| ATOM | 4099 | C | ASN | 631 | 62.367 | 36.370 | 75.003 | 1.00 | 6.75 | 0 |
| ATOM | 4100 | O | ASN | 631 | 62.059 | 37.486 | 75.438 | 1.00 | 6.80 | 0 |
| ATOM | 4101 | N | ARG | 632 | 63.555 | 35.810 | 75.189 | 1.00 | 2.00 | 0 |
| ATOM | 4103 | CA | ARG | 632 | 64.635 | 36.492 | 75.867 | 1.00 | 2.00 | 0 |
| ATOM | 4104 | CB | ARG | 632 | 65.873 | 35.595 | 75.909 | 1.00 | 6.06 | 0 |
| ATOM | 4105 | CG | ARG | 632 | 66.361 | 35.244 | 77.316 | 1.00 | 8.20 | 0 |
| ATOM | 4106 | CD | ARG | 632 | 67.436 | 36.202 | 77.839 | 1.00 | 8.31 | 0 |
| ATOM | 4107 | NE | ARG | 632 | 67.003 | 37.598 | 77.918 | 1.00 | 11.75 | 0 |
| ATOM | 4109 | CZ | ARG | 632 | 67.837 | 38.635 | 77.907 | 1.00 | 13.36 | 0 |
| ATOM | 4110 | NH1 | ARG | 632 | 69.144 | 38.423 | 77.811 | 1.00 | 13.50 | 0 |
| ATOM | 4113 | NH2 | ARG | 632 | 67.372 | 39.883 | 78.001 | 1.00 | 18.51 | 0 |
| ATOM | 4116 | C | ARG | 632 | 64.962 | 37.781 | 75.148 | 1.00 | 2.00 | 0 |
| ATOM | 4117 | O | ARG | 632 | 64.930 | 38.865 | 75.745 | 1.00 | 12.49 | 0 |
| ATOM | 4118 | N | ILE | 633 | 65.234 | 37.658 | 73.852 | 1.00 | 21.20 | 0 |
| ATOM | 4120 | CA | ILE | 633 | 65.608 | 38.788 | 73.014 | 1.00 | 19.86 | 0 |
| ATOM | 4121 | CB | ILE | 633 | 66.085 | 38.308 | 71.610 | 1.00 | 32.61 | 0 |
| ATOM | 4122 | CG2 | ILE | 633 | 66.132 | 39.471 | 70.625 | 1.00 | 29.80 | 0 |
| ATOM | 4123 | CG1 | ILE | 633 | 67.490 | 37.716 | 71.700 | 1.00 | 28.84 | 0 |
| ATOM | 4124 | CD1 | ILE | 633 | 67.619 | 36.496 | 72.594 | 1.00 | 35.23 | 0 |
| ATOM | 4125 | C | ILE | 633 | 64.550 | 39.866 | 72.815 | 1.00 | 22.19 | 0 |
| ATOM | 4126 | O | ILE | 633 | 64.864 | 41.053 | 72.878 | 1.00 | 30.44 | 0 |
| ATOM | 4127 | N | TYR | 634 | 63.303 | 39.473 | 72.588 | 1.00 | 32.62 | 0 |

TABLE A-continued

| ATOM | 4129 | CA | TYR | 634 | 62.276 | 40.471 | 72.316 | 1.00 | 31.19 | 0 |
| --- | --- | --- | --- | --- | --- | --- | --- | --- | --- | --- |
| ATOM | 4130 | CB | TYR | 634 | 61.395 | 40.006 | 71.147 | 1.00 | 13.98 | 0 |
| ATOM | 4131 | CG | TYR | 634 | 62.233 | 39.755 | 69.941 | 1.00 | 19.07 | 0 |
| ATOM | 4132 | CD1 | TYR | 634 | 62.652 | 40.805 | 69.147 | 1.00 | 17.28 | 0 |
| ATOM | 4133 | CE1 | TYR | 634 | 63.498 | 40.587 | 68.074 | 1.00 | 16.13 | 0 |
| ATOM | 4134 | CD2 | TYR | 634 | 62.668 | 38.474 | 69.639 | 1.00 | 15.20 | 0 |
| ATOM | 4135 | CE2 | TYR | 634 | 63.515 | 38.236 | 68.571 | 1.00 | 18.14 | 0 |
| ATOM | 4136 | CZ | TYR | 634 | 63.935 | 39.296 | 67.786 | 1.00 | 21.41 | 0 |
| ATOM | 4137 | OH | TYR | 634 | 64.789 | 39.069 | 66.720 | 1.00 | 20.11 | 0 |
| ATOM | 4139 | C | TYR | 634 | 61.430 | 41.025 | 73.446 | 1.00 | 28.63 | 0 |
| ATOM | 4140 | O | TYR | 634 | 60.380 | 41.637 | 73.188 | 1.00 | 19.20 | 0 |
| ATOM | 4141 | N | GLY | 635 | 61.851 | 40.807 | 74.690 | 1.00 | 38.67 | 0 |
| ATOM | 4143 | CA | GLY | 635 | 61.114 | 41.407 | 75.786 | 1.00 | 39.39 | 0 |
| ATOM | 4144 | C | GLY | 635 | 60.270 | 40.658 | 76.780 | 1.00 | 41.31 | 0 |
| ATOM | 4145 | O | GLY | 635 | 60.103 | 41.155 | 77.892 | 1.00 | 69.69 | 0 |
| ATOM | 4146 | N | PHE | 636 | 59.725 | 39.502 | 76.431 | 1.00 | 54.49 | 0 |
| ATOM | 4148 | CA | PHE | 636 | 58.905 | 38.786 | 77.404 | 1.00 | 56.26 | 0 |
| ATOM | 4149 | CB | PHE | 636 | 58.386 | 37.461 | 76.831 | 1.00 | 2.00 | 0 |
| ATOM | 4150 | CG | PHE | 636 | 57.275 | 36.845 | 77.639 | 1.00 | 2.00 | 0 |
| ATOM | 4151 | CD1 | PHE | 636 | 56.293 | 37.638 | 78.208 | 1.00 | 2.00 | 0 |
| ATOM | 4152 | CD2 | PHE | 636 | 57.214 | 35.478 | 77.824 | 1.00 | 2.00 | 0 |
| ATOM | 4153 | CE1 | PHE | 636 | 55.276 | 37.076 | 78.942 | 1.00 | 2.00 | 0 |
| ATOM | 4154 | CE2 | PHE | 636 | 56.210 | 34.919 | 78.549 | 1.00 | 2.00 | 0 |
| ATOM | 4155 | CZ | PHE | 636 | 55.238 | 35.716 | 79.111 | 1.00 | 2.00 | 0 |
| ATOM | 4156 | C | PHE | 636 | 59.761 | 38.522 | 78.646 | 1.00 | 55.84 | 0 |
| ATOM | 4157 | O | PHE | 636 | 59.321 | 38.728 | 79.791 | 1.00 | 2.00 | 0 |
| ATOM | 4158 | N | TYR | 637 | 61.005 | 38.114 | 78.415 | 1.00 | 2.00 | 0 |
| ATOM | 4160 | CA | TYR | 637 | 61.918 | 37.836 | 79.506 | 1.00 | 2.00 | 0 |
| ATOM | 4161 | CB | TYR | 637 | 63.266 | 37.419 | 78.947 | 1.00 | 18.03 | 0 |
| ATOM | 4162 | CG | TYR | 637 | 64.345 | 37.308 | 79.986 | 1.00 | 13.39 | 0 |
| ATOM | 4163 | CD1 | TYR | 637 | 64.560 | 36.116 | 80.668 | 1.00 | 15.45 | 0 |
| ATOM | 4164 | CE1 | TYR | 637 | 65.563 | 36.007 | 81.603 | 1.00 | 14.13 | 0 |
| ATOM | 4165 | CD2 | TYR | 637 | 65.163 | 38.390 | 80.273 | 1.00 | 14.83 | 0 |
| ATOM | 4166 | CE2 | TYR | 637 | 66.163 | 38.292 | 81.200 | 1.00 | 13.98 | 0 |
| ATOM | 4167 | CZ | TYR | 637 | 66.363 | 37.101 | 81.863 | 1.00 | 14.88 | 0 |
| ATOM | 4168 | OH | TYR | 637 | 67.379 | 37.015 | 82.784 | 1.00 | 13.10 | 0 |
| ATOM | 4170 | C | TYR | 637 | 62.091 | 39.056 | 80.411 | 1.00 | 2.00 | 0 |
| ATOM | 4171 | O | TYR | 637 | 62.362 | 38.920 | 81.605 | 1.00 | 20.03 | 0 |
| ATOM | 4172 | N | ASP | 638 | 61.919 | 40.240 | 79.833 | 1.00 | 2.00 | 0 |
| ATOM | 4174 | CA | ASP | 638 | 62.086 | 41.484 | 80.554 | 1.00 | 2.00 | 0 |
| ATOM | 4175 | CB | ASP | 638 | 62.701 | 42.522 | 79.614 | 1.00 | 57.25 | 0 |
| ATOM | 4176 | CG | ASP | 638 | 64.049 | 42.053 | 79.046 | 1.00 | 66.80 | 0 |
| ATOM | 4177 | OD1 | ASP | 638 | 64.078 | 41.539 | 77.905 | 1.00 | 65.06 | 0 |
| ATOM | 4178 | OD2 | ASP | 638 | 65.077 | 42.175 | 79.750 | 1.00 | 69.12 | 0 |
| ATOM | 4179 | C | ASP | 638 | 60.816 | 41.961 | 81.245 | 1.00 | 2.00 | 0 |
| ATOM | 4180 | O | ASP | 638 | 60.884 | 42.531 | 82.331 | 1.00 | 55.83 | 0 |
| ATOM | 4181 | N | GLU | 639 | 59.656 | 41.724 | 80.644 | 1.00 | 2.00 | 0 |
| ATOM | 4183 | CA | GLU | 639 | 58.405 | 42.074 | 81.317 | 1.00 | 2.00 | 0 |
| ATOM | 4184 | CB | GLU | 639 | 67.210 | 41.774 | 60.419 | 1.00 | 64.74 | 0 |
| ATOM | 4185 | CG | GLU | 639 | 57.051 | 42.726 | 79.261 | 1.00 | 71.70 | 0 |
| ATOM | 4186 | CD | GLU | 639 | 55.900 | 42.349 | 78.355 | 1.00 | 66.55 | 0 |
| ATOM | 4187 | OE1 | GLU | 639 | 54.748 | 42.718 | 78.667 | 1.00 | 65.31 | 0 |
| ATOM | 4188 | OE2 | GLU | 639 | 56.152 | 41.684 | 77.329 | 1.00 | 72.66 | 0 |
| ATOM | 4189 | C | GLU | 639 | 58.372 | 41.145 | 82.547 | 1.00 | 2.00 | 0 |
| ATOM | 4190 | O | GLU | 639 | 58.009 | 41.550 | 83.654 | 1.00 | 65.95 | 0 |
| ATOM | 4191 | N | CYS | 640 | 58.787 | 39.895 | 82.314 | 1.00 | 15.74 | 0 |
| ATOM | 4193 | CA | CYS | 640 | 58.859 | 38.843 | 83.323 | 1.00 | 15.74 | 0 |
| ATOM | 4194 | CB | CYS | 640 | 59.187 | 37.504 | 82.684 | 1.00 | 4.35 | 0 |
| ATOM | 4195 | SG | CYS | 640 | 57.734 | 36.587 | 82.208 | 1.00 | 13.44 | 0 |
| ATOM | 4196 | C | CYS | 640 | 59.859 | 39.081 | 84.426 | 1.00 | 15.74 | 0 |
| ATOM | 4197 | O | CYS | 640 | 59.590 | 38.723 | 85.564 | 1.00 | 11.73 | 0 |
| ATOM | 4198 | N | LYS | 641 | 61.028 | 39.631 | 84.110 | 1.00 | 2.00 | 0 |
| ATOM | 4200 | CA | LYS | 641 | 62.009 | 39.890 | 85.153 | 1.00 | 2.00 | 0 |
| ATOM | 4201 | CB | LYS | 641 | 63.425 | 39.454 | 84.721 | 1.00 | 32.33 | 0 |
| ATOM | 4202 | CG | LYS | 641 | 64.225 | 40.436 | 83.869 | 1.00 | 32.55 | 0 |
| ATOM | 4203 | CD | LYS | 641 | 65.735 | 40.154 | 83.954 | 1.00 | 38.99 | 0 |
| ATOM | 4204 | CE | LYS | 641 | 66.281 | 40.198 | 85.386 | 1.00 | 41.14 | 0 |
| ATOM | 4205 | NZ | LYS | 641 | 66.228 | 41.554 | 86.007 | 1.00 | 38.23 | 0 |
| ATOM | 4209 | C | LYS | 641 | 61.950 | 41.371 | 85.568 | 1.00 | 2.00 | 0 |
| ATOM | 4210 | O | LYS | 641 | 62.948 | 42.106 | 85.548 | 1.00 | 35.25 | 0 |
| ATOM | 4211 | N | ARG | 642 | 60.750 | 41.801 | 85.945 | 1.00 | 17.38 | 0 |
| ATOM | 4213 | CA | ARG | 642 | 60.502 | 43.168 | 86.384 | 1.00 | 17.38 | 0 |
| ATOM | 4214 | CB | ARG | 642 | 60.341 | 44.131 | 85.204 | 1.00 | 14.00 | 0 |
| ATOM | 4215 | CG | ARG | 642 | 61.636 | 44.613 | 84.561 | 1.00 | 23.15 | 0 |
| ATOM | 4216 | CD | ARG | 642 | 61.463 | 46.016 | 83.940 | 1.00 | 25.43 | 0 |
| ATOM | 4217 | NE | ARG | 642 | 60.488 | 46.077 | 82.846 | 1.00 | 33.87 | 0 |
| ATOM | 4219 | CZ | ARG | 642 | 60.816 | 46.208 | 81.560 | 1.00 | 39.98 | 0 |
| ATOM | 4220 | NH1 | ARG | 642 | 62.097 | 46.291 | 81.199 | 1.00 | 44.40 | 0 |
| ATOM | 4223 | NH2 | ARG | 642 | 59.867 | 46.253 | 80.631 | 1.00 | 41.77 | 0 |

TABLE A-continued

| | | | | | | | | | |
|---|---|---|---|---|---|---|---|---|---|
| ATOM | 4226 | C | ARG | 642 | 59.200 | 43.098 | 87.126 | 1.00 | 17.38 | 0 |
| ATOM | 4227 | O | ARG | 642 | 59.114 | 43.455 | 88.288 | 1.00 | 26.01 | 0 |
| ATOM | 4228 | N | ARG | 643 | 58.180 | 42.630 | 86.427 | 1.00 | 11.54 | 0 |
| ATOM | 4230 | CA | ARG | 643 | 56.869 | 42.500 | 87.018 | 1.00 | 11.54 | 0 |
| ATOM | 4231 | CB | ARG | 643 | 55.804 | 42.392 | 85.924 | 1.00 | 8.38 | 0 |
| ATOM | 4232 | CG | ARG | 643 | 55.526 | 43.749 | 85.304 | 1.00 | 8.38 | 0 |
| ATOM | 4233 | CD | ARG | 643 | 54.377 | 43.745 | 84.341 | 1.00 | 8.38 | 0 |
| ATOM | 4234 | NE | ARG | 643 | 53.121 | 43.351 | 84.949 | 1.00 | 8.38 | 0 |
| ATOM | 4236 | CZ | ARG | 643 | 51.939 | 43.569 | 84.390 | 1.00 | 8.38 | 0 |
| ATOM | 4237 | NH1 | ARG | 643 | 51.869 | 44.187 | 83.218 | 1.00 | 8.38 | 0 |
| ATOM | 4240 | NH2 | ARG | 643 | 50.825 | 43.157 | 84.985 | 1.00 | 8.38 | 0 |
| ATOM | 4243 | C | ARG | 643 | 56.841 | 41.304 | 87.939 | 1.00 | 11.54 | 0 |
| ATOM | 4244 | O | ARG | 643 | 56.156 | 41.309 | 88.969 | 1.00 | 8.38 | 0 |
| ATOM | 4245 | N | TYR | 644 | 57.606 | 40.285 | 87.565 | 1.00 | 2.00 | 0 |
| ATOM | 4247 | CA | TYR | 644 | 57.703 | 39.052 | 88.333 | 1.00 | 2.00 | 0 |
| ATOM | 4248 | CB | TYR | 644 | 56.784 | 37.972 | 87.741 | 1.00 | 14.67 | 0 |
| ATOM | 4249 | CG | TYR | 644 | 55.338 | 38.378 | 87.740 | 1.00 | 14.67 | 0 |
| ATOM | 4250 | CD1 | TYR | 644 | 54.695 | 38.723 | 86.554 | 1.00 | 14.67 | 0 |
| ATOM | 4251 | CE1 | TYR | 644 | 53.359 | 39.140 | 86.54B | 1.00 | 14.67 | 0 |
| ATOM | 4252 | CD2 | TYR | 644 | 54.617 | 38.453 | 88.922 | 1.00 | 14.67 | 0 |
| ATOM | 4253 | CE2 | TYR | 644 | 53.289 | 38.866 | 88.929 | 1.00 | 14.67 | 0 |
| ATOM | 4254 | CZ | TYR | 644 | 52.665 | 39.209 | 87.739 | 1.00 | 14.67 | 0 |
| ATOM | 4255 | OH | TYR | 644 | 51.349 | 39.629 | 87.741 | 1.00 | 14.67 | 0 |
| ATOM | 4257 | C | TYR | 644 | 59.160 | 38.598 | 88.330 | 1.00 | 2.00 | 0 |
| ATOM | 4258 | O | TYR | 644 | 60.062 | 39.412 | 88.575 | 1.00 | 14.67 | 0 |
| ATOM | 4259 | N | ASN | 645 | 59.399 | 37.321 | 88.028 | 1.00 | 2.00 | 0 |
| ATOM | 4261 | CA | ASN | 645 | 60.753 | 36.794 | 88.021 | 1.00 | 2.00 | 0 |
| ATOM | 4262 | CB | ASN | 645 | 61.103 | 36.147 | 89.379 | 1.00 | 16.19 | 0 |
| ATOM | 4263 | CG | ASN | 645 | 60.081 | 35.097 | 89.846 | 1.00 | 16.19 | 0 |
| ATOM | 4264 | OD1 | ASN | 645 | 59.466 | 34.378 | 89.054 | 1.00 | 16.19 | 0 |
| ATOM | 4265 | ND2 | ASN | 645 | 59.916 | 35.009 | 91.150 | 1.00 | 16.19 | 0 |
| ATOM | 4268 | C | ASN | 645 | 61.051 | 35.809 | 86.927 | 1.00 | 2.00 | 0 |
| ATOM | 4269 | O | ASN | 645 | 60.156 | 35.217 | 86.333 | 1.00 | 16.19 | 0 |
| ATOM | 4270 | N | ILE | 646 | 62.342 | 35.648 | 86.678 | 1.00 | 2.00 | 0 |
| ATOM | 4272 | CA | ILE | 646 | 62.856 | 34.716 | 85.689 | 1.00 | 2.00 | 0 |
| ATOM | 4273 | CB | ILE | 646 | 64.390 | 34.593 | 85.830 | 1.00 | 2.81 | 0 |
| ATOM | 4274 | CG2 | ILE | 646 | 64.917 | 33.316 | 85.196 | 1.00 | 2.59 | 0 |
| ATOM | 4275 | CG1 | ILE | 646 | 65.054 | 35.814 | 85.221 | 1.00 | 2.59 | 0 |
| ATOM | 4276 | CD1 | ILE | 646 | 66.492 | 35.955 | 85.666 | 1.00 | 8.72 | 0 |
| ATOM | 4277 | C | ILE | 646 | 62.214 | 33.339 | 85.886 | 1.00 | 2.00 | 0 |
| ATOM | 4278 | O | ILE | 646 | 61.875 | 32.675 | 84.915 | 1.00 | 6.42 | 0 |
| ATOM | 4279 | N | LYS | 647 | 62.031 | 32.918 | 87.137 | 1.00 | 2.00 | 0 |
| ATOM | 4281 | CA | LYS | 647 | 61.441 | 31.614 | 87.411 | 1.00 | 2.00 | 0 |
| ATOM | 4282 | CB | LYS | 647 | 61.347 | 31.387 | 88.920 | 1.00 | 79.29 | 0 |
| ATOM | 4283 | CG | LYS | 647 | 62.714 | 31.450 | 89.594 | 1.00 | 84.06 | 0 |
| ATOM | 4284 | CD | LYS | 647 | 63.727 | 30.622 | 88.804 | 1.00 | 88.57 | 0 |
| ATOM | 4285 | CE | LYS | 647 | 61.157 | 31.090 | 89.028 | 1.00 | 86.67 | 0 |
| ATDM | 4286 | NZ | LYS | 647 | 66.029 | 30.668 | 87.886 | 1.00 | 91.44 | 0 |
| ATOM | 4290 | C | LYS | 647 | 60.083 | 31.478 | 86.738 | 1.00 | 2.00 | 0 |
| ATOM | 4291 | O | LYS | 647 | 59.751 | 30.426 | 86.187 | 1.00 | 74.01 | 0 |
| ATOM | 4292 | N | LEU | 648 | 59.322 | 32.563 | 86.763 | 1.00 | 25.02 | 0 |
| ATOM | 4294 | CA | LEU | 648 | 58.012 | 32.599 | 86.136 | 1.00 | 23.81 | 0 |
| ATOM | 4295 | CB | LEU | 648 | 57.300 | 33.918 | 86.460 | 1.00 | 2.00 | 0 |
| ATOM | 4296 | CG | LEU | 648 | 55.802 | 33.929 | 86.178 | 1.00 | 2.00 | 0 |
| ATOM | 4297 | CD1 | LEU | 648 | 51.145 | 32.777 | 86.951 | 1.00 | 2.00 | 0 |
| ATOM | 4298 | CD2 | LEU | 648 | 55.206 | 35.262 | 86.574 | 1.00 | 2.00 | 0 |
| ATOM | 4299 | C | LEU | 648 | 58.245 | 32.495 | 84.637 | 1.00 | 28.16 | 0 |
| ATOM | 4300 | O | LEU | 648 | 57.562 | 31.751 | 83.934 | 1.00 | 2.00 | 0 |
| ATOM | 4301 | N | TRP | 649 | 59.227 | 33.243 | 84.151 | 1.00 | 42.46 | 0 |
| ATOM | 4303 | CA | TRP | 649 | 59.554 | 33.224 | 82.738 | 1.00 | 40.96 | 0 |
| ATOM | 4304 | CB | TRP | 649 | 60.719 | 34.161 | 82.465 | 1.00 | 11.77 | 0 |
| ATOM | 4305 | CG | TRP | 649 | 61.206 | 34.051 | 81.081 | 1.00 | 14.98 | 0 |
| ATOM | 4306 | CD2 | TRP | 649 | 62.393 | 33.394 | 80.653 | 1.00 | 14.05 | 0 |
| ATOM | 4307 | CE2 | TRP | 649 | 62.460 | 33.527 | 79.246 | 1.00 | 12.39 | 0 |
| ATOM | 4308 | CE3 | TRP | 649 | 63.412 | 32.703 | 81.320 | 1.00 | 25.06 | 0 |
| ATOM | 4309 | CD1 | TRP | 649 | 60.607 | 34.546 | 79.951 | 1.00 | 17.81 | 0 |
| ATOM | 4310 | NE1 | TRP | 649 | 61.356 | 34.232 | 78.846 | 1.00 | 15.30 | 0 |
| ATOM | 4312 | CZ2 | TRP | 649 | 63.510 | 32.995 | 78.495 | 1.00 | 13.58 | 0 |
| ATOM | 4313 | CZ3 | TRP | 649 | 64.456 | 32.174 | 80.576 | 1.00 | 15.93 | 0 |
| ATOM | 4314 | CH2 | TRP | 649 | 64.497 | 32.323 | 79.175 | 1.00 | 16.10 | 0 |
| ATOM | 4315 | C | TRP | 649 | 59.900 | 31.802 | 82.292 | 1.00 | 40.42 | 0 |
| ATOM | 4316 | O | TRP | 649 | 59.392 | 31.315 | 81.285 | 1.00 | 12.84 | 0 |
| ATOM | 4317 | N | LYS | 650 | 60.748 | 31.138 | 83.069 | 1.00 | 2.00 | 0 |
| ATOM | 4319 | CA | LYS | 650 | 61.179 | 29.776 | 82.796 | 1.00 | 2.00 | 0 |
| ATOM | 4320 | CB | LYS | 650 | 62.257 | 29.371 | 93.795 | 1.00 | 19.18 | 0 |
| ATOM | 4321 | CG | LYS | 650 | 63.420 | 30.343 | 83.820 | 1.00 | 4.52 | 0 |
| ATOM | 4322 | CD | LYS | 650 | 64.541 | 29.898 | 84.718 | 1.00 | 3.83 | 0 |
| ATOM | 4323 | CE | LYS | 650 | 65.148 | 28.593 | 84.221 | 1.00 | 11.09 | 0 |
| ATOM | 4324 | NZ | LYS | 650 | 66.096 | 27.974 | 85.202 | 1.00 | 11.03 | 0 |

TABLE A-continued

| ATOM | 4328 | C | LYS | 650 | 59.976 | 28.851 | 82.892 | 1.00 | 2.00 | 0 |
| ATOM | 4329 | O | LYS | 650 | 59.926 | 27.805 | 82.239 | 1.00 | 5.16 | 0 |
| ATOM | 4330 | N | THR | 651 | 58.997 | 29.234 | 83.702 | 1.00 | 10.53 | 0 |
| ATOM | 4332 | CA | THR | 651 | 57.792 | 28.422 | 83.838 | 1.00 | 14.10 | 0 |
| ATOM | 4333 | CB | THR | 651 | 56.915 | 28.882 | 85.038 | 1.00 | 23.55 | 0 |
| ATOM | 4334 | OG1 | THR | 651 | 57.613 | 28.622 | 86.268 | 1.00 | 23.26 | 0 |
| ATOM | 4336 | CG2 | THR | 651 | 55.582 | 28.150 | 85.047 | 1.00 | 24.53 | 0 |
| ATOM | 4337 | C | THR | 651 | 57.012 | 28.543 | 82.539 | 1.00 | 14.03 | 0 |
| ATOM | 4338 | O | THR | 651 | 56.599 | 27.534 | 81.951 | 1.00 | 23.01 | 0 |
| ATOM | 4339 | N | PHE | 652 | 56.837 | 29.779 | 82.082 | 1.00 | 2.00 | 0 |
| ATOM | 4341 | CA | PHE | 652 | 56.127 | 30.032 | 80.840 | 1.00 | 2.00 | 0 |
| ATOM | 4342 | CB | PHE | 652 | 56.225 | 31.511 | 80.440 | 1.00 | 2.00 | 0 |
| ATOM | 4343 | CG | PHE | 652 | 55.027 | 32.320 | 80.821 | 1.00 | 2.00 | 0 |
| ATOM | 4344 | CD1 | PHE | 652 | 55.164 | 33.486 | 81.536 | 1.00 | 2.00 | 0 |
| ATOM | 4345 | CD2 | PHE | 652 | 53.753 | 31.919 | 80.459 | 1.00 | 2.00 | 0 |
| ATOM | 4346 | CE1 | PHE | 652 | 54.039 | 34.245 | 81.884 | 1.00 | 2.00 | 0 |
| ATOM | 4347 | CE2 | PHE | 652 | 52.630 | 32.678 | 80.808 | 1.00 | 2.00 | 0 |
| ATOM | 4348 | CZ | PHE | 652 | 52.775 | 33.832 | 81.515 | 1.00 | 2.00 | 0 |
| ATOM | 4349 | C | PHE | 652 | 56.717 | 29.160 | 79.743 | 1.00 | 2.00 | 0 |
| ATOM | 4350 | O | PHE | 652 | 55.981 | 28.456 | 79.067 | 1.00 | 2.00 | 0 |
| ATOM | 4351 | N | THR | 653 | 58.039 | 29.143 | 79.608 | 1.00 | 2.00 | 0 |
| ATOM | 4353 | CA | THR | 653 | 58.631 | 28.344 | 78.552 | 1.00 | 2.00 | 0 |
| ATOM | 4354 | CB | THR | 653 | 60.126 | 28.538 | 78.429 | 1.00 | 2.14 | 0 |
| ATOM | 4355 | OG1 | THR | 653 | 60.804 | 27.592 | 79.255 | 1.00 | 2.14 | 0 |
| ATOM | 4357 | CG2 | THR | 653 | 60.499 | 29.945 | 78.787 | 1.00 | 2.14 | 0 |
| ATOM | 4358 | C | THR | 653 | 58.371 | 26.846 | 78.588 | 1.00 | 2.00 | 0 |
| ATOM | 4359 | O | THR | 653 | 58.452 | 26.196 | 77.555 | 1.00 | 4.20 | 0 |
| ATOM | 4360 | N | ASP | 654 | 58.064 | 26.271 | 79.743 | 1.00 | 2.00 | 0 |
| ATOM | 4362 | CA | ASP | 654 | 57.803 | 24.839 | 79.749 | 1.00 | 2.00 | 0 |
| ATOM | 4363 | CB | ASP | 654 | 58.083 | 24.225 | 81.119 | 1.00 | 25.83 | 0 |
| ATOM | 4364 | CG | ASP | 654 | 58.607 | 22.794 | 81.018 | 1.00 | 26.00 | 0 |
| ATOM | 4365 | CD1 | ASP | 654 | 59.163 | 22.420 | 79.960 | 1.00 | 29.22 | 0 |
| ATOM | 4366 | CD2 | ASP | 654 | 58.472 | 22.043 | 82.006 | 1.00 | 28.12 | 0 |
| ATOM | 4367 | C | ASP | 654 | 56.367 | 24.603 | 79.332 | 1.00 | 2.00 | 0 |
| ATOM | 4368 | O | ASP | 654 | 56.014 | 23.518 | 78.874 | 1.00 | 18.75 | 0 |
| ATOM | 4369 | N | CYS | 655 | 55.537 | 25.625 | 79.503 | 1.00 | 27.58 | 0 |
| ATOM | 4371 | CA | CYS | 655 | 54.146 | 25.546 | 79.095 | 1.00 | 27.58 | 0 |
| ATOM | 4372 | CB | CYS | 655 | 53.333 | 26.675 | 79.722 | 1.00 | 8.45 | 0 |
| ATOM | 4373 | SG | CYS | 655 | 51.756 | 26.978 | 78.901 | 1.00 | 8.45 | 0 |
| ATOM | 4374 | C | CYS | 655 | 54.162 | 25.683 | 77.575 | 1.00 | 27.58 | 0 |
| ATOM | 4375 | O | CYS | 655 | 53.565 | 24.863 | 76.865 | 1.00 | 8.45 | 0 |
| ATOM | 4376 | N | PHE | 656 | 54.871 | 26.709 | 77.088 | 1.00 | 7.64 | 0 |
| ATOM | 4378 | CA | PHE | 656 | 55.018 | 26.966 | 75.653 | 1.00 | 7.64 | 0 |
| ATOM | 4379 | CB | PHE | 656 | 55.967 | 28.145 | 75.402 | 1.00 | 12.44 | 0 |
| ATOM | 4380 | CG | PHE | 656 | 55.384 | 29.483 | 75.747 | 1.00 | 12.44 | 0 |
| ATOM | 4381 | CD1 | PHE | 656 | 54.073 | 29.591 | 76.242 | 1.00 | 12.44 | 0 |
| ATOM | 4382 | CD2 | PHE | 656 | 56.144 | 30.641 | 75.594 | 1.00 | 12.44 | 0 |
| ATOM | 4383 | CE1 | PHE | 656 | 53.525 | 30.840 | 76.585 | 1.00 | 12.44 | 0 |
| ATOM | 4384 | CE2 | PHE | 656 | 55.614 | 31.891 | 75.929 | 1.00 | 12.44 | 0 |
| ATOM | 4385 | CZ | PHE | 656 | 54.296 | 31.990 | 76.430 | 1.00 | 12.44 | 0 |
| ATOM | 4386 | C | PHE | 656 | 55.564 | 25.705 | 74.961 | 1.00 | 7.64 | 0 |
| ATOM | 4387 | O | PHE | 656 | 55.033 | 25.274 | 73.940 | 1.00 | 12.44 | 0 |
| ATOM | 4388 | N | ASN | 657 | 56.595 | 25.099 | 75.543 | 1.00 | 2.00 | 0 |
| ATOM | 4390 | CA | ASN | 657 | 57.198 | 23.896 | 75.006 | 1.00 | 2.00 | 0 |
| ATOM | 4391 | CB | ASN | 657 | 58.353 | 23.425 | 75.892 | 1.00 | 12.64 | 0 |
| ATOM | 4392 | CG | ASN | 657 | 59.614 | 24.233 | 75.690 | 1.00 | 12.64 | 0 |
| ATOM | 4393 | OD1 | ASN | 657 | 59.564 | 25.404 | 75.350 | 1.00 | 12.64 | 0 |
| ATOM | 4394 | ND2 | ASN | 657 | 60.757 | 23.607 | 75.896 | 1.00 | 12.64 | 0 |
| ATOM | 4397 | C | ASN | 657 | 56.202 | 22.772 | 74.881 | 1.00 | 2.00 | 0 |
| ATOM | 4398 | O | ASN | 657 | 56.585 | 21.668 | 74.532 | 1.00 | 12.64 | 0 |
| ATOM | 4399 | N | CYS | 658 | 54.934 | 23.017 | 75.196 | 1.00 | 2.00 | 0 |
| ATOM | 4401 | CA | CYS | 658 | 53.930 | 21.964 | 75.080 | 1.00 | 10.87 | 0 |
| ATOM | 4402 | CB | CYS | 658 | 53.543 | 21.468 | 76.475 | 1.00 | 10.87 | 0 |
| ATOM | 4403 | SG | CYS | 658 | 55.004 | 20.919 | 77.397 | 1.00 | 10.87 | 0 |
| ATOM | 4404 | C | CYS | 658 | 52.708 | 22.390 | 74.258 | 1.00 | 2.00 | 0 |
| ATOM | 4405 | O | CYS | 658 | 51.726 | 21.659 | 74.162 | 1.00 | 10.87 | 0 |
| ATOM | 4406 | N | LEU | 659 | 52.799 | 23.560 | 73.634 | 1.00 | 11.17 | 0 |
| ATOM | 4408 | CA | LEU | 659 | 51.739 | 24.085 | 72.781 | 1.00 | 11.17 | 0 |
| ATOM | 4409 | CB | LEU | 659 | 51.998 | 25.569 | 72.470 | 1.00 | 2.00 | 0 |
| ATOM | 4410 | CG | LEU | 659 | 51.757 | 26.629 | 73.542 | 1.00 | 2.00 | 0 |
| ATOM | 4411 | CD1 | LEU | 659 | 52.286 | 27.965 | 73.123 | 1.00 | 2.00 | 0 |
| ATOM | 4412 | CD2 | LEU | 659 | 50.307 | 26.759 | 73.767 | 1.00 | 2.00 | 0 |
| ATOM | 4413 | C | LEU | 659 | 51.651 | 23.298 | 71.450 | 1.00 | 11.17 | 0 |
| ATOM | 4414 | O | LEU | 659 | 52.681 | 22.845 | 70.900 | 1.00 | 2.00 | 0 |
| ATOM | 4415 | N | PRO | 660 | 50.415 | 23.109 | 70.931 | 1.00 | 14.96 | 0 |
| ATOM | 4416 | CD | PRO | 660 | 49.134 | 23.535 | 71.523 | 1.00 | 2.00 | 0 |
| ATOM | 4417 | CA | PRO | 660 | 50.166 | 22.398 | 69.680 | 1.00 | 14.96 | 0 |
| ATOM | 4418 | CB | PRO | 660 | 48.640 | 22.381 | 69.590 | 1.00 | 2.00 | 0 |
| ATOM | 4419 | CG | PRO | 660 | 48.194 | 22.472 | 71.028 | 1.00 | 2.00 | 0 |

TABLE A-continued

| ATOM | 4420 | C | PRO | 660 | 50.796 | 23.248 | 68.579 | 1.00 | 14.96 | 0 |
| --- | --- | --- | --- | --- | --- | --- | --- | --- | --- | --- |
| ATOM | 4421 | O | PRO | 660 | 50.888 | 24.474 | 68.709 | 1.00 | 2.00 | 0 |
| ATOM | 4422 | N | ILE | 661 | 51.195 | 22.603 | 67.488 | 1.00 | 28.66 | 0 |
| ATOM | 4424 | CA | ILE | 661 | 51.880 | 23.279 | 66.397 | 1.00 | 30.55 | 0 |
| ATOM | 4425 | CB | ILE | 661 | 53.126 | 22.480 | 66.036 | 1.00 | 19.83 | 0 |
| ATOM | 4426 | CG2 | ILE | 661 | 54.064 | 22.432 | 67.228 | 1.00 | 22.82 | 0 |
| ATOM | 4427 | CG1 | ILE | 661 | 52.728 | 21.050 | 65.669 | 1.00 | 24.89 | 0 |
| ATOM | 4428 | CD1 | ILE | 661 | 53.896 | 20.161 | 65.299 | 1.00 | 29.65 | 0 |
| ATOM | 4429 | C | ILE | 661 | 51.074 | 23.577 | 65.132 | 1.00 | 29.24 | 0 |
| ATOM | 4430 | O | ILE | 661 | 51.428 | 24.493 | 64.372 | 1.00 | 20.63 | 0 |
| ATOM | 4431 | N | ALA | 662 | 50.004 | 22.810 | 64.915 | 1.00 | 22.79 | 0 |
| ATOM | 4433 | CA | ALA | 662 | 49.112 | 22.970 | 63.751 | 1.00 | 22.79 | 0 |
| ATOM | 4434 | CB | ALA | 662 | 49.652 | 22.187 | 62.529 | 1.00 | 2.00 | 0 |
| ATOM | 4435 | C | ALA | 662 | 47.683 | 22.507 | 64.086 | 1.00 | 22.79 | 0 |
| ATOM | 4436 | O | ALA | 662 | 47.439 | 21.887 | 65.139 | 1.00 | 2.00 | 0 |
| ATOM | 4437 | N | ALA | 663 | 46.739 | 22.816 | 63.205 | 1.00 | 2.00 | 0 |
| ATOM | 4439 | CA | ALA | 663 | 45.347 | 22.438 | 63.410 | 1.00 | 2.00 | 0 |
| ATOM | 4440 | CB | ALA | 663 | 44.599 | 23.535 | 64.124 | 1.00 | 18.31 | 0 |
| ATOM | 4441 | C | ALA | 663 | 44.748 | 22.223 | 62.053 | 1.00 | 2.00 | 0 |
| ATOM | 4442 | O | ALA | 663 | 45.323 | 22.623 | 61.041 | 1.00 | 22.14 | 0 |
| ATOM | 4443 | N | ILE | 664 | 43.600 | 21.565 | 62.028 | 1.00 | 16.69 | 0 |
| ATOM | 4445 | CA | ILE | 664 | 42.892 | 21.300 | 60.788 | 1.00 | 16.69 | 0 |
| ATOM | 4446 | CB | ILE | 664 | 43.240 | 19.885 | 60.208 | 1.00 | 9.81 | 0 |
| ATOM | 4447 | CG2 | ILE | 664 | 42.396 | 19.597 | 58.976 | 1.00 | 9.81 | 0 |
| ATOM | 4448 | CG1 | ILE | 664 | 44.724 | 19.810 | 59.819 | 1.00 | 9.81 | 0 |
| ATOM | 4449 | CD1 | ILE | 664 | 45.161 | 18.450 | 59.316 | 1.00 | 9.81 | 0 |
| ATOM | 4450 | C | ILE | 664 | 41.408 | 21.397 | 61.118 | 1.00 | 16.69 | 0 |
| ATOM | 4451 | O | ILE | 664 | 40.880 | 20.603 | 61.899 | 1.00 | 9.81 | 0 |
| ATOM | 4452 | N | VAL | 665 | 40.754 | 22.408 | 60.561 | 1.00 | 14.09 | 0 |
| ATOM | 4454 | CA | VAL | 665 | 39.332 | 22.608 | 60.777 | 1.00 | 14.09 | 0 |
| ATOM | 4455 | CB | VAL | 665 | 38.954 | 24.091 | 60.742 | 1.00 | 2.00 | 0 |
| ATOM | 4456 | CG1 | VAL | 665 | 37.450 | 24.239 | 60.710 | 1.00 | 2.00 | 0 |
| ATOM | 4457 | CG2 | VAL | 665 | 38.500 | 24.788 | 61.950 | 1.00 | 2.00 | 0 |
| ATOM | 4458 | C | VAL | 665 | 38.509 | 21.873 | 59.729 | 1.00 | 14.09 | 0 |
| ATOM | 4459 | O | VAL | 665 | 38.768 | 21.972 | 58.524 | 1.00 | 2.00 | 0 |
| ATOM | 4460 | N | ASP | 666 | 37.517 | 21.137 | 60.219 | 1.00 | 2.00 | 0 |
| ATOM | 4462 | CA | ASP | 666 | 36.595 | 20.345 | 59.407 | 1.00 | 2.00 | 0 |
| ATOM | 4463 | CB | ASP | 666 | 35.443 | 21.235 | 58.934 | 1.00 | 65.64 | 0 |
| ATOM | 4464 | CG | ASP | 666 | 34.545 | 21.675 | 60.081 | 1.00 | 73.26 | 0 |
| ATOM | 4465 | OD1 | ASP | 666 | 33.763 | 20.838 | 60.578 | 1.00 | 71.65 | 0 |
| ATOM | 4466 | OD2 | ASP | 666 | 34.623 | 22.851 | 60.493 | 1.00 | 75.52 | 0 |
| ATOM | 4467 | C | ASP | 666 | 37.234 | 19.577 | 58.235 | 1.00 | 2.00 | 0 |
| ATOM | 4468 | O | ASP | 666 | 36.648 | 19.467 | 57.158 | 1.00 | 57.66 | 0 |
| ATOM | 4469 | N | GLU | 667 | 38.439 | 19.048 | 58.472 | 1.00 | 17.20 | 0 |
| ATOM | 4471 | CZ | GLU | 667 | 39.203 | 18.270 | 57.489 | 1.00 | 17.69 | 0 |
| ATOM | 4472 | CB | GLU | 667 | 38.455 | 16.981 | 57.138 | 1.00 | 42.87 | 0 |
| ATOM | 4473 | CG | GLU | 667 | 38.170 | 16.101 | 58.345 | 1.00 | 52.20 | 0 |
| ATOM | 4474 | CD | GLU | 667 | 37.457 | 14.806 | 57.988 | 1.00 | 53.85 | 0 |
| ATOM | 4475 | OB1 | GLU | 667 | 36.222 | 14.717 | 58.211 | 1.00 | 51.15 | 0 |
| ATOM | 4476 | OB2 | GLU | 667 | 38.139 | 13.877 | 57.494 | 1.00 | 55.67 | 0 |
| ATOM | 4477 | C | GLU | 667 | 39.584 | 19.015 | 56.207 | 1.00 | 17.24 | 0 |
| ATOM | 4478 | O | GLU | 667 | 40.146 | 18.421 | 55.286 | 1.00 | 34.30 | 0 |
| ATOM | 4479 | N | LYS | 668 | 39.314 | 20.319 | 56.172 | 1.00 | 26.53 | 0 |
| ATOM | 4481 | CA | LYS | 668 | 39.615 | 21.133 | 55.002 | 1.00 | 20.22 | 0 |
| ATOM | 4482 | CB | LYS | 668 | 38.318 | 21.709 | 54.410 | 1.00 | 13.48 | 0 |
| ATOM | 4483 | CC | LYS | 668 | 37.383 | 20.628 | 53.859 | 1.00 | 13.48 | 0 |
| ATOM | 4484 | CD | LYS | 668 | 38.119 | 19.779 | 52.819 | 1.00 | 13.48 | 0 |
| ATOM | 4485 | CE | LYS | 668 | 37.341 | 18.551 | 52.398 | 1.00 | 16.60 | 0 |
| ATOM | 4486 | NZ | LYS | 668 | 36.247 | 17.564 | 51.739 | 1.00 | 18.66 | 0 |
| ATOM | 4490 | C | LYS | 668 | 40.636 | 22.244 | 55.240 | 1.00 | 19.61 | 0 |
| ATOM | 4491 | O | LYS | 668 | 41.676 | 22.264 | 54.584 | 1.00 | 13.48 | 0 |
| ATOM | 4492 | N | ILE | 669 | 40.356 | 23.166 | 56.158 | 1.00 | 2.00 | 0 |
| ATOM | 4494 | CA | ILE | 669 | 41.295 | 24.263 | 56.424 | 1.00 | 2.00 | 0 |
| ATOM | 4495 | CB | ILE | 669 | 40.617 | 25.456 | 57.183 | 1.00 | 2.00 | 0 |
| ATOM | 4496 | CG2 | ILE | 669 | 41.521 | 26.680 | 57.166 | 1.00 | 2.00 | 0 |
| ATOM | 4497 | CG1 | ILE | 669 | 39.298 | 25.839 | 56.518 | 1.00 | 2.00 | 0 |
| ATOM | 4498 | CD1 | ILE | 669 | 38.581 | 26.960 | 57.189 | 1.00 | 2.00 | 0 |
| ATOM | 4499 | C | ILE | 669 | 42.439 | 23.721 | 57.279 | 1.00 | 2.00 | 0 |
| ATOM | 4500 | O | ILE | 669 | 42.201 | 23.034 | 58.269 | 1.00 | 2.00 | 0 |
| ATOM | 4501 | N | PHE | 670 | 43.673 | 24.010 | 56.892 | 1.00 | 2.00 | 0 |
| ATOM | 4503 | CA | PHE | 670 | 44.841 | 23.551 | 57.641 | 1.00 | 2.00 | 0 |
| ATOM | 4504 | CB | PHE | 670 | 45.804 | 22.801 | 56.718 | 1.00 | 2.00 | 0 |
| ATOM | 4505 | CG | PHE | 670 | 47.182 | 22.614 | 57.291 | 1.00 | 2.00 | 0 |
| ATOM | 4506 | CD1 | PHE | 670 | 47.503 | 21.473 | 58.007 | 1.00 | 2.00 | 0 |
| ATOM | 4507 | CD2 | PHE | 670 | 48.163 | 23.569 | 57.093 | 1.00 | 2.00 | 0 |
| ATOM | 4508 | CE1 | PHE | 670 | 48.769 | 21.288 | 58.506 | 1.00 | 2.00 | 0 |
| ATOM | 4509 | CE2 | PHE | 670 | 49.436 | 23.384 | 57.596 | 1.00 | 2.00 | 0 |
| ATOM | 4510 | CE | PHE | 670 | 49.737 | 22.241 | 58.302 | 1.00 | 2.00 | 0 |
| ATOM | 4511 | C | PHE | 670 | 45.528 | 24.780 | 58.190 | 1.00 | 2.00 | 0 |

TABLE A-continued

| | | | | | | | | | |
|---|---|---|---|---|---|---|---|---|---|
| ATOM | 4512 | O | PHE | 670 | 45.901 | 25.652 | 57.421 | 1.00 | 2.00 | 0 |
| ATOM | 4513 | N | CYS | 671 | 45.725 | 24.839 | 59.501 | 1.00 | 2.00 | 0 |
| ATOM | 4515 | CA | CYS | 671 | 46.353 | 25.992 | 60.120 | 1.00 | 2.00 | 0 |
| ATOM | 4516 | CB | CYS | 671 | 45.395 | 26.596 | 61.136 | 1.00 | 14.45 | 0 |
| ATOM | 4517 | SG | CYS | 671 | 43.708 | 26.779 | 60.568 | 1.00 | 25.33 | 0 |
| ATOM | 4518 | C | CYS | 671 | 47.685 | 25.701 | 60.816 | 1.00 | 2.00 | 0 |
| ATOM | 4519 | O | CYS | 671 | 47.921 | 24.589 | 61.310 | 1.00 | 8.01 | 0 |
| ATOM | 4520 | N | CYS | 672 | 48.546 | 26.714 | 60.845 | 1.00 | 2.00 | 0 |
| ATOM | 4522 | CA | CYS | 672 | 49.845 | 26.666 | 61.515 | 1.00 | 2.00 | 0 |
| ATOM | 4523 | CB | CYS | 672 | 50.826 | 25.741 | 60.792 | 1.00 | 9.00 | 0 |
| ATOM | 4524 | SG | CYS | 672 | 51.494 | 26.372 | 59.265 | 1.00 | 11.24 | 0 |
| ATOM | 4525 | C | CYS | 672 | 50.336 | 28.122 | 61.525 | 1.00 | 2.00 | 0 |
| ATOM | 4526 | O | CYS | 672 | 49.751 | 28.963 | 60.850 | 1.00 | 9.00 | 0 |
| ATOM | 4527 | N | HIS | 673 | 51.369 | 28.440 | 62.300 | 1.00 | 17.94 | 0 |
| ATOM | 4529 | CA | HIS | 673 | 51.855 | 29.817 | 62.360 | 1.00 | 17.94 | 0 |
| ATOM | 4530 | C | HIS | 673 | 52.456 | 30.359 | 61.065 | 1.00 | 17.94 | 0 |
| ATOM | 4531 | O | HIS | 673 | 51.960 | 31.349 | 60.514 | 1.00 | 2.00 | 0 |
| ATOM | 4532 | CB | HIS | 673 | 52.894 | 29.965 | 63.459 | 1.00 | 2.00 | 0 |
| ATOM | 4533 | CG | HIS | 673 | 53.283 | 31.383 | 63.724 | 1.00 | 2.00 | 0 |
| ATOM | 4534 | ND1 | HIS | 673 | 52.388 | 32.377 | 64.033 | 1.00 | 2.00 | 0 |
| ATOM | 4536 | CD2 | HIS | 673 | 54.503 | 31.975 | 63.718 | 1.00 | 2.00 | 0 |
| ATOM | 4537 | NE2 | HIS | 673 | 54.371 | 33.330 | 64.019 | 1.00 | 2.00 | 0 |
| ATOM | 4538 | CE1 | HIS | 673 | 53.072 | 33.512 | 64.199 | 1.00 | 2.00 | 0 |
| ATOM | 4539 | N | GLY | 674 | 53.545 | 29.721 | 60.626 | 1.00 | 2.00 | 0 |
| ATOM | 4541 | CA | GLY | 674 | 54.260 | 30.101 | 59.417 | 1.00 | 2.00 | 0 |
| ATOM | 4542 | C | GLY | 674 | 53.773 | 29.407 | 58.163 | 1.00 | 2.00 | 0 |
| ATOM | 4543 | O | GLY | 674 | 58.410 | 30.063 | 57.203 | 1.00 | 11.62 | 0 |
| ATOM | 4544 | N | GLY | 675 | 53.759 | 28.087 | 58.136 | 1.00 | 6.25 | 0 |
| ATOM | 4546 | CA | GLY | 675 | 53.286 | 27.440 | 56.931 | 1.00 | 6.25 | 0 |
| ATOM | 4547 | C | GLY | 675 | 53.823 | 26.061 | 56.604 | 1.00 | 6.25 | 0 |
| ATOM | 4548 | O | GLY | 675 | 53.867 | 25.173 | 57.452 | 1.00 | 28.15 | 0 |
| ATOM | 4549 | N | LEU | 676 | 54.241 | 25.883 | 55.356 | 1.00 | 2.00 | 0 |
| ATOM | 4551 | CA | LEU | 676 | 54.723 | 24.591 | 54.886 | 1.00 | 2.00 | 0 |
| ATOM | 4552 | CB | LEU | 676 | 54.336 | 24.409 | 53.418 | 1.00 | 2.00 | 0 |
| ATOM | 4553 | CG | LEU | 676 | 52.827 | 24.625 | 53.244 | 1.00 | 2.00 | 0 |
| ATOM | 4554 | CD1 | LEU | 676 | 52.412 | 24.556 | 51.777 | 1.00 | 2.00 | 0 |
| ATOM | 4555 | CD2 | LEU | 676 | 52.100 | 23.575 | 54.075 | 1.00 | 2.00 | 0 |
| ATOM | 4556 | C | LEU | 676 | 56.207 | 24.333 | 55.095 | 1.00 | 2.00 | 0 |
| ATOM | 4557 | O | LEU | 676 | 56.981 | 25.248 | 55.381 | 1.00 | 2.00 | 0 |
| ATOM | 4558 | N | SER | 677 | 56.582 | 23.069 | 54.945 | 1.00 | 12.63 | 0 |
| ATOM | 4560 | CA | SER | 677 | 57.946 | 22.617 | 55.141 | 1.00 | 12.63 | 0 |
| ATOM | 4561 | CB | SER | 677 | 58.083 | 21.985 | 56.539 | 1.00 | 2.43 | 0 |
| ATOM | 4562 | OG | SER | 677 | 59.248 | 21.192 | 56.649 | 1.00 | 2.03 | 0 |
| ATOM | 4564 | C | SER | 677 | 58.247 | 21.556 | 54.095 | 1.00 | 12.63 | 0 |
| ATOM | 4565 | O | SER | 677 | 57.405 | 20.684 | 53.838 | 1.00 | 10.72 | 0 |
| ATOM | 4566 | N | PRO | 678 | 59.449 | 21.605 | 53.484 | 1.00 | 2.00 | 0 |
| ATOM | 4567 | CD | PRO | 678 | 60.474 | 22.638 | 53.681 | 1.00 | 15.59 | 0 |
| ATOM | 4568 | CA | PRO | 678 | 59.887 | 20.647 | 52.469 | 1.00 | 2.00 | 0 |
| ATOM | 4569 | CB | PRO | 678 | 61.329 | 21.076 | 52.184 | 1.00 | 15.59 | 0 |
| ATOM | 4570 | CG | PRO | 678 | 61.299 | 22.517 | 52.416 | 1.00 | 15.59 | 0 |
| ATOM | 4571 | C | PRO | 678 | 59.859 | 19.234 | 53.032 | 1.00 | 2.00 | 0 |
| ATOM | 4572 | O | PRO | 678 | 59.990 | 18.269 | 52.293 | 1.00 | 15.59 | 0 |
| ATOM | 4573 | N | ASP | 679 | 59.685 | 19.112 | 54.342 | 1.00 | 2.00 | 0 |
| ATOM | 4575 | CA | ASP | 679 | 59.687 | 17.813 | 54.992 | 1.00 | 2.00 | 0 |
| ATOM | 4576 | CB | ASP | 679 | 60.510 | 17.926 | 56.271 | 1.00 | 26.28 | 0 |
| ATOM | 4577 | CG | ASP | 679 | 61.766 | 18.758 | 56.073 | 1.00 | 24.05 | 0 |
| ATOM | 4578 | CD1 | ASP | 679 | 62.687 | 18.269 | 55.383 | 1.00 | 32.92 | 0 |
| ATOM | 4579 | CD2 | ASP | 679 | 61.826 | 19.902 | 56.586 | 1.00 | 28.53 | 0 |
| ATOM | 4580 | C | ASP | 679 | 58.303 | 17.278 | 55.314 | 1.00 | 2.00 | 0 |
| ATOM | 4581 | O | ASP | 679 | 58.129 | 16.094 | 55.576 | 1.00 | 24.04 | 0 |
| ATOM | 4582 | N | LEU | 680 | 57.315 | 18.149 | 55.279 | 1.00 | 2.00 | 0 |
| ATOM | 4584 | CA | LEU | 680 | 55.970 | 17.747 | 55.622 | 1.00 | 2.00 | 0 |
| ATOM | 4585 | CB | LEU | 680 | 55.147 | 19.000 | 55.916 | 1.00 | 4.45 | 0 |
| ATOM | 4586 | CG | LEU | 680 | 53.683 | 18.788 | 56.262 | 1.00 | 2.86 | 0 |
| ATOM | 4587 | CD1 | LEU | 680 | 53.540 | 17.791 | 57.398 | 1.00 | 2.86 | 0 |
| ATOM | 4588 | CD2 | LEU | 680 | 53.085 | 20.134 | 56.582 | 1.00 | 2.86 | 0 |
| ATOM | 4589 | C | LEU | 680 | 55.262 | 16.862 | 54.588 | 1.00 | 2.00 | 0 |
| ATOM | 4590 | O | LEU | 680 | 54.421 | 17.331 | 53.814 | 1.00 | 15.95 | 0 |
| ATOM | 4591 | N | GLN | 681 | 55.588 | 15.578 | 54.561 | 1.00 | 2.00 | 0 |
| ATOM | 4593 | CA | GLN | 681 | 54.922 | 14.686 | 53.611 | 1.00 | 2.00 | 0 |
| ATOM | 4594 | CB | GLN | 681 | 55.719 | 13.410 | 53.885 | 1.00 | 36.99 | 0 |
| ATOM | 4595 | CG | GLN | 681 | 57.097 | 13.620 | 52.863 | 1.00 | 36.99 | 0 |
| ATOM | 4596 | CD | GLN | 681 | 57.716 | 12.321 | 52.468 | 1.00 | 36.99 | 0 |
| ATOM | 4597 | CE1 | GLN | 681 | 57.589 | 11.894 | 51.326 | 1.00 | 36.99 | 0 |
| ATOM | 4598 | NE2 | GLN | 681 | 58.377 | 11.663 | 53.409 | 1.00 | 36.99 | 0 |
| ATOM | 4601 | C | GLN | 681 | 53.551 | 14.319 | 54.159 | 1.00 | 2.00 | 0 |
| ATOM | 4602 | O | GLN | 681 | 52.547 | 14.392 | 53.445 | 1.00 | 11.55 | 0 |
| ATOM | 4603 | N | SER | 682 | 53.505 | 13.923 | 55.423 | 1.00 | 39.00 | 0 |
| ATOM | 4605 | CA | SER | 682 | 52.238 | 13.566 | 56.027 | 1.00 | 42.03 | 0 |

TABLE A-continued

| ATOM | 4606 | CB | SER | 682 | 52.131 | 12.048 | 56.224 | 1.00 | 2.00 | 0 |
| --- | --- | --- | --- | --- | --- | --- | --- | --- | --- | --- |
| ATOM | 4607 | CG | SER | 682 | 53.198 | 11.507 | 56.993 | 1.00 | 2.00 | 0 |
| ATOM | 4609 | C | SER | 682 | 52.003 | 14.284 | 57.343 | 1.00 | 38.75 | 0 |
| ATOM | 4610 | O | SER | 682 | 52.941 | 14.742 | 58.009 | 1.00 | 2.00 | 0 |
| ATOM | 4611 | N | MET | 683 | 50.730 | 14.397 | 57.698 | 1.00 | 15.16 | 0 |
| ATOM | 4613 | CA | MET | 683 | 50.338 | 15.029 | 58.938 | 1.00 | 15.16 | 0 |
| ATOM | 4614 | CB | MET | 683 | 48.820 | 15.069 | 59.044 | 1.00 | 11.68 | 0 |
| ATOM | 4615 | CG | MET | 683 | 48.099 | 15.565 | 57.799 | 1.00 | 12.75 | 0 |
| ATOM | 4616 | SD | MET | 683 | 48.197 | 17.328 | 57.477 | 1.00 | 11.68 | 0 |
| ATOM | 4617 | CE | MET | 683 | 49.486 | 17.429 | 56.200 | 1.00 | 12.61 | 0 |
| ATOM | 4618 | C | MET | 683 | 50.906 | 14.131 | 60.024 | 1.00 | 15.16 | 0 |
| ATOM | 4619 | O | MET | 683 | 51.215 | 14.585 | 61.116 | 1.00 | 15.01 | 0 |
| ATOM | 4620 | N | GLU | 684 | 51.050 | 12.848 | 59.705 | 1.00 | 40.22 | 0 |
| ATOM | 4622 | CA | GLU | 684 | 51.597 | 11.881 | 60.644 | 1.00 | 41.85 | 0 |
| ATOM | 4623 | CB | GLU | 684 | 52.007 | 10.594 | 59.937 | 1.00 | 63.04 | 0 |
| ATOM | 4624 | CG | GLU | 684 | 52.850 | 9.689 | 60.821 | 1.00 | 72.94 | 0 |
| ATOM | 4625 | CD | GLU | 684 | 53.111 | 8.343 | 60.206 | 1.00 | 77.43 | 0 |
| ATOM | 4626 | OE1 | GLU | 684 | 52.139 | 7.716 | 59.730 | 1.00 | 77.96 | 0 |
| ATOM | 4627 | OE2 | GLU | 684 | 54.285 | 7.909 | 60.201 | 1.00 | 79.67 | 0 |
| ATOM | 4628 | C | GLU | 684 | 52.819 | 12.471 | 61.297 | 1.00 | 40.42 | 0 |
| ATOM | 4629 | O | GLU | 684 | 52.932 | 12.495 | 62.517 | 1.00 | 62.00 | 0 |
| ATOM | 4630 | N | GLN | 685 | 53.727 | 12.959 | 60.466 | 1.00 | 2.00 | 0 |
| ATOM | 4632 | CA | GLN | 685 | 54.945 | 13.559 | 60.952 | 1.00 | 2.00 | 0 |
| ATOM | 4633 | CB | GLN | 685 | 55.703 | 14.200 | 59.797 | 1.00 | 52.45 | 0 |
| ATOM | 4634 | CG | GLN | 685 | 56.162 | 13.188 | 58.775 | 1.00 | 57.01 | 0 |
| ATOM | 4635 | CD | GLN | 685 | 56.779 | 13.832 | 57.574 | 1.00 | 58.68 | 0 |
| ATOM | 4636 | OE1 | GLN | 685 | 56.258 | 13.728 | 56.471 | 1.00 | 68.68 | 0 |
| ATOM | 4637 | NE2 | GLN | 685 | 57.895 | 14.510 | 57.778 | 1.00 | 65.77 | 0 |
| ATOM | 4640 | C | GLN | 685 | 54.627 | 14.585 | 62.029 | 1.00 | 2.00 | 0 |
| ATOM | 4641 | O | GLN | 685 | 55.312 | 14.631 | 63.056 | 1.00 | 54.77 | 0 |
| ATOM | 4642 | N | ILE | 686 | 53.579 | 15.387 | 61.816 | 1.00 | 16.80 | 0 |
| ATOM | 4644 | CA | ILE | 686 | 53.179 | 16.391 | 62.807 | 1.00 | 14.42 | 0 |
| ATOM | 4645 | CB | ILE | 686 | 51.990 | 17.270 | 62.307 | 1.00 | 2.00 | 0 |
| ATOM | 4646 | CG2 | ILE | 686 | 51.754 | 18.441 | 63.247 | 1.00 | 2.00 | 0 |
| ATOM | 4647 | CG1 | ILE | 686 | 52.304 | 17.869 | 60.944 | 1.00 | 2.00 | 0 |
| ATOM | 4648 | CD1 | ILE | 686 | 51.139 | 18.668 | 60.369 | 1.00 | 2.00 | 0 |
| ATOM | 4649 | C | ILE | 686 | 52.761 | 15.633 | 64.079 | 1.00 | 13.83 | 0 |
| ATOM | 4650 | O | ILE | 686 | 53.289 | 15.884 | 65.165 | 1.00 | 2.00 | 0 |
| ATOM | 4651 | N | ARG | 687 | 51.856 | 14.669 | 63.914 | 1.00 | 3.14 | 0 |
| ATOM | 4653 | CA | ARG | 687 | 51.367 | 13.855 | 65.027 | 1.00 | 3.14 | 0 |
| ATOM | 4654 | CB | ARG | 687 | 50.307 | 12.835 | 64.564 | 1.00 | 23.50 | 0 |
| ATOM | 4655 | CG | ARG | 687 | 49.266 | 13.324 | 63.559 | 1.00 | 26.96 | 0 |
| ATOM | 4656 | CD | ARG | 687 | 48.288 | 12.211 | 63.083 | 1.00 | 35.95 | 0 |
| ATOM | 4657 | NE | ARG | 687 | 48.878 | 11.199 | 62.190 | 1.00 | 41.22 | 0 |
| ATOM | 4659 | CZ | ARG | 687 | 49.583 | 10.138 | 62.594 | 1.00 | 45.24 | 0 |
| ATOM | 4660 | NH1 | ARG | 687 | 50.062 | 9.283 | 61.702 | 1.00 | 43.65 | 0 |
| ATOM | 4663 | NH2 | ARG | 687 | 49.827 | 9.922 | 63.887 | 1.00 | 36.26 | 0 |
| ATOM | 4666 | C | ARG | 687 | 52.504 | 13.060 | 65.665 | 1.00 | 3.14 | 0 |
| ATOM | 4667 | O | ARG | 687 | 52.260 | 12.327 | 66.613 | 1.00 | 18.08 | 0 |
| ATOM | 4668 | N | ARG | 688 | 53.722 | 13.157 | 65.136 | 1.00 | 11.08 | 0 |
| ATOM | 4670 | CA | ARG | 688 | 54.841 | 12.402 | 65.694 | 1.00 | 10.97 | 0 |
| ATOM | 4671 | CB | ARG | 688 | 55.576 | 11.624 | 64.595 | 1.00 | 52.72 | 0 |
| ATOM | 4672 | CG | ARG | 688 | 54.794 | 10.485 | 63.995 | 1.00 | 52.20 | 0 |
| ATOM | 4673 | CD | ARG | 688 | 54.421 | 9.463 | 65.035 | 1.00 | 55.85 | 0 |
| ATOM | 4674 | NE | ARG | 688 | 53.634 | 8.372 | 64.468 | 1.00 | 50.50 | 0 |
| ATOM | 4676 | CZ | ARG | 688 | 54.145 | 7.254 | 63.956 | 1.00 | 54.57 | 0 |
| ATOM | 4677 | NH1 | ARG | 688 | 53.335 | 6.326 | 63.465 | 1.00 | 53.02 | 0 |
| ATOM | 4680 | NH2 | ARG | 688 | 55.457 | 7.056 | 63.931 | 1.00 | 50.07 | 0 |
| ATOM | 4683 | C | ARG | 688 | 55.853 | 13.257 | 66.457 | 1.00 | 9.37 | 0 |
| ATOM | 4684 | O | ARG | 688 | 56.771 | 12.719 | 67.084 | 1.00 | 54.51 | 0 |
| ATOM | 4685 | N | ILE | 689 | 55.698 | 14.576 | 66.398 | 1.00 | 38.26 | 0 |
| ATOM | 4687 | CA | ILE | 689 | 56.614 | 15.487 | 67.081 | 1.00 | 36.62 | 0 |
| ATOM | 4688 | CB | ILE | 689 | 56.319 | 16.952 | 66.673 | 1.00 | 2.00 | 0 |
| ATOM | 4689 | CG2 | ILE | 689 | 57.248 | 17.901 | 67.399 | 1.00 | 2.00 | 0 |
| ATOM | 4690 | CG1 | ILE | 689 | 56.493 | 17.119 | 65.160 | 1.00 | 2.00 | 0 |
| ATOM | 4691 | CD1 | ILE | 689 | 56.670 | 18.556 | 64.711 | 1.00 | 2.00 | 0 |
| ATOM | 4692 | C | ILE | 689 | 56.552 | 15.347 | 68.620 | 1.00 | 42.28 | 0 |
| ATOM | 4693 | O | ILE | 689 | 55.468 | 15.462 | 69.226 | 1.00 | 2.00 | 0 |
| ATOM | 4694 | N | MET | 690 | 57.710 | 15.084 | 69.242 | 1.00 | 2.00 | 0 |
| ATOM | 4696 | CA | MET | 690 | 57.794 | 14.930 | 70.704 | 1.00 | 2.00 | 0 |
| ATOM | 4697 | CB | MET | 690 | 59.204 | 14.516 | 71.138 | 1.00 | 31.54 | 0 |
| ATOM | 4698 | CG | MET | 690 | 59.657 | 13.160 | 70.616 | 1.00 | 36.54 | 0 |
| ATOM | 4699 | SD | MET | 690 | 58.703 | 11.742 | 71.207 | 1.00 | 43.14 | 0 |
| ATOM | 4700 | CE | MET | 690 | 59.784 | 10.411 | 70.721 | 1.00 | 40.70 | 0 |
| ATOM | 4701 | C | MET | 690 | 57.491 | 16.313 | 71.227 | 1.00 | 2.00 | 0 |
| ATOM | 4702 | O | MET | 690 | 58.189 | 17.269 | 70.864 | 1.00 | 21.20 | 0 |
| ATOM | 4703 | N | ARG | 691 | 56.489 | 16.441 | 72.092 | 1.00 | 59.62 | 0 |
| ATOM | 4705 | CA | ARG | 691 | 56.135 | 17.780 | 72.507 | 1.00 | 65.12 | 0 |
| ATOM | 4706 | CB | ARG | 691 | 54.678 | 17.879 | 72.869 | 1.00 | 2.00 | 0 |

TABLE A-continued

| | | | | | | | | | |
|---|---|---|---|---|---|---|---|---|---|
| ATOM | 4707 | CG | ARG | 691 | 54.077 | 19.116 | 72.206 | 1.00 | 2.00 | 0 |
| ATOM | 4708 | CD | ARG | 691 | 52.598 | 19.166 | 72.384 | 1.00 | 2.00 | 0 |
| ATOM | 4709 | NE | ARG | 691 | 52.082 | 17.820 | 72.551 | 1.00 | 2.00 | 0 |
| ATOM | 4711 | CZ | ARG | 691 | 50.832 | 17.540 | 72.862 | 1.00 | 2.00 | 0 |
| ATOM | 4712 | NH1 | ARG | 691 | 49.957 | 18.525 | 71.024 | 1.00 | 2.00 | 0 |
| ATOM | 4715 | NH2 | ARG | 691 | 50.482 | 16.273 | 73.046 | 1.00 | 2.00 | 0 |
| ATOM | 4718 | C | ARG | 691 | 56.930 | 18.632 | 73.458 | 1.00 | 64.88 | 0 |
| ATOM | 4719 | O | ARG | 691 | 57.176 | 19.794 | 73.100 | 1.00 | 2.00 | 0 |
| ATOM | 4720 | N | PRO | 692 | 57.265 | 18.151 | 74.693 | 1.00 | 0.89 | 0 |
| ATOM | 4721 | CD | PRO | 692 | 56.930 | 16.947 | 75.482 | 1.00 | 19.88 | 0 |
| ATOM | 4722 | CA | PRO | 692 | 58.060 | 19.115 | 75.500 | 1.00 | 0.77 | 0 |
| ATOM | 4723 | CB | PRO | 692 | 58.305 | 18.357 | 76.811 | 1.00 | 21.87 | 0 |
| ATOM | 4724 | CG | PRO | 692 | 57.071 | 17.462 | 76.911 | 1.00 | 19.02 | 0 |
| ATOM | 4725 | C | PRO | 692 | 59.327 | 19.317 | 74.643 | 1.00 | 0.10 | 0 |
| ATOM | 4726 | O | PRO | 692 | 60.258 | 18.502 | 74.690 | 1.00 | 22.15 | 0 |
| ATOM | 4727 | N | THR | 693 | 59.310 | 20.362 | 73.811 | 1.00 | 2.00 | 0 |
| ATOM | 4729 | CA | THR | 693 | 60.395 | 20.605 | 72.896 | 1.00 | 2.00 | 0 |
| ATOM | 4730 | CB | THR | 693 | 60.153 | 19.842 | 71.569 | 1.00 | 39.91 | 0 |
| ATOM | 4731 | OG1 | THR | 693 | 61.310 | 19.947 | 70.728 | 1.00 | 47.46 | 0 |
| ATOM | 4733 | CG2 | THR | 693 | 58.944 | 20.419 | 70.830 | 1.00 | 46.31 | 0 |
| ATOM | 4734 | C | THR | 693 | 60.567 | 22.057 | 72.560 | 1.00 | 2.00 | 0 |
| ATOM | 4735 | O | THR | 693 | 59.640 | 22.848 | 72.678 | 1.00 | 41.07 | 0 |
| ATOM | 4736 | N | ASP | 694 | 61.782 | 22.399 | 72.154 | 1.00 | 4.51 | 0 |
| ATOM | 4738 | CA | ASP | 694 | 62.075 | 23.747 | 71.736 | 1.00 | 4.51 | 0 |
| ATOM | 4739 | CB | ASP | 694 | 63.429 | 24.203 | 72.283 | 1.00 | 83.74 | 0 |
| ATOM | 4740 | CG | ASP | 694 | 63.337 | 25.520 | 73.041 | 1.00 | 83.74 | 0 |
| ATOM | 4741 | OD1 | ASP | 694 | 63.231 | 25.484 | 74.285 | 1.00 | 83.74 | 0 |
| ATOM | 4742 | OD2 | ASP | 694 | 63.366 | 26.594 | 72.400 | 1.00 | 83.74 | 0 |
| ATOM | 4743 | C | ASP | 694 | 62.101 | 23.682 | 70.201 | 1.00 | 4.51 | 0 |
| ATOM | 4744 | O | ASP | 694 | 62.403 | 22.632 | 69.629 | 1.00 | 83.74 | 0 |
| ATOM | 4745 | N | VAL | 695 | 61.743 | 24.784 | 69.546 | 1.00 | 31.71 | 0 |
| ATOM | 4747 | CA | VAL | 695 | 61.760 | 24.864 | 68.087 | 1.00 | 37.86 | 0 |
| ATOM | 4748 | CB | VAL | 695 | 61.212 | 26.224 | 67.623 | 1.00 | 72.52 | 0 |
| ATOM | 4749 | CG1 | VAL | 695 | 61.120 | 26.268 | 66.113 | 1.00 | 68.63 | 0 |
| ATOM | 4750 | CG2 | VAL | 695 | 59.863 | 26.474 | 68.253 | 1.00 | 68.27 | 0 |
| ATOM | 4751 | C | VAL | 695 | 63.242 | 24.744 | 67.687 | 1.00 | 34.22 | 0 |
| ATOM | 4752 | O | VAL | 695 | 64.070 | 25.548 | 68.123 | 1.00 | 75.22 | 0 |
| ATOM | 4753 | N | PRO | 696 | 63.599 | 23.730 | 66.873 | 1.00 | 2.00 | 0 |
| ATOM | 4754 | CD | PRO | 696 | 62.777 | 22.616 | 66.373 | 1.00 | 5.25 | 0 |
| ATOM | 4755 | CA | PRO | 696 | 64.998 | 23.549 | 66.462 | 1.00 | 2.00 | 0 |
| ATOM | 4756 | CB | PRO | 696 | 64.997 | 22.163 | 65.803 | 1.00 | 5.25 | 0 |
| ATOM | 4757 | CG | PRO | 696 | 63.768 | 21.486 | 66.381 | 1.00 | 5.25 | 0 |
| ATOM | 4758 | C | PRO | 696 | 65.570 | 24.612 | 65.536 | 1.00 | 2.00 | 0 |
| ATOM | 4759 | O | PRO | 696 | 64.878 | 25.556 | 65.137 | 1.00 | 5.25 | 0 |
| ATOM | 4760 | N | ASP | 697 | 66.850 | 24.431 | 65.214 | 1.00 | 34.70 | 0 |
| ATOM | 4762 | CA | ASP | 697 | 67.598 | 25.311 | 64.321 | 1.00 | 35.10 | 0 |
| ATOM | 4763 | CB | ASP | 697 | 69.098 | 24.951 | 64.376 | 1.00 | 81.36 | 0 |
| ATOM | 4764 | CG | ASP | 697 | 69.630 | 24.774 | 65.825 | 1.00 | 81.80 | 0 |
| ATOM | 4765 | OD1 | ASP | 697 | 69.612 | 23.613 | 66.347 | 1.00 | 0.89 | 0 |
| ATOM | 4766 | OD2 | ASP | 697 | 70.075 | 25.792 | 66.436 | 1.00 | 0.05 | 0 |
| ATOM | 4767 | C | ASP | 697 | 67.037 | 25.099 | 62.894 | 1.00 | 36.63 | 0 |
| ATOM | 4768 | O | ASP | 697 | 67.014 | 26.022 | 62.069 | 1.00 | 0.75 | 0 |
| ATOM | 4769 | N | GLN | 698 | 66.576 | 23.877 | 62.620 | 1.00 | 8.48 | 0 |
| ATOM | 4771 | CA | GLN | 698 | 65.997 | 23.510 | 61.335 | 1.00 | 2.00 | 0 |
| ATOM | 4772 | CB | GLN | 698 | 67.089 | 23.346 | 60.285 | 1.00 | 43.65 | 0 |
| ATOM | 4773 | CG | GLN | 698 | 68.191 | 22.376 | 60.649 | 1.00 | 44.93 | 0 |
| ATOM | 4774 | CD | GLN | 698 | 69.158 | 22.169 | 59.501 | 1.00 | 43.25 | 0 |
| ATOM | 4775 | OE1 | GLN | 698 | 68.781 | 22.242 | 58.327 | 1.00 | 45.90 | 0 |
| ATOM | 4776 | NE2 | GLN | 698 | 70.411 | 21.911 | 59.830 | 1.00 | 44.14 | 0 |
| ATOM | 4779 | C | GLN | 698 | 65.211 | 22.216 | 61.482 | 1.00 | 2.32 | 0 |
| ATOM | 4780 | O | GLN | 698 | 65.396 | 21.486 | 62.452 | 1.00 | 42.62 | 0 |
| ATOM | 4781 | N | GLY | 699 | 64.324 | 21.939 | 60.530 | 1.00 | 2.00 | 0 |
| ATOM | 4783 | CA | GLY | 699 | 63.510 | 20.728 | 60.576 | 1.00 | 2.00 | 0 |
| ATOM | 4784 | C | GLY | 699 | 62.046 | 21.059 | 60.346 | 1.00 | 2.00 | 0 |
| ATOM | 4785 | O | GLY | 699 | 61.726 | 22.204 | 60.013 | 1.00 | 2.00 | 0 |
| ATOM | 4786 | N | LEU | 700 | 61.153 | 20.090 | 60.545 | 1.00 | 2.00 | 0 |
| ATOM | 4788 | CA | LEU | 700 | 59.700 | 20.297 | 60.352 | 1.00 | 2.00 | 0 |
| ATOM | 4789 | CB | LEU | 700 | 58.941 | 18.962 | 60.555 | 1.00 | 4.64 | 0 |
| ATOM | 4790 | CG | LEU | 700 | 57.436 | 18.836 | 60.273 | 1.00 | 8.84 | 0 |
| ATOM | 4791 | CD1 | LEU | 700 | 57.219 | 18.881 | 58.793 | 1.00 | 8.28 | 0 |
| ATOM | 4792 | CD2 | LEU | 700 | 56.879 | 17.536 | 60.803 | 1.00 | 5.23 | 0 |
| ATOM | 4793 | C | LEU | 700 | 59.086 | 21.400 | 61.247 | 1.00 | 2.00 | 0 |
| ATOM | 4794 | O | LEU | 700 | 58.365 | 22.261 | 60.763 | 1.00 | 8.77 | 0 |
| ATOM | 4795 | N | LEU | 701 | 59.394 | 21.381 | 62.540 | 1.00 | 12.05 | 0 |
| ATOM | 4797 | CA | LEU | 701 | 58.860 | 22.362 | 63.477 | 1.00 | 11.21 | 0 |
| ATOM | 4798 | CB | LEU | 701 | 59.278 | 22.039 | 64.908 | 1.00 | 2.00 | 0 |
| ATOM | 4799 | CG | LEU | 701 | 58.156 | 21.874 | 65.942 | 1.00 | 2.00 | 0 |
| ATOM | 4800 | CD1 | LEU | 701 | 58.759 | 21.879 | 67.354 | 1.00 | 2.00 | 0 |
| ATOM | 4801 | CD2 | LEU | 701 | 57.124 | 22.994 | 65.800 | 1.00 | 2.00 | 0 |

TABLE A-continued

| ATOM | 4802 | C | LEU | 701 | 59.339 | 23.747 | 63.153 | 1.00 | 6.49 | 0 |
| --- | --- | --- | --- | --- | --- | --- | --- | --- | --- | --- |
| ATOM | 4803 | O | LEU | 701 | 58.562 | 24.691 | 63.157 | 1.00 | 2.00 | 0 |
| ATOM | 4804 | N | CYS | 702 | 60.626 | 23.881 | 62.890 | 1.00 | 2.00 | 0 |
| ATOM | 4806 | CA | CYS | 702 | 61.158 | 25.191 | 62.572 | 1.00 | 2.00 | 0 |
| ATOM | 4807 | CB | CYS | 702 | 62.646 | 25.117 | 62.269 | 1.00 | 10.82 | 0 |
| ATOM | 4608 | SG | CYS | 702 | 63.290 | 26.639 | 61.543 | 1.00 | 10.82 | 0 |
| ATOM | 4809 | C | CYS | 702 | 60.442 | 25.786 | 61.365 | 1.00 | 2.00 | 0 |
| ATOM | 4810 | O | CYS | 702 | 60.022 | 26.954 | 61.384 | 1.00 | 10.82 | 0 |
| ATOM | 4811 | N | ASP | 703 | 60.292 | 24.980 | 60.316 | 1.00 | 2.00 | 0 |
| ATOM | 4813 | CA | ASP | 703 | 59.641 | 25.442 | 59.104 | 1.00 | 2.00 | 0 |
| ATOM | 4814 | CB | ASP | 703 | 59.790 | 24.391 | 58.010 | 1.00 | 9.22 | 0 |
| ATOM | 4815 | CG | ASP | 703 | 61.251 | 24.076 | 57.698 | 1.00 | 9.98 | 0 |
| ATOM | 4816 | OD1 | ASP | 703 | 62.126 | 24.940 | 57.943 | 1.00 | 9.22 | 0 |
| ATOM | 4817 | OD2 | ASP | 703 | 61.537 | 22.956 | 57.213 | 1.00 | 9.22 | 0 |
| ATOM | 4818 | C | ASP | 703 | 58.187 | 25.760 | 59.377 | 1.00 | 2.00 | 0 |
| ATOM | 4819 | O | ASP | 703 | 57.694 | 26.823 | 59.023 | 1.00 | 11.43 | 0 |
| ATOM | 4820 | N | LEU | 704 | 57.519 | 24.861 | 60.072 | 1.00 | 2.00 | 0 |
| ATOM | 4822 | CA | LEU | 704 | 56.113 | 25.051 | 60.391 | 1.00 | 2.00 | 0 |
| ATOM | 4823 | CB | LEU | 704 | 55.630 | 23.942 | 61.338 | 1.00 | 22.47 | 0 |
| ATOM | 4824 | CG | LEU | 704 | 55.412 | 22.533 | 60.780 | 1.00 | 21.16 | 0 |
| ATOM | 4825 | CD1 | LEU | 704 | 55.366 | 21.528 | 61.911 | 1.00 | 24.29 | 0 |
| ATOM | 4826 | CD2 | LEU | 704 | 54.132 | 22.489 | 59.973 | 1.00 | 22.40 | 0 |
| ATOM | 4827 | C | LEU | 704 | 55.809 | 26.417 | 61.006 | 1.00 | 2.00 | 0 |
| ATOM | 4828 | O | LEU | 704 | 54.736 | 26.979 | 60.773 | 1.00 | 15.38 | 0 |
| ATOM | 4829 | N | LEU | 705 | 56.757 | 26.967 | 61.763 | 1.00 | 39.58 | 0 |
| ATOM | 4831 | CA | LEU | 705 | 56.538 | 28.248 | 62.439 | 1.00 | 39.58 | 0 |
| ATOM | 4832 | CB | LEU | 705 | 56.884 | 28.108 | 63.913 | 1.00 | 2.00 | 0 |
| ATOM | 4833 | CG | LEU | 705 | 56.841 | 26.725 | 64.552 | 1.00 | 2.00 | 0 |
| ATOM | 4834 | CD1 | LEU | 705 | 57.376 | 26.870 | 65.950 | 1.00 | 2.00 | 0 |
| ATOM | 4835 | CD2 | LEU | 705 | 55.446 | 26.156 | 64.566 | 1.00 | 2.00 | 0 |
| ATOM | 4836 | C | LEU | 705 | 57.279 | 29.466 | 61.900 | 1.00 | 39.58 | 0 |
| ATOM | 4837 | O | LEU | 705 | 56.924 | 30.598 | 62.240 | 1.00 | 2.00 | 0 |
| ATOM | 4838 | N | TRP | 706 | 58.307 | 29.237 | 61.086 | 1.00 | 2.00 | 0 |
| ATOM | 4840 | CA | TRP | 706 | 59.117 | 30.319 | 60.523 | 1.00 | 2.00 | 0 |
| ATOM | 4841 | CB | TRP | 706 | 60.594 | 30.025 | 60.777 | 1.00 | 23.95 | 0 |
| ATOM | 4842 | CG | TRP | 706 | 61.025 | 30.261 | 62.165 | 1.00 | 23.95 | 0 |
| ATOM | 4843 | CD2 | TRP | 706 | 61.380 | 31.520 | 62.742 | 1.00 | 23.95 | 0 |
| ATOM | 4844 | CE2 | TRP | 706 | 61.735 | 31.278 | 64.083 | 1.00 | 23.95 | 0 |
| ATOM | 4845 | CE3 | TRP | 706 | 61.434 | 32.832 | 62.254 | 1.00 | 23.95 | 0 |
| ATOM | 4846 | CD1 | TRP | 706 | 61.173 | 29.329 | 63.150 | 1.00 | 23.95 | 0 |
| ATOM | 4847 | NE1 | TRP | 706 | 61.599 | 29.932 | 64.307 | 1.00 | 23.95 | 0 |
| ATOM | 4849 | CZ2 | TRP | 706 | 62.141 | 32.303 | 64.946 | 1.00 | 23.95 | 0 |
| ATOM | 4850 | CZ3 | TRP | 706 | 61.835 | 33.850 | 63.108 | 1.00 | 23.95 | 0 |
| ATOM | 4851 | CH2 | TRP | 706 | 62.184 | 33.580 | 64.439 | 1.00 | 23.95 | 0 |
| ATOM | 4852 | C | TRP | 706 | 58.947 | 30.619 | 59.028 | 1.00 | 2.00 | 0 |
| ATOM | 4853 | O | TRP | 706 | 59.186 | 31.751 | 58.598 | 1.00 | 23.95 | 0 |
| ATOM | 4854 | N | SER | 707 | 58.564 | 29.604 | 58.249 | 1.00 | 17.80 | 0 |
| ATOM | 4856 | CA | SER | 707 | 58.423 | 29.730 | 56.796 | 1.00 | 12.52 | 0 |
| ATOM | 4857 | CB | SER | 707 | 58.034 | 28.383 | 56.160 | 1.00 | 9.59 | 0 |
| ATOM | 4858 | OG | SER | 707 | 56.693 | 28.010 | 56.444 | 1.00 | 8.78 | 0 |
| ATOM | 4860 | C | SER | 707 | 57.459 | 30.806 | 56.328 | 1.00 | 18.86 | 0 |
| ATOM | 4861 | O | SER | 707 | 56.521 | 31.179 | 57.035 | 1.00 | 6.18 | 0 |
| ATOM | 4862 | N | ASP | 708 | 57.700 | 31.303 | 55.124 | 1.00 | 7.67 | 0 |
| ATOM | 4864 | CA | ASP | 708 | 56.860 | 32.328 | 54.547 | 1.00 | 7.67 | 0 |
| ATOM | 4865 | CB | ASP | 708 | 57.546 | 33.676 | 54.656 | 1.00 | 8.53 | 0 |
| ATOM | 4866 | CG | ASP | 708 | 57.720 | 34.104 | 56.079 | 1.00 | 10.12 | 0 |
| ATOM | 4867 | OD1 | ASP | 708 | 58.844 | 34.049 | 56.597 | 1.00 | 10.18 | 0 |
| ATOM | 4868 | OD2 | ASP | 708 | 56.717 | 34.483 | 56.689 | 1.00 | 10.95 | 0 |
| ATOM | 4869 | C | ASP | 708 | 56.609 | 31.998 | 53.104 | 1.00 | 7.67 | 0 |
| ATOM | 4870 | O | ASP | 708 | 57.461 | 31.432 | 52.444 | 1.00 | 11.43 | 0 |
| ATOM | 4871 | N | PRO | 709 | 55.425 | 32.328 | 52.596 | 1.00 | 2.00 | 0 |
| ATOM | 4872 | OD | PRO | 709 | 54.346 | 33.006 | 53.302 | 1.00 | 2.00 | 0 |
| ATOM | 4873 | CA | PRO | 709 | 55.029 | 32.078 | 51.214 | 1.00 | 2.00 | 0 |
| ATOM | 4874 | CB | PRO | 709 | 53.507 | 32.036 | 51.283 | 1.00 | 2.00 | 0 |
| ATOM | 4875 | CG | PRO | 709 | 53.169 | 32.316 | 52.728 | 1.00 | 2.00 | 0 |
| ATOM | 4876 | C | PRO | 709 | 55.475 | 33.269 | 50.406 | 1.00 | 2.00 | 0 |
| ATOM | 4877 | O | PRO | 709 | 55.071 | 34.393 | 50.712 | 1.00 | 2.00 | 0 |
| ATOM | 4878 | N | ASP | 710 | 56.306 | 33.046 | 49.393 | 1.00 | 2.57 | 0 |
| ATOM | 4880 | CA | ASP | 710 | 56.769 | 34.155 | 48.576 | 1.00 | 4.76 | 0 |
| ATOM | 4881 | CB | ASP | 710 | 58.297 | 34.215 | 48.537 | 1.00 | 18.70 | 0 |
| ATOM | 4882 | CG | ASP | 710 | 58.824 | 35.631 | 48.303 | 1.00 | 26.43 | 0 |
| ATOM | 4883 | OD1 | ASP | 710 | 58.070 | 36.497 | 47.793 | 1.00 | 26.58 | 0 |
| ATOM | 4884 | OD2 | ASP | 710 | 60.002 | 35.884 | 48.635 | 1.00 | 30.90 | 0 |
| ATOM | 4885 | C | ASP | 710 | 56.211 | 34.045 | 47.168 | 1.00 | 5.37 | 0 |
| ATOM | 4886 | O | ASP | 710 | 56.454 | 33.056 | 46.467 | 1.00 | 15.67 | 0 |
| ATOM | 4887 | N | LYS | 711 | 55.449 | 35.074 | 46.789 | 1.00 | 10.56 | 0 |
| ATOM | 4889 | CA | LYS | 711 | 54.802 | 35.217 | 45.480 | 1.00 | 16.19 | 0 |
| ATOM | 4890 | CB | LYS | 711 | 54.266 | 36.661 | 45.368 | 1.00 | 35.75 | 0 |
| ATOM | 4891 | CG | LYS | 711 | 53.743 | 37.109 | 44.007 | 1.00 | 43.76 | 0 |

TABLE A-continued

| ATOM | 4892 | CD | LYS | 711 | 54.843 | 37.750 | 43.146 | 1.00 | 49.83 | 0 |
|---|---|---|---|---|---|---|---|---|---|---|
| ATOM | 4893 | CE | LYS | 711 | 55.459 | 38.976 | 43.819 | 1.00 | 54.70 | 0 |
| ATOM | 4894 | NZ | LYS | 711 | 56.632 | 39.514 | 43.064 | 1.00 | 58.93 | 0 |
| ATOM | 4898 | C | LYS | 711 | 55.753 | 34.877 | 44.331 | 1.00 | 16.03 | 0 |
| ATOM | 4899 | O | LYS | 711 | 55.459 | 34.001 | 43.518 | 1.00 | 37.96 | 0 |
| ATOM | 4900 | N | ASP | 712 | 56.894 | 35.560 | 44.282 | 1.00 | 2.00 | 0 |
| ATOM | 4902 | CA | ASP | 712 | 57.890 | 35.330 | 43.252 | 1.00 | 2.00 | 0 |
| ATOM | 4903 | CB | ASP | 712 | 58.655 | 36.629 | 42.927 | 1.00 | 75.12 | 0 |
| ATOM | 4904 | CG | ASP | 712 | 59.362 | 37.231 | 44.134 | 1.00 | 75.41 | 0 |
| ATOM | 4905 | OD1 | ASP | 712 | 58.723 | 38.013 | 44.866 | 1.00 | 77.74 | 0 |
| ATOM | 4906 | OD2 | ASP | 712 | 60.561 | 36.937 | 44.341 | 1.00 | 84.37 | 0 |
| ATOM | 4907 | C | ASP | 712 | 58.863 | 34.189 | 43.597 | 1.00 | 2.00 | 0 |
| ATOM | 4908 | O | ASP | 712 | 60.083 | 34.366 | 43.607 | 1.00 | 77.12 | 0 |
| ATOM | 4909 | N | VAL | 713 | 58.298 | 33.016 | 43.866 | 1.00 | 27.09 | 0 |
| ATOM | 4911 | CA | VAL | 713 | 59.057 | 31.811 | 44.188 | 1.00 | 17.74 | 0 |
| ATOM | 4912 | CB | VAL | 713 | 59.166 | 31.579 | 45.727 | 1.00 | 2.00 | 0 |
| ATOM | 4913 | CG1 | VAL | 713 | 59.124 | 30.098 | 46.069 | 1.00 | 2.00 | 0 |
| ATOM | 4914 | CG2 | VAL | 713 | 60.481 | 32.120 | 46.224 | 1.00 | 2.00 | 0 |
| ATOM | 4915 | C | VAL | 713 | 58.319 | 30.653 | 43.538 | 1.00 | 21.93 | 0 |
| ATOM | 4916 | O | VAL | 713 | 57.092 | 30.567 | 43.593 | 1.00 | 2.00 | 0 |
| ATOM | 4917 | N | LEU | 714 | 59.063 | 29.766 | 42.903 | 1.00 | 15.32 | 0 |
| ATOM | 4919 | CA | LEU | 714 | 58.434 | 28.642 | 42.249 | 1.00 | 10.30 | 0 |
| ATOM | 4920 | CB | LEU | 714 | 59.285 | 28.147 | 41.078 | 1.00 | 48.90 | 0 |
| ATOM | 4921 | CG | LEU | 714 | 58.662 | 27.005 | 40.272 | 1.00 | 42.23 | 0 |
| ATOM | 4922 | CD1 | LEU | 714 | 57.229 | 27.357 | 39.909 | 1.00 | 43.72 | 0 |
| ATOM | 4923 | CD2 | LEU | 714 | 59.478 | 26.753 | 39.025 | 1.00 | 42.86 | 0 |
| ATOM | 4924 | C | LEU | 714 | 58.224 | 27.530 | 43.235 | 1.00 | 13.23 | 0 |
| ATOM | 4925 | O | LEU | 714 | 57.096 | 27.099 | 43.445 | 1.00 | 44.72 | 0 |
| ATOM | 4926 | N | GLY | 715 | 59.322 | 27.075 | 43.834 | 1.00 | 76.36 | 0 |
| ATOM | 4928 | CA | GLY | 715 | 59.263 | 25.995 | 44.800 | 1.00 | 76.36 | 0 |
| ATOM | 4929 | C | GLY | 715 | 59.630 | 26.420 | 46.206 | 1.00 | 76.36 | 0 |
| ATOM | 4930 | O | GLY | 715 | 58.814 | 26.974 | 46.929 | 1.00 | 19.62 | 0 |
| ATOM | 4931 | N | TRP | 716 | 60.875 | 26.183 | 46.583 | 1.00 | 4.87 | 0 |
| ATOM | 4932 | CA | TRP | 716 | 61.365 | 26.503 | 47.918 | 1.00 | 4.87 | 0 |
| ATOM | 4934 | CB | TRP | 716 | 61.944 | 25.241 | 48.554 | 1.00 | 2.00 | 0 |
| ATOM | 4935 | CG | TRP | 716 | 60.884 | 24.317 | 48.932 | 1.00 | 2.00 | 0 |
| ATOM | 4936 | CD2 | TRP | 716 | 59.936 | 24.529 | 49.962 | 1.00 | 2.00 | 0 |
| ATOM | 4937 | CE2 | TRP | 716 | 59.050 | 23.439 | 49.943 | 1.00 | 2.00 | 0 |
| ATOM | 4938 | CE3 | TRP | 716 | 59.750 | 25.541 | 50.909 | 1.00 | 2.00 | 0 |
| ATOM | 4939 | CD1 | TRP | 716 | 60.562 | 23.134 | 48.343 | 1.00 | 2.00 | 0 |
| ATOM | 4940 | NE1 | TRP | 716 | 59.454 | 22.597 | 48.940 | 1.00 | 2.00 | 0 |
| ATOM | 4942 | CZ2 | TRP | 716 | 57.994 | 23.334 | 50.830 | 1.00 | 2.00 | 0 |
| ATOM | 4943 | CZ3 | TRP | 716 | 58.715 | 25.438 | 51.783 | 1.00 | 2.00 | 0 |
| ATOM | 4944 | CH2 | TRP | 716 | 57.843 | 24.343 | 51.743 | 1.00 | 2.00 | 0 |
| ATOM | 4945 | C | TRP | 716 | 62.406 | 27.594 | 47.954 | 1.00 | 4.87 | 0 |
| ATOM | 4946 | O | TRP | 716 | 63.596 | 27.315 | 47.871 | 1.00 | 2.00 | 0 |
| ATOM | 4947 | N | GLY | 717 | 61.968 | 28.837 | 48.067 | 1.00 | 2.00 | 0 |
| ATOM | 4949 | CA | GLY | 717 | 62.911 | 29.937 | 48.124 | 1.00 | 2.00 | 0 |
| ATOM | 4950 | C | GLY | 717 | 63.725 | 30.031 | 49.414 | 1.00 | 2.00 | 0 |
| ATOM | 4951 | O | GLY | 717 | 63.443 | 29.343 | 50.404 | 1.00 | 2.00 | 0 |
| ATOM | 4952 | N | GLU | 718 | 64.752 | 30.880 | 49.387 | 1.00 | 4.99 | 0 |
| ATOM | 4954 | CA | GLU | 718 | 65.606 | 31.113 | 50.538 | 1.00 | 8.49 | 0 |
| ATOM | 4955 | CB | GLU | 718 | 66.980 | 31.619 | 50.092 | 1.00 | 86.14 | 0 |
| ATOM | 4956 | CG | GLU | 718 | 68.026 | 31.716 | 51.211 | 1.00 | 89.35 | 0 |
| ATOM | 4957 | CD | GLU | 718 | 68.627 | 30.371 | 51.633 | 1.00 | 87.67 | 0 |
| ATOM | 4958 | OE1 | GLU | 718 | 69.392 | 30.358 | 52.624 | 1.00 | 95.59 | 0 |
| ATOM | 4959 | OE2 | GLU | 718 | 68.353 | 29.336 | 50.986 | 1.00 | 88.92 | 0 |
| ATOM | 4960 | C | GLU | 718 | 64.883 | 32.182 | 51.340 | 1.00 | 9.60 | 0 |
| ATOM | 4961 | O | GLU | 718 | 64.597 | 33.269 | 50.828 | 1.00 | 90.23 | 0 |
| ATOM | 4962 | N | ASN | 719 | 64.560 | 31.863 | 52.590 | 1.00 | 32.81 | 0 |
| ATOM | 4964 | CA | ASN | 719 | 63.848 | 32.804 | 53.444 | 1.00 | 33.93 | 0 |
| ATOM | 4965 | CB | ASN | 719 | 63.159 | 32.083 | 54.591 | 1.00 | 14.30 | 0 |
| ATOM | 4966 | CG | ASN | 719 | 62.159 | 32.965 | 55.296 | 1.00 | 14.30 | 0 |
| ATOM | 4967 | OD1 | ASN | 719 | 62.533 | 33.912 | 55.983 | 1.00 | 14.30 | 0 |
| ATOM | 4968 | ND2 | ASN | 719 | 60.879 | 32.676 | 55.110 | 1.00 | 14.30 | 0 |
| ATOM | 4971 | C | ASN | 719 | 64.781 | 33.855 | 54.007 | 1.00 | 33.45 | 0 |
| ATOM | 4972 | O | ASN | 719 | 65.825 | 33.529 | 54.566 | 1.00 | 14.30 | 0 |
| ATOM | 4973 | N | ASP | 720 | 64.388 | 35.117 | 53.878 | 1.00 | 42.61 | 0 |
| ATOM | 4975 | CA | ASP | 720 | 65.212 | 36.222 | 54.351 | 1.00 | 47.00 | 0 |
| ATOM | 4976 | CB | ASP | 720 | 64.744 | 37.535 | 53.706 | 1.00 | 77.30 | 0 |
| ATOM | 4977 | CG | ASP | 720 | 65.025 | 37.574 | 52.200 | 1.00 | 92.85 | 0 |
| ATOM | 4978 | OD1 | ASP | 720 | 66.104 | 38.071 | 51.801 | 1.00 | 92.39 | 0 |
| ATOM | 4979 | OD2 | ASP | 720 | 64.172 | 37.094 | 51.416 | 1.00 | 90.51 | 0 |
| ATOM | 4980 | C | ASP | 720 | 65.328 | 36.352 | 55.869 | 1.00 | 39.89 | 0 |
| ATOM | 4981 | O | ASP | 720 | 66.255 | 36.986 | 56.370 | 1.00 | 74.64 | 0 |
| ATOM | 4992 | N | ARG | 721 | 64.411 | 35.728 | 56.602 | 1.00 | 13.83 | 0 |
| ATOM | 4994 | CA | ARG | 721 | 64.446 | 35.759 | 58.060 | 1.00 | 12.18 | 0 |
| ATOM | 4985 | CB | ARG | 721 | 63.262 | 35.007 | 58.649 | 1.00 | 15.37 | 0 |
| ATOM | 4986 | CG | ARG | 721 | 61.946 | 35.693 | 58.572 | 1.00 | 7.28 | 0 |

TABLE A-continued

| ATOM | 4987 | CD | ARG | 721 | 60.950 | 34.836 | 59.300 | 1.00 | 7.28 | 0 |
| --- | --- | --- | --- | --- | --- | --- | --- | --- | --- | --- |
| ATOM | 4988 | NE | ARG | 721 | 59.593 | 35.306 | 59.103 | 1.00 | 8.88 | 0 |
| ATOM | 4990 | CZ | ARG | 721 | 59.051 | 36.315 | 59.766 | 1.00 | 9.83 | 0 |
| ATOM | 4991 | NH1 | ARG | 721 | 59.751 | 36.965 | 60.690 | 1.00 | 8.95 | 0 |
| ATOM | 4994 | NH2 | ARG | 721 | 57.809 | 36.682 | 59.485 | 1.00 | 8.62 | 0 |
| ATOM | 4997 | C | ARG | 721 | 65.710 | 35.093 | 58.592 | 1.00 | 8.44 | 0 |
| ATOM | 4998 | O | ARG | 721 | 65.982 | 35.142 | 59.798 | 1.00 | 10.25 | 0 |
| ATOM | 4999 | N | GLY | 722 | 66.449 | 34.437 | 57.697 | 1.00 | 4.85 | 0 |
| ATOM | 5001 | CA | GLY | 722 | 67.668 | 33.752 | 58.083 | 1.00 | 4.85 | 0 |
| ATOM | 5002 | C | GLY | 722 | 67.392 | 32.344 | 58.592 | 1.00 | 4.85 | 0 |
| ATOM | 5003 | O | GLY | 722 | 68.305 | 31.655 | 59.052 | 1.00 | 76.68 | 0 |
| ATOM | 5004 | N | VAL | 723 | 66.134 | 31.918 | 58.508 | 1.00 | 10.85 | 0 |
| ATOM | 5006 | CA | VAL | 723 | 65.717 | 30.591 | 58.958 | 1.00 | 10.85 | 0 |
| ATOM | 5007 | CB | VAL | 723 | 65.259 | 30.574 | 60.471 | 1.00 | 2.00 | 0 |
| ATOM | 5008 | CG1 | VAL | 723 | 66.449 | 30.400 | 61.386 | 1.00 | 2.00 | 0 |
| ATOM | 5009 | CG2 | VAL | 723 | 64.504 | 31.858 | 60.825 | 1.00 | 2.00 | 0 |
| ATOM | 5010 | C | VAL | 723 | 64.546 | 30.100 | 58.105 | 1.00 | 10.85 | 0 |
| ATOM | 5011 | O | VAL | 723 | 63.667 | 30.883 | 57.714 | 1.00 | 2.00 | 0 |
| ATOM | 5012 | N | SER | 724 | 64.541 | 28.802 | 57.824 | 1.00 | 42.15 | 0 |
| ATOM | 5014 | CA | SER | 724 | 63.479 | 28.193 | 57.040 | 1.00 | 42.15 | 0 |
| ATOM | 5015 | CB | SER | 724 | 62.127 | 28.609 | 57.623 | 1.00 | 2.00 | 0 |
| ATOM | 5016 | OG | SER | 724 | 61.077 | 27.808 | 57.106 | 1.00 | 2.00 | 0 |
| ATOM | 5018 | C | SER | 724 | 63.583 | 28.588 | 55.561 | 1.00 | 42.15 | 0 |
| ATOM | 5019 | O | SER | 724 | 64.680 | 28.820 | 55.049 | 1.00 | 2.00 | 0 |
| ATOM | 5020 | N | PHE | 725 | 62.454 | 28.643 | 54.863 | 1.00 | 2.00 | 0 |
| ATOM | 5022 | CA | PHE | 725 | 62.464 | 29.007 | 53.457 | 1.00 | 2.00 | 0 |
| ATOM | 5023 | CB | PHE | 725 | 62.461 | 27.779 | 52.541 | 1.00 | 2.00 | 0 |
| ATOM | 5024 | CG | PHE | 725 | 62.891 | 26.551 | 53.205 | 1.00 | 2.00 | 0 |
| ATOM | 5025 | CD1 | PHE | 725 | 62.047 | 25.916 | 54.089 | 1.00 | 2.00 | 0 |
| ATOM | 5026 | CD2 | PHE | 725 | 64.151 | 26.044 | 52.984 | 1.00 | 2.00 | 0 |
| ATOM | 5027 | CE1 | PHE | 725 | 62.458 | 24.791 | 54.750 | 1.00 | 2.00 | 0 |
| ATOM | 5028 | CE2 | PHE | 725 | 64.578 | 24.906 | 53.646 | 1.00 | 2.00 | 0 |
| ATOM | 5029 | CZ | PHE | 725 | 63.733 | 24.280 | 54.530 | 1.00 | 2.00 | 0 |
| ATOM | 5030 | C | PHE | 725 | 61.222 | 29.787 | 53.146 | 1.00 | 2.00 | 0 |
| ATOM | 5031 | O | PHE | 725 | 60.382 | 30.040 | 54.009 | 1.00 | 2.00 | 0 |
| ATOM | 5032 | N | THR | 726 | 61.132 | 30.162 | 51.886 | 1.00 | 34.54 | 0 |
| ATOM | 5034 | CA | THR | 726 | 60.009 | 30.877 | 51.357 | 1.00 | 30.82 | 0 |
| ATOM | 5035 | CB | THR | 726 | 60.468 | 32.154 | 50.661 | 1.00 | 2.00 | 0 |
| ATOM | 5036 | OG1 | THR | 726 | 61.880 | 32.098 | 50.406 | 1.00 | 2.00 | 0 |
| ATOM | 5038 | CG2 | THR | 726 | 60.222 | 33.327 | 51.561 | 1.00 | 2.00 | 0 |
| ATOM | 5039 | C | THR | 726 | 59.450 | 29.866 | 50.382 | 1.00 | 34.20 | 0 |
| ATOM | 5040 | O | THR | 726 | 60.201 | 29.208 | 49.684 | 1.00 | 2.00 | 0 |
| ATOM | 5041 | N | PHE | 727 | 58.144 | 29.685 | 50.375 | 1.00 | 2.00 | 0 |
| ATOM | 5043 | CA | PHE | 727 | 57.555 | 28.712 | 49.483 | 1.00 | 2.00 | 0 |
| ATOM | 5044 | CB | PHE | 727 | 56.852 | 27.612 | 50.275 | 1.00 | 9.97 | 0 |
| ATOM | 5045 | CG | PHE | 727 | 55.698 | 28.096 | 51.105 | 1.00 | 15.33 | 0 |
| ATOM | 5046 | CD1 | PHE | 727 | 54.394 | 27.922 | 50.666 | 1.00 | 9.89 | 0 |
| ATOM | 5047 | CD2 | PHE | 727 | 55.916 | 28.726 | 52.323 | 1.00 | 15.65 | 0 |
| ATOM | 5048 | CE1 | PHE | 727 | 53.338 | 28.360 | 51.418 | 1.00 | 11.89 | 0 |
| ATOM | 5049 | CE2 | PHE | 727 | 54.852 | 29.171 | 53.087 | 1.00 | 6.87 | 0 |
| ATOM | 5050 | CZ | PHE | 727 | 53.563 | 28.986 | 52.631 | 1.00 | 11.72 | 0 |
| ATOM | 5051 | C | PHE | 727 | 56.580 | 29.398 | 48.553 | 1.00 | 2.00 | 0 |
| ATOM | 5052 | O | PHE | 727 | 55.848 | 30.312 | 48.982 | 1.00 | 18.77 | 0 |
| ATOM | 5053 | N | GLY | 728 | 56.576 | 28.956 | 47.289 | 1.00 | 13.14 | 0 |
| ATOM | 5055 | CA | GLY | 728 | 55.709 | 29.542 | 46.277 | 1.00 | 12.12 | 0 |
| ATOM | 5056 | C | GLY | 728 | 54.348 | 28.894 | 46.174 | 1.00 | 13.69 | 0 |
| ATOM | 5057 | O | GLY | 728 | 54.062 | 27.913 | 46.862 | 1.00 | 2.00 | 0 |
| ATOM | 5058 | N | ALA | 729 | 53.513 | 29.436 | 45.292 | 1.00 | 33.39 | 0 |
| ATOM | 5060 | CA | ALA | 729 | 52.161 | 28.916 | 45.080 | 1.00 | 33.11 | 0 |
| ATOM | 5061 | CB | ALA | 729 | 51.375 | 29.862 | 44.200 | 1.00 | 16.31 | 0 |
| ATOM | 5062 | C | ALA | 729 | 52.139 | 27.507 | 44.485 | 1.00 | 31.34 | 0 |
| ATOM | 5063 | O | ALA | 729 | 51.143 | 26.796 | 44.600 | 1.00 | 16.31 | 0 |
| ATOM | 5064 | N | GLU | 730 | 53.221 | 27.105 | 43.831 | 1.00 | 22.53 | 0 |
| ATOM | 5066 | CA | GLU | 730 | 53.284 | 25.761 | 43.281 | 1.00 | 26.87 | 0 |
| ATOM | 5067 | CB | GLU | 730 | 54.622 | 25.551 | 42.570 | 1.00 | 59.75 | 0 |
| ATOM | 5068 | CG | GLU | 730 | 54.893 | 24.117 | 42.142 | 1.00 | 62.63 | 0 |
| ATOM | 5069 | CD | GLU | 730 | 56.138 | 23.984 | 41.283 | 1.00 | 68.00 | 0 |
| ATOM | 5070 | OE1 | GLU | 730 | 57.213 | 23.624 | 41.822 | 1.00 | 74.97 | 0 |
| ATOM | 5071 | OE2 | GLU | 730 | 56.034 | 24.238 | 40.063 | 1.00 | 67.31 | 0 |
| ATOM | 5072 | C | GLU | 730 | 53.140 | 24.781 | 44.446 | 1.00 | 24.85 | 0 |
| ATOM | 5073 | O | GLU | 730 | 52.285 | 23.899 | 44.425 | 1.00 | 58.27 | 0 |
| ATOM | 5074 | N | VAL | 731 | 53.958 | 24.989 | 45.477 | 1.00 | 24.13 | 0 |
| ATOM | 5076 | CA | VAL | 731 | 53.985 | 24.157 | 46.679 | 1.00 | 19.42 | 0 |
| ATOM | 5077 | CB | VAL | 731 | 55.079 | 24.628 | 47.645 | 1.00 | 19.11 | 0 |
| ATOM | 5078 | CG1 | VAL | 731 | 55.159 | 23.699 | 48.824 | 1.00 | 19.11 | 0 |
| ATOM | 5079 | CG2 | VAL | 731 | 56.412 | 24.691 | 46.942 | 1.00 | 19.11 | 0 |
| ATOM | 5080 | C | VAL | 731 | 52.659 | 24.165 | 47.423 | 1.00 | 16.89 | 0 |
| ATOM | 5081 | O | VAL | 731 | 52.210 | 23.128 | 47.900 | 1.00 | 19.11 | 0 |
| ATOM | 5082 | N | VAL | 732 | 52.035 | 25.332 | 47.525 | 1.00 | 15.54 | 0 |

TABLE A-continued

| ATOM | 5084 | CA | VAL | 732 | 50.750 | 25.449 | 48.209 | 1.00 | 15.54 | 0 |
|---|---|---|---|---|---|---|---|---|---|---|
| ATOM | 5085 | CB | VAL | 732 | 50.254 | 26.898 | 48.240 | 1.00 | 20.17 | 0 |
| ATOM | 5086 | CG1 | VAL | 732 | 48.907 | 26.985 | 48.962 | 1.00 | 20.17 | 0 |
| ATOM | 5087 | CG2 | VAL | 732 | 51.272 | 27.764 | 48.902 | 1.00 | 20.17 | 0 |
| ATOM | 5088 | C | VAL | 732 | 49.653 | 24.609 | 47.554 | 1.00 | 15.54 | 0 |
| ATOM | 5089 | O | VAL | 732 | 49.011 | 23.791 | 48.222 | 1.00 | 20.17 | 0 |
| ATOM | 5090 | N | ALA | 733 | 49.437 | 24.822 | 46.253 | 1.00 | 16.29 | 0 |
| ATOM | 5092 | CA | ALA | 733 | 48.408 | 24.109 | 45.501 | 1.00 | 16.29 | 0 |
| ATOM | 5093 | CB | ALA | 733 | 48.260 | 24.717 | 44.131 | 1.00 | 17.33 | 0 |
| ATOM | 5094 | C | ALA | 733 | 48.703 | 22.618 | 45.390 | 1.00 | 16.29 | 0 |
| ATOM | 5095 | O | ALA | 733 | 47.776 | 21.795 | 45.349 | 1.00 | 17.78 | 0 |
| ATOM | 5096 | N | LYS | 734 | 49.996 | 22.287 | 45.348 | 1.00 | 2.00 | 0 |
| ATOM | 5098 | CA | LYS | 734 | 50.499 | 20.905 | 45.259 | 1.00 | 2.00 | 0 |
| ATOM | 5099 | CB | LYS | 734 | 52.012 | 20.936 | 45.015 | 1.00 | 23.03 | 0 |
| ATOM | 5100 | CG | LYS | 734 | 52.507 | 20.244 | 43.759 | 1.00 | 25.55 | 0 |
| ATOM | 5101 | CD | LYS | 734 | 52.696 | 21.212 | 42.594 | 1.00 | 35.13 | 0 |
| ATOM | 5102 | CE | LYS | 734 | 53.613 | 20.608 | 41.521 | 1.00 | 40.96 | 0 |
| ATOM | 5103 | NZ | LYS | 734 | 55.006 | 20.311 | 42.001 | 1.00 | 46.09 | 0 |
| ATOM | 5107 | C | LYS | 734 | 50.222 | 20.146 | 46.578 | 1.00 | 2.00 | 0 |
| ATOM | 5108 | O | LYS | 734 | 49.995 | 18.926 | 46.591 | 1.00 | 16.68 | 0 |
| ATOM | 5109 | N | PHE | 735 | 50.263 | 20.915 | 47.670 | 1.00 | 36.96 | 0 |
| ATOM | 5111 | CA | PHE | 735 | 50.036 | 20.478 | 49.047 | 1.00 | 33.73 | 0 |
| ATOM | 5112 | CB | PHE | 735 | 50.606 | 21.554 | 49.991 | 1.00 | 8.60 | 0 |
| ATOM | 5113 | CG | PHE | 735 | 50.320 | 21.323 | 51.465 | 1.00 | 8.60 | 0 |
| ATOM | 5114 | CD1 | PHE | 735 | 50.955 | 20.298 | 52.169 | 1.00 | 8.60 | 0 |
| ATOM | 5115 | CD2 | PHE | 735 | 49.412 | 22.135 | 52.142 | 1.00 | 8.60 | 0 |
| ATOM | 5116 | CE1 | PHE | 735 | 50.690 | 20.086 | 53.512 | 1.00 | 8.60 | 0 |
| ATOM | 5117 | CE2 | PHE | 735 | 49.143 | 21.929 | 53.483 | 1.00 | 8.60 | 0 |
| ATOM | 5118 | CZ | PHE | 735 | 49.784 | 20.900 | 54.168 | 1.00 | 8.60 | 0 |
| ATOM | 5119 | C | PHE | 735 | 46.546 | 20.256 | 49.334 | 1.00 | 34.15 | 0 |
| ATOM | 5120 | O | PHE | 735 | 48.151 | 19.181 | 49.801 | 1.00 | 8.60 | 0 |
| ATOM | 5121 | N | LEU | 736 | 47.731 | 21.281 | 49.075 | 1.00 | 2.00 | 0 |
| ATOM | 5123 | CA | LEU | 736 | 46.289 | 21.208 | 49.299 | 1.00 | 2.00 | 0 |
| ATOM | 5124 | CB | LEU | 736 | 45.599 | 22.451 | 48.770 | 1.00 | 2.00 | 0 |
| ATOM | 5125 | CG | LEU | 736 | 45.937 | 23.760 | 49.456 | 1.00 | 2.00 | 0 |
| ATOM | 5126 | CD1 | LEU | 736 | 45.314 | 24.887 | 48.689 | 1.00 | 2.00 | 0 |
| ATOM | 5127 | CD2 | LEU | 736 | 45.415 | 23.743 | 50.896 | 1.00 | 2.00 | 0 |
| ATOM | 5128 | C | LEU | 736 | 45.741 | 20.014 | 48.567 | 1.00 | 2.00 | 0 |
| ATOM | 5129 | O | LEU | 736 | 44.986 | 19.215 | 49.121 | 1.00 | 2.00 | 0 |
| ATOM | 5130 | N | HIS | 737 | 46.147 | 19.906 | 47.308 | 1.00 | 25.73 | 0 |
| ATOM | 5132 | CA | HIS | 737 | 45.747 | 18.818 | 46.427 | 1.00 | 25.73 | 0 |
| ATOM | 5133 | CB | HIS | 737 | 46.423 | 19.037 | 45.057 | 1.00 | 69.97 | 0 |
| ATOM | 5134 | CG | HIS | 737 | 46.638 | 17.784 | 44.263 | 1.00 | 68.65 | 0 |
| ATOM | 5135 | CD2 | HIS | 737 | 47.779 | 17.169 | 43.868 | 1.00 | 71.13 | 0 |
| ATOM | 5136 | ND1 | HIS | 737 | 45.601 | 17.012 | 43.783 | 1.00 | 76.45 | 0 |
| ATOM | 5138 | CE1 | HIS | 737 | 46.093 | 15.974 | 43.129 | 1.00 | 76.42 | 0 |
| ATOM | 5139 | NE2 | HIS | 737 | 47.412 | 16.046 | 43.166 | 1.00 | 74.54 | 0 |
| ATOM | 5141 | C | HIS | 737 | 46.088 | 17.440 | 47.037 | 1.00 | 25.73 | 0 |
| ATOM | 5142 | O | HIS | 737 | 45.223 | 16.570 | 47.166 | 1.00 | 61.28 | 0 |
| ATOM | 5143 | N | LYS | 738 | 47.347 | 17.266 | 47.422 | 1.00 | 11.82 | 0 |
| ATOM | 5145 | CA | LYS | 738 | 47.836 | 16.028 | 48.010 | 1.00 | 10.83 | 0 |
| ATOM | 5146 | CB | LYS | 738 | 49.343 | 16.163 | 48.256 | 1.00 | 10.15 | 0 |
| ATOM | 5147 | CG | LYS | 738 | 49.999 | 15.111 | 49.119 | 1.00 | 13.96 | 0 |
| ATOM | 5148 | CD | LYS | 738 | 51.516 | 15.253 | 49.005 | 1.00 | 16.98 | 0 |
| ATOM | 5149 | CE | LYS | 738 | 52.278 | 14.809 | 50.274 | 1.00 | 14.10 | 0 |
| ATOM | 5150 | NZ | LYS | 738 | 52.154 | 13.362 | 50.650 | 1.00 | 13.23 | 0 |
| ATOM | 5154 | C | LYS | 738 | 47.121 | 15.655 | 49.301 | 1.00 | 17.32 | 0 |
| ATOM | 5155 | O | LYS | 738 | 47.038 | 14.473 | 49.640 | 1.00 | 16.32 | 0 |
| ATOM | 5156 | N | HIS | 739 | 46.598 | 16.642 | 50.028 | 1.00 | 2.00 | 0 |
| ATOM | 5158 | CA | HIS | 739 | 45.935 | 16.319 | 51.284 | 1.00 | 2.00 | 0 |
| ATOM | 5159 | CB | HIS | 739 | 46.689 | 16.965 | 52.460 | 1.00 | 9.90 | 0 |
| ATOM | 5160 | CG | HIS | 739 | 48.099 | 16.482 | 52.597 | 1.00 | 8.91 | 0 |
| ATOM | 5161 | CD2 | HIS | 739 | 48.603 | 15.318 | 53.077 | 1.00 | 3.85 | 0 |
| ATOM | 5162 | ND1 | HIS | 739 | 49.182 | 17.212 | 52.148 | 1.00 | 7.65 | 0 |
| ATOM | 5164 | CE1 | HIS | 739 | 50.291 | 16.517 | 52.340 | 1.00 | 6.50 | 0 |
| ATOM | 5165 | NE2 | HIS | 739 | 49.966 | 15.364 | 52.901 | 1.00 | 3.85 | 0 |
| ATOM | 5167 | C | HIS | 739 | 44.442 | 16.598 | 51.378 | 1.00 | 2.00 | 0 |
| ATOM | 5168 | O | HIS | 739 | 43.913 | 16.722 | 52.477 | 1.00 | 18.58 | 0 |
| ATOM | 5169 | N | ASP | 740 | 43.763 | 16.678 | 50.236 | 1.00 | 2.00 | 0 |
| ATOM | 5171 | CA | ASP | 740 | 42.314 | 16.912 | 50.191 | 1.00 | 2.00 | 0 |
| ATOM | 5172 | CB | ASP | 740 | 41.567 | 15.695 | 50.758 | 1.00 | 37.08 | 0 |
| ATOM | 5173 | CG | ASP | 740 | 42.092 | 14.367 | 50.206 | 1.00 | 45.58 | 0 |
| ATOM | 5174 | OD1 | ASP | 740 | 42.974 | 13.754 | 50.856 | 1.00 | 45.42 | 0 |
| ATOM | 5175 | OD2 | ASP | 740 | 41.622 | 13.932 | 49.129 | 1.00 | 41.93 | 0 |
| ATOM | 5176 | C | ASP | 740 | 41.900 | 18.170 | 50.955 | 1.00 | 2.00 | 0 |
| ATOM | 5177 | O | ASP | 740 | 40.773 | 18.286 | 51.432 | 1.00 | 36.93 | 0 |
| ATOM | 5178 | N | LEU | 741 | 42.824 | 19.113 | 51.045 | 1.00 | 2.00 | 0 |
| ATOM | 5180 | CA | LEU | 741 | 42.610 | 20.357 | 51.764 | 1.00 | 2.00 | 0 |
| ATOM | 5181 | CB | LEU | 741 | 43.920 | 20.818 | 52.415 | 1.00 | 2.00 | 0 |

TABLE A-continued

| | | | | | | | | | |
|---|---|---|---|---|---|---|---|---|---|
| ATOM | 5182 | CG | LEU | 741 | 44.572 | 19.861 | 53.388 | 1.00 | 2.00 | 0 |
| ATOM | 5183 | CD1 | LEU | 741 | 45.906 | 20.394 | 53.859 | 1.00 | 2.00 | 0 |
| ATOM | 5184 | CD2 | LEU | 741 | 43.620 | 19.673 | 54.519 | 1.00 | 2.00 | 0 |
| ATOM | 5185 | C | LEU | 741 | 42.122 | 21.433 | 50.818 | 1.00 | 2.00 | 0 |
| ATOM | 5186 | O | LEU | 741 | 42.261 | 21.301 | 49.611 | 1.00 | 2.00 | 0 |
| ATOM | 5187 | N | ASP | 742 | 41.588 | 22.510 | 51.385 | 1.00 | 2.00 | 0 |
| ATOM | 5189 | CA | ASP | 742 | 41.080 | 23.620 | 50.607 | 1.00 | 2.00 | 0 |
| ATOM | 5190 | CB | ASP | 742 | 39.605 | 23.858 | 50.909 | 1.00 | 21.53 | 0 |
| ATOM | 5191 | CG | ASP | 742 | 38.717 | 22.741 | 50.433 | 1.00 | 26.90 | 0 |
| ATOM | 5192 | OD1 | ASP | 742 | 39.159 | 21.898 | 49.622 | 1.00 | 27.19 | 0 |
| ATOM | 5193 | OD2 | ASP | 742 | 37.555 | 22.714 | 50.876 | 1.00 | 25.88 | 0 |
| ATOM | 5194 | C | ASP | 742 | 41.810 | 24.913 | 50.887 | 1.00 | 2.00 | 0 |
| ATOM | 5195 | O | ASP | 742 | 42.064 | 25.698 | 49.970 | 1.00 | 14.77 | 0 |
| ATOM | 5196 | N | LEU | 743 | 42.141 | 25.152 | 52.149 | 1.00 | 5.78 | 0 |
| ATOM | 5198 | CA | LEU | 743 | 42.785 | 26.407 | 52.509 | 1.00 | 5.78 | 0 |
| ATOM | 5199 | CB | LEU | 743 | 41.744 | 27.312 | 53.185 | 1.00 | 2.00 | 0 |
| ATOM | 5200 | CG | LEU | 743 | 41.689 | 28.847 | 53.088 | 1.00 | 2.00 | 0 |
| ATOM | 5201 | CD1 | LEU | 743 | 40.947 | 29.364 | 54.297 | 1.00 | 2.00 | 0 |
| ATOM | 5202 | CD2 | LEU | 743 | 43.051 | 29.469 | 53.053 | 1.00 | 2.00 | 0 |
| ATOM | 5203 | C | LEU | 743 | 41.919 | 26.152 | 53.483 | 1.00 | 5.78 | 0 |
| ATOM | 5204 | O | LEU | 743 | 43.973 | 25.091 | 54.088 | 1.00 | 2.00 | 0 |
| ATOM | 5205 | N | ILE | 744 | 44.837 | 27.104 | 53.599 | 1.00 | 2.00 | 0 |
| ATOM | 5207 | CA | ILE | 744 | 45.916 | 27.031 | 54.574 | 1.00 | 2.00 | 0 |
| ATOM | 5208 | CB | ILE | 744 | 47.338 | 27.043 | 53.968 | 1.00 | 2.00 | 0 |
| ATOM | 5209 | CG2 | ILE | 744 | 48.360 | 27.214 | 55.089 | 1.00 | 2.00 | 0 |
| ATOM | 5210 | CG1 | ILE | 744 | 47.637 | 25.754 | 53.204 | 1.00 | 2.00 | 0 |
| ATOM | 5211 | CD1 | ILE | 744 | 49.117 | 25.602 | 52.856 | 1.00 | 2.00 | 0 |
| ATOM | 5212 | C | ILE | 744 | 45.770 | 28.330 | 55.356 | 1.00 | 2.00 | 0 |
| ATOM | 5213 | O | ILE | 744 | 45.830 | 29.423 | 54.788 | 1.00 | 2.00 | 0 |
| ATOM | 5214 | N | CYS | 745 | 45.557 | 28.226 | 56.655 | 1.00 | 71.57 | 0 |
| ATOM | 5216 | CA | CYS | 745 | 45.426 | 29.418 | 57.462 | 1.00 | 66.70 | 0 |
| ATOM | 5217 | CB | CYS | 745 | 44.204 | 29.301 | 58.363 | 1.00 | 17.55 | 0 |
| ATOM | 5218 | SG | CYS | 745 | 43.454 | 30.878 | 58.703 | 1.00 | 23.65 | 0 |
| ATOM | 5219 | C | CYS | 745 | 46.700 | 29.572 | 58.281 | 1.00 | 69.12 | 0 |
| ATOM | 5220 | O | CYS | 745 | 47.093 | 28.667 | 59.017 | 1.00 | 21.37 | 0 |
| ATOM | 5221 | N | ARG | 746 | 47.363 | 30.706 | 58.121 | 1.00 | 2.00 | 0 |
| ATOM | 5223 | CA | ARG | 746 | 48.594 | 30.982 | 58.837 | 1.00 | 2.00 | 0 |
| ATOM | 5224 | CB | ARG | 746 | 49.810 | 30.672 | 57.944 | 1.00 | 2.00 | 0 |
| ATOM | 5225 | CG | ARG | 746 | 49.860 | 31.394 | 56.609 | 1.00 | 2.00 | 0 |
| ATOM | 5226 | CD | ARG | 746 | 50.792 | 32.619 | 56.617 | 1.00 | 2.00 | 0 |
| ATOM | 5227 | NE | ARG | 746 | 52.220 | 32.293 | 56.560 | 1.00 | 2.00 | 0 |
| ATOM | 5229 | CZ | ARG | 746 | 53.212 | 33.184 | 56.626 | 1.00 | 2.00 | 0 |
| ATOM | 5230 | NH1 | ARG | 746 | 52.956 | 34.479 | 56.738 | 1.00 | 2.00 | 0 |
| ATOM | 5233 | NH2 | ARG | 746 | 54.468 | 32.778 | 56.603 | 1.00 | 2.00 | 0 |
| ATOM | 5236 | C | ARG | 746 | 48.597 | 32.439 | 59.271 | 1.00 | 2.00 | 0 |
| ATOM | 5237 | O | ARG | 746 | 47.739 | 33.220 | 58.847 | 1.00 | 2.00 | 0 |
| ATOM | 5238 | N | ALA | 747 | 49.524 | 32.802 | 60.146 | 1.00 | 2.00 | 0 |
| ATOM | 5240 | CA | ALA | 747 | 49.635 | 34.185 | 60.595 | 1.00 | 2.00 | 0 |
| ATOM | 5241 | CB | ALA | 747 | 49.410 | 34.264 | 62.106 | 1.00 | 2.00 | 0 |
| ATOM | 5242 | C | ALA | 747 | 51.073 | 34.588 | 60.193 | 1.00 | 2.00 | 0 |
| ATOM | 5243 | O | ALA | 747 | 51.378 | 34.658 | 58.999 | 1.00 | 2.00 | 0 |
| ATOM | 5244 | N | HIS | 748 | 51.943 | 34.854 | 61.168 | 1.00 | 2.00 | 0 |
| ATOM | 5246 | CA | HIS | 748 | 53.359 | 35.168 | 60.939 | 1.00 | 2.00 | 0 |
| ATOM | 5247 | C | HIS | 748 | 53.812 | 36.462 | 60.309 | 1.00 | 2.00 | 0 |
| ATOM | 5248 | O | HIS | 748 | 54.820 | 37.004 | 60.744 | 1.00 | 2.00 | 0 |
| ATOM | 5249 | CB | HIS | 748 | 54.032 | 34.028 | 60.187 | 1.00 | 2.00 | 0 |
| ATOM | 5250 | CG | HIS | 748 | 55.503 | 33.916 | 60.429 | 1.00 | 2.00 | 0 |
| ATOM | 5251 | ND1 | HIS | 748 | 56.023 | 33.803 | 61.694 | 1.00 | 2.00 | 0 |
| ATOM | 5252 | CE1 | HIS | 748 | 57.308 | 33.548 | 61.526 | 1.00 | 2.00 | 0 |
| ATOM | 5253 | CD2 | HIS | 748 | 56.493 | 33.737 | 59.527 | 1.00 | 2.00 | 0 |
| ATOM | 5254 | NE2 | HIS | 748 | 57.634 | 33.500 | 60.237 | 1.00 | 2.00 | 0 |
| ATOM | 5256 | N | GLN | 749 | 53.116 | 36.962 | 59.302 | 1.00 | 2.00 | 0 |
| ATOM | 5258 | CA | GLN | 749 | 53.556 | 38.197 | 58.677 | 1.00 | 2.00 | 0 |
| ATOM | 5259 | CB | GLN | 749 | 53.964 | 37.940 | 57.249 | 1.00 | 27.13 | 0 |
| ATOM | 5260 | CG | GLN | 749 | 55.257 | 37.222 | 57.143 | 1.00 | 28.03 | 0 |
| ATOM | 5261 | CD | GLN | 749 | 55.586 | 36.915 | 55.720 | 1.00 | 30.37 | 0 |
| ATOM | 5262 | OE1 | GLN | 749 | 56.425 | 37.580 | 55.107 | 1.00 | 30.92 | 0 |
| ATOM | 5263 | NE2 | GLN | 749 | 54.928 | 35.898 | 55.173 | 1.00 | 30.08 | 0 |
| ATOM | 5266 | C | GLN | 749 | 52.556 | 39.310 | 58.708 | 1.00 | 2.00 | 0 |
| ATOM | 5267 | O | GLN | 749 | 51.388 | 39.106 | 58.407 | 1.00 | 25.39 | 0 |
| ATOM | 5268 | N | VAL | 750 | 53.038 | 40.498 | 59.069 | 1.00 | 6.34 | 0 |
| ATOM | 5270 | CA | VAL | 750 | 52.193 | 41.682 | 59.157 | 1.00 | 6.34 | 0 |
| ATOM | 5271 | CB | VAL | 750 | 52.968 | 42.896 | 59.764 | 1.00 | 12.20 | 0 |
| ATOM | 5272 | CG1 | VAL | 750 | 54.183 | 43.216 | 58.935 | 1.00 | 12.20 | 0 |
| ATOM | 5273 | CG2 | VAL | 750 | 52.055 | 44.109 | 59.872 | 1.00 | 12.20 | 0 |
| ATOM | 5274 | C | VAL | 750 | 51.672 | 42.018 | 57.771 | 1.00 | 6.34 | 0 |
| ATOM | 5275 | O | VAL | 750 | 52.471 | 42.219 | 56.850 | 1.00 | 12.20 | 0 |
| ATOM | 5276 | N | VAL | 751 | 50.343 | 42.001 | 57.617 | 1.00 | 25.10 | 0 |
| ATOM | 5278 | CA | VAL | 751 | 49.685 | 42.327 | 56.348 | 1.00 | 25.10 | 0 |

TABLE A-continued

| ATOM | 5279 | CB | VAL | 751 | 48.617 | 41.298 | 55.902 | 1.00 | 2.00 | 0 |
| ATOM | 5280 | CG1 | VAL | 751 | 49.271 | 39.971 | 55.524 | 1.00 | 2.00 | 0 |
| ATOM | 5281 | CG2 | VAL | 751 | 47.570 | 41.138 | 56.976 | 1.00 | 2.00 | 0 |
| ATOM | 5282 | C | VAL | 751 | 48.996 | 43.654 | 56.540 | 1.00 | 25.10 | 0 |
| ATOM | 5283 | O | VAL | 751 | 48.606 | 43.995 | 57.646 | 1.00 | 2.00 | 0 |
| ATOM | 5284 | N | GLU | 752 | 48.820 | 44.389 | 55.453 | 1.00 | 2.00 | 0 |
| ATOM | 5286 | CA | GLU | 752 | 48.219 | 45.709 | 55.526 | 1.00 | 2.00 | 0 |
| ATOM | 5287 | CB | GLU | 752 | 48.430 | 46.435 | 54.190 | 1.00 | 39.24 | 0 |
| ATOM | 5288 | CG | GLU | 752 | 49.867 | 46.349 | 53.628 | 1.00 | 75.32 | 0 |
| ATOM | 5289 | CD | GLU | 752 | 50.962 | 46.804 | 54.611 | 1.00 | 75.31 | 0 |
| ATOM | 5290 | OE1 | GLU | 752 | 52.007 | 46.121 | 54.687 | 1.00 | 74.90 | 0 |
| ATOM | 5291 | OE2 | GLU | 752 | 50.792 | 47.837 | 55.300 | 1.00 | 91.76 | 0 |
| ATOM | 5292 | C | GLU | 752 | 46.744 | 45.716 | 55.913 | 1.00 | 2.00 | 0 |
| ATOM | 5293 | O | GLU | 752 | 46.326 | 46.469 | 56.796 | 1.00 | 38.94 | 0 |
| ATOM | 5294 | N | ASP | 753 | 45.968 | 44.860 | 55.259 | 1.00 | 31.76 | 0 |
| ATOM | 5296 | CA | ASP | 753 | 44.527 | 44.776 | 55.491 | 1.00 | 34.73 | 0 |
| ATOM | 5297 | CB | ASP | 753 | 43.787 | 44.470 | 54.170 | 1.00 | 79.26 | 0 |
| ATOM | 5298 | CG | ASP | 753 | 44.539 | 43.487 | 53.251 | 1.00 | 85.10 | 0 |
| ATOM | 5299 | OD1 | ASP | 753 | 44.040 | 43.240 | 52.130 | 1.00 | 88.01 | 0 |
| ATOM | 5300 | OD2 | ASP | 753 | 45.613 | 42.960 | 53.619 | 1.00 | 92.40 | 0 |
| ATOM | 5301 | C | ASP | 753 | 44.028 | 43.853 | 56.606 | 1.00 | 31.43 | 0 |
| ATOM | 5302 | O | ASP | 753 | 42.824 | 43.759 | 56.835 | 1.00 | 64.64 | 0 |
| ATOM | 5303 | N | GLY | 754 | 44.940 | 43.188 | 57.309 | 1.00 | 8.60 | 0 |
| ATOM | 5305 | CA | GLY | 754 | 44.535 | 42.309 | 58.393 | 1.00 | 5.10 | 0 |
| ATOM | 5306 | C | GLY | 754 | 44.577 | 40.849 | 58.007 | 1.00 | 3.66 | 0 |
| ATOM | 5307 | O | GLY | 754 | 44.781 | 39.959 | 58.853 | 1.00 | 2.00 | 0 |
| ATOM | 5308 | N | TYR | 755 | 44.361 | 40.611 | 56.718 | 1.00 | 27.09 | 0 |
| ATOM | 5310 | CA | TYR | 755 | 44.388 | 39.282 | 56.129 | 1.00 | 27.09 | 0 |
| ATOM | 5311 | CB | TYR | 755 | 43.004 | 38.632 | 56.128 | 1.00 | 28.14 | 0 |
| ATOM | 5312 | CG | TYR | 755 | 41.976 | 39.338 | 55.279 | 1.00 | 25.47 | 0 |
| ATOM | 5313 | CD1 | TYR | 755 | 41.236 | 40.393 | 55.797 | 1.00 | 23.65 | 0 |
| ATOM | 5314 | CE1 | TYR | 755 | 40.276 | 41.049 | 55.034 | 1.00 | 28.13 | 0 |
| ATOM | 5315 | CD2 | TYR | 755 | 41.736 | 38.949 | 53.964 | 1.00 | 30.24 | 0 |
| ATOM | 5316 | CE2 | TYR | 755 | 40.774 | 39.601 | 53.187 | 1.00 | 27.11 | 0 |
| ATOM | 5317 | CZ | TYR | 755 | 40.046 | 40.653 | 53.732 | 1.00 | 32.27 | 0 |
| ATOM | 5318 | OH | TYR | 755 | 39.086 | 41.311 | 52.996 | 1.00 | 28.90 | 0 |
| ATOM | 5320 | C | TYR | 755 | 44.844 | 39.530 | 54.713 | 1.00 | 27.09 | 0 |
| ATOM | 5321 | O | TYR | 755 | 44.772 | 40.654 | 54.238 | 1.00 | 25.53 | 0 |
| ATOM | 5322 | N | GLU | 756 | 45.288 | 38.483 | 54.035 | 1.00 | 8.71 | 0 |
| ATOM | 5324 | CA | GLU | 756 | 45.787 | 38.617 | 52.676 | 1.00 | 8.71 | 0 |
| ATOM | 5325 | CB | GLU | 756 | 47.170 | 39.251 | 52.740 | 1.00 | 5.76 | 0 |
| ATOM | 5326 | CG | GLU | 756 | 47.832 | 39.557 | 51.436 | 1.00 | 16.72 | 0 |
| ATOM | 5327 | CD | GLU | 756 | 49.127 | 40.303 | 51.671 | 1.00 | 23.34 | 0 |
| ATOM | 5328 | OE1 | GLU | 756 | 49.074 | 41.554 | 51.801 | 1.00 | 25.72 | 0 |
| ATOM | 5329 | OE2 | GLU | 756 | 50.194 | 39.636 | 51.751 | 1.00 | 25.15 | 0 |
| ATOM | 5330 | C | GLU | 756 | 45.853 | 37.240 | 52.044 | 1.00 | 8.71 | 0 |
| ATOM | 5331 | O | GLU | 756 | 46.400 | 36.306 | 52.638 | 1.00 | 6.14 | 0 |
| ATOM | 5332 | N | PHE | 757 | 45.269 | 37.105 | 50.858 | 1.00 | 28.33 | 0 |
| ATOM | 5334 | CA | PHE | 757 | 45.270 | 35.822 | 50.174 | 1.00 | 28.33 | 0 |
| ATOM | 5335 | CB | PHE | 757 | 44.055 | 35.683 | 49.253 | 1.00 | 2.00 | 0 |
| ATOM | 5336 | CG | PHE | 757 | 42.748 | 35.612 | 49.982 | 1.00 | 2.00 | 0 |
| ATOM | 5337 | CD1 | PHE | 757 | 41.961 | 36.747 | 50.137 | 1.00 | 2.00 | 0 |
| ATOM | 5338 | CD2 | PHE | 757 | 42.306 | 34.407 | 50.535 | 1.00 | 2.00 | 0 |
| ATOM | 5339 | CE1 | PHE | 757 | 40.751 | 36.695 | 50.833 | 1.00 | 2.00 | 0 |
| ATOM | 5340 | CE2 | PHE | 757 | 41.092 | 34.337 | 51.238 | 1.00 | 2.00 | 0 |
| ATOM | 5341 | CZ | PHE | 757 | 40.315 | 35.489 | 51.385 | 1.00 | 2.00 | 0 |
| ATOM | 5342 | C | PHE | 757 | 46.547 | 35.639 | 49.387 | 1.00 | 28.33 | 0 |
| ATOM | 5343 | O | PHE | 757 | 47.220 | 36.602 | 49.033 | 1.00 | 2.00 | 0 |
| ATOM | 5344 | N | PHE | 758 | 46.893 | 34.387 | 49.150 | 1.00 | 2.00 | 0 |
| ATOM | 5346 | CA | PHE | 758 | 48.075 | 34.050 | 48.397 | 1.00 | 2.00 | 0 |
| ATOM | 5347 | CB | PHE | 758 | 49.241 | 33.789 | 49.317 | 1.00 | 10.52 | 0 |
| ATOM | 5348 | CG | PHE | 758 | 50.450 | 33.263 | 48.618 | 1.00 | 7.54 | 0 |
| ATOM | 5349 | CD1 | PHE | 758 | 51.404 | 34.131 | 48.100 | 1.00 | 7.91 | 0 |
| ATOM | 5350 | CD2 | PHE | 758 | 50.654 | 31.895 | 48.492 | 1.00 | 7.80 | 0 |
| ATOM | 5351 | CE1 | PHE | 758 | 52.546 | 33.642 | 47.467 | 1.00 | 11.14 | 0 |
| ATOM | 5352 | CE2 | PHE | 758 | 51.796 | 31.398 | 47.858 | 1.00 | 11.57 | 0 |
| ATOM | 5353 | CZ | PHE | 758 | 52.741 | 32.272 | 47.347 | 1.00 | 10.83 | 0 |
| ATOM | 5354 | C | PHE | 758 | 47.725 | 32.786 | 47.636 | 1.00 | 2.00 | 0 |
| ATOM | 5355 | O | PHE | 758 | 46.826 | 32.034 | 48.042 | 1.00 | 13.46 | 0 |
| ATOM | 5356 | N | ALA | 759 | 48.415 | 32.573 | 46.518 | 1.00 | 17.88 | 0 |
| ATOM | 5358 | CA | ALA | 759 | 48.196 | 31.407 | 45.573 | 1.00 | 17.63 | 0 |
| ATOM | 5359 | CB | ALA | 759 | 48.767 | 30.155 | 46.334 | 1.00 | 2.00 | 0 |
| ATOM | 5360 | C | ALA | 759 | 46.733 | 31.180 | 45.314 | 1.00 | 19.54 | 0 |
| ATOM | 5361 | O | ALA | 759 | 46.187 | 30.106 | 45.547 | 1.00 | 2.00 | 0 |
| ATOM | 5362 | N | LYS | 760 | 46.086 | 32.205 | 44.786 | 1.00 | 3.38 | 0 |
| ATOM | 5364 | CA | LYS | 760 | 44.699 | 32.076 | 44.341 | 1.00 | 3.38 | 0 |
| ATOM | 5365 | CB | LYS | 760 | 44.639 | 31.068 | 43.184 | 1.00 | 64.10 | 0 |
| ATOM | 5366 | CG | LYS | 760 | 45.654 | 31.316 | 42.062 | 1.00 | 64.10 | 0 |
| ATOM | 5367 | CD | LYS | 760 | 45.843 | 30.068 | 41.205 | 1.00 | 64.10 | 0 |

TABLE A-continued

| ATOM | 5368 | CE | LYS | 760 | 44.506 | 29.540 | 40.699 | 1.00 | 64.10 | 0 |
| --- | --- | --- | --- | --- | --- | --- | --- | --- | --- | --- |
| ATOM | 5369 | NZ | LYS | 760 | 44.621 | 28.293 | 39.896 | 1.00 | 64.10 | 0 |
| ATOM | 5373 | C | LYS | 760 | 43.715 | 31.659 | 45.432 | 1.00 | 3.38 | 0 |
| ATOM | 5374 | O | LYS | 760 | 42.953 | 30.702 | 45.256 | 1.00 | 64.10 | 0 |
| ATOM | 5375 | N | ARG | 761 | 43.751 | 32.376 | 46.557 | 1.00 | 16.83 | 0 |
| ATOM | 5377 | CA | ARG | 761 | 42.869 | 32.139 | 47.721 | 1.00 | 16.83 | 0 |
| ATOM | 5378 | CB | ARG | 761 | 41.399 | 32.154 | 47.274 | 1.00 | 38.86 | 0 |
| ATOM | 5379 | CG | ARG | 761 | 41.012 | 33.375 | 46.458 | 1.00 | 38.86 | 0 |
| ATOM | 5380 | CD | ARG | 761 | 40.550 | 34.493 | 47.334 | 1.00 | 38.86 | 0 |
| ATOM | 5381 | NE | ARG | 761 | 40.635 | 35.785 | 46.669 | 1.00 | 38.86 | 0 |
| ATOM | 5383 | CZ | ARG | 761 | 39.799 | 36.793 | 46.898 | 1.00 | 38.86 | 0 |
| ATOM | 5384 | NH1 | ARG | 761 | 38.798 | 36.642 | 47.767 | 1.00 | 38.86 | 0 |
| ATOM | 5387 | NH2 | ARG | 761 | 39.988 | 37.963 | 46.291 | 1.00 | 38.86 | 0 |
| ATOM | 5390 | C | ARG | 761 | 43.145 | 30.844 | 48.508 | 1.00 | 16.83 | 0 |
| ATOM | 5391 | O | ARG | 761 | 42.596 | 30.639 | 49.585 | 1.00 | 38.86 | 0 |
| ATOM | 5392 | N | GLN | 762 | 44.021 | 30.002 | 47.971 | 1.00 | 24.54 | 0 |
| ATOM | 5394 | CA | GLN | 762 | 44.359 | 28.718 | 48.559 | 1.00 | 24.54 | 0 |
| ATOM | 5395 | CB | GLN | 762 | 45.167 | 27.908 | 47.553 | 1.00 | 19.81 | 0 |
| ATOM | 5396 | CG | GLN | 762 | 44.502 | 27.794 | 46.173 | 1.00 | 19.81 | 0 |
| ATOM | 5397 | CD | GLN | 762 | 45.309 | 26.959 | 45.196 | 1.00 | 19.81 | 0 |
| ATOM | 5398 | OE1 | GLN | 762 | 45.111 | 25.745 | 45.097 | 1.00 | 19.81 | 0 |
| ATOM | 5399 | NE2 | GLN | 762 | 46.230 | 27.596 | 44.476 | 1.00 | 19.81 | 0 |
| ATOM | 5402 | C | GLN | 762 | 45.126 | 28.856 | 49.857 | 1.00 | 24.54 | 0 |
| ATOM | 5403 | O | GLN | 762 | 45.278 | 27.893 | 50.599 | 1.00 | 19.81 | 0 |
| ATOM | 5404 | N | LEU | 763 | 45.631 | 30.053 | 50.119 | 1.00 | 2.00 | 0 |
| ATOM | 5406 | CA | LEU | 763 | 46.354 | 30.326 | 51.353 | 1.00 | 2.00 | 0 |
| ATOM | 5407 | CB | LEU | 763 | 47.882 | 30.319 | 51.127 | 1.00 | 13.68 | 0 |
| ATOM | 5408 | CG | LEU | 763 | 48.847 | 30.427 | 52.335 | 1.00 | 13.68 | 0 |
| ATOM | 5409 | CD1 | LEU | 763 | 50.117 | 29.641 | 52.066 | 1.00 | 13.68 | 0 |
| ATOM | 5410 | CD2 | LEU | 763 | 49.200 | 31.871 | 52.633 | 1.00 | 13.68 | 0 |
| ATOM | 5411 | C | LEU | 763 | 45.893 | 31.705 | 51.809 | 1.00 | 2.00 | 0 |
| ATOM | 5412 | O | LEU | 763 | 45.654 | 32.595 | 50.981 | 1.00 | 13.68 | 0 |
| ATOM | 5413 | N | VAL | 764 | 45.741 | 31.869 | 53.118 | 1.00 | 13.21 | 0 |
| ATOM | 5415 | CA | VAL | 764 | 45.340 | 33.140 | 53.680 | 1.00 | 13.65 | 0 |
| ATOM | 5416 | CB | VAL | 764 | 43.825 | 33.165 | 53.953 | 1.00 | 2.00 | 0 |
| ATOM | 5417 | CG1 | VAL | 764 | 43.452 | 32.097 | 54.933 | 1.00 | 2.00 | 0 |
| ATOM | 5418 | CG2 | VAL | 764 | 43.404 | 34.521 | 54.434 | 1.00 | 2.00 | 0 |
| ATOM | 5419 | C | VAL | 764 | 46.159 | 33.363 | 54.955 | 1.00 | 18.12 | 0 |
| ATOM | 5420 | O | VAL | 764 | 46.396 | 32.437 | 55.737 | 1.00 | 2.00 | 0 |
| ATOM | 5421 | N | THR | 765 | 46.646 | 34.587 | 55.111 | 1.00 | 2.00 | 0 |
| ATOM | 5423 | CA | THR | 765 | 47.453 | 34.992 | 56.254 | 1.00 | 2.00 | 0 |
| ATOM | 5424 | CB | THR | 765 | 48.731 | 35.660 | 55.798 | 1.00 | 2.00 | 0 |
| ATOM | 5425 | OG1 | THR | 765 | 49.474 | 34.740 | 54.991 | 1.00 | 2.00 | 0 |
| ATOM | 5427 | CG2 | THR | 765 | 49.542 | 36.119 | 56.973 | 1.00 | 2.00 | 0 |
| ATOM | 5428 | C | THR | 765 | 46.675 | 36.024 | 57.030 | 1.00 | 2.00 | 0 |
| ATOM | 5429 | O | THR | 765 | 46.201 | 37.016 | 56.454 | 1.00 | 2.00 | 0 |
| ATOM | 5430 | N | LEU | 766 | 46.549 | 35.797 | 58.333 | 1.00 | 5.65 | 0 |
| ATOM | 5432 | CA | LEU | 766 | 45.832 | 36.717 | 59.205 | 1.00 | 5.65 | 0 |
| ATOM | 5433 | CB | LEU | 766 | 44.848 | 35.943 | 60.059 | 1.00 | 2.00 | 0 |
| ATOM | 5434 | CG | LEU | 766 | 43.964 | 34.922 | 59.372 | 1.00 | 2.00 | 0 |
| ATOM | 5435 | CD1 | LEU | 766 | 43.703 | 33.794 | 60.327 | 1.00 | 2.00 | 0 |
| ATOM | 5436 | CD2 | LEU | 766 | 42.672 | 35.581 | 58.943 | 1.00 | 2.00 | 0 |
| ATOM | 5437 | C | LEU | 766 | 46.826 | 37.382 | 60.142 | 1.00 | 5.65 | 0 |
| ATOM | 5438 | O | LEU | 766 | 47.864 | 36.790 | 60.478 | 1.00 | 2.00 | 0 |
| ATOM | 5439 | N | PHE | 767 | 46.520 | 38.605 | 60.554 | 1.00 | 2.00 | 0 |
| ATOM | 5441 | CA | PHE | 767 | 47.342 | 39.320 | 61.530 | 1.00 | 2.00 | 0 |
| ATOM | 5442 | CB | PHE | 767 | 48.259 | 40.328 | 60.864 | 1.00 | 2.00 | 0 |
| ATOM | 5443 | CG | PHE | 767 | 49.494 | 40.612 | 61.649 | 1.00 | 2.00 | 0 |
| ATOM | 5444 | CD1 | PHE | 767 | 50.523 | 39.678 | 61.695 | 1.00 | 2.00 | 0 |
| ATOM | 5445 | CD2 | PHE | 767 | 49.647 | 41.811 | 62.317 | 1.00 | 2.00 | 0 |
| ATOM | 5446 | CE1 | PHE | 767 | 51.689 | 39.935 | 62.389 | 1.00 | 2.00 | 0 |
| ATOM | 5447 | CE2 | PHE | 767 | 50.813 | 42.078 | 63.018 | 1.00 | 2.00 | 0 |
| ATOM | 5448 | CZ | PHE | 767 | 51.838 | 41.134 | 63.050 | 1.00 | 2.00 | 0 |
| ATOM | 5449 | C | PHE | 767 | 46.325 | 40.033 | 62.418 | 1.00 | 2.00 | 0 |
| ATOM | 5450 | O | PHE | 767 | 45.957 | 41.184 | 62.171 | 1.00 | 2.00 | 0 |
| ATOM | 5451 | N | SER | 768 | 45.850 | 39.317 | 63.432 | 1.00 | 2.00 | 0 |
| ATOM | 5453 | CA | SER | 768 | 44.833 | 39.819 | 64.334 | 1.00 | 2.00 | 0 |
| ATOM | 5454 | CB | SER | 768 | 44.247 | 38.645 | 65.091 | 1.00 | 2.00 | 0 |
| ATOM | 5455 | OG | SER | 768 | 43.903 | 37.635 | 64.175 | 1.00 | 2.00 | 0 |
| ATOM | 5457 | C | SER | 768 | 45.261 | 40.872 | 65.336 | 1.00 | 2.00 | 0 |
| ATOM | 5458 | O | SER | 768 | 46.297 | 40.731 | 65.973 | 1.00 | 2.00 | 0 |
| ATOM | 5459 | N | ALA | 769 | 44.435 | 41.911 | 65.474 | 1.00 | 30.20 | 0 |
| ATOM | 5461 | CA | ALA | 769 | 44.619 | 43.009 | 66.428 | 1.00 | 27.69 | 0 |
| ATOM | 5462 | CB | ALA | 769 | 45.142 | 42.454 | 67.786 | 1.00 | 4.86 | 0 |
| ATOM | 5463 | C | ALA | 769 | 45.410 | 44.253 | 66.018 | 1.00 | 31.35 | 0 |
| ATOM | 5464 | O | ALA | 769 | 44.855 | 45.347 | 65.940 | 1.00 | 11.84 | 0 |
| ATOM | 5465 | N | PRO | 770 | 46.717 | 44.109 | 65.786 | 1.00 | 14.07 | 0 |
| ATOM | 5466 | CD | PRO | 770 | 47.556 | 42.904 | 65.939 | 1.00 | 2.00 | 0 |
| ATOM | 5467 | CA | PRO | 770 | 47.578 | 45.209 | 65.398 | 1.00 | 14.07 | 0 |

TABLE A-continued

| | | | | | | | | |
|---|---|---|---|---|---|---|---|---|
| ATOM | 5468 | CB | PRO | 770 | 48.615 | 44.494 | 64.540 | 1.00 | 2.00 | 0 |
| ATOM | 5469 | CG | PRO | 770 | 48.913 | 43.329 | 65.392 | 1.00 | 2.00 | 0 |
| ATOM | 5470 | C | PRO | 770 | 47.227 | 46.584 | 64.825 | 1.00 | 14.07 | 0 |
| ATOM | 5471 | O | PRO | 770 | 46.081 | 47.016 | 64.640 | 1.00 | 2.00 | 0 |
| ATOM | 5472 | N | ASN | 771 | 48.363 | 47.259 | 64.718 | 1.00 | 2.00 | 0 |
| ATOM | 5474 | CA | ASN | 771 | 48.703 | 48.578 | 64.220 | 1.00 | 2.00 | 0 |
| ATOM | 5475 | CB | ASN | 771 | 48.014 | 49.664 | 65.022 | 1.00 | 40.66 | 0 |
| ATOM | 5476 | CG | ASN | 771 | 48.270 | 51.032 | 64.457 | 1.00 | 47.17 | 0 |
| ATOM | 5477 | OD1 | ASN | 771 | 49.382 | 51.557 | 64.550 | 1.00 | 40.36 | 0 |
| ATOM | 5478 | ND2 | ASN | 771 | 47.249 | 51.617 | 63.841 | 1.00 | 43.79 | 0 |
| ATOM | 5481 | C | ASN | 771 | 50.174 | 48.414 | 64.666 | 1.00 | 2.00 | 0 |
| ATOM | 5482 | O | ASN | 771 | 50.811 | 49.318 | 65.208 | 1.00 | 50.90 | 0 |
| ATOM | 5483 | N | TYR | 772 | 50.657 | 47.191 | 64.417 | 1.00 | 6.11 | 0 |
| ATOM | 5485 | CA | TYR | 772 | 51.955 | 46.645 | 64.768 | 1.00 | 6.11 | 0 |
| ATOM | 5486 | CB | TYR | 772 | 52.366 | 45.641 | 63.705 | 1.00 | 8.06 | 0 |
| ATOM | 5487 | CG | TYR | 772 | 53.253 | 44.546 | 64.228 | 1.00 | 8.06 | 0 |
| ATOM | 5488 | CD1 | TYR | 772 | 52.992 | 43.949 | 65.453 | 1.00 | 8.06 | 0 |
| ATOM | 5489 | CE1 | TYR | 772 | 53.781 | 42.910 | 65.929 | 1.00 | 8.06 | 0 |
| ATOM | 5490 | CD2 | TYR | 772 | 54.335 | 44.084 | 63.487 | 1.00 | 8.06 | 0 |
| ATOM | 5491 | CE2 | TYR | 772 | 55.135 | 43.048 | 63.945 | 1.00 | 8.06 | 0 |
| ATOM | 5492 | CZ | TYR | 772 | 54.854 | 42.459 | 65.170 | 1.00 | 8.06 | 0 |
| ATOM | 5493 | OH | TYR | 772 | 55.634 | 41.403 | 65.632 | 1.00 | 8.06 | 0 |
| ATOM | 5495 | C | TYR | 772 | 53.130 | 47.557 | 65.074 | 1.00 | 6.11 | 0 |
| ATOM | 5496 | O | TYR | 772 | 53.499 | 48.428 | 64.271 | 1.00 | 19.22 | 0 |
| ATOM | 5497 | N | CYS | 773 | 53.724 | 47.335 | 66.244 | 1.00 | 15.64 | 0 |
| ATOM | 5499 | CA | CYS | 773 | 54.868 | 48.107 | 66.681 | 1.00 | 13.08 | 0 |
| ATOM | 5500 | CB | CYS | 773 | 56.059 | 47.798 | 65.777 | 1.00 | 21.47 | 0 |
| ATOM | 5501 | SG | CYS | 773 | 56.646 | 46.112 | 65.891 | 1.00 | 23.28 | 0 |
| ATOM | 5502 | C | CYS | 773 | 54.624 | 49.617 | 66.685 | 1.00 | 16.93 | 0 |
| ATOM | 5503 | O | CYS | 773 | 55.573 | 50.398 | 66.832 | 1.00 | 20.82 | 0 |
| ATOM | 5504 | N | GLY | 774 | 53.362 | 50.031 | 66.545 | 1.00 | 2.00 | 0 |
| ATOM | 5506 | CA | GLY | 774 | 53.059 | 51.452 | 66.482 | 1.00 | 2.00 | 0 |
| ATOM | 5507 | C | GLY | 774 | 53.821 | 52.023 | 65.288 | 1.00 | 2.00 | 0 |
| ATOM | 5508 | O | GLY | 774 | 54.051 | 53.233 | 65.188 | 1.00 | 60.37 | 0 |
| ATOM | 5509 | N | GLU | 775 | 54.219 | 51.130 | 64.383 | 1.00 | 22.26 | 0 |
| ATOM | 5511 | CA | GLU | 775 | 54.973 | 51.500 | 63.211 | 1.00 | 18.01 | 0 |
| ATOM | 5512 | CB | GLU | 775 | 56.253 | 50.683 | 63.133 | 1.00 | 40.50 | 0 |
| ATOM | 5513 | CG | GLU | 775 | 57.103 | 50.811 | 64.357 | 1.00 | 44.10 | 0 |
| ATOM | 5514 | CD | GLU | 775 | 58.496 | 50.246 | 64.190 | 1.00 | 42.58 | 0 |
| ATOM | 5515 | OE1 | GLU | 775 | 59.404 | 50.734 | 64.894 | 1.00 | 46.10 | 0 |
| ATOM | 5516 | OE2 | GLU | 775 | 58.687 | 49.324 | 63.367 | 1.00 | 44.55 | 0 |
| ATOM | 5517 | C | GLU | 775 | 54.181 | 51.268 | 61.945 | 1.00 | 16.06 | 0 |
| ATOM | 5518 | O | GLU | 775 | 54.133 | 52.117 | 61.051 | 1.00 | 34.47 | 0 |
| ATOM | 5519 | N | PHE | 776 | 53.530 | 50.125 | 61.874 | 1.00 | 21.64 | 0 |
| ATOM | 5521 | CA | PHE | 776 | 52.809 | 49.796 | 60.667 | 1.00 | 19.45 | 0 |
| ATOM | 5522 | CB | PHE | 776 | 52.828 | 48.279 | 60.517 | 1.00 | 7.64 | 0 |
| ATOM | 5523 | CG | PHE | 776 | 54.213 | 47.739 | 60.363 | 1.00 | 6.06 | 0 |
| ATOM | 5524 | CD1 | PHE | 776 | 54.056 | 47.656 | 61.452 | 1.00 | 6.54 | 0 |
| ATOM | 5525 | CD2 | PHE | 776 | 54.692 | 47.363 | 59.122 | 1.00 | 10.09 | 0 |
| ATOM | 5526 | CE1 | PHE | 776 | 56.370 | 47.206 | 61.313 | 1.00 | 6.06 | 0 |
| ATOM | 5527 | CE2 | PHE | 776 | 56.005 | 46.910 | 58.969 | 1.00 | 9.96 | 0 |
| ATOM | 5528 | CZ | PHE | 776 | 56.845 | 46.833 | 60.071 | 1.00 | 6.06 | 0 |
| ATOM | 5529 | C | PHE | 776 | 51.424 | 50.402 | 60.480 | 1.00 | 21.71 | 0 |
| ATOM | 5530 | O | PHE | 776 | 50.979 | 50.601 | 59.346 | 1.00 | 9.78 | 0 |
| ATOM | 5531 | N | ASP | 777 | 50.757 | 50.720 | 61.584 | 1.00 | 47.34 | 0 |
| ATOM | 5533 | CA | ASP | 777 | 49.427 | 51.322 | 61.532 | 1.00 | 47.73 | 0 |
| ATOM | 5534 | CB | ASP | 777 | 49.526 | 52.790 | 61.071 | 1.00 | 36.82 | 0 |
| ATOM | 5535 | CG | ASP | 777 | 50.299 | 53.677 | 62.059 | 1.00 | 86.03 | 0 |
| ATOM | 5536 | OD1 | ASP | 777 | 51.519 | 53.464 | 62.246 | 1.00 | 85.84 | 0 |
| ATOM | 5537 | OD2 | ASP | 777 | 49.685 | 54.595 | 62.644 | 1.00 | 85.92 | 0 |
| ATOM | 5538 | C | ASP | 777 | 48.456 | 50.547 | 60.632 | 1.00 | 47.70 | 0 |
| ATOM | 5539 | O | ASP | 777 | 47.458 | 51.095 | 60.164 | 1.00 | 37.69 | 0 |
| ATOM | 5540 | N | ASN | 778 | 48.756 | 49.268 | 60.419 | 1.00 | 12.97 | 0 |
| ATOM | 5542 | CA | ASN | 778 | 47.948 | 48.373 | 59.584 | 1.00 | 3.97 | 0 |
| ATOM | 5543 | CB | ASN | 778 | 48.760 | 47.123 | 59.221 | 1.00 | 17.34 | 0 |
| ATOM | 5544 | CG | ASN | 778 | 49.081 | 46.258 | 60.435 | 1.00 | 11.19 | 0 |
| ATOM | 5545 | OD1 | ASN | 778 | 49.928 | 46.613 | 61.275 | 1.00 | 10.18 | 0 |
| ATOM | 5546 | ND2 | ASN | 778 | 48.404 | 45.120 | 60.538 | 1.00 | 7.69 | 0 |
| ATOM | 5549 | C | ASN | 778 | 46.672 | 47.945 | 60.296 | 1.00 | 4.32 | 0 |
| ATOM | 5550 | O | ASN | 778 | 46.497 | 48.227 | 61.481 | 1.00 | 21.92 | 0 |
| ATOM | 5551 | N | ALA | 779 | 45.783 | 47.267 | 59.578 | 1.00 | 6.26 | 0 |
| ATOM | 5553 | CA | ALA | 779 | 44.537 | 46.799 | 60.168 | 1.00 | 6.26 | 0 |
| ATOM | 5554 | CB | ALA | 779 | 43.404 | 46.923 | 59.174 | 1.00 | 78.54 | 0 |
| ATOM | 5555 | C | ALA | 779 | 44.727 | 45.344 | 60.580 | 1.00 | 6.26 | 0 |
| ATOM | 5556 | O | ALA | 779 | 45.537 | 44.626 | 59.988 | 1.00 | 86.19 | 0 |
| ATOM | 5557 | N | GLY | 780 | 43.998 | 44.925 | 61.606 | 1.00 | 2.00 | 0 |
| ATOM | 5559 | CA | GLY | 780 | 44.091 | 43.560 | 62.077 | 1.00 | 2.00 | 0 |
| ATOM | 5560 | C | GLY | 780 | 42.800 | 42.848 | 61.747 | 1.00 | 2.00 | 0 |
| ATOM | 5561 | O | GLY | 780 | 41.725 | 43.433 | 61.869 | 1.00 | 21.77 | 0 |

TABLE A-continued

| ATOM | 5562 | N | ALA | 781 | 42.880 | 41.587 | 61.345 | 1.00 | 2.00 | 0 |
| --- | --- | --- | --- | --- | --- | --- | --- | --- | --- | --- |
| ATOM | 5564 | CA | ALA | 781 | 41.670 | 40.870 | 60.984 | 1.00 | 2.00 | 0 |
| ATOM | 5565 | CB | ALA | 781 | 41.671 | 40.567 | 59.492 | 1.00 | 14.58 | 0 |
| ATOM | 5566 | C | ALA | 781 | 41.474 | 39.587 | 61.763 | 1.00 | 2.00 | 0 |
| ATOM | 5567 | O | ALA | 781 | 42.396 | 39.076 | 62.398 | 1.00 | 14.58 | 0 |
| ATOM | 5568 | N | MET | 782 | 40.263 | 39.061 | 61.660 | 1.00 | 2.00 | 0 |
| ATOM | 5570 | CA | MET | 782 | 39.857 | 37.833 | 62.319 | 1.00 | 2.00 | 0 |
| ATOM | 5571 | CB | MET | 782 | 39.037 | 38.204 | 63.554 | 1.00 | 2.00 | 0 |
| ATOM | 5572 | CG | MET | 782 | 38.736 | 37.067 | 64.502 | 1.00 | 2.00 | 0 |
| ATOM | 5573 | SD | MET | 782 | 37.743 | 37.608 | 65.912 | 1.00 | 2.00 | 0 |
| ATOM | 5574 | CE | MET | 782 | 37.595 | 39.370 | 65.621 | 1.00 | 2.00 | 0 |
| ATOM | 5575 | C | MET | 782 | 39.010 | 37.029 | 61.306 | 1.00 | 2.00 | 0 |
| ATOM | 5576 | O | MET | 782 | 38.090 | 37.570 | 60.688 | 1.00 | 2.00 | 0 |
| ATOM | 5577 | N | MET | 783 | 39.325 | 35.752 | 61.116 | 1.00 | 2.00 | 0 |
| ATOM | 5579 | CA | MET | 783 | 38.570 | 34.955 | 60.165 | 1.00 | 2.00 | 0 |
| ATOM | 5580 | CB | MET | 783 | 39.482 | 34.182 | 59.209 | 1.00 | 16.43 | 0 |
| ATOM | 5581 | CG | MET | 783 | 38.688 | 33.363 | 58.165 | 1.00 | 19.34 | 0 |
| ATOM | 5582 | SD | MET | 783 | 39.689 | 32.337 | 57.060 | 1.00 | 18.69 | 0 |
| ATOM | 5583 | CE | MET | 783 | 39.780 | 30.793 | 57.975 | 1.00 | 21.53 | 0 |
| ATOM | 5584 | C | MET | 783 | 37.608 | 33.976 | 60.794 | 1.00 | 2.00 | 0 |
| ATOM | 5585 | O | MET | 783 | 38.004 | 33.010 | 61.447 | 1.00 | 10.33 | 0 |
| ATOM | 5586 | N | SER | 784 | 36.335 | 34.221 | 60.542 | 1.00 | 2.00 | 0 |
| ATOM | 5588 | CA | SER | 784 | 35.276 | 33.374 | 61.034 | 1.00 | 2.00 | 0 |
| ATOM | 5589 | CB | SER | 784 | 34.033 | 34.220 | 61.308 | 1.00 | 16.25 | 0 |
| ATOM | 5590 | OG | SER | 784 | 34.385 | 35.392 | 62.020 | 1.00 | 16.25 | 0 |
| ATOM | 5592 | C | SER | 784 | 34.953 | 32.301 | 59.990 | 1.00 | 2.00 | 0 |
| ATOM | 5593 | O | SER | 784 | 34.672 | 32.611 | 58.839 | 1.00 | 19.28 | 0 |
| ATOM | 5594 | N | VAL | 785 | 35.033 | 31.045 | 60.401 | 1.00 | 10.88 | 0 |
| ATOM | 5596 | CA | VAL | 785 | 34.706 | 29.907 | 59.557 | 1.00 | 16.53 | 0 |
| ATOM | 5597 | CB | VAL | 785 | 35.649 | 28.739 | 59.792 | 1.00 | 11.43 | 0 |
| ATOM | 5598 | CG1 | VAL | 785 | 35.183 | 27.538 | 58.975 | 1.00 | 11.43 | 0 |
| ATOM | 5599 | CG2 | VAL | 785 | 37.082 | 29.153 | 59.477 | 1.00 | 11.43 | 0 |
| ATOM | 5600 | C | VAL | 785 | 33.357 | 29.465 | 60.083 | 1.00 | 12.38 | 0 |
| ATOM | 5601 | O | VAL | 785 | 33.254 | 28.998 | 61.225 | 1.00 | 11.43 | 0 |
| ATOM | 5602 | N | ASP | 786 | 32.307 | 29.613 | 59.291 | 1.00 | 2.00 | 0 |
| ATOM | 5604 | CA | ASP | 786 | 31.024 | 29.200 | 59.807 | 1.00 | 2.00 | 0 |
| ATOM | 5605 | CB | ASP | 786 | 29.874 | 30.008 | 59.171 | 1.00 | 24.90 | 0 |
| ATOM | 5606 | CG | ASP | 786 | 28.403 | 29.458 | 57.842 | 1.00 | 30.71 | 0 |
| ATOM | 5607 | OD1 | ASP | 786 | 28.245 | 29.765 | 57.474 | 1.00 | 33.80 | 0 |
| ATOM | 5608 | OD2 | ASP | 786 | 30.165 | 28.737 | 57.163 | 1.00 | 32.56 | 0 |
| ATOM | 5609 | C | ASP | 786 | 30.860 | 27.699 | 59.656 | 1.00 | 2.00 | 0 |
| ATOM | 5610 | O | ASP | 786 | 31.677 | 27.029 | 59.031 | 1.00 | 23.30 | 0 |
| ATOM | 5611 | N | GLU | 787 | 29.803 | 27.195 | 60.268 | 1.00 | 7.48 | 0 |
| ATOM | 5613 | CA | GLU | 787 | 29.447 | 25.782 | 60.270 | 1.00 | 13.41 | 0 |
| ATOM | 5614 | CB | GLU | 787 | 27.983 | 25.636 | 60.696 | 1.00 | 2.00 | 0 |
| ATOM | 5615 | CG | GLU | 787 | 27.174 | 26.963 | 60.747 | 1.00 | 2.00 | 0 |
| ATOM | 5616 | CD | GLU | 787 | 27.384 | 27.758 | 62.053 | 1.00 | 2.00 | 0 |
| ATOM | 5617 | OE1 | GLU | 787 | 26.858 | 27.319 | 63.117 | 1.00 | 2.00 | 0 |
| ATOM | 5618 | OE2 | GLU | 787 | 28.070 | 28.817 | 62.024 | 1.00 | 2.00 | 0 |
| ATOM | 5619 | C | GLU | 787 | 29.665 | 25.015 | 58.965 | 1.00 | 11.86 | 0 |
| ATOM | 5620 | O | GLU | 787 | 30.002 | 23.830 | 58.994 | 1.00 | 2.00 | 0 |
| ATOM | 5621 | N | THR | 788 | 29.492 | 25.698 | 57.836 | 1.00 | 56.74 | 0 |
| ATOM | 5623 | CA | THR | 788 | 29.616 | 25.092 | 56.513 | 1.00 | 52.70 | 0 |
| ATOM | 5624 | CB | THR | 788 | 28.369 | 25.402 | 55.700 | 1.00 | 6.46 | 0 |
| ATOM | 5625 | OG1 | THR | 788 | 28.317 | 26.819 | 55.467 | 1.00 | 4.65 | 0 |
| ATOM | 5627 | CG2 | THR | 788 | 27.101 | 24.968 | 56.457 | 1.00 | 10.48 | 0 |
| ATOM | 5628 | C | THR | 788 | 30.835 | 25.536 | 55.683 | 1.00 | 51.86 | 0 |
| ATOM | 5629 | O | THR | 788 | 30.751 | 25.628 | 54.449 | 1.00 | 12.46 | 0 |
| ATOM | 5630 | N | LEU | 789 | 31.946 | 25.823 | 56.364 | 1.00 | 10.40 | 0 |
| ATOM | 5632 | CA | LEU | 789 | 33.194 | 26.245 | 55.734 | 1.00 | 6.34 | 0 |
| ATOM | 5633 | CB | LEU | 789 | 33.670 | 25.165 | 54.775 | 1.00 | 8.80 | 0 |
| ATOM | 5634 | CG | LEU | 789 | 34.458 | 24.017 | 55.405 | 1.00 | 15.93 | 0 |
| ATOM | 5635 | CD1 | LEU | 789 | 35.879 | 24.487 | 55.677 | 1.00 | 11.55 | 0 |
| ATOM | 5636 | CD2 | LEU | 789 | 33.785 | 23.525 | 56.682 | 1.00 | 14.98 | 0 |
| ATOM | 5637 | C | LEU | 789 | 33.173 | 27.619 | 55.042 | 1.00 | 4.53 | 0 |
| ATOM | 5638 | O | LEU | 789 | 34.065 | 27.948 | 54.248 | 1.00 | 8.97 | 0 |
| ATOM | 5639 | N | MET | 790 | 32.165 | 28.430 | 55.336 | 1.00 | 2.00 | 0 |
| ATOM | 5641 | CA | MET | 790 | 32.126 | 29.748 | 54.743 | 1.00 | 2.00 | 0 |
| ATOM | 5642 | CB | MET | 790 | 30.698 | 30.267 | 54.636 | 1.00 | 19.79 | 0 |
| ATOM | 5643 | CG | MET | 790 | 30.588 | 31.572 | 53.882 | 1.00 | 19.37 | 0 |
| ATOM | 5644 | SD | MET | 790 | 28.979 | 31.708 | 53.134 | 1.00 | 18.51 | 0 |
| ATOM | 5645 | CE | MET | 790 | 28.359 | 33.110 | 53.992 | 1.00 | 23.23 | 0 |
| ATOM | 5646 | C | MET | 790 | 32.945 | 30.667 | 55.627 | 1.00 | 2.00 | 0 |
| ATOM | 5647 | O | MET | 790 | 32.615 | 30.857 | 56.799 | 1.00 | 23.79 | 0 |
| ATOM | 5648 | N | CYS | 791 | 34.014 | 31.228 | 55.067 | 1.00 | 2.00 | 0 |
| ATOM | 5650 | CA | CYS | 791 | 34.882 | 32.133 | 55.803 | 1.00 | 2.00 | 0 |
| ATOM | 5651 | CB | CYS | 791 | 36.325 | 31.793 | 55.516 | 1.00 | 14.83 | 0 |
| ATOM | 5652 | SG | CYS | 791 | 36.570 | 30.052 | 55.766 | 1.00 | 15.43 | 0 |
| ATOM | 5653 | C | CYS | 791 | 34.616 | 33.591 | 55.502 | 1.00 | 2.00 | 0 |

TABLE A-continued

| | | | | | | | | | |
|---|---|---|---|---|---|---|---|---|---|
| ATOM | 5654 | O | CYS | 791 | 34.314 | 33.961 | 54.371 | 1.00 | 21.84 | 0 |
| ATOM | 5655 | N | SER | 792 | 34.697 | 34.412 | 56.540 | 1.00 | 2.00 | 0 |
| ATOM | 5657 | CA | SER | 792 | 34.480 | 35.849 | 56.430 | 1.00 | 2.00 | 0 |
| ATOM | 5658 | CB | SER | 792 | 33.073 | 36.221 | 56.903 | 1.00 | 2.93 | 0 |
| ATOM | 5659 | OG | SER | 792 | 32.887 | 35.867 | 58.256 | 1.00 | 3.41 | 0 |
| ATOM | 5661 | C | SER | 792 | 35.539 | 36.518 | 57.303 | 1.00 | 2.00 | 0 |
| ATOM | 5662 | O | SER | 792 | 36.290 | 35.826 | 57.994 | 1.00 | 2.56 | 0 |
| ATOM | 5663 | N | PHE | 793 | 35.609 | 37.842 | 57.270 | 1.00 | 2.00 | 0 |
| ATOM | 5665 | CA | PHE | 793 | 36.617 | 38.558 | 58.039 | 1.00 | 2.00 | 0 |
| ATOM | 5666 | CB | PHE | 793 | 37.765 | 39.025 | 57.129 | 1.00 | 38.05 | 0 |
| ATOM | 5667 | CG | PHE | 793 | 38.531 | 37.913 | 56.469 | 1.00 | 24.74 | 0 |
| ATOM | 5668 | CD1 | PHE | 793 | 38.055 | 37.314 | 55.306 | 1.00 | 28.08 | 0 |
| ATOM | 5669 | CD2 | PHE | 793 | 39.741 | 37.474 | 57.002 | 1.00 | 26.11 | 0 |
| ATOM | 5670 | CE1 | PHE | 793 | 38.774 | 36.295 | 54.680 | 1.00 | 27.84 | 0 |
| ATOM | 5671 | CE2 | PHE | 793 | 40.466 | 36.460 | 56.389 | 1.00 | 27.16 | 0 |
| ATOM | 5672 | CZ | PHE | 793 | 39.983 | 35.868 | 55.225 | 1.00 | 29.41 | 0 |
| ATOM | 5673 | C | PHE | 793 | 36.101 | 39.782 | 58.784 | 1.00 | 2.00 | 0 |
| ATOM | 5674 | O | PHE | 793 | 35.362 | 40.599 | 58.233 | 1.00 | 23.22 | 0 |
| ATOM | 5675 | N | GLN | 794 | 36.480 | 39.893 | 60.051 | 1.00 | 67.38 | 0 |
| ATOM | 5677 | CA | GLN | 794 | 36.128 | 41.064 | 60.837 | 1.00 | 63.52 | 0 |
| ATOM | 5678 | CB | GLN | 794 | 35.608 | 40.713 | 62.238 | 1.00 | 31.74 | 0 |
| ATOM | 5679 | CG | GLN | 794 | 34.294 | 39.954 | 62.289 | 1.00 | 36.03 | 0 |
| ATOM | 5680 | CD | GLN | 794 | 34.506 | 38.455 | 62.252 | 1.00 | 39.99 | 0 |
| ATOM | 5681 | OE1 | GLN | 794 | 34.622 | 37.858 | 61.179 | 1.00 | 39.14 | 0 |
| ATOM | 5682 | NE2 | GLN | 794 | 34.575 | 37.838 | 63.425 | 1.00 | 44.72 | 0 |
| ATOM | 5685 | C | GLN | 794 | 37.471 | 41.760 | 60.958 | 1.00 | 65.96 | 0 |
| ATOM | 5686 | O | GLN | 794 | 38.486 | 41.132 | 61.272 | 1.00 | 37.24 | 0 |
| ATOM | 5687 | N | ILE | 795 | 37.498 | 43.045 | 60.658 | 1.00 | 53.07 | 0 |
| ATOM | 5689 | CA | ILE | 795 | 38.732 | 43.790 | 60.748 | 1.00 | 54.05 | 0 |
| ATOM | 5690 | CB | ILE | 795 | 39.084 | 44.483 | 59.392 | 1.00 | 26.19 | 0 |
| ATOM | 5691 | CG2 | ILE | 795 | 40.115 | 45.589 | 59.608 | 1.00 | 28.70 | 0 |
| ATOM | 5692 | CG1 | ILE | 795 | 39.643 | 43.467 | 58.390 | 1.00 | 30.47 | 0 |
| ATOM | 5693 | CD1 | ILE | 795 | 38.659 | 42.449 | 57.906 | 1.00 | 28.83 | 0 |
| ATOM | 5694 | C | ILE | 795 | 38.543 | 44.847 | 61.817 | 1.00 | 53.94 | 0 |
| ATOM | 5695 | O | ILE | 795 | 37.476 | 45.452 | 61.903 | 1.00 | 27.08 | 0 |
| ATOM | 5696 | N | LEU | 796 | 39.544 | 45.008 | 62.674 | 1.00 | 30.60 | 0 |
| ATOM | 5698 | CA | LEU | 796 | 39.521 | 46.054 | 63.686 | 1.00 | 34.91 | 0 |
| ATOM | 5699 | CB | LEU | 796 | 39.839 | 45.528 | 65.089 | 1.00 | 41.88 | 0 |
| ATOM | 5700 | CG | LEU | 796 | 40.368 | 44.121 | 65.308 | 1.00 | 41.67 | 0 |
| ATOM | 5701 | CD1 | LEU | 796 | 40.976 | 44.038 | 66.702 | 1.00 | 39.26 | 0 |
| ATOM | 5702 | CD2 | LEU | 796 | 39.242 | 43.114 | 65.119 | 1.00 | 42.51 | 0 |
| ATOM | 5703 | C | LEU | 796 | 40.637 | 46.977 | 63.206 | 1.00 | 33.78 | 0 |
| ATOM | 5704 | O | LEU | 796 | 41.649 | 46.510 | 62.667 | 1.00 | 34.59 | 0 |
| ATOM | 5705 | N | LYS | 797 | 40.454 | 48.280 | 63.356 | 1.00 | 37.84 | 0 |
| ATOM | 5707 | CA | LYS | 797 | 41.475 | 49.207 | 62.902 | 1.00 | 40.12 | 0 |
| ATOM | 5708 | CB | LYS | 797 | 40.805 | 50.354 | 62.154 | 1.00 | 0.26 | 0 |
| ATOM | 5709 | CG | LYS | 797 | 39.959 | 49.929 | 60.932 | 1.00 | 0.34 | 0 |
| ATOM | 5710 | CD | LYS | 797 | 39.456 | 51.183 | 60.151 | 1.00 | 0.65 | 0 |
| ATOM | 5711 | CE | LYS | 797 | 39.134 | 50.875 | 58.662 | 1.00 | 0.12 | 0 |
| ATOM | 5712 | NZ | LYS | 797 | 38.852 | 52.117 | 57.851 | 1.00 | 0.70 | 0 |
| ATOM | 5716 | C | LYS | 797 | 42.356 | 49.727 | 64.053 | 1.00 | 50.42 | 0 |
| ATOM | 5717 | O | LYS | 797 | 42.961 | 50.809 | 63.985 | 1.00 | 0.89 | 0 |
| ATOM | 5718 | N | ALA | 400 | −8.399 | 33.628 | 131.469 | 1.00 | 75.56 | 0 |
| ATOM | 5720 | CA | ALA | 400 | −6.981 | 33.565 | 131.818 | 1.00 | 75.56 | 0 |
| ATOM | 5721 | CB | ALA | 400 | −6.134 | 33.160 | 130.576 | 1.00 | 21.27 | 0 |
| ATOM | 5722 | C | ALA | 400 | −6.530 | 34.922 | 132.352 | 1.00 | 75.56 | 0 |
| ATOM | 5723 | O | ALA | 400 | −7.350 | 35.762 | 132.744 | 1.00 | 21.27 | 0 |
| ATOM | 5724 | N | ARG | 401 | −5.218 | 35.116 | 132.374 | 1.00 | 2.00 | 0 |
| ATOM | 5726 | CA | ARG | 401 | −4.619 | 36.351 | 132.833 | 1.00 | 2.00 | 0 |
| ATOM | 5727 | CB | ARG | 401 | −4.586 | 36.395 | 134.359 | 1.00 | 2.00 | 0 |
| ATOM | 5728 | CG | ARG | 401 | −5.638 | 37.360 | 134.956 | 1.00 | 2.00 | 0 |
| ATOM | 5729 | CD | ARG | 401 | −5.639 | 37.340 | 136.471 | 1.00 | 2.00 | 0 |
| ATOM | 5730 | NE | ARG | 401 | −6.285 | 38.512 | 137.058 | 1.00 | 2.00 | 0 |
| ATOM | 5732 | CZ | ARG | 401 | −5.730 | 39.260 | 138.022 | 1.00 | 2.00 | 0 |
| ATOM | 5733 | NH1 | ARG | 401 | −6.338 | 40.369 | 138.457 | 1.00 | 2.00 | 0 |
| ATOM | 5736 | NH2 | ARG | 401 | −4.527 | 38.949 | 138.511 | 1.00 | 2.00 | 0 |
| ATOM | 5739 | C | ARG | 401 | −3.216 | 36.446 | 132.267 | 1.00 | 2.00 | 0 |
| ATOM | 5740 | O | ARG | 401 | −2.505 | 35.443 | 132.150 | 1.00 | 2.00 | 0 |
| ATOM | 5741 | N | VAL | 402 | −2.822 | 37.655 | 131.898 | 1.00 | 2.00 | 0 |
| ATOM | 5743 | CA | VAL | 402 | −1.516 | 37.882 | 131.311 | 1.00 | 2.00 | 0 |
| ATOM | 5744 | CB | VAL | 402 | −1.331 | 39.379 | 131.042 | 1.00 | 2.00 | 0 |
| ATOM | 5745 | CG1 | VAL | 402 | −0.063 | 39.632 | 130.283 | 1.00 | 2.00 | 0 |
| ATOM | 5746 | CG2 | VAL | 402 | −2.503 | 39.889 | 130.282 | 1.00 | 2.00 | 0 |
| ATOM | 5747 | C | VAL | 402 | −0.398 | 37.376 | 132.223 | 1.00 | 2.00 | 0 |
| ATOM | 5748 | O | VAL | 402 | −0.548 | 37.369 | 133.444 | 1.00 | 2.00 | 0 |
| ATOM | 5749 | N | SER | 403 | 0.701 | 36.920 | 131.625 | 1.00 | 19.26 | 0 |
| ATOM | 5751 | CA | SER | 403 | 1.882 | 36.461 | 132.361 | 1.00 | 23.92 | 0 |
| ATOM | 5752 | CB | SER | 403 | 1.894 | 34.942 | 132.528 | 1.00 | 22.54 | 0 |
| ATOM | 5753 | OG | SER | 403 | 1.503 | 34.298 | 131.333 | 1.00 | 14.30 | 0 |

TABLE A-continued

| | | | | | | | | | |
|---|---|---|---|---|---|---|---|---|---|
| ATOM | 5755 | C | SER | 403 | 3.070 | 36.913 | 131.514 | 1.00 | 21.44 | 0 |
| ATOM | 5756 | O | SER | 403 | 2.890 | 37.720 | 130.595 | 1.00 | 23.72 | 0 |
| ATOM | 5757 | N | PHE | 404 | 4.271 | 36.415 | 131.793 | 1.00 | 13.47 | 0 |
| ATOM | 5759 | CA | PHE | 404 | 5.439 | 36.827 | 131.013 | 1.00 | 13.06 | 0 |
| ATOM | 5760 | CB | PHE | 404 | 6.101 | 38.060 | 131.647 | 1.00 | 2.00 | 0 |
| ATOM | 5761 | CG | PHE | 404 | 5.228 | 39.270 | 131.627 | 1.00 | 2.00 | 0 |
| ATOM | 5762 | CD1 | PHE | 404 | 4.421 | 39.574 | 132.711 | 1.00 | 2.00 | 0 |
| ATOM | 5763 | CD2 | PHE | 404 | 5.171 | 40.080 | 130.505 | 1.00 | 2.00 | 0 |
| ATOM | 5764 | CE1 | PHE | 404 | 3.560 | 40.668 | 132.677 | 1.00 | 2.00 | 0 |
| ATOM | 5765 | CE2 | PHE | 404 | 4.313 | 41.178 | 130.463 | 1.00 | 2.00 | 0 |
| ATOM | 5766 | CZ | PHE | 404 | 3.507 | 41.472 | 131.549 | 1.00 | 2.00 | 0 |
| ATOM | 5767 | C | PHE | 404 | 6.476 | 35.735 | 130.791 | 1.00 | 16.54 | 0 |
| ATOM | 5768 | O | PHE | 404 | 6.472 | 34.720 | 131.489 | 1.00 | 2.00 | 0 |
| ATOM | 5769 | N | ALA | 405 | 7.341 | 35.960 | 129.802 | 1.00 | 2.00 | 0 |
| ATOM | 5771 | CA | ALA | 405 | 8.420 | 35.054 | 129.414 | 1.00 | 2.00 | 0 |
| ATOM | 5772 | CB | ALA | 405 | 9.762 | 30.742 | 129.619 | 1.00 | 85.03 | 0 |
| ATOM | 5773 | C | ALA | 405 | 8.434 | 33.682 | 130.078 | 1.00 | 2.00 | 0 |
| ATOM | 5774 | O | ALA | 405 | 8.380 | 32.654 | 129.401 | 1.00 | 85.03 | 0 |
| ATOM | 5775 | N | GLY | 899 | 32.968 | 17.226 | 49.661 | 1.00 | 95.94 | 0 |
| ATOM | 5777 | CA | GLY | 899 | 31.781 | 16.989 | 50.464 | 1.00 | 95.94 | 0 |
| ATOM | 5778 | C | GLY | 899 | 31.215 | 18.274 | 51.038 | 1.00 | 95.94 | 0 |
| ATOM | 5779 | O | GLY | 899 | 30.022 | 18.368 | 51.338 | 1.00 | 32.75 | 0 |
| ATOM | 5780 | N | ARG | 900 | 32.090 | 19.260 | 51.193 | 1.00 | 42.23 | 0 |
| ATOM | 5782 | CA | ARG | 900 | 31.732 | 20.569 | 51.722 | 1.00 | 42.23 | 0 |
| ATOM | 5783 | CB | ARG | 900 | 31.110 | 20.432 | 53.110 | 1.00 | 22.01 | 0 |
| ATOM | 5784 | CG | ARG | 900 | 30.578 | 21.718 | 53.694 | 1.00 | 22.01 | 0 |
| ATOM | 5785 | CD | ARG | 900 | 30.080 | 21.488 | 55.120 | 1.00 | 22.01 | 0 |
| ATOM | 5786 | NE | ARG | 900 | 31.005 | 20.664 | 55.909 | 1.00 | 22.01 | 0 |
| ATOM | 5788 | CZ | ARG | 900 | 31.111 | 20.691 | 57.237 | 1.00 | 22.01 | 0 |
| ATOM | 5789 | NH1 | ARG | 900 | 30.361 | 21.512 | 57.963 | 1.00 | 22.01 | 0 |
| ATOM | 5792 | NH2 | ARG | 900 | 31.957 | 19.865 | 57.839 | 1.00 | 22.01 | 0 |
| ATOM | 5795 | C | ARG | 900 | 33.034 | 21.365 | 51.774 | 1.00 | 42.23 | 0 |
| ATOM | 5796 | O | ARG | 900 | 33.795 | 21.309 | 52.735 | 1.00 | 22.01 | 0 |
| ATOM | 5797 | N | ARG | 901 | 33.284 | 22.091 | 50.697 | 1.00 | 8.39 | 0 |
| ATOM | 5799 | CA | ARG | 901 | 34.490 | 22.880 | 50.542 | 1.00 | 8.39 | 0 |
| ATOM | 5800 | CB | ARG | 901 | 34.793 | 23.036 | 49.045 | 1.00 | 2.00 | 0 |
| ATOM | 5801 | CG | ARG | 901 | 34.504 | 21.810 | 48.186 | 1.00 | 2.00 | 0 |
| ATOM | 5802 | CD | ARG | 901 | 34.584 | 22.175 | 46.699 | 1.00 | 2.00 | 0 |
| ATOM | 5803 | NE | ARG | 901 | 34.278 | 21.012 | 45.863 | 1.00 | 2.00 | 0 |
| ATOM | 5805 | CZ | ARG | 901 | 35.190 | 20.195 | 45.327 | 1.00 | 2.00 | 0 |
| ATOM | 5606 | NH1 | ARG | 901 | 36.498 | 20.416 | 45.509 | 1.00 | 2.00 | 0 |
| ATOM | 5809 | NH2 | ARG | 901 | 34.791 | 19.114 | 44.649 | 1.00 | 2.00 | 0 |
| ATOM | 5812 | C | ARG | 901 | 34.327 | 24.259 | 51.158 | 1.00 | 8.39 | 0 |
| ATOM | 5813 | O | ARG | 901 | 33.241 | 24.629 | 51.607 | 1.00 | 2.00 | 0 |
| ATOM | 5814 | N | VAL | 902 | 35.393 | 25.005 | 51.149 | 1.00 | 2.00 | 0 |
| ATOM | 5816 | CA | VAL | 902 | 35.425 | 26.384 | 51.650 | 1.00 | 2.00 | 0 |
| ATOM | 5817 | CB | VAL | 902 | 36.880 | 26.814 | 51.869 | 1.00 | 12.90 | 0 |
| ATOM | 5818 | CG1 | VAL | 902 | 37.039 | 28.332 | 51.992 | 1.00 | 12.90 | 0 |
| ATOM | 5819 | CG2 | VAL | 902 | 37.492 | 26.219 | 53.139 | 1.00 | 12.90 | 0 |
| ATOM | 5820 | C | VAL | 902 | 34.782 | 27.324 | 50.627 | 1.00 | 2.00 | 0 |
| ATOM | 5621 | O | VAL | 902 | 34.737 | 27.031 | 49.435 | 1.00 | 12.90 | 0 |
| ATOM | 5822 | N | SER | 903 | 34.288 | 28.438 | 51.120 | 1.00 | 2.00 | 0 |
| ATOM | 5824 | CA | SER | 903 | 33.673 | 29.487 | 50.271 | 1.00 | 2.00 | 0 |
| ATOM | 5825 | CB | SER | 903 | 32.173 | 29.205 | 50.008 | 1.00 | 2.00 | 0 |
| ATOM | 5826 | OG | SER | 903 | 31.477 | 28.917 | 51.209 | 1.00 | 2.00 | 0 |
| ATOM | 5828 | C | SER | 903 | 33.871 | 30.814 | 50.991 | 1.00 | 2.00 | 0 |
| ATOM | 5829 | O | SER | 903 | 34.386 | 30.866 | 52.115 | 1.00 | 2.00 | 0 |
| ATOM | 5830 | N | PHE | 904 | 33.482 | 31.903 | 50.376 | 1.00 | 2.00 | 0 |
| ATOM | 5832 | CA | PHE | 904 | 33.683 | 33.188 | 51.034 | 1.00 | 2.00 | 0 |
| ATOM | 5833 | CB | PHE | 904 | 34.894 | 33.898 | 50.455 | 1.00 | 17.14 | 0 |
| ATOM | 5834 | CG | PHE | 904 | 36.184 | 33.109 | 50.672 | 1.00 | 17.14 | 0 |
| ATOM | 5835 | CD1 | PHE | 904 | 36.511 | 32.067 | 49.605 | 1.00 | 17.14 | 0 |
| ATOM | 5836 | CD2 | PHE | 904 | 37.034 | 33.426 | 51.738 | 1.00 | 17.14 | 0 |
| ATOM | 5837 | CE1 | PHE | 904 | 37.690 | 31.343 | 49.994 | 1.00 | 17.14 | 0 |
| ATOM | 5838 | CE2 | PHE | 904 | 38.216 | 32.704 | 51.927 | 1.00 | 17.14 | 0 |
| ATOM | 5839 | CZ | PHE | 904 | 38.544 | 31.662 | 51.054 | 1.00 | 17.14 | 0 |
| ATOM | 5840 | C | PHE | 904 | 32.491 | 34.080 | 50.894 | 1.00 | 2.00 | 0 |
| ATOM | 5841 | O | PHE | 904 | 31.716 | 33.994 | 49.926 | 1.00 | 17.14 | 0 |
| ATOM | 5842 | N | ALA | 905 | 32.386 | 34.912 | 51.874 | 1.00 | 70.83 | 0 |
| ATOM | 5844 | CA | ALA | 905 | 31.311 | 35.857 | 51.949 | 1.00 | 69.99 | 0 |
| ATOM | 5845 | CB | ALA | 905 | 30.042 | 35.128 | 52.370 | 1.00 | 2.00 | 0 |
| ATOM | 5846 | C | ALA | 905 | 31.646 | 36.940 | 52.962 | 1.00 | 69.85 | 0 |
| ATOM | 5847 | O | ALA | 905 | 30.981 | 37.068 | 53.993 | 1.00 | 2.00 | 0 |
| ATOM | 5848 | N | ALA | 907 | 37.374 | 34.312 | 47.285 | 1.00 | 23.39 | 0 |
| ATOM | 5850 | CA | ALA | 907 | 36.215 | 33.651 | 46.695 | 1.00 | 23.39 | 0 |
| ATOM | 5851 | CB | ALA | 907 | 35.317 | 34.681 | 46.008 | 1.00 | 41.64 | 0 |
| ATOM | 5852 | C | ALA | 907 | 36.637 | 32.568 | 45.699 | 1.00 | 23.39 | 0 |
| ATOM | 5853 | O | ALA | 907 | 35.850 | 31.680 | 45.370 | 1.00 | 41.64 | 0 |
| ATOM | 5854 | N | ALA | 908 | 37.875 | 32.643 | 45.215 | 1.00 | 83.90 | 0 |

TABLE A-continued

| | | | | | | | | | |
|---|---|---|---|---|---|---|---|---|---|
| ATOM | 5856 | CA | ALA | 908 | 38.378 | 31.663 | 44.253 | 1.00 | 83.90 | 0 |
| ATOM | 5857 | CB | ALA | 908 | 39.439 | 32.296 | 43.337 | 1.00 | 22.84 | 0 |
| ATOM | 5858 | C | ALA | 908 | 38.961 | 30.466 | 44.992 | 1.00 | 83.90 | 0 |
| ATOM | 5859 | O | ALA | 908 | 38.459 | 30.074 | 46.046 | 1.00 | 22.84 | 0 |
| ATOM | 5860 | OW | WAT | 1 | 62.869 | 37.982 | 63.341 | 1.00 | 20.00 | 0 |
| ATOM | 5863 | OW | WAT | 103 | 57.039 | 39.062 | 61.228 | 1.00 | 20.00 | 0 |
| ATOM | 5866 | OW | WAT | 101 | 7.257 | 66.194 | 118.365 | 1.00 | 20.00 | 0 |
| ATOM | 5869 | OW | WAT | 2 | 12.341 | 60.209 | 123.464 | 1.00 | 20.00 | 0 |
| ATOM | 5872 | OW | WAT | 1 | 10.655 | 60.748 | 120.831 | 1.00 | 20.00 | 0 |
| ATOM | 5875 | OW | WAT | 104 | 55.432 | 36.306 | 63.901 | 1.00 | 20.00 | 0 |
| ATOM | 5878 | OW | WAT | 102 | 56.782 | 40.457 | 58.333 | 1.00 | 20.00 | 0 |
| ATOM | 5881 | OW | WAT | 4 | 5.787 | 57.856 | 118.686 | 1.00 | 20.00 | 0 |
| ATOM | 5884 | OW | WAT | 105 | 54.382 | 39.155 | 63.734 | 1.00 | 20.00 | 0 |
| ATOM | 5887 | OW | WAT | 5 | 8.964 | 57.595 | 118.151 | 1.00 | 20.00 | 0 |
| ATOM | 5890 | OW | WAT | 106 | 38.565 | 47.423 | 74.959 | 1.00 | 20.00 | 0 |
| ATOM | 5893 | OW | WAT | 6 | 16.086 | 42.169 | 105.289 | 1.00 | 20.00 | 0 |
| ATOM | 5896 | OW | WAT | 107 | 31.158 | 26.414 | 51.913 | 1.00 | 20.00 | 0 |
| ATOM | 5899 | OW | WAT | 7 | −0.781 | 32.787 | 131.574 | 1.00 | 20.00 | 0 |
| ATOM | 5902 | MN | MN2 | 430 | 4.422 | 59.061 | 119.360 | 1.00 | 15.61 | 0 |
| ATOM | 5903 | MN | MN2 | 431 | 7.458 | 57.871 | 117.661 | 1.00 | 16.53 | 0 |
| ATOM | 5904 | MN | MN2 | 930 | 56.038 | 34.500 | 63.727 | 1.00 | 16.67 | 0 |
| ATOM | 5905 | MN | MN2 | 931 | 54.402 | 37.798 | 64.756 | 1.00 | 15.40 | 0 |
| ATOM | 5906 | S | SO4 | 801 | 57.551 | 37.278 | 64.009 | 1.00 | 37.87 | 0 |
| ATOM | 5907 | O1 | SO4 | 801 | 57.600 | 35.652 | 63.897 | 1.00 | 42.46 | 0 |
| ATOM | 5908 | O2 | SO4 | 801 | 58.690 | 37.740 | 64.722 | 1.00 | 42.01 | 0 |
| ATOM | 5909 | O3 | SO4 | 801 | 56.355 | 37.648 | 64.705 | 1.00 | 45.08 | 0 |
| ATOM | 5910 | O4 | SO4 | 801 | 57.520 | 37.854 | 62.725 | 1.00 | 41.40 | 0 |
| ATOM | 5911 | S | SO4 | 800 | 6.866 | 60.776 | 118.643 | 1.00 | 37.87 | 0 |
| ATOM | 5912 | O1 | SO4 | 800 | 7.710 | 60.635 | 119.773 | 1.00 | 42.46 | 0 |
| ATOM | 5913 | O2 | SO4 | 800 | 7.044 | 62.063 | 118.053 | 1.00 | 42.01 | 0 |
| ATOM | 5914 | O3 | SO4 | 800 | 5.496 | 60.612 | 119.046 | 1.00 | 45.08 | 0 |
| ATOM | 5915 | O4 | SO4 | 800 | 7.194 | 59.728 | 117.703 | 1.00 | 41.40 | 0 |

References for Example 3

1. Hubbard, M. J. and Cohen, P. (1993) *Trends Biochem. Sci.* 18, 172–177.
2. Egloff, M. P., Johnson, D. F., Moorhead, G., Cohen, P. T., W., Cohen, P. and Barford, D., (1997) *EMBO J.* in press.
3. Dent, P., MacDougall, L. K., MacKintosh, C., Campbell, D. G. and Cohen, P. (1992) *Eur. J. Biochem.* 210, 1037–1044.
4. Alessi, D. R., MacDougall, L. K., Sola, M. M., Ikebe, M. and Cohen, P. (1992) *Eur. J. Biochem.* 210, 1023–1035.
5. Chen, Y-H., Chen, M-X., Alessi, D. R., Campbell, D. G., Shanahan, C., Cohen, P. and Cohen, P. T. W. (1994) *FEBS Lett* 356, 51–56.
6. Shirazi, A., Iizuka, K., Fadden, P., Mosse, C., Somlyo, A. P., Somlyo, A. V. and Haystead, T. A. J. (1994) *J. Biol. Chem.* 269, 31598–31606.
7. Johnson, D. F., Moorhead, G., Caudwell, F. B., Cohen, P., Chen, Y. H., Chen, M. X. and Cohen, P. T. W. (1996) *Eur. J. Biochem.* 239, 317–325.
8. Shimizu, H., Ito, M., Miyahara, M., Ichikawa, K., Okubo, S., Konishi, T., Naka, M., Tanaka, T., Hirano, K., Hartshorne, D. J. and Nakano, T. (1994) *J. Biol. Chem.* 269, 30407–30411.
9. Haystead, C. M. M., Gailly, P., Somlyo, A. P. and Somlyo, A. V. and Haystead, T. A. J. (1995) *FEBS Lett* 377, 123–127.
10. Ikebe, M. and Hartshorne, D. J. (1985) *J. Biol. Chem.* 260, 13146–13153.
11. Margossian, S. S. and Lowey, S. (1982) *Methods Enzymol.* 85, 55–71.
12. Hubbard, M. J. and Cohen, P. (1991) *Methods Enzymol.* 201, 414–427.
13. Laemmli, U. K. (1970) *Nature* 227, 680–685.
14. Schagger H. and von Jagow, G. (1987) *Anal. Biochem* 166, 368–379.
15. Bradford, M. M. (1976) *Anal. Biochem* 72, 248–254.
16. Sasaki, K., Shima, H., Kitagawa, Y., Irino, S., Sugimura, T. and Nagao, M. (1990) *Jap. J. Cancer Res.* 81, 1272–1280.
17. Takai, A., Sasaki, K., K., Nagai, H., Mieskes, G., Isobe, M., Isono, K. and Yasumoto, T. (1995) *Biochem. J.* 306, 657–665.
18. Gong, M. C., Cohen, P., Kitazawa, T., Ikebe, M., Masuo, M., Somlyo, A. P. and Somlyo, A. V. (1992) *J. Biol. Chem.* 267, 14662–14668.
19. Cohen, P., Klumpp, S. and Schelling, D. L. (1989) *FEBS Lett* 250, 596–600.
20. Pato, M. D. and Kerc, E. (1985) *J. Biol. Chem.* 260, 12359–12366.
21. Ichikawa, K., Hirano, K., Tanaka, J., Nakano, T. and Hartshorne, D. J. (1996) *Biochemistry* 35, 6313–6320.
22. Traverse, S., Cohen, P., Paterson, H., Marshall, C., Rapp, U. and Grand, R. J. A. (1993) *Oncogene* 8, 3175–3181.

References (other than those numbered in square brackets or otherwise given in full):

Aitken, A., Cohen, P. (1982) *FEBS. Lett*. 147, 54–58.
Aitken, A., Bilham, T. and Cohen, P. (1982) *Eur. J. Biochem.* 126, 235–246.
Alessi D. R., McDougall, L. K., Sola, M. M., Ikebe, M. and Cohen, P. (1992) *Eur. J. Biochem.* 210, 1023–1035.
Alessi, D. R., Street, A. J., Cohen, P. and Cohen, P. T. W. (1993) *Eur. J. Biochem.* 213, 1055–1066.
Barford, D. and Keller, J. C. (1994) *J. Mol. Biol.* 235, 763–766.
Barton, G. J., Cohen, P. T. W. and Barford, D. (1994) *Eur. J. Biochem.* 220, 225–237.
Brunger, A. T. (1992) X-PLOR: Yale University Press, New Haven, Conn.
Beullens, M., Van Eynde, A., Stalmans, W. and Bollen, M. (1992) *J. Biol. Chem.*, 267, 16538–16544.
Beullens, M., Van Eynde, A, Bollen, M., Stalmans, W. (1993) *J. Biol. Chem.*, 268, 13172–13177.

Beullens, M., Stalmans, W., Bollen, M. (1996) *Eur. J. Biochem.*, 239, 183–189.

Chen, Y. H., Chen M. X., Alessi, D. R., Campbell, D. G., Shanahan, C., Cohen, P. and Cohen, P. T. W. (1994) *FEBS Lett.* 356, 51–55.

Cohen, P., Alemany, S., Hemmings, B. A., Resink, T. J., Stralfors, P. and Tung, H. Y. L. (1988) *Methods Enzymol* 159, 390–408.

Cohen, P. (1989) *ANN. Rev. Biochem.*, 58, 453–508.

Cohen, P. (1992) *Trends Biochem. Sci.*, 17, 408–413.

Dent, P., Lavoinne, A., Nakielny, S., Caudwell, F. B., Watt, P. and Cohen, P. (1990) *Nature* 348, 302–307.

Desdouits, F., Cheetham, J. J., Huang, H. B., Jwon, Y. G., de Cruz e Silba, E. F., Denefle, P., Ehrlich, P., Nairn, A. C., Greengard, P., Girault, J. A. (1995) *Biochem. Biophys. Res. Comm.*, 206, 653–658.

Derrick, J. P. and Wigley, D. B. (1992) Nature 359, 752–754.

Doherty, M. J., Moorhead G., Morrice, N., Cohen, P. and Cohen, P. T. W. (1995) *FEBS Lett.* 375, 294–298.

Doyle, D. A., Lee, A., Lewis, J., Kim, E., Sheng, M., MacKinnon, R., (1996) *Cell* 85, 1067–1076.

Durfee, T., Becherer, K., Chen, P. L., Yeh, S. H., Yang, Y., Kilburn, A. E., Lee, W. H., Elledge, S. J. (1993) *Genes and Development*, 7, 555–569.

Endo, S., Zhou, X., Connor, J., Wang, B., Shnolikar, S. (1996) *Biochemistry*, 35, 5220–5228.

Faux, M. C., Scott, J. D. (1996) *Trends Biochem, Sci.*, 21, 312–315.

Francois, J. M., Thompson-Jaeger, S., Skroch, J., Zellenka, U., Spevak, W., Tatchell, K. (1992) *EMBO J.*, 11, 87–89.

Frederick, D. L., Tatchell, K. (1996) *Mol Cell Biol.* 16, 2922–2931. The REG2 gene.

Furey, W. and Swaminathan, S. (1990) *Am. Cryst. Acco. Meeting Summ.* 18, 73.

Helps, N., Barker, H., Elledge, S. J. and Cohen, P. T. W. (1995) *FEBS Lett.* 377, 295–300.

Hemmings, Jr., Nairn, A. C., Elliot, J. R., Greengard, P. (1990) *J. Biol. Chem.*, 265, 20369–20376.

Hirano, K., Ito, M., Hartshorne, D. J. (1995) *J. Biol. Chem.*, 270, 19786–19790.

Hirano, K., Erdodi, F., Patton, J. G. and Hartshorne, D. J. (1996) *FEBS Lett.* 389, 191–194.

Hubbard, M. J., Cohen, P. (1993) *Trends Biochem. Sci.*, 18, 172–177.

Hunter, T. (1995) *Cell*, 80, 225–236.

Goldberg, J., Huang, H., Kwon, Y., Greengard, P., Nairn, A. C. and Kuriyan, J. (1995) *Nature*, 376, 745–753.

Griffith, J. P., Kim, J. L., Kim, E. E., Sintchak, M. D., Thomson, J. A., Fitzgibbon, M. J., Fleming, M. A., Caron, P. R., Hsiao, K. and Navia, M. A. (1995) *Cell*, 82, 507–522.

Jagiello, I., Beullens, M., Stalmans, W., Bollen, M. (1995) *J. Biol. Chem.*, 270, 17257–17263.

Kissinger C. R., Parge, H. E., Knighton, D. R., Lewis, C. T., Pelletier, L. A., Tempczyk, A., Kalish, V. J., Tucker, K. D., Showalter, R. E., Moomaw, E. W., Gastinel, L. N., Habuka, N., Chen, X., Maldonado, F., Barker, J. E., Bacquet, R. and Villafranca, J. E. (1995) *Nature*, 378, 641–644.

Kraulis, P. (1991) *J. Appl. Cryst.*, 24, 946–950.

Johnson, D. F., Moorhead, G., Caudwell, F. B., Cohen, P., Chen, Y. H., Chen, M. X., Cohen, P. T. W. (1996) *Eur. J. Biochem.*, 239, 317–325.

Knighton D. R., Zheng, J., Ten Eyck, L. F., Xuong, N. H., Taylor, S. S., Sowadski, J. M., (1991) *Science*, 414–420.

Kraulis, P. J. (1991) *J. Appl. cryst.* 24, 946–950.

Kuehn, M. J., Ogg, D. J., Kihlberg, J., Slonim, L. N., Flemner, K., Bergfors, T. and Hultgren, S. J. (1993) *Science*, 262, 1234–1241.

Merrit, E. A., Murphy M. E. P., (1994) *Acra. Cryst.* D50, 869–873.

Moorhead, G., MacKintosh, W., Morrice, N., Gallagher, T., MacKintosh, C. (1994) *FEBS Lett.*, 356, 46–50.

Moorhead, G., MacKintosh, C., Morrice, N., Cohen, P. (1995) *FEBS Lett.*, 362, 101–105.

Nassar, N., Horn, G., Herrman, C., Scherer, A., McCormick, F. and Wittinghofer, A. (1995) *Nature*, 375, 554–560.

Navaza, J. (1992). AMoRe: In proceedings of the CCP4 Study Weekend. (Dodson, E. J et al) pp87–91, SERC, Daresbury Laboratory, Warrington, U. K. Nelson, K. K., Holmes, M., Lemmon, S. K. (1996) *Mol. Biol. Cell* 7, 245–260.

Nicholls, A. And Honig, B. (1991) *Comput. Chem.* 12, 435–445.

Otwinowski, Z. (1993) Denzo. In Data Collection and Processing. (Sawyer, L., Isaacs, N. and Bailey, S. eds), pp. 56–62, SERC Daresbury Laboratory, Warrington, UK.

Rost, B., Sander, C. (1993) *J. Mol. Biol.*, 232, 584–599.

Rost, B. (1996) *Meth. in Enzym.* 266, 525–539.

Schelling, D. L., Leader, D. P., Zammit, V. A. and Cohen, P. (1988) *Biochim. Biophys. Acta* 927, 221–231.

Shenolikar, S. (1994) *A M Rev. Cell. Biol.*, 10, 56–86.

Stralfors, P., Hiraga, A. and Cohen, P. (1986) *Eur. J. Biochem*, 149, 295–303.

Tang, P. M., Bondor, J. A., Swiderek,. K. M. and dePaoli-Roach, A. A. (1991) *J. Biol. Chem.* 266, 15782–15789.

Tu, J., Carlson, M. (1996) *EMBO J.*, 14, 5939–5946.

Tu, J. Song, W., Carlson, M. (1996) *Mol. Cell. Biol.* 16, 4199–4206.

Van Eynde, A., Beullens, M., Stalmans, W., Bollen, M. (1994) *Biochem. J.*, 297, 447–449.

Van Eynde, A., Wera, S., Beullens, M., Torrekens, S., Van Leuven, F., Stalmans, W. and Bollen, M. (1995) *J. Biol. Chem.* 270, 28068–28074.

Wera, S. and Hemmings, B. A. (1995) *Biochem. J.*, 311, 17–29.

Williams, K. R., Hemmings, H. C., LoPresti, M. B., Konigsberg, W. H. and Greengard, P. (1986) *J. Biol. Chem.* 261, 1890–1903.

Zhou, M. M. et al., Fesik, S. W. (1995) *Nature* 378 584–592.

References (Given as Numbers in Square Brackets, Except in Example 3)

1. Hubbard, M. J. and Cohen, P. (1993) *Trends Biochem. Sci.* 18, 172–177.
2. Bollen, M. and Stalmans, W. (1992) *Crit. Rev. Biochem. Mol. Biol.* 27, 227–281.
3. Mermoud, J. E., Cohen, P. and Lamond, A. I. (1992) *Nuc. Acids, Res.* 20, 5263–5269.

4. Tang, P. M., Bondor, H. A., Swiderek, K. M. and dePaoli-Roach, A. A. (1991) *J. Biol. Chem.* 266, 15782–15789.
5. Chen, Y. H., Hansen, L., Chen, M. X., Bjorbaek, C., Vestergaard, H., Hansen, T., Cohen, P. T. W. and Pedersen, O. (1994) *Diabetes* 43, 1234–1241.
6. Moorhead, G., MacKintosh, C., Morrice, N. and Cohen, P. (1995) *FEBS Lett* 362, 101–105.
7. Doherty, M. J., Moorhead, G., Morrice, N., Cohen, P. and Cohen, P. T. W. (1995) *FEBS Lett* 375, 294–298.
8. Moorhead, G., MacKintosh, R. W., Morrice, N., Gallagher, T. and MacKintosh, C. (1994) *FEBS Lett.* 356, 46–50.
9. Alessi, D. R., MacDougall, L. K., Sola, M. M., Ikebe, M. and Cohen, P. (1992) *Eur. J. Biochem.* 210, 1023–1035.
10. Chen. Y-H., Chen, M-X., Alessi, D. R., Campbell, D. G., Shanahan, C., Cohen, P. and Cohen, P. T. W. (1994) *FEBS Lett* 356, 51–56.
11. Shimizu, H., Ito, M., Miyahara, M., Ichikawa, K., Okubo, S., Konishi, T., Naka, M., Tanaka, T., Hirano, K., Hartshorne, D. J. and Nakano, T. (1994) *J. Biol. Chem.* 269–30407–30411.
12. Shirazi, A., Iizuka, K., Fadden, P. Mosse, C., Somlyo, A. V. and Haystead, T. A. J. (1994) *J. Biol. Chem.* 269, 31598–31606.
13. Helps, N., Barker, H., Elledge, S. J. and Cohen, P. T.,W. (1995) *FEBS Lett* 377, 295–300.
14. Ohkura, H. and Yanagida, M. (1991) *Cell* 64, 149–157.
15. Jagiello, I., Buellens, M., Stalmans, W. and Bollen, M. (1995) *J. Biol. Chem.* 270, 17257–17263.
16. Van Eynde, A., Wera, S., Beullens, M., Torrekens, S., Van Leuven, F., Stalmans, W. and Bollen, M. (1995) *J. Biol. Chem.* 270, 28068–28074.
17. Durphee, T., Becherer, K., Chen, P-L., Yeh, S. H., Yang, Y., Kilburn, A. E., Lee, W. H. and Elledge, S. J. (1993) *Genes and Development* 7, 555–569.
18. Hirano, K., Ito, M. and Hartshorne, D. J. (1995) *J. Biol. Chem.* 270, 19786–19790.
19. Cohen, P. (1992) *Trends Biochem. Sci.* 17, 408–413.
20. Alessi, D. R., Street, A. J., Cohen, P., and Cohen, P. T. W. (1993) *Eur. J. Biochem* 213, 1055–1066.
21. Hubbard, M. J., and Cohen, P. (1991) *Methods Enzymol.* 201, 414–427.
22. Schelling, D. L., Leader, D. P., Zammit, V. A. and Cohen, P. (1988) *Biochem. Biophys. Acta* 927, 221–231.
23. Cohen, P., Alemany, S., Hemmings, B. A., Resink, T. J., Stralfors, P. and Tung, H. Y. L. (1988) *Methods Enzymol.* 159, 390–408.
24. Stewart, A. A., Hemmings, B. A., Cohen, P., Goris, J. and Merlevede, W. (1991) *Eur. J. Biochem* 115, 197–205.
25. Gong, M. C., Fuglsang, A., Alessi, D. R., Kobayashi, S., Cohen, P., Somlyo, A. V. and Somlyo, A. P. (1992) *J. Biol. Chem.* 267, 21492–21498.
26. Alemany, S., Pelech, S. and Brierley, C. H. and Cohen, P. (1986) *Eur. J. Biochem.* 156, 101–110.
27. Stuart, J. S., Frederick, D. L., Varner, C. M. and Tatchell, K. (1994) *Mol. Cell. Biol.* 14, 896–905.
28. Desdouits, F., Cheetham. J. J., Huang, H-B., Kwon, Y. G., da Cruz C Silva, E. F., Denefle, P., Ehrlich, M. E., Nairn, A. C., Greengard. P. and Girault, J. A. (1995) *Biochem. Biophys. Res. Commun.* 206. 652–176 658.
29. Goldberg, J., Huang, H., Kwon, Y., Greengard, P., Nairn, A. C. and Kuriyan, J. (1995) *Nature* 376, 745–753.
30. Egloff, M-P., Cohen, P. T. W. and Renemer, P. and Barford, D. (1995) *J. Mol. Biol.* 254, 942–959.
31. Gailly, P., Somlyo, A. P. and Somlyo, A. (1996) submitted.
32. Traverse, S., Cohen, P., Paterson, H., Marshall, C., Rapp, U. and Grand, R. J. A. (1993) *Oncogene* 8, 3175–3181.

What is claimed is:

1. A method of identifying a compound which modulates the interaction between a PP1c and a regulatory subunit thereof, the method comprising assaying for the interaction between (a) a PP1c and (b) a regulatory subunit which is able to bind to PP1c or a PP1c-binding fragment or variant, wherein the fragment or variant comprises SEQ ID NO:35, or fusion of said subunit or a fusion of said fragment or variant, wherein the regulatory subunit is any one of $M_{110}$, $G_L$, $G_M$, M-complexes, p53 BP2, sds22, NIPPI, L5, Inhibitor-1, Inhibitor-2, or DARPP, and assaying for the interaction in the presence of a compound, to identify a compound which modulates the interaction.

2. A method of identifying a compound which mimics the effect of a regulatory subunit of PP1c, the method comprising assaying for the enzymatic or binding activity of PP1c in the presence of a given regulatory subunit, and contacting a compound with PP1c and determining whether, in the presence of the compound, PP1c adopts the enzymatic or binding activity of the PP1c in the presence of the given regulatory subunit, wherein if PP1c adopts the enzymatic or binding activity of the PP1c in the presence of a given regulatory subunit, the compound mimics the effect of the regulatory subunit of PP1c, and wherein the regulatory subunit is any one of $M_{110}$, $G_L$, $G_M$, M-complexes, p53 BP2, sds22, NIPPI, L5, Inhibitor-1, Inhibitor-2, or DARPP.

3. A method according to claim 1 or 2 wherein the regulatory subunit of PP1c is any one of $M_{110}$, $G_L$, $G_M$, M-complexes or p53BP2.

4. A method according to claim 3 wherein the regulatory subunit of PP1c is $M_{110}$ or $G_M$.

5. A method according to claim 1 wherein the fragment of a regulatory subunit which is able to bind to PP1c is any of the peptides G63-T93 of SEQ ID NO:32, G63-N75 of SEQ ID NO:32, E2-P243 of SEQ ID NO:34, E2-D118 of SEQ ID NO:34, and peptide 63–80 of SEQ ID NO:32 $G_M$ or peptides comprising said peptide sequences provided that they are not the complete $G_M$ regulatory subunit.

6. A method according to claim 1 wherein the fragment of a regulatory subunit which is able to bind to PP1c is any of the peptides M1-E309 of SEQ ID NO:33, M1-F38 of SEQ ID NO:33, M1-A150 of SEQ ID NO:33, or L24-Y496 of SEQ ID NO:33 of $M_{110}$ or peptides comprising said peptide sequences provided that they are not the complete $M_{110}$ regulatory subunit.

7. A method according to claim 1 wherein the PP1c-binding fragment or variant further comprises at least one basic residue in the four residues N-terminal of the consensus peptide sequence.

8. A method according to claim 1, wherein the third amimo acid in SEQ ID NO:35 is not Asp or Glu or a large hydrophobic residue.

9. A method according to claim 1 wherein the PP1c-binding fragment is a fragment of a regulatory subunit.

10. A method according to claim 8 wherein the PP1c-binding fragment is a fragment of any of the $M_{110}$, $G_L$, $G_M$, M-complexes, p53BP2, sds22, NIPPI, L5, Inhibitor-1, Inhibitor-2 or DARPP regulatory subunits comprising said SEQ ID NO:35.

11. A method according to claim 1 or 2 wherein the compound binds to a PP1c.

12. A method according to claim 1 wherein the compound binds to a regulatory subunit of PP1c.

13. A compound which modulates the interaction between a PP1c and a regulatory subunit thereof said compound comprising any of the peptides G63-T93 of SEQ ID NO:32, G63-N75 of SEQ ID NO:32, E2-P243 of SEQ ID NO:34, E2-D118 of SEQ ID NO:34, and peptide 63–80 of SEQ ID NO:32 $G_M$ or said compound comprising any of the peptides M1-E309 of SEQ ID NO:33, M1-F38 of SEQ ID NO:33, M1-A150 of SEQ ID NO:33 or L24-Y496 of SEQ ID NO:33 of $M_{110}$ or said compound comprising the consensus peptide sequence SEQ ID NO:35:Arg/Lys-Val/Ile-Xaa-Phe wherein Xaa is any naturally occurring amino acid, provided that said compound is not a complete regulatory subunit of PP1c.

14. A compound according to claim 13 consisting of the peptides G63-T93 of SEQ ID NO:32, G63-N75 of SEQ ID NO:32, E2-P243 of SEQ ID NO:34, E2-D118 of SEQ ID NO:34, or peptide 63–80 of SEQ ID NO:32 $G_M$ or consisting of the peptides M1-E309 of SEQ ID NO:33, M1-F38 of SEQ ID NO:33, M1-A150 of SEQ ID NO:33 or L24-Y496 of SEQ ID NO:33 of $M_{110}$.

15. A method of identifying a compound which modulates the interaction between a PP1c and a regulatory subunit thereof, or binds PP1c or mimics the effect of a regulatory subunit, the method comprising determining the conformation of a peptide bound to a regulatory subunit-binding site of PP1c and the conformation of the portion of PP1c which binds to the peptide, and selecting a compound which is capable of adopting the same conformation as the peptide bound to the regulatory subunit-binding site of PP1c or the same conformation as the portion of PP1c which binds to said peptide, wherein the selected compound modulates the interaction between a PP1c and a regulatory subunit thereof or binds PP1c and a regulatory subunit thereof or binds PP1c or mimics the effect of a regulatory subunit, wherein the regulatory subunit is any one of $M_{110}$, $G_L$, $G_M$, M-complexes, p53BP2, sds22, NIPPI, L5, Inhibitor-1, Inhibitor-2 or DARPP.

16. A method according to claim 15 wherein said peptide comprises the consensus peptide sequence SEQ ID NO:35: Arg/Lys-Val/Ile-Xaa-Phe wherein Xaa is any amino acid.

17. A method according to claim 16 wherein said peptide consists of residues 63 to 75 of SEQ ID NO: 32 $G_m$.

18. A composition comprising a compound according to claim 13 and an acceptable carrier.

19. A method according to claim 2 wherein the function or properties of the PP1c include the subcellular location of the PP1c, the substrate specificity of the PP1c, the activity of the PP1c towards one or more substrates, the activity of the PP1c in the presence of one or more extracellular agonists, the ability of the PP1c to bind to a regulatory subunit, or the ability of the PP1c to be modulated by reversible protein phosphorylation or second messengers.

* * * * *

SEQUENCE LISTING

<160> NUMBER OF SEQ ID NOS: 49

<210> SEQ ID NO 1
<211> LENGTH: 11
<212> TYPE: PRT
<213> ORGANISM: Homo sapiens

<400> SEQUENCE: 1

Thr Ala Ser Gly Val Ala Glu Thr Thr Asn Cys
 1               5                  10

<210> SEQ ID NO 2
<211> LENGTH: 7
<212> TYPE: PRT
<213> ORGANISM: RABBIT

<400> SEQUENCE: 2

Gly Arg Arg Val Ser Phe Ala
 1               5

<210> SEQ ID NO 3
<211> LENGTH: 6
<212> TYPE: PRT
<213> ORGANISM: RABBIT

<400> SEQUENCE: 3

```
Arg Arg Val Ser Phe Ala
 1               5

<210> SEQ ID NO 4
<211> LENGTH: 32
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 4

Gly Lys Arg Thr Asn Leu Arg Lys Thr Gly Ser Glu Arg Ile Ala His
 1               5                  10                  15

Gly Met Arg Val Lys Phe Asn Pro Leu Ala Leu Leu Asp Ser Cys
            20                  25                  30

<210> SEQ ID NO 5
<211> LENGTH: 4
<212> TYPE: PRT
<213> ORGANISM: CHICKEN

<400> SEQUENCE: 5

Lys Val Lys Phe
 1

<210> SEQ ID NO 6
<211> LENGTH: 31
<212> TYPE: PRT
<213> ORGANISM: RABBIT

<400> SEQUENCE: 6

Gly Arg Arg Val Ser Phe Ala Asp Asn Phe Gly Phe Asn Leu Val Ser
 1               5                  10                  15

Val Lys Glu Phe Asp Thr Trp Glu Leu Pro Ser Val Ser Thr Thr
            20                  25                  30

<210> SEQ ID NO 7
<211> LENGTH: 38
<212> TYPE: PRT
<213> ORGANISM: RAT

<400> SEQUENCE: 7

Met Lys Met Ala Asp Ala Lys Gln Lys Arg Asn Glu Gln Leu Lys Arg
 1               5                  10                  15

Trp Ile Gly Ser Glu Thr Asp Leu Glu Pro Pro Val Val Lys Arg Gln
            20                  25                  30

Lys Thr Lys Val Lys Phe
         35

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 8

Glu Phe Pro Val Val Val Val Glu Phe
 1               5

<210> SEQ ID NO 9
<211> LENGTH: 32
```

```
<212> TYPE: DNA
<213> ORGANISM: Artificial Sequence
<220> FEATURE:
<223> OTHER INFORMATION: Description of Artificial Sequence:PCR PRIMER

<400> SEQUENCE: 9
gccgaattca cacagaagaa tatgttttag cc                                    32

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence:PCR PRIMER

<400> SEQUENCE: 10
gccgaagctt atggaaaatt gactggatct gttg                                  34

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence:PCR PRIMER

<400> SEQUENCE: 11
cgcgcatatg tcgtcgctgt tcaccagg                                         28

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:PCR PRIMER

<400> SEQUENCE: 12
ggcggatccc tacttggaga gtttgc                                           26

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:PCR PRIMER

<400> SEQUENCE: 13
aggaagaatt cgttccacac gaac                                             24

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence:PCR PRIMER

<400> SEQUENCE: 14
cctagcccgg ggatgaagat ggcggac                                          27

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence:PCR PRIMER

<400> SEQUENCE: 15
```

```
gcggaagctt atgcttcctc ctctgcaata tc                              32
```

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence:PCR PRIMER

<400> SEQUENCE: 16

```
ctagaagctt ccatatttgc tgttgattca atc                             33
```

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence:PCR PRIMER

<400> SEQUENCE: 17

```
cctagcccgg gggacgatgg cgccgtcttc c                               31
```

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 18

Met Val Ala Asp
  1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 19

Gly Ser Pro Gly
  1

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 20

Gly Ser Pro Gly Ile Ser Gly Gly Gly Gly Ile Leu Asp Ser Met
  1               5                  10                  15

Gly Arg

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence:SYNTHETIC
      PEPTIDE

```
<400> SEQUENCE: 21

Ala Arg Val Ser Phe Ala
 1               5

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 22

Lys Ile Gln Phe
 1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 23

Arg Lys Asn Ser
 1

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 24

Thr Phe Ser Glu Asp Asp Glu
 1               5

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 25

Arg Val Ser Phe
 1

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 26

Arg Arg Pro Thr Pro
 1               5

<210> SEQ ID NO 27
<211> LENGTH: 13
<212> TYPE: PRT
```

```
<213> ORGANISM: Artificial Sequence
<220> FEATURE:
<223> OTHER INFORMATION: Description of Artificial Sequence:SYNTHETIC
      PEPTIDE

<400> SEQUENCE: 27

Ser Ala Ala Asn Ser Ile Ser Ser Leu Ile His Arg Asp
 1               5                  10

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 28

Gly Thr Gly Arg Arg Phe Thr Thr Ser
 1               5

<210> SEQ ID NO 29
<211> LENGTH: 1004
<212> TYPE: PRT
<213> ORGANISM: CHICKEN

<400> SEQUENCE: 29

Met Lys Met Ala Asp Ala Lys Gln Lys Arg Asn Glu Gln Leu Lys Arg
 1               5                  10                  15

Trp Ile Gly Ser Glu Thr Asp Leu Glu Pro Pro Val Val Lys Arg Lys
                20                  25                  30

Lys Thr Lys Val Lys Phe Asp Asp Gly Ala Val Phe Leu Ala Ala Cys
            35                  40                  45

Ser Ser Gly Asp Thr Glu Val Leu Arg Leu Leu Glu Arg Gly Ala
        50                  55                  60

Asp Ile Asn Tyr Ala Asn Val Asp Gly Leu Thr Ala Leu His Gln Ala
 65                  70                  75                  80

Cys Ile Asp Asp Asn Val Asp Met Val Lys Phe Leu Val Glu Asn Gly
                85                  90                  95

Ala Asn Ile Asn Gln Pro Asp Asn Glu Gly Trp Ile Pro Leu His Ala
                100                 105                 110

Ala Ala Ser Cys Gly Tyr Leu Asp Ile Ala Glu Tyr Leu Ile Ser Gln
            115                 120                 125

Gly Ala His Val Gly Ala Val Asn Ser Glu Gly Asp Thr Pro Leu Asp
        130                 135                 140

Ile Ala Glu Glu Glu Ala Met Glu Glu Leu Leu Gln Asn Glu Val Asn
145                 150                 155                 160

Arg Gln Gly Val Asp Ile Glu Ala Ala Arg Lys Glu Glu Arg Ile
                165                 170                 175

Met Leu Arg Asp Ala Arg Gln Trp Leu Asn Ser Gly His Ile Asn Asp
                180                 185                 190

Val Arg His Ala Lys Ser Gly Gly Thr Ala Leu His Val Ala Ala Ala
            195                 200                 205

Lys Gly Tyr Thr Glu Val Leu Lys Leu Leu Ile Gln Ala Arg Tyr Asp
        210                 215                 220

Val Asn Ile Lys Asp Tyr Asp Gly Trp Thr Pro Leu His Ala Ala Ala
225                 230                 235                 240

His Trp Gly Lys Glu Glu Ala Cys Arg Ile Leu Val Glu Asn Leu Cys
                245                 250                 255
```

-continued

```
Asp Met Glu Ala Val Asn Lys Val Gly Gln Thr Ala Phe Asp Val Ala
            260                 265                 270
Asp Glu Asp Ile Leu Gly Tyr Leu Glu Glu Leu Gln Lys Lys Gln Asn
            275                 280                 285
Leu Leu His Ser Glu Lys Arg Glu Lys Lys Ser Pro Leu Ile Glu Ser
            290                 295                 300
Thr Ala Asn Leu Asp Asn Asn Gln Thr Gln Lys Thr Phe Lys Asn Lys
305                 310                 315                 320
Glu Thr Leu Ile Met Glu Gln Glu Lys Asn Ala Ser Ser Ile Glu Ser
                325                 330                 335
Leu Glu His Glu Lys Ala Asp Glu Glu Glu Gly Lys Lys Asp Glu
            340                 345                 350
Ser Ser Cys Ser Ser Glu Glu Glu Asp Asp Ser Glu Ser Glu
            355                 360                 365
Ala Glu Thr Asp Lys Ala Lys Thr Leu Ala Asn Ala Asn Thr Thr Ser
            370                 375                 380
Thr Gln Ser Ala Ser Met Thr Ala Pro Ser Val Ala Gly Gly Gln Gly
385                 390                 395                 400
Thr Pro Thr Ser Pro Leu Lys Lys Phe Pro Thr Ser Thr Thr Lys Val
                405                 410                 415
Ser Pro Lys Glu Glu Arg Lys Asp Glu Ser Pro Ala Ser Trp Arg
            420                 425                 430
Leu Gly Leu Arg Lys Thr Gly Ser Tyr Gly Ala Leu Ala Glu Ile Thr
            435                 440                 445
Ala Ser Lys Glu Ala Gln Lys Glu Lys Asp Ser Ala Gly Val Ile Arg
450                 455                 460
Ser Ala Ser Ser Pro Arg Leu Ser Ser Ser Leu Asp Asn Lys Glu Lys
465                 470                 475                 480
Glu Lys Asp Gly Lys Gly Thr Arg Leu Ala Tyr Val Ala Pro Thr Ile
                485                 490                 495
Pro Arg Arg Leu Ala Ser Thr Ser Asp Ile Asp Glu Lys Glu Asn Arg
            500                 505                 510
Asp Ser Ser Ala Ser Ser Ile Arg Ser Gly Ser Ser Tyr Ala Arg Arg
            515                 520                 525
Lys Trp Glu Glu Asp Val Lys Lys Asn Ser Leu Asn Glu Gly Pro Thr
            530                 535                 540
Ser Leu Asn Thr Ser Tyr Gln Arg Ser Gly Ser Phe Gly Arg Arg Gln
545                 550                 555                 560
Asp Asp Leu Val Ser Ser Asn Val Pro Ser Thr Ala Ser Thr Val Thr
                565                 570                 575
Ser Ser Ala Gly Leu Gln Lys Thr Leu Pro Ala Ser Ala Asn Thr Thr
            580                 585                 590
Thr Lys Ser Thr Thr Gly Ser Thr Ser Ala Gly Val Gln Ser Ser Thr
            595                 600                 605
Ser Asn Arg Leu Trp Ala Glu Asp Ser Thr Glu Lys Glu Lys Asp Ser
            610                 615                 620
Val Pro Thr Ala Val Thr Val Pro Val Ala Pro Ser Val Val Asn Ala
625                 630                 635                 640
Ala Ala Thr Thr Thr Ala Met Thr Thr Ala Thr Ser Gly Thr Val Ser
                645                 650                 655
Ser Thr Ser Glu Val Arg Glu Arg Arg Arg Ser Tyr Leu Thr Pro Val
            660                 665                 670
```

-continued

```
Arg Asp Glu Glu Ser Glu Ser Gln Arg Lys Ala Arg Ser Arg Gln Ala
            675                 680                 685

Arg Gln Ser Arg Arg Ser Thr Gln Gly Val Thr Leu Thr Asp Leu Gln
        690                 695                 700

Glu Ala Glu Lys Thr Ile Gly Arg Ser Arg Ser Thr Arg Thr Arg Glu
705                 710                 715                 720

Gln Glu Asn Glu Lys Glu Lys Glu Lys Glu Lys Gln Asp Lys
                725                 730                 735

Glu Lys Gln Glu Glu Lys Lys Glu Ser Glu Thr Lys Asp Asp Asp Tyr
            740                 745                 750

Arg Gln Arg Tyr Ser Arg Thr Val Glu Glu Pro Tyr His Arg Tyr Arg
            755                 760                 765

Pro Thr Ser Thr Ser Thr Ser Thr Ser Ser Thr Ser Ser Leu Ser Thr
            770                 775                 780

Ser Thr Ser Ser Leu Ser Ser Ser Gln Leu Asn Arg Pro Asn Ser
785                 790                 795                 800

Leu Ile Gly Ile Thr Ser Ala Tyr Ser Arg Ser Gly Thr Lys Glu Ser
                805                 810                 815

Glu Arg Glu Gly Gly Lys Lys Glu Glu Glu Lys Glu Glu Asp Lys Ser
            820                 825                 830

Gln Pro Lys Ser Ile Arg Glu Arg Arg Pro Arg Glu Lys Arg Arg
            835                 840                 845

Ser Thr Gly Val Ser Phe Trp Thr Gln Asp Ser Asp Glu Asn Glu Gln
850                 855                 860

Glu His Gln Ser Asp Ser Glu Glu Gly Thr Asn Lys Lys Glu Thr Gln
865                 870                 875                 880

Ser Asp Ser Leu Ser Arg Tyr Asp Thr Gly Ser Leu Ser Val Ser Ser
            885                 890                 895

Gly Asp Arg Tyr Asp Ser Ala Gln Gly Arg Ser Gly Ser Gln Ser Tyr
            900                 905                 910

Leu Glu Asp Arg Lys Pro Tyr Cys Ser Arg Leu Glu Lys Glu Asp Ser
            915                 920                 925

Thr Asp Phe Lys Lys Leu Tyr Glu Gln Ile Leu Ala Glu Asn Glu Lys
            930                 935                 940

Leu Lys Ala Gln Leu His Asp Thr Asn Met Glu Leu Thr Asp Leu Lys
945                 950                 955                 960

Leu Gln Leu Glu Lys Thr Thr Gln Arg Gln Glu Arg Phe Ala Asp Arg
            965                 970                 975

Ser Leu Leu Glu Met Glu Lys Arg Val Ser Gly Lys Ser Gln Tyr Leu
            980                 985                 990

Leu Gly Gly Lys Lys Ser Arg Lys Lys Asp Ile
            995                 1000
```

<210> SEQ ID NO 30
<211> LENGTH: 951
<212> TYPE: PRT
<213> ORGANISM: RAT

<400> SEQUENCE: 30

```
Met Lys Met Ala Asp Ala Lys Gln Lys Arg Asn Glu Gln Leu Lys Arg
1               5                   10                  15

Trp Ile Gly Ser Glu Thr Asp Leu Glu Pro Pro Val Val Lys Arg Gln
            20                  25                  30

Lys Thr Lys Val Lys Phe Asp Asp Gly Ala Val Phe Leu Ala Ala Cys
        35                  40                  45
```

-continued

```
Ser Ser Gly Asp Thr Asp Glu Val Leu Lys Leu Leu His Arg Gly Ala
    50                  55                  60

Asp Ile Asn Tyr Ala Asn Val Asp Gly Leu Thr Ala Leu His Gln Ala
65                  70                  75                  80

Cys Ile Asp Asp Asn Val Asp Met Val Lys Phe Leu Val Glu Asn Gly
                85                  90                  95

Ala Asn Ile Asn Gln Pro Asp Asn Glu Gly Trp Ile Pro Leu His Ala
            100                 105                 110

Ala Ala Ser Cys Gly Tyr Leu Asp Ile Ala Glu Phe Leu Ile Gly Gln
        115                 120                 125

Gly Ala His Val Gly Ala Val Asn Ser Glu Gly Asp Thr Pro Leu Asp
    130                 135                 140

Ile Ala Glu Glu Glu Ala Met Glu Glu Leu Leu Gln Asn Glu Val Asn
145                 150                 155                 160

Arg Gln Gly Val Asp Ile Glu Ala Ala Arg Lys Glu Glu Arg Ile
                165                 170                 175

Met Leu Arg Asp Ala Arg Gln Trp Leu Asn Ser Gly His Ile Ser Asp
            180                 185                 190

Val Arg His Ala Lys Ser Gly Gly Thr Ala Leu His Val Ala Ala Ala
        195                 200                 205

Lys Gly Tyr Thr Glu Val Leu Lys Leu Leu Ile Gln Ala Gly Tyr Asp
    210                 215                 220

Val Asn Ile Lys Asp Tyr Asp Gly Trp Thr Pro Leu His Ala Ala Ala
225                 230                 235                 240

His Trp Gly Lys Glu Glu Ala Cys Arg Ile Leu Val Asp Asn Leu Cys
                245                 250                 255

Asp Met Glu Thr Val Asn Lys Val Gly Gln Thr Ala Phe Asp Val Ala
            260                 265                 270

Asp Glu Asp Ile Leu Gly Tyr Leu Glu Glu Leu Gln Lys Lys Gln Asn
        275                 280                 285

Leu Leu His Ser Glu Lys Arg Asp Lys Lys Ser Pro Leu Ile Glu Ser
    290                 295                 300

Thr Ala Asn Met Glu Asn Asn Gln Pro Gln Lys Thr Phe Lys Asn Lys
305                 310                 315                 320

Glu Thr Leu Ile Ile Glu Pro Glu Lys Asn Ala Ser Arg Ile Glu Ser
                325                 330                 335

Leu Glu Gln Glu Lys Ala Asp Glu Glu Glu Gly Lys Lys Asp Glu
            340                 345                 350

Ser Ser Cys Ser Ser Glu Glu Asp Glu Glu Asp Ser Glu Ser Glu
        355                 360                 365

Ala Glu Thr Asp Lys Thr Lys Pro Met Ala Ser Val Thr Asn Ala His
    370                 375                 380

Thr Ala Ser Thr Gln Ala Ala Pro Ala Ala Val Thr Thr Pro Thr Leu
385                 390                 395                 400

Ser Ser Asn Gln Gly Thr Pro Thr Ser Pro Val Lys Lys Phe Pro Thr
                405                 410                 415

Ser Thr Thr Lys Ile Ser Pro Lys Glu Glu Arg Lys Asp Glu Ser
            420                 425                 430

Pro Ala Ser Trp Arg Leu Gly Leu Arg Lys Thr Gly Ser Tyr Gly Ala
        435                 440                 445

Leu Ala Glu Ile Thr Ala Ser Lys Glu Ala Gln Lys Glu Lys Asp Thr
    450                 455                 460
```

-continued

```
Ala Gly Val Ile Arg Ser Ala Ser Ser Pro Arg Leu Ser Ser Ser Leu
465                 470                 475                 480

Asp Asn Lys Glu Lys Glu Lys Asp Asn Lys Gly Thr Arg Leu Ala Tyr
                    485                 490                 495

Val Ala Pro Thr Ile Pro Arg Arg Leu Gly Ser Thr Ser Asp Ile Glu
                500                 505                 510

Glu Lys Glu Asn Arg Glu Ser Ser Asn Leu Arg Thr Ser Ser Ser Tyr
                515                 520                 525

Thr Arg Arg Lys Trp Glu Asp Asp Leu Lys Lys Asn Ser Ser Ile Asn
            530                 535                 540

Glu Gly Ser Thr Tyr His Arg Ser Thr Ser Asn Arg Leu Trp Ala Glu
545                 550                 555                 560

Asp Ser Thr Glu Lys Glu Lys Asp Ser Ala Pro Thr Ala Ala Thr Ile
                565                 570                 575

Leu Val Ala Pro Thr Val Val Ser Ala Ala Ser Ser Thr Thr Ala
                580                 585                 590

Leu Thr Thr Thr Thr Ala Gly Thr Leu Ser Ser Thr Ser Glu Val Arg
        595                 600                 605

Glu Arg Arg Arg Ser Tyr Leu Thr Pro Val Arg Asp Glu Glu Ser Glu
        610                 615                 620

Ser Gln Arg Lys Ala Arg Ser Arg Gln Ala Arg Gln Ser Arg Arg Ser
625                 630                 635                 640

Thr Gln Gly Val Thr Leu Thr Asp Leu Gln Glu Ala Glu Lys Thr Ile
                645                 650                 655

Gly Arg Ser Arg Ser Thr Arg Thr Arg Glu Gln Glu Asn Glu Glu Lys
                660                 665                 670

Asp Lys Glu Glu Lys Glu Lys Gln Asp Lys Lys Gln Glu Glu Lys
                675                 680                 685

Lys Glu Ser Glu Val Ser Arg Glu Asp Glu Tyr Lys Gln Lys Tyr Ser
            690                 695                 700

Arg Thr Tyr Asp Glu Thr Tyr Ala Arg Tyr Arg Pro Val Ser Thr Ser
705                 710                 715                 720

Ser Ser Ser Thr Pro Ser Ser Ser Leu Ser Thr Leu Gly Ser Ser
                725                 730                 735

Leu Tyr Ala Ser Ser Gln Leu Asn Arg Pro Asn Ser Leu Val Gly Ile
            740                 745                 750

Thr Ser Ala Tyr Ser Arg Gly Leu Thr Lys Asp Asn Glu Arg Glu Gly
            755                 760                 765

Glu Lys Lys Glu Glu Glu Lys Glu Gly Glu Asp Lys Ser Gln Pro Lys
770                 775                 780

Ser Ile Arg Glu Arg Arg Arg Pro Arg Glu Lys Arg Arg Ser Thr Gly
785                 790                 795                 800

Val Ser Phe Trp Thr Gln Asp Ser Asp Glu Asn Glu Gln Glu Arg Gln
            805                 810                 815

Ser Asp Thr Glu Asp Gly Ser Ser Lys Arg Asp Thr Gln Thr Asp Ser
            820                 825                 830

Val Ser Arg Tyr Asp Ser Ser Thr Ser Ser Ser Asp Arg Tyr Asp
            835                 840                 845

Ser Leu Leu Gly Arg Ser Ala Ser Tyr Ser Tyr Leu Glu Glu Arg Lys
850                 855                 860

Pro Tyr Gly Ser Arg Leu Glu Lys Asp Asp Ser Thr Asp Phe Lys Lys
865                 870                 875                 880

Leu Tyr Glu Gln Ile Leu Ala Glu Asn Glu Lys Leu Lys Ala Gln Leu
```

-continued

```
                   885                 890                 895
His Asp Thr Asn Met Glu Leu Thr Asp Leu Lys Leu Gln Leu Glu Lys
            900                 905                 910
Ala Thr Gln Arg Gln Glu Arg Phe Ala Asp Arg Ser Leu Leu Glu Met
            915                 920                 925
Glu Lys Arg Val Thr Gly Lys Ser Gln Tyr Leu Leu Gly Gly Thr Lys
            930                 935                 940
Ser Ser Arg Lys Lys Asn Ile
945                 950

<210> SEQ ID NO 31
<211> LENGTH: 1032
<212> TYPE: PRT
<213> ORGANISM: RAT

<400> SEQUENCE: 31

Met Lys Met Ala Asp Ala Lys Gln Lys Arg Asn Glu Gln Leu Lys Arg
  1               5                  10                  15
Trp Ile Gly Ser Glu Thr Asp Leu Glu Pro Pro Val Val Lys Arg Gln
             20                  25                  30
Lys Thr Lys Val Lys Phe Asp Asp Gly Ala Val Phe Leu Ala Ala Cys
         35                  40                  45
Ser Ser Gly Asp Thr Asp Glu Val Leu Lys Leu Leu His Arg Gly Ala
     50                  55                  60
Asp Ile Asn Tyr Ala Asn Val Asp Gly Leu Thr Ala Leu His Gln Ala
 65                  70                  75                  80
Cys Ile Asp Asp Asn Val Asp Met Val Lys Phe Leu Val Glu Asn Gly
                 85                  90                  95
Ala Asn Ile Asn Gln Pro Asp Asn Glu Gly Trp Ile Pro Leu His Ala
            100                 105                 110
Ala Ala Ser Cys Gly Tyr Leu Asp Ile Ala Glu Phe Leu Ile Gly Gln
        115                 120                 125
Gly Ala His Val Gly Ala Val Asn Ser Glu Gly Asp Thr Pro Leu Asp
    130                 135                 140
Ile Ala Glu Glu Ala Met Glu Glu Leu Leu Gln Asn Glu Val Asn
145                 150                 155                 160
Arg Gln Gly Val Asp Ile Glu Ala Ala Arg Lys Glu Glu Arg Ile
                165                 170                 175
Met Leu Arg Asp Ala Arg Gln Trp Leu Asn Ser Gly His Ile Ser Asp
            180                 185                 190
Val Arg His Ala Lys Ser Gly Gly Thr Ala Leu His Val Ala Ala Ala
        195                 200                 205
Lys Gly Tyr Thr Glu Val Leu Lys Leu Leu Ile Gln Ala Gly Tyr Asp
    210                 215                 220
Val Asn Ile Lys Asp Tyr Asp Gly Trp Thr Pro Leu His Ala Ala Ala
225                 230                 235                 240
His Trp Gly Lys Glu Glu Ala Cys Arg Ile Leu Val Asp Asn Leu Cys
                245                 250                 255
Asp Met Glu Thr Val Asn Lys Val Gly Gln Thr Ala Phe Asp Val Ala
            260                 265                 270
Asp Glu Asp Ile Leu Gly Tyr Leu Glu Glu Leu Gln Lys Lys Gln Asn
        275                 280                 285
Leu Leu His Ser Glu Lys Arg Asp Lys Lys Ser Pro Leu Ile Glu Ser
    290                 295                 300
```

-continued

```
Thr Ala Asn Met Glu Asn Asn Gln Pro Gln Lys Thr Phe Lys Asn Lys
305                 310                 315                 320

Glu Thr Leu Ile Ile Glu Pro Glu Lys Asn Ala Ser Arg Ile Glu Ser
                325                 330                 335

Leu Glu Gln Glu Lys Ala Asp Glu Glu Glu Gly Lys Lys Asp Glu
            340                 345                 350

Ser Ser Cys Ser Ser Glu Glu Asp Glu Glu Asp Asp Ser Glu Ser Glu
            355                 360                 365

Ala Glu Thr Asp Lys Thr Lys Pro Met Ala Ser Val Thr Asn Ala His
        370                 375                 380

Thr Ala Ser Thr Gln Ala Ala Pro Ala Ala Val Thr Thr Pro Thr Leu
385                 390                 395                 400

Ser Ser Asn Gln Gly Thr Pro Thr Ser Pro Val Lys Lys Phe Pro Thr
                405                 410                 415

Ser Thr Thr Lys Ile Ser Pro Lys Glu Glu Arg Lys Asp Glu Ser
            420                 425                 430

Pro Ala Ser Trp Arg Leu Gly Leu Arg Lys Thr Gly Ser Tyr Gly Ala
                435                 440                 445

Leu Ala Glu Ile Thr Ala Ser Lys Glu Ala Gln Lys Glu Lys Asp Thr
450                 455                 460

Ala Gly Val Ile Arg Ser Ala Ser Ser Pro Arg Leu Ser Ser Ser Leu
465                 470                 475                 480

Asp Asn Lys Glu Lys Glu Lys Asp Asn Lys Gly Thr Arg Leu Ala Tyr
                485                 490                 495

Val Ala Pro Thr Ile Pro Arg Arg Leu Gly Ser Thr Ser Asp Ile Glu
                500                 505                 510

Glu Lys Glu Asn Arg Glu Ser Ser Asn Leu Arg Thr Ser Ser Ser Tyr
            515                 520                 525

Thr Arg Arg Lys Trp Glu Asp Asp Leu Lys Lys Asn Ser Ser Ile Asn
530                 535                 540

Glu Gly Ser Thr Tyr His Arg Ser Cys Ser Phe Gly Arg Arg Gln Asp
545                 550                 555                 560

Asp Leu Ile Ser Cys Ser Val Pro Ser Thr Thr Ser Thr Pro Thr Val
                565                 570                 575

Thr Ser Ala Ala Gly Leu Gln Lys Ser Phe Leu Ser Ser Thr Ser Thr
            580                 585                 590

Thr Ala Lys Thr Pro Pro Gly Ser Ser Pro Ala Gly Thr Gln Ser Ser
            595                 600                 605

Thr Ser Asn Arg Leu Trp Ala Glu Asp Ser Thr Glu Lys Glu Lys Asp
        610                 615                 620

Ser Ala Pro Thr Ala Ala Thr Ile Leu Val Ala Pro Thr Val Val Ser
625                 630                 635                 640

Ala Ala Ala Ser Ser Thr Thr Ala Leu Thr Thr Thr Ala Gly Thr
                645                 650                 655

Leu Ser Ser Thr Ser Glu Val Arg Glu Arg Arg Ser Tyr Leu Thr
                660                 665                 670

Pro Val Arg Asp Glu Glu Ser Glu Ser Gln Arg Lys Ala Arg Ser Arg
            675                 680                 685

Gln Ala Arg Gln Ser Arg Arg Ser Thr Gln Gly Val Thr Leu Thr Asp
        690                 695                 700

Leu Gln Glu Ala Glu Lys Thr Ile Gly Arg Ser Arg Ser Thr Arg Thr
705                 710                 715                 720

Arg Glu Gln Glu Asn Glu Glu Lys Asp Lys Glu Glu Lys Glu Lys Gln
```

```
                    725                 730                 735
Asp Lys Glu Lys Gln Glu Lys Glu Ser Glu Val Ser Arg Glu
            740                 745                 750
Asp Glu Tyr Lys Gln Lys Tyr Ser Arg Thr Tyr Asp Glu Thr Tyr Ala
            755                 760                 765
Arg Tyr Arg Pro Val Ser Thr Ser Ser Ser Thr Pro Ser Ser Ser
        770                 775                 780
Ser Leu Ser Thr Leu Gly Ser Ser Leu Tyr Ala Ser Ser Gln Leu Asn
785                 790                 795                 800
Arg Pro Asn Ser Leu Val Gly Ile Thr Ser Ala Tyr Ser Arg Gly Leu
                805                 810                 815
Thr Lys Asp Asn Glu Arg Glu Gly Lys Lys Glu Glu Lys Glu
            820                 825                 830
Gly Glu Asp Lys Ser Gln Pro Lys Ser Ile Arg Glu Arg Arg Pro
            835                 840                 845
Arg Glu Lys Arg Arg Ser Thr Gly Val Ser Phe Trp Thr Gln Asp Ser
        850                 855                 860
Asp Glu Asn Glu Gln Glu Arg Gln Ser Asp Thr Glu Asp Gly Ser Ser
865                 870                 875                 880
Lys Arg Asp Thr Gln Thr Asp Ser Val Ser Arg Tyr Asp Ser Ser Ser
                885                 890                 895
Thr Ser Ser Ser Asp Arg Tyr Asp Ser Leu Leu Gly Arg Ser Ala Ser
                900                 905                 910
Tyr Ser Tyr Leu Glu Glu Arg Lys Pro Tyr Gly Ser Arg Leu Glu Lys
            915                 920                 925
Asp Asp Ser Thr Asp Phe Lys Lys Leu Tyr Glu Gln Ile Leu Ala Glu
            930                 935                 940
Asn Glu Lys Leu Lys Ala Gln Leu His Asp Thr Asn Met Glu Leu Thr
945                 950                 955                 960
Asp Leu Lys Leu Gln Leu Glu Lys Ala Thr Gln Arg Gln Glu Arg Phe
                965                 970                 975
Ala Asp Arg Ser Leu Leu Glu Met Glu Lys Arg Glu Arg Arg Ala Leu
            980                 985                 990
Glu Arg Arg Ile Ser Glu Met Glu Glu Glu Leu Lys Met Leu Pro Asp
            995                 1000                1005
Leu Lys Ala Asp Asn Gln Arg Leu Lys Asp Glu Asn Gly Ala Leu Ile
    1010                1015                1020
Arg Val Ile Ser Lys Leu Ser Lys
1025                1030

<210> SEQ ID NO 32
<211> LENGTH: 31
<212> TYPE: PRT
<213> ORGANISM: RABBIT

<400> SEQUENCE: 32

Gly Arg Arg Val Ser Phe Ala Asp Asn Phe Gly Phe Asn Leu Val Ser
1               5                   10                  15

Val Lys Glu Phe Asp Thr Trp Glu Leu Pro Ser Val Ser Thr Thr
            20                  25                  30

<210> SEQ ID NO 33
<211> LENGTH: 976
<212> TYPE: PRT
<213> ORGANISM: RAT
```

```
<400> SEQUENCE: 33

Met Lys Met Ala Asp Ala Lys Gln Lys Arg Asn Glu Gln Leu Lys Arg
  1               5                  10                  15

Trp Ile Gly Ser Glu Thr Asp Leu Glu Pro Pro Val Val Lys Arg Gln
             20                  25                  30

Lys Thr Lys Val Lys Phe Asp Asp Gly Ala Val Phe Leu Ala Ala Cys
         35                  40                  45

Ser Ser Gly Asp Thr Asp Glu Val Leu Lys Leu Leu His Arg Gly Ala
     50                  55                  60

Asp Ile Asn Tyr Ala Asn Val Asp Gly Leu Thr Ala Leu His Gln Ala
 65                  70                  75                  80

Cys Ile Asp Asp Asn Val Asp Met Val Lys Phe Leu Val Glu Asn Gly
                 85                  90                  95

Ala Asn Ile Asn Gln Pro Asp Asn Glu Gly Trp Ile Pro Leu His Ala
                100                 105                 110

Ala Ala Ser Cys Gly Tyr Leu Asp Ile Ala Glu Phe Leu Ile Gly Gln
            115                 120                 125

Gly Ala His Val Gly Ala Val Asn Ser Glu Gly Asp Thr Pro Leu Asp
130                 135                 140

Ile Ala Glu Glu Glu Ala Met Glu Glu Leu Leu Gln Asn Glu Val Asn
145                 150                 155                 160

Arg Gln Gly Val Asp Ile Glu Ala Ala Arg Lys Glu Glu Arg Ile
                165                 170                 175

Met Leu Arg Asp Ala Arg Gln Trp Leu Asn Ser Gly His Ile Ser Asp
            180                 185                 190

Val Arg His Ala Lys Ser Gly Gly Thr Ala Leu His Val Ala Ala Ala
        195                 200                 205

Lys Gly Tyr Thr Glu Val Leu Lys Leu Leu Ile Gln Ala Gly Tyr Asp
    210                 215                 220

Val Asn Ile Lys Asp Tyr Asp Gly Trp Thr Pro Leu His Ala Ala Ala
225                 230                 235                 240

His Trp Gly Lys Glu Glu Ala Cys Arg Ile Leu Val Asp Asn Leu Cys
                245                 250                 255

Asp Met Glu Thr Val Asn Lys Val Gly Gln Thr Ala Phe Asp Val Ala
            260                 265                 270

Asp Glu Asp Ile Leu Gly Tyr Leu Glu Glu Leu Gln Lys Lys Gln Asn
        275                 280                 285

Leu Leu His Ser Glu Lys Arg Asp Lys Lys Ser Pro Leu Ile Glu Ser
    290                 295                 300

Thr Ala Asn Met Glu Asn Asn Gln Pro Gln Lys Thr Phe Lys Asn Lys
305                 310                 315                 320

Glu Thr Leu Ile Ile Glu Pro Glu Lys Asn Ala Ser Arg Ile Glu Ser
                325                 330                 335

Leu Glu Gln Glu Lys Ala Asp Glu Glu Glu Gly Lys Lys Asp Glu
            340                 345                 350

Ser Ser Cys Ser Ser Glu Glu Asp Glu Glu Asp Asp Ser Glu Ser Glu
        355                 360                 365

Ala Glu Thr Asp Lys Thr Lys Pro Met Ala Ser Val Thr Asn Ala His
    370                 375                 380

Thr Ala Ser Thr Gln Ala Ala Pro Ala Ala Val Thr Thr Pro Thr Leu
385                 390                 395                 400

Ser Ser Asn Gln Gly Thr Pro Ser Pro Val Lys Lys Phe Pro Thr
                405                 410                 415
```

```
Ser Thr Thr Lys Ile Ser Pro Lys Glu Glu Arg Lys Asp Glu Ser
            420                 425                 430

Pro Ala Ser Trp Arg Leu Gly Leu Arg Lys Thr Gly Ser Tyr Gly Ala
            435                 440                 445

Leu Ala Glu Ile Thr Ala Ser Lys Glu Ala Gln Lys Glu Lys Asp Thr
            450                 455                 460

Ala Gly Val Ile Arg Ser Ala Ser Pro Arg Leu Ser Ser Ser Leu
465                 470                 475                 480

Asp Asn Lys Glu Lys Glu Lys Asp Asn Lys Gly Thr Arg Leu Ala Tyr
                485                 490                 495

Val Ala Pro Thr Ile Pro Arg Arg Leu Gly Ser Thr Ser Asp Ile Glu
            500                 505                 510

Glu Lys Glu Asn Arg Glu Ser Ser Asn Leu Arg Thr Ser Ser Ser Tyr
            515                 520                 525

Thr Arg Arg Lys Trp Glu Asp Asp Leu Lys Lys Asn Ser Ser Ile Asn
            530                 535                 540

Glu Gly Ser Thr Tyr His Arg Ser Thr Ser Asn Arg Leu Trp Ala Glu
545                 550                 555                 560

Asp Ser Thr Glu Lys Glu Lys Asp Ser Ala Pro Thr Ala Ala Thr Ile
                565                 570                 575

Leu Val Ala Pro Thr Val Val Ser Ala Ala Ser Ser Thr Thr Ala
            580                 585                 590

Leu Thr Thr Thr Thr Ala Gly Thr Leu Ser Ser Thr Ser Glu Val Arg
            595                 600                 605

Glu Arg Arg Arg Ser Tyr Leu Thr Pro Val Arg Asp Glu Glu Ser Glu
            610                 615                 620

Ser Gln Arg Lys Ala Arg Ser Arg Gln Ala Arg Gln Ser Arg Arg Ser
625                 630                 635                 640

Thr Gln Gly Val Thr Leu Thr Asp Leu Gln Glu Ala Glu Lys Thr Ile
                645                 650                 655

Gly Arg Ser Arg Ser Thr Arg Thr Arg Glu Gln Glu Asn Glu Glu Lys
            660                 665                 670

Asp Lys Glu Glu Lys Glu Lys Gln Asp Lys Glu Lys Gln Glu Glu Lys
            675                 680                 685

Lys Glu Ser Glu Val Ser Arg Glu Asp Tyr Lys Gln Lys Tyr Ser
            690                 695                 700

Arg Thr Tyr Asp Glu Thr Tyr Ala Arg Tyr Arg Pro Val Ser Thr Ser
705                 710                 715                 720

Ser Ser Ser Thr Pro Ser Ser Ser Leu Ser Thr Leu Gly Ser Ser
                725                 730                 735

Leu Tyr Ala Ser Ser Gln Leu Asn Arg Pro Asn Ser Leu Val Gly Ile
            740                 745                 750

Thr Ser Ala Tyr Ser Arg Gly Leu Thr Lys Asp Asn Glu Arg Glu Gly
            755                 760                 765

Glu Lys Lys Glu Glu Glu Lys Glu Gly Glu Asp Lys Ser Gln Pro Lys
            770                 775                 780

Ser Ile Arg Glu Arg Arg Arg Pro Arg Glu Lys Arg Arg Ser Thr Gly
785                 790                 795                 800

Val Ser Phe Trp Thr Gln Asp Ser Asp Glu Asn Glu Gln Glu Arg Gln
                805                 810                 815

Ser Asp Thr Glu Asp Gly Ser Ser Lys Arg Asp Thr Gln Thr Asp Ser
            820                 825                 830
```

-continued

```
Val Ser Arg Tyr Asp Ser Ser Thr Ser Ser Asp Arg Tyr Asp
        835                 840                 845

Ser Leu Leu Gly Arg Ser Ala Ser Tyr Ser Tyr Leu Glu Glu Arg Lys
    850                 855                 860

Pro Tyr Gly Ser Arg Leu Glu Lys Asp Asp Ser Thr Asp Phe Lys Lys
865                 870                 875                 880

Leu Tyr Glu Gln Ile Leu Ala Glu Asn Glu Lys Leu Lys Ala Gln Leu
                885                 890                 895

His Asp Thr Asn Met Glu Leu Thr Asp Leu Lys Leu Gln Leu Glu Lys
            900                 905                 910

Ala Thr Gln Arg Gln Glu Arg Phe Ala Asp Arg Ser Leu Leu Glu Met
        915                 920                 925

Glu Lys Arg Glu Arg Arg Ala Leu Glu Arg Arg Ile Ser Glu Met Glu
    930                 935                 940

Glu Glu Leu Lys Met Leu Pro Asp Leu Lys Ala Asp Asn Gln Arg Leu
945                 950                 955                 960

Lys Asp Glu Asn Gly Ala Leu Ile Arg Val Ile Ser Lys Leu Ser Lys
                965                 970                 975
```

<210> SEQ ID NO 34
<211> LENGTH: 1122
<212> TYPE: PRT
<213> ORGANISM: Homo sapiens

<400> SEQUENCE: 34

```
Met Glu Pro Ser Glu Val Pro Ser Gln Ile Ser Lys Asp Asn Phe Leu
1               5                   10                  15

Glu Val Pro Asn Leu Ser Asp Ser Leu Cys Glu Asp Glu Glu Val Thr
                20                  25                  30

Phe Gln Pro Gly Phe Ser Pro Gln Pro Ser Arg Arg Gly Ser Asp Ser
            35                  40                  45

Ser Glu Asp Ile Tyr Leu Asp Thr Pro Ser Ser Gly Thr Arg Arg Val
    50                  55                  60

Ser Phe Ala Asp Ser Phe Gly Phe Asn Leu Val Ser Val Lys Glu Phe
65                  70                  75                  80

Asp Cys Trp Glu Leu Pro Ser Ala Ser Thr Thr Phe Asp Leu Gly Thr
                85                  90                  95

Asp Ile Phe His Thr Glu Glu Tyr Val Leu Ala Pro Leu Phe Asp Leu
            100                 105                 110

Pro Ser Ser Lys Glu Asp Leu Met Gln Gln Leu Gln Ile Gln Lys Ala
    115                 120                 125

Ile Leu Glu Ser Thr Glu Ser Leu Leu Gly Ser Thr Ser Ile Lys Gly
130                 135                 140

Ile Ile Arg Val Leu Asn Val Ser Phe Glu Lys Leu Val Tyr Val Arg
145                 150                 155                 160

Met Ser Leu Asp Asp Trp Gln Thr His Tyr Asp Ile Leu Ala Glu Tyr
                165                 170                 175

Val Pro Asn Ser Cys Asp Gly Glu Thr Asp Gln Phe Ser Phe Lys Ile
            180                 185                 190

Val Leu Val Pro Pro Tyr Gln Lys Asp Gly Ser Lys Val Glu Phe Cys
    195                 200                 205

Ile Arg Tyr Glu Thr Ser Val Gly Thr Phe Trp Ser Asn Asn Asn Gly
210                 215                 220

Thr Asn Tyr Thr Phe Ile Cys Gln Lys Lys Glu Gln Glu Pro Glu Pro
225                 230                 235                 240
```

-continued

```
Val Lys Pro Trp Lys Glu Val Pro Asn Arg Gln Ile Lys Gly Cys Leu
                245                 250                 255
Lys Val Lys Ser Ser Lys Glu Ser Ser Val Thr Ser Glu Glu Asn
            260                 265                 270
Asn Phe Glu Asn Pro Lys Asn Thr Asp Thr Tyr Ile Pro Thr Ile Ile
            275                 280                 285
Cys Ser His Glu Asp Lys Glu Asp Leu Glu Ala Ser Asn Arg Asn Val
290                 295                 300
Lys Asp Val Asn Arg Glu His Asp Glu His Asn Glu Lys Glu Leu Glu
305                 310                 315                 320
Leu Met Ile Asn Gln His Leu Ile Arg Thr Arg Ser Thr Ala Ser Arg
                325                 330                 335
Asp Glu Arg Asn Thr Phe Ser Thr Asp Pro Val Asn Phe Pro Asn Lys
                340                 345                 350
Ala Glu Gly Leu Glu Lys Lys Gln Ile His Gly Glu Ile Cys Thr Asp
                355                 360                 365
Leu Phe Gln Arg Ser Leu Ser Pro Ser Ser Ala Glu Ser Ser Val
370                 375                 380
Lys Gly Asp Phe Tyr Cys Asn Glu Lys Tyr Ser Ser Gly Asp Asp Cys
385                 390                 395                 400
Thr His Gln Pro Ser Glu Glu Thr Thr Ser Asn Met Gly Glu Ile Lys
                405                 410                 415
Pro Ser Leu Gly Asp Thr Ser Asp Glu Leu Val Gln Leu His Thr
                420                 425                 430
Gly Ser Lys Glu Val Leu Asp Asp Asn Ala Asn Pro Ala His Gly Asn
            435                 440                 445
Gly Thr Met Gln Ile Pro Cys Pro Ser Ser Asp Gln Leu Met Ala Gly
            450                 455                 460
Asn Leu Asn Lys Lys His Glu Gly Gly Ala Lys Lys Ile Glu Val Lys
465                 470                 475                 480
Asp Leu Gly Cys Leu Arg Arg Asp Phe His Ser Asp Thr Ser Ala Cys
                485                 490                 495
Leu Lys Glu Ser Thr Glu Glu Gly Ser Ser Lys Glu Asp Tyr Tyr Gly
                500                 505                 510
Asn Gly Lys Asp Asp Glu Glu Gln Arg Ile Tyr Leu Gly Val Asn Glu
            515                 520                 525
Lys Gln Arg Lys Asn Phe Gln Thr Ile Leu His Asp Gln Glu Arg Lys
530                 535                 540
Met Gly Asn Pro Lys Ile Ser Val Ala Gly Ile Gly Ala Ser Asn Arg
545                 550                 555                 560
Asp Leu Ala Thr Leu Leu Ser Glu His Thr Ala Ile Pro Thr Arg Ala
                565                 570                 575
Ile Thr Ala Asp Val Ser His Ser Pro Arg Thr Asn Leu Ser Trp Glu
                580                 585                 590
Glu Ala Val Leu Thr Pro Glu His His His Leu Thr Ser Glu Gly Ser
                595                 600                 605
Ala Leu Gly Gly Ile Thr Gly Gln Val Cys Ser Ser Arg Thr Gly Asn
            610                 615                 620
Val Leu Arg Asn Asp Tyr Leu Phe Gln Val Glu Lys Ser Gly Gly
625                 630                 635                 640
Ile Asn Ser Glu Asp Gln Asp Asn Ser Pro Gln His Lys Gln Ser Trp
                645                 650                 655
```

-continued

```
Asn Val Leu Glu Ser Gln Gly Lys Ser Arg Glu Asn Lys Thr Asn Ile
            660                 665                 670

Thr Glu His Ile Lys Gly Gln Thr Asp Cys Glu Asp Val Trp Gly Lys
            675                 680                 685

Arg Asp Asn Thr Arg Ser Leu Lys Ala Thr Thr Glu Glu Leu Phe Thr
            690                 695                 700

Cys Gln Glu Thr Val Cys Cys Glu Leu Ser Ser Leu Ala Asp His Gly
705                 710                 715                 720

Ile Thr Glu Lys Ala Glu Ala Gly Thr Ala Tyr Ile Ile Lys Thr Thr
                725                 730                 735

Ser Glu Ser Thr Pro Glu Ser Met Ser Ala Arg Glu Lys Ala Ile Ile
            740                 745                 750

Ala Lys Leu Pro Gln Glu Thr Ala Arg Ser Asp Arg Pro Ile Glu Val
            755                 760                 765

Lys Glu Thr Ala Phe Asp Pro His Glu Gly Arg Asn Asp Asp Ser His
            770                 775                 780

Tyr Thr Leu Cys Gln Arg Asp Thr Val Gly Val Ile Tyr Asp Asn Asp
785                 790                 795                 800

Phe Glu Lys Glu Ser Arg Leu Gly Ile Cys Asn Val Arg Val Asp Glu
                805                 810                 815

Met Glu Lys Glu Glu Thr Met Ser Met Tyr Asn Pro Arg Lys Thr His
            820                 825                 830

Asp Arg Glu Lys Cys Gly Thr Gly Asn Ile Thr Ser Val Glu Glu Ser
            835                 840                 845

Ser Trp Val Ile Thr Glu Tyr Gln Lys Ala Thr Ser Lys Leu Asp Leu
            850                 855                 860

Gln Leu Gly Met Leu Pro Thr Asp Lys Thr Val Phe Ser Glu Asn Arg
865                 870                 875                 880

Asp His Arg Gln Val Gln Glu Leu Ser Lys Lys Thr Asp Ser Asp Ala
                885                 890                 895

Ile Val His Ser Ala Phe Asn Ser Asp Thr Asn Arg Ala Pro Gln Asn
            900                 905                 910

Ser Ser Pro Phe Ser Lys His His Thr Glu Ile Ser Val Ser Thr Asn
            915                 920                 925

Glu Gln Ala Ile Ala Val Glu Asn Ala Val Thr Thr Met Ala Ser Gln
            930                 935                 940

Pro Ile Ser Thr Lys Ser Glu Asn Ile Cys Asn Ser Thr Arg Glu Ile
945                 950                 955                 960

Gln Gly Ile Glu Lys His Pro Tyr Pro Glu Ser Lys Pro Glu Glu Val
                965                 970                 975

Ser Arg Ser Ser Gly Ile Val Thr Ser Gly Ser Arg Lys Glu Arg Cys
            980                 985                 990

Ile Gly Gln Ile Phe Gln Thr Glu Glu Tyr Ser Val Glu Lys Ser Leu
            995                 1000                1005

Gly Pro Met Ile Leu Ile Asn Lys Pro Leu Glu Asn Met Glu Glu Ala
            1010                1015                1020

Arg His Glu Asn Glu Gly Leu Val Ser Ser Gly Gln Ser Leu Tyr Thr
1025                1030                1035                1040

Ser Gly Glu Lys Glu Ser Asp Ser Ser Ala Ser Thr Ser Leu Pro Val
                1045                1050                1055

Glu Glu Ser Gln Ala Gln Gly Asn Glu Ser Leu Phe Ser Lys Tyr Thr
            1060                1065                1070

Asn Ser Lys Ile Pro Tyr Phe Leu Leu Phe Leu Ile Phe Leu Ile Thr
```

-continued

```
                      1075                1080                1085
Val Tyr His Tyr Asp Leu Met Ile Gly Leu Thr Phe Tyr Val Leu Ser
        1090                1095                1100

Leu Ser Trp Leu Ser Trp Glu Glu Gly Arg Gln Lys Glu Ser Val Lys
1105                1110                1115                1120

Lys Lys

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence:SYNTHETIC
      CONSENSUS SEQUENCE
<220> FEATURE:
<223> OTHER INFORMATION: RESIDUE 1 IS ARG OR LYS
<220> FEATURE:
<223> OTHER INFORMATION: RESIDUE 2 IS VAL OR ILE
<220> FEATURE:
<223> OTHER INFORMATION: RESIDUE 3 IS VARIABLE IN THE CONSENSUS SEQUENCE

<400> SEQUENCE: 35

Xaa Xaa Xaa Phe
  1

<210> SEQ ID NO 36
<211> LENGTH: 9
<212> TYPE: PRT
<213> ORGANISM: Homo sapiens

<400> SEQUENCE: 36

Ala Val Lys Phe Asp Met Gly Ala Tyr
  1               5

<210> SEQ ID NO 37
<211> LENGTH: 186
<212> TYPE: PRT
<213> ORGANISM: CHICKEN

<400> SEQUENCE: 37

Met Ser Ser Leu Phe Thr Arg Ser Lys Glu Tyr Thr Arg Ser Arg Lys
  1               5                  10                  15

Ser Gln Ser Asp Ser Pro Pro Ser Ser Pro Ser Ile Ala Lys Thr
                 20                  25                  30

Leu Arg His Glu Arg Leu Ser Arg Leu Glu Ala Ala Thr Thr Pro Ala
             35                  40                  45

Thr Ser Asp Ser Tyr Ser Asp Arg Ala Ser Ser Arg Ser Ser Ala Tyr
         50                  55                  60

Ser Arg Arg Glu Asn Arg Leu Ala Ala Leu Ser Ser Arg Ala Glu Glu
 65                  70                  75                  80

Glu Ser Asn Arg Asp Tyr Lys Lys Leu Tyr Glu Ser Ala Leu Ser Glu
                 85                  90                  95

Asn Gln Lys Leu Lys Ser Lys Leu Gln Glu Ala Gln Leu Glu Leu Ala
                100                 105                 110

Asp Ile Lys Ser Lys Leu Glu Lys Ala Ala Gln Gln Lys His Glu Lys
            115                 120                 125

Thr Ser Asp Arg Ser Ser Met Leu Glu Met Glu Lys Arg Glu Lys Arg
        130                 135                 140

Ala Leu Glu Arg Lys Leu Ser Glu Met Glu Glu Glu Met Lys Ile Leu
145                 150                 155                 160
```

```
Thr Glu Leu Lys Ser Asp Asn Gln Arg Leu Lys Asp Glu Asn Gly Ala
            165                 170                 175

Leu Ile Arg Val Ile Ser Lys Leu Ser Lys
            180                 185

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 38

Gln Leu Asn Ser Ser
  1               5

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 39

Ser Pro Glu Lys Asn Val Arg Phe Ala Ile Glu
  1               5                  10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 40

Ser Ser Gly Lys Ser Val Arg Phe Ala Ala His
  1               5                  10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 41

Ile Arg Ser Lys Ser Val His Phe Asp Gln Ala
  1               5                  10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 42

Gln Arg Ser Lys Ser Val His Phe Asp Arg Val
  1               5                  10

<210> SEQ ID NO 43
<211> LENGTH: 11
```

-continued

```
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 43

Val Phe Val Lys Asn Ile Tyr Phe Ser Asn Ala
 1               5                  10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 44

Thr Lys Asn Arg His Ile His Phe Asn Asp Arg
 1               5                  10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 45

Pro Arg Glu Arg His Ile Lys Phe Asn Asp Asn
 1               5                  10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 46

Phe Lys Ser Lys Lys Val Arg Phe Ser Glu His
 1               5                  10

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 47

Leu Ser Glu Lys Phe Ile Pro Phe Asn Asn Leu
 1               5                  10

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 48

Lys Lys Lys Arg Cys Val Asn Phe Arg Asn Lys
```

-continued

```
                  1               5               10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence:SYNTHETIC
      PEPTIDE

<400> SEQUENCE: 49

Lys Val Thr Arg Glu Ile Thr Phe Trp Lys Glu
  1               5                  10
```